(12) United States Patent
Renz et al.

(10) Patent No.: US 7,855,321 B2
(45) Date of Patent: Dec. 21, 2010

(54) PLANT ACYLTRANSFERASES SPECIFIC FOR LONG-CHAINED, MULTIPLY UNSATURATED FATTY ACIDS

(75) Inventors: Andreas Renz, Limburgerhof (DE); Jörg Bauer, Ludwigshafen (DE); Margit Frentzen, Aachen (DE); Nursen Sözer, Übach-Palenberg (DE); Stobart Keith, Bristol (GB); Thomas Fraser, Bristol (GB); Colin M. Lazarus, Bristol (GB); Baoxiu Qi, Bath (GB); Amine Abbadi, Hamburg (DE); Ernst Heinz, Hamburg (DE)

(73) Assignee: University of Bristol, Bristol (GB)

( * ) Notice: Subject to any disclaimer, the term of this patent is extended or adjusted under 35 U.S.C. 154(b) by 333 days.

(21) Appl. No.: 10/552,013

(22) PCT Filed: Mar. 26, 2004

(86) PCT No.: PCT/EP2004/003224

§ 371 (c)(1),
(2), (4) Date: Sep. 30, 2005

(87) PCT Pub. No.: WO2004/087902

PCT Pub. Date: Oct. 14, 2004

(65) Prior Publication Data

US 2006/0174376 A1 Aug. 3, 2006

(30) Foreign Application Priority Data

Mar. 31, 2003 (DE) .................. 103 14 759
Oct. 17, 2003 (DE) .................. 103 48 996

(51) Int. Cl.
*A01H 5/00* (2006.01)
*C12N 15/82* (2006.01)
*C12N 1/20* (2006.01)
*C07H 21/04* (2006.01)

(52) U.S. Cl. .............. 800/281; 536/23.2; 800/298; 435/252.3; 435/254.2

(58) Field of Classification Search .................. None
See application file for complete search history.

(56) References Cited

U.S. PATENT DOCUMENTS

| 5,614,393 | A | 3/1997 | Thomas et al. |
| 5,968,791 | A | 10/1999 | Davies et al. |
| 6,043,411 | A | 3/2000 | Nishizawa et al. |
| 2004/0111763 | A1 | 6/2004 | Heinz et al. |

FOREIGN PATENT DOCUMENTS

| DE | 102 19 203 | 11/2003 |
| EP | 0 550 162 | 7/1993 |
| EP | 0 794 250 | 9/1997 |
| WO | WO-91/13972 | 9/1991 |
| WO | WO-93/06712 | 4/1993 |
| WO | WO-93/10241 | 5/1993 |
| WO | WO-93/11245 | 6/1993 |
| WO | WO-94/11516 | 5/1994 |
| WO | WO-94/13814 | 6/1994 |
| WO | WO-94/18337 | 8/1994 |
| WO | WO-95/18222 | 7/1995 |
| WO | WO-95/27791 | 10/1995 |
| WO | WO-96/21022 | 7/1996 |
| WO | WO-96/24674 | 8/1996 |
| WO | WO-97/21340 | 6/1997 |
| WO | WO-97/30582 | 8/1997 |
| WO | WO-98/27203 | 6/1998 |
| WO | WO-98/46763 | 10/1998 |
| WO | WO-98/46764 | 10/1998 |
| WO | WO-98/46765 | 10/1998 |
| WO | WO-98/46776 | 10/1998 |
| WO | WO-98/54302 | 12/1998 |
| WO | WO-98/54303 | 12/1998 |
| WO | WO-98/55625 | 12/1998 |
| WO | WO-98/55631 | 12/1998 |
| WO | WO-98/55632 | 12/1998 |

(Continued)

OTHER PUBLICATIONS

Broun et al, Science 282:1315-1317, Nov. 13, 1998.*
Van de Loo et al , PNAS, USA 92:6743-6747, Jul. 1995.*
Doerks et al, TIG 14(6): 248-250, Jun. 1998.*
Smith et al, Nature Biotechnology 15: 1222-1223, Nov. 15, 1997.*
Brenner, S.E., TIG 15(4): 132-133, Apr. 1999.*
Bork et al, TIG 12(10): 425-427, Oct. 1996.*
DeLuca, V. AgBiotech News and Information 5(6): 225N-229N, 1993.*
McCreath et al, Nature 405: 1066-1069, Jul. 29, 2000.*
Yamashita, A. et al., "ATP-independent Fatty Acyl-Coenzyme A synthesis from Phospholipid", The Journal of Biological Chemistry 276(29) (2001), pp. 26745-26752.

(Continued)

*Primary Examiner*—Elizabeth F McElwain
(74) *Attorney, Agent, or Firm*—Connolly Bove Lodge & Hutz, LLP

(57) ABSTRACT

The present invention relates to a process for the production of long-chain polyunsaturated fatty acids in an organism by introducing, into the organism, nucleic acids which code for polypeptides with acyl transferase activity. These nucleic acid sequences, if appropriate together with further nucleic acid sequences which code for polypeptides of the fatty acid or lipid metabolism biosynthesis, can advantageously be expressed in the organism. Furthermore, the invention relates to a method for the production of oils and/or triacylglycerides with an elevated content of long-chain polyunsaturated fatty acids.

The invention furthermore relates to the nucleic acid sequences, nucleic acid constructs, vectors and organisms comprising the nucleic acid sequences according to the invention, vectors comprising the nucleic acid sequences and/or the nucleic acid constructs and to transgenic organisms comprising the abovementioned nucleic acid sequences, nucleic acid constructs and/or vectors.

A further part of the invention relates to oils, lipids and/or fatty acids produced by the process according to the invention and to their use.

21 Claims, 37 Drawing Sheets

FOREIGN PATENT DOCUMENTS

| | | | |
|---|---|---|---|
| WO | WO-99/27111 | | 6/1999 |
| WO | WO-99/64616 | | 12/1999 |
| WO | WO 00/18889 | * | 4/2000 |
| WO | WO-00/18889 | | 4/2000 |
| WO | WO-00/21557 | | 4/2000 |
| WO | WO-00/42195 | | 7/2000 |
| WO | WO-01/59128 | | 8/2001 |
| WO | WO-02/72742 | | 9/2002 |

OTHER PUBLICATIONS

Zou, J. et al., "The *Arabidopsis thaliana TAG1M*utant Has a Mutation in a Diacylglycerol Acyltransferase Gene", The Plant Journal 19(6) (1999), pp. 645-653.

Wang, X. M. et al., "Biosynthesis and Regulation of Linolenic Acid in Higher Plants", Plant Physiol. Biochem., 26(6) 1988, pp. 777-792.

Zank, T. K. et al., "Cloning and Functional Expression of the First Plant Fatty Acid Elongase Specific For Δ6-Polyunsaturated Fatty Acids", Biochemical Society Transactions 28(6) (2000), pp. 654-658.

Tumaney, A. W. et al., "Synthesis of Azidophospholipids and Labeling of Lysophosphatidylcholine Acyltransferase from Developing Soybean Cotyledons", Biochimica et Biophysica Acta 1439 (1999), pp. 47-56.

Stymne, S. et al., "Evidence for the Reversibility of the Acyl-CoA: Lysophosphatidylcholine Acyltransferase in Microsomal Preparations from Developing Safflower (*Carthamus tinctorius* L.) Cotyledons and Rat Liver", Biochem. J. 223 (1984), pp. 305-314.

Stukey, J. E. et al., "The *OLE1* Gene of *Saccharomyces cerevisiae* Encodes the Δ9 Fatty Acid Desaturase and Can Be Functionally Replaced by the Rat Stearoyl-CoA Desaturase Gene", The Journal of Biologica Chemistry 265(33) (1990), pp. 20144-20149.

Cases, S. et al., "Identification of a Gene Encoding an Acyl CoA: Diacylglycerol Acyltransferase, A Key Enzyme in Triacylglycerol Synthesis", Proc. Natl. Acad. Sci. USA 95 (1998), pp. 13018-13023.

Mishra, S. et al., "Purification and Characterization of Thiol-Reagent-Sensitive Glycerol-3-Phosphate Acyltransferase from the Membrane Fraction of an Oleaginous Fungus", Biochem. J. 355 (2001), pp. 315-322.

Vazhappilly, R. et al., "Heterotrophic Production Potential of Omega-3 Polyunsaturated Fatty Acids by Microalgae and Algae-like Microorganisms", Botanica Marina 41 (1998), pp. 553-558.

Oelkers, P. et al., "A Lecithin Cholesterol Acyltransferase-like Gene Mediates Diacylglycerol Esterification in Yeast", The Journal of Biological Chemistry, 275(21) (2000), pp. 15609-15612.

McLean, J. et al., "Cloning and Expression of Human Lecithin-Cholesterol Acyltransferase cDNA", Proc. Natl. Acad. Sci. Usa, 83 (1986), pp. 2335-2339.

Wada, H. et al., "Enhancement of Chilling Tolerance of a Cyanobacterium by Genetic Manipulation of Fatty Acid Desaturation", Nature 347 (1990), pp. 200-203.

Stymne, S. et al., "Triacylglycerol Biosynthesis", Chapter 8 from the Biochemistry of Plants, A Comprehensive Treatise, vol. 9 (1987), Stump, P. K. Ed., Academic Press, NY, pp. 175-214.

Frentzen, M., "Acyltransferases from Basic Science to Modified Seed Oils", Fett/Lipid 100(4-5) (1998), pp. 161-166.

Database EMBL, "Vicia faba putative glycerol-3-phosphate acyltransferase (GPAT) mRNA", Database Accession No. AF090734, Sep. 23, 1998.

Hobbs, D. H. et al., "Cloning of a cDNA Encoding Diacylglycerol Acyltransferase from *Arabidopsis thaliana* and Its Functional Expression", FEBS Letters 452 (1999), pp. 145-149.

Huang, Y-S. et al., "Cloning of Δ2- and Δ6-Desaturases from *Mortierella alpina* and Recombinant Production of γ-Linolenic Acid in *Saccharomyces cerevisiae*", Lipids 34(7) (1999), pp. 649-659.

Lands, W. E. M., "Metabolism of Glycerolipids", The Journal of Biological Chemistry, 235(8) (1960), pp. 2233-2237.

Metz, J. G. et al., "Production of Polyunsaturated Fatty Acids by Polyketide Synthases in Both Prokaryotes and Eukaryotes", Science 293 (2001), pp. 290-293.

Jako, C. et al., "Seed-Specific Over-Expression of an Arabidopsis cDNA Encoding a Diacylglycerol Acyltransferase Enhances Seed oil Content and Seed Weight", Plant Physiology, 126 (2001), pp. 861-874.

Totani, N. et al., "The Filamentous Fungus *Mortierella alpine*, High in Arachidonic Acid", Lipids 22(12) (1987), pp. 1060-1062.

Knutzon, D. S. et al., "Cloning of a Coconut Endosperm cDNA Encoding a 1-Acyl-*sn*Glycerl-3-Phosphate Acyltransferase That Accepts Medium-Chain-Length Substrates", Plant Physiol. 109 (1995), pp. 999-1006.

Alonso, D. L. et al., "Plants as 'Chemical Factories' for the Production of Polyunsaturated Fatty Acids", Biotechnology Advances 18 (2000), pp. 481-497.

Lassner, M. W. et al., "Lysophosphatidic Acid Acyltransferase from Meadowfoam Mediates Insertion of Erucic Acid at the *sn*-2 Position of Triacylglycerol in Transgenic Rapeseed Oil", Plant Physiol 109 (1995), pp. 1389-1394.

Akimoto, M. et al., "Carbon Dioxide Fixation and Polyunsaturated Fatty Acid Production by the Red Alga *Porphyridium Cruentum*", Applied Biochemistry and Biotechnology, 73 (1998), pp. 269-278.

Slabas, A. R. et al., "Acyltransferases and Their Role in the Biosynthesis of Lipids-Opportunities for New Oils", J. Plant Physiol. 158 (2001), pp. 505-513.

Abbadi, A. et al., "Transgenic Oilseeds as Sustainable Source of Nutritionally Relevant C20 and C22 Polyunsaturated Fatty Acids?", Eur. J. Lipid Sci. Technol. 103 (2001), pp. 106-113.

Akermoun, M. et al., "Solubilization of the Plastidial Lysophosphatidylcholine Acyltransferase from *Allium porrum* Leaves: Towards Plants Devoid of Eukaryotic Plastid Lipids?", Biochemical Soc. Transactions 28 (2000), pp. 713-715.

Fraser, T., et al., "Partial purification and photoaffinity labeling of sunflower acyl-CoA: lysophosphatidylcholine acyltransferase", Biochemical Soc. Transactions 28 (2000), pp. 715-718.

* cited by examiner

Figure 1: Vector map of pSUN3CeLPLAT
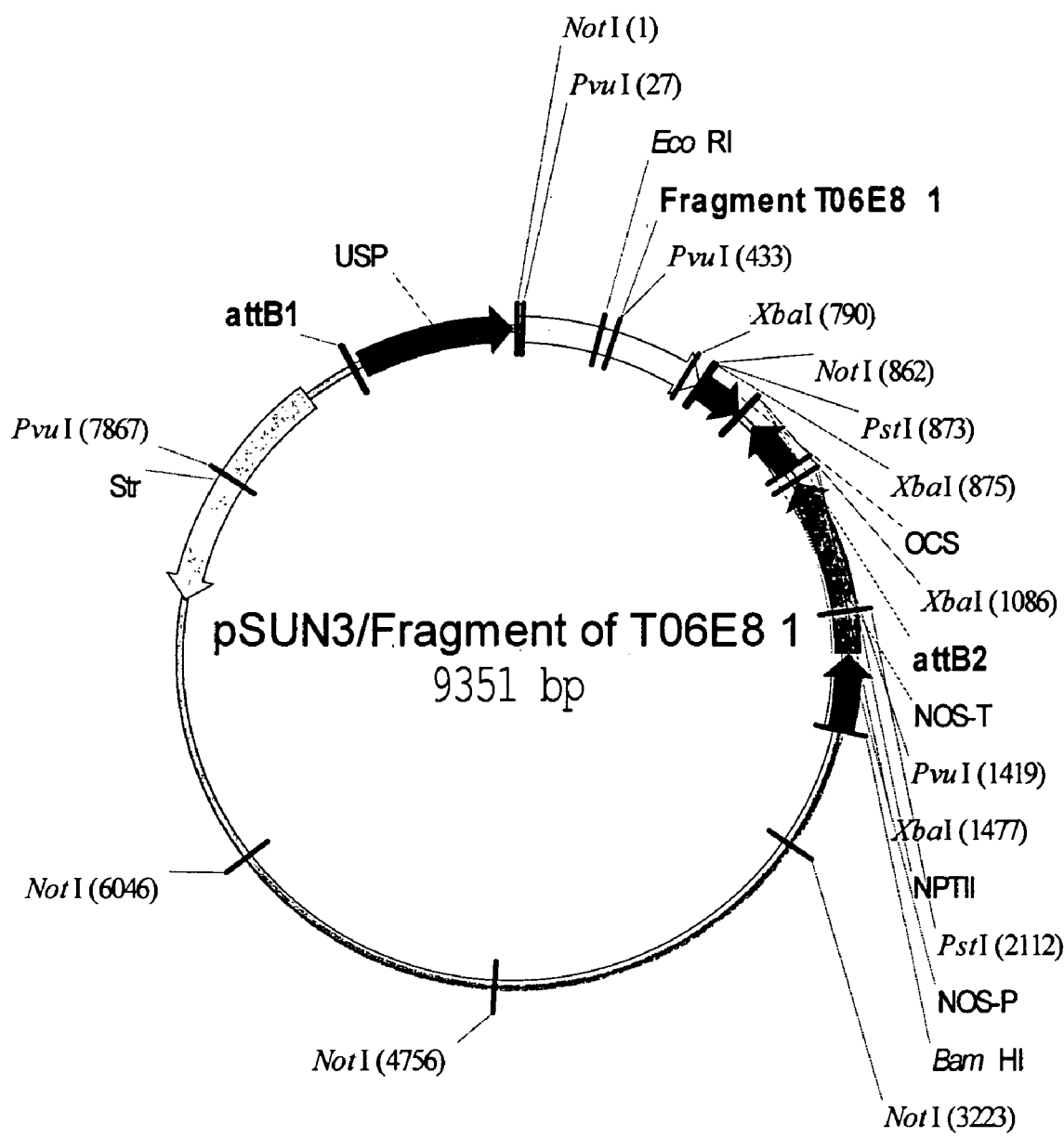

Figure 2: Amino acid sequence alignment of C. elegans LPLATs (Ce-T06E8.1 and Ce-F59F4.4) with the M. musculus LPAAT (Mm-NP061350).

```
              1                                                              50
Mm-NP061350   MELWPGAWTA LLLLLELLLS TLWFCSSSAK YEFKMAFYNG WELFLAILAI
Ce-T06E8.1    ...MENFWSI VVFFLLSILF ILYNISTVCH YYMRISFYYF TLLLHGMEVC
Ce-F59F4.4    .......MTF LAILFVIAVL LLLAQLPVIG EYIRAVYFGM CLIIGGFLGG 51                                                             100
Mm-NP061350   PVCAVRGRNV ENMKIERLLL LHAKYLYGIR VEVRGAHHFP PTQDYVVVSN
Ce-T06E8.1    VTMIPSWLNG KGADYVFHSF FYWCKWTGVH TTVYGYEKTQ VEGPAVVICN
Ce-F59F4.4    LASIPFGKSP NNHFRMFKIF QAMTWPMGVR FELRNSEILH DKKPYIIIAN 101                                                            150
Mm-NP061350   HQSSLDLLGM MEVLPDRCVP IAKRELLWAG SAGLACWLAG ITFIDRKRTG
Ce-T06E8.1    HQSSLDILSM ASIWPKNCVV MMKRILAYVP FFNLGAYFSN TLFIDRYNRE
Ce-F59F4.4    HQSALDVLGM SFAWPVDCVV MLKSSLKYLP GFNLCAYLCD SVYINRFSKE 151                                                            200
Mm-NP061350   DALSVMSEVA QTLLTQDVRV WVFPEGTRNH NGSMIPFKRG AFHIAVQAQV
Ce-T06E8.1    RAMASVDYCA SEMKNRNLKL WVFPEGTRNR EGGFIPFKKG AFNIAVRAQI
Ce-F59F4.4    KALKTVDTTL HELVTKKRKV WLYPEGTRNA EPELLPFKKG AFILAKQAKI 201                                                            250
Mm-NP061350   PIIPIVMSSY QDFYSKKERR FTSPGRCQVR VLPPVSTEGL TPDDVPALAD
Ce-T06E8.1    PIIPVVFSDY RDFYSKPGRY FKNDGEVVIR VLDALPIKGL TLDDVSELSD
Ce-F59F4.4    PIVPCVFSSH KFFYSHAEKR LTS.GNCILD ILPEVDSS... KFDSIDDLSA 251                          285
Mm-NP061350   SVRHSMLTIF REISTDGLGG GDCLKKPGGA GEARL
Ce-T06E8.1    MCRDVMLAAY KEVTLEAQQR NATRRGETKD GKKSE
Ce-F59F4.4    HCRKIMQAHR EKIDAEAANL NI........ .....
```

Figure 3: Fatty acid profiles of transgenic C13ABYS86 S. cerevisiae cells
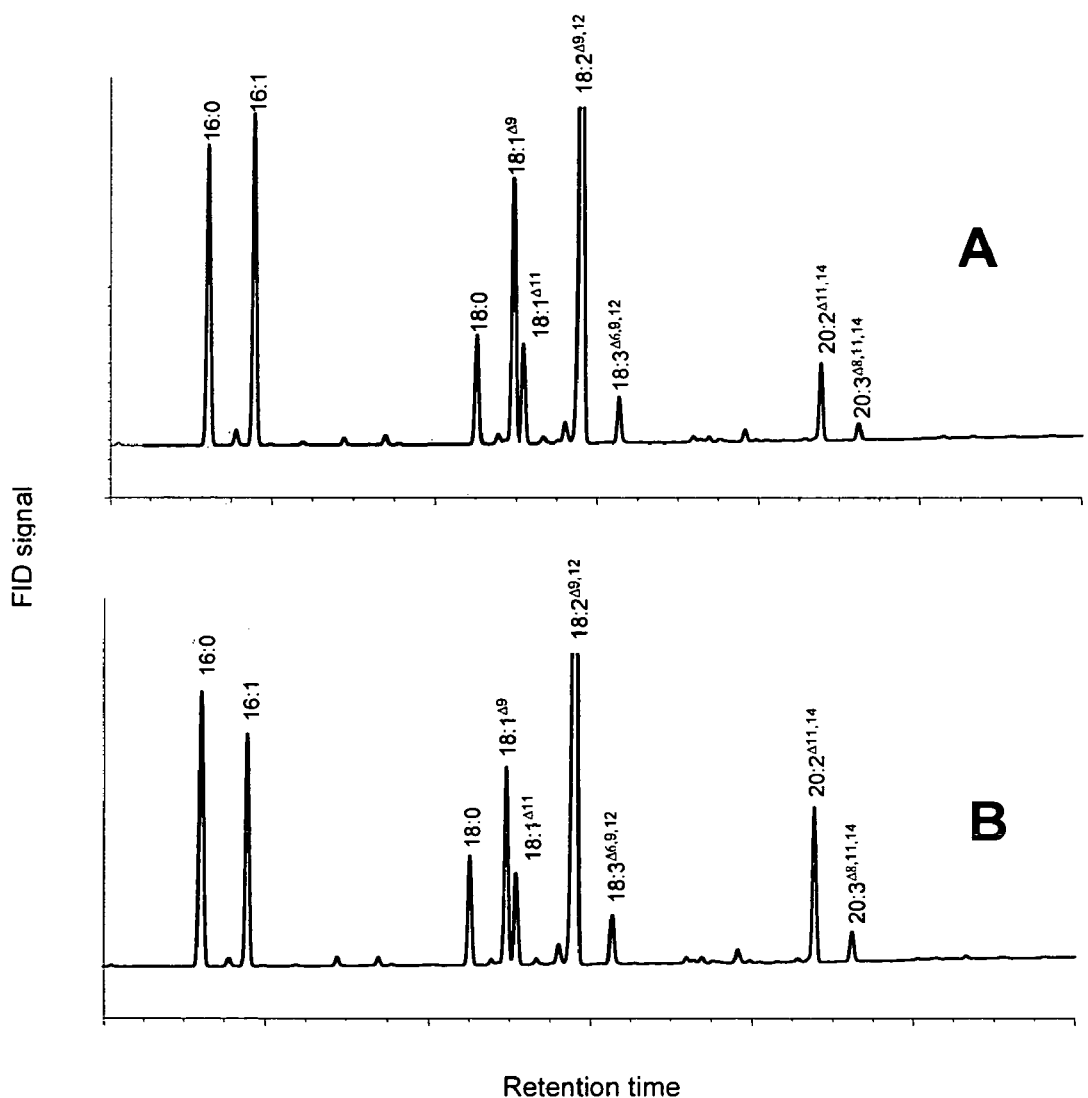

Figure 4: Elongation of exogenously applied $18:2^{\Delta 9,12}$ and $18:3^{\Delta 9,12,15}$, respectively, following their endogenous Δ-6-desaturation (data from figs 2 and 3).
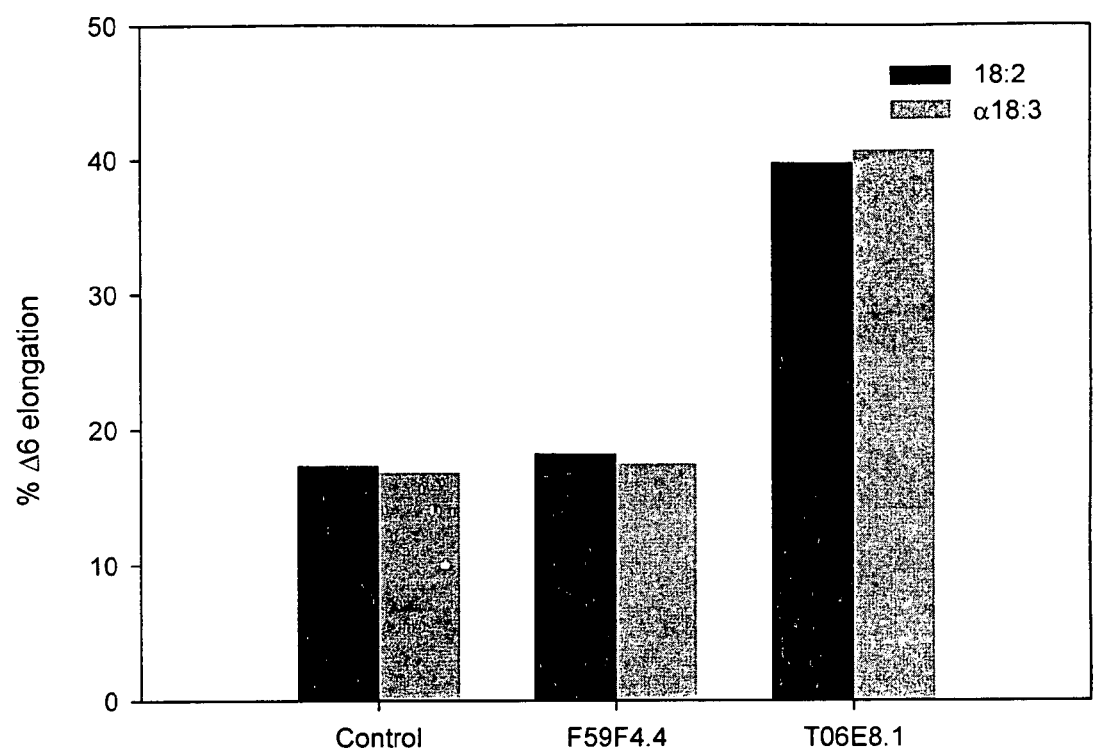

Figure 5: Fatty acid profiles of transgenic C13ABYS86 S. cerevisiae cells
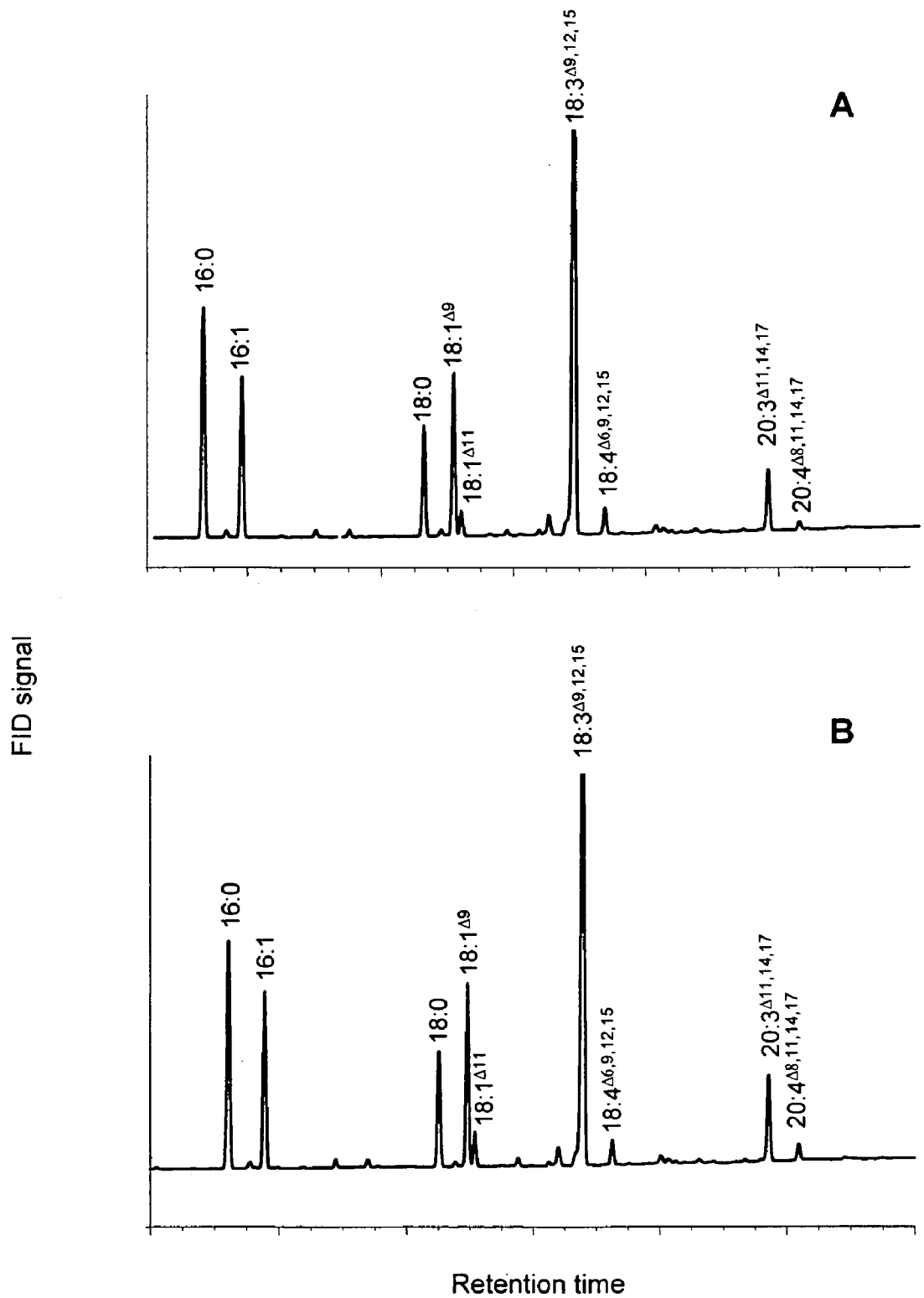

Figure 6: Acyl-CoA composition of transgenic INVSc1 yeasts which had been transformed with the vectors pESCLeu PpD6Pse1/pYes2 (A) or pESCLeu-PpD6-Pse1/pYes2-T06E8.1 (B).
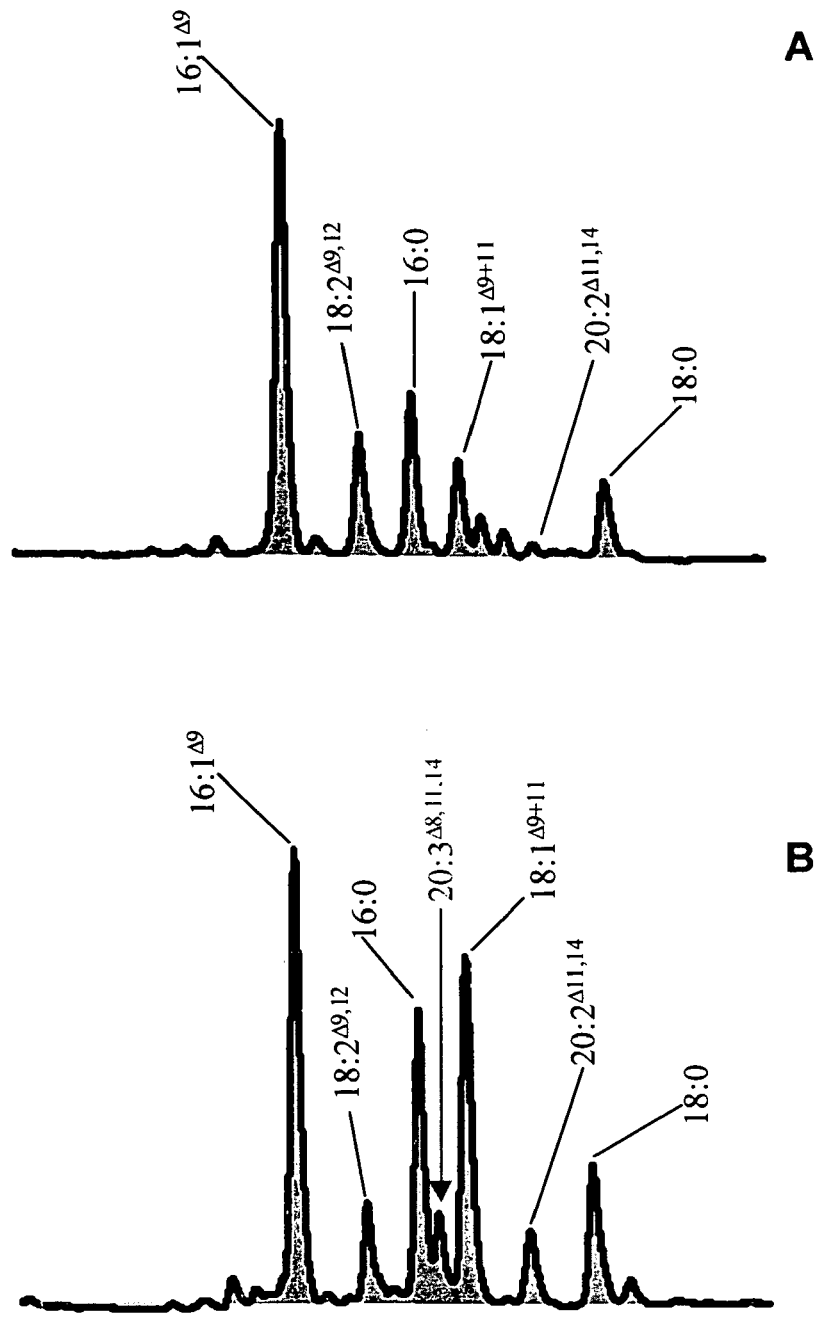

Figure 7: Fatty acid profiles of transgenic INVSc1 *S. cerevisiae* cells
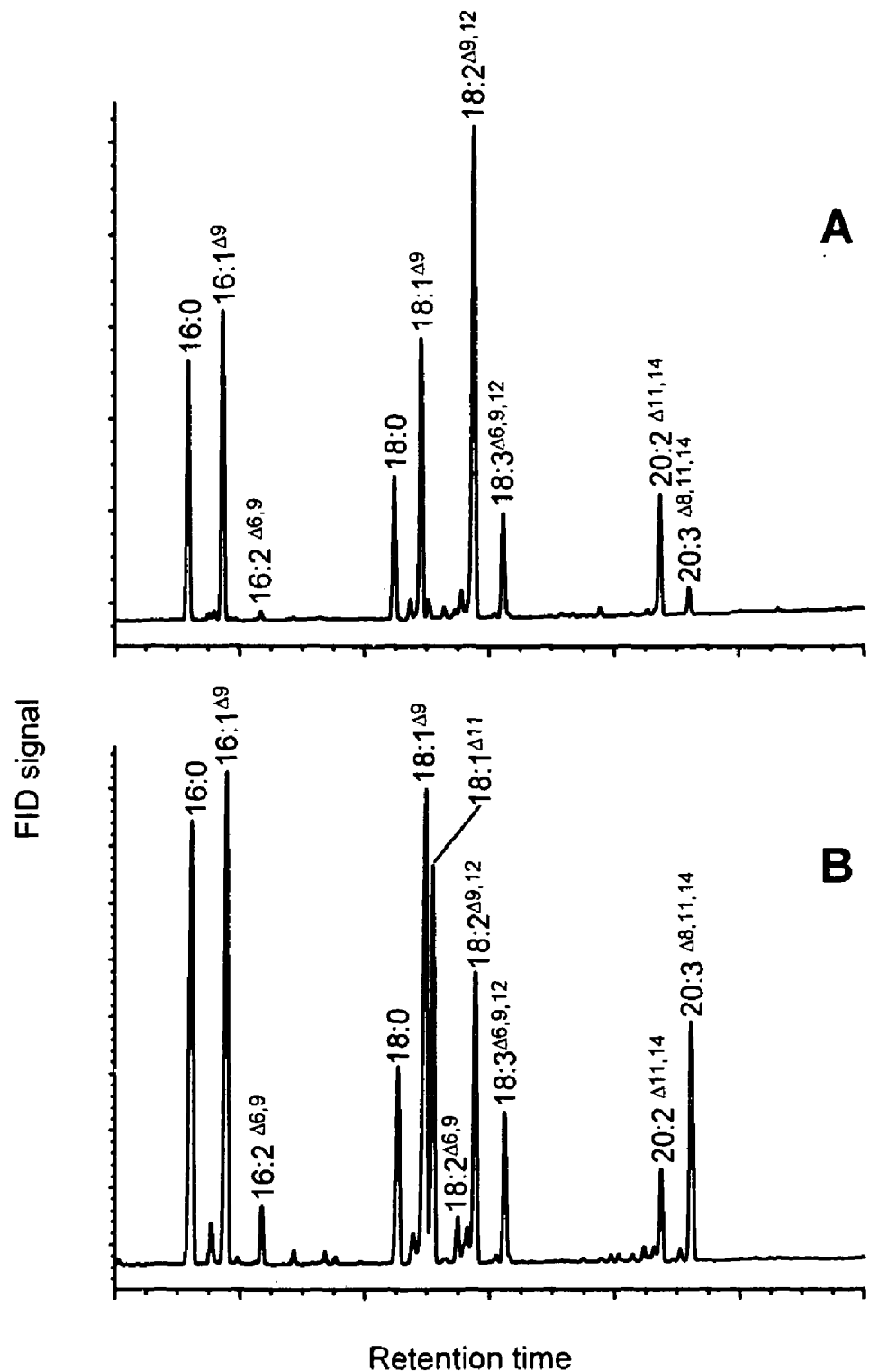

Figure 8: Fatty acid profiles of transgenic INVSc1 *S. cerevisiae* cells.
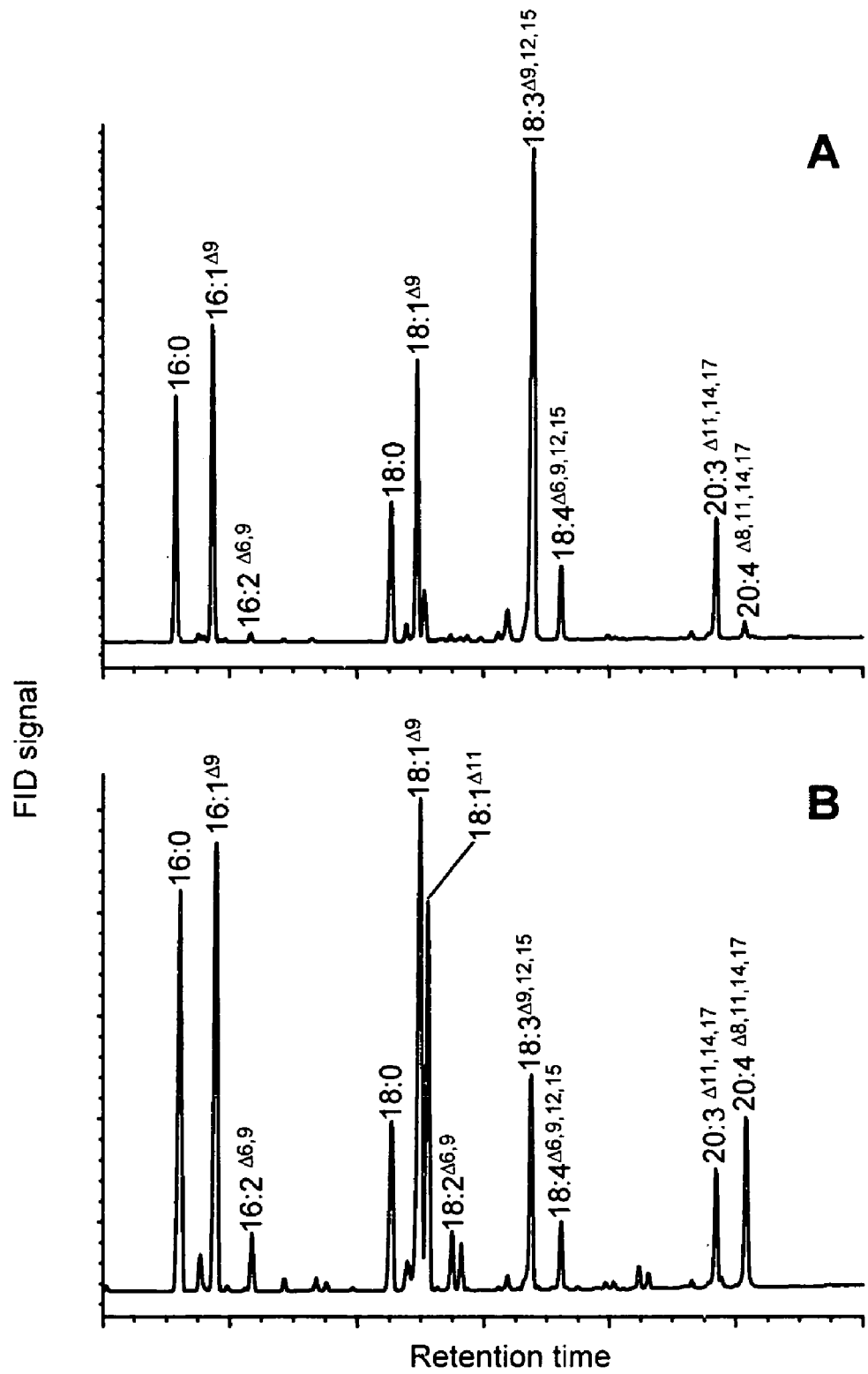

Figure 9A: Vector map of pGPTV LeB4-700 + T06E8.1
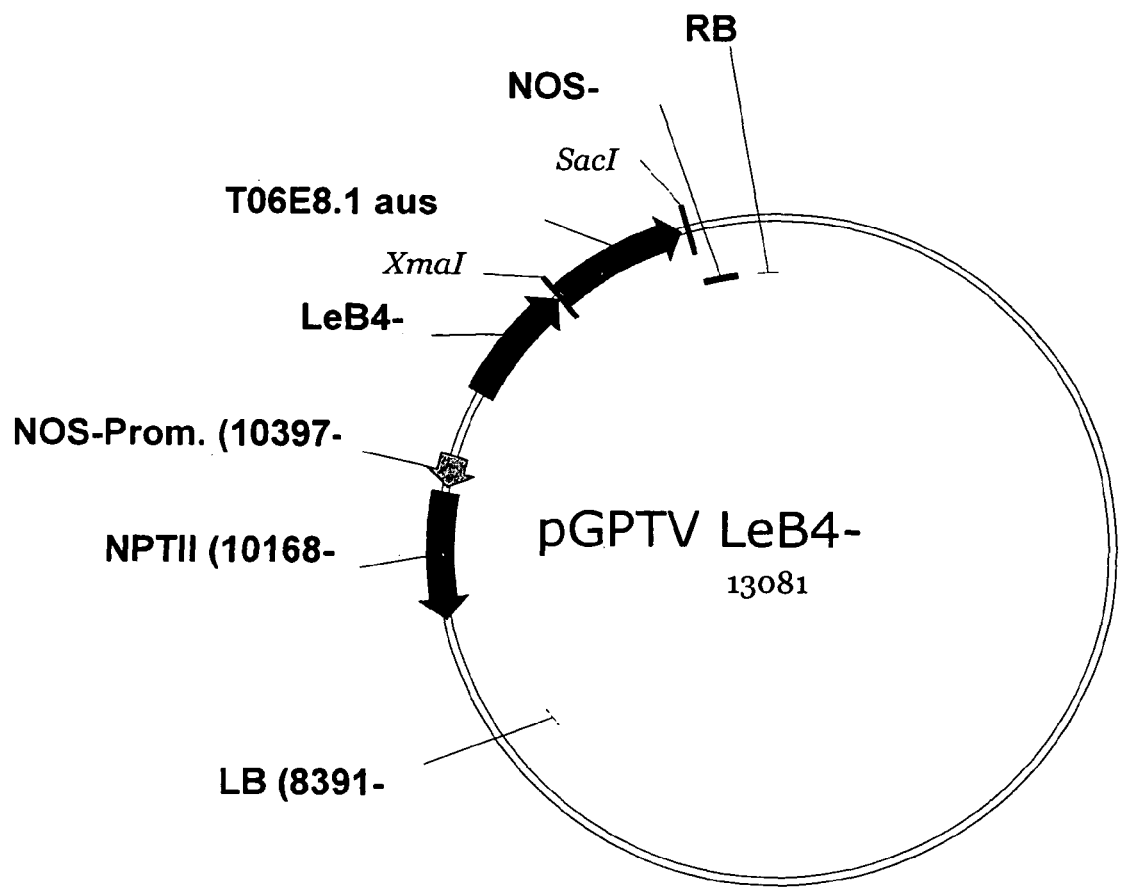

Figure 9B: Vector map of pGPTV USP/OCS-1,2,3 PSE1(Pp)+D6-Des(Pt)+2AT (T06E8-1)
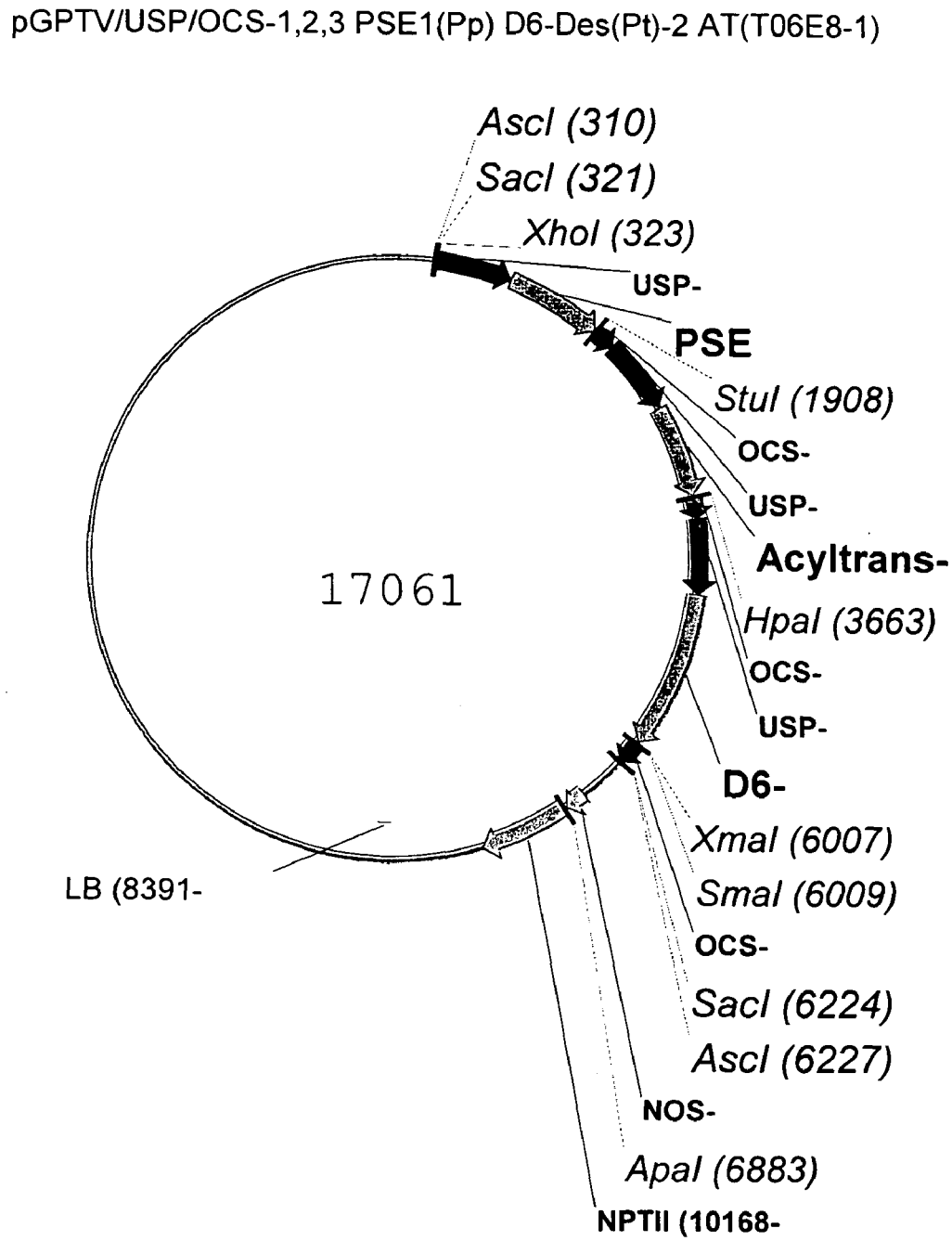

Figure 10A: Biosynthetic pathway of LCPUFAs
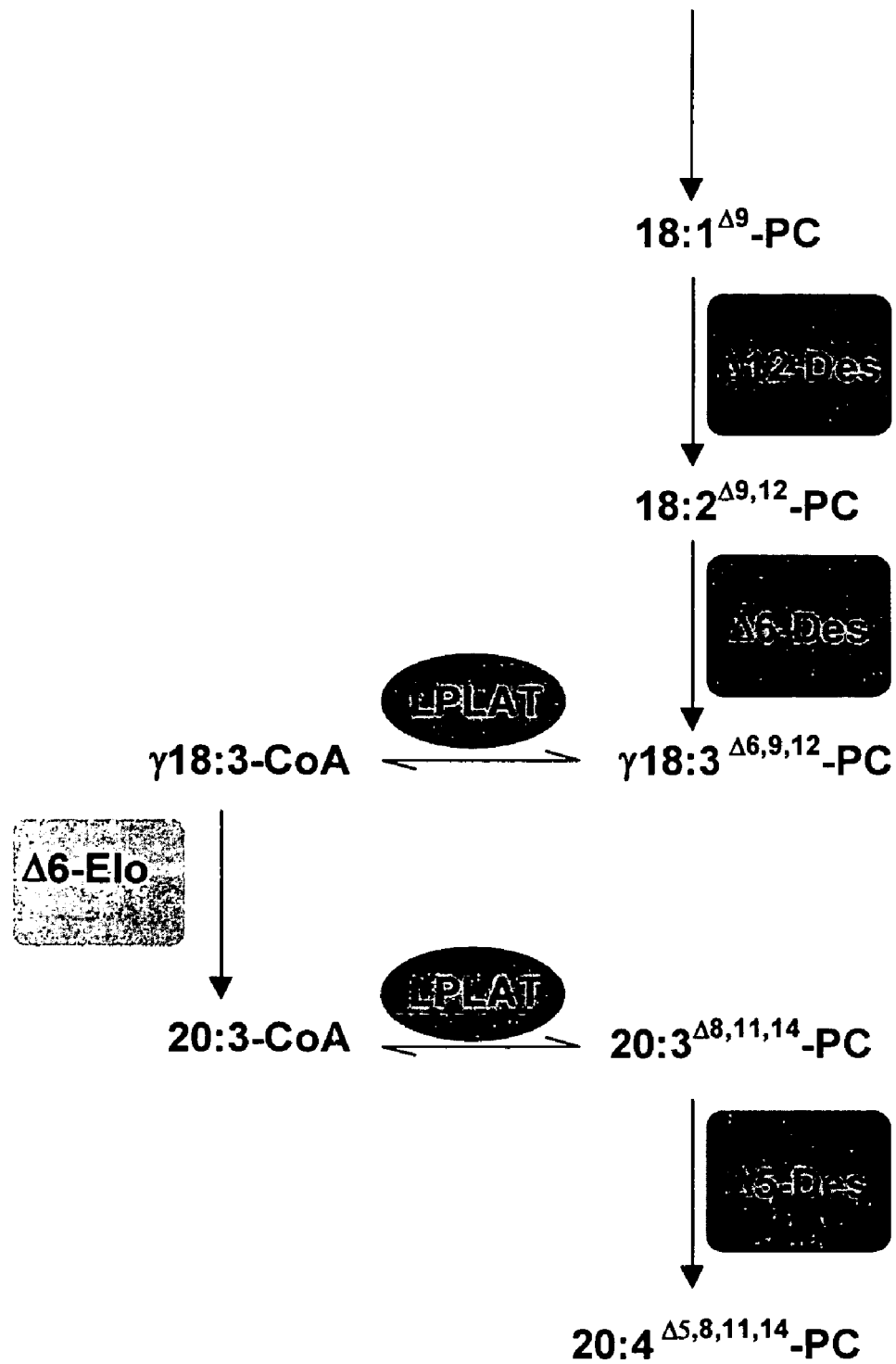

Figure 10B: Biosynthetic pathway of LCPUFAs
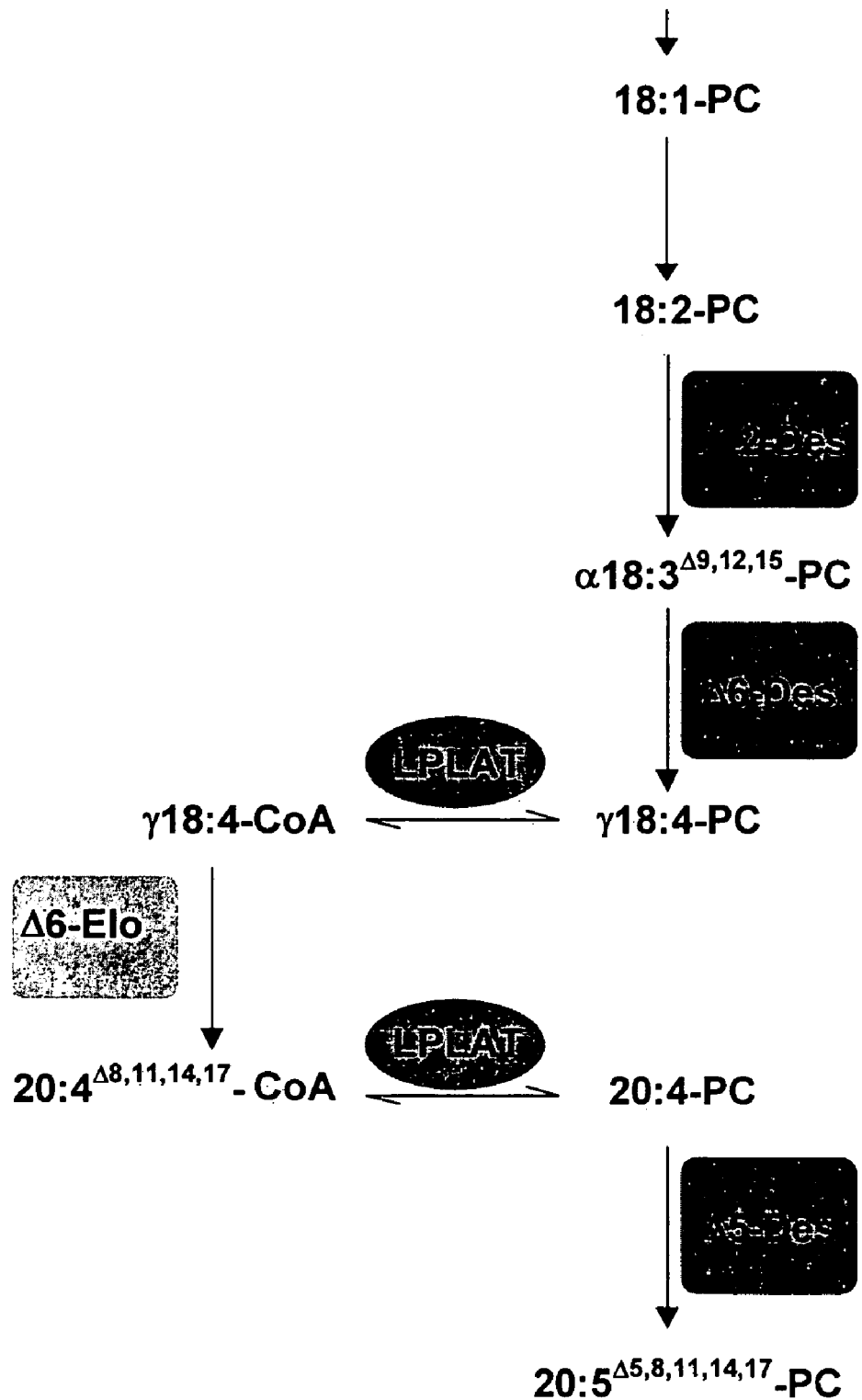

Figure 11: Comparison of GPAT and LPAAT substrate specificities in linseed, sunflower and *Mortierella alpina*
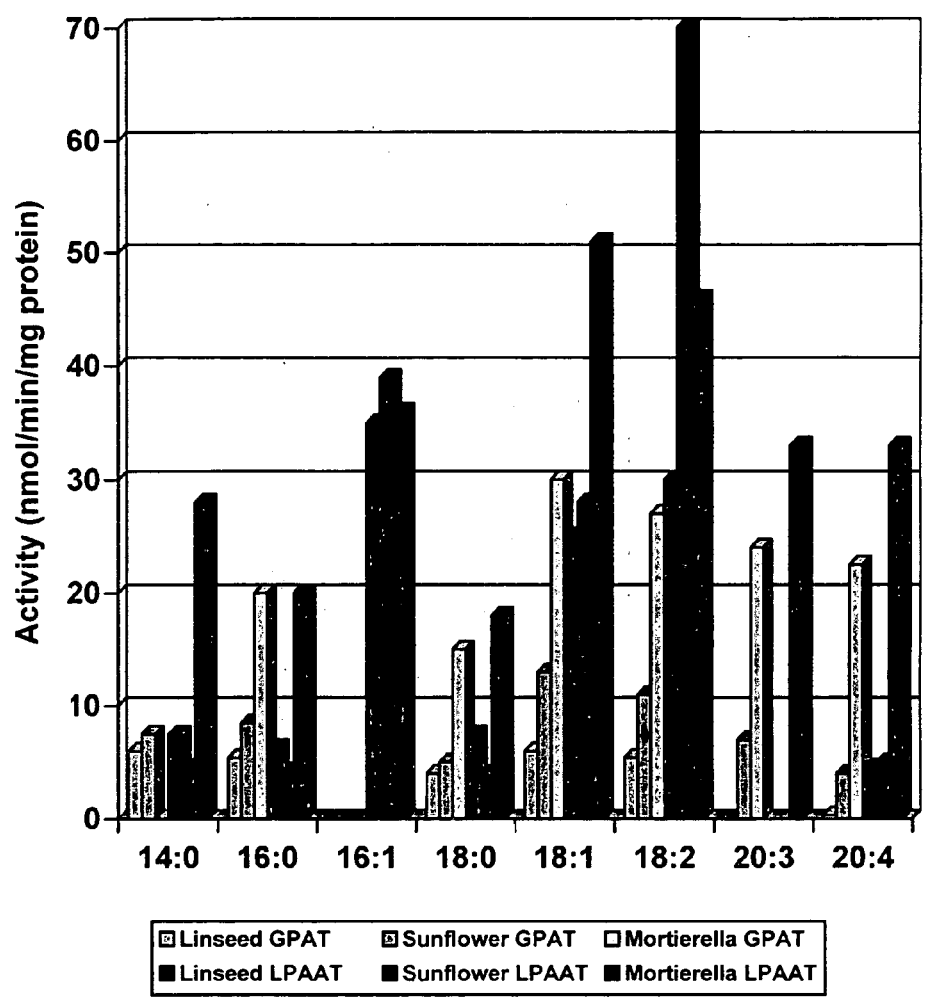

Figure 12: Comparison of LPCAT substrate specificity in linseed, sunflower and - *Mortierella alpina*
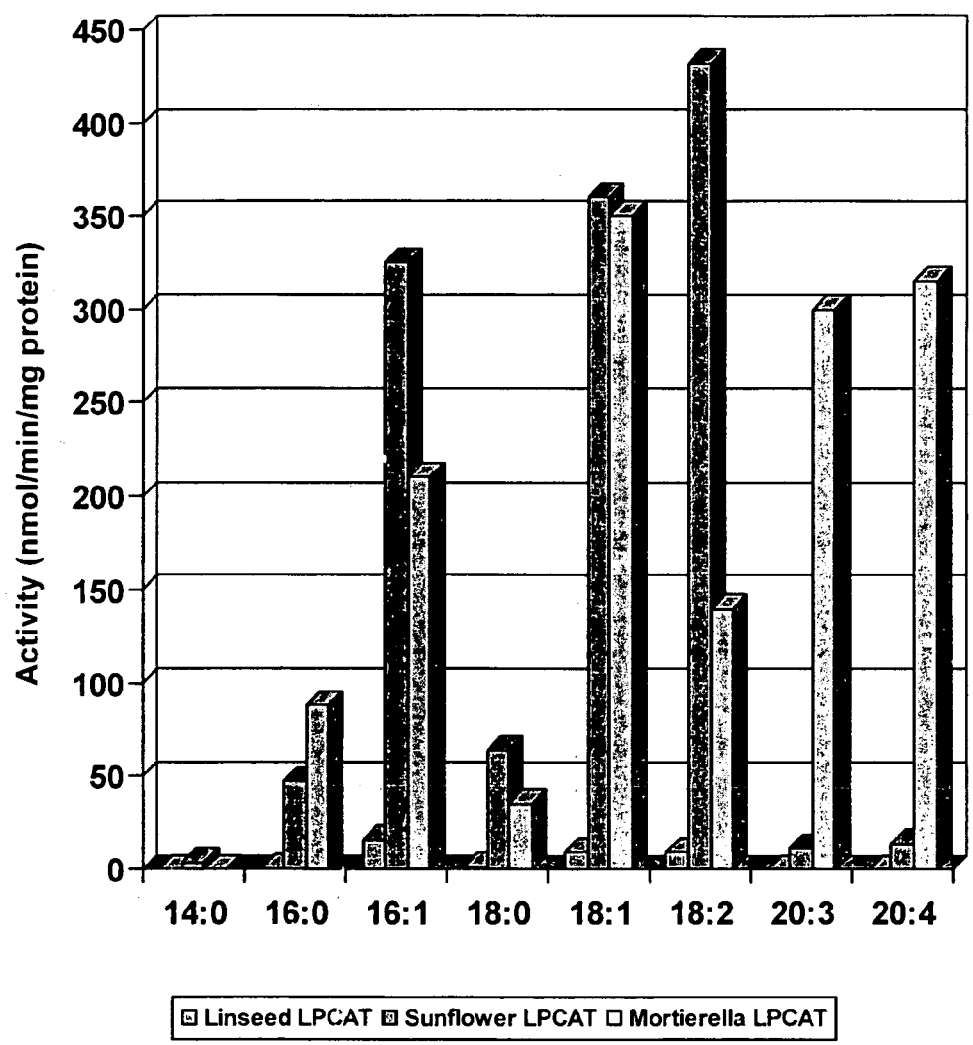

Figure 13: Alignment of SEQ ID NO: 2 with Swiss Prot database

```
                       1                                                50
Q9JZ47            ..................................MSSNKASFFTRL
Q9JU41            ..................................MSSNKASFFTRL
Q59601            ..................................MSSNKASFFTRL
Q9HW50            ................................MARLRLLLRSARL
SEQ ID NO: 2      ................................MSAWTRAKTAVGL
O35259            METIMDDEVTKRTSAEELESWNLLSRTNYNFQYISLRLTILWGLGVLIRY 51                                               100
Q9JZ47            RRLCRLAVWLFKTGKNLRGIDGG.CPESRNRAVIELGRGVLAALD.....
Q9JU41            RRLCRLTVWLFKTGKNLRGIDGG.CPESRNRAVIELGRGVLAALD.....
Q59601            RRLCRLTVWLFKTGKNLRGIDGG.CPKSRNRAVIALGKGALAALD.....
Q9HW50            LGLVALGLGLAAWVSLRERLPGADVTPLRQRLTRWWLARLCAALP.....
SEQ ID NO: 2      LTLAPARIVFLVTVLGTYGLTVAACTRLGVPKSFVLGLTRCVARLTLWGL
O35259            CFLLPLRIALAFTGIGLLVVGTTMVGYLPNGRFKEFLSKHVHLMCYRICV 101                                               150
Q9JZ47            ..IGLEVGRPAPEHPNG..VLVAANHVSWLDIFAMS.AVYPSSFIAKQEI
Q9JU41            ..IGLEVGRPAPEHPNG..VLVAANHVSWLDIFAMS.AVYPSSFIAKQEI
Q59601            ..IGLEVGRPAPEHPNG..VLVAANHVSWLDIFAMS.AVYPSSFIAKQEI
Q9HW50            ..FEVRVSGEAPRQP....MLWVANHVSWTDIPLLG.ALAPLTFLSKAEV
SEQ ID NO: 2      GFYHIEVSCDAQGLREWP.RVIVANHVSYLEILYFMSTVHCPSFVMKKTC
O35259            RALTAIITYHNRKNRPRNGGICVANHTSRIDVIIFASDGYYAMVGQVHGG 151                                               200
Q9JZ47            KSWPVLGKMGQNAGTVFINRNSRR.........DIEPINRAVCETLQRGQ
Q9JU41            KSWPVLGKMGQNAGTVFINRNSRR.........DIEPINRAVCETLQRGQ
Q59601            KSWPVLGKMGQNAGTVFINRNSRR.........DIEPINRAVCETLQRGQ
Q9HW50            RAWPLAGWLAEKAGTLFIRRGSG..........DSRLINQRLAEQLHRGR
SEQ ID NO: 2      LRVPLVGYIAMELGGVIVDREGGGQSASAIIRDRVQEPPRDSSSEKHHAQ
O35259            LMGVIQRAMVKACPHVWFERSEVK.........DRHLVAKRLTEHVQDKS 201                                               250
Q9JZ47            ..NVSFFPEARTSSGLGLLPFKAALFQSAIDAGAKVLAVALRYYDETGKR
Q9JU41            ..NVSFFPEARTSSGLGLLPFKAALFQSAIDAGAKVLAVALRYYDETGKR
Q59601            ..NVSFFPEARTSSGLGLLPFKAALFQSAIDAGAKVLAVALRYYDETGKR
Q9HW50            ..NLLIFPEGTTTNGESLRTFHGRLMASALEAGVAVQPVAISYRRDGVPD
SEQ ID NO: 2      ..PLLVFPEGTTTNGSCLLQFKTGAFR...PG.APVLPVVLEFPIDKARG
O35259            KLPILIFPEGTCINNTSVMMFKKGSFEIG....ATVYPVAIKY..DPQFG
```

Figure 13 (continued)

```
              251                                                300
Q9JZ47        TARPSYADVGLPTCLWRIVSMKKLTIRVDFVCVADAAE.............
Q9JU41        TARPSYADVGLPTCLWRIVSMKKLTIKVDFVCVADAAE.............
Q59601        TARPSYADVGLPTCLWRIVSMKKLTIKVDFVCVADAAE.............
Q9HW50        AQAPFIGDDDLLSHLGRLLRGERGSVHIQLLEPIPSQ..............
SEQ ID NO: 2  DFSPAYESVHTPAHLLRMLAQWRHRLRVRYLPLYEPSAAEKVDADLYARN
O35259        DAFWNSSKYGMVTYLLRMMTSWAIVCSVWYLPPMTRE..............

301                                           349
Q9JZ47        ...SEDRYALKDKIEESIRAVVADDADIAV....................
Q9JU41        ...SEDRYALKDKIEESIRAVVADDADIAV....................
Q59601        ...SEDRYALKDKIEESIRAVVADDADIAV....................
Q9HW50        ...GLDRAELARQAQQAVRLALFGTAAPTQTRRAA...............
SEQ ID NO: 2  VRDEMARALKVPTVEQSYRDKLVYHADLMPHYQKAGPGALYLYVRPDLL
O35259        ......KDEDAVQFANRVKSAIARQEDW......................
```

Figure 14:  Alignment of SEQ ID NO: 5 with Swiss Prot database

```
              1                                                  50
Q9C9P8        MEVCGDLKSDNLKNRPLTPLRILRGLMILLVFLSTAFMFLLYFAPIAALG
Q9SFJ1        MEVCGDLKSDNLKNRPLTPLRILRGLMILLVFLSTAFMFLLYFAPIAALG
Q9LHN4        .....MEKKSVPNSDKLSLIRVLRGIICLMVLVSTAFMMLIFWGFLSAVV
SEQ ID NO: 5  ..................................................
Q9SDN3        ..................................................
Q9XFW4        ................MAMAAAVIVPLGILFFISGLVVNLLQAVCYVLV 51                                                 100
Q9C9P8        LRLLSVQQSRKVVSLIFGLWLALWPYLFETVNGTTVVFSGDIIP...VEK
Q9SFJ1        LRLLSVQQSRKVVSLIFGLWLALWPYLFETVNGTTVVFSGDIIP...VEK
Q9LHN4        LRLFSIRYSRKCVSFFFGSWLALWPFLFEKINKTKVIFSGDKVP...CED
SEQ ID NO: 5  ........................MDVVKVIFAGDKVP...KEN
Q9SDN3        ..............................................MGKE
Q9XFW4        RPMSKNTYRKINRVVAETLWLELVWIVDWWAGVKIQVFADDETFNRMGKE 101                                                150
Q9C9P8        RVLLIANHRTEVDWMYLWNIALRKGCLGYIKYVLKSSLMKLPIFGWGFHV
Q9SFJ1        RVLLIANHRTEVDWMYLWNIALRKGCLGYIKYVLKSSLMKLPIFGWGFHV
Q9LHN4        RVLLIANHRTEVDWMYFWDLALRKGQIGNIKYVLKSSLMKLPLFGWAFHL
SEQ ID NO: 5  RVMVMCNHRTEVDWMYIWNLAIRKGKIGYCKYAVKNSVKNLPLFGWAFYV
Q9SDN3        HALVISNHRSDIDWLVGWVLAQRSGCLGSSLAVMKKSSKFLPVIGWSMWF
Q9XFW4        HALVVCNHRSDIDWLVGWILAQRSGCLGSALAVMKKSSKFLPVIGWSMWF 151                                                200
Q9C9P8        LEFIPVERKREVDEPVLLQMLSSFKDPQEPLWLALFPEGTDFTEEKCKRS
Q9SFJ1        LEFIPVERKREVDEPVLLQMLSSFKDPQEPLWLALFPEGTDFTEEKCKRS
Q9LHN4        FEFIPVERRWEVDEANLRQIVSSFKDPRDALWLALFPEGTDYTEAKCQRS
SEQ ID NO: 5  FEFLMLHRKWEVDAPVIKTYIDSFQDKRDPLWLVVFPEGTDFSEAKRDTG
Q9SDN3        SEYLFLERSWAKDEGTLKSGVQRLKDFPQPFWLALFVEGTRFTQAKLLAA
Q9XFW4        SEYLFLERNWAKDESTLQSGLQRLNDFPRPFWLALFVEGTRFTEAKLKAA 201                                                250
Q9C9P8        QKFAAEVGLPALSNVLLPKTRGFGVCLEVLHNSLDAVYDLTIAYKPRCP.
Q9SFJ1        QKFAAEVGLPALSNVLLPKTRGFGVCLEVLHNSLDAVYDLTIAYKPRCP.
Q9LHN4        KKFAAENGLPILNNVLLPRTKGFVSCLQELSCSLDAVYDVTIGYKTRCP.
SEQ ID NO: 5  NAIGREKGYPELVNVLQPRTRGFVTCLSQSRCSLDAVYDLTIGYKKRCP.
Q9SDN3        QEYAAATGLPVPRNVLIPRTKGFVTAVSQMRSFAPAIYDVTVAIPKSSPA
Q9XFW4        QEYAASSELPVPRNVLIPRTKGFVSAVSNMRSFVPAIYDMTVAIPKTSPP
```

Figure 14 (continued)

```
                  251                                                300
Q9C9P8            SFMDNVFGTDPSEVHIHVRRVLLKEIPANEAESSAWLMDSFKLKDKLLSD
Q9SFJ1            SFMDNVFGTDPSEVHIHVRRVLLKEIPANEAESSAWLMDSFKLKDKLLSD
Q9LHN4            SFLDNVYGIEPSEVHIHIRRINLTQIPNQEKDINAWLMNTFQLKDQLLND
SEQ ID NO: 5      LFINNVFGTDPSEVHIHIRRIPISEIPQSEDGMTQWLYDLFYQKDQMLAS
Q9SDN3            PTMLRLFEGRPSVVHVHIKRHVMRDLPETDEAVAQWCKDIFVAKDALLDK
Q9XFW4            PTMLRLFKGQPSVVHVHIKCHSMKDLPEPEDEIAQWCRDQFVAKDALLDK 301                                                350
Q9C9P8            FNAQGKFPNQRPEEELSVLKCIATFAGKQQQVTKPSCQKVFLLLNQSSDE
Q9SFJ1            FNAQGKFPNQRPEEELSVLKCIATFAGKQQQVTKPSCQKVFLLLNQSSDE
Q9LHN4            FYSNGHFPNEGTEKEFNTKKYLINCLAVIAFTTICTHLTFFSSMIWFRIY
SEQ ID NO: 5      FSKTGSFPDSGIE.ESPLNIVEGVCNVALHVVLSGWVFWCLFHSVWLKLY
Q9SDN3            HTVEQTFGDQQLKVTGRPLKSLLVVTAWACLLILGALKFLYWSSLLSSWK
Q9XFW4            HIAADTFPGQKEQNIGRPIKSLAVVVSWACLLTLGAMKFLHWSNLFSSWK 351                                                400
Q9C9P8            KESKKAVAQHPFTDTLDHLFQVEHSISCFLYMHIYNLSTCHLISLYE...
Q9SFJ1            KESKKAVAQHPFTDTLDHLFQVEHSISCFLYMHIYNLSTCHLISLYE...
Q9LHN4            VSLACVYLTSATHFNLRSVPLVETAKNSLKLVNK................
SEQ ID NO: 5      VAFASLLLAFSTYFDWRPKPVYSSLRTKRKIV..................
Q9SDN3            GIAFSALGLGVVTVLMQILIRFSQSERSTPAPVAPTNNKNKGESSGKPEK
Q9XFW4            GIALSAFGLGIITLCMQILIRSSQSERSTPAKVAPAKPKDNHQSGPSSQT

401
Q9C9P8            .......
Q9SFJ1            .......
Q9LHN4            .......
SEQ ID NO: 5      .......
Q9SDN3            QQ.....
Q9XFW4            EVEEKQK
```

Figure 15: Alignment of SEQ ID NO: 35 with Swiss Prot database

```
                1                                                50
P04180          ..............................................MGP
Q08758          ..............................................MGP
Q9MZ04          ..............................................MGL
Q9DDJ6          ..............................................MGR
Q9Y2B3          ..............................................MGL
SEQ ID NO: 35   MCSISCGSTPQQLCHYRKSGELITRKSRAAIRWWRYGQQCKVLLPLDLIR 51                                               100
P04180          PGSPWQWVTLLLGLLLPP..............AAPFWLLNVLFPPHTTPK
Q08758          PGSPWQWVPLLLGLLLPP..............AAPFWLLNVLFPPHTTPK
Q9MZ04          PGSPWQWVLLLLELLLPT..............AAPFWLLNVLFPPHTTPK
Q9DDJ6          TGAGFALLTLLLLLPQP...............ASQFWLFNVLFPPTSTPE
Q9Y2B3          HLRPYRVGLLPDGLLFLL..............LLLMLLADPALP......
SEQ ID NO: 35   SSSQFFIVVLTLTLFLFTTCGAVHTAAQDRSFATLSQRSRASLFSVGRAQ 101                                              150
P04180          AELSNHTRPVILVPGCLGNQLEAKLDKPDVVN.WMCYRKTEDFFTIWLDL
Q08758          AELSNHTRPVILVPGCLGNQLEAKLDKPDVVN.WMCYRKTEDFFTIWLDL
Q9MZ04          AELSNHTRPVILVPGCLGNQLEAKLDKPDVVN.WMCYRKTEDFFTIWLDL
Q9DDJ6          APPTNSTPPVVLVPGCLGNQLEAKLDKPDVVN.WMCYRKTEDYFTIWLNL
Q9Y2B3          ...AGRHPPVVLVPGDLGNQLEAKLDKPTVVH.YLCSKKTESYFTIWLNL
SEQ ID NO: 35   ARNKHHLAPVVIVPGTGGNQLEARLTADYEANKPWCYSFRKDYFRLWLDV 151                                              200
P04180          NMFLPLGVDCWIDNTRVVYNRSSGLVSNAPGVQIRVPGFGKTYSVEYLDS
Q08758          NMFLPLGVDCWIDNTRVVYNRSSGLVSNAPGVQIRVPGFGKTYSVEYLDS
Q9MZ04          NMFLPLGVDCWIDNTRVTYNHSSGRVSNAPGVQIRVPGFGKTYPVEYLDN
Q9DDJ6          NTFLPVGVDCWIDNTRVVYNRTSRKMSNAPGVHIRVPGFGKTYSVEYLDQ
Q9Y2B3          ELLLPVIIDCWIDNIRLVYNKTSRATQFPDGVDVRVPGFGKTFSLEFLDP
SEQ ID NO: 35   KTLFPPFTTCFADRLSLDYNPQSDAYSNIKGVKTRVPFFGTTEGMEYLDP 201                                              250
P04180          SK..LAGYLHTLVQNLVNNGYVRDETVRAAPYDWRLEPGQQE.....EYY
Q08758          SK..LAGYLHTLVQNLVNNGYVRDETVRAAPYDWRLEPGQQE.....EYY
Q9MZ04          SK..LAGYMHTLVQNLVNNGYVRDETVRAAPYDWRLGPKQQE.....EYY
Q9DDJ6          SK..LAGYLHTLVQNLVNNGYVRDQTVRAAPYDWRVGPQEQP.....EYF
Q9Y2B3          SKSSVGSYFHTMVESLVGWGYTRGEDVRGAPYDWRRAPNENG.....PYF
SEQ ID NO: 35   SLKFLTGYMIHLVNALKAHGYENGKSLYGAPYDFRFAPGPHASNVALEYL
```

Figure 15 (continued)

```
                  251                                               300
P04180            RKLAGLVEEMHAAYG.KPVFLIGHSLGCLHLLYFLLRQPQAWKDRFIDGF
Q08758            HKLAGLVEEMHAAYG.KPVFLIGHSLGCLHLLYFLLRQPQAWKDRFIDGF
Q9MZ04            RDLARLVEEMHATYG.KPVFLIGHSLGCLHLLHFLLHPQSWKDRFIDGF
Q9DDJ6            QNLKALIEEMHDEYQ.QRVFLIAHSMGNLNVLYFLLQQRQAWKDQYIGGF
Q9Y2B3            LALREMIEEMYQLYG.GPVVLVAHSMGNMYTLYFLQRQPQAWKDKYIRAF
SEQ ID NO: 35     KDLKDLIETAYSVNANEPVVILAHSMGGLWTLFFLNQQSMEWRNKYVSRF 301                                               350
P04180            ISLGAPWGGSIKPMLVLASGDNQGIPIMSSIKLKEEQRITTTSPWMFPSR
Q08758            ISLGAPWGGSIKPMLVLASGDNQGIPIMSSIKLKEEQRITTTSPWMFPSR
Q9MZ04            ISLGAPWGGSIKPMQVLASGDNQGIPIMSSIKLKEEQRITTTSPWMFPSS
Q9DDJ6            ISLGAPWGGSVKPLRVLASGDNQGIPLMSNIKLREEQRMTTTSPWMFPTS
Q9Y2B3            VSLGAPWGGVAKTLRVLASGDNNRIPVIGPLKIREQQRSAVSTSWLLPYN
SEQ ID NO: 35     VSVATPWGGAVEQMMTFASGNPEGVPFVNSLVVREEQRRSESNLWLLPVR 351                                               400
P04180            MAWPEDHVFISTPSFNYTGRDFQRFFADLHFEEGWYMWLQ.SRDLLAGLP
Q08758            LAWPEDHVFISTPSFNYTGRDFQRFFADLHFEEGWYMWLQ.SRDLLAGLP
Q9MZ04            EVWPEDHVFISTPSFNYTIRDYQRFFVDVHFEEGWYMWLQ.SRDLLAGLP
Q9DDJ6            LAWPEDHIFISTPSYNYTYRDYKQFFTDVNLEDGWYMWED.MKDLLKGLP
Q9Y2B3            YTWSPEKVFVQTPTINYTLRDYRKFFQDIGFEDGWLMRQD.TEGLVEATM
SEQ ID NO: 35     RCFR.DRPLVITSSRNYTAGDMEQFLCDIGFPEGVAPYKSRIPHLTDILQ 401                                               450
P04180            APGVEVYCLYGVGLPTPRTYIYDHGFPYTDPVGVLYEDGDDTVATRST.E
Q08758            APGVEVYCLYGVGLPTPRTYIYDHGFPYTDPVDVLYEDGDDTVATRST.E
Q9MZ04            APGVEVYCLYGVGLPTPSTYIYDHDFPYTDPLDVLYEDGDNTVATRSM.E
Q9DDJ6            PPGVDTYCLYGTGYPTVETYIYDEHFPYEDPVDMIYGDGDDTVNRRSS.E
Q9Y2B3            PPGVQLHCLYGTGVPTPDSFYYES.FPDRDPK.ICFGDGDGTVNLKSA.L
SEQ ID NO: 35     PPQVPVTLIHGYGVPTAETLSYEK.KGFDNHPEITEGDGDGTVNVCSLTA 451                                               500
P04180            LCGLWQGRQPQPVHLLPLHGIQHLNMVFSNLTLEHINAILLGAYRQGPPA
Q08758            LCGLWQGRQPQPVHLLPLRGIQHLNMVFSNQTLEHINAILLGAYRQGPPA
Q9MZ04            LCSQWQGRQPQPVHLLPLHRIQHLNMVFSNQTLEHINDILLGAYRHGNPV
Q9DDJ6            LCKRWRNQQKQKVHIQELRGIDHLNMVFSNLTLSSINEILLGSSQVGAGT
Q9Y2B3            QCQAWQSRQEHQVLLQELPGSEHIEMLANATTLAYLKRVLLGP.......
SEQ ID NO: 35     VVEEWERVAGQELEMIALHGKQHMQILHDDHSVQVIVDAILNVTPQEQLM 501             524
P04180            SPTASPEPPPPE............
Q08758            SLTASPEPPPPE............
Q9MZ04            PPAASPRPLTPE............
Q9DDJ6            KEHGELGQMGALKSSLEAGRRGKN
Q9Y2B3            ........................
SEQ ID NO: 35     FH......................
```

Figure 16: Alignment of SEQ ID NO: 23 with Swiss Prot database

```
                  1                                                50
P10349            ..................................................
Q9FEP9            .......MFILSSSSSTLPSAPPFSSTTSIFLSFSRVSLPPSSSSLK...
Q39639            MFILSAVSSSSSSSSVPSSLPPFSLSPSISLSFSRVSLPPSSSSSSSSL
Q9FEQ0            ...............MFILSSSSSLPSPLSLSSSRVSLPPPSSSSLN..
Q9M4V1            ...............MLVPSALPRVSRSVSAARFSVSGVGSSPALSSRS
SEQ ID NO: 23     ....................MPSLFRAKRNGRRTPGNAVTN...

51                                              100
P10349            ......................MAELIQDKESAQSAATAAAAS
Q9FEP9            ..LLPLSLQFGPPKLAS.SCSLRFSASRAMAELIQDKESAQSAATAAAAS
Q39639            KLFLPLSLHFTPPKLSSPHSFLRFSASRAMAELIQDKESAHTPSTTDVTR
Q9FEQ0            ..LLPLSPHFQPPNLAC...SCSVASRSTAELLHDFKHSAHTAASADEAR
Q9M4V1            CTSLDSSVRSSLRRCPCGIYTSRTKAVVEAVESKASAREWRSAVKRAVLA
SEQ ID NO: 23     ..........FGKSEFH.....R..EIS...GSTRATTQVAEATTAGLRE 101                                             150
P10349            SGYERRNEPAHSRKFLDVRSEEELLSCIKKETEAGKLPPNVAAGMEELYQ
Q9FEP9            SGYERRNEPAHSRKFLDVRSEEELLSCIKKETEAGKLPPNVAAGMEELYQ
Q39639            N......DPPHSRAFLDLRSEEELLSCIRRETEAGKLPSNVAAGMEELYQ
Q9FEQ0            N......HLPHSRAFLDVRSEQELLSYIRREAEAGKLPSNVAAGMEELYQ
Q9M4V1            SDTGAEEEVGHSRSFLRARSEEELLSYIRKEVETGRLSSDIANGLEELYY
SEQ ID NO: 23     TIEDRAIIDGHSHSFEGIQSEEELMQVIEKEVESGRLPKRAGAGMVELYR 151                                             200
P10349            NYRNAVIESGNPKADEIVLSNMTVALDRILLDVEDPFVFSSHHKAIREPF
Q9FEP9            NYRNAVIESGNPKADEIVLSNMTVALDRILLDVEDPFVFSSHHKAIREPF
Q39639            NYKNAVFESGNPKADEIVLSNMTVALDRILLDVEDPFMFSPHHKAIREPF
Q9FEQ0            NYKNAVLKSGNPKADEIVLSNMTVALDRILLDVEEPFVFSPHHKAVREPF
Q9M4V1            NYRNAVLQSGDPRANKIILSNMAVAFDRILLDVEDPFTFSPHHQAIREPF
SEQ ID NO: 23     NYRDAVVSSGVENAMDIVVKVMSTVLDRILLQFEEPFTFGSHHKRMVEPY 201                                             250
P10349            DYYIFGQNYIRPLIDFGNSFVGNLSLFKDIEEKLQQGHNVVLISNHQTEA
Q9FEP9            DYYIFGQNYIRPLIDFGNSFVGNLSLFKDIEEKLQQGHNVVLISNHQTEA
Q39639            DYYTFGQNYVRPLIDFENSFVGNLSLFKDIEEKLHQGHNVVLISNHQTEA
Q9FEQ0            DYYTFGQNYVRPLIDFGNSFVGNPFLFKDIEEKLHQGHNVVLISNHQTEA
Q9M4V1            DYYMFGQNYIRPLIDFRRSYIGNISIFSDMEEKLQQGHNIVLMSNHQTEA
SEQ ID NO: 23     DYYTFGQNYVRPLLDFRNSYLGNLKIFDQIEKNLKEGHNVIFLSNHQTEA
```

Figure 16 (continued)

```
                    251                                               300
P10349              DPAIISLLLEKTNPYIAENTIFVAGDRVLADPLCKPFSIGRNLICVYSKK
Q9FEP9              DPAIISLLLEKTNPYIAENTIFVAGDRVLADPLCKPFSIGRNLICVYSKK
Q39639              DPAIISLLLEKTNPYIAENMIYVAGDRVIADPLCKPFSIGRNLICVYSKK
Q9FEQ0              DPAIISLLLEKTSPYIAENMIYVAGDRVIVDPLCKPFSIGRNLICVYSKK
Q9M4V1              DPAIIALLLERTNSHIAETMVFVAGDRVLTDPLCKPFSMGRNLLCVYSKK
SEQ ID NO: 23       DPAVMALLLEHSHPYLAENLTYVAGDRVVLDPFCKPFSMGRNLLCVYSKK 301                                               350
P10349              HMFDIPELTETKRKANTRSLKEMALLLRGGSQLIWIAPSGGRDRPDPSTG
Q9FEP9              HMFDIPELTETKRKANTRSLKEMALLLRGGSQLIWIAPSGGRDRPDPSTG
Q39639              HMLDIPELAETKRKANTRSLKEMALLLRGGSQLIWIAPSGGRDRPDPSTG
Q9FEQ0              HMFDIPELAETKRKANTRSLKEMALLLRGGSQLIWIAPSGGRDRLDPSSG
Q9M4V1              HMDDVPELIEMKRRANTRSLKEMALLLRGGSQIIWIAPSGGRDRPDPSTG
SEQ ID NO: 23       HIHDVPDLAEMKIKANAKTLRQMTILLRQGGQYYG...............

351                                               400
P10349              EWYPAPFDASSVDNMRRLIQHSDVPGHLFPLALLCHDIMPPPSQVEIEIG
Q9FEP9              EWYPAPFDASSVDNMRRLIQHSDVPGHLFPLALLCHDIMPPPSQVEIEIG
Q39639              EWYPAPFDASSVDNMRRLLQHSGAPGHLYPLALLCYDIMPPPSQVEIEIG
Q9FEQ0              EWLPAPFDASSMDNMRRLIQHSGVPGHLCPLALLCYDIMPPPSKVEIEIG
Q9M4V1              EWHPAPFDVSSVDNMRRLVEHSSVPGHIYPLSLLCYEVMPPPQQVEKQIG
SEQ ID NO: 23       .................................................

401                                               450
P10349              EKRVIAFNGAGLSVAPEISFEEIAATHKNPEEVREAYSKALFDSVAMQYN
Q9FEP9              EKRVIAFNGAGLSVAPEISFEEIAATHKNPEEVREAYSKALFDSVAMQYN
Q39639              EKRVISFNGTGLSVGPEISFDEIAASRDNPDEVREAYSKALYDSVAKQYN
Q9FEQ0              EKRVISFNGVGLSLAPAISFEAIAATHRNPDEAREAYSKALFDSVSMQYN
Q9M4V1              ERRTISFHGVGLSVAPELNFNELTAGCETPEEAKEAFSQALYNSVGEQYN
SEQ ID NO: 23       .................................................

451                       476
P10349              VLKTAISGKQGLGASTADVSLSQPW.
Q9FEP9              VLKTAISGKQGLGASTADVSLSQPW.
Q39639              VLKAAIDGKQELEASVADVSLSQPWI
Q9FEQ0              VLKAAIYGRQALRASTADVSLSQPWI
Q9M4V1              VLKSAIHEHRGLNASNSIISLSQPWQ
SEQ ID NO: 23       ..........................
```

Figure 17: Alignment of SEQ ID NO: 27 with Swiss Prot database

```
                 1                                                50
SEQ ID NO: 27    MEGGGSIIALPLGLMFLFSGFFINILQLLSVLFILPFSRRAYRVVNMIMM
Q9XFW4           .MAMAAAVIVPLGILFFISGLVVNLLQAVCYVLVRPMSKNTYRKINRVVA
Q40119           MAIPAAAFIVPISLLFFMSGLVVNFIQAVFYVLVRPISKDTYRRINTLVA
Q9SDN3           ..................................................
Q41745           MAIPLVLVVLPLGLLFLLSGLIVNAIQAVLFVTIRPFSKSFYRRINRFLA
Q9SYC8           MKIPAALVFIPVGVLFLISGLIVNIIQLVFFIIVRPFSRSLYRRINKNVA 51                                               100
SEQ ID NO: 27    EVLWSELIWLLDWWANVKVKVYTPKESWEHLGKEHALLICNHRSDIDWLV
Q9XFW4           ETLWLELVWIVDWWAGVKIQVFADDETFNRMGKEHALVVCNHRSDIDWLV
Q40119           ELLWLELVWVIDWWAGVKVQLYTDTESFRLMGKEHALLICNHRSDIDWLI
Q9SDN3           ..............................MGKEHALVISNHRSDIDWLV
Q41745           ELLWLQLVWVVDWWAGVKVQLHADEETYRSMGKEHALIISNHRSDIDWLI
Q9SYC8           ELLWLQLIWLFDWWACIKINLYVDAETLELIGKEHALVLSNHRSDIDWLI 101                                              150
SEQ ID NO: 27    GWIIAQRLGCLGGTRAVMKKSTKFLPVIGWSMWFSEYVFLSRDWAKDEKV
Q9XFW4           GWILAQRSGCLGSALAVMKKSSKFLPVIGWSMWFSEYLFLERNWAKDEST
Q40119           GWVLAQRCGCLSSSIAVMKKSSKFLPVIGWSMWFSEYLFLERNWAKDENT
Q9SDN3           GWVLAQRSGCLGSSLAVMKKSSKFLPVIGWSMWFSEYLFLERSWAKDEGT
Q41745           GWILAQRSGCLGSTLAVMKKSSKFLPVIGWSMWFAEYLFLERSWAKDEKT
Q9SYC8           GWVMAQRVGCLGSSLAIMKKEAKYLPIIGWSMWFSDYIFLERSWAKDENT 151                                              200
SEQ ID NO: 27    LKNGYSSLKGFPRTLWVALFVEGTRFTKAKLEAAQKFAADTGLRVPRHVL
Q9XFW4           LQSGLQRLNDFPRPFWLALFVEGTRFTEAKLKAAQEYAASSELPVPRNVL
Q40119           LKSGLQRLNDFPKPFWLALFVEGTRFTKAKLLAAQEYAASAGLPVPRNVL
Q9SDN3           LKSGVQRLKDFPQPFWLALFVEGTRFQAKLLAAQEYAAATGLPVPRNVL
Q41745           LKWGLQRLKDFPRPFWLALFVEGTRFTPAKLLAAQEYAASQGLPAPRNVL
Q9SYC8           LKAGFKRLEDFPMTFWLALFVEGTRFTQEKLEAAQEYASIRSLPSPRNVL 201                                              250
SEQ ID NO: 27    VPRTKGFVSAVENLREFVPVVYDMTVAISKELPNPTMIRIFRGQPSVVHV
Q9XFW4           IPRTKGFVSAVSNMRSFVPAIYDMTVAIPKTSPPPTMLRLFKGQPSVVHV
Q40119           IPRTKGFVSAVSNMRSFVPAIYDLTVAIPKTTEQPTMLRLFRGKSSVVHV
Q9SDN3           IPRTKGFVTAVSQMRSFAPAIYDVTVAIPKSSPAPTMLRLFEGRPSVVHV
Q41745           IPRTKGFVSAVSIMRDFVPAIYDTTVIVPKDSPQPTMLRILKGQSSVIHV
Q9SYC8           IPRTKGFVSAVSEIRSFVPAIYDCTLTVHNNQPTPTLLRMFSGQSSEINL
```

Figure 17 (continued)

```
                   251                                              300
SEQ ID NO: 27      HVRRVPMSDLPEGANAISKWCHDAFHIKDDRLEQHEKENTFGEDLYIPIE
Q9XFW4             HIKCHSMKDLPEPEDEIAQWCRDQFVAKDALLDKHIAADTFPGQKEQNIG
Q40119             HLKRHLMKDLPKTDDGVAQWCKDQFISKDALLDKHVAEDTFSGLEVQDIG
Q9SDN3             HIKRHVMRDLPETDEAVAQWCKDIFVAKDALLDKHTVEQTFGDQQLKVTG
Q41745             RMKRHAMSEMPKSDEDVSKWCKDIFVAKDALLDKHLATGTFD.EEIRPIG
Q9SYC8             QMRRHKMSELPETDDGIAQWCQDLFITKDAQLEKYFTKDVFSDLEVHQIN 301                                              350
SEQ ID NO: 27      RPLKPLIIVISWAITLLAAAWWFLRR..VLSTWKGIAWVAGVLVVVMLCV
Q9XFW4             RPIKSLAVVVSWACLLTLGAMKFLHWSNLFSSWKGIALSAFGLGIITLCM
Q40119             RPMKSLVVVVSWMCLLCLGLVKFLQWSALLSSWKGMMITTFVLGIVTVLM
Q9SDN3             RPLKSLLVVTAWACLLILGALKFLYWSSLLSSWKGIAFSALGLGVVTVLM
Q41745             RPVKSLLVTLFWSCLLLFGAIEFFKWTQLLSTWRGVAFTAAGMALVTGVM
Q9SYC8             RPIKPLIVVIIWLGFLVFGGFKLLQWLSIVASWKIILLFVFFLVIATITM 351                 391
SEQ ID NO: 27      QILVMSSQSERSSDPAAKKANQKQAASVAHLGKTD......
Q9XFW4             QILIRSSQSERSTPAKVAPAKPKDNHQSGPSSQTEVEEKQK
Q40119             HILIRSSQSEHSTPAKTRARQTAENPK..............
Q9SDN3             QILIRFSQSERSTPAVAPTNNKNKGESSGKPEKQQ.....
Q41745             HVFIMFSQAERSSSARAARNRVKKE................
Q9SYC8             QILIQSSESQRSTPAKRPLQEQLISA...............
```

Figure 18: Alignment of SEQ ID NO: 8 with Swiss Prot database

```
               1                                                  50
SEQ ID NO: 8   MESTADVGMSDDDPILLNGLETPLLAEFPLGERPTIGPEAPVNPFHEPDG
P42322         ..................................................
Q9NKW7         ..................................................
Q9XFJ4         ......MGQREDIRTLSNEYEVTDIPRRGGLSVVRRGTRRRTLHSGQHHE
O35259         ..................................................
Q9FF57         ..................................................

51                                                 100
SEQ ID NO: 8   GWKTNNEWNYFQMMKSILLIPLLLVRLVSMITIVAFGYVWIRICLIGVTD
P42322         ..................................................
Q9NKW7         ..................................................
Q9XFJ4         VVAIKTLR.RFGPPPAPEKKSLNKSRVPQAALISETLLTNELLVMIKIVE
O35259         ..................METIMDDEVTKRTSAEELESWNLLSRTNYN.
Q9FF57         ..............MIEQLGLIIIMGLIHYQSERVKPREWLKLSSSENSR 101                                                150
SEQ ID NO: 8   PLFKPFNPCRRFMLWGIRLVARAVMFTMGYYYIPIKGKPAHRSEAPIIVS
P42322         ..................................................
Q9NKW7         ..................................................
Q9XFJ4         DVSPHPNVIHLYDVCEDPSGVHLILELCSGGELFDRIAGQARYNEEGAAA
O35259         ...FQYISLRLTILWGLGVLIRYCFLLPLRIALAFTGIGLLVVGTTMVGY
Q9FF57         LG.NTKTNHRRSETGDVSYEQRDLLDISPTLTEAAGAIVDFHCFKTCRCF 151                                                200
SEQ ID NO: 8   NHIGFLDPIFVFYRHLPAIVSAKENVEMPIIGLFLQALQIIPVDRTDAQS
P42322         ..................................................
Q9NKW7         ..................................................
Q9XFJ4         VVRQIAKGLEALHGASIVHRDLKPENCLFLNKDENSPLKIMDFGLSSIED
O35259         LPNGRFKEFLSKHVHLMCYR..............................
Q9FF57         TLAFGWIIFLSLFIPVNALLK.............................

201                                                250
SEQ ID NO: 8   RHHAAGNVRRRAVDNMWSHVMLFPQGTTTNGRAIIAFKTGAFSPGLPVQP
P42322         ..................................................
Q9NKW7         ..................................................
Q9XFJ4         FANPVVGLFGSIDYVSPEALSREKITTKSDIWSLGVILYILLSGYPPFIA
O35259         ..................................................
Q9FF57         .........................................GQDRLRKKIER
```

Figure 18 (continued)

```
                     251                                          300
SEQ ID NO:  8  MVIRYPHKYVNPSWCDQGGPLVVVLQLMTQFINHMEVEYLPVMKPTVREM
P42322         ..................................................
Q9NKW7         ..................................................
Q9XFJ4         PSNRQKQQMILNGQFSFDEKTWKNISSSAKQLISSLLKVDPNMRPTAQEI
O35259         ICVR.ALTAIITYHN...................................
Q9FF57         VLVEMICSFFVASWTG..................................

301                                          350
SEQ ID NO:  8  KYPHEFASRVRSEMAKALGIVCTEHSFLD...IKLALAAEKLKQPSGRSL
P42322         ........................................MGTNTSSLRP
Q9NKW7         .................................................MGN
Q9XFJ4         LEHPWVTGDLAKQEQMDAEIVSRLQSFNARRKFRAAAMASILSSSFSLRT
O35259         ................................RKNRPRN........GG
Q9FF57         .............................VVKYHGPRPSIRP...KQ 351                                          400
SEQ ID NO:  8  VEFARMEKLFRLDFPTAKEYLEKFSAMDRTHSGF..VTFEELCTALDLP.
P42322         EEVEEMQKGTNFTQKEIKKLYKRFKKLDKDGNGT..ISKDEFLMIPELA.
Q9NKW7         ENSLPMELCSNFDPDEIKRLGKRFRKLDLDNSGS..LSVDEFMTLPELQ.
Q9XFJ4         KKLKKLVGSYDLKPEELENLSHNFKKICKNGENSTLLEFEEVLKAMEMSS
O35259         ICVANHTSRIDVIIFASDGYYAMVGQVHGGLMGVIQRAMVKACPHVWFE.
Q9FF57         VYVANHTSMIDFIVLEQMTAFAVIMQKHPGWVGLLQSTILESVGCIWFN.

401                                          450
SEQ ID NO:  8  RSPITKQVFNLFDKDGHGSINFREFLAGLAFVSSHTSFSSTMEAAFKACD
P42322         VNPLVKRVISIFDENGDGSVNFKEFIAALSVFNAQGDKQRKLEFAFKVYD
Q9NKW7         QNPLVQRVIDIFDTDGNGEVDFKEFIEGVSQFSVKGDKLSKLRFAFKIYD
Q9XFJ4         LVPLAPRIFDLFDNNRDGTVDMREIIGGFSSLKYSQGD.DALRLCFQVYD
O35259         RSEVKDRHLVAKRLTEHVQDKSKLPILIFPEGTCINNT.SVMMFKKGSFE
Q9FF57         RSEAKDREIVAKKLRDHVQGADSNPLLIFPEGTCVNNN.YTVMFKKGAFE 451                                          500
SEQ ID NO:  8  VNGDGTLSRDEVERSLLDIFPELPPI......TVFKLFDTLDINHDEKIS
P42322         IDGDGYISNGELFTVLKMMVGNNLSD.VQLQQIVDKTILEADEDGDGKIS
Q9NKW7         MDKDGYISNGELFQVLKMMVGNNLKD.TQLQQIVDKTIIHADADGDGKIS
Q9XFJ4         TDRSGCISKEEVESMLRALPEDCLPINITEPGKLDEIFDLMDANSDGKVT
O35259         IGATVYPVAIKYDPQFGDAFWNSSKYG.....MVTYLLRMMTSWAIVCSV
Q9FF57         LDCTVCPIAIKYNKIFVDAFWNSRKQS.....FTMHLLQLMTSWAVVCEV
```

Figure 18 (continued)

```
              501                                               550
SEQ ID NO: 8  WEEFSSFLQRNPEYLAIIIYAHPTLLKPPTSTS.................
P42322        FEEFAKTLSHQDLENKMTIRL.............................
Q9NKW7        FEEFCAVVGNMDVHKKMVVDV.............................
Q9XFJ4        FDEFKAAMQRDSSLQDVVLSSLRPN.........................
O35259        WYLPPMTREKDEDAVQFANRVKSAIARQEDW...................
Q9FF57        WYLEPQTIRPGETGIEFAERVRDMISLRAGLKKVPWDGYLKYSRPSPKHS 551           568
SEQ ID NO: 8  ..................
P42322        ..................
Q9NKW7        ..................
Q9XFJ4        ..................
O35259        ..................
Q9FF57        ERKQQSFAESILARLEEK
```

Figure 19: Alignment of SEQ ID NO: 10 with Swiss Prot database

```
                    1                                                  50
Q24214              ..................................................
P28470              ..................................................
SEQ ID NO: 10       MTSTENTAMFTEDTSTLNGSTEANHAEFPLGERPTIGPEPPVNPFHESST
O35259              ........................METIMDDEVTKRTSAEEL
Q9XFJ4              MGQREDIRTLSNEYEVTDIPRRGGLSVVRRGTRRRTLHSGQHHEVVAIKT 51                                                 100
Q24214              ..................................................
P28470              ..................................................
SEQ ID NO: 10       WSIPQVIKTILLVPLLVIRLLSMFALMMLGYICVKVAMIGCKDPLFKPFN
O35259              ESWNLLSRTNYNFQYISLRLTILWGLGVLIRYCFLLP..............
Q9XFJ4              LRRFGPPPAPEKKSLNKSRVPQAALISETLLTNELLVMIKIVEDVSPHPN 101                                                150
Q24214              ..................................................
P28470              ..................................................
SEQ ID NO: 10       PLRRLLLVSVRLIARGVMVAMGYYYILVKGKPAHRSVAPIIVSNHIGFVD
O35259              ..............LRIALAFTGIGLLVVG.............TTMVG...
Q9XFJ4              VIHLYDVCEDPSGVHLILELCSGGELFDRIAGQARYNEEGAAAVVRQIAK 151                                                200
Q24214              ..................................................
P28470              ..................................................
SEQ ID NO: 10       PIFVFYRHLPVIVSAKEIVEMPIIGMFLQALQIIPVDRINPASRHHAAGN
O35259              ..........................YLPNGRFKEFLSKH....
Q9XFJ4              GLEALHGASIVHRDLKPENCLFLNKDENSPLKIMDFGLSSIEDFANPVVG 201                                                250
Q24214              ..................................................
P28470              ..................................................
SEQ ID NO: 10       IRRRAMDNEWPHVMLFPEGTTTNGKALISFKTGAFSPGLPVQPMVIKYPH
O35259              ..........VHLMCYR...........................
Q9XFJ4              LFGSIDYVSPEALSREKITTKSDIWSLGVILYILLSGYPPFIAPSNRQKQ 251                                                300
Q24214              ..................................................
P28470              ..................................................
SEQ ID NO: 10       KYVNPCWCNQGGPLVILFQLMTQFVNYMEVEYLPVMTPNVHEIKNPHEFA
O35259              ..................ICVR..............ALTAIITYHNRK
Q9XFJ4              QMILNGQFSFDEKTWKNISSSAKQLISSLLKVDPNMRPTAQEILEHPWVT
```

Figure 19 (continued)

```
                  301                                    350
Q24214            .........................................MGNETSLPME
P28470            .........................................GNEASYHSE
SEQ ID NO: 10     NRVRTEMAKALGVVCTEHNF...LDIKLKMAAEKLKQPSGRSLVEFARME
O35259            NRPR....................N...........GGICVANHT
Q9XFJ4            GDLAKQEQMDAEIVSRLQSFNARRKFRAAAMASILSSSFSLRTKKLKKLV 351                                    400
Q24214            MCSNFDADEIRRLGKRFRKLDLD..NSGALSVDEFMSLPELQ.QNPLVQR
P28470            MGTHFDHDEIKRLGRSFKKMDLD..KSGSLSVDEFMSLPELQ.QNPLVGR
SEQ ID NO: 10     KLFRLDYSKAQEYLEKFSAMDPS..HSGYVTYDEFLKALHLP.PTQITEQ
O35259            SRIDVIIFASDGYYAMVGQVHGG..LMGVIQRAMVKACPHVW.FERSEVK
Q9XFJ4            GSYDLKPEELENLSHNFKKICKNGENSTLLEFEEVLKAMEMSSLVPLAPR 401                                    450
Q24214            VIDIFDADGNGEVDFKEFIQGVSQFS.VKGDKLSKLRFAFRIYDMDNDGY
P28470            VIDIFDTDGNGEVDFREFIVGTSQFS.VKGDEEQKLRFAFRIYDMDNDGF
SEQ ID NO: 10     VFNLFDKNGHGSINFREFVAGLAFLS.THTSFQTTMKAAFKACDVDGDGT
O35259            DRHLVAKRLTEHVQDKSKLPILIFPEGTCINNTSVMMFKKGSFEIGATVY
Q9XFJ4            IFDLFDNNRDGTVDMREIIGGFSSLK..YSQGDDALRLCFQVYDTDRSGC 451                                    500
Q24214            ISNGELFQVLKMMVGNNLKD.TQLQQIVDKTIGFADKDEDGKISFDEFCS
P28470            ISNGELFQVLKMMVGNNLKD.WQLQQLVDKSILVLDKDGDGRISFEEFRD
SEQ ID NO: 10     LTRNEVESSLMAVFP......ELPPATVLKLFDTLDLNRDGSINWEEFSS
O35259            PVAIKYDPQFGDAFWN............SSKYGMVTYLLRMMTSWAIVCS
Q9XFJ4            ISKEEVESMLRALPEDCLPINITEPGKLDEIFDLMDANSDGKVTFDEFKA 501            532
Q24214            VVGNTDIHKKMVVDV................
P28470            VVRTMEIHKKLVVFVDHGQED...........
SEQ ID NO: 10     FLQRNPEYLAIILAAHPTLLQAPKSEESETNI
O35259            VWYLPPMTREKDEDAVQFANRVKSAIARQEDW
Q9XFJ4            AMQRDSSLQDVVLSSLRPN.............
```

Figure 20: Alignment of SEQ ID NO: 12 with Swiss Prot database

```
                    1                                                50
Q9XFW4              .MAMAAAVIVPLGILFFISGLVVNLLQAVCYVLVRPMSKNTYRKINRVVA
Q9SDN3              ..................................................
Q40119              MAIPAAAFIVPISLLFFMSGLVVNFIQAVFYVLVRPISKDTYRRINTLVA
Q41745              MAIPLVLVVLPLGLLFLLSGLIVNAIQAVLFVTIRPFSKSFYRRINRFLA
Q9SYC8              MKIPAALVFIPVGVLFLISGLIVNIIQLVFFIIVRPFSRSLYRRINKNVA
SEQ ID NO: 12       ..............................................MIMM 51                                               100
Q9XFW4              ETLWLELVWIVDWWAGVKIQVFADDETFNRMGKEHALVVCNHRSDIDWLV
Q9SDN3              ........................MGKEHALVISNHRSDIDWLV
Q40119              ELLWLELVWVIDWWAGVKVQLYTDTESFRLMGKEHALLICNHRSDIDWLI
Q41745              ELLWLQLVWVVDWWAGVKVQLHADEETYRSMGKEHALIISNHRSDIDWLI
Q9SYC8              ELLWLQLIWLFDWWACIKINLYVDAETLELIGKEHALVLSNHRSDIDWLI
SEQ ID NO: 12       EVLWSELIWLLDWWANVKVKVYTPKESWEHLGKEHALLICNHRSDIDWLV 101                                              150
Q9XFW4              GWILAQRSGCLGSALAVMKKSSKFLPVIGWSMWFSEYLFLERNWAKDEST
Q9SDN3              GWVLAQRSGCLGSSLAVMKKSSKFLPVIGWSMWFSEYLFLERSWAKDEGT
Q40119              GWVLAQRCGCLSSSIAVMKKSSKFLPVIGWSMWFSEYLFLERNWAKDENT
Q41745              GWILAQRSGCLGSTLAVMKKSSKFLPVIGWSMWFAEYLFLERSWAKDEKT
Q9SYC8              GWVMAQRVGCLGSSLAIMKKEAKYLPIIGWSMWFSDYIFLERSWAKDENT
SEQ ID NO: 12       GWIIAQRLGCLGGTRAVMKKSTKFLPVIGWSMWFSEYVFLSRDWAKDEKV 151                                              200
Q9XFW4              LQSGLQRLNDFPRPFWLALFVEGTRFTEAKLKAAQEYAASSELPVPRNVL
Q9SDN3              LKSGVQRLKDFPQPFWLALFVEGTRFTQAKLLAAQEYAAATGLPVPRNVL
Q40119              LKSGLQRLNDFPKPFWLALFVEGTRFTKAKLLAAQEYAASAGLPVPRNVL
Q41745              LKWGLQRLKDFPRPFWLALFVEGTRFTPAKLLAAQEYAASQGLPAPRNVL
Q9SYC8              LKAGFKRLEDFPMTFWLALFVEGTRFTQEKLEAAQEYASIRSLPSPRNVL
SEQ ID NO: 12       LKNGYSSLKGFPRTLWVALFVEGTRFTKAKLEVAQKFAADTGLRVPRYVL 201                                              250
Q9XFW4              IPRTKGFVSAVSNMRSFVPAIYDMTVAIPKTSPPPTMLRLFKGQPSVVHV
Q9SDN3              IPRTKGFVTAVSQMRSFAPAIYDVTVAIPKSSPAPTMLRLFEGRPSVVHV
Q40119              IPRTKGFVSAVSNMRSFVPAIYDLTVAIPKTTEQPTMLRLFRGKSSVVHV
Q41745              IPRTKGFVSAVSIMRDFVPAIYDTTVIVPKDSPQPTMLRILKGQSSVIHV
Q9SYC8              IPRTKGFVSAVSEIRSFVPAIYDCTLTVHNNQPTPTLLRMFSGQSSEINL
SEQ ID NO: 12       VPRTKGFVSAVENLREFVPVVYDMTVAISKELPNPTMIRIFRGQPSVVHV
```

Figure 20 (continued)

```
              251                                               300
Q9XFW4        HIKCHSMKDLPEPEDEIAQWCRDQFVAKDALLDKHIAADTFPGQKEQNIG
Q9SDN3        HIKRHVMRDLPETDEAVAQWCKDIFVAKDALLDKHTVEQTFGDQQLKVTG
Q40119        HLKRHLMKDLPKTDDGVAQWCKDQFISKDALLDKHVAEDTFSGLEVQDIG
Q41745        RMKRHAMSEMPKSDEDVSKWCKDIFVAKDALLDKHLATGTFD.EEIRPIG
Q9SYC8        QMRRHKMSELPETDDGIAQWCQDLFITKDAQLEKYFTKDVFSDLEVHQIN
SEQ ID NO: 12 YVRRVPMSDLPEGANAISKWCHDAFHIKDDRLEQHEKENTFGEDLYIPIE 301                                               350
Q9XFW4        RPIKSLAVVVSWACLLTLGAMKFLHWSNLFSSWKGIALSAFGLGIITLCM
Q9SDN3        RPLKSLLVVTAWACLLILGALKFLYWSSLLSSWKGIAFSALGLGVVTVLM
Q40119        RPMKSLVVVVSWMCLLCLGLVKFLQWSALLSSWKGMMITTFVLGIVTVLM
Q41745        RPVKSLLVTLFWSCLLLFGAIEFFKWTQLLSTWRGVAFTAAGMALVTGVM
Q9SYC8        RPIKPLIVVIIWLGFLVFGGFKLLQWLSIVASWKIILLFVFFLVIATITM
SEQ ID NO: 12 RPLKPLIIVISWAITLLAAAWWFLRR..VLSTWKGIAWVAGVLVVVMLCV 351                               391
Q9XFW4        QILIRSSQSERSTPAKVAPAKPKDNHQSGPSSQTEVEEKQK
Q9SDN3        QILIRFSQSERSTPAPVAPTNNKNKGESSGKPEKQQ.....
Q40119        HILIRSSQSEHSTPAKTRARQTAENPK..............
Q41745        HVFIMFSQAERSSSARAARNRVKKE................
Q9SYC8        QILIQSSESQRSTPAKRPLQEQLISA...............
SEQ ID NO: 12 QILVMSSQSERSSDPAAKKANQKQAASVAHLGKTD......
```

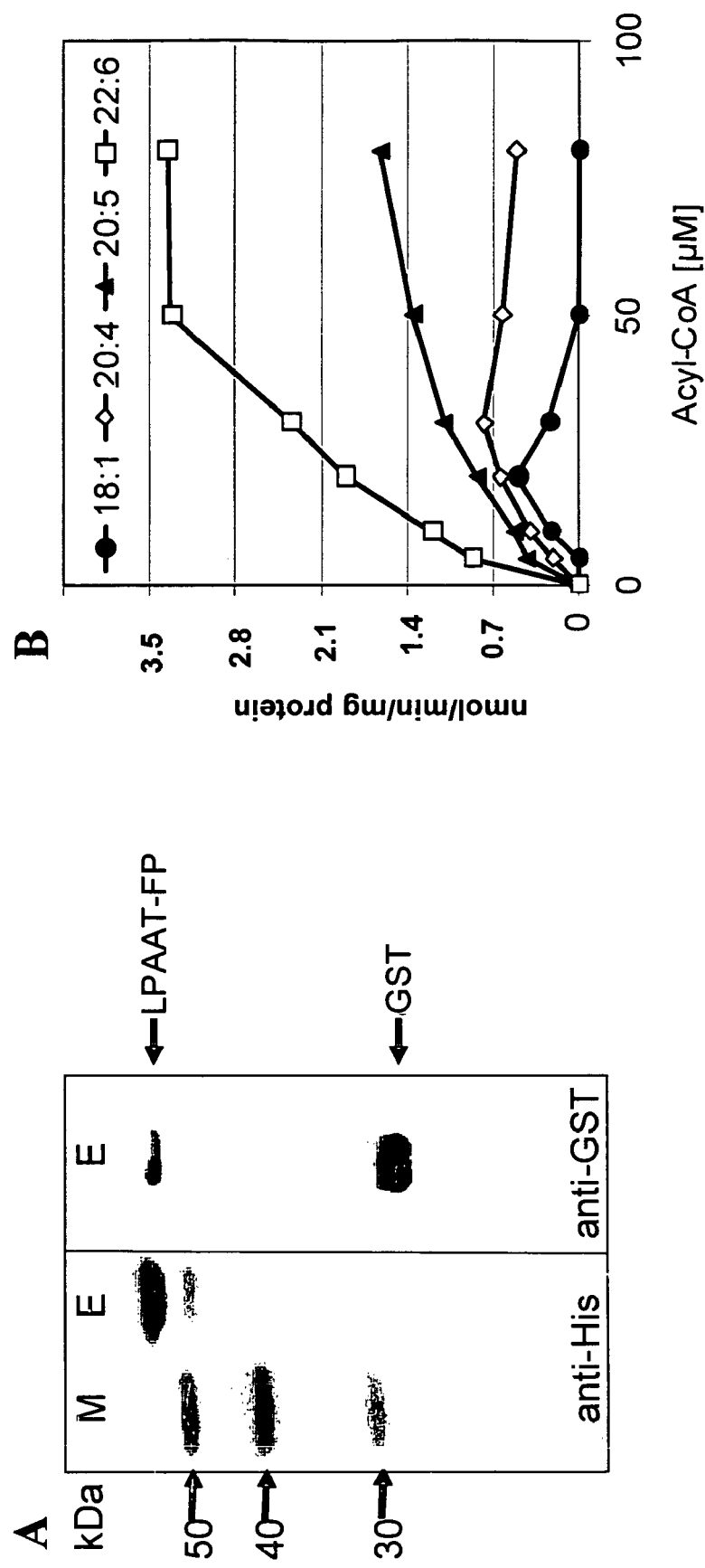
Figure 21: A. Western blot analyses of the *Thraustochytrium* LPAAT expressed in *E. coli* as fusion protein (LPAAT-FP) with N-terminal GST tag and C-terminal His tag.
B Acyl-CoA specificity of the *Thraustochytrium* LPAAT expressed as GST fusion protein in *E. coli*

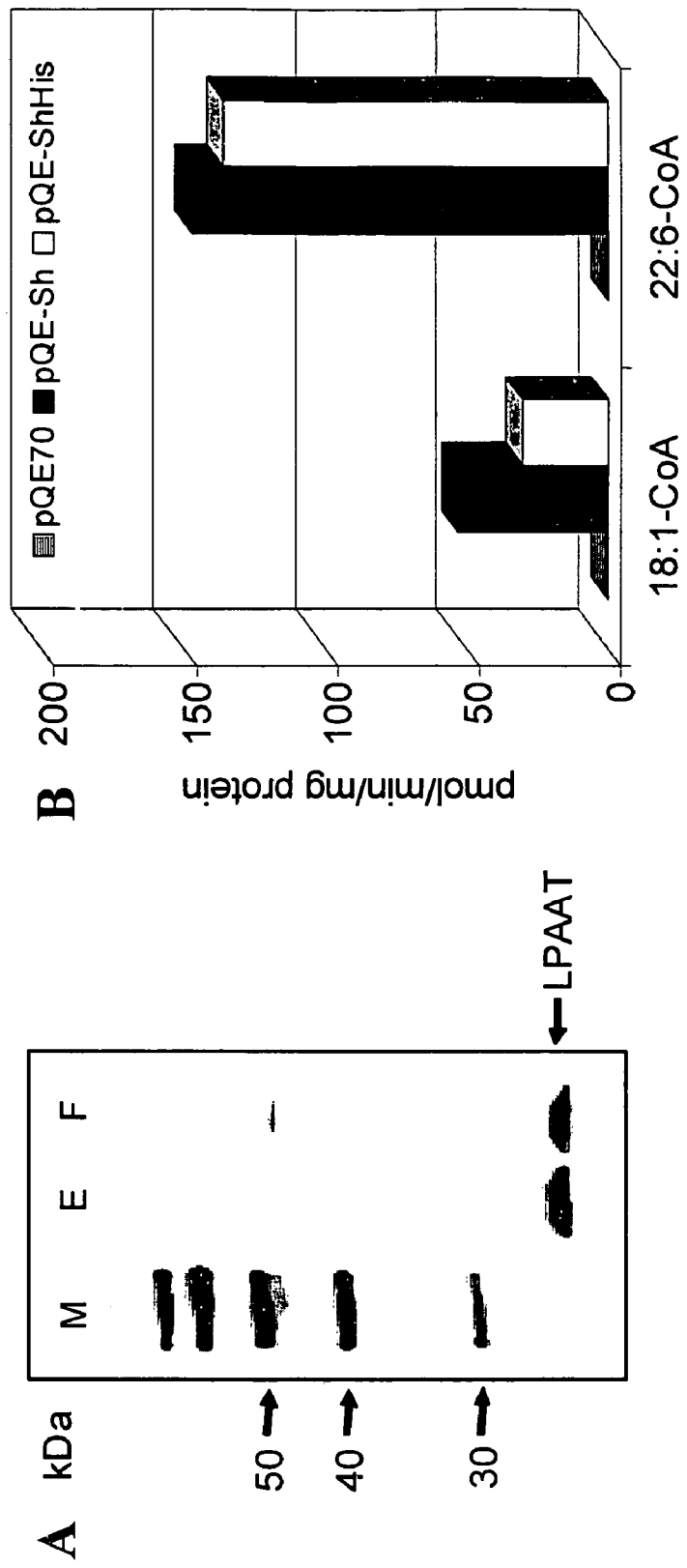
Figure 22: A: Western blot analysis of the *Shewanella* LPAAT expressed in *E. coli* as fusion protein with C-terminal His tag.
B: Functional expression of the *Shewanella* LPAAT in *E. coli*

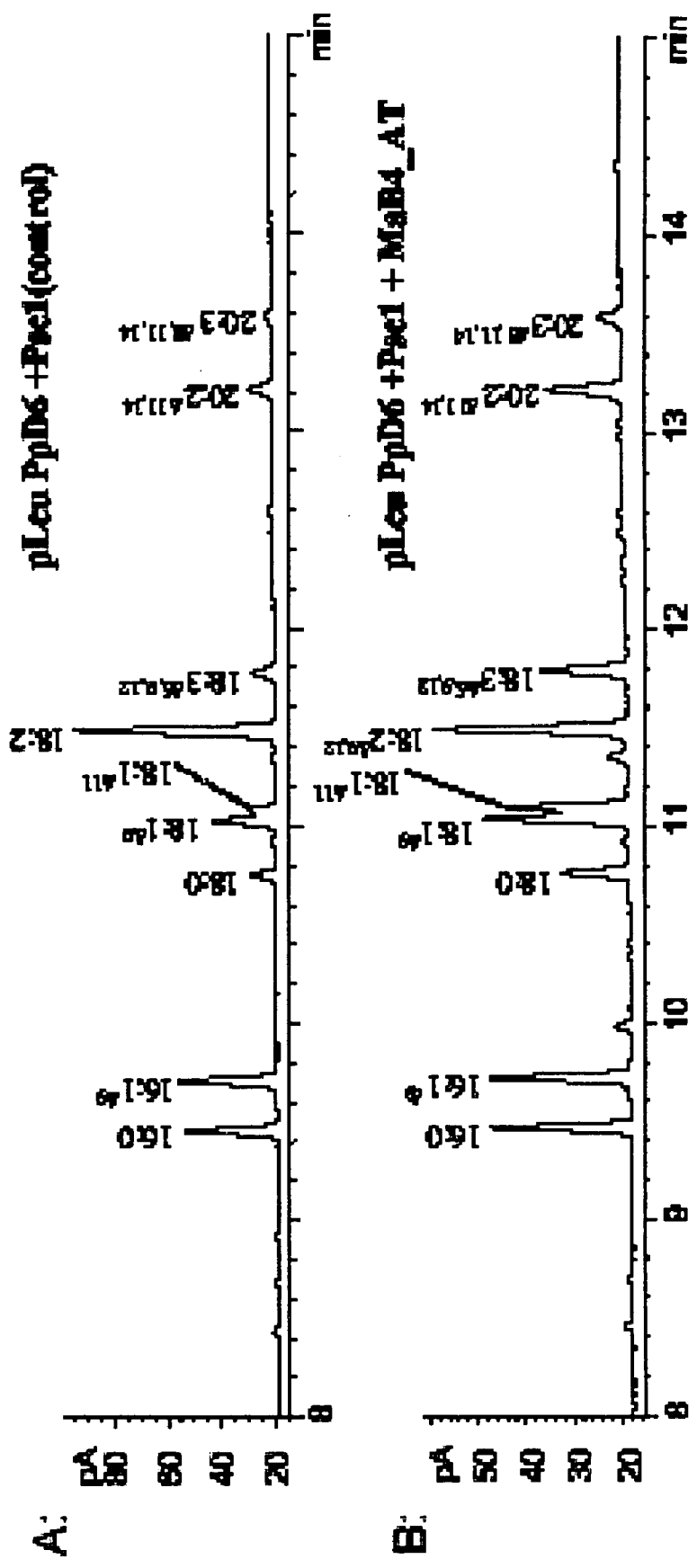
Figure 23: Expression of Mortierella LPAAT (MaB4_AT) in yeast, and feeding of 18:2 Δ9,12 fatty acids (A + B)

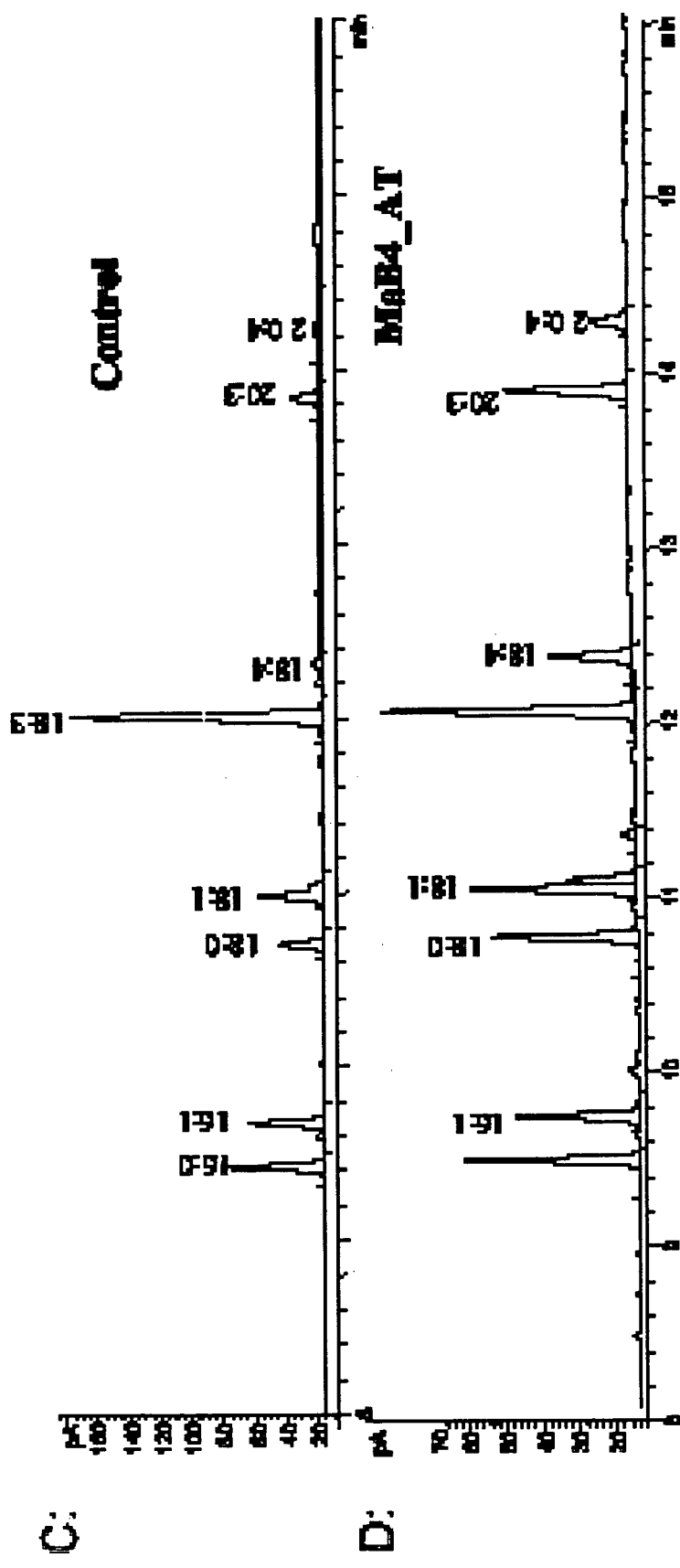
Figure 24: Expression of Mortierella LPAAT (MaB4_AT) in yeast, and feeding of 18:3 Δ9,12,15 fatty acids (C + D)

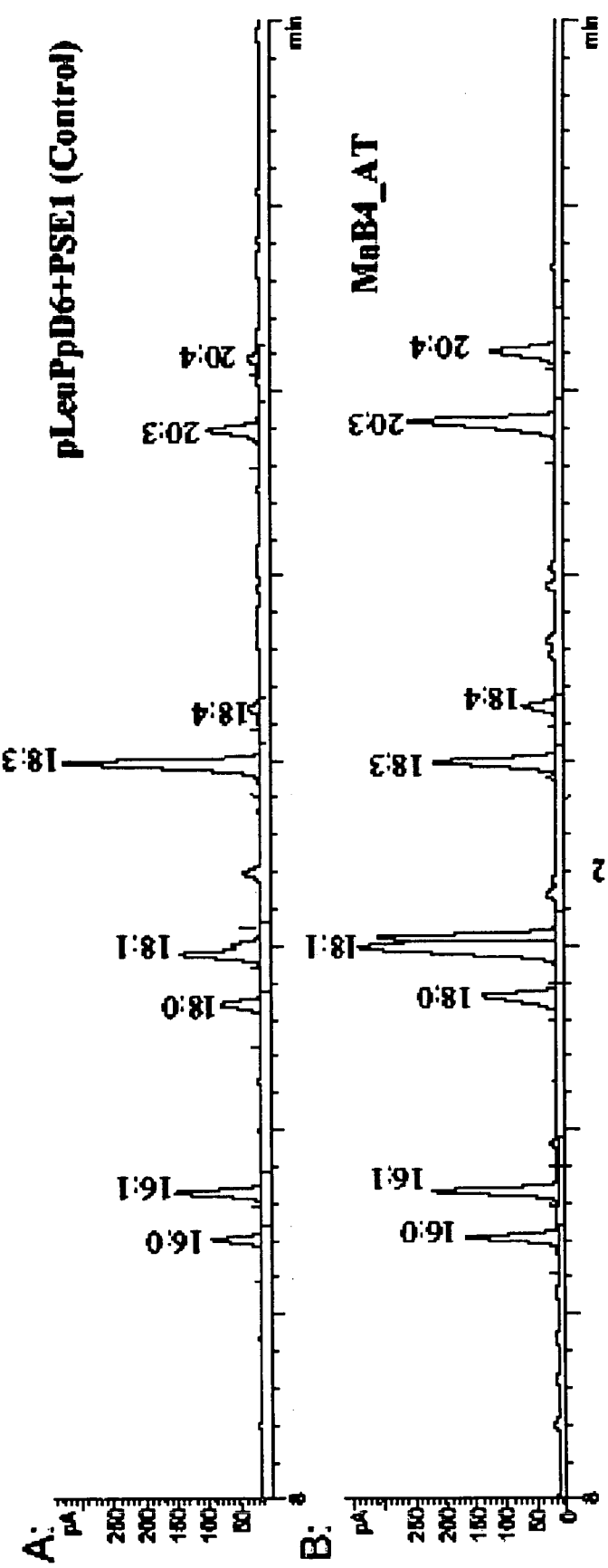
Figure 25: Expression of Mortierella LPAAT (MaB4_AT) in yeast, and feeding of 18:2 Δ9,12 fatty acids (A + B). Analysis of the neutral lipids.

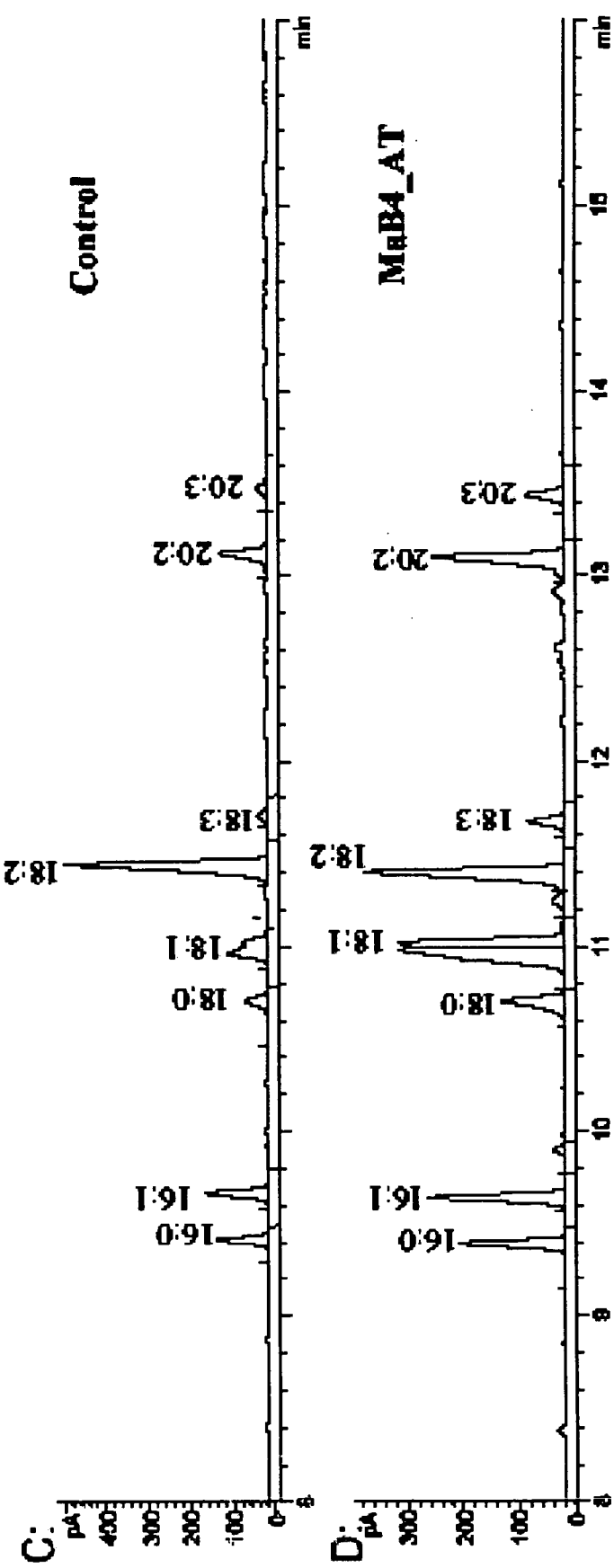
Figure 26: Expression of Mortierella LPAAT (MaB4_AT) in yeast, and feeding of 18:3 Δ9,12,15 fatty acids (C + D). Analysis of the neutral lipids.

PLANT ACYLTRANSFERASES SPECIFIC FOR LONG-CHAINED, MULTIPLY UNSATURATED FATTY ACIDS

RELATED APPLICATIONS

This application is a national stage application (under 35 U.S.C. 371) of PCT/EP2004/003224 filed Mar. 26, 2004 which claims benefit to German application 103 14 759.4 filed Mar. 31, 2003 and German application 103 48 996.7 filed Oct. 17, 2003.

The Sequence Listing associated with this application is filed in electronic format via EFS-Web and hereby incorporated by reference into the specification in its entirety. The name of the text file containing the Sequence Listing is Sequence_Listing_13478_00002 US. The size of the text file is 412 KB, and the text file was created on Jan. 18, 2010.

FIELD OF THE INVENTION

The present invention relates to a process for the production of long-chain polyunsaturated fatty acids in an organism by introducing, into the organism, nucleic acids which code for polypeptides with acyltransferase activity. These nucleic acid sequences, if appropriate together with further nucleic acid sequences which code for polypeptides of the fatty acid or lipid metabolism biosynthesis, can advantageously be expressed in the organism. Furthermore, the invention relates to a method for the production of oils and/or triacylglycerides with an elevated content of long-chain polyunsaturated fatty acids.

The invention furthermore relates to the nucleic acid sequences, nucleic acid constructs, vectors and organisms comprising the nucleic acid sequences according to the invention, vectors comprising the nucleic acid sequences and/or the nucleic acid constructs and to transgenic organisms comprising the abovementioned nucleic acid sequences, nucleic acid constructs and/or vectors.

A further part of the invention relates to oils, lipids and/or fatty acids produced by the process according to the invention and to their use.

DESCRIPTION OF RELATED ART

Fatty acids and triacylglycerides have a multiplicity of applications in the food industry, in animal nutrition, in cosmetics and in the pharmacological sector. Depending on whether they are free saturated or unsaturated fatty acids or else triacylglycerides with an elevated content of saturated or unsaturated fatty acids, they are suitable for very different applications. Polyunsaturated ω-3-fatty acids and ω-6-fatty acids are therefore an important constituent in animal and human food. Owing to the present-day composition of human food, an addition of polyunsaturated ω-3-fatty acids, which are preferentially found in fish oils, to the food is particularly important. Thus, for example, polyunsaturated fatty acids such as docosahexaenoic acid (=DHA, $C22:6^{\Delta4,7,10,13,16,19}$) or eicosapentaenoic acid (=EPA, $C20:5^{\Delta5,8,11,14,17}$) are added to baby formula to improve the nutritional value. The unsaturated fatty acid DHA is said to have a positive effect on the development of the brain.

Hereinbelow, polyunsaturated fatty acids are referred to as PUFA, PUFAs, LCPUFA or LCPUFAs (holy unsaturated fatty acids, PUFA, long chain holy unsaturated fatty acids, LCPUFA).

The various fatty acids and triglycerides are mainly obtained from microorganisms such as *Mortierella* and *Schizochytrium* or from oil-producing plants such as soybean, oilseed rape, algae such as *Crypthecodinium* or *Phaeodactylum* and others, where they are obtained, as a rule, in the form of their triacylglycerides (=triglycerides=triglycerols). However, they can also be obtained from animals, such as, for example, fish. The free fatty acids are advantageously prepared by hydrolysis. Higher polyunsaturated fatty acids such as DHA, EPA, arachidonic acid (=ARA, $C20:4^{\Delta5,8,11,14}$), dihomo-γ-linolenic acid ($C20:3^{\Delta8,11,14}$) or docosapentaenoic acid (DPA, $C22:5^{\Delta7,10,13,16,19}$) can not be isolated from oil crop plants such as oilseed rape, soybean, sunflower or safflower. Conventional natural sources of these fatty acids are fish such as herring, salmon, sardine, redfish, eel, carp, trout, halibut, mackerel, zander or tuna, or algae.

Depending on the intended use, oils with saturated or unsaturated fatty acids are preferred. In human nutrition, for example, lipids with unsaturated fatty acids, specifically polyunsaturated fatty acids, are preferred. The polyunsaturated ω-3-fatty acids are said to have a positive effect on the cholesterol level in the blood and thus on the possibility of preventing heart disease. The risk of heart disease, stroke or hypertension can be reduced markedly by adding these ω-3-fatty acids to the food. Also, ω-3-fatty acids have a positive effect on inflammatory, specifically on chronically inflammatory, processes in association with immunological diseases such as rheumatoid arthritis. They are therefore added to foodstuffs, specifically to dietetic foodstuffs, or are employed in medicaments. ω-6-Fatty acids such as arachidonic acid tend to have a negative effect on these disorders in connection with these rheumatic diseases on account of our usual dietary intake.

ω-3- and ω-6-fatty acids are precursors of tissue hormones, known as eicosanoids, such as the prostaglandins, which are derived from dihomo-γ-linolenic acid, arachidonic acid and eicosapentaenoic acid, and of the thromxanes and leukotrienes, which are derived from arachidonic acid and eicosapentaenoic acid. Eicosanoids (known as the $PG_2$ series) which are formed from ω-6-fatty acids generally promote inflammatory reactions, while eicosanoids (known as the $PG_3$ series) from ω-3-fatty acids have little or no proinflammatory effect.

Owing to the positive characteristics of the polyunsaturated fatty acids, there has been no lack of attempts in the past to make available genes which are involved in the synthesis of fatty acids or triglycerides for the production of oils in various organisms with a modified content of unsaturated fatty acids. Thus, WO 91/13972 and its US equivalent describe a Δ-9-desaturase. WO 93/11245 claims a Δ-15-desaturase and WO 94/11516 a Δ-12-desaturase. Further desaturases are described, for example, in EP-A-0 550 162, WO 94/18337, WO 97/30582, WO 97/21340, WO 95/18222, EP-A-0 794 250, Stukey et al., J. Biol. Chem., 265, 1990: 20144-20149, Wada et al., Nature 347, 1990: 200-203 or Huang et al., Lipids 34, 1999: 649-659. However, the biochemical characterization of the various desaturases has been insufficient to date since the enzymes, being membrane-bound proteins, present great difficulty in their isolation and characterization (McKeon et al., Methods in Enzymol. 71, 1981: 12141-2147, Wang et al., Plant Physiol. Biochem., 26, 1988: 777-792). As a rule, membrane-bound desaturases are characterized by being introduced into a suitable organism which is subsequently analyzed for enzyme activity by analyzing the starting materials and the products. Δ-6-Desaturases are described in WO 93/06712, U.S. Pat. No. 5,614,393, WO 96/21022, WO 00/21557 and WO 99/27111 and the application for the production in transgenic organisms is described in WO 98/46763, WO 98/46764 and WO 98/46765. In this context, the expression of various desaturases and the formation of polyunsaturated fatty acids are also described and claimed in WO 99/64616 or WO 98/46776. As regards the expression efficacy of desaturases and its effect on the formation of polyunsaturated fatty acids, it must be noted that the expression of a single desaturase as described to date has only resulted in low contents of unsaturated fatty acids/lipids such as, for example, γ-linolenic acid and stearidonic acid. Moreover, a mixture of ω-3- and ω-6-fatty acids was obtained, as a rule.

Especially suitable microorganisms for the production of PUFAs are microalgae such as *Phaeodactylum tricornutum, Porphoridium* species, *Thraustochytrium* species, *Schizochytrium* species or *Crypthecodinium* species, ciliates such as *Stylonychia* or *Colpidium*, fungi such as *Mortierella, Entomophthora* or *Mucor* and/or mosses such as *Physcomitrella, Ceratodon* and *Marchantia* (R. Vazhappilly & F. Chen (1998) Botanica Marina 41: 553-558; K. Totani & K. Oba (1987) Lipids 22: 1060-1062; M. Akimoto et al. (1998) Appl. Biochemistry and Biotechnology 73: 269-278). Strain selection has resulted in the development of a number of mutant strains of the microorganisms in question which produce a series of desirable compounds including PUFAs. However, the mutation and selection of strains with an improved production of a particular molecule such as the polyunsaturated fatty acids is a time-consuming and difficult process. This is why recombinant methods as described above are preferred whenever possible. However, only limited amounts of the desired polyunsaturated fatty acids such as DPA, EPA or ARA can be produced with the aid of the above mentioned microorganisms, and, depending on the microorganism used, these are generally obtained as fatty acid mixtures of, for example, EPA, DPA and DHA.

The biosynthesis of LCPUFAs and the incorporation of LCPUFAs into membranes or triacylglycerides proceeds via various metabolic pathways (A. Abbadi et al. (2001) European Journal of Lipid Science & Technology 103:106-113). In bacteria such as *Vibrio*, and microalgae, such as *Schizochytrium*, malonyl-CoA is converted into LCPUFAs via an LCPUFA-producing polyketide synthase (J. G. Metz et al. (2001) Science 293: 290-293; WO 00/42195; WO 98/27203; WO 98/55625). In microalgae, such as *Phaeodactylum*, and mosses, such as *Physcomitrella*, unsaturated fatty acids such as linoleic acid or linolenic acid are converted, in the form of their acyl-CoAs, in a plurality of desaturation and elongation steps to give LCPUFAs (T. K. Zank et al. (2000) Biochemical Society Transactions 28: 654-658). In mammals, the biosynthesis of DHA comprises a chain shortening via beta-oxidation, in addition to desaturation and elongation steps.

In microorganisms and lower plants, LCPUFAs are present either exclusively in the form of membrane lipids, as is the case in *Physcomitrella* and *Phaeodactylum*, or in membrane lipids and triacylglycerides, as is the case in *Schizochytrium* and *Mortierella*. Incorporation of LCPUFAs into lipids and oils is catalyzed by various acyltransferases and transacylases. These enzymes are, already known to carry out the incorporation of saturated and unsaturated fatty acids [A. R. Slabas (200.1) J. Plant Physiology 158: 505-513; M. Frentzen (1998) Fett/Lipid 100: 161-166); S. Cases et al. (1998) Proc. Nat. Acad. Sci. USA 95: 13018-13023]. The acyltransferases are enzymes of the "Kennedy pathway", which are located on the cytoplasmic side of the membrane system of the endoplasmic reticulum, referred to as "ER" hereinbelow. ER membranes may be isolated experimentally as "microsomal fractions" from various organisms [D. S. Knutzon et al. (1995) Plant Physiology 109: 999-1006; S. Mishra & Y. Kamisaka (2001) Biochemistry 355: 315-322; U.S. Pat. No. 5,968,791]. These ER-bound acyltransferases in the microsomal fraction use acyl-CoA as the activated form of fatty acids. Glycerol-3-phosphate acyltransferase, referred to as GPAT hereinbelow, catalyzes the incorporation of acyl groups at the sn-1 position of glycerol-3-phosphate. 1-Acylglycerol-3-phosphate acyltransferase (E.C. 2.3.1.51), also known as lysophosphatidic acid acyltransferase and referred to as LPAAT hereinbelow, catalyzes the incorporation of acyl groups at the sn-2 position of lysophosphatidic acid, abbreviated as LPA hereinbelow. After dephosphorylation of phosphatidic acid by phosphatidic acid phosphatase, diacylglycerol acyltransferase, referred to as DAGAT hereinbelow, catalyzes the incorporation of acyl groups at the sn-3 position of diacylglycerols. Apart from these Kennedy pathway enzymes, further enzymes capable of incorporating acyl groups from membrane lipids into triacylglycerides are involved in the incorporation of fatty acids into triacylglycerides, namely phospholipid diacylglycerol acyltransferase, referred to as PDAT hereinbelow, and lysophosphatidylcholine acyltransferase, referred to as LPCAT. Other enzymes too, such as lecithin cholesterol acyltransferase (LCAT) can be involved in the transfer of acyl groups from membrane lipids into triacylglycerides.

In WO 98/54302, Tjoelker et al. disclose a human lysophosphatidic acid acyltransferase and its potential use for the therapy of diseases, as a diagnostic, and a method for identifying modulators of the human LPAAT. In WO 98/54303, Leung et al. describe mammalian lysophosphatidic acid acyltransferases. Moreover, Leung et al. disclose a method for screening pharmaceutical compounds for use, for example, in the treatment of inflammations.

Moreover, a multiplicity of acyltransferases with a wide range of enzymatic functions have been described in the literature and patents; thus, for example, WO 98/55632 and WO 93/10241 describe fatty acid alcohol acyltransferases which are involved in wax synthesis. WO 98/55631 describes a DAGAT (diacylglycerol acyltransferase) from *Mortierella ramanniana* and a wax synthase from jojoba which also has DAGAT activity. Slabas et al. (WO 94/13814) disclose a membrane-bound sn2-specific acyltransferase which has a different selectivity in the incorporation of monounsaturated erucic acid for the sn2 position and thus makes possible an increased erucic acid yield in oilseed rape. WO 96/24674 describes a corresponding enzyme or gene from *Limnanthes douglasii*. In WO 95/27791, Davies et al. describe LPAATs which are specific for medium-length fatty acids and incorporate these into the sn2 position of triglycerides. Further novel plant acyltransferase sequences which have been found via homology comparisons with sequences from public databases are described by Lassner et al. (WO 00/18889). Information on the specific function of these acyltransferase sequences or biochemical data on the corresponding enzymes cannot be found in WO 00/18889.

The enzymic activity of an LPCAT was first described in rats [Land (1960) Journal of Biological Chemistry 235: 2233-2237]. A plastidic LPCAT isoform [Akermoun et al. (2000) Biochemical Society Transactions 28: 713-715] and an ER-bound isoform [Tumaney and Rajasekharan (1999) Biochimica et Biophysica Acta 1439: 47-56; Fraser and Stobart, Biochemical Society Transactions (2000) 28: 715-7718] exist in plants. LPCAT is involved in the biosynthesis and transacylation of polyunsaturated fatty acids in animals as well as in plants [Stymne and Stobart (1984) Biochem. J. 223: 305-314; Stymne and Stobart (1987) in 'The Biochemistry of Plants: a Comprehensive Treatise', Vol. 9 (Stumpf, P. K. ed.) pp. 175-214, Academic Press, New York]. An important function of LPCAT or, more generally, of an acyl-CoA:lysophospholipid acyltransferase, referred to as LPLAT hereinbelow, in the ATP-independent synthesis of acyl-CoA from phospholipids has been described by Yamashita et al. (2001; Journal of Biological Chemistry 276: 26745-26752).

Despite a lot of biochemical data, no genes coding for LPCAT have been identified previously. Genes of various other plant acyltransferases have been isolated and are described in WO 00/18889 (Novel Plant Acyltransferases).

Higher plants comprise polyunsaturated fatty acids such as linoleic acid (C18:2) and linolenic acid (C18:3). ARA, EPA and DHA are found not at all in the seed oil of higher plants, or only in traces (E. Ucciani: Nouveau Dictionnaire des Huiles Végétales. Technique & Documentation—Lavoisier, 1995. ISBN: 2-7430-0009-0). It is advantageous to produce LCPUFAs in higher plants, preferably in oil seeds such as oilseed rape, linseed, sunflower and soybean, since large amounts of high-quality LCPUFAs for the food industry, animal nutrition and pharmaceutical purposes may be obtained at low costs in this way. To this end, it is advantageous to introduce into and express in oil seeds genes coding for enzymes of the biosynthesis of LCPUFAs by genetic engineering methods. Said genes code, for example, for Δ-6-desaturase, Δ-6-elongase, Δ-5-desaturase, Δ-5-elongase and Δ-4-desaturase. These genes may advantageously be isolated from microorganisms and lower plants which produce LCPUFAs and incorporate them in the membranes or triacylglycerides. Thus, Δ-6-desaturase genes have already been isolated from the moss *Physcomitrella patens* and Δ-6-elongase genes have already been isolated from *P. patens* and the nematode *C. elegans*.

Transgenic plants which express genes coding for enzymes of LCPUFA biosynthesis are suitable for producing small amounts of these LCPUFAs; however, there is the risk that the latter are incorporated not into triacylglycerides, but into membranes, since the endogenous acyltransferases and transacylases may not recognize LCPUFAs as substrate and, accordingly, do not incorporate them into triacylglycerides. This is undesired for the following reasons: (i) the main lipid fraction in oil seeds are triacylglycerides. This is why, for economical reasons, it is necessary to concentrate LCPUFAs in triacylglycerides. LCPUFAs which are incorporated into membranes can modify the physical characteristics of the membranes and thus have harmful effects on the integrity and transport characteristics of the membranes and on the stress tolerance of plants.

First transgenic plants which comprise and express genes coding for enzymes of LCPUFA biosynthesis and produce LCPUFAs have been described for the first time, for example, in DE 102 19 203 (process for the production of polyunsaturated fatty acids in plants). However, these plants produce LCPUFAs in amounts which require further optimization for processing the oils present in said plants.

In order to enable food and feed to be enriched with these polyunsaturated fatty acids, there is therefore a great need for a simple, inexpensive process for producing said polyunsaturated fatty acids, especially in eukaryotic systems.

BRIEF DESCRIPTION OF THE DRAWINGS

FIG. 1 shows vector map of pSUN3CeLPLAT.

FIG. 2 shows amino acid sequence alignment of *C. elegans* LPLATs (Ce-T06E8.1 and Ce-F59F4.4) with the *M. musculus* LPAAT (Mm-NP061350).

FIG. 3 shows fatty acid profiles of transgenic C13ABYS86 *S. cerevisiae* cells.

FIG. 4 shows elongation of exogenously applied $18:2^{\Delta 9,12}$ and $18:3^{\Delta 9,12,15}$, respectively, following their endogenous Δ-6-desaturation (data from FIGS. 2 and 3).

FIG. 5 shows fatty acid profiles of transgenic C13ABYS86 *S. cerevisiae* cells.

FIG. 6 shows acyl-CoA composition of transgenic INVSc1 yeasts which had been transformed with the vectors pESCLeu PpD6Pse1/pYes2 (A) or pESCLeu-PpD6-Pse1/pYes2-T06E8.1 (B).

FIG. 7 shows fatty acid profiles of transgenic INVSc1 *S. cerevisiae* cells.

FIG. 8 shows fatty acid profiles of transgenic INVSc1 *S. cerevisiae* cells.

FIG. 9A shows vector map of pGPTV LeB4-700+ T06E8.1.

FIG. 9B shows vector map of pGPTV USP/OCS-1,2,3 PSE1(Pp)+D6-Des(Pt)+2AT (T06E8-1).

FIGS. 10A and 10B show biosynthetic pathway of LCPUFAs.

FIG. 11 shows comparison of GPAT and LPAAT substrate specificities in linseed, sunflower and *Mortierella alpine*.

FIG. 12 shows comparison of LPCAT substrate specificity in linseed, sunflower and *Mortierella alpine*.

FIG. 13 shows alignment of SEQ ID NO: 2 with Swiss Prot database.

FIG. 14 shows alignment of SEQ ID NO: 5 with Swiss Prot database.

FIG. 15 shows alignment of SEQ ID NO: 35 with Swiss Prot database.

FIG. 16 shows alignment of SEQ ID NO: 23 with Swiss Prot database.

FIG. 17 shows alignment of SEQ ID NO: 27 with Swiss Prot database.

FIG. 18 shows alignment of SEQ ID NO: 8 with Swiss Prot database.

FIG. 19 shows alignment of SEQ ID NO: 10 with Swiss Prot database.

FIG. 20 shows alignment of SEQ ID NO: 12 with Swiss Prot database.

FIG. 21 shows Western blot analyses of the *Thraustochytrium* LPAAT expressed in *E. coli* as fusion protein (LPAAT-FP) with N-terminal GST tag and C-terminal His tag (A) and acyl-CoA specificity of the *Thraustochytrium* LPAAT expressed as GST fusion protein in *E. coli* (B).

FIG. 22 shows Western blot analysis of the *Shewanella* LPAAT expressed in *E. coli* as fusion protein with C-terminal His tag (A) and functional expression of the *Shewanella* LPAAT in *E. coli* (B).

FIG. 23 shows expression of *Mortierella* LPAAT (MaB4_AT) in yeast, and feeding of 18:2 Δ9,12 fatty acids (A+B).

FIG. 24 shows expression of *Mortierella* LPAAT (MaB4_AT) in yeast, and feeding of 18:3 Δ9,12,15 fatty acids (C+D).

FIG. 25 shows expression of *Mortierella* LPAAT (MaB4_AT) in yeast, and feeding of 18:2 Δ9,12 fatty acids (A+B). Analysis of the neutral lipids.

FIG. 26 shows expression of *Mortierella* LPAAT (MaB4_AT) in yeast, and feeding of 18:3 Δ9,12,15 fatty acids (C+D). Analysis of the neutral lipids.

DETAILED DESCRIPTION OF THE INVENTION

It was therefore the object to develop a process for the production of polyunsaturated fatty acids in an organism, advantageously in a eukaryotic organism, preferably in a plant. This object was achieved by the process according to the invention for the production of polyunsaturated fatty acids in an organism, which comprises the following steps:

a) introducing, into the organism, at least one nucleic acid sequence with the sequence shown in SEQ ID NO: 1, SEQ ID NO: 3, SEQ ID NO: 4, SEQ ID NO: 6, SEQ ID NO: 7, SEQ ID NO: 9, SEQ ID NO: 11, SEQ ID NO: 13, SEQ ID NO: 14, SEQ ID NO: 16, SEQ ID NO: 18 or SEQ ID NO: 20, which codes for a polypeptide with lysophosphatidic acid acyltransferase activity; or b) introducing, into the organism, at least one nucleic acid sequence with the sequence shown in SEQ ID NO: 22, SEQ ID NO: 24 or SEQ ID NO: 26, which codes for a polypeptide with glycerol-3-phosphate acyltransferase activity; or c) introducing, into the organism, at least one nucleic acid sequence with the sequence shown in SEQ ID NO: 28, SEQ ID NO: 30 or SEQ ID NO: 32 which codes for a polypeptide with diacylglycerol acyltransferase activity; or d) introducing, into the organism, at least one nucleic acid sequence with the sequence shown in SEQ ID NO: 34 or SEQ ID NO: 36, which codes for a polypeptide with lecithin cholesterol acyltransferase activity; or e) introducing, into the organism, at least one nucleic acid sequence which can be derived from the coding sequence in SEQ ID NO: 1, SEQ ID NO: 3, SEQ ID NO: 4, SEQ ID NO: 6, SEQ ID NO: 7, SEQ ID NO: 9, SEQ ID NO: 11, SEQ ID NO: 13, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34 or SEQ ID NO: 36 as the result of the degeneracy of the genetic code, or f) introducing, into the organism, at least one derivative of the nucleic acid sequence shown in SEQ ID NO: 1, SEQ ID NO: 3, SEQ ID NO: 4, SEQ ID NO: 6, SEQ ID NO: 7, SEQ ID NO: 9, SEQ ID NO: 11, SEQ ID NO: 13, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34 or SEQ ID NO: 36, which code for polypeptides with the amino acid sequence shown in SEQ ID NO: 2, SEQ ID NO: 5, SEQ ID NO: 8, SEQ ID NO: 10, SEQ ID NO: 12, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35 or SEQ ID NO: 37 and which have at least 40% homology at the amino acid level with SEQ ID NO: 2, SEQ ID NO: 5, SEQ ID NO: 8, SEQ ID NO: 10, SEQ ID NO: 12, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35 or SEQ ID NO: 37 and have an equivalent lysophosphatidic acid acyltransferase activity, glycerol-3-phosphate acyltransferase activity, diacylglycerol acyltransferase activity or lecithin cholesterol acyltransferase activity, and g) culturing and harvesting the organism.

Advantageously, the polyunsaturated fatty acids produced in the process of the invention comprise at least two, advantageously three, four or five, double bonds. The fatty acids particularly advantageously comprise four or five double bonds. Fatty acids produced in the process advantageously have 18, 20, 22 or 24 carbon atoms in the fatty acid chain; preferably, the fatty acids comprise 20, 22 or 24 carbon atoms in the fatty acid chain. Advantageously, saturated fatty acids are reacted to a minor extent, or not at all, with the nucleic acids used in the process. A minor extent is understood as meaning that the saturated fatty acids are reacted with less than 5%, advantageously less than 3%, especially advantageously with less than 2% of the activity in comparison with polyunsaturated fatty acids. These fatty acids which are produced may be produced in the process as a single product or be present in a fatty acid mixture.

The nucleic acid sequences used in the process of the invention are isolated nucleic acid sequences which code for polypeptides with lysophosphatidic acid acyltransferase activity, glycerol-3-phosphate acyltransferase activity, diacylglycerol acyltransferase activity and/or lecithin cholesterol acyltransferase activity.

The polyunsaturated fatty acids produced in the process are advantageously bound in membrane lipids and/or triacylglycerides but may also occur in the organisms as free fatty acids or else bound in the form of other fatty acid esters. In this context, they may be present as stated as "pure products" or else advantageously in the form of mixtures of various fatty acids or mixtures of different glycerides. The various fatty acids bound in the triacylglycerides can be derived here from short-chain fatty acids having from 4 to 6 carbon atoms, medium-chain fatty acids having from 8 to 12 carbon atoms or long-chain fatty acids having from 14 to 24 carbon atoms, with preference being given to the long-chain fatty acids and particular preference being given to the long-chain fatty acids, LCPUFAs, of $C_{18}$-, $C_{20}$-, $C_{22}$- and/or $C_{24}$-fatty acids.

The process of the invention advantageously produces fatty acid esters with polyunsaturated $C_{18}$-, $C_{20}$-, $C_{22}$- and/or $C_{24}$-fatty acid molecules, with at least two double bonds being present in the fatty acid ester. These fatty acid molecules preferably comprise three, four or five double bonds and advantageously lead to the synthesis of hexadecadienoic acid (C6:$2^{\Delta 9,12}$), γ-linolenic acid (=GLA, C18:$3^{\Delta 6,9,12}$), stearidonic acid (=SDA, C18:$4\Delta^{6,9,12,15}$), dihomo-γ-linolenic acid (=DGLA, 20:$3^{\Delta 8,11,14}$), eicosatetraenoic acid (=ETA, C20:$4^{\Delta 5,8,11,14}$), arachidonic acid (ARA), eicosapentaenoic acid (EPA) or mixtures thereof, preferably EPA and/or ARA.

The fatty acid esters with polyunsaturated $C_{18}$-, $C_{20}$-, $C_{22}$- and/or $C_{24}$-fatty acid molecules can be isolated, from the organisms which have been used for the preparation of the fatty acid esters, in the form of an oil or lipid, for example in the form of compounds such as sphingolipids, phosphoglycerides, lipids, glycolipids such as glycosphingolipid, phospholipids such as phosphatidylethanolamine, phosphatidylcholine, phosphatidylserine, phosphatidylglycerol, phosphatidylinositol or diphosphatidylglycerol, monoacylglycerides, diacylglycerides, triacylglycerides or other fatty acid esters such as the acetyl-coenzyme A esters which comprise the polyunsaturated fatty acids with at least two, preferably three double bonds; advantageously they are isolated in the form of their diacylglycerides, triacylglycerides and/or in the form of phosphatidylcholine, especially preferably in the form of the triacylglycerides. In addition to these esters, the polyunsaturated fatty acids are also present in the organisms, advantageously the plants, as free fatty acids or bound in other compounds. As a rule, the various abovementioned compounds (fatty acid esters and free fatty acids) are present in the organisms with an approximate distribution of 80 to 90% by weight of triglycerides, 2 to 5% by weight of diglycerides, 5 to 10% by weight of monoglycerides, 1 to 5% by weight of free fatty acids, 2 to 8% by weight of phospholipids, the total of the various compounds amounting to 100% by weight.

The process according to the invention yields the LCPUFAs produced in a content of at least 3% by weight, advantageously at least 5% by weight, preferably at least 8% by weight, especially preferably at least 10% by weight, most preferably at least 15% by weight, based on the total fatty acids in the transgenic organisms, advantageously in a transgenic plant. The fatty acids are advantageously produced in bound form. With the aid of the nucleic acids used in the process according to the invention, these unsaturated fatty acids can be brought into the sn1, sn2 and/or sn3 position of the triglycerides which are advantageously prepared. Since a plurality of reaction steps are performed by the starting compounds hexadecadienoic acid (C16:2), linoleic acid (C18:2) and linolenic acid (C18:3) in the process according to the invention, the end products of the process such as, for example, arachidonic acid (ARA) or eicosapentaenoic acid (EPA) are not obtained as absolutely pure products; minor traces of the precursors are always present in the end product. If, for example, both linoleic acid and linolenic acid are present in the starting organism and the starting plant, the end products such as ARA and EPA are present as mixtures. The precursors should advantageously not amount to more than 20% by weight, preferably not to more than 15% by weight, especially preferably not to more than 10% by weight, most preferably not to more than 5% by weight, based on the amount of the end product in question. Advantageously, only ARA or only EPA, bound or as free acids, are produced as end products in a transgenic plant in the process according to the invention. If both compounds (ARA and EPA) are produced simultaneously, they are advantageously produced in a ratio of at least 1:2 (EPA:ARA), advantageously of at least 1:3, preferably 1:4, especially preferably 1:5.

Owing to the nucleic acid sequences according to the invention, an increase in the yield of polyunsaturated fatty acids of at least 50%, advantageously of at least 80%, especially advantageously of at least 100%, very especially advantageously of at least 150%, in comparison with the nontransgenic starting organism, can be obtained by comparison in GC analysis (see examples). In a further advantageous embodiment, the yield of polyunsaturated fatty acids can be increased by at least 200%, preferably by at least 250%, very especially preferably by at least 300%.

Chemically pure polyunsaturated fatty acids or fatty acid compositions can also be synthesized by the processes described above. To this end, the fatty acids or the fatty acid compositions are isolated from the organism, such as the microorganisms or the plants or the culture medium in or on which the organisms have been grown, or from the organism and the culture medium, in the known manner, for example via extraction, distillation, crystallization, chromatography or combinations of these methods. These chemically pure fatty acids or fatty acid compositions are advantageous for applications in the food industry sector, the cosmetics industry sector and especially the pharmacological industry sector.

Suitable organisms for the production in the process according to the invention are, in principle, any organisms such as microorganisms, nonhuman animals or plants. Advantageously the process according to the invention employs transgenic organisms such as fungi, such as *Mortierella* or *Traustochytrium*, yeasts such as *Saccharomyces* or *Schizosaccharomyces*, mosses such as *Physcomitrella* or *Ceratodon*, nonhuman animals such as *Caenorhabditis*, algae such as *Crypthecodinium* or *Phaeodactylum* or plants such as dicotyledonous or monocotyledonous plants. Organisms which are especially advantageously used in the process according to the invention are organisms which belong to the oil-producing organisms, that is to say which are used for the production of oils, such as fungi, such as *Mortierella* or *Traustochytrium*, algae such as *Crypthecodinium, Phaeodactylum*, or plants, in particular plants, preferably oil crop plants which comprise large amounts of lipid compounds, such as peanut, oilseed rape, canola, sunflower, safflower, poppy, mustard, hemp, castor-oil plant, olive, sesame, *Calendula*, Punica, evening primrose, verbascum, thistle, wild roses, hazelnut, almond, *macadamia*, avocado, bay, pumpkin/squash, linseed, soybean, pistachios, borage, trees (oil palm, coconut or walnut) or arable crops such as maize, wheat, rye, oats, triticale, rice, barley, cotton, cassava, pepper, Tagetes, Solanaceae plants such as potato, tobacco, eggplant and tomato, *Vicia* species, pea, alfalfa or bushy plants (coffee, cacao, tea), *Salix* species, and perennial grasses and fodder crops. Preferred plants according to the invention are oil crop plants such as peanut, oilseed rape, canola, sunflower, safflower, poppy, mustard, hemp, castor-oil plant, olive, *Calendula*, Punica, evening primrose, pumpkin/squash, linseed, soybean, borage, trees (oil palm, coconut). Especially preferred are plants which are high in C18:2- and/or C18:3-fatty acids, such as sunflower, safflower, tobacco, verbascum, sesame, cotton, pumpkin/squash, poppy, evening primrose, walnut, linseed, hemp, thistle or safflower. Very especially preferred plants are plants such as safflower, sunflower, poppy, evening primrose, walnut, linseed or hemp.

It is advantageous to the inventive process described to introduce, in addition to the nucleic acids introduced in step (a) to (f) of the process, further nucleic acids which code for enzymes of the fatty acid or lipid metabolism into the organism.

In principle, all genes of the fatty acid or lipid metabolism can be used in the process for the production of polyunsaturated fatty acids, advantageously in combination with the inventive acyl-CoA:lysophospholipid acyltransferase. Genes of the fatty acid or lipid metabolism selected from the group consisting of acyl-CoA dehydrogenase(s), acyl-ACP [=acyl carrier protein] desaturase(s), acyl-ACP thioesterase(s), fatty acid acyltransferase(s), acyl-CoA:lysophospholipid acyltransferases, fatty acid synthase(s), fatty acid hydroxylase(s), acetyl-coenzyme. A carboxylase(s), acyl-coenzyme A oxidase(s), fatty acid desaturase(s), fatty acid acetylenases, lipoxygenases, triacylglycerol lipases, alleneoxide synthases, hydroperoxide lyases or fatty acid elongase(s) are advantageously used in combination with the acyl-CoA:lysophospholipid acyltransferase. Genes selected from the group of the acyl-CoA:lysophospholipid acyltransferases, Δ-4-desaturases, Δ-5-desaturases, Δ-6-desaturases, Δ-8-desaturases, Δ-9-desaturases, Δ-12-desaturases, Δ-5-elongases, Δ-6-elongases or Δ-9-elongases are especially preferably used in combination with the abovementioned genes for lysophosphatidic acid acyltransferase, glycerol-3-phosphate acyltransferase, diacylglycerol acyltransferase or lecithin cholesterol acyltransferase, it being possible to use individual genes or a plurality of genes in combination.

Owing to the enzymatic activity of the nucleic acids used in the process according to the invention which code for polypeptides with lysophosphatidic acid acyltransferase glycerol-3-phosphate acyltransferase, diacylglycerol acyltransferase or lecithin cholesterol acyltransferase activity, advantageously in combination with nucleic acid sequences which code for polypeptides of the fatty acid or lipid metabolism, such as the acyl-CoA:lysophospholipid acyltransferase activity, the Δ-4-, Δ-5-, Δ-6-, Δ-8-desaturase or the Δ-5-, Δ-6- or Δ-9-elongase activity, a wide range of polyunsaturated fatty acids can be produced in the process according to the invention. Depending on the choice of the organisms, such as the advantageous plant, used for the process according to the invention, mixtures of the various polyunsaturated fatty acids or individual polyunsaturated fatty acids, such as EPA or ARA, can be produced in free or bound form. Depending on the prevailing fatty acid composition in the starting plant (C18:2- or C18:3-fatty acids), fatty acids which are derived from C18:2-fatty acids, such as GLA, DGLA or ARA, or fatty acids which are derived from C18:3-fatty acids, such as SDA, ETA or EPA, are thus obtained. If only linoleic acid (=LA, $C18:2^{\Delta 9,12}$) is present as unsaturated fatty acid in the plant used for the process, the process can only afford GLA, DGLA and ARA as products, all of which can be present as free fatty acids or in bound form. If only α-linolenic acid (=ALA, $C18:3^{\Delta 9,12,15}$) is present as unsaturated fatty acid in the plant used for the process, as is the case, for example, in linseed, the process can only afford SDA, ETA and EPA as products, all of which can be present as free fatty acids or in bound form, as described above. By modifying the activity of the enzymes involved in the synthesis, lysophosphatidic acid acyltransferase, glycerol-3-phosphate acyltransferase, diacylglycerol acyltransferase or lecithin cholesterol acyltransferase advantageously in combination with acyl-CoA:lysophospholipid acyltransferase, Δ-5-, Δ-6-desaturase and/or Δ-6-elongase or with acyl-CoA:lysophospholipid acyltransferase, Δ-5-, Δ-8-desaturase and/or Δ-9-elongase or in combination with only the first three genes, acyl-CoA:lysophospholipid acyltransferase, Δ-6-desaturase and/or Δ-6-elongase or acyl-CoA:lysophospholipid acyltransferase, Δ-8-desaturase and Δ-9-elongase, of the synthesis cascade, it is possible to produce, in a targeted fashion, only individual products in the abovementioned organisms, advantageously in the abovementioned plants. Owing to the activity of Δ-6-desaturase and Δ-6-elongase, for example, GLA and DGLA, or SDA and ETA, are formed, depending on the starting plant and unsaturated fatty acid. DGLA or ETA or mixtures of these are preferably formed. If Δ-5-desaturase is additionally introduced into the organisms, advantageously into the plant, ARA or EPA is additionally formed. This also applies to organisms into which Δ-8-desaturase and Δ-9-elongase have been introduced previously. Advantageously, only ARA or EPA or mixtures of these are synthesized, depending on the fatty acid present in the organism, or in the plant, which acts as starting substance for the synthesis. Since biosynthetic cascades are involved, the end products in question are not present in pure form in the organisms. Small amounts of the precursor compounds are always additionally present in the end product. These small amounts amount to less than 20% by weight, advantageously less than 15% by weight, especially advantageously less than 10% by weight, most advantageously less than 5, 4, 3, 2 or 1% by weight, based on the end product DGLA, ETA or their mixtures, or ARA, EPA or their mixtures.

To increase the yield in the described method for the production of oils and/or triglycerides with an advantageously elevated content of polyunsaturated fatty acids, it is advantageous to increase the amount of starting product for the synthesis of fatty acids; this can be achieved for example by introducing, into the organism, a nucleic acid which codes for a polypeptide with Δ-12-desaturase. This is particularly advantageous in oil-producing organisms such as oilseed rape which are high in oleic acid. Since these organisms are only low in linoleic acid (Mikoklajczak et al., Journal of the American Oil Chemical Society, 38, 1961, 678-681), the use of the abovementioned Δ-12-desaturases for producing the starting material linoleic acid is advantageous.

Nucleic acids used in the process according to the invention are advantageously derived from plants such as algae such as Isochrysis or Crypthecodinium, algae/diatoms such as Phaeodactylum, mosses such as *Physcomitrella* or Ceratodon, or higher plants such as the Primulaceae such as *Aleuritia, Calendula stellata, Osteospermum spinescens* or *Osteospermum hyoseroides*, microorganisms such as fungi, such as *Aspergillus, Thraustochytrium, Phytophthora, Entomophthora, Mucor* or *Mortierella*, bacteria such as *Shewanella*, yeasts or animals such as nematodes such as *Caenorhabditis*, insects or humans. The nucleic acids are advantageously derived from fungi, animals, or from plants such as algae or mosses, preferably from nematodes such as *Caenorhabditis*.

The process according to the invention advantageously employs the above mentioned nucleic acid sequences or their derivative or homologs which code for polypeptides which retain the enzymatic activity of the proteins encoded by nucleic acid sequences. These sequences, individually or in combination with the nucleic acid sequences which code for lysophosphatidic acid acyltransferase, glycerol-3-phosphate acyltransferase, diacylglycerol acyltransferase and/or lecithin cholesterol acyltransferase are cloned into expression constructs and used for the introduction into, and expression in, organisms. Owing to their construction, these expression constructs make possible an advantageous optimal synthesis of the polyunsaturated fatty acids produced in the process according to the invention.

In a preferred embodiment, the process furthermore comprises the step of obtaining a cell or an intact organism which comprises the nucleic acid sequences used in the process, where the cell and/or the organism is transformed with a nucleic acid sequence according to the invention which codes for the lysophosphatidic acid acyltransferase, glycerol-3-phosphate acyltransferase, diacylglycerol acyltransferase and/or lecithin cholesterol acyltransferase, a gene construct or a vector as described below, alone or in combination with further nucleic acid sequences which code for proteins of the fatty acid or lipid metabolism. In a further preferred embodiment, this process furthermore comprises the step of obtaining the fine chemical from the culture. The culture can, for example, take the form of a fermentation culture, for example in the case of the cultivation of microorganisms, such as, for example, *Mortierella, Saccharomyces* or *Traustochytrium*, or a greenhouse- or field-grown culture of a plant. The cell or the organism produced thus is advantageously a cell of an oil-producing organism, such as an oil crop plant, such as, for example, peanut, oilseed rape, canola, linseed, hemp, soybean, safflower, sunflowers or borage.

In the case of plant cells, plant tissue or plant organs, "growing" is understood as meaning, for example, the cultivation on or in a nutrient medium, or of the intact plant on or in a substrate, for example in a hydroponic culture, potting compost or on arable land.

For the purposes of the invention, "transgenic" or "recombinant" means, with regard to the example of a nucleic acid sequence, an expression cassette (=gene construct) or a vector comprising the nucleic acid sequence according to the invention or an organism transformed with the nucleic acid sequences, expression cassette or vector according to the invention, all those constructions brought about by recombinant methods in which either a) the nucleic acid sequence according to the invention, or
b) a genetic control sequence which is operably linked with the nucleic acid sequence according to the invention, for example a promoter, or
c) (a) and (b)

are not located in their natural genetic environment or have been modified by recombinant methods, it being possible for the modification to take the form of, for example, a substitution, addition, deletion, inversion or insertion of one or more nucleotide residues. The natural genetic environment is understood as meaning the natural genomic or chromosomal locus in the original organism or the presence in a genomic library. In the case of a genomic library, the natural genetic environment of the nucleic acid sequence is preferably retained, at least in part. The environment flanks the nucleic acid sequence at least on one side and has a sequence length of at least 50 bp, preferably at least 500 bp, especially preferably at least 1000 bp, most preferably at least 5000 bp. A naturally occurring expression cassette—for example the naturally occurring combination of the natural promoter of the inventive nucleic acid sequences with the corresponding lysophosphatidic acid acyltransferase, glycerol-3-phosphate acyltransferase, diacylglycerol acyltransferase and/or lecithin cholesterol acyltransferase genes—becomes a transgenic expression cassette when this expression cassette is modified by nonnatural, synthetic ("artificial") methods such as, for example, mutagenic treatment. Suitable methods are described, for example, in U.S. Pat. No. 5,565,350 or WO 00/15815.

A transgenic organism or transgenic plant for the purposes of the invention is understood as meaning, as above, that the nucleic acids used in the process are not at their natural locus in the genome of an organism, it being possible for the nucleic acids to be expressed homologously or heterologously. However, as mentioned, transgenic also means that, while the nucleic acids according to the invention are at their natural position in the genome of an organism, the sequence has been modified with regard to the natural sequence, and/or that the regulatory sequences of the natural sequences have been modified. Transgenic is preferably understood as meaning the expression of the nucleic acids according to the invention at an unnatural locus in the genome, i.e. homologous or, preferably, heterologous expression of the nucleic acids takes place. Preferred transgenic organisms are fungi such as *Mortierella*, mosses such as *Physcomitrella*, algae such as *Cryptocodinium* or plants such as the oil crop plants.

Suitable organisms or host organisms for the nucleic acids, the expression cassette or the vector used in the process according to the invention are, in principle, advantageously all organisms which are capable of synthesizing fatty acids, specifically unsaturated fatty acids, and/or which are suitable for the expression of recombinant genes. Examples which may be mentioned are plants such as *Arabidopsis, Asteraceae* such as *Calendula* or crop plants such as soybean, peanut, castor-oil plant, sunflower, maize, cotton, flax, oilseed rape, coconut, oil palm, safflower (*Carthamus tinctorius*) or cacao bean, microorganisms, such as fungi, for example the genus *Mortierella, Thraustochytrium, Saprolegnia*, or *Pythium*, bacteria, such as the genus *Escherichia*, or *Shewanella*, yeasts, such as the genus *Saccharomyces*, cyanobacteria, ciliates, algae or protozoans such as dinoflagellates, such as *Crypthecodinium*. Preferred organisms are those which are naturally capable of synthesizing substantial amounts of oil, such as fungi, such as *Mortierella alpina, Pythium insidiosum*, or plants such as soybean, oilseed rape, coconut, oil palm, safflower, flax, hemp, castor-oil plant, *Calendula*, peanut, cacao bean or sunflower, or yeasts such as *Saccharomyces cerevisiae*, with soybean, flax, oilseed rape, safflower, sunflower, *Calendula, Mortierella* or *Saccharomyces cerevisiae* being especially preferred. In principle, suitable host organisms are, in addition to the abovementioned transgenic organisms, also transgenic animals, advantageously nonhuman animals, for example *C. elegans*.

Further utilizable host cells are detailed in: Goeddel, Gene Expression Technology: Methods in Enzymology 185, Academic Press, San Diego, Calif. (1990).

Expression strains which can be used, for example those with a lower protease activity, are described in: Gottesman, S., Gene Expression Technology: Methods in Enzymology 185, Academic Press, San Diego, Calif. (1990) 119-128.

These include plant cells and certain tissues, organs and parts of plants in all their phenotypic forms such as anthers, fibers, root hairs, stalks, embryos, calli, cotyledons, petioles, harvested material, plant tissue, reproductive tissue and cell cultures which are derived from the actual transgenic plant and/or can be used for giving rise to the transgenic plant.

Transgenic plants which comprise the polyunsaturated fatty acids synthesized in the process according to the invention can advantageously be marketed directly without there being any need for the oils, lipids or fatty acids synthesized to be isolated. Plants for the process according to the invention are listed as meaning intact plants and all plant parts, plant organs or plant parts such as leaf, stem, seeds, root, tubers, anthers, fibers, root hairs, stalks, embryos, calli, cotyledons, petioles, harvested material, plant tissue, reproductive tissue and cell cultures which are derived from the transgenic plant and/or can be used for giving rise to the transgenic plant. In this context, the seed comprises all parts of the seed such as the seed coats, epidermal cells, seed cells, endosperm or embryonic tissue. However, the compounds produced in the process according to the invention can also be isolated from the organisms, advantageously plants, in the form of their oils, fat, lipids and/or free fatty acids. Polyunsaturated fatty acids produced by this process can be obtained by harvesting the organisms, either from the crop in which they grow, or from the field. This can be done via pressing or extraction of the plant parts, preferably the plant seeds. In this context, the oils, fats, lipids and/or free fatty acids can be obtained by what is known as cold-beating or cold-pressing without applying heat by pressing. To allow for greater ease of disruption of the plant parts, specifically the seeds, they are previously comminuted, steamed or roasted. The seeds which have been pretreated in this manner can subsequently be pressed or extracted with solvents such as warm hexane. The solvent is subsequently removed again. In the case of microorganisms, the latter are, after harvesting, for example extracted directly without further processing steps or else, after disruption, extracted via various methods with which the skilled worker is familiar. In this manner, more than 96% of the compounds produced in the process can be isolated. Thereafter, the resulting products are processed further, i.e. refined. In this process, substances such as the plant mucilages and suspended matter are first removed. What is known as desliming can be effected enzymatically or, for example, chemico-physically by addition of acid such as phosphoric acid. Thereafter, the free fatty acids are removed by treatment with a base, for example sodium hydroxide solution. The resulting product is washed thoroughly with water to remove the alkali remaining in the product and then dried. To remove the pigments remaining in the product, the products are subjected to bleaching, for example using fuller's earth or active charcoal. At the end, the product is deodorized, for example using steam.

The PUFAs or LCPUFAs produced by this process are preferably $C_{18}$-, $C_{20}$-, $C_{22}$- or $C_{24}$-fatty acid molecules with at least two double bonds in the fatty acid molecule, preferably three, four, five or six double bonds. These $C_{18}$-, $C_{20}$-, $C_{22}$- or $C_{24}$-fatty acid molecules can be isolated from the organism in the form of an oil, a lipid or a free fatty acid. Suitable organisms are, for example, those mentioned above. Preferred organisms are transgenic plants.

One embodiment of the invention is therefore oils, lipids or fatty acids or fractions thereof which have been produced by the above-described process, especially preferably oil, lipid or a fatty acid composition comprising PUFAs and being derived from transgenic plants.

A further embodiment according to the invention is the use of the oil, lipid, the fatty acids and/or the fatty acid composition in feedstuffs, foodstuffs, cosmetics or pharmaceuticals.

The term "oil", "lipid" or "fat" is understood as meaning a fatty acid mixture comprising unsaturated or saturated, preferably esterified, fatty acid(s). The oil, lipid or fat is preferably high in polyunsaturated free or, advantageously, esterified fatty acid(s), in particular linoleic acid, γ-linolenic acid, dihomo-γ-linolenic acid, arachidonic acid, α-linolenic acid, stearidonic acid, eicosatetraenoic acid, eicosapentaenoic acid, docosapentaenoic acid or docosahexaenoic acid. The content of unsaturated esterified fatty acids preferably amounts to approximately 30%, a content of 50% is more preferred, a content of 60%, 70%, 80% or more is even more preferred. For the analysis, the fatty acid content can, for example, be determined by gas chromatography after converting the fatty acids into the methyl esters by transesterification. The oil, lipid or fat can comprise various other saturated or unsaturated fatty acids, for example calendulic acid, palmitic acid, palmitoleic acid, stearic acid, oleic acid and the like. The content of the various fatty acids in the oil or fat can vary in particular, depending on the starting organism.

The polyunsaturated fatty acids with advantageously at least two double bonds which are produced in the process are, as described above, for example sphingolipids, phosphoglycerides, lipids, glycolipids, phospholipids, monoacylglycerol, diacylglycerol, triacylglycerol or other fatty acid esters.

Starting from the polyunsaturated fatty acids with advantageously at least two double bonds, which acids have been prepared in the process according to the invention, the polyunsaturated fatty acids which are present can be liberated for example via treatment with alkali, for example aqueous KOH or NaOH, or acid hydrolysis, advantageously in the presence of an alcohol such as methanol or ethanol, or via enzymatic cleavage, and isolated via, for example, phase separation and subsequent acidification via, for example, $H_2SO_4$. The fatty acids can also be liberated directly without the above-described processing step.

After their introduction into an organism, advantageously a plant cell or plant, the nucleic acids used in the process can either be present on a separate plasmid or integrated into the genome of the host cell. In the case of integration into the genome, integration can be random or else be effected by recombination such that the native gene is replaced by the copy introduced, whereby the production of the desired compound by the cell is modulated, or by the use of a gene in trans, so that the gene is linked functionally with a functional expression unit which comprises at least one sequence which ensures the expression of a gene and at least one sequence which ensures the polyadenylation of a functionally transcribed gene. The nucleic acids are advantageously introduced into the organisms via multiexpression cassettes or constructs for multiparallel expression, advantageously into the plants for the multiparallel seed-specific expression of genes.

Mosses and algae are the only known plant systems which produce substantial amounts of polyunsaturated fatty acids such as arachidonic acid (ARA) and/or eicosapentaenoic acid (EPA) and/or docosahexaenoic acid (DHA). Mosses comprise PUFAs in membrane lipids, while algae, organisms which are related to algae and a few fungi also accumulate substantial amounts of PUFAs in the triacylglycerol fraction. This is why nucleic acid molecules are suitable which are isolated from such strains which also accumulate PUFAs in the triacylglycerol fraction, particularly advantageously for the process according to the invention and thus for the modification of the lipid and PUFA production system in a host, in particular plants such as oil crop plants, for example oilseed rape, canola, linseed, hemp, soybeans, sunflowers and borage. They can therefore be used advantageously in the process according to the invention.

Substrates of the nucleic acids used in the process according to the invention which code for polypeptides with lysophosphatidic acid acyltransferase activity, glycerol-3-phosphate acyltransferase activity, diacylglycerol acyltransferase activity or lecithin cholesterol acyltransferase activity, and/or of the further nucleic acids used, such as the nucleic acids which code for polypeptides of the fatty acid metabolism or lipid metabolism selected from the group consisting of acyl-CoA dehydrogenase(s), acyl-ACP[=acyl carrier protein] desaturase(s), acyl-ACP thioesterase(s), fatty acid acyltransferase(s), acyl-CoA:lysophospholipid acyltransferase(s), fatty acid synthase(s), fatty acid hydroxylase(s), acetyl coenzyme A carboxylase(s), acyl coenzyme A oxidase(s), fatty acid desaturase(s), fatty acid acetylenase(s), lipoxygenase(s), triacylglycerol lipase(s), allene oxide synthase(s), hydroperoxide lyase(s) or fatty acid elongase(s) which are advantageously suitable are $C_{16}$-, $C_{18}$-, $C_{20}$- or $C_{22}$-fatty acids. The fatty acids converted in the process in the form of substrates are preferably converted in the form of their acyl-CoA esters.

To produce the long-chain PUFAs according to the invention, the polyunsaturated $C_{16}$- or $C_{18}$-fatty acids must first be desaturated by the enzymatic activity of a desaturase and subsequently be elongated by at least two carbon atoms via an elongase. After one elongation cycle, this enzyme activity gives $C_{18}$- or $C_{20}$-fatty acids and after two or three elongation cycles $C_{22}$- or $C_{24}$-fatty acids. The activity of the desaturases and elongases used in the process according to the invention preferably leads to $C_{18}$-, $C_{20}$-, $C_{22}$- and/or $C_{24}$-fatty acids, advantageously with at least two double bonds in the fatty acid molecule, preferably with three, four or five double bonds, especially preferably to give $C_{20}$- and/or $C_{22}$-fatty acids with at least two double bonds in the fatty acid molecule, preferably with three, four or five double bonds in the molecule. After a first desaturation and the elongation have taken place, further desaturation steps such as, for example, one in the Δ5 position may take place. Products of the process according to the invention which are especially preferred are dihomo-γ-linolenic acid, arachidonic acid, eicosapentaenoic acid, docosapentaenoic acid and/or docosahexaenoic acid. The $C_{18}$-fatty acids with at least two double bonds in the fatty acid can be elongated by the enzymatic activity according to the invention in the form of the free fatty acid or in the form of the esters, such as phospholipids, glycolipids, sphingolipids, phosphoglycerides, monoacylglycerol, diacylglycerol or triacylglycerol.

The preferred biosynthesis site of fatty acids, oils, lipids or fats in the plants which are advantageously used is, for example, in general the seed or cell strata of the seed, so that seed-specific expression of the nucleic acids used in the process makes sense. However, it is obvious that the biosynthesis of fatty acids, oils or lipids need not be limited to the seed tissue, but can also take place in a tissue-specific manner in all the other parts of the plant, for example in epidermal cells or in the tubers.

If microorganisms such as yeasts, such as *Saccharomyces* or *Schizosaccharomyces*, fungi such as *Mortierella*, *Aspergillus*, *Phytophtora*, *Entomophthora*, *Mucor* or *Thraustochytrium*, algae such as *Isochrysis*, *Phaeodactylum* or *Crypthecodinium* are used as organisms in the process according to the invention, these organisms are advantageously grown in fermentation cultures.

Owing to the use of the nucleic acids according to the invention which code for a lysophosphatidic acid acyltransferase, glycerol-3-phosphate acyltransferase, diacylglycerol acyltransferase and/or lecithin cholesterol acyltransferase, the polyunsaturated fatty acids produced in the process can be increased by at least 5%, preferably by at least 10%, especially preferably by at least 20%, very especially preferably by at least 50% in comparison with the wild type of the organisms which do not comprise the nucleic acids recombinantly.

In principle, the polyunsaturated fatty acids produced by the process according to the invention in the organisms used in the process can be increased in two different ways. Advantageously, the pool of free polyunsaturated fatty acids and/or the content of the esterified polyunsaturated fatty acids produced via the process can be enlarged. Advantageously, the pool of esterified polyunsaturated fatty acids in the transgenic organisms is enlarged by the process according to the invention.

If microorganisms are used as organisms in the process according to the invention, they are grown or cultured in the manner with which the skilled worker is familiar, depending on the host organism. As a rule, microorganisms are grown in a liquid medium comprising a carbon source, usually in the form of sugars, a nitrogen source, usually in the form of organic nitrogen sources such as yeast extract or salts such as ammonium sulfate, trace elements such as salts of iron, manganese and magnesium and, if appropriate, vitamins, at temperatures of between 0° C. and 100° C., preferably between 10° C. and 60° C., while gassing in oxygen. The pH of the liquid medium can either be kept constant, that is to say regulated during the culturing period, or not. The cultures can be grown batchwise, semibatchwise or continuously. Nutrients can be provided at the beginning of the fermentation or fed in semicontinuously or continuously: The polyunsaturated fatty acids produced can be isolated from the organisms as described above by processes known to the skilled worker, for example by extraction, distillation, crystallization, if appropriate precipitation with salt, and/or chromatography. To this end, the organisms can advantageously be disrupted beforehand.

If the host organisms are microorganisms, the process according to the invention is advantageously carried out at a temperature of between 0° C. and 95° C., preferably between 10° C. and 85° C., especially preferably between 15° C. and 75° C., very especially preferably between 15° C. and 45° C.

In this process, the pH value is advantageously kept between pH 4 and 12, preferably between pH 6 and 9, especially preferably between pH 7 and 8.

The process according to the invention can be operated batchwise, semibatchwise or continuously. An overview of known cultivation methods can be found in the textbook by Chmiel (Bioprozeßtechnik 1. Einführung in die Bioverfahrenstechnik [Bioprocess technology 1. Introduction to Bioprocess technology] (Gustav Fischer Verlag, Stuttgart, 1991)) or in the textbook by Storhas (Bioreaktoren und periphere Einrichtungen [Bioreactors and peripheral equipment] (Vieweg Verlag, Brunswick/Wiesbaden, 1994)).

The culture medium to be used must suitably meet the requirements of the strains in question. Descriptions of culture media for various microorganisms can be found in the textbook "Manual of Methods for General Bacteriology" of the American Society for Bacteriology (Washington D.C., USA, 1981).

As described above, these media which can be employed in accordance with the invention usually comprise one or more carbon sources, nitrogen sources, inorganic salts, vitamins and/or trace elements.

Preferred carbon sources are sugars, such as mono-, di- or polysaccharides. Examples of very good carbon sources are glucose, fructose, mannose, galactose, ribose, sorbose, ribulose, lactose, maltose, sucrose, raffinose, starch or cellulose. Sugars can also be added to the media via complex compounds such as molasses or other by-products from sugar refining. The addition of mixtures of a variety of carbon sources may also be advantageous. Other possible carbon sources are oils and fats such as, for example, soya oil, sunflower oil, peanut oil and/or coconut fat, fatty acids such as, for example, palmitic acid, stearic acid and/or linoleic acid, alcohols and/or polyalcohols such as, for example, glycerol, methanol and/or ethanol, and/or organic acids such as, for example, acetic acid and/or lactic acid.

Nitrogen sources are usually organic or inorganic nitrogen compounds or materials comprising these compounds. Examples of nitrogen sources comprise ammonia in liquid or gaseous form or ammonium salts such as ammonium sulfate, ammonium chloride, ammonium phosphate, ammonium carbonate or ammonium nitrate, nitrates, urea, amino acids or complex nitrogen sources such as cornsteep liquor, soya meal, soya protein, yeast extract, meat extract and others. The nitrogen sources can be used individually or as a mixture.

Inorganic salt compounds which may be present in the media comprise the chloride, phosphorus and sulfate salts of calcium, magnesium, sodium, cobalt, molybdenum, potassium, manganese, zinc, copper and iron.

Inorganic sulfur-containing compounds such as, for example, sulfates, sulfites, dithionites, tetrathionates, thiosulfates, sulfides, or else organic sulfur compounds such as mercaptans and thiols may be used as sources of sulfur for the production of sulfur-containing fine chemicals, in particular of methionine.

Phosphoric acid, potassium dihydrogenphosphate or dipotassium hydrogenphosphate or the corresponding sodium-containing salts may be used as sources of phosphorus.

Chelating agents may be added to the medium in order to keep the metal ions in solution. Particularly suitable chelating agents comprise dihydroxyphenols such as catechol or protocatechuate and organic acids such as citric acid.

The fermentation media used according to the invention for culturing microorganisms usually also comprise other growth factors such as vitamins or growth promoters, which include, for example, biotin, riboflavin, thiamine, folic acid, nicotinic acid, panthothenate and pyridoxine. Growth factors and salts are frequently derived from complex media components such as yeast extract, molasses, cornsteep liquor and the like. It is moreover possible to add suitable precursors to the culture medium. The exact composition of the media compounds heavily depends on the particular experiment and is decided upon individually for each specific case. Information on the optimization of media can be found in the textbook "Applied Microbiol. Physiology, A Practical Approach" (Editors P. M. Rhodes, P. F. Stanbury, IRL Press (1997) pp. 53-73, ISBN 0 19 963577 3). Growth media can also be obtained from commercial suppliers, for example Standard 1 (Merck) or BHI (brain heart infusion, DIFCO) and the like.

All media components are sterilized, either by heat (20 min at 1.5 bar and 121° C.) or by filter sterilization. The components may be sterilized either together or, if required, separately. All media components may be present at the start of the cultivation or added continuously or batchwise, as desired.

The culture temperature is normally between 15° C. and 45° C., preferably at from 25° C. to 40° C., and may be kept constant or may be altered during the experiment. The pH of the medium should be in the range from 5 to 8.5, preferably around 7.0. The pH for cultivation can be controlled during cultivation by adding basic compounds such as sodium hydroxide, potassium hydroxide, ammonia and aqueous ammonia or acidic compounds such as phosphoric acid or sulfuric acid. Foaming can be controlled by employing antifoams such as, for example, fatty acid polyglycol esters. To maintain the stability of plasmids it is possible to add to the medium suitable substances having a selective effect, for example antibiotics. Aerobic conditions are maintained by introducing oxygen or oxygen-containing gas mixtures such as, for example, ambient air into the culture. The temperature of the culture is normally 20° C. to 45° C. and preferably 25° C. to 40° C. The culture is continued until formation of the desired product is at a maximum. This aim is normally achieved within 10 to 160 hours.

The fermentation broths obtained in this way, in particular those comprising polyunsaturated fatty acids, usually contain a dry mass of from 7.5 to 25% by weight.

The fermentation broth can then be processed further. The biomass may, according to requirement, be removed completely or partially from the fermentation broth by separation methods such as, for example, centrifugation, filtration, decanting or a combination of these methods or be left completely in said broth. It is advantageous to process the biomass after its separation.

However, the fermentation broth can also be thickened or concentrated without separating the cells, using known methods such as, for example, with the aid of a rotary evaporator, thin-film evaporator, falling-film evaporator, by reverse osmosis or by nanofiltration. Finally, this concentrated fermentation broth can be processed to obtain the fatty acids present therein.

The fatty acids obtained in the process are also suitable as starting material for the chemical synthesis of further products of interest. For example, they can be used in combination with one another or alone for the preparation of pharmaceuticals, foodstuffs, animal feeds or cosmetics.

The invention furthermore relates to isolated nucleic acid sequences coding for polypeptides having lysophosphatidic acid acyltransferase activity, glycerol-3-phosphate acyltransferase activity, diacylglycerol acyltransferase activity or lecithin cholesterol acyltransferase activity, wherein the lysophosphatidic acid acyltransferases, glycerol-3-phosphate acyltransferases, diacylglycerol acyltransferases and/or lecithin cholesterol acyltransferases encoded by the nucleic acid sequences specifically convert $C_{18}$-, $C_{20}$-, $C_{22}$- or $C_{24}$-fatty acids with at least one double bonds in the fatty acid molecule and advantageously ultimately incorporate these into diacylglycerides and/or triacylglycerides.

Advantageous isolated nucleic acid sequences are sequences selected from the group consisting of:
a) a nucleic acid sequence with the sequence shown in SEQ ID NO: 1, SEQ ID NO: 3, SEQ ID NO: 4, SEQ ID NO: 6, SEQ ID NO: 7, SEQ ID NO: 9, SEQ ID NO: 11, SEQ ID NO: 13, SEQ ID NO: 14, SEQ ID NO: 16, SEQ ID NO: 18 or SEQ ID NO: 20,
b) nucleic acid sequences which, as the result of the degeneracy of the genetic code, can be derived from the coding sequence in SEQ ID NO: 1, SEQ ID NO: 3, SEQ ID NO: 4, SEQ ID NO: 6, SEQ ID NO: 7, SEQ ID NO: 9, SEQ ID NO: 11, SEQ ID NO: 13, SEQ ID NO: 14, SEQ ID NO: 16, SEQ ID NO: 18 or SEQ ID NO: 20,
c) derivatives of the nucleic acid sequence shown in SEQ ID NO: 1, SEQ ID NO: 3, SEQ ID NO: 4, SEQ ID NO: 6, SEQ ID NO: 7, SEQ ID NO: 9, SEQ ID NO: 11, SEQ ID NO: 13, SEQ ID NO: 14, SEQ ID NO: 16, SEQ ID NO: 18 or SEQ ID NO: 20 which code for polypeptides with the amino acid sequence shown in SEQ ID NO: 2, SEQ ID NO: 5, SEQ ID NO: 8, SEQ ID NO: 10, SEQ ID NO: 12, SEQ ID NO: 15, SEQ ID NO: 17, SEQ ID NO: 19 or SEQ ID NO: 21 and which have at least 40% homology at the amino acid level with SEQ ID NO: 2, SEQ ID NO: 5, SEQ ID NO: 8, SEQ ID NO: 10, SEQ ID NO: 12, SEQ ID NO: 15, SEQ ID NO: 17, SEQ ID NO: 19 or SEQ ID NO: 21 and have lysophosphatidic acid acyltransferase activity.

Further advantageous isolated nucleic acid sequences according to the invention are sequences selected from the group consisting of:
a) a nucleic acid sequence with the sequence shown in SEQ ID NO: 22, SEQ ID NO: 24 or SEQ ID NO: 26,
b) nucleic acid sequences which, as the result of the degeneracy of the genetic code, can be derived from the coding sequence in SEQ ID NO: 22, SEQ ID NO: 24 or SEQ ID NO: 26,
c) derivatives of the nucleic acid sequence shown in SEQ ID NO: 22, SEQ ID NO: 24 or SEQ ID NO: 26, which code for polypeptides with the amino acid sequence shown in SEQ ID NO: 23, SEQ ID NO: 25 or SEQ ID NO: 27 and have at least 40% homology at the amino acid level with SEQ ID NO: 23, SEQ ID NO: 25 or SEQ ID NO: 27 and have glycerol-3-phosphate acyltransferase activity.

Additional advantageous isolated nucleic acid sequences according to the invention are sequences selected from the group consisting of:
a) a nucleic acid sequence with the sequence shown in SEQ ID NO: 28, SEQ ID NO: 30 or SEQ ID NO: 32,
b) nucleic acid sequences which, as the result of the degeneracy of the genetic code, can be derived from the coding sequence in SEQ ID NO: 28, SEQ ID NO: 30 or SEQ ID NO: 32,
c) derivatives of the nucleic acid sequence shown in SEQ ID NO: 28, SEQ ID NO: 30 or SEQ ID NO: 32, which code for polypeptides with the amino acid sequence shown in SEQ ID NO: 29, SEQ ID NO: 31 or SEQ ID NO: 33 and have at least 40% homology at the amino acid level with SEQ ID NO: 29, SEQ ID NO: 31 or SEQ ID NO: 33 and which have diacylglycerol acyltransferase activity.

A further group of advantageous isolated nucleic acid sequences according to the invention are sequences selected from the group consisting of:
a) a nucleic acid sequence with the sequence shown in SEQ ID NO: 34 or SEQ ID NO: 36,
b) nucleic acid sequences which, as the result of the degeneracy of the genetic code, can be derived from the coding sequence in SEQ ID NO: 34 or SEQ ID NO: 36,
c) derivatives of the nucleic acid sequence shown in SEQ ID NO: 34 or SEQ ID NO: 36, which code for polypeptides with the amino acid sequence shown in SEQ ID NO: 35 or SEQ ID NO: 37 and which have at least 40% homology at the amino acid level with SEQ ID NO: 35 or SEQ ID NO: 37 and have lecithin cholesterol acyltransferase activity.

With the aid of these isolated nucleic acids according to the invention, LCPUFAs can be incorporated, in LCPUFA-producing organisms, at all positions of, for example, a triacylglycerol, as indicated by the position analyses of the lipids from LCPUFA-producing organisms.

The abovementioned isolated nucleic acid sequences according to the invention can advantageously be combined with the following nucleic acid sequences, which code for polypeptides with acyl-CoA:lysophospholipid acyltransferase activity, selected from the group consisting of:
a) a nucleic acid sequence with the sequence shown in SEQ ID NO: 39, SEQ ID NO: 41, SEQ ID NO: 43 or SEQ ID NO: 45, b) nucleic acid sequences which can be derived from the coding sequence present in SEQ ID NO: 39, SEQ ID NO: 41, SEQ ID NO: 43 or SEQ ID NO: 45 as the result of the degeneracy of the genetic code, c) derivatives of the nucleic acid sequence shown in SEQ ID NO: 39, SEQ ID NO: 41, SEQ ID NO: 43 or SEQ ID NO: 45, which code for polypeptides with the amino acid sequence shown in SEQ ID NO: 40, SEQ ID NO: 42, SEQ ID NO: 44 or SEQ ID NO: 46 and which have at least 40% homology at the amino acid level with SEQ ID NO: 40, SEQ ID NO: 42, SEQ ID NO: 44 or SEQ ID NO: 46 and which have an acyl-CoA:lysophospholipid acyltransferase activity.

All of the nucleic acid sequences used in the process according to the invention are advantageously derived from a eukaryotic organism.

The nucleic acid sequences used in the process which code for proteins with lysophosphatidic acid acyltransferase activity, glycerol-3-phosphate acyltransferase activity, diacylglycerol acyltransferase activity or lecithin cholesterol acyltransferase activity or for proteins of the fatty acid or lipid metabolism, advantageously for proteins with acyl-CoA: lysophospholipid acyltransferase, Δ-4-desaturase, Δ-5-desaturase, Δ-6-desaturase, Δ-8-desaturase, Δ-9-desaturase, Δ-12-desaturase, Δ-5-elongase, Δ-6-elongase or Δ-9-elongase activity are, advantageously alone or preferably in combination, introduced in an expression cassette (=nucleic acid construct) which makes possible the expression of the nucleic acids in an organism, advantageously a plant or a microorganism.

To introduce the nucleic acids used in the process, the latter are advantageously amplified and ligated in the known manner. Preferably, a procedure following the protocol for Pfu DNA polymerase or a Pfu/Taq DNA polymerase mixture is followed. The primers are selected taking into consideration the sequence to be amplified. The primers should expediently be chosen in such a way that the amplificate comprises the entire codogenic sequence from the start codon to the stop codon. After the amplification, the amplificate is expediently analyzed. For example, a gel-electrophoretic separation can be carried out with regards to quality and quantity. Thereafter, the amplificate can be purified following a standard protocol (for example Qiagen). An aliquot of the purified amplificate is then available for the subsequent cloning step. Suitable cloning vectors are generally known to the skilled worker. These include, in particular, vectors which are capable of replication in microbial systems, that is to say mainly vectors which ensure efficient cloning in yeasts or fungi and which make possible the stable transformation of plants. Those which must be mentioned in particular are various binary and cointegrated vector systems which are suitable for the T-DNA-mediated transformation. Such vector systems are, as a rule, characterized in that they comprise at least the vir genes required for the *Agrobacterium*-mediated transformation and the T-DNA-delimiting sequences (T-DNA border). These vector systems preferably also comprise further cis-regulatory regions such as promoters and terminators and/or selection markers, by means of which suitably transformed organisms can be identified. While in the case of cointegrated vector systems vir genes and T-DNA sequences are arranged on the same vector, binary systems are based on at least two vectors, one of which bears vir genes, but no T-DNA, while a second one bears T-DNA, but no vir gene. Owing to this fact, the last-mentioned vectors are relatively small, easy to manipulate and to replicate both in *E. coli* and in *Agrobacterium*. These binary vectors include vectors from the series pBIB-HYG, pPZP, pBecks, pGreenU. In accordance with the invention, Bin19, pBI101, pBinAR, pGPTV and pCAMBIA are used by preference. An overview of binary vectors and their use is found in Hellens et al., Trends in Plant Science (2000) 5, 446-451. In order to prepare the vectors, the vectors can first be linearized with restriction endonuclease(s) and then modified enzymatically in a suitable manner. Thereafter, the vector is purified, and an aliquot is employed for the cloning step. In the cloning step, the enzymatically cleaved and, if appropriate, purified amplificate is cloned using vector fragments which have been prepared in a similar manner, using ligase. In this context, a particular nucleic acid construct, or vector or plasmid construct, can have one or else more than one codogenic gene segment. The codogenic gene segments in these constructs are preferably linked functionally with regulatory sequences. The regulatory sequences include, in particular, plant sequences such as the above-described promoters and terminators. The constructs can advantageously be stably propagated in microorganisms, in particular in *Escherichia coli* and *Agrobacterium tumefaciens*, under selective conditions and make possible the transfer of heterologous DNA into plants or microorganisms.

The nucleic acids used in the process, the inventive nucleic acids and nucleic acid constructs, can be introduced into organisms such as microorganisms or advantageously plants, advantageously using cloning vectors, and thus be used in the transformation of plants such as those which are published and cited in: Plant Molecular Biology and Biotechnology (CRC Press, Boca Raton, Fla.), Chapter 6/7, pp. 71-119 (1993); F. F. White, Vectors for Gene Transfer in Higher Plants; in: Transgenic Plants, Vol. 1, Engineering and Utilization, Ed.: Kung and R. Wu, Academic Press, 1993, 15-38; B. Jenes et al., Techniques for Gene Transfer, in: Transgenic Plants, Vol. 1, Engineering and Utilization, Ed.: Kung and R. Wu, Academic Press (1993), 128-143; Potrykus, Annu. Rev. Plant Physiol. Plant Molec. Biol. 42 (1991), 205-225. Thus, the nucleic acids, the inventive nucleic acids and nucleic acid constructs, and/or vectors used in the process can be used for the recombinant modification of a broad spectrum of organisms, advantageously plants, so that the latter become better and/or more efficient PUFA producers.

A series of mechanisms exists by which the modification of a lysophosphatidic acid acyltransferase, glycerol-3-phosphate acyltransferase, diacylglycerol acyltransferase, or lecithin cholesterol acyltransferase protein according to the invention can influence directly the yield, production and/or production efficiency of a fine chemical from an oil crop plant or a microorganism, owing to a modified protein. The number or activity of the lysophosphatidic acid acyltransferase, glycerol-3-phosphate acyltransferase, diacylglycerol acyltransferase, or lecithin cholesterol acyltransferase protein or gene and also of gene combinations of acyl-CoA:lysophospholipid acyltransferases, desaturases and/or elongases for example may have increased, so that greater amounts of the compounds produced are produced de novo, since the organisms lacked this activity and ability to biosynthesize prior to introduction of the corresponding gene(s). This applies analogously to the combination with further desaturases or elongases or further enzymes of the fatty acid and lipid metabolism. The use of various divergent sequences, i.e. sequences which differ at the DNA sequence level, may also be advantageous in this context, or else the use of promoters for gene expression which makes possible a different gene expression in the course of time, for example as a function of the degree of maturity of a seed or an oil-storing tissue.

Owing to the introduction of a lysophosphatidic acid acyltransferase, glycerol-3-phosphate acyltransferase, diacylglycerol acyltransferase, lecithin cholesterol acyltransferase, acyl-CoA:lysophospholipid acyltransferase, desaturase and/ or elongase gene or more lysophosphatidic acid acyltransferase, glycerol-3-phosphate acyltransferase, diacylglycerol acyltransferase, lecithin cholesterol acyltransferase, acyl-CoA:lysophospholipid acyltransferase, desaturase and/or elongase genes into an organism, alone or in combination with other genes in a cell, it is not only possible to increase biosynthesis flux towards the end product, but also to increase, or to create de novo, the corresponding triacylglycerol composition. Likewise, the number or activity of other genes which are involved in the import of nutrients which are required for the biosynthesis of one or more fine chemicals (e.g. fatty acids, polar and neutral lipids), can be increased, so that the concentration of these precursors, cofactors or intermediates within the cells or within the storage compartment is increased, whereby the ability of the cells to produce PUFAs as described below is enhanced further. Fatty acids and lipids are themselves desirable as fine chemicals; by optimizing the activity or increasing the number of one or more lysophosphatidic acid acyltransferase, glycerol-3-phosphate acyltransferase, diacylglycerol acyltransferase, lecithin cholesterol acyltransferase, acyl-CoA:lysophospholipid acyltransferase, desaturase and/or elongase genes which are involved in the biosynthesis of these compounds, or by destroying the activity of one or more genes which are involved in the degradation of these compounds, an enhanced yield, production and/or efficiency of production of fatty acid and lipid molecules from organisms, advantageously from plants, is made possible.

The isolated nucleic acid molecules used in the process according to the invention code for proteins or parts of these, where the proteins or the individual protein or parts thereof comprise(s) an amino acid sequence with sufficient homology to an amino acid sequence of the sequence SEQ ID NO: 2, SEQ ID NO: 5, SEQ ID NO: 8, SEQ ID NO: 10, SEQ ID NO: 12, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35 or SEQ ID NO: 37, so that the protein or part thereof have a and retains an equivalent lysophosphatidic acid acyltransferase, glycerol-3-phosphate acyltransferase, diacylglycerol acyltransferase or lecithin cholesterol acyltransferase activity. The protein or part thereof which is encoded by the nucleic acid molecule preferably retains its essential enzymatic activity and the ability to participate in the metabolism of compounds required for the synthesis of cell membranes or lipid bodies in organisms, advantageously in plants, or in the transport of molecules across these membranes. Advantageously, the protein encoded by the nucleic acid molecules is at least approximately 40%, preferably at least approximately 60% and more preferably at least approximately 70%, 80% or 90% and most preferably at least approximately 95%, 96%, 97%, 98%, 99% or more homologous to an amino acid sequence of the sequence SEQ ID NO: 2, SEQ ID NO: 5, SEQ ID NO: 8, SEQ ID NO: 10, SEQ ID NO: 12, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35 or SEQ ID NO: 37. For the purposes of the invention homology or homologous are to be understood as meaning identity or identical.

Essential enzymatic activity of the inventive lysophosphatidic acid acyltransferases, glycerol-3-phosphate acyltransferases, diacylglycerol acyltransferases or lecithin cholesterol acyltransferases used is understood as meaning that they retain at least an enzymatic activity of at least 10%, preferably 20%, especially preferably 30% and very especially 40% in comparison with the proteins/enzymes encoded by the sequence with SEQ ID NO: 1, SEQ ID NO: 3, SEQ ID NO: 4, SEQ ID NO: 6, SEQ ID NO: 7, SEQ ID NO: 9, SEQ ID NO: 11, SEQ ID NO: 13, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34 or SEQ ID NO: 36 and their derivatives and can thus participate in the metabolism of compounds required for the synthesis of fatty acids, fatty acid esters such as diacylglycerides and/or triacylglycerides in an organism, advantageously a plant cell, or in the transport of molecules across membranes, meaning desaturated $C_{18}$-, $C_{20}$-, $C_{22}$- or $C_{24}$-carbon chains in the fatty acid molecule with double bonds at least two, advantageously three, four or five positions.

Nucleic acids which can advantageously be used in the process are derived from bacteria, fungi or plants such as algae or mosses, such as the genera *Shewanella, Physcomitrella, Thraustochytrium, Fusarium, Phytophtora, Ceratodon, Isochrysis, Aleurita, Muscarioides, Mortierella, Borago, Phaeodactylum, Crypthecodinium* or from nematodes such as *Caenorhabditis*, specifically from the genera and species *Shewanella hanedai, Physcomitrella patens, Phytophtora infestans, Fusarium graminaeum, Cryptocodinium cohnii, Ceratodon purpureus, Isochrysis galbana, Aleurita farinosa, Muscarioides viallii, Mortierella alpina, Borago officinalis, Phaeodactylum tricornutum*, or especially advantageously from *Caenorhabditis elegans*.

Alternatively, the isolated nucleotide sequences used may code for lysophosphatidic acid acyltransferases, glycerol-3-phosphate acyltransferases, diacylglycerol acyltransferases or lecithin cholesterol acyltransferases which hybridize with a nucleotide sequence of SEQ ID NO: 1, SEQ ID NO: 3, SEQ ID NO: 4, SEQ ID NO: 6, SEQ ID NO: 7, SEQ ID NO: 9, SEQ ID NO: 11, SEQ ID NO: 13, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34 or SEQ ID NO: 36, for example under stringent conditions.

The nucleic acid sequences used in the process are advantageously introduced into an expression cassette which makes possible the expression of the nucleic acids in organisms such as microorganisms or plants.

In doing so, the nucleic acid sequences which code for the lysophosphatidic acid acyltransferases, glycerol-3-phosphate acyltransferases, diacylglycerol acyltransferases or lecithin cholesterol acyltransferases of the invention, and the nucleic acid sequences which code for the acyl-CoA:lysophospholipid acyltransferases used in combination, the desaturases and/or the elongases are linked functionally with one or more regulatory signals, advantageously for enhancing gene expression. These regulatory sequences are intended to make possible the specific expression of the genes and proteins. Depending on the host organism, this may mean, for example, that the gene is expressed and/or overexpressed only after induction has taken place, or else that it expresses and/or overexpresses immediately. For example, these regulatory sequences take the form of sequences to which inductors or repressors bind, thus controlling the expression of the nucleic acid. In addition to these novel regulatory sequences, or instead of these sequences, the natural regulation of these sequences may still be present before the actual structural genes and, if appropriate, may have been genetically modified in such a way that natural regulation has been eliminated and expression of the genes has been enhanced. However, the expression cassette (=expression construct=gene construct) can also be simpler in construction, that is to say no additional regulatory signals have been inserted before the nucleic acid sequence or its derivatives, and the natural promoter together with its regulation has not been removed. Instead, the natural regulatory sequence has been mutated in such a way that regulation no longer takes place and/or gene expression is enhanced. These modified promoters can also be positioned on their own before the natural gene in the form of part-sequences (=promoter with parts of the nucleic acid sequences of the invention) in order to enhance the activity. Moreover, the gene construct may advantageously also comprise one or more of what are known as enhancer sequences in functional linkage with the promoter, which make possible an enhanced expression of the nucleic acid sequence. Additional advantageous sequences, such as further regulatory elements or terminators, may also be inserted at the 3' end of the DNA sequences. The lysophosphatidic acid acyltransferase, glycerol-3-phosphate acyltransferase, diacylglycerol acyltransferase or lecithin cholesterol acyltransferase genes and the advantageously used acyl-CoA:lysophospholipid acyltransferase, Δ-4-desaturase, Δ5-desaturase, Δ-6-desaturase and/or Δ-8-desaturase genes and/or Δ-5-elongase, Δ-6-elongase and/or Δ-9-elongase genes may be present in one or more copies in the expression cassette (=gene construct). Preferably, only one copy of the genes is present in each expression cassette. This gene construct or the gene constructs can be expressed together in the host organism. In this context, the gene construct(s) can be inserted in one or more vectors and be present in the cell in free form, or else be inserted in the genome. It is advantageous for the insertion of further genes in the host genome when the genes to be expressed are present together in one gene construct.

In this context, the regulatory sequences or factors can, as described above, preferably have a positive effect on the gene expression of the genes introduced, thus enhancing it. Thus, an enhancement of the regulatory elements, advantageously at the transcriptional level, may take place by using strong transcription signals such as promoters and/or enhancers. In addition, however, enhanced translation is also possible, for example by improving the stability of the mRNA.

A further embodiment of the invention is one or more gene constructs which comprise one or more sequences which are defined by SEQ ID NO: 1, SEQ ID NO: 3, SEQ ID NO: 4, SEQ ID NO: 6, SEQ ID NO: 7, SEQ ID NO: 9, SEQ ID NO: 11, SEQ ID NO: 13, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34 or SEQ ID NO: 36 or its derivatives and which code for polypeptides as shown in SEQ ID NO: 2, SEQ ID NO: 5, SEQ ID NO: 8, SEQ ID NO: 10, SEQ ID NO: 12, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35 or SEQ ID NO: 37. The abovementioned lysophosphatidic acid acyltransferases, glycerol-3-phosphate acyltransferases, diacylglycerol acyltransferases or lecithin cholesterol acyltransferases lead advantageously to an exchange or incorporation of fatty acids between the mono-, di- and/or triglyceride pool of the cell and the CoA-fatty acid ester pool, the substrate advantageously having one, two, three, four or five double bonds and advantageously 18, 20, 22 or 24 carbon atoms in the fatty acid molecule. The same applies to their homologs, derivatives or analogs, which are linked functionally with one or more regulatory signals, advantageously for enhancing gene expression.

Advantageous regulatory sequences for the novel process are present for example in promoters such as the cos, tac, trp, tet, trp-tet, lpp, lac, lpp-lac, laclq, T7, T5, T3, gal, trc, ara, SP6, λ-PR or λ-PL promoter and are advantageously employed in Gram-negative bacteria. Further advantageous regulatory sequences are, for example, present in the Gram-positive promoters amy and SPO2, in the yeast or fungal promoters ADC1, MFα, AC, P-60, CYC1, GAPDH, TEF; rp28, ADH or in the plant promoters CaMV/35S [Franck et al., Cell 21 (1980) 285-294], PRP1 [Ward et al., Plant. Mol. Biol. 22 (1993)], SSU, OCS, lib4, usp, STLS1, B33, nos or in the ubiquitin or phaseolin promoter. Advantageous in this context are also inducible promoters, such as the promoters described in EP-A-0 388 186 (benzylsulfonamide-inducible), Plant J. 2, 1992:397-404 (Gatz et al., tetracycline-inducible), EP-A-0 335 528 (abscisic acid-inducible) or WO 93/21334 (ethanol- or cyclohexenol-inducible). Further suitable plant promoters are the cytosolic FBPase promoter or the ST-LSI promoter of potato (Stockhaus et al., EMBO J. 8, 1989, 2445), the *glycine max* phosphoribosyl-pyrophosphate amidotransferase promoter (Genbank Accession No. U87999) or the node-specific promoter described in EP-A-0 249 676. Especially advantageous promoters are promoters which make possible the expression in tissues which are involved in the biosynthesis of fatty acids. Very especially advantageous are seed-specific promoters, such as the USP promoter as described, but also other promoters such as the LeB4, DC3, phaseolin or napin promoter. Further especially advantageous promoters are seed-specific promoters which can be used for monocotyledonous or dicotyledonous plants and which are described in U.S. Pat. No. 5,608,152 (oilseed rape napin promoter), WO 98/45461 (*Arabidopsis* oleosin promoter), U.S. Pat. No. 5,504,200 (*Phaseolus vulgaris* phaseolin promoter), WO 91/13980 (*Brassica* Bce4 promoter), by Baeumlein et al., Plant J., 2, 2, 1992:233-239 (LeB4 promoter from a legume), these promoters being suitable for dicots. Examples of promoters which are suitable for monocots are the barley Ipt-2 or Ipt-1 promoter (WO 95/15389 and WO 95/23230), the barley hordein promoter and other suitable promoters described in WO 99/16890.

In principle, it is possible to use all natural promoters together with their regulatory sequences, such as those mentioned above, for the novel process. It is also possible and advantageous to use synthetic promoters, either in addition or alone, in particular when they mediate seed-specific expression, such as those described in WO 99/16890.

In order to achieve a particularly high PUFA content, especially in transgenic plants, the PUFA biosynthesis genes should advantageously be expressed in oil crops in a seed-specific manner. To this end, seed-specific promoters can be used, or those promoters which are active in the embryo and/or in the endosperm. In principle, seed-specific promoters can be isolated both from dicotyledonous and from monocotyledonous plants. Advantageous preferred promoters are listed hereinbelow: USP (=unknown seed protein) and vicilin (*Vicia faba*) [Bäumlein et al., Mol. Gen Genet., 1991, 225(3)], napin (oilseed rape) [U.S. Pat. No. 5,608,152], acyl carrier protein (oilseed rape) [U.S. Pat. No. 5,315,001 and WO 92/18634], oleosin (*Arabidopsis thaliana*) [WO 98/45461 and WO 93/20216], phaseolin (*Phaseolus vulgaris*) [U.S. Pat. No. 5,504,200], Bce4 [WO 91/13980], legumes B4 (LegB4 promoter) [Bäumlein et al., Plant J., 2,2, 1992], Lpt2 and Ipt1 (barley) [WO 95/15389 and WO 95/23230], seed-specific promoters from rice, maize and wheat [WO 99/16890], Amy32b, Amy 6-6 and aleurain [U.S. Pat. No. 5,677,474], Bce4 (oilseed rape) [U.S. Pat. No. 5,530,149], glycinin (soybean) [EP 571 741], phosphoenol pyruvate carboxylase (soybean) [JP 06/62870], ADR12-2 (soybean) [WO 98/08962], isocitrate lyase (oilseed rape) [U.S. Pat. No. 5,689,040] or α-amylase (barley) [EP 781 849].

Plant gene expression can also be facilitated via a chemically inducible promoter (see review in Gatz 1997, Annu. Rev. Plant Physiol. Plant Mol. Biol., 48:89-108). Chemically inducible promoters are particularly suitable when it is desired that gene expression should take place in a time-specific manner. Examples of such promoters are a salicylic-acid-inducible promoter (WO 95/19443), a tetracycline-inducible promoter (Gatz et al. (1992) Plant J. 2, 397-404) and an ethanol-inducible promoter.

To ensure the stable integration of the biosynthesis genes into the transgenic plant over a plurality of generations, each of the nucleic acids which code for lysophosphatidic acid acyltransferase, glycerol-3-phosphate acyltransferase, diacylglycerol acyltransferase and/or lecithin cholesterol acyltransferase, the advantageous acyl-CoA:lysophospholipid acyltransferase, $\Delta$-4-desaturase, $\Delta$-5-desaturase, $\Delta$-6-desaturase, $\Delta$-8-desaturase and/or $\Delta$-5-elongase, $\Delta$-6-elongase and/or $\Delta$-9-elongase and which are used in the process should be expressed under the control of a separate promoter, preferably a promoter which differs from the other promoters, since repeating sequence motifs can lead to instability of the T-DNA, or to recombination events. In this context, the expression cassette is advantageously constructed in such a way that a promoter is followed by a suitable cleavage site, advantageously in a polylinker, for insertion of the nucleic acid to be expressed and, if appropriate, a terminator is positioned behind the polylinker. This sequence is repeated several times, preferably three, four or five times, so that up to five genes can be combined in one construct and introduced into the transgenic plant in order to be expressed. Advantageously, the sequence is repeated up to three times. To express the nucleic acid sequences, the latter are inserted behind the promoter via the suitable cleavage site, for example in the polylinker. Advantageously, each nucleic acid sequence has its own promoter and, if appropriate, its own terminator. However, it is also possible to insert a plurality of nucleic acid sequences behind a promoter and, if appropriate, before a terminator. Here, the insertion site, or the sequence, of the inserted nucleic acids in the expression cassette is not of critical importance, that is to say a nucleic acid sequence can be inserted at the first or last position in the cassette without its expression being substantially influenced thereby. Advantageously, different promoters such as, for example, the USP, LegB4 or DC3 promoter, and different terminators can be used in the expression cassette. However, it is also possible to use only one type of promoter in the cassette. This, however, may lead to undesired recombination events.

As described above, the transcription of the genes which have been introduced should advantageously be terminated by suitable terminators at the 3' end of the biosynthesis genes which have been introduced (behind the stop codon). An example of a sequence which can be used in this context is the OCS1 terminator. As is the case with the promoters, different terminator sequences should be used for each gene.

As described above, the gene construct can also comprise further genes to be introduced into the organisms. It is possible and advantageous to introduce into the host organisms, and to express therein, regulatory genes such as genes for inductors, repressors or enzymes which, owing to their enzyme activity, engage in the regulation of one or more genes of a biosynthetic pathway. These genes can be of heterologous or of homologous origin. Moreover, further biosynthesis genes of the fatty acid or lipid metabolism can advantageously be present in the nucleic acid construct, or gene construct; however, these genes can also be positioned on one or more further nucleic acid constructs. Biosynthesis genes of the fatty acid or lipid metabolism which are advantageously used are a gene selected from the group consisting of acyl-CoA dehydrogenase(s), acyl-ACP [=acyl carrier protein] desaturase(s), acyl-ACP thioesterase(s), fatty acid acyltransferase(s), acyl-CoA:lysophospholipid acyltransferase(s), fatty acid synthase(s), fatty acid hydroxylase(s), acetyl-coenzyme A carboxylase(s), acyl-coenzyme A oxidase(s), fatty acid desaturase(s), fatty acid acetylenases, lipoxygenase(s), triacylglycerol lipase(s), allenoxide synthase(s), hydroperoxide lyase(s) or fatty acid elongase(s) or combinations thereof. Especially advantageous nucleic acid sequences are biosynthesis genes of the fatty acid or lipid metabolism selected from the group consisting of acyl-CoA: lysophospholipid acyltransferase, $\Delta$-4-desaturase, $\Delta$-5-desaturase, $\Delta$-6-desaturase, $\Delta$-8-desaturase, $\Delta$-9-desaturase, $\Delta$-12-desaturase, $\Delta$-5-elongase, $\Delta$-6-elongase or $\Delta$-9-elongase.

In this context, the abovementioned nucleic acids and genes can be cloned into expression cassettes of the invention in combination with other elongases and desaturases and used for transforming plants with the aid of *Agrobacterium*.

Here, the regulatory sequences or factors can, as described above, preferably have a positive effect on, and thus enhance, the expression of the genes which have been introduced. Thus, enhancement of the regulatory elements can advantageously take place at the transcriptional level by using strong transcription signals such as promoters and/or enhancers. However, an enhanced translation is also possible, for example by improving the stability of the mRNA. In principle, the expression cassettes can be used directly for introduction into the plant or else be introduced into a vector.

These advantageous vectors, preferably expression vectors, comprise the nucleic acids which code for lysophosphatidic acid acyltransferases, glycerol-3-phosphate acyltransferases, diacylglycerol acyltransferases or lecithin cholesterol acyltransferases and which are used in the process, or else a nucleic acid construct which comprises the nucleic acid used either alone or in combination with further biosynthesis genes of the fatty acid or lipid metabolism such as the acyl-CoA:lysophospholipid acyltransferases, $\Delta$-4-desaturase, $\Delta$-5-desaturase, $\Delta$-6-desaturase, $\Delta$-8-desaturase, $\Delta$-9-desaturase, $\Delta$-12-desaturase, $\Delta$-5-elongase, $\Delta$-6-elongase and/or $\Delta$-9-elongase. As used in the present context, the term "vector" refers to a nucleic acid molecule which is capable of transporting another nucleic acid to which it is bound. One type of vector is a "plasmid", a circular double-stranded DNA loop into which additional DNA segments can be ligated. A further type of vector is a viral vector, it being possible for additional DNA segments to be ligated into the viral genome. Certain vectors are capable of autonomous replication in a host cell into which they have been introduced (for example bacterial vectors with bacterial replication origin). Other vectors are advantageously integrated into the genome of a host cell when they are introduced into the host cell, and thus replicate together with the host genome. Moreover, certain vectors can govern the expression of genes with which they are in functional linkage. These vectors are referred to in the present context as "expression vectors". Usually, expression vectors which are suitable for DNA recombination techniques take the form of plasmids. In the present description, "plasmid" and "vector" can be used exchangeably since the plasmid is the form of vector which is most frequently used. However, the invention is intended to comprise these other forms of expression vectors, such as viral vectors, which exert similar functions. Furthermore, the term "vector" is also intended to comprise other vectors with which the skilled worker is familiar, such as phages, viruses such as SV40, CMV, TMV, transposons, IS elements, phasmids, phagemids, cosmids, linear or circular DNA.

The recombinant expression vectors advantageously used in the process comprise the nucleic acids described below or the above-described gene construct in a form which is suitable for expressing the nucleic acids used in a host cell, which means that the recombinant expression vectors comprise one or more regulatory sequences, selected on the basis of the host cells to be used for the expression, which regulatory sequence(s) is/are linked functionally with the nucleic acid sequence to be expressed. In a recombinant expression vector, "linked functionally" means that the nucleotide sequence of interest is bound to the regulatory sequence(s) in such a way that the expression of the nucleotide sequence is possible and they are bound to each other in such a way that both sequences carry out the predicted function which is ascribed to the sequence (for example in an in-vitro transcription/translation system, or in a host cell if the vector is introduced into the host cell). The term "regulatory sequence" is intended to comprise promoters, enhancers and other expression control elements (for example polyadenylation signals). These regulatory sequences are described, for example, in Goeddel: Gene Expression Technology: Methods in Enzymology 185, Academic Press, San Diego, Calif. (1990), or see: Gruber and Crosby, in: Methods in Plant Molecular Biology and Biotechnology, CRC Press, Boca Raton, Fla., Ed.: Glick and Thompson, Chapter 7, 89-108, including the references cited therein. Regulatory sequences comprise those which govern the constitutive expression of a nucleotide sequence in many types of host cell and those which govern the direct expression of the nucleotide sequence only in specific host cells under specific conditions. The skilled worker knows that the design of the expression vector can depend on factors such as the choice of host cell to be transformed, the expression level of the desired protein and the like.

The recombinant expression vectors used can be designed for the expression of lysophosphatidic acid acyltransferases, glycerol-3-phosphate acyltransferases, diacylglycerol acyltransferases or lecithin cholesterol acyltransferases, acyl-CoA:lysophospholipid acyltransferases, desaturases and elongases in prokaryotic or eukaryotic cells. This is advantageous since intermediate steps of the vector construction are frequently carried out in microorganisms for the sake of simplicity. For example, lysophosphatidic acid acyltransferase, glycerol-3-phosphate acyltransferase, diacylglycerol acyltransferase, lecithin cholesterol acyltransferase, acyl-CoA: lysophospholipid acyltransferases, desaturase and/or elongase genes can be expressed in bacterial cells, insect cells (using Baculovirus expression vectors), yeast and other fungal cells (see Romanos, M. A., et al. (1992)"Foreign gene expression in yeast: a review", Yeast 8:423-488; van den Hondel, C. A. M. J. J., et al. (1991) "Heterologous gene expression in filamentous fungi", in: More Gene Manipulations in Fungi, J. W. Bennet & L. L. Lasure, Ed., pp. 396-428: Academic Press: San Diego; and van den Hondel, C. A. M. J. J., & Punt, P. J. (1991) "Gene transfer systems and vector development for filamentous fungi, in: Applied Molecular Genetics of Fungi, Peberdy, J. F., et al., Ed., pp. 1-28, Cambridge University Press: Cambridge), algae (Falciatore et al., 1999, Marine Biotechnology. 1, 3:239-251), ciliates of the types: *Holotrichia, Peritrichia, Spirotrichia, Suctoria, Tetrahymena, Paramecium, Colpidium, Glaucoma, Platyophrya, Potomacus, Desaturaseudocohnilembus, Euplotes, Engelmaniella* and *Stylonychia*, in particular of the genus *Stylonychia lemnae*, using vectors in a transformation method as described in WO 98/01572 and, preferably, in cells of multi-celled plants (see Schmidt, R. and Willmitzer, L. (1988) "High efficiency *Agrobacterium tumefaciens*-mediated transformation of *Arabidopsis thaliana* leaf and cotyledon explants" Plant Cell Rep.: 583-586; Plant Molecular Biology and Biotechnology, C Press, Boca Raton, Fla., Chapter 617, pp. 71-119 (1993); F. F. White, B. Jenes et al., Techniques for Gene Transfer, in: Transgenic Plants, Vol. 1, Engineering and Utilization, Ed.: Kung and R. Wu, Academic Press (1993), 128-43; Potrykus, Annu. Rev. Plant Physiol. Plant Molec. Biol. 42 (1991), 205-225 (and references cited therein)). Suitable host cells are furthermore discussed in Goeddel, Gene Expression Technology: Methods in Enzymology 185, Academic Press, San Diego, Calif. (1990). As an alternative, the recombinant expression vector can be transcribed and translated in vitro, for example using T7-promoter regulatory sequences and T7-polymerase.

In most cases, the expression of proteins in prokaryotes involves the use of vectors comprising constitutive or inducible promoters which govern the expression of fusion or nonfusion proteins. Typical fusion expression vectors are, inter alia, pGEX (Pharmacia Biotech Inc; Smith, D. B., and Johnson, K. S. (1988) Gene 67:31-40), pMAL (New England Biolabs, Beverly, Mass.) and pRIT5 (Pharmacia, Piscataway, N.J.), where glutathione S-transferase (GST), maltose-E binding protein and protein A, respectively, is fused with the recombinant target protein.

Examples of suitable inducible nonfusion *E. coli* expression vectors are, inter alia, pTrc (Amann et al. (1988) Gene 69:301-315) and pET 11d (Studier et al., Gene Expression Technology: Methods in Enzymology 185, Academic Press, San Diego, Calif. (1990) 60-89). The target gene expression from the pTrc vector is based on the transcription from a hybrid trp-lac fusion promoter by the host RNA polymerase. The target gene expression from the vector pET 11d is based on the transcription of a T7-gn10-lac fusion promoter, which is mediated by a viral RNA polymerase (T7 gn1), which is coexpressed. This viral polymerase is provided by the host strains BL21 (DE3) or HMS174 (bE3) from a resident λ-prophage which harbors a T7 gn1 gene under the transcriptional control of the lacUV 5 promoter.

Other vectors which are suitable for prokaryotic organisms are known to the skilled worker, these vectors are, for example in *E. coli* pLG338, pACYC184, the pBR series such as pBR322, the pUC series such as pUC18 or pUC19, the M113 mp series, pKC30, pRep4, pHS1, pHS2, pPLc236, pMBL24, pLG200, pUR290, pIN-III113-B1, λgt11 or pBdCl, in *Streptomyces* pIJ101, pIJ364, pIJ702 or pIJ361, in *Bacillus* pUB110, pC194 or pBD214, in *Corynebacterium* pSA77 or pAJ667.

In a further embodiment, the expression vector is a yeast expression vector. Examples for vectors for expression in the yeast *S. cerevisiae* comprise pYeDesaturasec1 (Baldari et al. (1987) Embo J. 6:229-234), pMFa (Kurjan and Herskowitz (1982) Cell 30:933-943), pJRY88 (Schultz et al. (1987) Gene 54:113-123) and pYES2 (Invitrogen Corporation, San Diego, Calif.). Vectors and processes for the construction of vectors which are suitable for use in other fungi, such as the filamentous fungi, comprise those which are described in detail in: van den Hondel, C. A. M. J. J., & Punt, P. J. (1991) "Gene transfer systems and vector development for filamentous fungi, in: Applied Molecular Genetics of fungi, J. F. Peberdy et al., Ed., pp. 1-28, Cambridge University Press: Cambridge, or in: More Gene Manipulations in Fungi [J. W. Bennet & L. L. Lasure, Ed., pp. 396-428: Academic Press: San Diego]. Further suitable yeast vectors are, for example, pAG-1, YEp6, YEp13 or pEMBLYe23.

As an alternative, the lysophosphatidic acid acyltransferases, glycerol-3-phosphate acyltransferases, diacylglycerol acyltransferases, lecithin cholesterol acyltransferases, acyl-CoA:lysophospholipid acyltransferases, desaturases and/or elongases can be expressed in insect cells using Baculovirus expression vectors. Baculovirus vectors which are available for the expression of proteins in cultured insect cells (for example Sf9 cells) comprise the pAc series (Smith et al. (1983) Mol. Cell Biol. 3:2156-2165) and the pVL series (Lucklow and Summers (1989) Virology 170:31-39).

The abovementioned vectors offer only a small overview of suitable vectors which are possible. Further plasmids are known to the skilled worker and are described, for example, in: Cloning Vectors (Ed. Pouwels, P. H., et al., Elsevier, Amsterdam-New York-Oxford, 1985, ISBN 0 444 904018). For further suitable expression systems for prokaryotic and eukaryotic cells, see the Chapters 16 and 17 in Sambrook, J., Fritsch, E. F., and Maniatis, T., Molecular Cloning: A Laboratory Manual, 2nd edition, Cold Spring Harbor Laboratory, Cold Spring Harbor Laboratory Press, Cold Spring Harbor, N.Y., 1989.

In a further embodiment of the process, the lysophosphatidic acid acyltransferases, glycerol-3-phosphate acyltransferases, diacylglycerol acyltransferases, lecithin cholesterol acyltransferases, acyl-CoA:lysophospholipid acyltransferases, desaturases and/or elongases can be expressed in single-celled plant cells (such as algae), see Falciatore et al., 1999, Marine Biotechnology 1 (3):239-251 and references cited therein, and in plant cells from higher plants (for example spermatophytes such as arable crops). Examples of plant expression vectors comprise those which are described in detail in: Becker, D., Kemper, E., Schell, J., and Masterson, R. (1992) "New plant binary vectors with selectable markers located proximal to the left border", Plant Mol. Biol. 20:1195-1197; and Bevan, M. W. (1984) "Binary *Agrobacterium* vectors for plant transformation", Nucl. Acids Res. 12:8711-8721; Vectors for Gene Transfer in Higher Plants; in: Transgenic Plants, Vol. 1, Engineering and Utilization, Ed.: Kung and R. Wu, Academic Press, 1993, pp. 15-38.

A plant expression cassette preferably comprises regulatory sequences which are capable of governing the expression of genes in plant cells and which are linked functionally so that each sequence can fulfill its function, such as transcriptional termination, for example polyadenylation signals. Preferred polyadenylation signals are those which are derived from *Agrobacterium tumefaciens* T-DNA, such as gene 3 of the Ti plasmid pTiACH5 (Gielen et al., EMBO J. 3 (1984) 835 et seq.), which is known as octopine synthase, or functional equivalents thereof, but all other terminators which are functionally active in plants are also suitable.

Since plant gene expression is very often not limited to transcriptional levels, a plant expression cassette preferably comprises other sequences which are linked functionally, such as translation enhancers, for example the overdrive sequence, which comprises the tobacco mosaic virus 5'-untranslated leader sequence, which increases the protein/RNA ratio (Gallie et al., 1987, Nucl. Acids Research 15:8693-8711).

As described above, plant gene expression must be linked functionally with a suitable promoter which triggers gene expression with the correct timing or in a cell- or tissue-specific manner. Utilizable promoters are constitutive promoters (Benfey et al., EMBO J. 8 (1989) 2195-2202), such as those which are derived from plant viruses, such as 35S CAMV (Franck et al., Cell 21 (1980) 285-294), 19S CaMV (see also U.S. Pat. No. 5,352,605 and WO 84/02913), or plant promoters, such as the promoter of the small rubisco subunit, which is described iii U.S. Pat. No. 4,962,028.

Other preferred sequences for use in functional linkage in plant gene expression cassettes are targeting sequences, which are required for steering the gene product into its corresponding cell compartment (see a review in Kermode, Crit. Rev. Plant Sci. 15, 4 (1996) 285-423 and references cited therein), for example into the vacuole, into the nucleus, all types of plastids, such as amyloplasts, chloroplasts, chromoplasts, the extracellular space, the mitochondria, the endoplasmic reticulum, elaioplasts, peroxisomes and other compartments of plant cells.

As described above, plant gene expression can also be facilitated via a chemically inducible promoter (see review in Gatz 1997, Annu. Rev. Plant Physiol. Plant Mol. Biol., 48:89-108). Chemically inducible promoters are particularly suitable when it is desired that the gene expression takes place in a time-specific manner. Examples of such promoters are a salicylic-acid-inducible promoter (WO 95/19443), a tetracyclin-inducible promoter (Gatz et al. (1992) Plant J. 2, 397404) and an ethanol-inducible promoter.

Promoters which respond to biotic or abiotic stress conditions are also suitable, for example the pathogen-induced PRP1 gene promoter (Ward et al., Plant. Mol. Biol. 22 (1993) 361-366), the heat-inducible tomato hsp80 promoter (U.S. Pat. No. 5,187,267), the chill-inducible potato alpha-amylase promoter (WO 96/12814) or the wound-inducible pinII promoter (EP-A-0 375 091).

Especially preferred are those promoters which bring about the gene expression in tissues and organs in which the biosynthesis of fatty acids, lipids and oils takes place, in seed cells, such as cells of the endosperm and of the developing embryo. Suitable promoters are the oilseed rape napin gene promoter (U.S. Pat. No. 5,608,152), the *Vicia faba* USP promoter (Baeumlein et al., Mol Gen Genet, 1991, 225 (3):459-67), the *Arabidopsis* oleosin promoter (WO 98/45461), the *Phaseolus vulgaris* phaseolin promoter (U.S. Pat. No. 5,504,200), the *Brassica* Bce4 promoter (WO 91/13980) or the legumine B4 promoter (LeB4; Baeumlein et al., 1992, Plant Journal, 2 (2):233-9), and promoters which bring about the seed-specific expression in monocotyledonous plants such as maize, barley, wheat, rye, rice and the like. Suitable noteworthy promoters are the barley Ipt2 or Ipt1 gene promoter (WO 95/15389 and WO 95/23230) or the promoters from the barley hordein gene, the rice glutelin gene, the rice oryzin gene, the rice prolamine gene, the wheat gliadine gene, the wheat glutelin gene, the maize zeine gene, the oat glutelin gene, the sorghum kasirin gene or the rye secalin gene, which are described in WO 99/16890.

In particular, it may be desired to bring about the multiparallel expression of the lysophosphatidic acid acyltransferases, glycerol-3-phosphate acyltransferases, diacylglycerol acyltransferases or lecithin cholesterol acyltransferases used in the process alone or in combination with acyl-CoA:lysophospholipid acyltransferases, desaturases and/or elongases. Such expression cassettes can be introduced via the simultaneous transformation of a plurality of individual expression constructs or, preferably, by combining a plurality of expression cassettes on one construct. Also, a plurality of vectors can be transformed with in each case a plurality of expression cassettes and then transferred onto the host cell.

Promoters which are likewise especially suitable are those which bring about plastid-specific expression, since plastids constitute the compartment in which the precursors and some end products of lipid biosynthesis are synthesized. Suitable promoters, such as the viral RNA polymerase promoter, are described in WO 95/16783 and WO 97/06250, and the clpP promoter from *Arabidopsis*, described in WO 99/46394.

Vector DNA can be introduced into prokaryotic or eukaryotic cells via conventional transformation or transfection techniques. The terms "transformation" and "transfection", conjugation and transduction, as used in the present context, are intended to comprise a multiplicity of methods known in the prior art for the introduction of foreign nucleic acid (for example DNA) into a host cell, including calcium phosphate or calcium chloride coprecipitation, DEAE-dextran-mediated transfection, lipofection, natural competence, chemically mediated transfer, electroporation or particle bombardment. Suitable methods for the transformation or transfection of host cells, including plant cells, can be found in Sambrook et al. (Molecular Cloning: A Laboratory Manual., 2nd ed., Cold Spring Harbor Laboratory, Cold Spring Harbor Laboratory Press, Cold Spring Harbor, N.Y., 1989) and other laboratory textbooks such as Methods in Molecular Biology, 1995, Vol. 44, *Agrobacterium* protocols, Ed.: Gartland and Davey, Humana Press, Totowa, N.J.

Host cells which are suitable in principle for taking up the nucleic acid according to the invention, the gene product according to the invention or the vector according to the invention are all prokaryotic or eukaryotic organisms. The host organisms which are advantageously used are microorganisms such as fungi or yeasts, or plant cells, preferably plants or parts thereof. Fungi, yeasts or plants are preferably used, especially preferably plants, very especially preferably plants such as oil crop plants, which are high in lipid compounds, such as oilseed rape, evening primrose, hemp, thistle, peanut, canola, linseed, soybean, safflower, sunflower, borage, or plants such as maize, wheat, rye, oats, triticale, rice, barley, cotton, cassava, pepper, Tagetes, Solanaceae plants such as potato, tobacco, eggplant and tomato, *Vicia* species, pea, alfalfa, bushy plants (coffee, cacao, tea), *Salix* species, trees (oil palm, coconut), and perennial grasses and fodder crops. Especially preferred plants according to the invention are oil crop plants such as soybean, peanut, oilseed rape, canola, linseed, hemp, evening primrose, sunflower, safflower, trees (oil palm, coconut).

The invention furthermore relates to isolated nucleic acid sequences as described above coding for polypeptides having lysophosphatidic acid acyltransferase activity, glycerol-3-phosphate acyltransferase activity, diacylglycerol acyltransferase activity or lecithin cholesterol acyltransferase activity, where the lysophosphatidic acid acyltransferases, glycerol-3-phosphate acyltransferases, diacylglycerol acyltransferases or lecithin cholesterol acyltransferases encoded by the nucleic acid sequences specifically convert $C_{18}$-, $C_{20}$-, $C_{22}$- or $C_{24}$-fatty acids with at least one double bonds in the fatty acid molecule.

Advantageous isolated nucleic acid sequences are sequences selected from the group consisting of:
a) a nucleic acid sequence with the sequence shown in SEQ ID NO: 1, SEQ ID NO: 3, SEQ ID NO: 4, SEQ ID NO: 6, SEQ ID NO: 7, SEQ ID NO: 9, SEQ ID NO: 11, SEQ. ID NO: 13, SEQ ID NO: 14, SEQ ID NO: 16, SEQ ID NO: 18 or SEQ ID NO: 20,
b) nucleic acid sequences which, as the result of the degeneracy of the genetic code, can be derived from the coding sequence in SEQ ID NO: 1, SEQ ID NO: 3, SEQ ID NO: 4, SEQ ID NO: 6, SEQ ID NO: 7, SEQ ID NO: 9, SEQ ID NO: 11, SEQ ID NO: 13, SEQ ID NO: 14, SEQ ID NO: 16, SEQ ID NO: 18 or SEQ ID NO: 20,
c) derivatives of the nucleic acid sequence shown in SEQ ID NO: 1, SEQ ID NO: 3, SEQ ID NO: 4, SEQ ID NO: 6, SEQ ID NO: 7, SEQ ID NO: 9, SEQ ID NO: 11, SEQ ID NO: 13, SEQ ID NO: 14, SEQ ID NO: 16, SEQ ID NO: 18 or SEQ ID NO: 20, which code for polypeptides with the amino acid sequence shown in SEQ ID NO: 2, SEQ ID NO: 5, SEQ ID NO: 8, SEQ ID NO: 10, SEQ ID NO: 12, SEQ ID NO: 15, SEQ ID NO: 17, SEQ ID NO: 19 or SEQ ID NO: 21 and which have at least 40% homology at the amino acid level with SEQ ID NO: 2, SEQ ID NO: 5, SEQ ID NO: 8, SEQ ID NO: 10, SEQ ID NO: 12, SEQ ID NO: 15, SEQ ID NO: 17, SEQ ID NO: 19 or SEQ ID NO: 21 and have lysophosphatidic acid acyltransferase activity.

Further advantageous isolated nucleic acid sequences are sequences selected from the group consisting of:
a) a nucleic acid sequence with the sequence shown in SEQ ID NO: 22, SEQ ID NO: 24 or SEQ ID NO: 26,
b) nucleic acid sequences which, as the result of the degeneracy of the genetic code, can be derived from the coding sequence in SEQ ID NO: 22, SEQ ID NO: 24 or SEQ ID NO: 26,
c) derivatives of the nucleic acid sequence shown in SEQ ID NO: 22, SEQ ID NO: 24 or SEQ ID NO: 26, which code for polypeptides with the amino acid sequence shown in SEQ ID NO: 23, SEQ ID NO: 25 or SEQ ID NO: 27 and have at least 40% homology at the amino acid level with SEQ ID NO: 23, SEQ ID NO: 25 or SEQ ID NO: 27 and have glycerol-3-phosphate acyltransferase activity.

Further advantageous isolated nucleic acid sequences are sequences selected from the group consisting of:
a) a nucleic acid sequence with the sequence shown in SEQ ID NO: 28, SEQ ID NO: 30 or SEQ ID NO: 32,
b) nucleic acid sequences which, as the result of the degeneracy of the genetic code, can be derived from the coding sequence in SEQ ID NO: 28, SEQ ID NO: 30 or SEQ ID NO: 32,
c) derivatives of the nucleic acid sequence shown in SEQ ID NO: 28, SEQ ID NO: 30 or SEQ ID NO: 32, which code for polypeptides with the amino acid sequence shown in SEQ ID NO: 29, SEQ ID NO: 31 or SEQ ID NO: 33 and have at least 40% homology at the amino acid level with SEQ ID NO: 29, SEQ ID NO: 31 or SEQ ID NO: 33 and which have diacylglycerol acyltransferase activity.

Further advantageous isolated nucleic acid sequences are sequences selected from the group consisting of:
a) a nucleic acid sequence with the sequence shown in SEQ ID NO: 34 or SEQ ID NO: 36,
b) nucleic acid sequences which, as the result of the degeneracy of the genetic code, can be derived from the coding sequence in SEQ ID NO: 34 or SEQ ID NO: 36,
c) derivatives of the nucleic acid sequence shown in SEQ ID NO: 34 or SEQ ID NO: 36, which code for polypeptides with the amino acid sequence shown in SEQ ID NO: 35 or SEQ ID NO: 37 and which have at least 40% homology at the amino acid level with SEQ ID NO: 35 or SEQ ID NO: 37 and have lecithin cholesterol acyltransferase activity.

The abovementioned nucleic acids according to the invention are derived from organisms such as animals, ciliates, fungi, plants such as algae or dinoflagellates which are capable of synthesizing PUFAs.

In an advantageous embodiment, the term "nucleic acid (molecule)" as used in the present context additionally comprises the untranslated sequence at the 3' and at the 5' end of the coding gene region: at least 500, preferably 200, especially preferably 100 nucleotides of the sequence upstream of the 5' end of the coding region and at least 100, preferably 50, especially preferably 20 nucleotides of the sequence downstream of the 3' end of the coding gene region. An "isolated" nucleic acid molecule is separated from other nucleic acid molecules which are present in the natural source of the nucleic acid. An "isolated" nucleic acid preferably has no sequences which naturally flank the nucleic acid in the genomic DNA of the organism from which the nucleic acid is derived (for example sequences which are located at the 5' and 3' ends of the nucleic acid). In various embodiments, the isolated lysophosphatidic acid acyltransferase, glycerol-3- phosphate acyltransferase, diacylglycerol acyltransferase and/or lecithin cholesterol acyltransferase molecule can comprise for example fewer than approximately 5 kb, 4 kb, 3 kb, 2 kb, 1 kb, 0.5 kb or 0.1 kb of nucleotide sequences which naturally flank the nucleic acid molecule in the genomic DNA of the cell from which the nucleic acid is derived.

The nucleic acid molecules used in the process, for example a nucleic acid molecule with a nucleotide sequence of SEQ ID NO: 1, SEQ ID NO: 3, SEQ ID NO: 4, SEQ ID NO: 6, SEQ ID NO: 7, SEQ ID NO: 9, SEQ ID NO: 11, SEQ ID NO: 13, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34 or SEQ ID NO: 36 or of a part thereof can be isolated using molecular-biological standard techniques and the sequence information provided herein. Also, for example a homologous sequence or homologous, conserved sequence regions can be identified at the DNA or amino acid level with the aid of comparative algorithms. They can be used as hybridization probe together with standard hybridization techniques (such as, for example, those described in Sambrook et al., Molecular Cloning: A Laboratory Manual. 2nd ed., Cold Spring Harbor Laboratory, Cold Spring Harbor Laboratory Press, Cold Spring Harbor, N.Y., 1989) for isolating further nucleic acid sequences which can be used in the process. Moreover, a nucleic acid molecule comprising a complete sequence of SEQ ID NO: 1, SEQ ID NO: 3, SEQ ID NO: 4, SEQ ID NO: 6, SEQ ID NO: 7, SEQ ID NO: 9, SEQ ID NO: 11, SEQ ID NO: 13, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34 or SEQ ID NO: 36 or a part thereof can be isolated by polymerase chain reaction, where oligonucleotide primers which are based on this sequence or on parts thereof are used (for example a nucleic acid molecule comprising the complete sequence or a part thereof can be isolated by polymerase chain reaction using oligonucleotide primers which have been generated based on this same sequence). For example, mRNA can be isolated from cells (for example by means of the guanidinium thiocyanate extraction method of Chirgwin et al. (1979) Biochemistry 18:5294-5299) and cDNA by means of reverse transcriptase (for example Moloney MLV reverse transcriptase, available from Gibco/BRL, Bethesda, Md., or AMV reverse transcriptase, available from Seikagaku America, Inc., St. Petersburg, Fla.). Synthetic oligonucleotide primers for the amplification by means of polymerase chain reaction can be generated based on one of the sequences shown in SEQ ID NO: 1, SEQ ID NO: 3, SEQ ID NO: 4, SEQ ID NO: 6, SEQ ID NO: 7, SEQ ID NO: 9, SEQ ID NO: 11, SEQ ID NO: 13, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34 or SEQ ID NO: 36 or with the aid of the amino acid sequences detailed in SEQ ID NO: 2, SEQ ID NO: 5, SEQ ID NO: 8, SEQ ID NO: 10, SEQ ID NO: 12, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35 or SEQ ID NO: 37. A nucleic acid according to the invention can be amplified by standard PCR amplification techniques using cDNA or, alternatively, genomic DNA as template and suitable oligonucleotide primers. The nucleic acid amplified thus can be cloned into a suitable vector and characterized by means of DNA sequence analysis. Oligonucleotides which correspond to a desaturase nucleotide sequence can be generated by standard synthetic methods, for example Using an automatic DNA synthesizer.

Homologs of the lysophosphatidic acid acyltransferase, glycerol-3-phosphate acyltransferase, diacylglycerol acyltransferase or lecithin cholesterol acyltransferase nucleic acid sequences used with the sequence SEQ ID NO: 1, SEQ ID NO: 3, SEQ ID NO: 4, SEQ ID NO: 6, SEQ ID NO: 7, SEQ ID NO: 9, SEQ: ID NO: 11, SEQ ID NO: 13, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34 or SEQ ID NO: 36 means, for example, allelic variants with at least approximately 40 to 60%, preferably at least approximately from 60 to 70%, more preferably at least approximately from 70 to 80%, 80 to 90% or 90 to 95% and even more preferably at least approximately 95%, 96%, 97%; 98%, 99% or more homology with a nucleotide sequence shown in SEQ ID NO: 1, SEQ ID NO: 3, SEQ ID NO: 4, SEQ ID NO: 6, SEQ ID NO: 7, SEQ ID NO: 9, SEQ ID NO: 11, SEQ ID NO: 13, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34 or SEQ ID NO: 36 or its homologs, derivatives or analogs or parts thereof. Furthermore, isolated nucleic acid molecules of a nucleotide sequence which hybridize with one of the nucleotide sequences shown in SEQ ID NO: 1, SEQ ID NO: 3, SEQ ID NO: 4, SEQ ID NO: 6, SEQ ID NO: 7, SEQ ID NO: 9, SEQ ID NO: 11, SEQ ID NO: 13, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34 or SEQ ID NO: 36 or with a part thereof, for example hybridized under stringent conditions. Allelic variants comprise in particular functional variants which can be obtained by deletion, insertion or substitution of nucleotides from/into the sequence detailed in SEQ ID NO: 1, SEQ ID NO: 3, SEQ ID NO: 4, SEQ ID NO: 6, SEQ ID NO: 7, SEQ ID NO: 9, SEQ ID NO: 11, SEQ ID NO: 13, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34 or SEQ ID NO: 36 it being intended, however, that the enzyme activity of the resulting proteins which are synthesized is advantageously retained for the insertion of one or more genes. Proteins which retain the enzymatic activity of lysophosphatidic acid acyltransferase, glycerol-3-phosphate acyltransferase, diacylglycerol acyltransferase or lecithin cholesterol acyltransferase, i.e. whose activity is essentially not reduced, means proteins with at least 10%, preferably 20%, especially preferably 30%, very especially preferably 40% of the original enzyme activity in comparison with the protein encoded by SEQ ID NO: 1, SEQ ID NO: 3, SEQ ID NO: 4, SEQ ID NO: 6, SEQ ID NO: 7, SEQ ID NO: 9, SEQ ID NO: 11, SEQ ID NO: 13, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34 or SEQ ID NO: 36.

Homologs of SEQ ID NO: 1, SEQ ID NO: 3, SEQ ID NO: 4, SEQ ID NO: 6, SEQ ID NO: 7, SEQ ID NO: 9, SEQ ID NO: 11, SEQ ID NO: 13, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34 or SEQ ID NO: 36 mean for example also bacterial, fungal and plant homologs, truncated sequences, single-stranded DNA or RNA of the coding and noncoding DNA sequence.

Homologs of SEQ ID NO: 1, SEQ ID NO: 3, SEQ ID NO: 4, SEQ ID NO: 6, SEQ ID NO: 7, SEQ ID NO: 9, SEQ ID NO: 11, SEQ ID NO: 13, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34 or SEQ ID NO: 36 also mean derivatives such as, for example, promoter variants. The promoters upstream of the nucleotide sequences detailed can be modified by one or more nucleotide exchanges, by insertion(s) and/or deletion(s) without the functionality or activity of the promoters being adversely affected, however. It is furthermore possible that the modification of the promoter sequence enhances their activity or that they are replaced entirely by more active promoters, including those from heterologous organisms.

The abovementioned nucleic acids and protein molecules with lysophosphatidic acid acyltransferase, glycerol-3-phosphate acyltransferase, diacylglycerol acyltransferase or lecithin cholesterol acyltransferase activity which are involved in the metabolism of lipids and fatty acids, PUFA cofactors and enzymes or in the transport of lipophilic compounds across membranes are used in the process according to the invention for the modulation of the production of PUFAs in transgenic organisms, advantageously in plants, such as maize, wheat, rye, oats, triticale, rice, barley, soybean, peanut, cotton, *Linum* species such as linseed or flax, *Brassica* species such as oilseed rape, canola and turnip rape, pepper, sunflower, borage, evening primrose and Tagetes, Solanaceae plants such as potato, tobacco, eggplant and tomato, *Vicia* species, pea, cassava, alfalfa, bushy plants (coffee, cacao, tea), *Salix* species, trees (oil palm, coconut) and perennial grasses and fodder crops, either directly (for example when the overexpression or optimization of a fatty acid biosynthesis protein has a direct effect on the yield, production and/or production efficiency of the fatty acid from modified organisms) and/or can have an indirect effect which nevertheless leads to an enhanced yield, production and/or production efficiency of the PUFAs or a reduction of undesired compounds (for example when the modulation of the metabolism of lipids and fatty acids, cofactors and enzymes leads to modifications of the yield, production and/or production efficiency or the composition of the desired compounds within the cells, which, in turn, can affect the production of one or more fatty acids).

The combination of various precursor molecules and biosynthesis enzymes leads to the production of various fatty acid molecules, which has a decisive effect on lipid composition, since polyunsaturated fatty acids (=PUFAs) are not only incorporated into triacylglycerol but also into membrane lipids.

Lipid synthesis can be divided into two sections: the synthesis of fatty acids and their binding to sn-glycerol-3-phosphate, and the addition or modification of a polar head group. Usual lipids which are used in membranes comprise phospholipids, glycolipids, sphingolipids and phosphoglycerides. Fatty acid synthesis starts with the conversion of acetyl-CoA into malonyl-CoA by acetyl-CoA carboxylase or into acetyl-ACP by acetyl transacylase. After a condensation reaction, these two product molecules together form acetoacetyl-ACP, which is converted via a series of condensation, reduction and dehydratization reactions so that a saturated fatty acid molecule with the desired chain length is obtained. The production of the unsaturated fatty acids from these molecules is catalyzed by specific desaturases, either aerobically by means of molecular oxygen or anaerobically (regarding the fatty acid synthesis in microorganisms, see F. C. Neidhardt et al. (1996) *E. coli* and *Salmonella*. ASM Press: Washington, D.C., pp. 612-636 and references cited therein; Lengeler et al. (Ed.) (1999) Biology of Procaryotes. Thieme: Stuttgart, New York, and the references therein, and Magnuson, K., et al. (1993) Microbiological Reviews 57:522-542 and the references therein). To undergo the further elongation steps, the resulting phospholipid-bound fatty acids must then be returned from the phospholipids to the fatty acid CoA ester pool. This is made possible by acyl-CoA:lysophospholipid acyltransferases. Moreover, these enzymes are capable of transferring the elongated fatty acids from the CoA esters back to the phospholipids. If appropriate, this reaction sequence can be followed repeatedly.

Examples of precursors for the biosynthesis of PUFAs are oleic acid, linoleic acid and linolenic acid. These $C_{18}$-carbon fatty acids must be elongated to $C_{20}$ and $C_{22}$ in order to obtain fatty acids of the eicosa and docosa chain type. With the aid of the lysophosphatidic acid acyltransferases, glycerol-3-phosphate acyltransferases, diacylglycerol acyltransferases, lecithin cholesterol acyltransferases used in the process, advantageously in combination with acyl-CoA:lysophospholipid acyltransferases, desaturases such as Δ-4-, Δ-5-, Δ-6- and Δ-8-desaturases and/or Δ-5-, Δ-6-, Δ-9-elongases, arachidonic acid, eicosapentaenoic acid, docosapentaenoic acid or docosahexaenoic acid and various other long-chain PUFAs can be obtained, extracted and employed in various applications regarding foodstuffs, feedstuffs, cosmetics or pharmaceuticals. Preferably, C18-, $C_{20}$-, $C_{22}$- and/or $C_{24}$-fatty acids with at least two, advantageously at least three, four, five or six, double bonds in the fatty acid molecule can be prepared using the abovementioned enzymes, to give preferably $C_{20}$-, $C_{22}$- and/or $C_{24}$-fatty acids with advantageously three, four or five double bonds in the fatty acid molecule. Desaturation may take place before or after elongation of the fatty acid in question. This is why the products of the desaturase activities and the further desaturation and elongation steps which are possible result in preferred PUFAs with a higher degree of desaturation, including a further elongation from $C_{20}$- to $C_{22}$-fatty acids, to fatty acids such as γ-linolenic acid, dihomo-γ-linolenic acid, arachidonic acid, stearidonic acid, eicosatetraenoic acid or eicosapentaenoic acid. Substrates of the lysophosphatidic acyltransferases, glycerol-3-phosphate acyltransferases, diacylglycerol acyltransferases or lecithin cholesterol acyltransferases in the process according to the invention are $C_{18}$-, $C_{20}$- or $C_{22}$-fatty acids such as, for example, linoleic acid, γ-linolenic acid, α-linolenic acid, dihomo-γ-linolenic acid, eicosatetraenoic acid or stearidonic acid. Preferred substrates are linoleic acid, γ-linolenic acid and/or α-linolenic acid, dihomo-γ-linolenic acid, arachidonic acid, eicosatetraenoic acid or eicosapentaenoic acid. The $C_{18}$-, $C_{20}$- or $C_{22}$-fatty acids with at least two double bonds in the fatty acid are obtained in the process according to the invention in the form of the free fatty acid or in the form of their esters, for example in the form of their glycerides.

The term "glyceride" is understood as meaning a glycerol esterified with one, two or three carboxyl radicals (mono-, di- or triglyceride). "Glyceride" is also understood as meaning a mixture of various glycerides. The glyceride or glyceride mixture may comprise further additions, for example free fatty acids, antioxidants, proteins, carbohydrates, vitamins and/or other substances.

For the purposes of the process of the invention, a "glyceride" is furthermore understood as meaning glycerol derivatives. In addition to the above-described fatty acid glycerides, these also include glycerophospholipids and glyceroglycolipids. Preferred examples which may be mentioned in this context are the glycerophospholipids such as lecithin (phosphatidylcholine), cardiolipin, phosphatidylglycerol, phosphatidylserine and alkylacylglycerophospholipids.

Furthermore, fatty acids must subsequently be translocated to various modification sites and incorporated into the triacylglycerol storage lipid. A further important step in lipid synthesis is the transfer of fatty acids to the polar head groups, for example by glycerol fatty acid acyltransferase (see Frentzen, 1998, Lipid, 100(4-5):161-166).

For publications on plant fatty acid biosynthesis and on the desaturation, the lipid metabolism and the membrane transport of lipidic compounds, on beta-oxidation, fatty acid modification and cofactors, triacylglycerol storage and triacylglycerol assembly, including the references therein, see the following papers: Kinney, 1997, Genetic Engineering, Ed.: J K Setlow, 19:149-166; Ohlrogge and Browse, 1995, Plant Cell 7:957-970; Shanklin and Cahoon, 1998, Annu. Rev. Plant Physiol. Plant Mol. Biol. 49:611-641; Voelker, 1996, Genetic Engineering, Ed.: J K Setlow, 18:111-13; Gerhardt, 1992, Prog. Lipid R. 31:397-417; Gühnemann-Schäfer& Kindl, 1995, Biochim. Biophys Acta 1256:181-186; Kunau et al., 1995, Prog. Lipid Res. 34:267-342; Stymne et al., 1993, in: Biochemistry and Molecular Biology of Membrane and Storage Lipids of Plants, Ed.: Murata and Somerville, Rockville, American Society of Plant Physiologists, 150-158, Murphy & Ross 1998, Plant Journal. 13(1):1-16.

The PUFAs produced in the process comprise a group of molecules which higher animals are no longer capable of synthesizing and must therefore take up, or which higher animals are no longer capable of synthesizing themselves in sufficient quantity and must therefore take up additional quantities, although they are synthesized readily by other organisms such as bacteria; for example, cats are no longer capable of synthesizing arachidonic acid.

The term "lysophosphatidic acid acyltransferase, glycerol-3-phosphate acyltransferase, diacylglycerol acyltransferase or lecithin cholesterol acyltransferase" comprises for the purposes of the invention proteins which participate in the biosynthesis of fatty acids and their homologs, derivatives and analogs. Phospholipids for the purposes of the invention are understood as meaning phosphatidylcholine, phosphatidylethanolamine, phosphatidylserine, phosphatidylglycerol and/or phosphatidylinositol, advantageously phosphatidylcholine. The terms lysophosphatidic acid acyltransferase, glycerol-3-phosphate acyltransferase, diacylglycerol acyltransferase or lecithin cholesterol acyltransferase nucleic acid sequence(s) comprise nucleic acid sequences which code for a lysophosphatidic acid acyltransferase, glycerol-3-phosphate acyltransferase, diacylglycerol acyltransferase or lecithin cholesterol acyltransferase and part of which may be a coding region and likewise corresponding 5' and 3' untranslated sequence regions. The terms production or productivity are known in the art and encompass the concentration of the fermentation product (compounds of the formula I) which is formed within a specific period of time and in a specific fermentation volume (for example kg of product per hour per liter). The term production efficiency comprises the time required for obtaining a specific production quantity (for example the time required by the cell to establish a certain throughput rate of a fine chemical). The term yield or product/carbon yield is known in the art and comprises the efficiency of the conversion of the carbon source into the product (i.e. the fine chemical). This is usually expressed for example as kg of product per kg of carbon source. By increasing the yield or production of the compound, the amount of the molecules obtained of this compound, or of the suitable molecules of this compound obtained in a specific culture quantity over a specified period of time is increased. The terms biosynthesis or biosynthetic pathway are known in the art and comprise the synthesis of a compound, preferably of an organic compound, by a cell from intermediates, for example in a multi-step and strongly regulated process. The terms catabolism or catabolic pathway are known in the art and comprise the cleavage of a compound, preferably of an organic compound, by a cell to give catabolites (in more general terms, smaller or less complex molecules), for example in a multi-step and strongly regulated process. The term metabolism is known in the art and comprises the totality of the biochemical reactions which take place in an organism. The metabolism of a certain compound (for example the metabolism of a fatty acid) thus comprises the totality of the biosynthetic pathways, modification pathways and catabolic pathways of this compound in the cell which relate to this compound.

In a further embodiment, derivatives of the nucleic acid molecule according to the invention represented in SEQ ID NO: 1, SEQ ID NO: 3, SEQ ID NO: 4, SEQ ID NO: 6, SEQ ID NO: 7, SEQ ID NO: 9, SEQ ID NO: 11, SEQ ID NO: 13, SEQ ID NO: 14, SEQ ID NO; 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34 or SEQ ID NO: 36 code for proteins with at least 40%, advantageously from approximately 50 to 60%, preferably at least from approximately 60 to 70% and more preferably at least from approximately 70 to 80%, 80 to 90%, 90 to 95% and most preferably at least approximately 96%, 97%, 98%, 99% or more homology (=identity) with a complete amino acid sequence of SEQ ID NO: 2, SEQ ID NO: 5, SEQ ID NO: 8, SEQ ID NO: 10, SEQ ID NO: 12, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35 or SEQ ID NO: 37. The homology was calculated over the entire amino acid or nucleic acid sequence region. The program PileUp (J. Mol. Evolution., 25, 351-360, 1987, Higgins et al., CABIOS, 5 1989: 151-153) or the programs Gap and BestFit [Needleman and Wunsch (J. Mol. Biol. 48; 443-453 (1970) and Smith and Waterman (Adv. Appl. Math. 2; 482-489 (1981)], which are part of the GCG software packet [Genetics Computer Group, 575 Science Drive, Madison, Wis., USA 53711 (1991)], were used for the sequence alignment. The sequence homology values which are indicated above as percentages were determined over the entire sequence region using the program BestFit and the following settings: Gap Weight: 8, Length Weight: 2.

Moreover, the invention comprises nucleic acid molecules which differ from one of the nucleotide sequences shown in SEQ ID NO: 1, SEQ ID NO: 3, SEQ ID NO: 4, SEQ ID NO: 6, SEQ ID NO: 7, SEQ ID NO: 9, SEQ ID NO: 11, SEQ ID NO: 13, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34 or SEQ ID NO: 36 (and parts thereof) owing to the degeneracy of the genetic code and which thus code for the same lysophosphatidic acid acyltransferase, glycerol-3-phosphate acyltransferase, diacylglycerol acyltransferase or lecithin cholesterol acyltransferase as those encoded by the nucleotide sequences shown in SEQ ID NO: 1, SEQ ID NO: 3, SEQ ID NO: 4, SEQ ID NO: 6, SEQ ID NO: 7, SEQ ID NO: 9, SEQ ID NO: 11, SEQ ID NO: 13, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34 or SEQ ID NO: 36.

In addition to the lysophosphatidic acid acyltransferase, glycerol-3-phosphate acyltransferase, diacylglycerol acyltransferase or lecithin cholesterol acyltransferase nucleotide sequences shown in SEQ ID NO: 1, SEQ ID NO: 3, SEQ ID NO: 4, SEQ ID NO: 6, SEQ ID NO: 7, SEQ ID NO: 9, SEQ ID NO: 11, SEQ ID NO: 13, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34 or SEQ ID NO: 36, the skilled worker will recognize that DNA sequence polymorphisms which lead to changes in the amino acid sequences of the lysophosphatidic acid acyltransferase, glycerol-3-phosphate acyltransferase, diacylglycerol acyltransferase or lecithin cholesterol acyltransferase may exist within a population. These genetic polymorphisms in the lysophosphatidic acid acyltransferase, glycerol-3-phosphate acyltransferase, diacylglycerol acyltransferase or lecithin cholesterol acyltransferase gene may exist between individuals within a population owing to natural variation. These natural variants usually bring about a variance of 1 to 5% in the nucleotide sequence of the lysophosphatidic acid acyltransferase, glycerol-3-phosphate acyltransferase, diacylglycerol acyltransferase or lecithin cholesterol acyltransferase gene. Each and every one of these nucleotide variations and resulting amino acid polymorphisms in the lysophosphatidic acid acyltransferase, glycerol-3-phosphate acyltransferase, diacylglycerol acyltransferase or lecithin cholesterol acyltransferase which are the result of natural variation and do not modify the functional activity of are to be encompassed by the invention.

Owing to their homology to the lysophosphatidic acid acyltransferase, glycerol-3-phosphate acyltransferase, diacylglycerol acyltransferase or lecithin cholesterol acyltransferase nucleic acids disclosed here, nucleic acid molecules which are advantageous for the process according to the invention can be isolated following standard hybridization techniques under stringent hybridization conditions, using the sequences or part thereof as hybridization probe. In this context it is possible, for example, to use isolated nucleic acid molecules which are at least 15 nucleotides in length and which hybridize under stringent conditions with the nucleic acid molecules which comprise a nucleotide sequence of SEQ ID NO: 1, SEQ ID NO: 3, SEQ ID NO: 4, SEQ ID NO: 6, SEQ ID NO: 7, SEQ ID NO: 9, SEQ ID NO: 11, SEQ ID NO: 13, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34 or SEQ ID NO: 36. Nucleic acids with at least 25, 50, 100, 250 or more nucleotides can also be used. The term "hybridizes under stringent conditions" as used in the present context is intended to describe hybridization and washing conditions under which nucleotide sequences with at least 60% homology to one another usually remain hybridized with one another. Conditions are preferably such that sequences with at least approximately 65%, preferably at least approximately 70% and especially preferably at least approximately 75% or more homology to one another usually remain hybridized with one another. These stringent conditions are known to the skilled worker and can be found in Current Protocols in Molecular Biology, John Wiley & Sons, N.Y. (1989), 6.3.1-6.3.6. A preferred nonlimiting example of stringent hybridization conditions is hybridizations in 6× sodium chloride/sodium citrate (=SSC) at approximately 45° C., followed by one or more washing steps in 0.2×SSC, 0.1% SDS at 50 to 65° C. The skilled worker knows that these hybridization conditions differ depending on the type of nucleic acid and, for example when organic solvents are present, regarding temperature and buffer concentration. Under "standard hybridization conditions", for example, the temperature is, depending on the type of nucleic acid, between 42° C. and 58° C. in aqueous buffer with a concentration of 0.1 to 5×SSC (pH 7.2). If organic solvent, for example 50% formamide, is present in the abovementioned buffer, the temperature under standard conditions is approximately 42° C. The hybridization conditions for DNA:DNA hybrids, for example, are preferably 0.1×SSC and 20° C. to 45° C., preferably 30° C. to 45° C. The hybridization conditions for DNA:RNA hybrids are, for example, preferably 0.1×SSC and 30° C. to 55° C., preferably 45° C. to 55° C. The abovementioned hybridization temperatures are determined by way of example for a nucleic acid with approximately 100 bp (=base pairs) in length and with a G+C content of 50% in the absence of formamide. The skilled worker knows how to determine the required hybridization conditions on the basis of the abovementioned textbooks or textbooks such as Sambrook et al., "Molecular Cloning", Cold Spring Harbor Laboratory, 1989; Hames and Higgins (Ed.) 1985, "Nucleic Acids Hybridization: A Practical Approach", IRL Press at Oxford University Press, Oxford; Brown (Ed.) 1991, "Essential Molecular Biology: A Practical Approach", IRL Press at Oxford University Press, Oxford.

In order to determine the percentage of homology (=identity) of two amino acid sequences (for example one of the sequences of SEQ ID NO: 2, SEQ ID NO: 5, SEQ ID NO: 8, SEQ ID NO: 10, SEQ ID NO: 12, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35 or SEQ ID NO: 37) or of two nucleic acids (for example SEQ ID NO: 1, SEQ ID NO: 3, SEQ ID NO: 4, SEQ ID NO: 6, SEQ ID NO: 7, SEQ ID NO: 9, SEQ ID NO: 11, SEQ ID NO: 13, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34 or SEQ ID NO: 36), the sequences are written one under the other for an optimal comparison (for example, gaps may be introduced into the sequence of a protein or of a nucleic acid in order to generate an optimal alignment with the other protein or the other nucleic acid). Then, the amino acid residues or nucleotides at the corresponding amino acid positions or nucleotide positions are compared. If a position in a sequence is occupied by the same amino acid residue or the same nucleotide as the corresponding position in the other sequence, then the molecules are homologous at this position (i.e. amino acid or nucleic acid "homology" as used in the present context corresponds to amino acid or nucleic acid "identity"). The percentage of homology between the two sequences is a function of the number of identical positions which the sequences share (i.e. % homology=number of identical positions/total number of positions×100). The terms homology and identity are therefore to be considered as synonymous. The programs and algorithms used are described above.

An isolated nucleic acid molecule which codes for a lysophosphatidic acid acyltransferase, glycerol-3-phosphate acyltransferase, diacylglycerol acyltransferase or lecithin cholesterol acyltransferase which is homologous to a protein sequence of SEQ ID NO: 2, SEQ ID NO: 5, SEQ ID NO: 8, SEQ ID NO: 10, SEQ ID NO: 12, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35 or SEQ ID NO: 37 can be generated by introducing one or more nucleotide substitutions, additions or deletions into a nucleotide sequence of SEQ ID NO: 1, SEQ ID NO: 3, SEQ ID NO: 4, SEQ ID NO: 6, SEQ ID NO: 7, SEQ ID NO: 9, SEQ ID NO: 11, SEQ ID NO: 13, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34 or SEQ ID NO: 36 so that one or more amino acid substitutions, additions or deletions are introduced into the protein which is encoded. Mutations in one of the sequences of SEQ ID NO: 1, SEQ ID NO: 3, SEQ ID NO: 4, SEQ ID NO: 6, SEQ ID NO: 7, SEQ ID NO: 9, SEQ ID NO: 11, SEQ ID NO: 13, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34 or SEQ ID NO: 36 can be introduced by standard techniques such as site-specific mutagenesis and PCR-mediated mutagenesis: It is preferred to generate conservative amino acid substitutions in one or more of the predicted nonessential amino acid residues. In a "conservative amino acid substitution", the amino acid residue is replaced by an amino acid residue with a similar side chain. Families of amino acid residues with similar side chains have been defined in the art. These families comprise amino acids with basic-side chains (for example lysine, arginine, histidine), acidic side chains (for example aspartic acid, glutamic acid), uncharged polar side chains (for example glycine, asparagine, glutamine, serine, threonine, tyrosine, cysteine), unpolar side chains (for example alanine, valine, leucine, isoleucine, proline, phenylalanine, methionine, tryptophan), beta-branched side chains (for example threonine, valine, isoleucine) and aromatic side chains (for example tyrosine, phenylalanine, tryptophan, histidine). A predicted nonessential amino acid residue in a lysophosphatidic acid acyltransferase, glycerol-3-phosphate acyltransferase, diacylglycerol acyltransferase or lecithin cholesterol acyltransferase is thus preferably replaced by another amino acid residue from the same family of side chains. In another embodiment, the mutations can, alternatively, be introduced randomly over all or part of the sequence coding for lysophosphatidic acid acyltransferase, glycerol-3-phosphate acyltransferase, diacylglycerol acyltransferase or lecithin cholesterol acyltransferase, for example by saturation mutagenesis, and the resulting mutants can be screened by the herein-described lysophosphatidic acid acyltransferase, glycerol-3-phosphate acyltransferase, diacylglycerol acyltransferase or lecithin cholesterol acyltransferase activity in order to identify mutants which have retained the lysophosphatidic acid acyltransferase, glycerol-3-phosphate acyltransferase, diacylglycerol acyltransferase or lecithin cholesterol acyltransferase activity. Following the mutagenesis of one of the sequences of SEQ ID NO: 1, SEQ ID NO: 3, SEQ ID NO: 4, SEQ ID NO: 6, SEQ ID NO: 7, SEQ ID NO: 9, SEQ ID NO: 11, SEQ ID NO: 13, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34 or SEQ ID NO: 36, the protein which is encoded can be expressed recombinantly, and the activity of the protein can be determined, for example using the tests described in the present text.

The present invention is illustrated in greater detail by the examples which follow, which are not to be construed as limiting. The content of all of the references, patent applications, patents and published patent applications cited in the present patent application is herewith incorporated by reference.

EXAMPLES

Example 1

General Methods a) General Cloning Methods:

Cloning methods such as, for example, restriction cleavages, agarose gel electrophoresis, purification of DNA fragments, transfer of nucleic acids to nitrocellulose and nylon membranes, linking of DNA fragments, transformation of *Escherichia coli* and yeast cells, cultivation of bacteria and sequence analysis of recombinant DNA were carried out as described in Sambrook et al. (1989) (Cold Spring Harbor Laboratory Press: ISBN 0-87969-309-6) or Kaiser, Michaelis and Mitchell (1994) "Methods in Yeast Genetics" (Cold Spring Harbor Laboratory Press: ISBN 0-87969-451-3).

b) Chemicals

Unless stated otherwise in the text, the chemicals used were obtained in analytical-grade quality from Fluka (Neu-Ulm, Germany), Merck (Darmstadt, Germany), Roth (Karlsruhe, Germany), Serva (Heidelberg, Germany) and Sigma (Deisenhofen, Germany). Solutions were prepared using purified, pyrogen-free water, referred to as $H_2O$ hereinbelow, from a Milli-Q Water System water purification system (Millipore, Eschborn, Germany). Restriction endonucleases, DNA-modifying enzymes and molecular-biological kits were obtained from AGS (Heidelberg, Germany), Amersham (Brunswick, Germany), Biometra (Göttingen, Germany), Boehringer (Mannheim, Germany), Genomed (Bad Oeynhausen, Germany), New England Biolabs (Schwalbach/Taunus, Germany), Novagen (Madison, Wis., USA), Perkin-Elmer (Weiterstadt, Germany), Pharmacia (Freiburg, Germany), Qiagen (Hilden, Germany) and Stratagene (Amsterdam, the Netherlands). Unless stated otherwise, they were used according to the manufacturer's instructions.

c) Cloning and Expression of Desaturases and Elongases

The *Escherichia coli* strain XL1 Blue MRF' kan (Stratagene) was used for subcloning Δ-6-desaturase from *Physcomitrella patens*. This gene was functionally expressed using the *Saccharomyces cerevisiae* strain INVSc 1 (Invitrogen Co.). *E. coli* was cultured in Luria-Bertani broth (LB, Duchefa, Haarlem, the Netherlands) at 37° C. If necessary, ampicillin (100 mg/liter) was added and 1.5% (w/v) agar was added for solid LB media. *S. cerevisiae* was cultured at 30° C. either in YPG medium or in complete minimal medium without uracil (CMdum; see in: Ausubel, F. M., Brent, R., Kingston, R. E., Moore, D. D., Seidman, J. G., Smith, J. A., Struhl, K., Albright, L. B., Coen, D. M., and Varki, A. (1995) Current Protocols in Molecular Biology, John Wiley & Sons, New York) with either 2% (w/v) raffinose or glucose. For solid media, 2% (w/v) Bacto™-Agar (Difco) were added. The plasmids used for cloning and expression are pUC18 (Pharmacia) and pYES2 (Invitrogen Co.).

d) Cloning and Expression of PUFA-Specific Desaturases and Elongases

For expression in plants, cDNA clones of SEQ ID NO: 46 (*Physcomitrella patens* Δ-6-desaturase), 48 (*Physcomitrella patens* Δ-6-elongase) or 50 (*Phaeodactylum tricornutum* Δ-5-desaturase) were modified so as for only the coding region to be amplified by means of polymerase chain reaction with the aid of two oligonucleotides. Care was taken here to observe a consensus sequence upstream of the start codon, for efficient translation. To this end, either the ATA or the AAA base sequence was chosen and inserted into the sequence upstream of the ATG [Kozak, M. (1986) Point mutations define a sequence flanking the AUG initiator codon that modulates translation by eukaryotic ribosomes, Cell 44, 283-2929]. In addition, a restriction cleavage site was introduced upstream of this consensus triplet, which must be compatible with the cleavage site of the target vector into which the fragment is to be cloned and with the aid of which gene expression is to be carried out in micro-organisms or plants.

The PCR reaction was carried out in a thermocycler (Biometra), using plasmid DNA as template and Pfu DNA polymerase (Stratagene) and the following temperature program: 3 min at 96° C., followed by 30 cycles of 30 s at 96° C., 30 s at 55° C. and 2 min at 72° C., 1 cycle of 10 min at 72° C. and stop at 4° C. The annealing temperature was varied depending on the oligonucleotides chosen. A synthesis time of about one minute per kilobase pair of DNA has to be taken as starting point. Other parameters which influence the PCR, such as, for example, Mg ions, salt, DNA polymerase etc., are familiar to the skilled worker in the field and may be varied as required.

The correct size of the amplified DNA fragment was confirmed by means of agarose-TBE gel electrophoresis. The amplified DNA was extracted from the gel using the QIAquick gel extraction kit (QIAGEN) and ligated into the SmaI restriction site of the dephosphorylated pUC18 vector, using the Sure Clone Ligations Kit (Pharmacia), resulting in the pUC derivatives. After transformation of E. coli XL1 Blue MRF' kan a DNA minipreparation [Riggs, M. G., & McLachlan, A. (1986) A simplified screening procedure for large numbers of plasmid mini-preparation. BioTechniques 4, 310-313] of ampicillin-resistant transformants was carried out, and positive clones were identified by means of BamHI restriction analysis. The sequence of the cloned PCR product was confirmed by means of resequencing using the ABI PRISM Big Dye Terminator Cycle Sequencing Ready Reaction Kit (Perkin-Elmer, Weiterstadt, Germany).

e) Transformation of *Agrobacterium*

Unless described otherwise, *Agrobacterium*-mediated plant transformation was carried out with the aid of an *Agrobacterium tumefaciens* strain, as by Deblaere et al. (1984, Nucl. Acids Res. 13, 4777-4788).

f) Plant Transformation

Unless described otherwise, *Agrobacterium*-mediated plant transformation was carried out using standard transformation and regeneration techniques (Gelvin, Stanton B., Schilperoort, Robert A., Plant Molecular Biology Manual, 2nd ed., Dordrecht: Kluwer Academic Publ., 1995, in Sect., Ringbuc Zentrale Signatur: BT11-P ISBN 0-7923-2731-4; Glick, Bernard R., Thompson, John E., Methods in Plant Molecular Biology and Biotechnology, Boca Raton: CRC Press, 1993, 360 S., ISBN 0-8493-5164-2).

According thereto, it is possible to transform, for example, oilseed rape by means of cotyledon or hypocotyl transformation (Moloney et al., Plant Cell 8 (1989) 238-242; De Block et al., Plant Physiol. 91 (1989) 694-701). The use of antibiotics for the selection of *agrobacteria* and plants depends on the binary vector used for transformation and the *Agrobacterium* strain. Normally, oilseed rape is selected using kanamycin as selectable plant marker.

The transformation of soybean may be carried out using, for example, a technique described in EP-A-0 0424 047 (Pioneer Hi-Bred International) or in EP-A-0 0397 687, U.S. Pat. No. 5,376,543, U.S. Pat. No. 5,169,770 (University Toledo).

The transformation of plants using particle bombardment, polyethylene glycol-mediated DNA uptake or via the silicon carbonate fiber technique is described, for example, by Freeling and Walbot "The maize handbook" (1993) ISBN 3-540-97826-7, Springer Verlag New York).

Unless described otherwise, *Agrobacterium*-mediated gene transfer into linseed (*Linum usitatissimum*) was carried out by the technique as described in Mlynarova et al. [(1994) Plant Cell Report 13:282-285].

G) Plasmids for Plant Transformation

Binary vectors based on the vectors pBinAR (Höfgen and Willmitzer, Plant Science 66 (1990) 221-230) or pGPTV (Becker et al. 1992, Plant Mol. Biol. 20:1195-1197) were used for plant transformation. The binary vectors which comprise the nucleic acids to be expressed are constructed by ligating the cDNA in sense orientation into the T-DNA. 5' of the cDNA, a plant promoter activates cDNA transcription. A polyadenylation sequence is located 3' of the cDNA. The binary vectors may carry different marker genes such as, for example, the acetolactate synthase gene (AHAS or ALS) [Ott et al., J. Mol. Biol. 1996, 263:359-360] which imparts a resistance to the imidazolinones or the nptII marker gene which codes for a kanamycin resistance imparted by neomycin phosphotransferase.

Tissue-specific expression of the nucleic acids can be achieved using a tissue-specific promoter. Unless described otherwise, the LeB4 or the USP promoter or the phaseolin promoter was cloned 5' of the cDNA. Terminators used were the NOS terminator and the OCS terminator (see FIG. 1). FIG. 1 depicts a vector map of the vector used for expression, pSUN3CeLPLAT.

It is also possible to use any other seed-specific promoter element such as, for example, the napin or arcelin promoter (Goossens et al. 1999, Plant Phys. 120(4):1095-1103 and Gerhardt et al. 2000, Biochimica et Biophysica Acta 1490(1-2): 87-98).

The CaMV-35S promoter or a v-ATPase C1 promoter can be used for constitutive expression in the whole plant.

The nucleic acids used in the process which code for acyl-CoA:lysophospholipid acyltransferases; desaturases or elongases were cloned into a binary vector one after the other by constructing a plurality of expression cassettes, in order to mimic the metabolic pathway in plants.

Within an expression cassette, the protein to be expressed may be targeted into a cellular compartment by using a signal peptide, for example for plastids, mitochondria or the endoplasmic reticulum (Kermode, Crit. Rev. Plant Sci. 15, 4 (1996) 285-423). The signal peptide is cloned 5' of and in-frame with the cDNA in order to achieve the subcellular localization of the fusion protein.

Examples of multiexpression cassettes were disclosed in DE 102 19 203 and are given again below.

i.) Promoter-Terminator Cassettes

Expression cassettes consist of at least two functional units such as a promoter and a terminator. Further desired gene sequences such as targeting sequences, coding regions of genes or parts thereof etc. may be inserted between promoter and terminator. To construct the expression cassettes, promoters and terminators (USP promoter: Baeumlein et al., Mol Gen Genet, 1991, 225 (3):459-67); OCS terminator: Gielen et al. EMBO J. 3 (1984) 835ff.) were isolated with the aid of the polymerase chain reaction and tailor-made with flanking sequences of choice on the basis of synthetic oligonucleotides.

Examples of oligonucleotides which may be used are the following:

USP1 upstream (SEQ ID NO: 75):
-CCGGAATTCGGCGCGCCGAGCTCCTCGAGCAAATTTACACATTGCCA- USP2 upstream (SEQ ID NO: 76):
-CCGGAATTCGGCGCGCCGAGCTCCTCGAGCAAATTTACACATTGCCA- USP3 upstream (SEQ ID NO: 77):
-CCGGAATTCGGCGCGCCGAGCTCCTCGAGCAAATTTACACATTGCCA- USP1 downstream (SEQ ID NO: 78):
-AAAACTGCAGGCGGCCGCCCACCGCGGTGGGCTGGCTATGAAGAAATT- USP2 downstream (SEQ ID NO: 79):
-CGCGGATCCGCTGGCTATGAAGAAATT-

```
-continued
USP3 downstream (SEQ ID NO: 80):
-TCCCCCGGGATCGATGCCGGCAGATCTGCTGGCTATGAAGAAATT- OCS1 upstream (SEQ ID NO: 81):
-AAAACTGCAGTCTAGAAGGCCTCCTGCTTTAATGAGATAT- OCS2 upstream (SEQ ID NO: 82):
-CGCGGATCCGATATCGGGCCCGCTAGCGTTAACCCTGCTTTAATGAGAT
AT- OCS3 upstream (SEQ ID NO: 83):
-TCCCCCGGGCCATGGCCTGCTTTAATGAGATAT- OCS1 downstream (SEQ ID NO: 84):
-CCCAAGCTTGGCGCGCCGAGCTCGAATTCGTCGAGCGGACAATCAGTAA
ATTGA- OCS2 downstream (SEQ ID NO: 85):
-CCCAAGCTTGGCGCGCCGAGCTCGAATTCGTCGACGGACAATCAGTAAA
TTGA- OCS3 downstream (SEQ ID NO: 86):
-CCCAAGCTTGGCGCGCCGAGCTCGTCGACGGACAATCAGTAAATTGA-
```

The methods are known to the skilled worker in the field and are well known from the literature.

In a first step, a promoter and a terminator were amplified via PCR. The terminator was then cloned into a recipient plasmid and, in a second step, the promoter was inserted upstream of the terminator. As a result, an expression cassette was cloned into the basic plasmid. The plasmids pUT1, 2 and 3 were thus generated on the basis of the pUC19 plasmid.

The corresponding constructs or plasmids are defined in SEQ ID NO: 52, 53 and 54. They comprise the USP promoter and the OCS terminator. Based on these plasmids, the construct pUT12 was generated by cutting pUT1 by means of SalI/ScaI and pUT2 by means of XhoI/ScaI. The fragments comprising the expression cassettes were ligated and transformed into E. coli XL1 blue MRF. After isolating ampicillin-resistant colonies, DNA was prepared and those clones which comprise two expression cassettes were identified by restriction analysis. The XhoI/SalI ligation of compatible ends has eliminated here the two cleavage sites, XhoI and SalI, between the expression cassettes. The resulting plasmid, pUT12, is indicated in SEQ ID NO: 55. Subsequently, pUT12 was cut again by means of Sal/ScaI and pUT3 was cut by means of XhoI/ScaI. The fragments comprising the expression cassettes were ligated and transformed into E. coli XLI blue MRF. After isolation from ampicillin-resistant colonies, DNA was again prepared, and those clones which comprise three expression cassettes were identified by restriction analysis. In this manner, a set of multiexpression cassettes was produced which can be utilized for insertion of desired DNA and which is described in table 1 and which moreover can incorporate further expression cassettes.

Said cassettes comprise the following elements:

TABLE 1

| PUC19 derivative | Cleavage sites upstream of the USP promoter | Multiple cloning cleavage sites | Cleavage sites downstream of the OCS terminator |
|---|---|---|---|
| PUT1 | EcoRI/AscI/SacI/XhoI | BstXI/NotI/PstI/XbaI/StuI | SalI/EcoRI/SacI/AscI/HindIII |
| PUT2 | EcoRI/AscI/SacI/XhoI | BamHI/EcoRV/ApaI/NheI/HpaI | SalI/EcoRI/SacI/AscI/HindIII |
| PUT3 | EcoRI/AscI/SacI/XhoI | BglII/NaeI/ClaI/SmaI/NcoI | SalI/SacI/AscI/HindIII |
| PUT12 double expression cassette | EcoRI/AscI/SacI/XhoI | BstXI/NotI/PstI/XbaI/StuI and BamHI/EcoRV/ApaI/NheI/HpaI | SalI/EcoRI/SacI/AscI/HindIII |
| PUT123 triple expression cassette | EcoRI/AscI/SacI/XhoI | 1. BstXI/NotI/PstI/XbaI/StuI and 2. BamHI/EcoRV/ApaI/NheI/HpaI and 3. BglII/NaeI/ClaI/SmaI/NcoI | SalI/SacI/AscI/HindIII |

Furthermore, further multiexpression cassettes may be generated, as described and as specified in more detail in table 2, with the aid of the i) USP promoter or with the aid of the ii) 700 base pair 3' fragment of the LeB4 promoter or with the aid of the iii) DC3 promoter and employed for seed-specific gene expression.

The DC3 promoter is described in Thomas, Plant Cell 1996, 263:359-368 and consists merely of the region from −117 to +26, which is why it therefore constitutes one of the smallest known seed-specific promoters. The expression cassettes may comprise several copies of the same promoter or else be constructed via three different promoters.

Advantageously used polylinker- or polylinker-terminator-polylinkers can be found in the sequences SEQ ID NO: 60 to 62.

TABLE 2

| Multiple expression cassettes | | | |
|---|---|---|---|
| Plasmid name of the pUC19 derivative | Cleavage sites upstream of the particular promoter | Multiple cloning cleavage sites | Cleavage sites downstream of the OCS terminator |
| pUT1 (pUC19 with USP-OCS1) | EcoRI/AscI/SacI/XhoI | (1) BstXI/NotI/PstI/XbaI/StuI | SalI/EcoRI/SacI/AscI/HindIII |
| PDCT (pUC19 with DC3-OCS) | EcoRI/AscI/SacI/XhoI | (2) BamHI/EcoRV/ApaI/NheI/HpaI | SalI/EcoRI/SacI/AscI/HindIII |

TABLE 2-continued

Multiple expression cassettes

| Plasmid name of the pUC19 derivative | Cleavage sites upstream of the particular promoter | Multiple cloning cleavage sites | Cleavage sites downstream of the OCS terminator |
| --- | --- | --- | --- |
| PleBT (pUC19 with LeB4(700)-OCS) | EcoRI/AscI/SacI/XhoI | (3) BglII/NaeI/ClaI/SmaI/NcoI | SalI/SacI/AscI/HindIII |
| PUD12 (pUC 19 with USP-OCS1 and with DC3-OCS) | EcoRI/AscI/SacI/XhoI | (1) BstXI/NotI/PstI/XbaI/StuI and (2) BamHI/EcoRV/ApaI/NheI/HpaI | SalI/EcoRI/SacI/AscI/HindIII |
| PUDL123 Triple expression cassette (pUC19 with USP/DC3 and LeB4-700) | EcoRI/AscI/SacI/XhoI | (1) BstXI/NotI/PstI/XbaI/StuI and (2) BamHI/(EcoRV*)/ApaI/NheI/HpaI and (3) BglII/NaeI/ClaI/SmaI/NcoI | SalI/SacI/AscI/HindIII |

*EcoRV cleavage site cuts in the 700 base pair fragment of the LeB4 promoter (LeB4-700)

Further promoters for multigene constructs can be generated analogously, in particular by using the a) 2.7 kB fragment of the LeB4 promoter or with the aid of the b) phaseolin promoter or with the aid of the c) constitutive v-ATPase c1 promoter.

It may be particularly desirable to use further particularly suitable promoters for constructing seed-specific multiexpression cassettes, such as, for example, the napin promoter or the arcelin-5 promoter.

Further vectors which can be utilized in plants and which have one or two or three promoter-terminator expression cassettes can be found in the sequences SEQ ID NO: 63 to SEQ ID NO: 68.

ii.) Generation of expression constructs which comprise promoter, terminator and desired gene sequence for the expression of PUFA genes in plant expression cassettes.

The Δ-6-elongase Pp_PSE1 is first inserted into the first cassette in pUT123 via BstXI and XbaI. Then, the moss Δ-6-desaturase (Pp_des6) is inserted via BamHI/NaeI into the second cassette and, finally, the Phaeodactylum Δ-5-desaturase (Pt_des5) is inserted via BglII/NcoI into the third cassette (see SEQ ID NO: 56). The triple construct is named pARA1. Taking into consideration sequence-specific restriction cleavage sites, further expression cassettes, as set out in table 3 and referred to as pARA2, pARA3 and pARA4, may be generated.

TABLE 3

Combinations of desaturases and elongases

| Gene plasmid | Δ-6-Desaturase | Δ-5-Desaturase | Δ-6-Elongase |
| --- | --- | --- | --- |
| pARA1 | Pp_des6 | Pt_des5 | Pp_PSE1 |
| pARA2 | Pt_des6 | Pt_des5 | Pp_PSE1 |
| pARA3 | Pt_des6 | Ce_des5 | Pp_PSE1 |
| PARA4 | Ce_des6 | Ce_des5 | Ce_PSE1 | des5 = PUFA-specific Δ-5-desaturase
des6 = PUFA-specific Δ-6-desaturase
PSE = PUFA-specific Δ-6-elongase
Pt_des5 = Δ-5-desaturase from *Phaeodactylum tricornutum*
Pp_des6 or Pt_des6 = Δ-6-desaturase from *Physcomitrella patens* or *Phaeodactylum tricornutum*
Pp = *Physcomitrella patens*, Pt = *Phaeodactylum tricornutum*
Pp_PSE1 = Δ-6-elongase from *Physcomitrella patens*
Pt_PSE1 = Δ-6-elongase from *Phaeodactylum tricornutum*
Ce_des5 = Δ-5-desaturase from *Caenorhabditis elegans* (Genbank Acc. No. AF078796)
Ce_des6 = Δ-6-desaturase from *Caenorhabditis elegans* (Genbank Acc. No. AF031477, bases 11–1342)
Ce_PSE1 = Δ-6-elongase from *Caenorhabditis elegans* (Genbank Acc. No. AF244356, bases 1–867)

Further desaturases or elongase gene sequences may also be inserted into expression cassettes of the type described, such as, for example, Genbank Acc. No. AF231981, NM_013402, AF206662, AF268031, AF226273, AF110510 or AF110509.

iii.) Transfer of expression cassettes into vectors for the transformation of *Agrobacterium tumefaciens* and for the transformation of plants The constructs thus generated were inserted into the binary vector pGPTV by means of AscI. For this purpose, the multiple cloning sequence was extended by an AscI cleavage site. For this purpose, the polylinker was synthesized de novo in the form of two double-stranded oligonucleotides, with an additional AscI DNA sequence being inserted. The oligonucleotide was inserted into the pGPTV vector by means of EcoRI and HindIII. The cloning techniques required are known to the skilled worker and may readily be found in the literature as described in example 1.

The nucleic acid sequences for Δ-5-desaturase (SEQ ID NO: 50), Δ-6-desaturase (SEQ ID NO: 46) and Δ-6-elongase (SEQ ID NO: 48), which were used for the experiments described below, were the sequences from *Physcomitrella patens* and *Phaeodactylum tricornutum*. The corresponding amino acid sequences can be found in the sequences SEQ ID NO: 47, SEQ ID NO: 49 and SEQ ID NO: 51. A vector which comprises all of the abovementioned genes is indicated in SEQ ID NO: 56. The corresponding amino acid sequences of the genes can be found in SEQ ID NO: 57, SEQ ID NO: 58 and SEQ ID NO: 59.

Example 2

Cloning and Characterization of the ceLPLATs (SEQ ID NO: 38-44)

a) Database Search

The ceLPLATs (=acyl-CoA:lysophospholipid acyltransferase from *Caenorhabditis elegans*) were identified by sequence comparisons with known LPA-ATs. The search was restricted to the nematode genome (*Caenorhabditis elegans*) with the aid of the BLAST-Psi algorithm (Altschul et al., J. Mol. Biol. 1990, 215: 403-410), since this organism synthesizes LCPUFAs. The probe employed in the sequence comparison was an LPAAT protein sequence from *Mus musculus* (MsLPAAT Accession No. NP_061350). LPLAT catalyzes, by a reversible transferase reaction, the ATP-independent synthesis of acyl-CoAs from phospholipids with the aid of CoA as cofactor (Yamashita et al., J. Biol. Chem. 2001, 20: 26745-26752). Sequence comparisons enabled two putative ceLPLAT sequences to be identified (Accession No. T06E8.1 and F59F4.4). The identified sequences are most similar to each other and to MsLPAATs (FIG. 2). The alignment was generated using the Clustal program.

b) Cloning of the CeLPLATs

Primer pairs were synthesized on the basis of the ceLPLAT nucleic acid sequences (table 4) and the corresponding cDNAs were isolated from a *C. elegans* cDNA library by means of PCR processes. The respective primer pairs were selected so as to carry, apart from the start codon, the yeast consensus sequence for high-efficiency translation (Kozak, Cell 1986, 44:283-292). The LPLAT cDNAs were amplified in each case using 2 µl of cDNA-library solution as template, 200 µM dNTPs, 2.5 U of "proof-reading" pfu polymerase and 50 pmol of each primer in a total volume of 50 µl. The conditions for the PCR were as follows: first denaturation at 95° C. for 5 minutes, followed by 30 cycles at 94° C. for 30 seconds, 58° C. for one minute and 72° C. for 2 minutes, and a final extension step at 72° C. for 10 minutes. The sequence of the LPLAT cDNAs was confirmed by DNA sequencing.

TABLE 4

Nucleotide sequences of the PCR primers for cloning CeLPLATs

| Primer | Nucleotide sequence |
| --- | --- |
| 5' T06E8.1f* (SEQ ID NO: 87) | 5' ACATAATGGAGAACTTCTGGTCGATCGTC 3' |
| 3' T06E8.1r* (SEQ ID NO: 88) | 5' TTACTCAGATTTCTTCCCGTCTTT 3' |
| 5' F59F4.4f* (SEQ ID NO: 89) | 5' ACATAATGACCTTCCTAGCCATATTA 3' |
| 3' F59F4.4r* (SEQ ID NO: 90) | 5' TCAGATATTCAAATTGGCGGCTTC 3' |

*f: forward, r: reverse

Example 3

Analysis of the Effect of the Recombinant Proteins on Production of the Desired Product A) Possible Preparation Methods The effect of genetic modification in fungi, algae, ciliates or, as described in the examples hereinabove, on the production of the polyunsaturated fatty acids in yeasts, or in plants may be determined by growing the modified microorganisms or the modified plant under suitable conditions (such as those described above) and studying the medium and/or the cellular components for increased production of the lipids or fatty acids. These analytical techniques are known to the skilled worker and comprise spectroscopy, thin-layer chromatography, various types of staining methods, enzymic and microbiological methods and analytical chromatography such as high-performance liquid, chromatography (see, for example, Ullmann, Encyclopedia of Industrial Chemistry, vol. A2, pp. 89-90 and pp. 443-613, VCH: Weinheim (1985); Fallon, A., et al., (1987) "Applications of HPLC in Biochemistry" in: Laboratory Techniques in Biochemistry and Molecular Biology, vol. 17; Rehm et al. (1993) Biotechnology, vol. 3, chapter III: "Product recovery and purification", pp. 469-714, VCH: Weinheim; Belter, P. A., et al. (1988) Bioseparations: downstream processing for Biotechnology, John Wiley and Sons; Kennedy, J. F., and Cabral, J. M. S. (1992) Recovery processes for biological Materials, John Wiley and Sons; Shaeiwitz, J. A., and Henry, J. D. (1988) Biochemical Separations, in: Ullmann's Encyclopedia of Industrial Chemistry, vol. B3; chapter 11, pp. 1-27, VCH: Weinheim; and Dechow, F. J. (1989) Separation and purification techniques in biotechnology, Noyes Publications).

Apart from the abovementioned methods for detecting fatty acids in yeasts, plant lipids are extracted from plant material as described by Cahoon et al. (1999) Proc. Natl. Acad. Sci. USA 96 (22):12935-12940, and Browse et al. (1986) Analytic Biochemistry 152:141-145. The qualitative and quantitative analysis of lipids or fatty acids is described in Christie, William W., Advances in Lipid Methodology, Ayr/Scotland: Oily Press (Oily Press Lipid Library; 2); Christie, William W., Gas Chromatography and Lipids. A Practical Guide-Ayr, Scotland: Oily Press, 1989, Repr. 1992, IX, 307 S. (Oily Press Lipid Library; 1); "Progress in Lipid Research, Oxford: Pergamon Press, 1 (1952)-16 (1977) under the title: Progress in the Chemistry of Fats and Other Lipids CODEN.

Thus, fatty acids or triacylglycerol (=TAG, abbreviations indicated in brackets) may be analyzed, for example, by means of fatty acid methyl esters (=FAME), gas liquid chromatography-mass spectrometry (=GC-MS) or thin-layer chromatography (TLC).

Unequivocal proof of the presence of fatty acid products may be obtained by means of analyzing recombinant organisms following standard analytical procedures: GC, GC-MS or TLC, as variously described by Christie and references therein (1997, in: Advances on Lipid Methodology, fourth ed.: Christie, Oily Press, Dundee, 119-169; 1998, Gaschromatographie-Massenspektrometrie-Verfahren [Gas chromatography-mass spectrometry methods], Lipide 33:343-353).

The plant material to be analyzed may for this purpose be disrupted either by sonification, glass milling, liquid nitrogen and grinding or via other applicable processes. After the material has been disrupted, it is then centrifuged. The sediment is then resuspended in distilled water, heated at 100° C. for 10 min, cooled on ice and centrifuged again, followed by extraction in 0.5 M sulfuric acid in methanol containing 2% dimethoxypropane for 1 h at 90° C., leading to hydrolyzed oil and lipid compounds which result in transmethylated lipids. These fatty acid methyl esters may then be extracted in petroleum ether and finally be subjected to GC analysis using a capillary column (Chrompack, WCOT Fused Silica, CP-Wax-52 CB, 25 µm, 0.32 mm), with a temperature gradient of between 170° C. and 240° C. for 20 min and at 240° C. for 5 min. The identity of the resulting fatty acid methyl esters can be defined using standards available from commercial sources (i.e. Sigma).

In the case of fatty acids for which no standards are available, the identity may be shown via derivatization and subsequent GC-MS analysis. For example, the localization of triple-bond fatty acids is shown via GC-MS after derivatization with 4,4-dimethoxyoxazoline derivatives (Christie, 1998, see above).

B) Fatty Acid Analysis in Plants

Total fatty acids were extracted from plant seeds and analyzed by means of gas chromatography.

The seeds were taken up with 1% sodium methoxide in methanol and incubated at RT (approx. 22° C.) for 20 min. This was followed by washing with NaCl solution and taking up the FAMEs in 0.3 ml of heptane.

The samples were fractionated on a ZEBRON-ZB Wax capillary column (30 m, 0.32 mm, 0.25 µm; Phenomenex) in a Hewlett Packard 6850 gas chromatograph with flame ionization detector. The oven temperature was programmed from 70° C. (hold for 1 min) to 200° C. at a rate of 20° C./min, then to 250° C. (hold for 5 min) at a rate of 5° C./min and finally to 260° C. at a rate of 5° C./min. The carrier gas used was nitrogen (4.5 ml/min at 70° C.). The fatty acids were identified by comparison with retention times of FAME standards (SIGMA).

Example 4

Functional Characterization of CeLPLATs in Yeast a) Heterologous Expression in *Saccharomyces cerevisiae*

To characterize the function of the *C. elegans*, CeLPLATs (SEQ ID NO: 38-44), the open reading frames of the particular cDNAs were cloned downstream of the galactose-inducible GALL promoter of pYes2.1Topo, using the pYes2.1TOPO TA Expression Kit (Invitrogen), resulting in pYes2-T06E8.1 and pYes2-F59F4.4.

Since expression of the CeLPLATs should result in an efficient exchange of the acyl substrates, the double construct pESCLeu-PpD6-Pse1 which includes the open reading frames of a Δ6-desaturase (PpD6) and a Δ6-elongase (PSE1) from *Physcomitrella patens* (see DE 102 19 203) was also prepared. The nucleic acid sequence of said Δ6-desaturase (PpD6) and said Δ6-elongase (Pse1) are indicated in each case in SEQ ID NO: 46 and SEQ ID NO: 48. The corresponding amino acid sequences can be found in SEQ ID NO: 47 and SEQ ID NO: 49.

The *Saccharomyces cerevisiae* strains C 13ABYS86 (protease-deficient) and INVSc1 were transformed simultaneously with the vectors pYes2-T06E8.1 and pESCLeu-PpD6-Pse1 and, respectively, pYes2-F59F4.4 and pESCLeu-PpD6-Pse1 by means of a modified PEG/lithium acetate protocol. The control used was a yeast which was transformed with the pESCLeu-PpD6-Pse1 vector and the empty vector pYes2. The transformed yeasts were selected on complete minimal medium (CMdum) agar plates containing 2% glucose but no uracil or leucine. After selection, 4 transformants, two pYes2-T06E8.1/pESCLeu-PpD6-Pse1 and two pYes2-F59F4.4/pESCLeu-PpD6-Pse1 and one pESCLeu-PpD6-Pse1/pYes2 were selected for further functional expression. The experiments described were also carried out in the yeast strain INVSc1.

In order to express the CeLPAATs, precultures of in each case 2 ml of CMdum liquid medium containing 2% (w/v) raffinose but no uracil or leucine were first inoculated with the selected transformants and incubated at 30° C., 200 rpm, for 2 days. 5 ml of CMdum liquid medium (without uracil and leucine) containing 2% raffinose, 1% (v/v) Tergitol NP-40 and 250 μM linoleic acid ($18:2^{\Delta9,12}$) or linolenic acid ($18:3^{\Delta9,12,15}$) were then inoculated with the precultures to an $OD_{600}$ of 0.08. Expression was induced at an $OD_{600}$ of 0.2-0.4 by adding 2% (w/v) galactose. The cultures were incubated at 20° C. for a further 48 h.

Fatty Acid Analysis

The yeast cells from the main cultures were harvested by centrifugation (100×g, 10 min, 20° C.) and washed with 100 mM $NaHCO_3$, pH 8.0 in order to remove residual medium and fatty acids. Fatty acid methyl esters (FAMEs) were prepared from the yeast cell sediments by acidic methanolysis. For this, the cell sediments were incubated with 2 ml of 1N methanolic sulfuric acid and 2% (v/v) dimethoxypropane at 80° C. for 1 h. Extraction of the FAMES was carried out by extracting twice with petroleum ether (PE). Nonderivatized fatty acids were removed by washing the organic phases in each case once with 2 ml of 100 mM $NaHCO_3$, pH 8.0 and 2 ml of distilled water. The PE phases were subsequently dried with $Na_2SO_4$, evaporated under argon and taken up in 100 μl of PE. The samples were separated on a DB-23 capillary column (30 m, 0.25 mm, 0.25 μm, Agilent) in a Hewlett Packard 6850 gas chromatograph with flame ionization detector. The conditions for the GLC analysis were as follows: the oven temperature was programmed from 50° C. to 250° C. at a rate of 5° C./min and finally at 250° C. (hold) for 10 min.

The signals were identified by comparing the retention times with those of corresponding fatty acid standards (Sigma).

Acyl-CoA Analysis

The acyl-CoA analysis was carried out as described in Larson and Graham (2001; Plant Journal 25: 115-125).

Expression Analysis

FIGS. 2 A and B and FIGS. 3 A and B depict the fatty acid profiles of transgenic C13ABYS86 yeasts fed with $18:2^{\Delta9,12}$ and $18:3^{\Delta9,12,15}$, respectively. The substrates fed can be detected in large amounts in all transgenic yeasts. All four transgenic yeasts display synthesis of $18:3^{\Delta6,9,12}$ and $20:3^{\Delta8,11,14}$ and, respectively, $18:4^{\Delta6,9,12,15}$ and $20:4^{\Delta8,11,14,17}$, the products of the Δ-6-desaturase and Δ-6-elongase reactions, meaning that the genes PpD6 and Pse1 were able to be functionally expressed.

FIG. 3 depicts, as described above, the fatty acid profiles of transgenic C13ABYS86 *S. cerevisiae* cells. The fatty acid methyl esters were synthesized by acidic methanolysis of intact cells which had been transformed either with the pESCLeu-PpD6-Pse1/pYes2 (A) or with the pYes2-T06E8.1/pESCLeu-PpD6-Pse1 (B) vectors. The yeasts were cultured in minimal medium in the presence of $18:2^{\Delta9,12}$. The fatty acid methyl esters were subsequently analyzed by GLC.

In the control yeasts transformed with the pESCLeu-PpD6-Pse1/pYes2 vectors, the proportion of $20:3^{\Delta8,11,14}$ to which $18:3^{\Delta6,9,12}$ is elongated by Pse1 is substantially lower than in the yeasts which additionally express LPLAT T06E8.1. In fact, elongation of $18:3^{\Delta6,9,12}$ and $18:4^{\Delta6,9,12,15}$ was improved by 100-150% by additional expression of CeLPLAT (T06E8.1) (FIG. 4). This significant increase in the LCPUFA content can be explained only as follows: the exogenously fed fatty acids ($18:2^{\Delta9,12}$ and $18:3^{\Delta9,12,15}$ respectively) are first incorporated into phospholipids and desaturated there by Δ-6-desaturase to give $18:3^{\Delta6,9,12}$ and $18:4^{\Delta6,9,12,15}$. Only after reequilibration with the acyl-CoA pool can $18:3^{\Delta6,9,12}$ and $18:4^{\Delta6,9,12,15}$ be elongated by the elongase to give $20:3^{\Delta8,11,14}$- and $20:4^{\Delta8,11,14,17}$-CoA, respectively and then incorporated again into the lipids. LPLAT T06E8.1 is capable of converting the Δ6-desaturated acyl groups very efficiently back to CoA thioesters. Interestingly, it was also possible to improve the elongation of the fed fatty acids $18:2^{\Delta9,12}$ and $18:3^{\Delta9,12,15}$. (FIGS. 2 A and B and FIGS. 5 A and B, respectively).

FIG. 5 indicates the fatty acid profiles of transgenic C13ABYS86 *S. cerevisiae* cells. Synthesis of the fatty acid methyl esters was carried out by acidic methanolysis of intact cells which had been transformed either with the vectors pESCLeu-PpD6-Pse1/pYes2 (A) or with the vectors pYes2-T06E8.1/pESCLeu-PpD6-Pse1 (B). The yeasts were cultured in minimal medium in the presence of $18:3^{\Delta9,12,15}$. The fatty acid methyl esters were subsequently analyzed via GLC.

In contrast, expression of a different CeLPLAT (F59F4.4) has no influence on elongation (FIG. 4). F59F4.4 evidently does not code for an LPLAT. Thus, not every putative LPLAT nucleic acid sequence is enzymatically active in the reaction found according to the invention.

FIG. 4 indicates the elongation of exogenously applied $18:2^{\Delta 9,12}$ and $18:3^{\Delta 9,12,15}$ following their endogenous $\Delta$-6-desaturation (data of FIGS. 2 and 5). The exogenously fed fatty acids are first incorporated into phospholipids and desaturated there to give $18:3^{\Delta 6,9,12}$ and $18:4^{\Delta 6,9,12,15}$. Only after reequilibration with the acyl-CoA pool can $18:3^{\Delta 6,9,12}$ and $18:4^{\Delta 6,9,12,15}$ be elongated by the elongase to give $20:3^{\Delta 8,11,14}$- and $20:4^{\Delta 8,11,14,17}$-CoA, respectively, and then incorporated again into the lipids. LPLAT T06E8.1 is capable of converting the $\Delta$-6-desaturated acyl groups efficiently back to CoA-thioesters.

These results show that CeLPLAT (T06E8.1), after coexpression with $\Delta$-6-desaturase and $\Delta$-6-elongase, leads to efficient production of C20-PUFAs. These results can be explained by the fact that CeLPLAT (T06E8.1) makes possible an efficient exchange of the newly synthesized fatty acids between lipids and the acyl-CoA pool (see FIG. 6).

FIG. 6 indicates the acyl-CoA composition of transgenic INVSc1 yeasts transformed with the pESCLeu PpD6Pse1/pYes2 (A) or pESCLeu-PpD6-Pse1/pYes2-T06E8.1 (B) vectors. The yeast cells were cultured in minimal medium without uracil and leucine in the presence of 250 μM $18:2^{\Delta 9,12}$. The acyl-CoA derivatives were analyzed via HPLC.

When using the yeast strain INVSc1 for coexpression of CeLPLAT (T06E8.1) together with PpD6 and Pse1, the following picture emerges: control yeasts expressing PpD6 and Pse1 comprise, as already shown when using the strain C13ABYS86, only small amounts of the elongation product ($20:3_{\Delta 8,11,14}$, with 18:2 feed, and $20:4^{\Delta 8,11,14,17}$, with 18:3 feed; see FIGS. 7A and 8A, respectively). Additional expression of CeLPLAT (T06E8.1) results in a marked increase in these elongation products (see FIGS. 7B and 8B). Table 5 indicates that additional expression of CeLPLAT surprisingly causes an 8-fold increase in the $20:3^{\Delta 8,11,14}$ (with 18:2 feed) and, respectively, the $20:4^{\Delta 8,11,14,17}$ (with 18:3 feed) content. It is also revealed that $C16:2^{\Delta 6,9}$ is also elongated more efficiently to give $C18:2^{\Delta 6,9}$.

The fatty acid profiles of transgenic INVSc1 *S. cerevisiae* cells can be seen from FIG. 7. Synthesis of the fatty acid methyl esters was carried out by acid methanolysis of intact cells which had been transformed either with the vectors pESCLeu-PpD6-Pse1/pYes2 (A) or pYes2-T06E8.1/pESCLeu-PpD6-Pse1 (B). The yeasts were cultured in minimal medium in the presence of $18:2^{\Delta 9,12}$. The fatty acid methyl esters were subsequently analyzed via GLC.

The fatty acid profiles of transgenic INVSc1 *S. cerevisiae* cells can be seen from FIG. 8. Synthesis of the fatty acid methyl esters was carried out by acid methanolysis of intact cells which had been transformed either with the vectors pESCLeu-PpD6-Pse1/pYes2 (A) or pYes2-T06E8.1/pESCLeu-PpD6-Pse1 (B). The yeasts were cultured in minimal medium in the presence of $18:3^{\Delta,12,15}$. The fatty acid methyl esters were subsequently analyzed via GLC.

TABLE 5

Fatty acid composition (in mol %) of transgenic yeasts transformed with the pESCLeu PpD6Pse1/pYes2 (PpD6 Pse1) or pESCLeu-PpD6-Pse1/pYes2-T06E8.1 (PpD6 Pse1 + T06E8) vectors. The yeast cells were cultured in minimal medium without uracil and leucine in the presence of 250 μM $18:2^{\Delta 9,12}$ or $18:3^{\Delta 9,12,15}$. The fatty acid methyl esters were obtained by acidic methanolysis of whole cells and analyzed via GLC. Each value indicates the average (n = 4) ± standard deviation.

| | Feeding with 250 μM $18:2^{\Delta 9,12}$ | | Feeding with 250 μM $18:3^{\Delta 9,12,15}$ | |
|---|---|---|---|---|
| Fatty acids | PpΔ6/Pse1 | PpΔ6/Pse1 + T06E8 | PpΔ6/Pse1 | PpΔ6/Pse1 + T06E8 |
| 16:0 | 15.31 ± 1.36 | 15.60 ± 1.36 | 12.20 ± 0.62 | 16.25 ± 1.85 |
| $16:1^{\Delta 9}$ | 23.22 ± 2.16 | 15.80 ± 3.92 | 17.61 ± 1.05 | 14.58 ± 1.93 |
| 18:0 | 5.11 ± 0.63 | 7.98 ± 1.28 | 5.94 ± 0.71 | 7.52 ± 0.89 |
| $18:1^{\Delta 9}$ | 15.09 ± 0.59 | 16.01 ± 2.53 | 15.62 ± 0.34 | 15.14 ± 2.61 |
| $18:1^{\Delta 11}$ | 4.64 ± 1.09 | 11.80 ± 1.12 | 4.56 ± 0.18 | 13.07 ± 1.66 |
| $18:2^{\Delta 9,12}$ | 28.72 ± 3.25 | 14.44 ± 1.61 | — | — |
| $18:3^{\Delta 6,9,12}$ | 3.77 ± 0.41 | 4.72 ± 0.72 | — | — |
| $18:3^{\Delta 9,12,15}$ | — | — | 32.86 ± 1.20 | 14.14 ± 2.52 |
| $18:4^{\Delta 6,9,12,15}$ | — | — | 5.16 ± 1.04 | 3.31 ± 1.15 |
| $20:2^{\Delta 11,14}$ | 2.12 ± 0.86 | 4.95 ± 4.71 | — | — |
| $20:3^{\Delta 8,11,14}$ | 1.03 ± 0.14 | 8.23 ± 1.59 | — | — |
| $20:3^{\Delta 11,14,17}$ | — | — | 4.12 ± 1.54 | 6.95 ± 2.52 |
| $20:4^{\Delta 8,11,14,17}$ | — | — | 1.34 ± 0.28 | 8.70 ± 1.11 |

A measure for the efficiency of LCPUFA biosynthesis in transgenic yeast is the quotient of the content of the desired $\Delta$-6-elongation product after $\Delta$-6-desaturation ($20:3^{\Delta 8,11,14}$ and $20:4^{\Delta 8,11,14,17}$, respectively) to the content of fatty acid fed in ($18:2^{\Delta 9,12}$ and $18:3^{\Delta 9,12,15}$, respectively). This quotient is 0:04 in INVSc1 control yeasts expressing PpD6 and Pse1, and 0.60 in yeasts expressing CeLPLAT in addition to PpD6 and Pse1. In other words: the content of desired $\Delta$-6-elongation product after $\Delta$-6-desaturation with coexpression of CeLPLAT is 60% of the content of the fatty acid fed in in each case. In control yeasts, this content is only approx. 4%, meaning a 15-fold increase in the efficiency of LCPUFA biosynthesis in transgenic yeast due to coexpression of LPLAT.

Interestingly, coexpression of CeLPLAT causes not only an increase in the elongation products mentioned, $20:3^{\Delta 8,11,14}$ and $20:4^{\Delta 8,11,14,17}$, but also an increase in the $20:3^{\Delta 8,11,14}:20:2^{\Delta 11,14}$ ratio and the $20:4^{\Delta 8,11,14,17}:20:3^{\Delta 11,14,17}$ ratio, respectively. This means that, in the presence of LPLAT, $\Delta$-6-elongase preferably uses polyunsaturated fatty acids ($18:3^{\Delta 6,9,12}$ and $18:4^{\Delta 6,9,12,15}$) as substrate, while no distinct substrate specificity is discernible in the absence of LPLAT ($18:2^{\Delta 9,12}$ and $18:3^{\Delta 9,12,15}$ are also elongated). The reason for this may be protein-protein interactions between $\Delta$-6-elongase, $\Delta$-6-desaturase and LPLAT or posttranslational modifications (partial proteolysis, for example). This will also explain why the above-described rise in Δ-6-elongation products with coexpression of Δ-6-desaturase, Δ-6-elongase and LPLAT is smaller when a protease-deficient yeast strain is used.

Acyl-CoA analyses of transgenic INVSc1 yeasts fed with $18:2^{\Delta9,12}$ gave the following result: no $18:3^{\Delta6,9,12}$-CoA and $20:3^{\Delta8,11,14}$-CoA is detectable in control yeasts expressing PpD6 and Pse1, indicating that neither the substrate ($18:3^{\Delta6,9,12}$-CoA) nor the product ($20:3^{\Delta8,11,14}$-CoA) of Δ-6-elongase is present in detectable amounts in control yeasts. This suggests that the transfer of $18:3^{\Delta6,9,12}$ from membrane lipids into the acyl-CoA pool does not take place or does not take place correctly, meaning that there is hardly any substrate available for the Δ-6-elongase present, and this in turn explains the low elongation product content in control yeasts. INVSc1 yeasts which express CeLPLAT in addition to PpD6 and Pse1 and which had been fed with $18:2^{\Delta9,12}$ have substantial amounts of $20:3^{\Delta8,11,14}$-CoA but not of $18:3^{\Delta6,9,12}$-CoA. This indicates that LPLAT transfers $18:3^{\Delta6,9,12}$ from the membrane lipids to the acyl-CoA pool very efficiently. $18:3^{\Delta6,9,12}$-CoA is then elongated by Δ-6-elongase so that $20:3^{\Delta8,11,14}$-CoA but not any $18:3^{\Delta6,9,12}$-CoA is detectable.

b) Functional Characterization of the CeLPLATs in Transgenic Plants

Expression of Functional CeLPLAT in Transgenic Plants

DE 102 19 203 describes transgenic plants whose seed oil comprises small amounts of ARA and EPA, due to seed-specific expression of functional genes coding for Δ-6-desaturase, Δ-6-elongase and Δ-5-desaturase. The vector exploited for transformation of these plants can be found in SEQ ID NO: 56. In order to increase the content of these LCPUFAs, the gene CeLPLAT (T06E8.1) was additionally expressed in seeds in the transgenic plants mentioned.

For this purpose, the coding region of CeLPLAT was amplified via PCR.

Table 6 indicates the primers used for cloning another ceLPLAT clone into binary vectors.

TABLE 6

Nucleotide sequences of the PCR primers for cloning CeLPLAT (T06E8.1) into the binary vector pSUN3

| Primer | Nucleotide sequence |
|---|---|
| ARe503f* (SEQ ID NO: 91) | 5' TTAAGCGCGGCCGCATGGAGAACTTCTGGTCG 3' |
| ARe504r* (SEQ ID NO: 92) | 5' ACCTCGGCGGCCGCCCTTTTACTCAGATTTC 3' |

* f: forward, r: reverse

The PCR product was cloned into a pENTRY vector between USP promoter and OCS terminator. The expression cassette was then cloned into the binary pSUN300 vectors. The vector obtained was referred to as pSUN3CeLPLAT (FIG. 1). In addition, the CeLPLAT coding regions were amplified and cloned between LegB4 promoter and OCS terminator. This vector was referred to as pGPTVCeLPLAT (FIG. 9A).

In addition, the CeLPLAT coding region was amplified via PCR and cloned between LegB4 promoter and OCS terminator. The PCR primers used for this were selected so as for an efficient Kosak sequence to be introduced into the PCR product. Moreover, the CeLPLAT DNA sequence was modified so as to adapt it to the codon usage of higher plants.

The following primers were used for the PCR:

Forward primer (SEQ ID NO: 93):
5'-ACATAATGGAGAACTTCTGGTCTATTGTTGTGTTTTTCTA-3'

Reverse primer (SEQ ID NO: 94):
5'-CTAGCTAGCTTACTCAGAT1TCTTCCCGTCTTTTGTTTCTC-3'

The PCR product was cloned into the cloning vector pCR Script and cloned via the restriction enzymes XmaI and SacI into the vector pGPTV LegB4-700. The resulting plasmid was referred to as pGPTV LegB4-700+T06E8.1 (FIG. 9A).

The same PCR product was in addition cloned into a multi-gene expression vector which already comprised the genes for a *Phaeodactylum tricornutum* delta-6-desaturase (SEQ ID NO: 69, amino acid sequence SEQ ID NO: 70) and a *P. patens* delta-6-elongase. The resulting plasmid was referred to as pGPTV USP/OCS-1,2,3 PSE1 (Pp)+D6-Des(Pt)+2AT (T06E8-1) (FIG. 9B). The sequences of the vector and of the genes can be found in SEQ ID NO: 71, SEQ ID NO: 72, SEQ ID NO: 73 and SEQ ID NO: 74. The *Phaeodactylum tricornutum* Δ-6-desaturase extends from nucleotide 4554 to 5987 in SEQ ID NO: 71. The *Physcomitrella patens* Δ-6-elongase extends from nucleotide 1026 to 1898 and that of *Caenorhabditis elegans* LPLAT extends from nucleotide 2805 to 3653 in SEQ ID NO: 71.

Tobacco plants were cotransformed with the pSUN3CeLPLAT vector and the vector described in DE 102 19 203 and SEQ ID NO: 56, which comprises genes coding for Δ-6-desaturase, Δ-6-elongase and Δ-5-desaturase, with transgenic plants being selected using kanamycin.

Tobacco plants were moreover transformed with the pGPTV USP/OCS-1,2,3 PSE1 (Pp)+D6-Des(Pt)+2AT (T06E8-1) vector [see SEQ ID NO: 71, SEQ ID NO: 72, SEQ ID NO: 73 and SEQ ID NO: 74].

Linseed was transformed with the pSUN3CeLPLAT vector. The resulting transgenic plants were crossed with those transgenic linseed plants which already comprised small amounts of ARA and EPA, owing to functional gene expression of Δ-6-desaturase, Δ-6-elongase and Δ-5-desaturase.

Linseed was furthermore transformed with the pGPTV LegB4-700+T06E8.1 vector. The resulting transgenic plants were crossed with those transgenic linseed plants which already comprised small amounts of ARA and EPA, owing to functional expression of Δ-6-desaturase, Δ-6-elongase and Δ-5-desaturase.

The seeds of transgenic tobacco and linseed plants were, as described hereinbefore [example 3 b)], studied for increased LCPUFA contents.

The function of acyl-CoA:lysophospholipid acyltransferase (LPLAT) can be deduced from the studies presented herein as depicted in FIGS. 10 A and 10 B. The biosynthetic pathway of LCPUFAS is thus as follows.

Desaturases catalyze the introduction of double bonds into lipid-coupled fatty acids (sn2-acyl-phosphatidylcholine), while the elongases exclusively catalyze the elongation of coenzyme A-esterified fatty acids (acyl-CoAs). According to this mechanism, the alternating action of desaturases and elongases requires continuous exchange of acyl substrates between phospholipids and acyl-CoA pool and thus the existence of an additional activity which converts the acyl substrates to the substrate form required in each case, i.e. lipids (for desaturases) or CoA thioesters (for elongases). This exchange between acyl-CoA pool and phospholipids is made possible by LCPUFA-specific LPLAT. The biosynthesis of ARA (A) takes place analogously to that of EPA (B), but with the difference that, in the case of EPA, a Δ-15-desaturation takes place upstream of the Δ-6-desaturation so that α18:3-PC acts as a substrate for Δ-6-desaturase. The biosynthesis of DHA requires a further exchange between phospholipids and acyl-CoA pool via LPLAT: $20:5^{\Delta5,8,11,14,17}$ is transferred from the phospholipids pool to the CoA pool and, after Δ-5-elongation, $22:5^{\Delta7,10,13,16,19}$ is transferred from the CoA pool to the phospholipids pool and finally converted by Δ-4-desaturase to give DHA. The same applies to the exchange in the biosynthetic pathway using Δ-8-desaturase, Δ-9-elongase and Δ-5-desaturase.

Example 5

Functional Characterization of the Acyltransferases

To compare the substrate specificity of acyltransferases of higher plants and LCPUFA-producing organisms, microsomal fractions were isolated from the LCPUFA-producing organism *Mortierella alpina* and from sunflower. The GPAT and LPAAT activities were assayed with different acyl-CoAs as substrate.

A position analysis of the lipids was carried out to verify whether the LCPUFA producer *Thraustochytrium* does indeed incorporate DHA at the sn-2 position of the lipids.

To isolate LCPUFA-specific acyltransferases, cDNA libraries were established starting from mRNA of the LCPUFA-producing organisms *Thraustochytrium, Physcomitrella, Cryptecodinium cohnii* and *Fusarium* and a *Shewanella* genomic library was established, and these libraries were analyzed in greater detail via DNA sequencing. Acyltransferase clones were identified via sequence homologies. As an alternative, acyltransferases were amplified via PCR techniques.

Transgenic *E. coli* cells, yeasts, insect cells and plant cells with an elevated expression of at least one LCPUFA-specific acyltransferase have an elevated LCPUFA content in their lipids.

Example 6

Isolation of Microsomal Fractions from *Mortierella*, Sunflower and Linseed, and Analysis of the Substrate Specificity of Acyltransferases for Different Acyl-CoAs To find out whether higher plants, in particular oil seed plants such as sunflower, linseed, oilseed rape or soybean, can incorporate LCPUFAs into their lipids, microsomes were prepared from sunflower and linseed, and different acyltransferase activities were studied for their substrate specificity for LCPUFA-CoAs. Specifically, GPAT, LPAAT and LPCAT activities were studied. These results were compared with the corresponding acyltransferase activities of the LCPUFA producers *Mortierella alpina*, which, as is known, comprises high levels of the LCPUFA arachidonic acid in its lipids and in the triacylglycerol (C. Ming et al. (1999) Bioresource Technology 67: 101-110).

Preparation of Microsomal Membranes from Cotyledons of Maturing Seeds of Sunflower and Linseed All the procedures were carried out at 4° C. The cotyledons of maturing sunflower seeds and linseed were harvested approximately 10 days after anthesis and suspended in 0.1 M sodium phosphate buffer (pH 7.2), comprising 0.33 M sucrose and 0.1% BSA (free from fatty acids). After comminution in a glass homogenizer, the homogenate was centrifuged for 30 minutes at 20 000×g. The supernatant was filtered through one layer of Miracloth and centrifuged for 90 minutes in an ultracentrifuge at 100 000×g. The pelleted microsomal membranes were washed with 0.1 M sodium phosphate buffer (pH 7.2) and resuspended in a small volume of buffer, using a glass homogenizer. The microsomal membrane preparations were either immediately processed or stored at −80° C.

Preparation of Microsomal Membranes from *Mortierella*

*Mortierella* cultures were harvested after 5 days and placed on ice. All further procedures were carried out at 4° C. The mycelium was suspended in 0.1 M sodium phosphate buffer (pH 7.2), comprising 0.33 M sucrose, 0.1% BSA (free from fatty acids), 1000 units of catalase/ml and 1 mM Pefabloc. The following steps were carried out as described under "preparations of microsomal membranes from cotyledons of maturing seeds of sunflower and linseed".

Acyl-CoA Substrate Specificity of GPAT: Conversion of Individual Acyl-CoA Substrates in the Acylation of [$^{14}$C] Glycerol-3-Phosphate The specificity of the GPAT was studied to verify whether the enzyme has a preference for certain acyl-CoAs, in particular to determine whether the GPAT from oil seed plants converts LCPUFA-CoAs. Microsomal membranes were incubated with 0.5 mM (*Mortierella*) or 0.2 mM (sunflower and linseed) of one of the following acyl-CoAs: myristoyl-CoA (14:0-CoA), palmitoyl-CoA (16:0-CoA), palmitoleoyl-CoA (16:1-CoA), stearoyl-CoA (18:0-CoA), oleoyl-CoA (18:1-CoA), linoleoyl-CoA (18:2-CoA), dihomo-gamma-linolenoyl-CoA (20:3-CoA) or arachidonyl-CoA (20:4-CoA) and 5 mM [$^{14}$C] G3P. Microsomal membranes (equivalent to 50 μg of protein in the case of sunflower and *Mortierella* and 150 μg of protein in the case of linseed) were added to the reaction mixture in order to start the reaction. After incubation for 5 minutes, the lipids were extracted by the method of Bligh & Dyer, and the radioactivity incorporated in complex lipids was determined.

FIG. 11 and table 7a and 7b show the GPAT activities of *Mortierella*, sunflower and linseed for different acyl-CoA substrates.

The GPAT of *Mortierella* incorporates unsaturated fatty acids more efficiently than saturated fatty acids. Oleate and linoleate were converted with similar incorporation rates (100% and 90%, respectively). The incorporation of polyunsaturated fatty acids (20:3-CoA and 20:4-CoA) was only marginally lower (80% and 75%, respectively).

Oleate and linoleate are also the best substrates for GPAT in microsomal membranes (100% and 85% activity, respectively). Acyl-CoAs of the saturated fatty acids stearate and palmitate are only incorporated approximately half as efficiently (40% and 64%, respectively). This also applies analogously for 20:3-CoA (55%). Arachidonyl-CoA is a relatively poor substrate for sunflower GPAT (23%).

The GPAT in microsomal membranes of linseed has the lowest specific activity of all GPAT enzymes studied. With 6 nmol/min/mg protein, it is only half as active as sunflower GPAT and 5 times less active than the enzyme from *Mortierella*. As regards the substrate specificities behaves The most efficient acyl-CoA substrates of the linseed GPAT are oleate and linoleate (100% and 90%, respectively), as is the case with sunflower. The incorporation rates of the saturated fatty acids stearate and palmitate, at 65% and 90%, are markedly higher than in the case of sunflower. In contrast, arachidonyl-CoA is a very poor substrate for linseed GPAT (5%).

Acyl-CoA Substrate Specificity of LPAAT: Conversion of Individual Acyl-CoA Substrates in the Acylation of Lysophosphatidic Acid The specificity of the LPAAT was studied in order to verify whether the enzyme has a preference for certain acyl-CoAs, in particular to determine whether the LPAAT from oil seed plants converts LCPUFA-CoAs. LPAAT activity was determined in a continuous spectraphotometric assay in which 5,5-dithiobis-2-nitrobenzoate (DTNB) was used, and the change in absorption at 409 nm and 25° C. was monitored (F. M. Jackson et al. (1998) Microbiology 144: 2639-2645). The assay comprised sn-1-oleoyl-lysophosphatidic acid (30 nmol), DTNB (50 nmol) and 20 nmol of one of the following acyl-CoAs: palmitoyl-CoA (16:0-CoA), stearoyl-CoA (18:0-CoA), oleoyl-CoA (18:1-CoA), linoleoyl-CoA (18:2-CoA), dihomo-gamma-linolenyl-CoA (20:3-CoA) or arachidonyl-CoA (20:4-CoA) in 1 ml of 0.1 M phosphate buffer, pH 7.2. The CoA liberated in the reaction was determined quantitatively with the aid of the initial increase and the absorption coefficient of 13.6 mM-1×cm-1. Microsomal membranes (equivalent to 10 µg of protein in the case of *Mortierella* and 40 µg of protein in the case of sunflower and linseed) were added to the reaction mixture in order to start the reaction.

FIG. 11 and table 7a and 7b show the LPAAT activities of *Mortierella*, sunflower and linseed for different acyl-CoA substrates.

The *Mortierella* LPAAT incorporates oleoyl-CoA most efficiently (100%). Linoleoyl-CoA is likewise converted very efficiently (90%). While the saturated fatty acid substrates 16:0-CoA and 18:0-CoA are only incorporated at 40% and 36%, respectively, the LCPUFA substrates 20:3-CoA and 20:4-CoA are incorporated with a relatively high efficiency (in each case 65%).

In sunflower microsomal membranes, linoleoyl-CoA is the LPAAT substrate which is most efficiently incorporated into phosphatidic acid (250% relative to oleoyl-CoA). Both saturated and polyunsaturated acyl-CoA were poor substrates for sunflower LPAAT (relative activities less than 20%).

A very similar picture emerges for linseed LPAAT: linoleoyl-CoA is the best substrate (120% relative to oleoyl-CoA). Saturated fatty acids are poor LPAAT substrates (25% and 30% for 16:0-CoA and 18:0-CoA). Arachidonyl-CoA is converted least (19% relative activity).

Acyl-CoA Substrate Specificity of LPCAT: Conversion of Individual Acyl-CoA Substrates in the Acylation of Lysophosphatidylcholine In higher plants and fungi, fatty acids are desaturated for the production of polyunsaturated fatty acids while esterified with phosphatidylcholine (PC) (A. K. Stobart and S. Stymne (1985) Planta 163: 119-125; F. M. Jackson et al. (1998) Microbiology 144: 2639-2645). The involvement of PC in the desaturation of fatty acids also in fungi requires the existence of a functional transfer system for fatty acids into and from the sn-2 position of PC, analogously to the system which has been described for developing oil seeds (Jackson et al., 1998; Stobart et al., 1983). It is assumed that this transfer of the acyl group from acyl-CoA to the sn-2 position of PC is catalyzed by LPCAT. In the present context, the specificity of LPCAT was studied in order to verify whether the enzyme has a preference for certain acyl-CoAs, in particular in order to determine whether the oil seed LPCAT converts LCPUFA-CoAs.

LPCAT activity was determined in a continuous spectraphotometric assay in which 5,5-dithiobis-2-nitrobenzoate (DTNB) was used, and the change in absorption at 409 nm and 25° C. was monitored. The assay comprised sn-1-palmitolysophosphatidylcholine (30 nmol) as acyl acceptor, DTNB (50 nmol) and 20 nmol of one of the following acyl-CoAs: myristoyl-CoA (14:0-CoA), palmitoyl-CoA (16:0-CoA), palmitoleoyl-CoA (16:1-CoA), stearoyl-CoA (18:0-CoA), oleoyl-CoA (18:1-CoA), linoleoyl-CoA (18:2-CoA), dihomo-gamma-linolenyl-CoA (20:3-CoA) or arachidonyl-CoA (20:4-CoA) in 1 ml of 0.1 M phosphate buffer, pH 7.2. The reaction was started by addition of microsomal membrane preparation. The amount of microsomal membrane preparation added was 5 µg (*Mortierella* and sunflower) or 30 µg (linseed). The CoA liberated in the reaction was determined quantitatively with the aid of the initial increase and the absorption coefficient of 13.6 mM-1×cm-1 at 409 nm.

FIG. 12 and table 7a and 7b show the LPCAT activities of *Mortierella*, sunflower and linseed for different acyl-CoA substrates.

The results demonstrate that LPCAT is considerably more active in microsomal membranes of sunflower and *Mortierella* than in the case of linseed (see tables 10a and 10b). Besides 18:1 (100%), *Mortierella* LPCAT also converts 18:2 (40%), 20:3 (85%) and 20:4 (90%) with high efficiency. Saturated fatty acids are virtually not converted (relative activity less than 25%).

Sunflower LPCAT converts oleoyl-CoA and linoleoyl-CoA with similar efficiency (100% and 120% relative activities, respectively). Palmitoyl-CoA and stearoyl-CoA are poor substrates (relative activity less than 20%). 20:3-CoA and 20:4-CoA are virtually not converted (relative activities less than 5%).

The behavior of linseed LPCAT is similar: while oleoyl-CoA and linoleoyl-CoA are converted equally efficiently, no LPCAT activity was detected for 20:3-CoA and 20:4-CoA.

Discussion of the Data for the Acyl-CoA Specificity of GPAT, LPAAT and LPCAT

The substrate specificity of G3P-acylating enzymes was studied intensively in order to understand the mechanism of the distribution of fatty acids in phospholipids and triacylglycerol. Mammalian microsomal GPAT utilizes saturated and unsaturated acyl-CoAs (Yamada & Okuyama, 1978; Haldar et al., 1979; Tamai & Lands, 1974). The same was demonstrated for plant microsomal GPATs (Frentzen, 1993; Bafor et al. 1990). Jackson et al. (1998) furthermore demonstrated that neither GPAT nor LPAAT from the fungus *Mucor circinelloides* has a pronounced substrate specificity for acyl-CoAs. In the case of *Mucor*, both saturated and unsaturated fatty acids are acylated at both positions. A purified GPAT from the membrane fraction of *Mortierella ramanniana*, in contrast, showed a clear preference for oleoyl-CoA in contrast to palmitoyl-CoA (Mishra & Kamisaka, 2001).

In order to study whether GPAT in microsomal membranes from *Mortierella*, sunflower and linseed has a pronounced specificity for certain acyl-CoA species, individual acyl-CoAs were added to the microsomes. The *Mortierella* GPAT has a similarity with other plant, animal and fungal GPATs in as far as it has a broad specificity for acyl-CoAs, i.e. saturated and unsaturated fatty acids are acylated at the sn-1 position of G3P. The GPATs from sunflower and linseed microsomal membranes also utilize saturated and unsaturated acyl donors in a manner similar to what has been demonstrated for safflower and turnip rape (Bafor et al., 1990), albeit with a preference for unsaturated fatty acids. In general, the *Mortierella* GPAT is less discriminating than the sunflower and linseed enzyme. However, it is noticeable that sunflower and linseed GPATs virtually fails to convert arachidonyl-CoA, whereas the *Mortierella* enzyme acylates arachidonyl-CoA in a highly efficient manner.

In the second acylation step, *Mortierella*, sunflower and linseed LPAAT is active with sn-1-oleoyl lysophosphatidic acid as acyl acceptor. Similarly to GPAT, *Mortierella* LPAAT also has a broad specificity for acyl-CoAs. These data resemble those from guinea pig and rat liver microsomes, where, with the exception of stearoyl-CoA, LPAAT esterifies all acyl-CoAs with 16 and 18 carbon atoms, independently of the degree of saturation (Hill and Lands, 1968). In the present work, the sunflower and linseed LPAATs showed a pronounced specificity for linoleate and oleate. Saturated fatty acids, in contrast, were scarcely converted. These data agree with the observation that, in most oil seed crops, LPAATs show a higher specificity for unsaturated fatty acids (Griffiths et al, 1985; Ichihara et al., 1987). In sunflower and linseed, arachidonyl-CoA is a poor substrate, even for LPAAT. In comparison with GPAT, the LPAAT activity of sunflower and linseed is somewhat higher, however.

The specificity of LPCAT in microsomal preparations of *Mortierella* and sunflower was likewise studied. In *Mortierella*, LPCAT showed a broad spectrum of substrate specificity. The activity of the enzyme with different acyl-CoAs decreased in the order 18:1-CoA>20:4-CoA>20:3-CoA>16:1-CoA>18:2-CoA. Sunflower and linseed LPCAT showed virtually no activity with 20:3 and 20:4-CoA. LPCAT in bovine brain microsomes also showed a weak activity with saturated acyl-CoAs and a more pronounced activity with linoleoyl- and oleoyl-CoA (Deka et al., 1986). LPCAT from bovine heart muscle microsomes accept a wide range of substrates, although the activity is particularly high with arachidonyl-, linoleoyl- and oleoyl-CoA substrates (Sanjawara et al., 1988). In plants, the acyl specificity and selectivity of LPCAT was studied in microsomes of safflower (Stymne et al., 1983; Griffith et al., 1985) and linseed (Stymne & Stobart, 1985a). Oleate and linoleate were acylated with approximately the same conversion rate at the sn-2 position of PC. The activity with alpha-linoleate was only approximately half as much. Palmitate and stearate were considerably poorer LPCAT substrates when they were offered as individual acyl-CoAs. If a mixture of saturated and unsaturated acyl-CoAs was offered, palmitate and stearate were completely excluded by the PC. LPCAT in microsomal membranes of *Mucor circinelloides* too utilizes oleoyl- and linoleoyl-CoA much more efficiently than saturated fatty acids. There is thus a great degree of agreement in the specificity of plant, animal and fungal LPCATs. The fact that LPCAT from *Mortierella* microsomal membranes only shows poor activity with stearoyl-CoA and good activity with oleoyl- and linoleoyl-CoA might suggest that phosphatidylcholine acts as substrate for desaturases. It was demonstrated that oleate at the sn-1 and the sn-2 position of PC acts as substrate for Δ-12-deseturase in oil seed plants (Stymne & Stobart, 1986; Griffiths et al., 1988). Similar results were reported for *Mucor circinelloides* (Jackson et al., 1998). Δ-6-Desaturase also utilizes linoleate at the sn-2 position of PC in microsomal membrane preparations of *Mucor* (Jackson et al., 1998). The Δ-6-desaturase from borage, too, utilizes exclusively linoleate at the sn-2 position of the phospholipid (Stymne & Stobart, 1986; Griffiths et al., 1988).

The results described in example 6 demonstrate that acyltransferases from sunflower and linseed are not capable of efficiently incorporating LCPUFAs such as dihomo-γ-linolenate and arachidonate into the membrane and storage lipids. While LCPUFAs can be produced in oil seed plants such as sunflower, linseed or soybean, by functionally expressing the biosynthetic genes in question, it can be assumed that the resulting LCPUFAs are not efficiently incorporated into triacylglycerol as the result of lacking acyltransferase activities, which leads to a poor yield. Thus, acyltransferases with a high specificity for LCPUFA-CoAs must be transformed into oil seed plants in addition to LCPUFA biosynthetic genes (for example desaturases and elongases or polyketide synthases). Suitable for this purpose are acyltransferases from LCPUFA-producing organisms such as *Mortierella, Phaeodactylum, Crypthecodinium, Physcomitrella, Euglena* and *Thraustochytrium*.

Table 7a and 7b indicate the activity and acyl specificity of linseed, sunflower and *Mortierella alpina* acyltransferases.

TABLE 7a

Activity and acyl specificity of linseed and sunflower acyltransferases

| Enzyme activity | Linseed | | | Sunflower | | |
| --- | --- | --- | --- | --- | --- | --- |
| | GPAT | LPAAT | LPCAT | GPAT | LPAAT | LPCAT |
| Rate (nmol/min/mg protein) of the incorporation of oleic acid | 6 | 25 | 9 | 13 | 28 | 360 |
| Percentage incorporation in comparison with the incorporation of oleic acid | | | | | | |
| Myristoyl-CoA | 100 | 30 | 0 | 57 | 16 | 1 |
| SSA Palmitoyl-CoA | 90 | 25 | 5 | 64 | 15 | 13 |
| Palmitololeoyl-CoA | | 140 | 180 | | 140 | 90 |
| Stearoyl-CoA | 65 | 30 | 15 | 40 | 14 | 18 |
| Oleoyl-CoA | 100 | 100 | 100 | 100 | 100 | 100 |
| Linoleoyl-CoA | 90 | 120 | 100 | 85 | 250 | 120 |
| 20:3-CoA | | | 0 | 55 | | 3 |
| Arachidonoyl-CoA | 5 | 19 | 0 | 23 | 18 | 4 |

TABLE 7b

Activity and acyl specificity of *Mortierella alpine* acyltransferases

| | *Mortierella alpina* | | |
| --- | --- | --- | --- |
| Enzyme activity | GPAT | LPAAT | LPCAT |
| Rate (nmol/min/mg protein) of the incorporation of oleic acid | 30 | 51 | 350 |
| Percentage incorporation in comparison with the incorporation of oleic acid | | | |
| Myristoyl-CoA | | 55 | 0 |
| Palmitoyl-CoA | 66 | 40 | 25 |
| Palmitololeoyl-CoA | | 70 | 60 |
| Stearoyl-CoA | 50 | 36 | 10 |
| Oleoyl-CoA | 100 | 100 | 100 |
| Linoleoyl-CoA | 90 | 90 | 40 |

TABLE 7b-continued

Activity and acyl specificity of *Mortierella alpine* acyltransferases

| Enzyme activity | Mortierella alpina | | |
|---|---|---|---|
| | GPAT | LPAAT | LPCAT |
| 20:3-CoA | 80 | 65 | 85 |
| Arachidonoyl-CoA | 75 | 65 | 90 |

Example 7

Position Analysis of the Lipids from *Thraustochytrium*

It was demonstrated in example 6 that LCPUFA producers such as *Mortierella* have membrane-bound acyltransferase activities which incorporate LCPUFA-CoAs into membrane and storage lipids. Position analyses of the lipids from LCPUFA producers allow conclusions to be drawn regarding the in-vivo activities of the individual acyltransferases. This is why the question of which fatty acids are esterified at the individual positions of the lipids of the DHA producer *Thraustochytrium* was studied herein below.

a) Cultivation of *Thraustochytrium* spec. (TS) ATCC 26185

Cultivation of the fungus TS was performed in TS liquid culture and by streaking onto TS plates. Every three weeks, the fungi were transferred to fresh plates, stored for two days at 28° C. and thereafter stored at RT (approx. 23° C.). The liquid culture was incubated with shaking at 30° C. and harvested after 6 days. Shaking the culture with exposure to light increases the lipid yield (data not shown).

I) TS medium: (Bajpai et al. (1991) JAOCS 68: 507-514)

| a) 10× solution A (g/l): | |
|---|---|
| 250 g/l | NaCl |
| 50 g/l | MgSO$_4$.7H$_2$O |
| 10 g/l | KCl |
| 20 g/l | Na glutamate |
| 2 g/l | (NH4)$_2$SO$_4$ |
| 20 g/l | glucose |
| Autoclave solution. | |
| b) 10× solution B (g/l) | |
| 200 g/l | glucose |
| 20 g/l | yeast extract |
| Solution B was filter-sterilized. | |
| c) 10× solution C (g/l) | |
| 2 g/l | CaCO$_3$ |

To dissolve the CaCO$_3$, the solution was acidified with HCl and thereafter autoclaved.

| d) 10× solution D (g/l) | |
|---|---|
| 1 g/l | KH$_2$PO$_4$ |
| 1 g/l | NaHCO$_3$ |

The solution was autoclaved.

Supplements: thiamine and vitamin B$_{12}$

In each case 100 ml of the 10× solutions a) to d) and 10 µg/l thiamine and 1 g/l vitamin B$_{12}$ were added to 600 ml of autoclaved distilled water.

b) Lipid Analysis of *Thraustochytrium* (Bligh & Dyer (1959) Canadian J. Biochem. 37: 911-917)

To extract the total lipids from TS in liquid culture, the former were sedimented by centrifugation for 10 minutes at 3000 g. Resuspension of the cells in 10 ml of 0.45% NaCl was followed by boiling for 10 minutes in a water bath. After a further centrifugation step (as above) of the suspension, which had been transferred into 40 ml ground-glass tubes, the sediment was taken up in trichloromethane/methanol 1:2 (v/v). Here, the volume of the solvent mixture depended on the volume of the sediment. In general, 10 ml of the mixture were required for extracting a 100 ml culture. The first extraction took place for at least 6 hours, but mostly overnight at 8° C. on a shaker. Thereafter, what remained of the cells was resedimented and the supernatant was stored at 8° C. The second extraction was performed analogously to the first extraction, however using trichloromethane/methanol 2:1 (v/v) overnight. After the second extraction, what was left of the cells was resedimented, and the supernatant was combined with that of the first extraction. Then, the combined extracts were brought to a trichloromethane/methanol/0.45% NaCl ratio of 2:1:0.7 and shaken. Here, undesired coextracted substances such as sugars are extracted by shaking and then enter aqueous phase. Then, the extract was centrifuged until phase separation occurred, the organic bottom phase was removed and filtered through cotton wool into a round-bottomed flask to remove suspended matter. The lipid extract was evaporated to dryness on a rotary evaporator, the total lipids were transferred into trichloromethane/methanol 2:1 (v/v) and into a ground-glass tube. Then, the extract was again evaporated to dryness under nitrogen and finally taken up in trichloromethane/methanol 2:1 (v/v) in a defined volume.

c) Lipid Analysis from *Thraustochytrium* Membranes

Isolated *Thraustochytrium* membranes were transferred into a ground-glass tube, taken up in 0.45% NaCl and boiled for 5 minutes in a water bath to inactivate lipid-degrading enzymes. After centrifugation (5 minutes, 3000×g), the aqueous supernatant was decanted off. The lipids were extracted for one hour at 4° C. in trichloromethane/methanol (2:1). After addition of ⅓ volume of 0.45% NaCl, the samples were centrifuged to improve phase separation (5 minutes, 3000×g). The lipid-containing bottom phase was removed and concentrated in vacuo. The lipids were taken up in a suitable volume of trichloromethane.

Directly thereafter, the lipids were applied to silica gel plates (silica gel 60, 20×20 cm, 0.25 mm layer thickness; Merck, Darmstadt) for subjecting the phospholipids to thin-layer chromatographic separation, together with suitable standards. The mobile phase used was trichloromethane/methanol/glacial acetic acid/H$_2$O 91/30/4/4 (v/v/v/v). The development time was 1.5 hours. After the solvent had been evaporated, the plates were stained with 2',7'-dichlorofluorescein (Merck, Darmstadt; in 0.3% isopropanol) and visualized under UV light (366 nm).

d) Lipase Digestion of the *Thraustochytrium* Total Lipids

The enzymatic digestion is performed by means of pancreatic lipase (EC 3.1.1.3). The hydrolytic cleavage takes place at the phase boundary between fat and water, the enzyme specifically attacking the terminal ester bonds in the sn-1 and sn-3 positions in triacylglycerols (TAGs). An intermediary concentration of 1,2- and 2,3-diacyl-sn-glycerols, which are subsequently digested further to give sn-2 monoacylglycerols, takes place. Following separation by thin-layer chromatography and recovery of the sn-2 monoacylglycerol fraction, the fatty acid composition of the TAGs in the middle position is determined.

50 mg of the total lipid were weighed into a ground-glass tube. After addition of 0.5 ml of Tris buffer, 0.1 ml of $CaCl_2$ solution and 0.25 ml of bile salt solution (0.05% (w/v) bile salt; Sigma, Deisenhofen), the ground tube was sealed. The mixture was mixed for one minute and subsequently pre-warmed for one minute in a water bath at 40° C. in order to emulsify the sample.

Hydrolysis was effected after addition of pancreatic lipase (EC 3.1.1.3; Sigma, Deisenhofen; 2 mg of lipase per 5 mg of lipid; lipase freshly dissolved in 0.5 ml of Tris buffer) at 38° C. and high shaking frequency (if possible 1200 rpm). After 30 minutes, the reaction was stopped by addition of 1 ml of HCl (6 N) and 1 ml of ethanol.

The reaction mixture was extracted twice in the centrifuge glass, using in each case 4 ml of diethyl ether. In doing so, the ether phase, which was the top phase, was removed. The aqueous phase which remained was reextracted with diethyl ether. The formation of emulsions was additionally prevented in each extraction step by centrifugation. The combined ether phases were washed by shaking with in each case 3 ml of water (distilled). The organic phase was transferred into a fresh tube and dried using sodium sulfate. After centrifugation for 2 minutes at 3000×g, the clear supernatant was removed and the sodium sulfate pellet was again extracted by shaking with diethyl ether, centrifuged as stated above, and the organic phases were combined. After concentration of the ether extract in vacuo, the extract was immediately thereafter applied to silica gel plates (silica gel 60, 20×20 cm, 0.25 mm layer thickness; Merck, Darmstadt) in order to subject the partial glycerides to separation by thin-layer chromatography. The mobile phase used was diisopropyl ether/glacial acetic acid 40:1 (v/v). The development time was 35-45 minutes. After evaporation of the solvent, the plates were stained using 2',7'-dichlorofluorescein (Merck, Darmstadt; in 0.3% isopropanol) and visualized under UV light. The individual lipid fractions were separated in the following order: monoacylglycerols (sn-2 MAGs, immediately above the starting line), diacylglycerols (sn-1,2- and sn-2,3-DAGs), free fatty acids (FFA) and the unreacted TAGs.

The MAG band was scraped off from the silica gel plate. The fatty acid composition of the TAGs was determined by means of transmethylation, followed by gas-chromatographic separation of the fatty acid methyl esters (FAMEs).

Tris buffer:
1M Tris/HCl, bring to pH 8.0 using HCl
CaCl solution
2.2% (w/v) $CaCl_2$ e) Lipase Digestion of the *Thraustochytrium* Membrane Lipids (Fischer et al., 1973)

The position analysis of the membrane lipids was carried out by enzymatic hydrolysis of the sn-2 ester bond with phospholipase $A_2$ (EC 3.1.1.4).

The isolated membrane lipids were concentrated in vacuo, treated with 0.5 ml of hydrolysis buffer and dispersed for 5 minutes using a sonicator. Hydrolysis was effected at RT after addition of 50 U of phospholipase $A_2$. The reaction was stopped by addition of 4 ml of trichloromethane/methanol 2:1 (v/v) and 0.45% NaCl. The organic, bottom phase was transferred into a fresh vessel, evaporated on a rotary evaporator and taken up in 200 μl of trichloromethane/methanol 2:1 (v/v).

Directly thereafter, the mixture was applied to silica gel plates (silica gel 60, 20×20 cm, 0.25 mm layer thickness; Merck, Darmstadt) in order to subject the phospholipids to thin-layer chromatographic separation. The mobile phase used was trichloromethane/methanol/glacial acetic acid/$H_2O$ 91/30/4/4 (v/v/v/v). The development time was 1.5 hours. After evaporation of the solvent, the plates were stained using 2',7'-dichlorofluorescein (Merck, Darmstadt; in 0.3% isopropanol) and visualized under UV light. Bands of interest were scraped off from the silica gel plate, transmethylated and thereafter analyzed in a gas chromatograph.

| Hydrolysis buffer | |
|---|---|
| 0.1 M | boric acid, pH 8.0 |
| 3 mM | $CaCl_2$ |
| 1.4 mM | sodium deoxycholate | f) Transmethylation of Fatty Acids with Sodium Methylate (Method of Lühs)

After the solvent had been evaporated, or after material had been scraped from the thin-layer plate (for example in the case of sn-2 analysis of the total lipids), lipid samples were treated with 2 ml of sodium methylate solution for transesterification purposes. The mixture was shaken thoroughly and, in order to subject the fatty acids to transmethylation, incubated for approximately 30 minutes at room temperature. Thereafter, 1.5 ml of isooctane were added and the samples were carefully shaken twice. The mixture was stored for 30 minutes at 4° C., during which time the fatty acid methyl esters (FAMEs) enter the isooctane phase. After clear phase separation had occurred, the top phase, which was the isooctane phase, was pipetted into a GC tube and the sample was analyzed in a gas chromatograph.

Sodium Methylate Solution 5 g of sodium methylate were dissolved in 800 ml of methanol (99%) at 50° C., using a magnetic stirrer, and, after cooling, made up to 1000 ml with isooctane.

g) Methylation of Free Fatty Acids with Methanolic Sulfuric Acid

In a Pyrex tube with screw top, 1 ml of 1 N methanolic sulfuric acid was added to the concentrated lipid extract. The mixture was incubated for one hour at 80° C. After the mixture had been cooled briefly, it was treated with 1 ml of 0.9% NaCl and mixed. Thereafter, an equal volume of hexane was added, and the mixture was mixed thoroughly and incubated at 4° C. for 30 minutes until phase separation took place. The hexane phase, which was the top phase, was transferred into a GC tube and analyzed in a gas chromatograph.

Methanolic Sulfuric Acid 2 ml of dimethoxypropanes and 0.5 M $H_2SO_4$ were added to 100 ml of (anhydrous) methanol.

h) Gas-Chromatographic Analysis

The following parameters of the gas-chromatographic system were maintained for the GC analyses:

| | |
|---|---|
| Equipment type | HP 6890 GC |
| Injector | HP GC injector |
| Detector | flame ionization detector (FID), temp. 250° C. |
| Column | J&W DW23 50% cyanopropyl/methylsiloxanes, 30 m, 0.5 mm diameter |
| Oven temperature | 220° C. |
| Carrier gas | hydrogen |
| Autosampler | HP 7673, injection volume 1 μl of sample | i) The Lipid Analysis of the *Thraustochytrium* Lipids Gave the Following Results

| Lipid fraction | Fatty acid composition | | | |
|---|---|---|---|---|
|  | 16:0 | 22:3 ω-3 | 22:4 ω-3 | 22:6 ω-3 |
| Total TAG | 24% | 12% | 31% | 23% |
| TAG sn-2 | 21% | 26% |  | 43% |
| Total membrane lipids | 16% | 13% |  | 23% |
| Membrane lipids sn-2 | 34% | 18% |  | 36% |

The results show that *Thraustochytrium* has a high DHA content in its lipids. With besides palmitate, DHA is the main component of the triacylglycerols and dominating fatty acid of the membrane lipids. It is noticeable that DHA is markedly concentrated at the sn-2 position of both the triacylglycerol and the membrane lipids: 36-43% of the fatty acids at the sn-2 position is DHA. As a result of this data, it can be assumed that *Thraustochytrium* has an active LPAAT with a high specificity for DHA-CoA.

Example 8

Isolation of Total RNA and Poly(A)$^+$ RNA

Total RNA was isolated from plants such as linseed and oilseed rape etc. by a method described by Logemann et al. (Anal. Biochem. (1987) 163: 21). The total RNA can be obtained from the moss *Physcomitrella patens* from protonemal tissue using the GTC method (Reski et al. (1994) Mol. Gen. Genet. 244: 351-359).

a) RNA Isolation from *Thraustochytrium, Cryptecodinium* and *Shewanella*:

Frozen algal samples (−70° C.) were comminuted in an ice-cold mortar under liquid nitrogen to give a fine powder. 2 volumes of homogenization medium (12.024 g sorbitol, 40.0 ml 1 M Tris-RC1, pH 9 (0.2 M); 12.0 ml 5 M NaCl (0.3 M), 8.0 ml 250 mM EDTA, 761.0 mg EGTA, 40.0 ml 10% SDS were made up to 200 ml with H$_2$O and the pH was brought to 8.5) and 4 volumes of phenol comprising 0.2% of mercaptoethanol were added to the frozen cell powder at 40-50° C., with thorough mixing. Thereafter, 2 volumes of chloroform were added and the mixture was stirred vigorously for 15 minutes. The mixture was centrifuged for 10 minutes at 10 000 g and the aqueous phase was extracted with phenol/chloroform (2 vol/2 vol) and finally with chloroform.

The resulting volume of the aqueous phase was treated with 1/20 vol of 4 M sodium acetate (pR 6) and 1 vol of isopropanol (ice-cold), and the nucleic acids were precipitated ON (=Overnight) at −20° C. The mixture was centrifuged for 30 minutes at 10 000 g and the supernatant was pipetted off. This was followed by a wash step with 70% EtOH and another centrifugation. The sediment was in Tris borate buffer (80 mM Tris borate buffer, 10 mM EDTA, pH 7.0). Then, the supernatant was mixed with ⅓ vol of 8 M LiCl, mixed and incubated for 30 minutes at 4° C. After recentrifugation, the sediment was washed with 70% ethanol and centrifuged, and the sediment was subsequently dissolved in RNAse-free water.

Poly(A}+ RNA was isolated using Dyna Beads (Dynal, Oslo, Finland) following the instructions in the manufacturer's protocol.

After the RNA or poly(A}+ RNA concentration had been determined, the RNA was precipitated by addition of 1/10 volume of 3 M sodium acetate, pH 4.6, and 2 volumes of ethanol and stored at −70° C.

For the analysis, in each case 20 μg of RNA were separated in a formaldehyde-comprising, 1.5% strength agarose gel and transferred onto nylon membranes (Hybond, Amersham). Specific transcripts were detected as described by Amasino (Amasino (1986) Anal. Biochem. 152: 304).

Example 9

Construction of cDNA Libraries

To construct the cDNA libraries from *Physcomitrella, Thraustochytrium* and *Fusarium*, the first-strand synthesis was carried out using reverse transcriptase from murine leukemia virus (Roche, Mannheim, Germany) and oligo-d(T) primers, while the second-strand synthesis was achieved by incubation with DNA polymerase 1, Klenow enzyme and RNAse H cleavage at 12° C. (2 hours), 16° C. (1 hour) and 22° C. (1 hour): the reaction was stopped by incubation at 65° C. (10 minutes) and subsequently transferred onto ice. Double-stranded DNA molecules were made blunt-ended using T4 DNA polymerase (Roche, Mannheim) at 37° C. (30 minutes). The nucleotides were removed by means of phenol/chloroform extraction and Sephadex G50 centrifugation columns. EcoRI/XhoI adapters (Pharmacia, Freiburg, Germany) were ligated onto the cDNA ends by means of T4 DNA ligase (Roche, 12° C., overnight), cut again with XhoI and phosphorylated by incubation with polynucleotide kinase (Roche, 37° C., 30 min). This mixture was subjected to separation on a low-melting agarose gel. DNA molecules of above 300 base pairs were eluted from the gel, extracted with phenol, concentrated on Elutip D columns (Schleicher and Schüll, Dassel, Germany) and ligated with vector arms and packaged in lambda-ZAPII phages or lambda-ZAP Express phages using the Gigapack Gold kit (Stratagene, Amsterdam, the Netherlands), using the manufacturer's material and following their instructions.

Example 10

DNA Sequencing and Computer Analysis cDNA libraries as described in example 9 were used for DNA sequencing by standard methods, in particular by means of the chain termination method using the ABI PRISM Big Dye Terminator Cycle Sequencing Ready Reaction kit (Perkin-Elmer, Weiterstadt, Germany). Random individual clones were sequenced after plasmid preparation from cDNA libraries via in-vivo mass excision and retransformation of DH10B on agar plates (details on materials and protocol from Stratagene, Amsterdam, the Netherlands). Plasmid DNA was prepared from *E. coli* overnight cultures which had been grown in Luria broth with ampicillin (see Sambrook et al. (1989) (Cold Spring Harbor Laboratory Press: ISBN 0-87969-309-6)) on a Qiagen DNA preparation robot (Qiagen, Hilden) following the manufacturer's protocol. Sequencing primers with the following nucleotide sequences were used:

5'-CAGGAAACAGCTATGACC-3' (SEQ ID NO: 95)

5'-CTAAAGGGAACAAAAGCTG-3' (SEQ ID NO: 96)

5'-TGTAAAACGACGGCCAGT-3' (SEQ ID NO: 97)

The sequences were processed and annotated using the standard software package EST-MAX, which is commercially available from Bio-Max (Munich, Germany). Using comparative algorithms, and using a search sequence, the BLAST program was used for searching for homologous genes (Altschul et al. (1997) "Gapped BLAST and PSI-BLAST: A new generation of protein database search programs", Nucleic Acids Res. 25: 3389-3402).

Example 11

Identification of Genes by Means of Hybridization

Gene sequences can be used for identifying homologous or heterologous genes from cDNA or genomic libraries.

Homologous genes (i.e. full-length cDNA clones which are homologous, or homologs) can be isolated via nucleic acid hybridization using, for example, cDNA libraries: depending on the frequency of the gene of interest, 100 000 up to 1 000 000 recombinant bacteriophages are plated and transferred onto a nylon membrane. After denaturation with alkali, the DNA is immobilized on the membrane, for example by UV crosslinking. Hybridization is effected under high-stringency conditions. The wash steps and the hybridization are carried out in aqueous solution at a ionic strength of 1 M NaCl and a temperature of 68° C. Hybridization probes were prepared for example by labeling by means of radioactive (32P) nick transcription (High Prime, Roche, Mannheim, Germany). The signals are detected by means of autoradiography.

Partially homologous or heterologous genes which are related, but not identical, can be identified analogously to the above-described method using low-stringency hybridization and wash conditions. The ionic strength for the aqueous hybridization was usually kept at 1 M NaCl, the temperature being lowered gradually from 68 to 42° C.

Gene sequences with homologies with only a single domain of, for example, 10 to 20 amino acids can be isolated using synthetic radiolabeled oligonucleotide probes. Radiolabeled oligonucleotides are prepared by phosphorylating the 5' end of two complementary oligonucleotides with T4 polynucleotide kinase. The complementary oligonucleotides are hybridized with one another and ligated so that concatemers are formed. The double-stranded concatemers are radiolabeled, for example by Nick transcription. Hybridization is usually effected under low-stringency conditions, using high oligonucleotide concentrations.

Oligonucleotide Hybridization Solution:
  6×SSC
  0.01 M sodium phosphate
  1 mM EDTA (pH 8)
  0.5% SDS
  100 µg/ml denatured salmon sperm DNA
  0.1% dry skim milk During the hybridization, the temperature was gradually reduced to 5-10° C. below the calculated oligonucleotide Tm or down to room temperature means RT=23° C. in all experiments, unless otherwise specified), followed by wash steps and autoradiography. Washing was carried out with extremely low stringency, for example 3 wash steps using 4×SSC. Further details are as described by Sambrook, J., et al. (1989), "Molecular Cloning: A Laboratory Manual", Cold Spring Harbor Laboratory Press, or Ausubel, F. M., et al. (1994) "Current Protocols in Molecular Biology", John Wiley & Sons.

Example 12

Isolation and Cloning of an LPAAT Full-Length Clone from *Thraustochytrium* Screening a *Thraustochytrium* cDNA Library Analogously to what has been described for example 9, a *Thraustochytrium* cDNA library was generated. In the next step, the phage library was converted into a plasmid library by means of a helper phage, following the manufacturer's instruction. The plasmid library was plated on LB medium, 0.8% agar, 100 mg/l ampicillin and incubated. Grown bacterial colonies were selected randomly, grown in liquid medium (LB, 100 mg/l ampicillin) and sequenced as described in example 10.

The sequences obtained were searched for redundancies, and these were removed. This gave rise to an assortment of sequences which describes a unigene set. This sequence set was input into the Pedant database (Biomax AG, Martinsried, Germany). A short sequence section with a low degree of similarity to known acyltransferases was found by means of BLAST analysis, using conserved regions within acyltransferases. The existing sequence information was used for generating primers (LPAAT069-5' and LPAAT069-3'). Using this fragment, the cDNA library was then searched for a full-length clone (table 8).

TABLE 8

Sequences of the primers employed

| Primer | Sequence | $T_m$ (° C.) |
|---|---|---|
| LPAAT069-5' | 5'-GCT ACA TTG CCA TGG AGC-3' (SEQ ID NO: 98) | 56 |
| LPAAT069-3' | 5'-GCT ACA AGA GGT CAG GTC G-3' (SEQ ID NO: 99) | 59 |
| ACtrau-5' | 5'-CTG GAT CCA TGA GCG CGT GGA CGA G-3' (SEQ ID NO: 100) | 69 (52) |
| ACtrau-3' | 5'-TTG GAT CCC AAG AGG TCA GGT CGG A-3' (SEQ ID NO: 101) | 66 (54) |
| ACtrau-3'stop | 5'-TTG GAT CCC TAC AAG AGG TCA GGT CG-3' (SEQ ID NO: 102) | 66 (48) |
| YES-HIS-5' | 5'-CTG AGC TCA TGA GCG CGT GGA G-3' (SEQ ID NO: 103) | 69 (56) |
| YES-HIS-3' | 5'-ATG GAT CCG TGA TGG TGA TGG TGA TGC AAG AGG TC-3' (SEQ ID NO: 104) | 72 (40) |

The melting point $T_m$ (° C.) of the oligonucleotides was calculated by the method of Suggs et al. (1981): $T_m$ (° C.) = 4 (G + C) + 2 (A + T) $T_m$ values in brackets refer to actually binding nucleotides of primers whose ends have been modified by additionally introduced cleavage sites.

In the PCR experiments, the constituents of a PCR standard mix, shown hereinbelow, were pipetted into a PCR reaction vessel on ice, placed into the thermoblock, and the temperature profile shown hereinbelow was started. The polymerase employed was in almost all cases Taq polymerase (Gibco BRL), with Pfu polymerase (Stratagene) only being used for amplifications for the purposes of functional expression in *E. coli* JC201. In all experiments, the polymerase was added via what is known as a "hot start", where the enzyme is added only after the DNA template has been subjected to denaturation for 5 minutes. The annealing temperatures ($T_a$) were chosen to be 3-5° C. below the mean melting point $T_m$ of the primer pairs.

PCR Standard Mix (for Taq Polymerase)
 5 μp 10×PCR buffer (100 mM Tri-HCl, pH 8.3; 15 mM $MgCl_2$, 500 mM KCl)
 1 μl dNTP mix (10 mM dATP, dGTP, dTTP and dCTP)
 1 μl primer 1 (30 μM)
 1 μl primer 2 (30 μM)
 1 U Taq polymerase
 50-100 no plasmid DNA template
 make up to 50 μl with distilled water Hot-Start Program
 1. denaturation 95° C., 5 min
 2. hot start 25° C., 3 min→addition of the polymerase
 3. denaturation 94° C. 30 s
 4. annealing $T_m$-5° C., 30 s
 5. polymerization 72° C., 1-3 min (approx. 60 s for 1.0 kbp)
 Steps 3. to 5. were repeated cyclically 25 to 30 times.
 6. polymerization 72° C., 5 min
 7. termination 4° C.

a) Cold Labeling of DNA

DNA probes were cold-labeled using the "PCR DIG PROBE SYNTHESIS KIT" (Boehringer Mannheim). To do so, DNA fragments were labeled in a PCR reaction with digoxigenin-labeled deoxyuridine triphosphate (DIG-dUTP). The detection was subsequently carried out by means of an anti-digoxygenin antibody which is conjugated with alkaline phosphatase, and addition of chemiluminescence or color substrates.

To avoid background signals which can be attributed to vector sequences, the PCR labeling first involved, in a first PCR, the amplification of the desired DNA with unlabeled dNTPs, the linear fragment was purified via an agarose gel and used as template for the actual PCR labeling, in which, in turn, the primer pair of the first PCR was employed. The labeling reaction was carried out as specified in the manufacturer's instructions. The chosen primer combinations are compiled in the table which follows.

| Primer | Sequence |
|---|---|
| LPAAT069-5' | 5'-GCT ACA TTG CCA TGG AGC-3' (SEQ ID NO: 105) |
| LPAAT069-3' | 5'-GCT ACA AGA GGT CAG GTC G-3' (SEQ ID NO: 98) | b) Screening a cDNA Library

To isolate a complete clone, a *Thraustochytrium* cDNA library (in λTriplEx2) was searched with the DIG-labeled probe. The probe was generated using the primers LPAAT069-3' and LPAAT069-5, derived from the EST clone s_t002038069 known cDNA sequence which might code for a *Thraustochytrium* LPAAT.

$5×10^4$ plaques were plated in each: case on 10 large NZY plates, following the manufacturer's instructions (Stratagene). To transfer the phages onto nitrocellulose filters (Hybond™-C, Amersham), the filters were placed on the plates for 1 minute, and their precise position was marked by 3 stamps with a cannula. The filters, stamped side uppermost, were subsequently treated first for 5 minutes with denaturation solution, then for 5 minutes with neutralization solution and finally for 15 minutes with 2×SSC solution. This was carried out using 3 sheets of Whatman 3 MM paper which had been impregnated with the solutions. After the filters had dried for 5 minutes, the DNA was immobilized by UV treatment with 0.12 Joule/$cm^2$ (UV-Crosslinker, Hoefer Scientific Instruments). Hybridization and calorimetric detection were carried out using the "Dig System für Filter Hybridisierung" from Boehringer (Mannheim) in accordance with the manufacturer's instructions. The hybridization buffers used were standard buffers, the hybridization being carried out in 80 ml of hybridization buffer using 15 μl of the probe PCR mix. After detection had been effected, the precise position of the signals and the three reference points of the filters were transferred to plastic films in order to identify the positive plaques on the plates, using the former as stencil. The positive plaques were then excised using a flamed cork borer (diameter 5 mm), transferred into 1 ml of SM buffer supplemented with 20 μl of $CHCl_3$, and the phages were eluted from the agar plugs overnight at 40° C. Accurate excision of the plaques was almost impossible as the result of their high density and small size. This is why, as a rule, one to two rescreens are carried out. In this case, the phage lysates were studied for approx. 570 bp fragments by means of PCR and the primers LPAAT069-3' and LPAAt-5. To this end, aliquots of the phage lysates were treated with EDTA (final concentration 10 mM), and 1 μl of this was employed as template for the PCR. Using positive lysates, in-vivo excisions were carried out as specified in the "ZAP-cDNA® Gigapack® II Gold Cloning Kit" (Stratagene), but instead of the 10-50 μL as stated, only 2 μl of the infected SOLR cells were plated onto LB-Amp plates and incubated overnight at 37° C. The plasmids from the resulting colonies were analyzed directly by means of PCR and the primers LPAAT-3' and LPAAT-5'. To this end, pools were generated by rubbing in each case 6 colonies into 20 μl of distilled water in an Eppendorf tube, using sterile toothpicks, and the tubes were subjected to 3× freeze-thaw cycles in order to lyze the cells, centrifuged for 5 minutes at 14 000×g, and 2 μl of the supernatant was employed as template in the PCR reaction. Positive pools were isolated, and the plasmids were isolated via plasmid minipreps and analyzed via PCR, restriction analyses and DNA sequencing reactions.

Finally, a *Thraustochytrium* LPAAT full-length clone was identified; its DNA sequence is shown in SEQ ID NO: 1. The derived amino acid sequence is shown in SEQ ID NO: 2.

NZY Medium (Per Liter, NZY Plates made with 15 g Agar)
 5 g NaCl
 5 g yeast extract
 10 g NZ amine (casein hydrolysate)
 pH 7.5 (NaOH)
 2 g $MgSO_4$ (filter-sterilized)

Denaturation Solution
 0.5 M NaOH
 1.5 M NaCl

Neutralization Solution
 1.0 M Tris-HCl, pH 7.5
 1.5 M NaCl

20×SSC
 3.0 M NaCl
 0.3 M sodium citrate, pH 7.0

Standard Buffer
 5×SSC
 0.1% (w/v) N-laurylsarcosine
 0.02% (w/v) SDS
 1% blocking reagent SM Buffer (Per Liter)
  5.8 g NaCl
  2 g MgSO$_4$
  50 ml 1 M Tris-HCl, pH 7.5
  5 ml 2% strength gelatin Example 13

Isolation and Cloning of Full-Length Clones for PUFA-Specific Acyltransferases from *Physcomitrella patens*, *Mortierella alpina* and *Shewanella hanedai*

RNA was isolated, and a cDNA library generated, from *Physcomitrella patens* and *Mortierella alpina* as described in examples 8 and 9.

In the next step, the phage library was converted into a plasmid library by means of a helper phage, following the manufacturer's instructions. The plasmid library was plated on LB medium, 0.8% agar, 100 mg/l ampicillin and incubated. Grown bacterial colonies were selected randomly, grown in liquid medium (LB, 100 mg/l ampicillin) and sequenced as described in example 10.

The sequences obtained were searched for redundancies, and these were removed. This gave rise to an assortment of sequences which describes a unigene set. This sequence set was input into the Pedant database (Biomax AG, Martinsried, Germany). Short sequence sections with a low degree of similarity to known acyltransferases were found by means of BLAST analysis, using conserved regions within acyltransferases (table 9). The existing sequence information was used for generating primers (table 10). Using these primers, the full-length clone was amplified.

For the *Shewanella hanedai* acyltransferase, the public database of *Shewanella putrefaciens* MR1 (TIGR database http://tigrblast.tigr.org/ufmg/) was searched for acyltransferases. A sequence with homology to acyltransferases was found in the database. A PCR fragment of this sequence was generated by means of standard primers T7 and T3. The resulting product was illustrated as in example 10 a) and b), labeled and employed for searching a genomic *Shewanella hanedai* library.

*Shewanella hanedai* genomic DNA was isolated by the following protocol:

A 100 ml culture was grown at 30° C. to an optical density of 1.0. 60 ml of this were centrifuged for 3 minutes at 3000×g. The pellet was resuspended in 6 ml of twice-distilled H$_2$O and divided between 1.5 ml vessels, centrifuged, and the supernatant was discarded. The pellets were resuspended and lyzed by vortexing with 200 μl of solution A, 200 μL of phenol/chloroform (1:1) and 0.3 g of glass beads. After addition of 200 μl of TE buffer pH 8.0, the mixture was centrifuged for 5 minutes. The supernatant was subjected to ethanol precipitation with 1 ml of ethanol. After the precipitation, the resulting pellet was dissolved in 400 μl of TE buffer pH 8.0+30 μg/ml Rnase A. After incubation for 5 minutes at 37° C., 18 μl of 3 M sodium acetate solution pH 4.8 and 1 ml of ethanol were added, and the precipitated DNA was pelleted by centrifugation. The DNA pellet was dissolved in 25 μl of twice-distilled H$_2$O. The concentration of the genomic DNA was determined by its absorption at 260 nm.

Solution A:
  2% Trition-X100
  1% SDS
  0.1 M NaCl
  0.01 M Tris-HCl pH 8.0
  0.001 M EDTA The resulting genomic DNA was incubated with the restriction enzyme Sau3A (New England Biolabs) for 1 hour at 25° C. following the manufacturer's instructions. The resulting fragments were then ligated into a BamHI-digested pUC18 plasmid, using T4 ligase (Roche). The resulting library was then searched in the same manner as described in example 10. A clone comprising a 1.7 kb genomic fragment and having a 687 bp coding sequence with similarity to acyltransferases was found.

The *Shewanella hanedai* sequence has a particularly high degree of similarity to the *Chaenorabdidis elegans* LPCAT. The similarity of the two sequences at the amino acid level is 26%.

TABLE 9

Identified acyltransferase from the abovementioned cDNA libraries

| Clone No. | Organism | Homology with |
|---|---|---|
| MaLPAAT1.1 | *M. alpina* | LPAAT |
| MaLPAAT1.2 | *M. alpina* | LPAAT |
| ShLPAAT | *S. hanedai* | LPAAT |
| T6 | *Thrausto.* | LPAAT |
| pp004064045r | *P. patens* | LPAAT |
| pp020064227r | *P. patens* | LPAAT |
| pp015052144r | *P. patens* | GPAT/LPAT |
| pp004034225r | *P. patens* | GPAT |
| pp004104272r | *P. patens* | Ca-LPAAT |
| pp020018156r | *P. patens* | Ca-LPAAT |
| pp015034341r | *P. patens* | LPAAT |
| pp015033362r | *P. patens* | LCAT |
| Fg003028298 | *Fusarium* | LCAT |

TABLE 10

Sequences of the primers employed:

| Clone No. | Organism | Primer sequence in 5'-3' orientation | Length in bp |
|---|---|---|---|
| MaLPAAT1.1 | *M. alpina* | atggatgaatccaccacgacc (SEQ ID NO: 123) atcagcccgatgcttgctgc (SEQ ID NO: 124) | 1254 |
| MaLPAAT1.2 | *M. alpina* | atgaaccctatctacaagggt (SEQ ID NO: 125) tcagcccgatgcttgctgc (SEQ ID NO: 126) | 1170 |
| ShLPAAT | *S. hanedai* | atgttactgctagcatttgt (SEQ ID NO: 127) ttactttgccattaagg (SEQ ID NO: 128) | 687 |
| T6 | *Thrausto.* | atgagcgcgtggacgagggc (SEQ ID NO: 129) ctacaagaggtcaggtcgga cgtaca (SEQ ID NO: 130) | 918 |
| Pp00406404 | *P. patens* | Atggctttgatgtatatctg (SEQ ID NO: 131) ttacacgattttctttttag (SEQ ID NO: 132) | 714 |
| Pp02006422 | *P. patens* | atgctgatattacagcccttc (SEQ ID NO: 133) ctaatgaacaggaagaccgt (SEQ ID NO: 134) | 657 |
| Pp01505214 | *P. patens* | atgatccggattttcagag (SEQ ID NO: 135) tcagtccgttttgccgaggt (SEQ ID NO: 136) | 444 |

TABLE 10-continued

Sequences of the primers employed:

| Clone No. | Organism | Primer sequence in 5'-3' orientation | Length in bp |
|---|---|---|---|
| Pp00403422 | P. patens | atgccgtcgctgtttcggg (SEQ ID NO: 137) tcaatcagttcgcctgcttc (SEQ ID NO: 138) | 1305 |
| Pp00410427 | P. patens | atgctgatattacagcccttc (SEQ ID NO: 139) ctaatgaacaggaagaccgt (SEQ ID NO: 140) | 1566 |
| Pp02001815 | P. patens | atgaccagcacggaaaatac (SEQ ID NO: 141) ctagatgttagtttcactc (SEQ ID NO: 142) | 1560 |
| Pp01503434 | P. patens | atgattatgatggaggtgctg (SEQ ID NO: 143) tcagtccgttttgccgagg (SEQ ID NO: 144) | 1014 |
| Pp01503336 | P. patens | atgtgttcaatttcttgtgg (SEQ ID NO: 145) ttagtggaacataagctgtt (SEQ ID NO: 146) | 1503 |
| Fg003028298 | Fusarium | atgggaaagtccactttac (SEQ ID NO: 147) ctatgaagtctcctcatca tcg (SEQ ID NO: 148) | 1893 |

In the PCR experiments, the constituents of a PCR standard mix, shown hereinbelow, were pipetted into a PCR reaction vessel on ice, placed into the thermoblock, and the temperature profile shown hereinbelow was started. The polymerase employed was in almost all cases Taq polymerase (Gibco BRL), with Pfu polymerase (Stratagene) only being used for amplifications for the purposes of functional expression in *E. coli* JC201. In all experiments, the polymerase was added via what is known as a "hot start", where the enzyme is added only after the DNA template has been subjected to denaturation for 5 minutes. The annealing, temperatures ($T_a$) were chosen to be 3-5° C. below the mean melting point $T_m$ of the primer pairs.

PCR Standard Mix (for Taq Polymerase)

5 µl 10×PCR buffer (100 mM Tri-HCl, pH 8.3; 15 mM MgCl$_2$, 500 mM KCl)

1 µl dNTP mix (10 mM dATP, dGTP, dTTP and dCTP)

1 µl primer 1 (30 µM)

1 µl primer 2 (30 µM)

1 U Taq polymerase 50-100 ng plasmid DNA template make up to 50 µl with distilled water Hot-Start Program 1. denaturation 95° C., 5 min
2. hot start 25° C., 3 min→addition of the polymerase
3. denaturation 94° C. 30 s
4. annealing $T_m$-5° C., 30 s
5. polymerization 72° C., 1-3 min (approx. 60 s for 1.0 kbp)

Steps 3. to 5. were repeated cyclically 25 to 30 times.

6. polymerization 72° C., 5 min
7. termination 4° C.

GSP (SEQ ID NO: 120):
TCT CTT TTT CGT GCT GCT CCA GCC GAT (Are 297)

PCR Program: 10 min. 95° C.
  1 min. 95° C. (40 cycles)
  1 min. 65° C.
  2 min. 72° C.
  10 min. 72° C. interval 4° C.

PCR Apparatus: Biometra Trio Thermoblock

First PCR on the RACE library moss with AP1 and GSP, when size correct PCR with nested AP2 and GSP, positives are cloned into pCRII-TOPO-TA cloning vector for sequencing purposes.

Example 14

Expression of *Thraustochytrium* LPAAT (ThLPAAT) in Yeast

To detect the functionality of ThLPAAT, the coding region of the cDNA was, in a first approach, cloned into a yeast expression vector and expressed in *S. cerevisiae*. The LPAAT produced in the yeast should be detected added via acyltransferase activity in microsomal fractions.

All solid and liquid media for yeast were prepared by protocols of Ausubel et al. (Current Protocols in Molecular Biology, John Wiley & Sons, New York, 1995).

The ThLPAAT cDNA was excised from the vector pGEM-T by a restriction digest with HindIII/BamHI, cloned into the HindIII/BamHI-cut shuttle vector pYES2 (Invitrogen, Carlsbad, USA), and the resulting vector pYES2-ThLPAAT was transformed into *E. coli* XL1 Blue. With the aid of the LiAc method, pYES2-ThLPAAT was transformed into *S. cerevisiae* INCSc1 (Invitrogen, Carlsbad, USA), where the expression of the ThLPAAT cDNA was under the control of the GALL promoter.

The expression of ThLPAAT in *S. cerevisiae* INVSc1 was carried out by a modified method of Avery et al. (Appl. Environ. Microbiol., 62, 1996: 3960-3966) and Girke et al. (The Plant Journal, 5, 1998: 39-48). To prepare a starter culture, 20 ml of SD medium supplemented with glucose and amino acid solution, but without histidine, were inoculated with an individual yeast colony and incubated overnight at 30° C. at 140 rpm. The cell culture was washed twice by centrifugation and resuspended in SD medium without supplements and without sugar. The washed cells were used to inoculate a main culture to an OD$_{600}$ of from 0.1 to 0.3. The main culture was grown in 25 ml of SD medium supplemented with 2% (w/v) galactose, amino acid solution without histidine, 0.02% linoleic acid (2% strength stock solution in 5% Tergitol NP40), 10% Tergitol NP40 for 72 hours at 30° C. The main culture was harvested by centrifugation. The cell pellet was frozen at −20° C. and then lyophilized for approximately 18 hours.

After expression of the construct pYES2-ThLPAAT in yeast, no active protein was purified, nor did the subcellular fractions from the different transgenic cells show higher LPAAT activities than the corresponding control fractions.

To increase the solubility of the expressed protein, a further construct pDest15-GST-ThLPAAT (pDest15 vektor from Invitrogen) was generated via the Gateway reaction. To this end, the following primers were synthesized following the manufacturer's instructions:

5' primer att1ThLPAAT (SEQ ID NO: 121):
GGGGACAAGTTTGTACAAAAAAGCAGGCTCCATGAGCGCGTGGACGAGGG
CC 3' primer att2ThLPAAT (SEQ ID NO: 122):
GGGGACCACTTTGTACAAGAAAGCTGGGTCTAGTGGTGGTGGTGGTGGTG
CAAGAGGTCAGGTCGGACGTAC These primers were used to carry out the following PCR reaction:

PCR Standard Mix (for Taq Polymerase)
  5 µl 10×PCR buffer (100 mM Tri-HCl, pH 8.3; 15 mM MgCl$_2$, 500 mM KCl)
  1 µl dNTP mix (10 mM dATP, dGTP, dTTP and dCTP)
  1 µl primer 1 (30 µM)
  1 µl primer 2 (30 µM)
  1 U Taq polymerase
  50-100 ng pYES2-ThLPAAT
  make up to 50 µl with distilled water PCR Program: 2 min. 95° C.
  1 min. 95° C. (30 cycles)
  1 min. 65° C.
  2 min. 72° C.
  10 min. 72° C. interval 4° C.

PCR Apparatus: Biometra Trio Thermoblock

The PCR product was transferred into the vector pDO-NOR221 by Gateway reaction (BP reaction; Invitrogen) following the manufacturer's instructions, and the sequence was verified by sequencing. In a next step, the ThLPAAT sequence was then transferred into the vector pDES15 by the LR reaction and employed for expression in E. coli BL21 cells. The ThLPAAT sequence was attached to the open reading frame of the glutathione-S transferase (GST) encoded in the plasmid, in accordance with the manufacturer's instructions. This gave rise to a fusion protein of GST and ThLPAAT.

Expressed protein was detected after expression under standard conditions in E. coli (FIG. 21A) and purified via a glutathione column.

The purified fusion protein showed LPAAT activity, as shown in FIG. 21B. The highest activity was obtained for DHA-CoA (22:6), which makes possible a utilization of this acyltransferase for the production of PUFA.

FIG. 21A shows the Western blot analyses of the Thraustochytrium LPAAT expressed in E. coli as fusion protein (LPAAT-FP) with N-terminal GST tag and C-terminal His tag (lines E: 7 µg soluble protein fraction, line M: size standard). FIG. 21B shows the acyl-CoA specificity of the Thraustochytrium LPAAT, expressed as GST fusion protein, in E. coli. The enzyme assays were determined using 0.4 µg of soluble protein fraction in the presence of 100 mM Tricine-NaOH (pH 8.2), 30 µM 1-oleoyl[U-$^{14}$C]glycerol-3-phosphate and increasing concentrations of the thioesters detailed.

Example 15

Expression of Shewanella LPAAT

To clone an LPAAT gene from the prokaryotic organism Shewanella, the genomic DNA from Shewanella hanedai was isolated, partially digested with Sau3a and ligated into the vector pUC18. This genomic library was screened for LPAAT genes by a PCR using different primer combinations. This method has made it possible to identify a 1486 bp clone whose open reading frame codes for a 25.2 kDa LPAAT protein. The ShLPAAT sequence was introduced into the vector pQE70 (Qiagen) in accordance with the manufacturer's instructions. The resulting plasmids pQE70-Sh and pQE70-ShHis and the blank vector pQE70 were transformed into E. coli BL21 cells and expressed at 10° C. (FIG. 22A). Active protein was obtained at this temperature only (FIG. 22B). The membrane fractions were used for this purpose in the further experiments. In both expression forms, this fraction showed a high level of activity with regard to the incorporation of DHA-CoA (22:6-CoA). The high incorporation rate with regard to PUFA acyl-CoA residues is required for the use for the production of PUFA.

FIG. 22A: shows the Western blot analysis of the Shewanella LPAAT expressed in E. coli as fusion protein with C-terminal His-tag (line E: 7 µg of inclusion body fraction, line F: 7 µg of membrane fraction, line M: size standard). FIG. 22B: shows the functional expression of the Shewanella LPAAT in E. coli enzyme assays. The assays were carried out with extracts (1 µg) from E. coli comprising the blank vector (pQE70) or a Shewanella construct without (pQE-Sh) or with His-Tag sequence at the 3' end (pQE-ShHis) in the presence of 30 µM 1-oleoyl[U-14C]glycerol-3-phosphate and 30 µM of the detailed thioesters.

Example 16

Expression of Mortierella LPAAT (MaLPAAT, MaB4) in yeast

The MaLPAAT cDNA was amplified via PCR with the stated primers MaLPAAT1.1, the PCR product was cloned into the vector pENTR-SD-D-TOPO (Invitrogen, Carlsbad, USA) in accordance with the manufacturer's instructions and transformed into E. coli XL1 Blue. The MaLPAAT fragment was transferred from the resulting vector pENTR-SD-D-MaLPAAT via Gateway reaction in accordance with the manufacturer's instructions (Invitrogen, Carlsbad, USA) into the vector pYES54Dest, resulting in the vector pYES52Dest-MaLPAAT. PYES52Dest-MaLPAAT was transformed into S. cerevisiae INCSc1 (Invitrogen, Carlsbad, USA) with the aid of the LiAc method.

Yeast cells which had been transformed with the plasmid pYES52Dest-MaLPAAT were analyzed as follows:

Yeast colonies which, after transformation, were capable of growing on dropout uracil minimal medium were again streaked on dropout uracil minimal medium and then grown on, liquid minimal medium to an OD600 of 0.8. This preculture was then used for inoculating the main culture which, besides the minimal medium, additionally comprised 2% (w/v) galactose and 250 µM of the fatty acids. After incubation of the main culture for 24 hours at 30° C., the cells were harvested by centrifugation (100×g, 10 min, 20° C.) and washed with 100 mM NaHCO$_3$, pH 8.0, in order to remove residual medium and fatty acids. Fatty acid methyl esters (FAMEs) were prepared from the yeast cell sediments by acid methanolysis. To this end, the cell sediments were incubated for 1 hour at 80° C. with 2 ml of 1N methanolic sulfuric acid and 2% (v/v) dimethoxypropane. The FAMEs were extracted by two extractions with petroleum ether (PE). To remove nonderivatized fatty acids, the organic phases were washed in each case once with 2 ml of 100 mM NaHCO$_3$, pH 8.0, and 2 ml of distilled water. Thereafter, the PE phases were dried with Na$_2$SO$_4$, evaporated under argon and taken up in 100 µl of PE. The samples were separated on a DB-23 capillary column (30 m, 0.25 mm, 0.25 µm, Agilent) in a Hewlett Packard 6850 gaschromatograph equipped with flame ionization detector. The conditions for the GLC analysis were as follows: the oven temperature was programmed from 50° C. to 250° C. with an increment of 5° C./min and finally 10 minutes at 250° C. (holding).

The signals were identified by comparing the retention times with corresponding fatty acid standards (Sigma).

The methodology is described for example in Napier and Michaelson, 2001, Lipids. 36(8):761-766; Sayanova et al., 2001, Journal of Experimental Botany. 52(360):1581-1585, Sperling et al., 2001, Arch. Biochem. Biophys. 388(2):293-298 and Michaelson et al., 1998, FEBS Letters. 439(3):215-218.

FIG. 23 shows the results of the feeding experiments with the yeast cells which comprise plasmid pYES52Dest-MaL-PAAT (MaB4_AT). In FIG. 23, A/B, the yeast cultures were fed linoleic acid (18:2 Δ9,12). In comparison with the control culture (FIG. 23, A), the yeast cells with the MaLPAAT showed a markedly higher conversion (increased 4-fold) of 18:2 into γ-linolenic acid (18:3 Δ6,9,12), and a 3.5-fold increase of the fatty acid 20:2 Δ11,14 elongated from 18:2. Analogously, when feeding linolenic acid (18:3 Δ9, 12, 15), a markedly higher conversion rate to give stearidonic acid (18:4 Δ6, 9, 12, 15) and isoarachidonic acid (20:4 Δ8, 11, 14, 17) was observed in comparison with the controls (FIG. 24).

Besides this activity, an enhanced conversion of 16:1 Δ9 (endogenous fatty acid in yeast) to give cis-vaccenic acid (18:1 Δ11) was observed in both feeding experiments.

FIG. 25 and FIG. 26 show that the observed enhanced conversion rates of the substrates by the desaturase and the elongase also leads to an increase in the polyunsaturated fatty acids in the neutral lipid (oil). After the yeasts had been fed linoleic or linolenic acid, the yeast cells were extracted in chloroform:methanol (2:1) and applied to a silica thin-layer plate (Machery&Nagel, Düren). The thin-layer plate was incubated for 45 minutes with chloroform-methanol-$H_2O$ (65:25:4) in a chamber. In doing so, the neutral lipids (triacylglycerides) migrate with the solvent front. After the incubation had ended, the neutral lipids were scraped off from the plate, extracted with chloroform:methanol and analyzed by gas chromatography.

The increase in the conversion rate of PUFAs, which had been observed for the total extracts, was clearly also monitored in the neutral lipids. As regards the feeding of linoleic acid (FIG. 25 A and B), a 2-fold increase in the conversion of linoleic acid into γ-linolenic acid (18:3 Δ6, 9, 12) and a 3-fold increase in the 20:2 Δ9,12 content was observed. The feeding of linolenic acid (FIG. 26, C and D) gave similar data (conversion of 18:3 into 18:4 3-fold, of 18:3 into 20:3 3-fold).

Thus, it was demonstrated that the increase in the PUFA content as the result of MaLPAAT leads to an increase in PUFAs in the oil (neutral lipids) of the yeasts.

Example 16

Plasmids for Plant Transformation

Binary vectors such as pBinAR can be used for transforming plants (Höfgen and Willmitzer (1990) Plant Science 66: 5221-230). The binary vectors can be constructed by ligating the cDNA in sense or antisense orientation into T-DNA. 5' of the cDNA, a plant promoter activates the transcription of the cDNA. A polyadenylation sequence is located 3' of the cDNA.

Tissue-specific expression can be achieved using a tissue-specific promoter. For example, seed-specific expression can be achieved by cloning the napin or the LeB4 or USP promoter 5' of the cDNA. Any other seed-specific promoter element can also be used. The CaMV-35S promoter can be used for obtaining constitutive expression in all of the plant. The expressed protein can be targeted into a cellular compartment using a signal peptide, for example for plastids, mitochondria or the endoplasmic reticulum (Kermode (1996) Crit. Rev. Plant Sci. 15: 285-423). The signal peptide is cloned 5' in the reading frame with the cDNA in order to obtain the subcellular localization of the fusion protein.

Example 17

Transformation of *Agrobacterium*

The *Agrobacterium*-mediated transformation of plants can be carried out for example using the *Agrobacterium tumefaciens* strain GV3101 (pMP90) (Koncz and Schell (1986) Mol. Gen. Genet. 204: 383-396) or LBA4404 (Clontech). The transformation can be carried out by standard transformation techniques (Deblaere et al. (1984) Nucl. Acids. Res. 13: 4777-4788).

Example 18

Plant Transformation and Expression of PUFA-Specific Acyltransferases in Plants

The expression of LCPUFA-specific acyltransferases in transgenic plants is advantageous in order to increase the LCPUFA content in these plants. To this end, the acyltransferase cDNAs according to the invention were cloned into binary vectors and transferred into *Arabidopsis thaliana*, *Nicotiana tabacum*, *Brassica napus* and *Linum usitatissimum* via *Agrobacterium*-mediated DNA transfer. Here, the expression of the acyltransferase cDNA was under the control of the constitutive CaMV 35 S promoter or the seed-specific USP promoter.

Especially preferred in this context are transgenic plants which already express the desaturases and elongases required for the synthesis of LCPUFAs and which produce small amounts of these LCPUFAs.

The expression vectors used were the vector pBinAR (Höfgen and Willmitzer, Plant Science, 66, 1990: 221-230) or the pBinAR derivative pBinAR-USP, in which the CaMV 35 S promoter had been replaced by the *V. faba* USP promoter. The vectors pGPTV and pGPTV-USP were also used. To carry out the recloning step, it was necessary to excise the CalDes cDNA from the vector pGEM-T and clone it into pBinAR or pBinAR-USP. A further binary vector which was used was pSUN.

The resulting binary vectors with acyltransferase genes were transformed into *Agrobacterium tumefaciens* (Höfgen and Willmitzer, Nucl. Acids Res., 16, 1988: 9877). *A. thaliana* was transformed by means of floral dip (Clough and Bent, Plant Journal, 16, 1998: 735-743), and *N. tabacum* via coculturing tobacco leaf segments with transformed *A. tumefaciens* cells, and linseed and oilseed rape by coculturing hypocotyl segments with transformed *A. tumefaciens* cells.

The expression of the acyltransferase genes in transgenic *Arabidopsis*, tobacco, oilseed rape and linseed plants was analyzed via Northern blot analysis. Selected plants were analyzed for their content in punicic acid or other conjugated fatty acids such as CLA in the seed oil.

To obtain seed-specific expression of PuFADX and PuFAD12, it is also possible to use the napin promoter analogously to the USP promoter.

The *Agrobacterium*-mediated transformation of plants can be carried out using standard transformation and regeneration techniques (Gelvin, Stanton B., Schilperoort, Robert A., Plant Molecular Biology Manual, 2$^{nd}$ Ed., Dordrecht: Kluwer Academic Publ., 1995, in Sect., Ringbuc Zentrale Signatur: BT11-P ISBN 0-7923-2731-4; Glick, Bernard R., Thompson, John E., Methods in Plant Molecular Biology and Biotechnology, B. Raton: CRC Press, 1993, 360 S., ISBN 0-8493-5164-2).

For example, oilseed rape can be transformed by cotyledon or hypocotyl transformation (Moloney et al., Plant Cell Report 8 (1989) 238-242; De Block et al., Plant Physiol. 91 (1989) 694-701). The use of antibiotics for the selection of Agro-bacteria and plants depends on the binary vector and the agrobacterial strain used for the transformation. Oilseed rape is usually selected using kanamycin as selectable plant marker. The *agrobacterium*-mediated gene transfer into linseed (*Linum usitatissimum*) can be carried out for example using a technique described by Mlynarova et al. (1994) Plant Cell Report 13: 282-285.

Soybean can be transformed for example using a technique described in EP-A-O 0424047 (Pioneer Hi-Bred International) or in EP-A-O 0397687, U.S. Pat. No. 5,376,543, U.S. Pat. No. 5,169,770 (University Toledo). The transformation of plants using particle bombardment, polyethylene glycol-mediated DNA uptake or via the silicon carbonate fiber technique is described for example by Freeling and Walbot "The maize handbook" (1993) ISBN 3-540-97826-7, Springer Verlag New York).

Example 19

Analysis of the Expression of a Recombinant Gene Product in a Transformed Organism The activity of a recombinant gene product in the transformed host organism was measured at the transcriptional and/or the translational level.

A suitable method for determining the amount of transcription of the gene (an indication of the amount of RNA available for the translation of the gene product) is to carry out a Northern blot as detailed hereinbelow (reference, see Ausubel et al. (1988) Current Protocols in Molecular Biology, Wiley: New York, or the abovementioned examples section), where a primer which is such that it binds to the gene of interest is labeled with a detectable label (usually a radioactive or chemiluminescent label) so that, when the total RNA of a culture of the organism is extracted, separated on a gel, transferred to a stable matrix and incubated with this probe, the binding, and the degree of the binding, of the probe indicates the presence and also the amount of the mRNA for this gene. This information indicates the degree of the transcription of the transformed gene. Cellular total RNA can be prepared from cells, tissues or organs using a plurality of methods, all of which are known in the art, such as, for example, the method described by Bormann, E. R., et al. (1992) Mol. Microbiol. 6:317-326.

Northern Hybridization:

To carry out the RNA hybridization, 20 μg of total RNA or 1 μg of poly(A)$^+$ RNA were separated as described in Amasino (1986, Anal. Biochem. 152, 304) by means of gel electrophoresis in agarose gels with a strength of 1.25% using formaldehyde, transferred by capillary attraction using 10×SSC to positively charged nylon membranes (Hybond N$^+$, Amersham, Brunswick), immobilized by means of UV light and prehybridized for 3 hours at 68° C. using hybridization buffer (10% dextran sulfate weight/vol., 1 M NaCl, 1% SDS, 100 mg herring sperm DNA). The DNA probe was labeled with the Highprime DNA labeling kit (Roche, Mannheim, Germany) during the prehybridization step, using alpha-32P-dCTP (Amersham, Brunswick, Germany). The hybridization was carried out at 68° C. overnight in the same buffer after addition of the labeled DNA probe. The wash steps were carried out twice for 15 minutes using 2×SSC and twice for 30 minutes using 1×SSC, 1% SDS, at 68° C. The sealed filters were exposed at −70° C. for a period of from 4 hours to 3 days.

To analyze the presence or the relative amount of protein translated by this mRNA, it is possible to employ standard techniques such as a Western blot (see, for example, Ausubel et al. (1988) Current Protocols in Molecular Biology, Wiley: New York). In this method, the cellular total proteins are extracted, separated by means of gel electrophoresis, transferred to a matrix such as nitrocellulose, and incubated with a probe, such as an antibody, which binds specifically to the desired protein. This probe is usually provided with a chemiluminescent or calorimetric label which is easy to detect. The presence and the amount of the observed labeling indicates the presence and the amount of the desired mutated protein which is present in the cell.

Example 20

Analysis of the Effect of the Recombinant Proteins on the Production of the Desired Product The effect of the genetic modification in plants, fungi, algae, ciliates, or on the production of a desired compound (such as a fatty acid) can be determined by growing the modified microorganisms or the modified plant under suitable conditions (like those described above) and analyzing the medium and/or the cellular components for the increased production of the desired product (i.e. of lipids or a fatty acid). These analytical techniques are known to the skilled worker and comprise spectroscopy, thin-layer chromatography, various types of staining methods, enzymatic processes, microbiological processes and analytical chromatography such as high-performance liquid chromatography (see, for example, Ullmann, Encyclopedia of Industrial Chemistry, Vol. A2, pp. 89-90 and pp. 443-613, VCH: Weinheim (1985); Fallon, A., et al., (1987) "Applications of HPLC in Biochemistry" in: Laboratory Techniques in Biochemistry and Molecular Biology, Vol. 17; Rehm et al. (1993) Biotechnology, Vol. 3, Chapter III: "Product recovery and purification", pp. 469-714, VCH: Weinheim; Belter, P. A., et al. (1988) Bioseparations: downstream processing for Biotechnology, John Wiley and Sons; Kennedy, J. F., and Cabral, J. M. S. (1992) Recovery processes for biological Materials, John Wiley and Sons; Shaeiwitz, J. A., and Henry, J. D. (1988) Biochemical Separations, in: Ullmann's Encyclopedia of Industrial Chemistry, Vol. B3; Chapter 11, pp. 1-27, VCH: Weinheim; and Dechow, F. J. (1989) Separation and purification techniques in biotechnology, Noyes Publications).

In addition to the abovementioned processes, plant lipids are extracted from plant material as described by Cahoon et al. (1999) Proc. Natl. Acad. Sci. USA 96 (22) 12935-12940, and Browse et al. (1986) Analytic Biochemistry 152:141-145. Qualitative and quantitative lipid or fatty acid analysis is described by Christie, William W., Advances in Lipid Methodology, Ayr/Scotland: Oily Press (Oily Press Lipid Library; 2); Christie, William W., Gas Chromatography and Lipids. A Practical Guide-Ayr, Scotland: Oily Press, 1989, Repr. 1992, IX, 307 pp. (Oily Press Lipid Library; 1); "Progress in Lipid Research, Oxford: Pergamon Press, 1 (1952)-16 (1977) under the title: Progress in the Chemistry of Fats and Other Lipids CODEN.

Besides measuring the end product of the fermentation, it is also possible to analyze other components of the metabolic pathways which are used for the production of the desired compound, such as intermediate and secondary products, in order to determine the overall efficiency of the production of the compound. The analytical methods comprise measuring the amounts of nutrient in the medium (for example sugars, hydrocarbons, nitrogen sources, phosphate and other ions), measuring the biomass composition and the growths, analysis of the production of common metabolites of biosynthetic pathways and measuring gases which are generated during the fermentation. Standard methods for these measurements are described in Applied Microbial Physiology; A Practical Approach, P. M. Rhodes and P. F. Stanbury, Ed., IRL Press, pp. 131-163 and 165-192 (ISBN: 0199635773) and references cited therein.

One example is the analysis of fatty acids (abbreviations: FAMEs, fatty acid methyl esters; GC-MS, gas-liquid chromatography-mass spectrometry; TAG, triacylglycerol; TLC, thin-layer chromatography).

The unambiguous detection for the presence of fatty acid products can be obtained by means of analyzing recombinant organisms by analytical standard methods: GC, GC-MS or TLC, as described repeatedly by Christie and the references cited therein (1997, in: Advances on Lipid Methodology, Fourth Ed.: Christie, Oily Press, Dundee, 119-169; 1998, Gas-chromatography/mass spectrometry methods, Lipids 33:343-353).

The material to be analyzed can be disrupted by sonication, grinding in a glass mill, liquid nitrogen and grinding, or via other suitable methods. After disruption, the material must be centrifuged. The sediment is resuspended in distilled water, heated for 10 minutes at 100° C., cooled on ice and recentrifuged, followed by extraction in 0.5 M sulfuric acid in methanol supplemented with 2% dimethoxypropane for 1 hour at 90° C., which leads to hydrolyzed oil and lipid compounds, which give transmethylated lipids. These fatty acid methyl esters are extracted in petroleum ether and finally subjected to GC analysis using a capillary column (Chrompack, WCOT Fused Silica, CP-Wax-52 CB, 25 micrometers, 0.32 mm) at a temperature gradient between 170° C. and 240° C. for 20 minutes and 5 minutes at 240° C. The identity of the resulting fatty acid methyl esters must be defined using standards which are available from commercial sources (i.e. Sigma).

In the case of fatty acids for which no standards are available, the identity must be shown via derivatization and subsequent GC-MS analysis. For example, the localization of fatty acids with triple bond must be shown via GC-MS after derivatization with 4,4-dimethoxyoxazoline derivatives (Christie, 1998, see above).

EQUIVALENTS

The skilled worker recognizes, or will find, a multiplicity of equivalents of the specific embodiments according to the invention described herein by simply using routine experiments. The patent claims are intended to encompass these equivalents.

We claim:

1. A process for the production of polyunsaturated fatty acids in an organism comprising (a) introducing, into the organism, at least one nucleic acid comprising the sequence shown in SEQ ID NO: 16 which codes for a polypeptide with lysophosphatidic acid acyltransferase activity; or (b) introducing, into the organism, at least one nucleic acid comprising a nucleic acid sequence having at least 95% identity with the sequence of SEQ ID NO: 16, wherein the nucleic acid codes for a polypeptide with lysophosphatidic acid acyltransferase activity, or (c) introducing, into the organism, at least one nucleic acid which codes for a polypeptide comprising the amino acid sequence shown in SEQ ID NO: 17 or comprising an amino acid sequence having at least 95% identity with SEQ ID NO: 17 and has lysophosphatidic acid acyltransferase activity, and
(d) culturing and harvesting the organism
wherein the organism is a microorganism, yeast, or a plant.

2. The process for the production of polyunsaturated fatty acids according to claim 1, wherein, additionally to the nucleic acid sequence mentioned under (a) to (c), at least one further nucleic acid sequence which codes for a polypeptide of the fatty acid metabolism or lipid metabolism selected from the group consisting of acyl-CoA dehydrogenase(s), acyl-ACP[=acyl carrier protein] desaturase(s), acyl-ACP thioesterase(s), fatty acid acyltransferase(s), acyl-CoA:lysophospholipid acyltransferase(s), fatty acid synthase(s), fatty acid hydroxylase(s), acetyl-coenzyme A carboxylase(s), acyl-coenzyme A oxidase(s), fatty acid desaturase(s), fatty acid acetylenase(s), lipoxygenase(s), triacylglycerol lipase(s), allene oxide synthase(s), hydroperoxide lyase(s) and fatty acid elongase(s) is introduced into the organism.

3. The process for the production of polyunsaturated fatty acids according to claim 1, wherein, additionally to the nucleic acid sequence mentioned under (a) to (c), at least one further nucleic acid sequence which codes for a polypeptide selected from the group consisting of acyl-CoA:lysophospholipid acyltransferase, Δ-4-desaturase, Δ-5-desaturase, Δ-6-desaturase, Δ-8-desaturase, Δ-9-desaturase, Δ-12-desaturase, Δ-5-elongase, Δ-6-elongase and Δ-9-elongase, is introduced into the organism.

4. The process for the production of polyunsaturated fatty acids according to claim 1, wherein the polyunsaturated fatty acids produced are $C_{18}$-, $C_{20}$-, $C_{22}$- or $C_{24}$-fatty acids.

5. The process for the production of polyunsaturated fatty acids according to claim 1, wherein the polyunsaturated fatty acids are isolated from the organism in the form of an oil, a lipid or a free fatty acid.

6. The process for the production of polyunsaturated fatty acids according to claim 1, wherein the polyunsaturated fatty acids produced in the process are $C_{18}$-, $C_{20}$-, $C_{22}$- or $C_{24}$-fatty acids with at least three double bonds.

7. The process for the production of polyunsaturated fatty acids according to claim 1, wherein a polyunsaturated fatty acid selected from the group consisting of dihomo-γ-linolenic acid, arachidonic acid, eicosapentaenoic acid, docosapentaenoic acid and docosahexaenoic acid is produced in the process.

8. The process for the production of polyunsaturated fatty acids according to claim 1, wherein the organism is a transgenic plant.

9. The process for the production of polyunsaturated fatty acids according to claim 8, wherein the transgenic plant is an oil crop plant.

10. An isolated nucleic acid comprising a nucleic acid sequence selected from the group consisting of:
(a) the nucleic acid sequence shown in SEQ ID NO: 16,
(b) a nucleic acid sequence having at least 95% identity with the sequence of SEQ ID NO: 16 and coding for a polypeptide having lysophosphatidic acid acyltransferase activity,
(c) a nucleic acid sequence encoding a polypeptide comprising the amino acid sequence shown in SEQ ID NO: 17, and
(d) a nucleic acid sequence encoding a polypeptide comprising an amino acid sequence having at least 95% identity with the sequence of SEQ ID NO: 17 and having lysophosphatidic acid acyltransferase activity.

11. The isolated nucleic acid of claim 10, wherein the nucleic acid sequence originates from a eukaryote.

12. A gene construct comprising the isolated nucleic acid of claim 10, where the nucleic acid is linked functionally to one or more regulatory signals.

13. The gene construct of claim 12, wherein the gene construct comprises an additional biosynthesis gene of the fatty acid metabolism or lipid metabolism selected from the group consisting of acyl-CoA dehydrogenase(s), acyl-ACP [=acyl carrier protein] desaturase(s), acyl-ACP thioesterase(s), fatty acid acyltransferase(s), acyl-CoA:lysophospholipid acyltransferase(s), fatty acid synthase(s), fatty acid hydroxylase(s), acetyl-coenzyme A carboxylase(s), acyl-coenzyme A oxidase(s), fatty acid desaturase(s), fatty acid acetylenase(s), lipoxygenase(s), triacylglycerol lipase(s), allene oxide synthase(s), hydroperoxide lyase(s) and fatty acid elongase(s).

14. The gene construct of claim 12, wherein the gene construct comprises an additional biosynthesis gene of the fatty acid metabolism or lipid metabolism selected from the group consisting of acyl-CoA:lysophospholipid acyltransferase, Δ-4-desaturase, Δ-5-desaturase, Δ-6-desaturase, Δ-8-desaturase, Δ-9-desaturase, Δ-12-desaturase, Δ-5-elongase, Δ-6-elongase and Δ-9-elongase.

15. A vector comprising the nucleic acid of claim 10 or a gene construct comprising said nucleic acid.

16. A transgenic organism comprising the nucleic acid of claim 10, wherein the organism is a microorganism, yeast, or a plant.

17. The transgenic organism of claim 16, wherein the organism is a plant.

18. A transgenic organism comprising the gene construct of claim 12, wherein the transgenic organism is a microorganism, yeast, or a plant.

19. A transgenic organism comprising the vector of claim 15, wherein the transgenic organism is a microorganism, yeast, or a plant.

20. The nucleic acid of claim 10, wherein the nucleic acid sequence comprises the sequence of SEQ ID NO: 16.

21. The nucleic acid of claim 10, wherein the nucleic acid sequence encodes a polypeptide comprising the amino acid sequence of SEQ ID NO: 17.

* * * * *

SEQUENCE LISTING

```
<160> NUMBER OF SEQ ID NOS: 148

<210> SEQ ID NO 1
<211> LENGTH: 1047
<212> TYPE: DNA
<213> ORGANISM: Thraustochytrium
<220> FEATURE:
<221> NAME/KEY: CDS
<222> LOCATION: (38)..(952)
<223> OTHER INFORMATION: LPAAT

<400> SEQUENCE: 1
gggcggtgtc cggccgttcg agcgcgtgga cgccaac atg agc gcg tgg acg agg        55
                                        Met Ser Ala Trp Thr Arg
                                         1               5 gcc aag acc gcc gtg ggc ctc ctg acg ctg gcg cct gcg cgg ata gtg       103
Ala Lys Thr Ala Val Gly Leu Leu Thr Leu Ala Pro Ala Arg Ile Val
             10                  15                  20 ttc ctc gtg act gtc ctg ggc acg tac ggg ctc acg gtc gcg gcc tgc       151
Phe Leu Val Thr Val Leu Gly Thr Tyr Gly Leu Thr Val Ala Ala Cys
         25                  30                  35 acg cga ctt ggc gtc ccg aaa agc ttc gtg ctg ggc ctg acg cgg tgc       199
Thr Arg Leu Gly Val Pro Lys Ser Phe Val Leu Gly Leu Thr Arg Cys
     40                  45                  50 gtc gcg cga ctc acg ctc tgg ggg ctt ggg ttc tac cac att gag gtc       247
Val Ala Arg Leu Thr Leu Trp Gly Leu Gly Phe Tyr His Ile Glu Val
 55                  60                  65                  70 tct tgc gac gcc caa ggc ctt cgg gag tgg ccg cgc gtg att gtc gcg       295
Ser Cys Asp Ala Gln Gly Leu Arg Glu Trp Pro Arg Val Ile Val Ala
                 75                  80                  85 aac cac gtc tcg tac ctg gag atc ttg tac ttc atg tcg acc gtg cac       343
```

-continued

```
                Asn His Val Ser Tyr Leu Glu Ile Leu Tyr Phe Met Ser Thr Val His
                             90                  95                 100 tgc ccg tct ttc gtc atg aag aag acc tgc ctc cga gtc ccg ctt gtc          391
Cys Pro Ser Phe Val Met Lys Lys Thr Cys Leu Arg Val Pro Leu Val
            105                 110                 115 ggc tac att gcc atg gag ctg ggc ggt gtg att gtg gac cgc gag ggc          439
Gly Tyr Ile Ala Met Glu Leu Gly Gly Val Ile Val Asp Arg Glu Gly
        120                 125                 130 ggc ggt caa agc gca tcg gcg atc att cgc gac cgc gtg cag gag cct          487
Gly Gly Gln Ser Ala Ser Ala Ile Ile Arg Asp Arg Val Gln Glu Pro
135                 140                 145                 150 cct cga gat tcg tcg agc gag aag cac cac gcg cag ccg ctt ctt gtg          535
Pro Arg Asp Ser Ser Ser Glu Lys His His Ala Gln Pro Leu Leu Val
                155                 160                 165 ttc ccc gag ggg acc acc acc aat gga agc tgc ctg ctc caa ttc aag          583
Phe Pro Glu Gly Thr Thr Thr Asn Gly Ser Cys Leu Leu Gln Phe Lys
            170                 175                 180 acg gga gcc ttt cgt cct ggg gct ccg gtg ctt ccg gtc gtg ctt gag          631
Thr Gly Ala Phe Arg Pro Gly Ala Pro Val Leu Pro Val Val Leu Glu
        185                 190                 195 ttt ccg att gac aaa gcg cgt ggt gac ttt tcc ccg gcg tac gaa tcg          679
Phe Pro Ile Asp Lys Ala Arg Gly Asp Phe Ser Pro Ala Tyr Glu Ser
200                 205                 210 gtc cac acg cca gct cac ctc ctt cgc atg ctc gca caa tgg agg cac          727
Val His Thr Pro Ala His Leu Leu Arg Met Leu Ala Gln Trp Arg His
215                 220                 225                 230 cgg ctt cgg gtg cgc tat ctt cct ctg tat gag ccc tct gcg gct gag          775
Arg Leu Arg Val Arg Tyr Leu Pro Leu Tyr Glu Pro Ser Ala Ala Glu
                235                 240                 245 aag gtt gat gca gac ctt tat gcg cgg aac gtg cgc gac gaa atg gcg          823
Lys Val Asp Ala Asp Leu Tyr Ala Arg Asn Val Arg Asp Glu Met Ala
            250                 255                 260 cgc gcg ctc aag gta ccc act gtg gag cag tct tac cgc gac aag ctc          871
Arg Ala Leu Lys Val Pro Thr Val Glu Gln Ser Tyr Arg Asp Lys Leu
        265                 270                 275 gtc tac cac gcg gat ctc atg ccg cac tac cag aag gcc ggc ccc gga          919
Val Tyr His Ala Asp Leu Met Pro His Tyr Gln Lys Ala Gly Pro Gly
280                 285                 290 gcg ctc tat ctg tac gtc cga cct gac ctc ttg tagcactcat gcgcgtccca       972
Ala Leu Tyr Leu Tyr Val Arg Pro Asp Leu Leu
295                 300                 305 agcggtccag caacgggaga ttaaaacacg atttcttagc ctacaaaaaa aaaaaaaaaa      1032
aaaaaaaaaa aaaaa                                                       1047

<210> SEQ ID NO 2
<211> LENGTH: 305
<212> TYPE: PRT
<213> ORGANISM: Thraustochytrium

<400> SEQUENCE: 2

Met Ser Ala Trp Thr Arg Ala Lys Thr Ala Val Gly Leu Leu Thr Leu
1               5                   10                  15

Ala Pro Ala Arg Ile Val Phe Leu Val Thr Val Leu Gly Thr Tyr Gly
            20                  25                  30

Leu Thr Val Ala Ala Cys Thr Arg Leu Gly Val Pro Lys Ser Phe Val
        35                  40                  45

Leu Gly Leu Thr Arg Cys Val Ala Arg Leu Thr Leu Trp Gly Leu Gly
    50                  55                  60
```

| | | | | | | | | | | | | | | | |
|---|---|---|---|---|---|---|---|---|---|---|---|---|---|---|---|
|Phe|Tyr|His|Ile|Glu|Val|Ser|Cys|Asp|Ala|Gln|Gly|Leu|Arg|Glu|Trp|
|65| | | |70| | | |75| | | |80| | | |

Pro Arg Val Ile Val Ala Asn His Val Ser Tyr Leu Glu Ile Leu Tyr
                         85                               90                             95

Phe Met Ser Thr Val His Cys Pro Ser Phe Val Met Lys Lys Thr Cys
            100                 105                 110

Leu Arg Val Pro Leu Val Gly Tyr Ile Ala Met Glu Leu Gly Gly Val
        115                 120                 125

Ile Val Asp Arg Glu Gly Gly Gln Ser Ala Ser Ala Ile Ile Arg
    130                 135                 140

Asp Arg Val Gln Glu Pro Pro Arg Asp Ser Ser Glu Lys His His
145                 150                 155                 160

Ala Gln Pro Leu Leu Val Phe Pro Glu Gly Thr Thr Thr Asn Gly Ser
            165                 170                 175

Cys Leu Leu Gln Phe Lys Thr Gly Ala Phe Arg Pro Gly Ala Pro Val
            180                 185                 190

Leu Pro Val Val Leu Glu Phe Pro Ile Asp Lys Ala Arg Gly Asp Phe
        195                 200                 205

Ser Pro Ala Tyr Glu Ser Val His Thr Pro Ala His Leu Leu Arg Met
    210                 215                 220

Leu Ala Gln Trp Arg His Arg Leu Arg Val Arg Tyr Leu Pro Leu Tyr
225                 230                 235                 240

Glu Pro Ser Ala Ala Glu Lys Val Asp Ala Asp Leu Tyr Ala Arg Asn
            245                 250                 255

Val Arg Asp Glu Met Ala Arg Ala Leu Lys Val Pro Thr Val Glu Gln
            260                 265                 270

Ser Tyr Arg Asp Lys Leu Val Tyr His Ala Asp Leu Met Pro His Tyr
        275                 280                 285

Gln Lys Ala Gly Pro Gly Ala Leu Tyr Leu Tyr Val Arg Pro Asp Leu
    290                 295                 300

Leu
305

<210> SEQ ID NO 3
<211> LENGTH: 1701
<212> TYPE: DNA
<213> ORGANISM: Physcomitrella patens
<220> FEATURE:
<221> NAME/KEY: misc_feature
<223> OTHER INFORMATION: LPAAT

<400> SEQUENCE: 3

```
ggcacgaggg aaattggctt tctatgtggc cgtacttatt cgaggaggtc aacgaaacaa        60
aggtatgtct tattaatgaa aatgtctcca cacatgtatg ttgtttaggt atattctgtc       120
aactgaaaac ttgttttaat tttttcttaa attgaaattc tgtgcctgaa agccaactct       180
aggtccatca taatgtagca atatgatcag aagcgctcaa atgtgtcgtg aaagtttgct       240
tttgcaattt tcttttgctg ttaacctatt gattatgttg gaaccacaat acagacgctg       300
cttcacttca ttcttatggc aatgaatgtc gtgatgattc cggttaattt catcctacag       360
ggatatggat gttgtaaagg tgattttttgc aggtgataaa gtacctaagg agaaccgtgt      420
gatggtcatg tgcaaccatc gtaccgaagt ggactggatg tacatttgga acttagcaat       480
tcggaaaggc aagattgggt actgcaagta tgcggtgaag aactcagtga aaaacttacc       540
cttgtttggt tgggcatttt acgttttttga gtttctgatg ctgcatagaa agtgggaagt      600
```

-continued

| | |
|---|---|
| ggatgctccc gtcatcaaga catacattga cagttttcaa gataaaagag atcctctctg | 660 |
| gctagtcgtg tttcctgaag gcacagattt ttcgtaaggc tgaagtaccc atccatggct | 720 |
| ttgatgtata tctgcaatct tctctataat ctgcatttat tctctgttgt ttctctagca | 780 |
| agtaaatcat acttgcttaa tgtacttagc aatttgtcat ttttgactta ttgtgatgta | 840 |
| aatgtgattg actactatga cagtgaagcg aaacgggaca cgggcaatgc aattggaaga | 900 |
| gagaaaggct atccggagct tgtcaatgtg cttcaacctc gcactcgtgg ctttgtgact | 960 |
| tgcctttctc aatcgcgctg ctctttggat gcagtttatg acctcactat agggtacaag | 1020 |
| aagcggtgtc ccttgttcat caacaatgta ttcggaaccg atccatcgga agtgcacatt | 1080 |
| cacattcgcc gaataccaat ttctgagatt cctcaatcag aagacggtat gacgcagtgg | 1140 |
| ctgtatgatc tattttatca aaaggaccag atgttggcca gttttagtaa gacaggctct | 1200 |
| ttccctgaca gtggaattga agagagccct tgaacatag tggaaggtgt ttgcaatgtt | 1260 |
| gctctacacg tagtccttag cggttgggta ttctggtgct tgtttcattc ggtttggttg | 1320 |
| aagctttatg tggctttcgc tagtttgctg ctcgcgttta gtacctattt tgattggaga | 1380 |
| cctaaaccgg tttactctag tctacgtact aaaagaaaaa tcgtgtaaaa taaattcgtt | 1440 |
| agttgtaatt ggtttgttta ttccgattcc aaagctgagt ttaagggtga ggctcctctt | 1500 |
| taagctgatt tttgctatta attggctgct cccttgtttg tctgccgtaa attggcttta | 1560 |
| atacggttgt cttctgctga tgaacctcag tgcttcaaga cgatgtggcc ttttagcctt | 1620 |
| ctcctttacc catcttgacc agatgccaaa ctcgcaataa agcagatcaa taggtcgtgc | 1680 |
| cccaaaaaaa aaaaaaaaaa a | 1701 |

```
<210> SEQ ID NO 4
<211> LENGTH: 714
<212> TYPE: DNA
<213> ORGANISM: Physcomitrella patens
<220> FEATURE:
<221> NAME/KEY: CDS
<222> LOCATION: (1)..(714)
<223> OTHER INFORMATION: LPAAT
```

<400> SEQUENCE: 4

| | |
|---|---|
| atg gct ttg atg tat atc tgc aat ctt ctc tat aat ctg cat tta ttc<br>Met Ala Leu Met Tyr Ile Cys Asn Leu Leu Tyr Asn Leu His Leu Phe<br>1               5               10             15 | 48 |
| tct gtt gtt tct cta gca agt aaa tca tac ttg ctt aat gta ctt agc<br>Ser Val Val Ser Leu Ala Ser Lys Ser Tyr Leu Leu Asn Val Leu Ser<br>                20               25               30 | 96 |
| aat ttg tca ttt ttg act tat tgt gat gta aat gtg att gac tac tat<br>Asn Leu Ser Phe Leu Thr Tyr Cys Asp Val Asn Val Ile Asp Tyr Tyr<br>         35               40               45 | 144 |
| gac agt gaa gcg aaa cgg gac acg ggc aat gca att gga aga gag aaa<br>Asp Ser Glu Ala Lys Arg Asp Thr Gly Asn Ala Ile Gly Arg Glu Lys<br>50               55               60 | 192 |
| ggc tat ccg gag ctt gtc aat gtg ctt caa cct cgc act cgt ggc ttt<br>Gly Tyr Pro Glu Leu Val Asn Val Leu Gln Pro Arg Thr Arg Gly Phe<br>65               70               75               80 | 240 |
| gtg act tgc ctt tct caa tcg cgc tgc tct ttg gat gca gtt tat gac<br>Val Thr Cys Leu Ser Gln Ser Arg Cys Ser Leu Asp Ala Val Tyr Asp<br>                85               90               95 | 288 |
| ctc act ata ggg tac aag aag cgg tgt ccc ttg ttc atc aac aat gta<br>Leu Thr Ile Gly Tyr Lys Lys Arg Cys Pro Leu Phe Ile Asn Asn Val<br>         100              105            110 | 336 |
| ttc gga acc gat cca tcg gaa gtg cac att cac att cgc cga ata cca | 384 |

```
Phe Gly Thr Asp Pro Ser Glu Val His Ile His Ile Arg Arg Ile Pro
        115                 120                 125 att tct gag att cct caa tca gaa gac ggt atg acg cag tgg ctg tat       432
Ile Ser Glu Ile Pro Gln Ser Glu Asp Gly Met Thr Gln Trp Leu Tyr
130                 135                 140 gat cta ttt tat caa aag gac cag atg ttg gcc agt ttt agt aag aca       480
Asp Leu Phe Tyr Gln Lys Asp Gln Met Leu Ala Ser Phe Ser Lys Thr
145                 150                 155                 160 ggc tct ttc cct gac agt gga att gaa gag agc cct ttg aac ata gtg       528
Gly Ser Phe Pro Asp Ser Gly Ile Glu Glu Ser Pro Leu Asn Ile Val
                165                 170                 175 gaa ggt gtt tgc aat gtt gct cta cac gta gtc ctt agc ggt tgg gta       576
Glu Gly Val Cys Asn Val Ala Leu His Val Val Leu Ser Gly Trp Val
            180                 185                 190 ttc tgg tgc ttg ttt cat tcg gtt tgg ttg aag ctt tat gtg gct ttc       624
Phe Trp Cys Leu Phe His Ser Val Trp Leu Lys Leu Tyr Val Ala Phe
        195                 200                 205 gct agt ttg ctg ctc gcg ttt agt acc tat ttt gat tgg aga cct aaa       672
Ala Ser Leu Leu Leu Ala Phe Ser Thr Tyr Phe Asp Trp Arg Pro Lys
210                 215                 220 ccg gtt tac tct agt cta cgt act aaa aga aaa atc gtg taa               714
Pro Val Tyr Ser Ser Leu Arg Thr Lys Arg Lys Ile Val
225                 230                 235

<210> SEQ ID NO 5
<211> LENGTH: 237
<212> TYPE: PRT
<213> ORGANISM: Physcomitrella patens

<400> SEQUENCE: 5

Met Ala Leu Met Tyr Ile Cys Asn Leu Leu Tyr Asn Leu His Leu Phe
1               5                   10                  15

Ser Val Val Ser Leu Ala Ser Lys Ser Tyr Leu Leu Asn Val Leu Ser
            20                  25                  30

Asn Leu Ser Phe Leu Thr Tyr Cys Asp Val Asn Val Ile Asp Tyr Tyr
        35                  40                  45

Asp Ser Glu Ala Lys Arg Asp Thr Gly Asn Ala Ile Gly Arg Glu Lys
    50                  55                  60

Gly Tyr Pro Glu Leu Val Asn Val Leu Gln Pro Arg Thr Arg Gly Phe
65                  70                  75                  80

Val Thr Cys Leu Ser Gln Ser Arg Cys Ser Leu Asp Ala Val Tyr Asp
                85                  90                  95

Leu Thr Ile Gly Tyr Lys Lys Arg Cys Pro Leu Phe Ile Asn Asn Val
            100                 105                 110

Phe Gly Thr Asp Pro Ser Glu Val His Ile His Ile Arg Arg Ile Pro
        115                 120                 125

Ile Ser Glu Ile Pro Gln Ser Glu Asp Gly Met Thr Gln Trp Leu Tyr
130                 135                 140

Asp Leu Phe Tyr Gln Lys Asp Gln Met Leu Ala Ser Phe Ser Lys Thr
145                 150                 155                 160

Gly Ser Phe Pro Asp Ser Gly Ile Glu Glu Ser Pro Leu Asn Ile Val
                165                 170                 175

Glu Gly Val Cys Asn Val Ala Leu His Val Val Leu Ser Gly Trp Val
            180                 185                 190

Phe Trp Cys Leu Phe His Ser Val Trp Leu Lys Leu Tyr Val Ala Phe
        195                 200                 205

Ala Ser Leu Leu Leu Ala Phe Ser Thr Tyr Phe Asp Trp Arg Pro Lys
```

```
                  210                 215                 220
Pro Val Tyr Ser Ser Leu Arg Thr Lys Arg Lys Ile Val
225                 230                 235

<210> SEQ ID NO 6
<211> LENGTH: 507
<212> TYPE: DNA
<213> ORGANISM: Physcomitrella patens
<220> FEATURE:
<221> NAME/KEY: misc_feature
<223> OTHER INFORMATION: LPAAT

<400> SEQUENCE: 6
accaggtcga gatgcccatt attggactgt ttttgcaagc tttgcaaata atacccgtgg       60
accggactga tgctcagtct aggcaccatg cggctggcaa cgttcggcga agggctgtgg     120
acaatatgtg gtcccacgtc atgttgttcc cggagggcac taccaccaat ggcagagcaa     180
taatcgcctt caaaacagga gcattttcgc ctggtctccc tgtgcagcca atggttatta     240 gatacccctca caagtatgtc aaccctctt ggtgtgacca aggaggtccg ttggtcgttg     300
tgttgcagct gatgactcag ttcatcaacc acatggaggt tgaatatttg ccggtcatga     360
agccaactgt gagagagatg aaatacctc atgaattcgc aagtagagtt cgcagcgaga     420
tggctaaagc gttaggcatc gtgtgcacag aacacagctt tctggatatt aagctagcgc     480
tggctgcaga aaagctcaaa cagcctt                                        507

<210> SEQ ID NO 7
<211> LENGTH: 1566
<212> TYPE: DNA
<213> ORGANISM: Physcomitrella patens
<220> FEATURE:
<221> NAME/KEY: CDS
<222> LOCATION: (1)..(1566)
<223> OTHER INFORMATION: LPAAT

<400> SEQUENCE: 7 atg gag agc aca gca gat gtc gga atg tcc gac gac gat cct atc ctt       48
Met Glu Ser Thr Ala Asp Val Gly Met Ser Asp Asp Asp Pro Ile Leu
1               5                   10                  15 ctc aac ggg ctc gaa acg cca cta ctg gct gaa ttt cct ctt ggc gaa       96
Leu Asn Gly Leu Glu Thr Pro Leu Leu Ala Glu Phe Pro Leu Gly Glu
            20                  25                  30 cgg cct aca ata ggg ccg gag gca cca gta aat ccc ttc cat gaa ccc      144
Arg Pro Thr Ile Gly Pro Glu Ala Pro Val Asn Pro Phe His Glu Pro
        35                  40                  45 gat ggt ggt tgg aag acc aac aac gag tgg aat tac ttt caa atg atg      192
Asp Gly Gly Trp Lys Thr Asn Asn Glu Trp Asn Tyr Phe Gln Met Met
    50                  55                  60 aaa tcc att ttg ctg att cca ctt ctt ctc gtt cgt cta gtg agc atg      240
Lys Ser Ile Leu Leu Ile Pro Leu Leu Leu Val Arg Leu Val Ser Met
65                  70                  75                  80 ata aca atc gta gca ttt gga tat gtg tgg atc agg att tgt ctg atc      288
Ile Thr Ile Val Ala Phe Gly Tyr Val Trp Ile Arg Ile Cys Leu Ile
                85                  90                  95 ggc gtc aca gat ccc ttg ttt aag cct ttc aat ccg tgt cga cgg ttc      336
Gly Val Thr Asp Pro Leu Phe Lys Pro Phe Asn Pro Cys Arg Arg Phe
            100                 105                 110 atg ctg tgg ggc ata cgg tta gta gca aga gca gtg atg ttt acc atg      384
Met Leu Trp Gly Ile Arg Leu Val Ala Arg Ala Val Met Phe Thr Met
        115                 120                 125 ggt tat tac tac att ccc atc aag gga aaa ccg gct cac cga tca gag      432
```

```
                Gly Tyr Tyr Tyr Ile Pro Ile Lys Gly Lys Pro Ala His Arg Ser Glu
                    130                 135                 140 gcg ccc att att gtg tcc aat cac att gga ttt ctg gat ccc atc ttt        480
Ala Pro Ile Ile Val Ser Asn His Ile Gly Phe Leu Asp Pro Ile Phe
145                 150                 155                 160 gtg ttc tat cgg cac ttg ccg gcc atc gtc tca gcc aag gag aac gtc        528
Val Phe Tyr Arg His Leu Pro Ala Ile Val Ser Ala Lys Glu Asn Val
                165                 170                 175 gag atg ccc att att gga ctg ttt ttg caa gct ttg caa ata ata ccc        576
Glu Met Pro Ile Ile Gly Leu Phe Leu Gln Ala Leu Gln Ile Ile Pro
            180                 185                 190 gtg gac cgg act gat gct cag tct agg cac cac gcg gct ggc aac gtt        624
Val Asp Arg Thr Asp Ala Gln Ser Arg His His Ala Ala Gly Asn Val
        195                 200                 205 cgg cga agg gct gtg gac aat atg tgg tcc cac gtc atg ttg ttc ccg        672
Arg Arg Arg Ala Val Asp Asn Met Trp Ser His Val Met Leu Phe Pro
    210                 215                 220 cag ggc act acc acc aat ggc aga gca ata atc gcc ttc aaa aca gga        720
Gln Gly Thr Thr Thr Asn Gly Arg Ala Ile Ile Ala Phe Lys Thr Gly
225                 230                 235                 240 gca ttt tcg cct ggt ctc cct gtg cag cca atg gtt att aga tac cct        768
Ala Phe Ser Pro Gly Leu Pro Val Gln Pro Met Val Ile Arg Tyr Pro
                245                 250                 255 cac aag tat gtc aac ccc tct tgg tgt gac caa gga ggt ccg ttg gtc        816
His Lys Tyr Val Asn Pro Ser Trp Cys Asp Gln Gly Gly Pro Leu Val
            260                 265                 270 gtt gtg ttg cag ctg atg act cag ttc atc aac cac atg gag gtt gaa        864
Val Val Leu Gln Leu Met Thr Gln Phe Ile Asn His Met Glu Val Glu
        275                 280                 285 tat ttg ccg gtc atg aag cca act gtg aga gag atg aaa tac cct cat        912
Tyr Leu Pro Val Met Lys Pro Thr Val Arg Glu Met Lys Tyr Pro His
    290                 295                 300 gaa ttc gca agt aga gtt cgc agc gag atg gct aaa gcg tta ggc atc        960
Glu Phe Ala Ser Arg Val Arg Ser Glu Met Ala Lys Ala Leu Gly Ile
305                 310                 315                 320 gtg tgc aca gaa cac agc ttt ctg gat att aag cta gcg ctg gct gca       1008
Val Cys Thr Glu His Ser Phe Leu Asp Ile Lys Leu Ala Leu Ala Ala
                325                 330                 335 gaa aag ctc aaa cag cct tca ggt cgg tcg ttg gtt gag ttt gct cgc       1056
Glu Lys Leu Lys Gln Pro Ser Gly Arg Ser Leu Val Glu Phe Ala Arg
            340                 345                 350 atg gag aag tta ttt cgg ctg gat ttt cct acg gcg aag gaa tac ttg       1104
Met Glu Lys Leu Phe Arg Leu Asp Phe Pro Thr Ala Lys Glu Tyr Leu
        355                 360                 365 gaa aag ttc agc gcc atg gac cgc aca cac agt ggc ttt gtt aca ttt       1152
Glu Lys Phe Ser Ala Met Asp Arg Thr His Ser Gly Phe Val Thr Phe
    370                 375                 380 gag gag tta tgt acg gca ctg gat ctt cca cgc tca cca att act aag       1200
Glu Glu Leu Cys Thr Ala Leu Asp Leu Pro Arg Ser Pro Ile Thr Lys
385                 390                 395                 400 cag gtg ttc aac ctt ttc gat aag gat ggg cat gga agc ata aac ttt       1248
Gln Val Phe Asn Leu Phe Asp Lys Asp Gly His Gly Ser Ile Asn Phe
                405                 410                 415 cga gag ttt ttg gca ggg ctc gcc ttt gtg tcc agc cac aca tca ttt       1296
Arg Glu Phe Leu Ala Gly Leu Ala Phe Val Ser Ser His Thr Ser Phe
            420                 425                 430 tca agt aca atg gag gct gca ttt aaa gca tgt gat gtg aat ggc gat       1344
Ser Ser Thr Met Glu Ala Ala Phe Lys Ala Cys Asp Val Asn Gly Asp
        435                 440                 445
```

```
ggc act ctt tct cgt gat gaa gtg gag agg agt ttg ctt gat atc ttt      1392
Gly Thr Leu Ser Arg Asp Glu Val Glu Arg Ser Leu Leu Asp Ile Phe
    450                 455                 460 cca gag ctc cct cca ata acg gtc ttc aag ctt ttt gac acg tta gat      1440
Pro Glu Leu Pro Pro Ile Thr Val Phe Lys Leu Phe Asp Thr Leu Asp
465                 470                 475                 480 ata aat cat gat gag aaa atc agc tgg gag gag ttc agt agc ttt ctg      1488
Ile Asn His Asp Glu Lys Ile Ser Trp Glu Glu Phe Ser Ser Phe Leu
                485                 490                 495 cag cga aac cca gag tat ctg gcc atc att ata tat gcg cac cct act      1536
Gln Arg Asn Pro Glu Tyr Leu Ala Ile Ile Ile Tyr Ala His Pro Thr
            500                 505                 510 ctg ctg aag cca ccc aca tcg act agc tga                              1566
Leu Leu Lys Pro Pro Thr Ser Thr Ser
        515                 520

<210> SEQ ID NO 8
<211> LENGTH: 521
<212> TYPE: PRT
<213> ORGANISM: Physcomitrella patens

<400> SEQUENCE: 8

Met Glu Ser Thr Ala Asp Val Gly Met Ser Asp Asp Pro Ile Leu
1               5                   10                  15

Leu Asn Gly Leu Glu Thr Pro Leu Ala Glu Phe Pro Leu Gly Glu
            20                  25                  30

Arg Pro Thr Ile Gly Pro Glu Ala Pro Val Asn Pro Phe His Glu Pro
        35                  40                  45

Asp Gly Gly Trp Lys Thr Asn Asn Glu Trp Asn Tyr Phe Gln Met Met
    50                  55                  60

Lys Ser Ile Leu Leu Ile Pro Leu Leu Leu Val Arg Leu Val Ser Met
65                  70                  75                  80

Ile Thr Ile Val Ala Phe Gly Tyr Val Trp Ile Arg Ile Cys Leu Ile
                85                  90                  95

Gly Val Thr Asp Pro Leu Phe Lys Pro Phe Asn Pro Cys Arg Arg Phe
            100                 105                 110

Met Leu Trp Gly Ile Arg Leu Val Ala Arg Ala Val Met Phe Thr Met
        115                 120                 125

Gly Tyr Tyr Tyr Ile Pro Ile Lys Gly Lys Pro Ala His Arg Ser Glu
    130                 135                 140

Ala Pro Ile Ile Val Ser Asn His Ile Gly Phe Leu Asp Pro Ile Phe
145                 150                 155                 160

Val Phe Tyr Arg His Leu Pro Ala Ile Val Ser Ala Lys Glu Asn Val
                165                 170                 175

Glu Met Pro Ile Ile Gly Leu Phe Leu Gln Ala Leu Gln Ile Ile Pro
            180                 185                 190

Val Asp Arg Thr Asp Ala Gln Ser Arg His His Ala Ala Gly Asn Val
        195                 200                 205

Arg Arg Arg Ala Val Asp Asn Met Trp Ser His Val Met Leu Phe Pro
    210                 215                 220

Gln Gly Thr Thr Thr Asn Gly Arg Ala Ile Ile Ala Phe Lys Thr Gly
225                 230                 235                 240

Ala Phe Ser Pro Gly Leu Pro Val Gln Pro Met Val Ile Arg Tyr Pro
                245                 250                 255

His Lys Tyr Val Asn Pro Ser Trp Cys Asp Gln Gly Gly Pro Leu Val
            260                 265                 270
```

```
Val Val Leu Gln Leu Met Thr Gln Phe Ile Asn His Met Glu Val Glu
        275                 280                 285

Tyr Leu Pro Val Met Lys Pro Thr Val Arg Glu Met Lys Tyr Pro His
        290                 295                 300

Glu Phe Ala Ser Arg Val Arg Ser Glu Met Ala Lys Ala Leu Gly Ile
305                 310                 315                 320

Val Cys Thr Glu His Ser Phe Leu Asp Ile Lys Leu Ala Leu Ala Ala
                325                 330                 335

Glu Lys Leu Lys Gln Pro Ser Gly Arg Ser Leu Val Glu Phe Ala Arg
                340                 345                 350

Met Glu Lys Leu Phe Arg Leu Asp Phe Pro Thr Ala Lys Glu Tyr Leu
            355                 360                 365

Glu Lys Phe Ser Ala Met Asp Arg Thr His Ser Gly Phe Val Thr Phe
        370                 375                 380

Glu Glu Leu Cys Thr Ala Leu Asp Leu Pro Arg Ser Pro Ile Thr Lys
385                 390                 395                 400

Gln Val Phe Asn Leu Phe Asp Lys Asp Gly His Gly Ser Ile Asn Phe
                405                 410                 415

Arg Glu Phe Leu Ala Gly Leu Ala Phe Val Ser Ser His Thr Ser Phe
                420                 425                 430

Ser Ser Thr Met Glu Ala Ala Phe Lys Ala Cys Asp Val Asn Gly Asp
            435                 440                 445

Gly Thr Leu Ser Arg Asp Glu Val Glu Arg Ser Leu Leu Asp Ile Phe
        450                 455                 460

Pro Glu Leu Pro Pro Ile Thr Val Phe Lys Leu Phe Asp Thr Leu Asp
465                 470                 475                 480

Ile Asn His Asp Glu Lys Ile Ser Trp Glu Glu Phe Ser Ser Phe Leu
                485                 490                 495

Gln Arg Asn Pro Glu Tyr Leu Ala Ile Ile Tyr Ala His Pro Thr
                500                 505                 510

Leu Leu Lys Pro Pro Thr Ser Thr Ser
        515                 520

<210> SEQ ID NO 9
<211> LENGTH: 2217
<212> TYPE: DNA
<213> ORGANISM: Physcomitrella patens
<220> FEATURE:
<221> NAME/KEY: CDS
<222> LOCATION: (281)..(1837)
<223> OTHER INFORMATION: LPAAT2

<400> SEQUENCE: 9
ggcgcgccag aggacgagac aagggggggcg ctgtggactt ggtacaactc caaatgtggc     60
tctgaatcat caactaaggg tatggttata caaagtgcgt gccgccgaag agacagacct    120
tcttggttac ccaagactga atgaagatgg gaagtggaac gatagtatga tggctcagag    180
acgagtggct ccgagttttt tggtactcag taggaagttg caagtggggt ttgcatgctg    240
aagaatcgac actgcacagg cctcaccatc gacggatagc atg acc agc acg gaa    295
                                              Met Thr Ser Thr Glu
                                                1               5 aat act gcg atg ttc aca gaa gac act agc act cta aac ggc tcc aca    343
Asn Thr Ala Met Phe Thr Glu Asp Thr Ser Thr Leu Asn Gly Ser Thr
            10                  15                  20 gag gca aat cat gct gag ttt cct ctt gga gag cgg ccg acg ata ggg    391
Glu Ala Asn His Ala Glu Phe Pro Leu Gly Glu Arg Pro Thr Ile Gly
        25                  30                  35
```

```
                                                       -continued ccg gag cca cca gtg aac ccc ttc cac gag tcc agc acg tgg agc atc       439
Pro Glu Pro Pro Val Asn Pro Phe His Glu Ser Ser Thr Trp Ser Ile
        40                  45                  50 ccc caa gtg atc aag acc att ctg cta gtc ccc ttg ctc gtc ata cgc       487
Pro Gln Val Ile Lys Thr Ile Leu Leu Val Pro Leu Leu Val Ile Arg
55                  60                  65 ttg ctc agc atg ttc gct ctc atg atg ttg ggc tac ata tgc gtc aag       535
Leu Leu Ser Met Phe Ala Leu Met Met Leu Gly Tyr Ile Cys Val Lys
70                  75                  80                  85 gtc gct atg atc gga tgc aaa gac ccg ttg ttc aag cct ttc aat cct       583
Val Ala Met Ile Gly Cys Lys Asp Pro Leu Phe Lys Pro Phe Asn Pro
                90                  95                  100 ttg cgg cga ctc ttg ttg gta agt gtg agg tta ata gca aga ggg gtg       631
Leu Arg Arg Leu Leu Leu Val Ser Val Arg Leu Ile Ala Arg Gly Val
        105                 110                 115 atg gtg gcc atg ggg tat tac tat atc ctc gtc aag gga aaa cca gcc       679
Met Val Ala Met Gly Tyr Tyr Tyr Ile Leu Val Lys Gly Lys Pro Ala
        120                 125                 130 cac cgg tct gtg gcg ccc att atc gta tcc aac cac atc ggc ttt gtg       727
His Arg Ser Val Ala Pro Ile Ile Val Ser Asn His Ile Gly Phe Val
        135                 140                 145 gat ccc att ttt gtg ttc tat agg cac ttg ccg gtc atc gtc tca gcc       775
Asp Pro Ile Phe Val Phe Tyr Arg His Leu Pro Val Ile Val Ser Ala
150                 155                 160                 165 aag gaa att gtg gag atg ccc ata atc gga atg ttc tta caa gct ctg       823
Lys Glu Ile Val Glu Met Pro Ile Ile Gly Met Phe Leu Gln Ala Leu
                170                 175                 180 cag atc ata cct gtg gac cga ata aac ccc gcg tcc agg cac cat gcg       871
Gln Ile Ile Pro Val Asp Arg Ile Asn Pro Ala Ser Arg His His Ala
        185                 190                 195 gct gga aat atc cga cga aga gct atg gac aac gag tgg ccg cat gtc       919
Ala Gly Asn Ile Arg Arg Arg Ala Met Asp Asn Glu Trp Pro His Val
        200                 205                 210 atg ctg ttt cca gag ggg act acc aca aat ggc aaa gcg ttg atc tcc       967
Met Leu Phe Pro Glu Gly Thr Thr Thr Asn Gly Lys Ala Leu Ile Ser
215                 220                 225 ttc aaa aca gga gca ttt tcg cct ggt cta cct gtg caa ccc atg gtc      1015
Phe Lys Thr Gly Ala Phe Ser Pro Gly Leu Pro Val Gln Pro Met Val
230                 235                 240                 245 att aaa tac ccc cac aag tat gtg aat ccg tgt tgg tgt aac caa ggg      1063
Ile Lys Tyr Pro His Lys Tyr Val Asn Pro Cys Trp Cys Asn Gln Gly
                250                 255                 260 ggg cca ttg gtc att ctc ttt cag ctg atg act cag ttt gta aat tac      1111
Gly Pro Leu Val Ile Leu Phe Gln Leu Met Thr Gln Phe Val Asn Tyr
        265                 270                 275 atg gag gtg gag tat ttg cct gtg atg acg cca aat gtg cat gag att      1159
Met Glu Val Glu Tyr Leu Pro Val Met Thr Pro Asn Val His Glu Ile
        280                 285                 290 aaa aat ccc cat gaa ttt gct aat aga gta cgg act gag atg gcc aaa      1207
Lys Asn Pro His Glu Phe Ala Asn Arg Val Arg Thr Glu Met Ala Lys
        295                 300                 305 gcg ctg ggc gtt gtg tgc acg gaa cat aac ttt cta gat atc aaa cta      1255
Ala Leu Gly Val Val Cys Thr Glu His Asn Phe Leu Asp Ile Lys Leu
310                 315                 320                 325 aaa atg gct gca gag aag ctc aag cag cct tca gga cgc tca ttg gtt      1303
Lys Met Ala Ala Glu Lys Leu Lys Gln Pro Ser Gly Arg Ser Leu Val
                330                 335                 340 gaa ttc gca cgc atg gag aag ctt ttt cga ctg gac tat tcc aag gcc      1351
Glu Phe Ala Arg Met Glu Lys Leu Phe Arg Leu Asp Tyr Ser Lys Ala
```

-continued

```
                    345                 350                 355
cag gaa tac ttg gaa aaa ttc agt gct atg gat cct tca cac agt ggt    1399
Gln Glu Tyr Leu Glu Lys Phe Ser Ala Met Asp Pro Ser His Ser Gly
            360                 365                 370 tat gtc aca tac gat gag ttc ctt aaa gca ctc cat ctt ccg ccc acc    1447
Tyr Val Thr Tyr Asp Glu Phe Leu Lys Ala Leu His Leu Pro Pro Thr
        375                 380                 385 cag atc act gag cag gtg ttc aac ctt ttc gac aag aac gga cac ggt    1495
Gln Ile Thr Glu Gln Val Phe Asn Leu Phe Asp Lys Asn Gly His Gly
390                 395                 400                 405 tct ata aac ttt cga gag ttt gtg gca ggg ctt gct ttc ctg tct acc    1543
Ser Ile Asn Phe Arg Glu Phe Val Ala Gly Leu Ala Phe Leu Ser Thr
                410                 415                 420 cac act tca ttc cag act aca atg aag gct gca ttc aaa gct tgt gat    1591
His Thr Ser Phe Gln Thr Thr Met Lys Ala Ala Phe Lys Ala Cys Asp
            425                 430                 435 gtg gat ggc gat ggc acc ctc act cgt aat gag gtg gaa agc agc ttg    1639
Val Asp Gly Asp Gly Thr Leu Thr Arg Asn Glu Val Glu Ser Ser Leu
        440                 445                 450 atg gcc gta ttc ccg gag ctc ccc cca gca acg gtg tta aaa ctt ttc    1687
Met Ala Val Phe Pro Glu Leu Pro Pro Ala Thr Val Leu Lys Leu Phe
455                 460                 465 gac acg ctg gat tta aat cgt gac ggg agc att aac tgg gag gag ttc    1735
Asp Thr Leu Asp Leu Asn Arg Asp Gly Ser Ile Asn Trp Glu Glu Phe
470                 475                 480                 485 agc agc ttt ctg caa cga aat cct gag tat ttg gcc atc ata ttg gct    1783
Ser Ser Phe Leu Gln Arg Asn Pro Glu Tyr Leu Ala Ile Ile Leu Ala
                490                 495                 500 gca cac cct act ctg ttg cag gca cca aag tcg gaa gag agt gaa act    1831
Ala His Pro Thr Leu Leu Gln Ala Pro Lys Ser Glu Glu Ser Glu Thr
            505                 510                 515 aac atc tagagttctg tcaatcgata tctattagat catctctttc acatgctgtg    1887
Asn Ile ggacctttg gagctgcaat tcctcgagca tgatataacc actctattac agttgcgctt    1947
agtgggtgca tcttctggat ttgaatcgac tcggggacta aaaagcagca gtggtttgct    2007
gtcaccgttg acatggttta ggaacttagc atcgagatag atccttactt gagatcattt    2067
tgtatttcca cagactattg ctgttaccag tagctctgct agagctagaa tttctatgat    2127
gtggacgaaa gtcaacttat tcttaagaat caaaagttaa gctccggtct ttgtaacgtt    2187
tttactgcaa aaaaaaaaaa aaaaaaaaa                                      2217
```

<210> SEQ ID NO 10
<211> LENGTH: 519
<212> TYPE: PRT
<213> ORGANISM: Physcomitrella patens

<400> SEQUENCE: 10

```
Met Thr Ser Thr Glu Asn Thr Ala Met Phe Thr Glu Asp Thr Ser Thr
1               5                   10                  15

Leu Asn Gly Ser Thr Glu Ala Asn His Ala Glu Phe Pro Leu Gly Glu
            20                  25                  30

Arg Pro Thr Ile Gly Pro Glu Pro Val Asn Pro Phe His Glu Ser
        35                  40                  45

Ser Thr Trp Ser Ile Pro Gln Val Ile Lys Thr Ile Leu Leu Val Pro
    50                  55                  60

Leu Leu Val Ile Arg Leu Leu Ser Met Phe Ala Leu Met Met Leu Gly
65                  70                  75                  80
```

-continued

```
Tyr Ile Cys Val Lys Val Ala Met Ile Gly Cys Lys Asp Pro Leu Phe
                85                  90                  95
Lys Pro Phe Asn Pro Leu Arg Arg Leu Leu Val Ser Val Arg Leu
            100                 105                 110
Ile Ala Arg Gly Val Met Val Ala Met Gly Tyr Tyr Ile Leu Val
            115                 120                 125
Lys Gly Lys Pro Ala His Arg Ser Val Ala Pro Ile Ile Val Ser Asn
130                 135                 140
His Ile Gly Phe Val Asp Pro Ile Phe Val Phe Tyr Arg His Leu Pro
145                 150                 155                 160
Val Ile Val Ser Ala Lys Glu Ile Val Glu Met Pro Ile Ile Gly Met
                165                 170                 175
Phe Leu Gln Ala Leu Gln Ile Ile Pro Val Asp Arg Ile Asn Pro Ala
                180                 185                 190
Ser Arg His His Ala Ala Gly Asn Ile Arg Arg Arg Ala Met Asp Asn
            195                 200                 205
Glu Trp Pro His Val Met Leu Phe Pro Glu Gly Thr Thr Thr Asn Gly
            210                 215                 220
Lys Ala Leu Ile Ser Phe Lys Thr Gly Ala Phe Ser Pro Gly Leu Pro
225                 230                 235                 240
Val Gln Pro Met Val Ile Lys Tyr Pro His Lys Tyr Val Asn Pro Cys
                245                 250                 255
Trp Cys Asn Gln Gly Gly Pro Leu Val Ile Leu Phe Gln Leu Met Thr
            260                 265                 270
Gln Phe Val Asn Tyr Met Glu Val Glu Tyr Leu Pro Val Met Thr Pro
            275                 280                 285
Asn Val His Glu Ile Lys Asn Pro His Glu Phe Ala Asn Arg Val Arg
            290                 295                 300
Thr Glu Met Ala Lys Ala Leu Gly Val Val Cys Thr Glu His Asn Phe
305                 310                 315                 320
Leu Asp Ile Lys Leu Lys Met Ala Ala Glu Lys Leu Lys Gln Pro Ser
                325                 330                 335
Gly Arg Ser Leu Val Glu Phe Ala Arg Met Glu Lys Leu Phe Arg Leu
            340                 345                 350
Asp Tyr Ser Lys Ala Gln Glu Tyr Leu Glu Lys Phe Ser Ala Met Asp
            355                 360                 365
Pro Ser His Ser Gly Tyr Val Thr Tyr Asp Glu Phe Leu Lys Ala Leu
            370                 375                 380
His Leu Pro Pro Thr Gln Ile Thr Glu Gln Val Phe Asn Leu Phe Asp
385                 390                 395                 400
Lys Asn Gly His Gly Ser Ile Asn Phe Arg Glu Phe Val Ala Gly Leu
                405                 410                 415
Ala Phe Leu Ser Thr His Thr Ser Phe Gln Thr Thr Met Lys Ala Ala
                420                 425                 430
Phe Lys Ala Cys Asp Val Asp Gly Asp Gly Thr Leu Thr Arg Asn Glu
            435                 440                 445
Val Glu Ser Ser Leu Met Ala Val Phe Pro Glu Leu Pro Pro Ala Thr
450                 455                 460
Val Leu Lys Leu Phe Asp Thr Leu Asp Leu Asn Arg Asp Gly Ser Ile
465                 470                 475                 480
Asn Trp Glu Glu Phe Ser Ser Phe Leu Gln Arg Asn Pro Glu Tyr Leu
                485                 490                 495
```

```
Ala Ile Ile Leu Ala Ala His Pro Thr Leu Leu Gln Ala Pro Lys Ser
            500                 505                 510

Glu Glu Ser Glu Thr Asn Ile
        515

<210> SEQ ID NO 11
<211> LENGTH: 1014
<212> TYPE: DNA
<213> ORGANISM: Physcomitrella patens
<220> FEATURE:
<221> NAME/KEY: CDS
<222> LOCATION: (1)..(1014)
<223> OTHER INFORMATION: LPAAT

<400> SEQUENCE: 11 atg att atg atg gag gtg ctg tgg tcg gag ctt ata tgg ctg ctg gat      48
Met Ile Met Met Glu Val Leu Trp Ser Glu Leu Ile Trp Leu Leu Asp
1               5                   10                  15 tgg tgg gca aat gtg aag gtg aag gtt tac acg cca aag gag tcg tgg     96
Trp Trp Ala Asn Val Lys Val Lys Val Tyr Thr Pro Lys Glu Ser Trp
                20                  25                  30 gag cac tta gga aag gag cac gca tta ctc att tgt aat cac cgc agt    144
Glu His Leu Gly Lys Glu His Ala Leu Leu Ile Cys Asn His Arg Ser
            35                  40                  45 gac att gat tgg ctc gta gga tgg att att gcc cag aga ttg ggg tgt    192
Asp Ile Asp Trp Leu Val Gly Trp Ile Ile Ala Gln Arg Leu Gly Cys
        50                  55                  60 cta ggt ggg act cga gct gtt atg aag aag tcc acc aaa ttt ctt ccg    240
Leu Gly Gly Thr Arg Ala Val Met Lys Lys Ser Thr Lys Phe Leu Pro
65                  70                  75                  80 gtc att ggc tgg tct atg tgg ttt tca gag tat gtg ttt tta tca aga    288
Val Ile Gly Trp Ser Met Trp Phe Ser Glu Tyr Val Phe Leu Ser Arg
                85                  90                  95 gat tgg gcc aaa gat gag aag gtc ttg aag aat ggt tat tca agt ctt    336
Asp Trp Ala Lys Asp Glu Lys Val Leu Lys Asn Gly Tyr Ser Ser Leu
            100                 105                 110 aag ggc ttc ccc agg acc ttg tgg gtg gct ctt ttt gtg gaa ggc act    384
Lys Gly Phe Pro Arg Thr Leu Trp Val Ala Leu Phe Val Glu Gly Thr
        115                 120                 125 cga ttt acg aag gct aaa ctt gag gtt gcc caa aaa ttt gcg gcg gat    432
Arg Phe Thr Lys Ala Lys Leu Glu Val Ala Gln Lys Phe Ala Ala Asp
    130                 135                 140 aca ggg cta cgt gtt cca agg tat gtg ctt gtt cct cgc aca aaa ggg    480
Thr Gly Leu Arg Val Pro Arg Tyr Val Leu Val Pro Arg Thr Lys Gly
145                 150                 155                 160 ttc gtt tcg gct gtg gag aac ttg cgt gaa ttt gtt ccg gta gtt tat    528
Phe Val Ser Ala Val Glu Asn Leu Arg Glu Phe Val Pro Val Val Tyr
                165                 170                 175 gac atg acc gtt gct ata tct aaa gag ctg ccc aat cct aca atg atc    576
Asp Met Thr Val Ala Ile Ser Lys Glu Leu Pro Asn Pro Thr Met Ile
            180                 185                 190 cgg att ttc aga ggg caa cca tct gtg gtt cat gtg tac gtg agg cgg    624
Arg Ile Phe Arg Gly Gln Pro Ser Val Val His Val Tyr Val Arg Arg
        195                 200                 205 gtc cct atg tct gat ctg cct gag gga gcc aac gcg att tct aaa tgg    672
Val Pro Met Ser Asp Leu Pro Glu Gly Ala Asn Ala Ile Ser Lys Trp
    210                 215                 220 tgt cac gat gcc ttt cac atc aag gac gat cgg ctg gag cag cac gaa    720
Cys His Asp Ala Phe His Ile Lys Asp Asp Arg Leu Glu Gln His Glu
225                 230                 235                 240 aaa gag aat acg ttt ggg gag gac ttg tat att cct att gaa cgg cca    768
```

-continued

```
Lys Glu Asn Thr Phe Gly Glu Asp Leu Tyr Ile Pro Ile Glu Arg Pro
                245                 250                 255 ctt aaa cct ctt att att gtg atc tcc tgg gcc atc act ttg ctg gct    816
Leu Lys Pro Leu Ile Ile Val Ile Ser Trp Ala Ile Thr Leu Leu Ala
        260                 265                 270 gca gca tgg tgg ttt cta aga cga gtt tta tcc act tgg aaa gga atc    864
Ala Ala Trp Trp Phe Leu Arg Arg Val Leu Ser Thr Trp Lys Gly Ile
            275                 280                 285 gcc tgg gtg gca gga gta ctc gtg gtc gtc atg ctg tgt gtc cag att    912
Ala Trp Val Ala Gly Val Leu Val Val Val Met Leu Cys Val Gln Ile
        290                 295                 300 tta gtg atg tcg tca caa tcg gaa aga agt tca gat cct gca gct aag    960
Leu Val Met Ser Ser Gln Ser Glu Arg Ser Ser Asp Pro Ala Ala Lys
305                 310                 315                 320 aag gcc aat caa aaa cag gcg gct tct gtt gct cac ctc ggc aaa acg    1008
Lys Ala Asn Gln Lys Gln Ala Ala Ser Val Ala His Leu Gly Lys Thr
                325                 330                 335 gac tga                                                            1014
Asp

<210> SEQ ID NO 12
<211> LENGTH: 337
<212> TYPE: PRT
<213> ORGANISM: Physcomitrella patens

<400> SEQUENCE: 12

Met Ile Met Met Glu Val Leu Trp Ser Glu Leu Ile Trp Leu Leu Asp
1               5                   10                  15

Trp Trp Ala Asn Val Lys Val Lys Val Tyr Thr Pro Lys Glu Ser Trp
            20                  25                  30

Glu His Leu Gly Lys Glu His Ala Leu Leu Ile Cys Asn His Arg Ser
        35                  40                  45

Asp Ile Asp Trp Leu Val Gly Trp Ile Ile Ala Gln Arg Leu Gly Cys
    50                  55                  60

Leu Gly Gly Thr Arg Ala Val Met Lys Ser Thr Lys Phe Leu Pro
65                  70                  75                  80

Val Ile Gly Trp Ser Met Trp Phe Ser Glu Tyr Val Phe Leu Ser Arg
                85                  90                  95

Asp Trp Ala Lys Asp Glu Lys Val Leu Lys Asn Gly Tyr Ser Ser Leu
            100                 105                 110

Lys Gly Phe Pro Arg Thr Leu Trp Val Ala Leu Phe Val Glu Gly Thr
        115                 120                 125

Arg Phe Thr Lys Ala Lys Leu Glu Val Ala Gln Lys Phe Ala Ala Asp
    130                 135                 140

Thr Gly Leu Arg Val Pro Arg Tyr Val Leu Val Pro Arg Thr Lys Gly
145                 150                 155                 160

Phe Val Ser Ala Val Glu Asn Leu Arg Glu Phe Val Pro Val Val Tyr
                165                 170                 175

Asp Met Thr Val Ala Ile Ser Lys Glu Leu Pro Asn Pro Thr Met Ile
            180                 185                 190

Arg Ile Phe Arg Gly Gln Pro Ser Val Val His Val Tyr Val Arg Arg
        195                 200                 205

Val Pro Met Ser Asp Leu Pro Glu Gly Ala Asn Ala Ile Ser Lys Trp
    210                 215                 220

Cys His Asp Ala Phe His Ile Lys Asp Asp Arg Leu Glu Gln His Glu
225                 230                 235                 240
```

-continued

```
Lys Glu Asn Thr Phe Gly Glu Asp Leu Tyr Ile Pro Ile Glu Arg Pro
            245                 250                 255
Leu Lys Pro Leu Ile Ile Val Ile Ser Trp Ala Ile Thr Leu Leu Ala
        260                 265                 270
Ala Ala Trp Trp Phe Leu Arg Arg Val Leu Ser Thr Trp Lys Gly Ile
    275                 280                 285
Ala Trp Val Ala Gly Val Leu Val Val Met Leu Cys Val Gln Ile
290                 295                 300
Leu Val Met Ser Ser Gln Ser Glu Arg Ser Ser Asp Pro Ala Ala Lys
305                 310                 315                 320
Lys Ala Asn Gln Lys Gln Ala Ala Ser Val Ala His Leu Gly Lys Thr
                325                 330                 335
Asp
```

<210> SEQ ID NO 13
<211> LENGTH: 643
<212> TYPE: DNA
<213> ORGANISM: Physcomitrella patens
<220> FEATURE:
<221> NAME/KEY: misc_feature
<223> OTHER INFORMATION: LPAAT2

<400> SEQUENCE: 13

```
ggcgcgccag aggacgagac aagggagtc aattggaatg cctgaagacc tgcatgaaac    60
tggttaaaga aggtgtgtct gctctgtttt tccctgaggg cacaaggaca acggatggag   120
caatggctgc cttcaagaaa ggagctttct ctgtggcggc caagggaggt gtgtcagttg   180
tacctataac gttaattggc tcaggcaagt tgatgccaaa tggtttagaa tatacattac   240
ggcctggcgt tgtgaaaatg attgtccacc cagctatccg cagtaaaaat gccgatgagc   300
tttgtgatca gtctaggaag gttattgcag agaccttgat caaacacggt cttcctgttc   360
attagttgct gtgattgatg atcgccatc aggatgatgc gatcaagtga tcaagccctg   420
tttgtcgttc ttagtgatta aggagtcatt tctgtccatc gtttatgccc cgcaagagat   480
ttaaggagat cacaaagtcg gttgtagcaa gagagttgga cactgtgata agcccaatta   540
acttatgttg aagtgtcatt tattctttga aaaaaaaaa aataaaaaaa aaaaaaaaa   600
aaaaaaaaa aaaaaaaaa aaaaaaaaa aaaaagcggc cgc                        643
```

<210> SEQ ID NO 14
<211> LENGTH: 657
<212> TYPE: DNA
<213> ORGANISM: Physcomitrella patens
<220> FEATURE:
<221> NAME/KEY: CDS
<222> LOCATION: (1)..(657)
<223> OTHER INFORMATION: LPAAT

<400> SEQUENCE: 14

```
atg ctg ata tta cag ccc ttc gta ctc tta ctc gac aag caa cgt aga    48
Met Leu Ile Leu Gln Pro Phe Val Leu Leu Leu Asp Lys Gln Arg Arg
1               5                  10                  15 aga gct cag cac ctt gtg aac aag gtg tgg gca att tgg aca acg tct    96
Arg Ala Gln His Leu Val Asn Lys Val Trp Ala Ile Trp Thr Thr Ser
            20                  25                  30 ttg ttt tat aaa act gag att gaa ggt tgg gaa aat ctt cca gca tct   144
Leu Phe Tyr Lys Thr Glu Ile Glu Gly Trp Glu Asn Leu Pro Ala Ser
        35                  40                  45 gat gag ggt gca gtg tat gtt gcc aat cat caa agc ttt ttg gac atc   192
Asp Glu Gly Ala Val Tyr Val Ala Asn His Gln Ser Phe Leu Asp Ile
```

```
                50                  55                  60
tat aca ctc ttt caa tta gga cga cca ttt aag ttt att agc aag acc      240
Tyr Thr Leu Phe Gln Leu Gly Arg Pro Phe Lys Phe Ile Ser Lys Thr
 65                  70                  75                  80 agc aat ttt ctc att ccg att att ggt tgg tcc atg tac atg acg ggc      288
Ser Asn Phe Leu Ile Pro Ile Ile Gly Trp Ser Met Tyr Met Thr Gly
                 85                  90                  95 cac att ccc cta aag cgt atg gac aag agg agt caa ttg gaa tgc ctg      336
His Ile Pro Leu Lys Arg Met Asp Lys Arg Ser Gln Leu Glu Cys Leu
            100                 105                 110 aag acc tgc atg aag ctg gtt aaa gaa ggt gtg tct gtt ctg ttt ttc      384
Lys Thr Cys Met Lys Leu Val Lys Glu Gly Val Ser Val Leu Phe Phe
        115                 120                 125 cct gag ggc aca agg aca acg gat gga gca atg gct gcc ttc aag aaa      432
Pro Glu Gly Thr Arg Thr Thr Asp Gly Ala Met Ala Ala Phe Lys Lys
    130                 135                 140 gga gct ttc tct gtg gcg gcc aag gga ggt gtg cca gtt gta cct ata      480
Gly Ala Phe Ser Val Ala Ala Lys Gly Gly Val Pro Val Val Pro Ile
145                 150                 155                 160 acg tta att ggc tca ggc aag ttg atg cca aat ggt tta gaa tat aca      528
Thr Leu Ile Gly Ser Gly Lys Leu Met Pro Asn Gly Leu Glu Tyr Thr
                165                 170                 175 tta cgg cct ggc gtt gtg aaa atg att gtc cac cca gct atc cgc agt      576
Leu Arg Pro Gly Val Val Lys Met Ile Val His Pro Ala Ile Arg Ser
            180                 185                 190 aaa aat gcc gat gag ctt tgt gat cag tct agg aag gtt att gca gag      624
Lys Asn Ala Asp Glu Leu Cys Asp Gln Ser Arg Lys Val Ile Ala Glu
        195                 200                 205 acc ttg atc caa cac ggt ctt cct gtt cat tag                          657
Thr Leu Ile Gln His Gly Leu Pro Val His
    210                 215

<210> SEQ ID NO 15
<211> LENGTH: 218
<212> TYPE: PRT
<213> ORGANISM: Physcomitrella patens

<400> SEQUENCE: 15

Met Leu Ile Leu Gln Pro Phe Val Leu Leu Asp Lys Gln Arg Arg
1               5                   10                  15

Arg Ala Gln His Leu Val Asn Lys Val Trp Ala Ile Leu Thr Thr Ser
            20                  25                  30

Leu Phe Tyr Lys Thr Glu Ile Glu Gly Trp Glu Asn Leu Pro Ala Ser
        35                  40                  45

Asp Glu Gly Ala Val Tyr Val Ala Asn His Gln Ser Phe Leu Asp Ile
    50                  55                  60

Tyr Thr Leu Phe Gln Leu Gly Arg Pro Phe Lys Phe Ile Ser Lys Thr
65                  70                  75                  80

Ser Asn Phe Leu Ile Pro Ile Ile Gly Trp Ser Met Tyr Met Thr Gly
                85                  90                  95

His Ile Pro Leu Lys Arg Met Asp Lys Arg Ser Gln Leu Glu Cys Leu
            100                 105                 110

Lys Thr Cys Met Lys Leu Val Lys Glu Gly Val Ser Val Leu Phe Phe
        115                 120                 125

Pro Glu Gly Thr Arg Thr Thr Asp Gly Ala Met Ala Ala Phe Lys Lys
    130                 135                 140

Gly Ala Phe Ser Val Ala Ala Lys Gly Gly Val Pro Val Val Pro Ile
145                 150                 155                 160
```

-continued

Thr Leu Ile Gly Ser Gly Lys Leu Met Pro Asn Gly Leu Glu Tyr Thr
                165                 170                 175

Leu Arg Pro Gly Val Val Lys Met Ile Val His Pro Ala Ile Arg Ser
            180                 185                 190

Lys Asn Ala Asp Glu Leu Cys Asp Gln Ser Arg Lys Val Ile Ala Glu
        195                 200                 205

Thr Leu Ile Gln His Gly Leu Pro Val His
        210                 215

<210> SEQ ID NO 16
<211> LENGTH: 1254
<212> TYPE: DNA
<213> ORGANISM: Mortierella alpina
<220> FEATURE:
<221> NAME/KEY: CDS
<222> LOCATION: (1)..(1251)
<223> OTHER INFORMATION: LPAAT

<400> SEQUENCE: 16

| | |
|---|---:|
| atg gat gaa tcc acc acg acc acc acg cac cac tca gag acc agc agc<br>Met Asp Glu Ser Thr Thr Thr Thr Thr His His Ser Glu Thr Ser Ser<br>1               5                   10                  15 | 48 |
| aag acg tcc tcg cac ccc cgc cgg ctc ggt ccc gag atg aac cct atc<br>Lys Thr Ser Ser His Pro Arg Arg Leu Gly Pro Glu Met Asn Pro Ile<br>            20                  25                  30 | 96 |
| tac aag ggt ctg cga gcc att gtc tgg gcc ttt tac ttc aac ctg gga<br>Tyr Lys Gly Leu Arg Ala Ile Val Trp Ala Phe Tyr Phe Asn Leu Gly<br>        35                  40                  45 | 144 |
| gcg tcg ctt ata tcg atc acg cag gtg ctg tcg ctg cct ctg gcg ttg<br>Ala Ser Leu Ile Ser Ile Thr Gln Val Leu Ser Leu Pro Leu Ala Leu<br>    50                  55                  60 | 192 |
| att gct cca ggg gtc tac cag tgg cac atc agc aaa aca cag ggt cac<br>Ile Ala Pro Gly Val Tyr Gln Trp His Ile Ser Lys Thr Gln Gly His<br>65                  70                  75                  80 | 240 |
| ttt gga gct ttc ctg ctc cgg atg aac cag ctc ttt gcg ccg tca gat<br>Phe Gly Ala Phe Leu Leu Arg Met Asn Gln Leu Phe Ala Pro Ser Asp<br>                85                  90                  95 | 288 |
| att gtc ttg aca ggg gac gag agt gtc agg gga atc gtc aag gtc tac<br>Ile Val Leu Thr Gly Asp Glu Ser Val Arg Gly Ile Val Lys Val Tyr<br>            100                 105                 110 | 336 |
| aaa gga cgg aac ctg aag gag gcc ggt gag cca ggc agc ggt cag gga<br>Lys Gly Arg Asn Leu Lys Glu Ala Gly Glu Pro Gly Ser Gly Gln Gly<br>        115                 120                 125 | 384 |
| gag gac att ctt ctg gat atg ccc gag agg atg gtt ttc att gcg aac<br>Glu Asp Ile Leu Leu Asp Met Pro Glu Arg Met Val Phe Ile Ala Asn<br>    130                 135                 140 | 432 |
| cac cag atc tac tct gac tgg atg tac ctc tgg tgc ttc tcc tat ttt<br>His Gln Ile Tyr Ser Asp Trp Met Tyr Leu Trp Cys Phe Ser Tyr Phe<br>145                 150                 155                 160 | 480 |
| gca gag agg cac agg gca ctg aag att att ctt cgg ggc gac ctg acc<br>Ala Glu Arg His Arg Ala Leu Lys Ile Ile Leu Arg Gly Asp Leu Thr<br>                165                 170                 175 | 528 |
| tgg atc cct gtc ttt ggc tgg ggt atg cgg ttc ttt gac ttt atc ttt<br>Trp Ile Pro Val Phe Gly Trp Gly Met Arg Phe Phe Asp Phe Ile Phe<br>            180                 185                 190 | 576 |
| ttg aaa cgt aat gac tgg gca cac gat cgc cgt gcc att gag gaa aac<br>Leu Lys Arg Asn Asp Trp Ala His Asp Arg Arg Ala Ile Glu Glu Asn<br>        195                 200                 205 | 624 |
| ttg gga cgt gtc aag gaa aag gat ccc ctc tgg ctc gtg gtc ttc ccc<br>Leu Gly Arg Val Lys Glu Lys Asp Pro Leu Trp Leu Val Val Phe Pro | 672 |

```
              210                 215                 220
gag gga aca gtc gtc tcc aag gaa acg cgt ctc cga tcc gtt gcc ttt      720
Glu Gly Thr Val Val Ser Lys Glu Thr Arg Leu Arg Ser Val Ala Phe
225                 230                 235                 240 tca aag aag gct agt ctg tcg gat cac cgc cat gtg ctg ctt cca agg      768
Ser Lys Lys Ala Ser Leu Ser Asp His Arg His Val Leu Leu Pro Arg
            245                 250                 255 acc agc ggt ctg ttt gtg tgc atc aac aag ttg cgt gga tct gtc gac      816
Thr Ser Gly Leu Phe Val Cys Ile Asn Lys Leu Arg Gly Ser Val Asp
        260                 265                 270 tac ttg tac gat gca acc gtt ggc tac tcg aat gtc gag tat ggc gag      864
Tyr Leu Tyr Asp Ala Thr Val Gly Tyr Ser Asn Val Glu Tyr Gly Glu
    275                 280                 285 att ccg cag gag ctt tac ccg tta cca gga ctg tat atc aac aaa gca      912
Ile Pro Gln Glu Leu Tyr Pro Leu Pro Gly Leu Tyr Ile Asn Lys Ala
290                 295                 300 cag ccc aag gag atc aac atg cac ctg cgt cga ttt gcg atc aag gat      960
Gln Pro Lys Glu Ile Asn Met His Leu Arg Arg Phe Ala Ile Lys Asp
305                 310                 315                 320 atc ccc acg tca gaa ccc gaa ttt gtg gaa tgg gtc cga gct cgg tgg     1008
Ile Pro Thr Ser Glu Pro Glu Phe Val Glu Trp Val Arg Ala Arg Trp
            325                 330                 335 gtg gag aag gat gag ttg atg gaa gag ttt tat acc aag ggc cga ttt     1056
Val Glu Lys Asp Glu Leu Met Glu Glu Phe Tyr Thr Lys Gly Arg Phe
        340                 345                 350 cca tca caa ctg acg gcc gcc gac att ggt gag aag gag gtc aag acg     1104
Pro Ser Gln Leu Thr Ala Ala Asp Ile Gly Glu Lys Glu Val Lys Thr
    355                 360                 365 gca gga ggt cca acg gag gga cag agt gtc agg atc ccg ctc aag gcg     1152
Ala Gly Gly Pro Thr Glu Gly Gln Ser Val Arg Ile Pro Leu Lys Ala
370                 375                 380 cga ggc atg atg gac tac ctc atg ccc tcg gtc atg aat ctg atc gcc     1200
Arg Gly Met Met Asp Tyr Leu Met Pro Ser Val Met Asn Leu Ile Ala
385                 390                 395                 400 ctt cct gtg ctg gcg ttt gcg atg aga tat gca gtg cag caa gca tcg     1248
Leu Pro Val Leu Ala Phe Ala Met Arg Tyr Ala Val Gln Gln Ala Ser
            405                 410                 415 ggc tga                                                              1254
Gly
```

<210> SEQ ID NO 17
<211> LENGTH: 417
<212> TYPE: PRT
<213> ORGANISM: Mortierella alpina

<400> SEQUENCE: 17

```
Met Asp Glu Ser Thr Thr Thr Thr His His Ser Glu Thr Ser Ser
1               5                   10                  15

Lys Thr Ser Ser His Pro Arg Arg Leu Gly Pro Glu Met Asn Pro Ile
            20                  25                  30

Tyr Lys Gly Leu Arg Ala Ile Val Trp Ala Phe Tyr Phe Asn Leu Gly
        35                  40                  45

Ala Ser Leu Ile Ser Ile Thr Gln Val Leu Ser Leu Pro Leu Ala Leu
    50                  55                  60

Ile Ala Pro Gly Val Tyr Gln Trp His Ile Ser Lys Thr Gln Gly His
65                  70                  75                  80

Phe Gly Ala Phe Leu Leu Arg Met Asn Gln Leu Phe Ala Pro Ser Asp
            85                  90                  95
```

```
Ile Val Leu Thr Gly Asp Glu Ser Val Arg Gly Ile Val Lys Val Tyr
            100                 105                 110

Lys Gly Arg Asn Leu Lys Glu Ala Gly Glu Pro Gly Ser Gly Gln Gly
            115                 120                 125

Glu Asp Ile Leu Leu Asp Met Pro Glu Arg Met Val Phe Ile Ala Asn
        130                 135                 140

His Gln Ile Tyr Ser Asp Trp Met Tyr Leu Trp Cys Phe Ser Tyr Phe
145                 150                 155                 160

Ala Glu Arg His Arg Ala Leu Lys Ile Ile Leu Arg Gly Asp Leu Thr
                165                 170                 175

Trp Ile Pro Val Phe Gly Trp Gly Met Arg Phe Phe Asp Phe Ile Phe
            180                 185                 190

Leu Lys Arg Asn Asp Trp Ala His Asp Arg Arg Ala Ile Glu Glu Asn
            195                 200                 205

Leu Gly Arg Val Lys Glu Lys Asp Pro Leu Trp Leu Val Phe Pro
        210                 215                 220

Glu Gly Thr Val Val Ser Lys Glu Thr Arg Leu Arg Ser Val Ala Phe
225                 230                 235                 240

Ser Lys Lys Ala Ser Leu Ser Asp His Arg His Val Leu Leu Pro Arg
                245                 250                 255

Thr Ser Gly Leu Phe Val Cys Ile Asn Lys Leu Arg Gly Ser Val Asp
            260                 265                 270

Tyr Leu Tyr Asp Ala Thr Val Gly Tyr Ser Asn Val Glu Tyr Gly Glu
            275                 280                 285

Ile Pro Gln Glu Leu Tyr Pro Leu Pro Gly Leu Tyr Ile Asn Lys Ala
        290                 295                 300

Gln Pro Lys Glu Ile Asn Met His Leu Arg Arg Phe Ala Ile Lys Asp
305                 310                 315                 320

Ile Pro Thr Ser Glu Pro Glu Phe Val Glu Trp Val Arg Ala Arg Trp
                325                 330                 335

Val Glu Lys Asp Glu Leu Met Glu Glu Phe Tyr Thr Lys Gly Arg Phe
            340                 345                 350

Pro Ser Gln Leu Thr Ala Ala Asp Ile Gly Glu Lys Val Lys Thr
        355                 360                 365

Ala Gly Gly Pro Thr Glu Gly Gln Ser Val Arg Ile Pro Leu Lys Ala
    370                 375                 380

Arg Gly Met Met Asp Tyr Leu Met Pro Ser Val Met Asn Leu Ile Ala
385                 390                 395                 400

Leu Pro Val Leu Ala Phe Ala Met Arg Tyr Ala Val Gln Gln Ala Ser
                405                 410                 415

Gly

<210> SEQ ID NO 18
<211> LENGTH: 1170
<212> TYPE: DNA
<213> ORGANISM: Mortierella alpina
<220> FEATURE:
<221> NAME/KEY: CDS
<222> LOCATION: (1)..(1167)
<223> OTHER INFORMATION: LPAAT

<400> SEQUENCE: 18 atg aac cct atc tac aag ggt ctg cga gcc att gtc tgg gcc ttt tac     48
Met Asn Pro Ile Tyr Lys Gly Leu Arg Ala Ile Val Trp Ala Phe Tyr
1               5                   10                  15 ttc aac ctg gga gcg tcg ctt ata tcg atc acg cag gtg ctg tcg ctg     96
```

```
                Phe Asn Leu Gly Ala Ser Leu Ile Ser Ile Thr Gln Val Leu Ser Leu
                                 20                  25                  30 cct ctg gcg ttg att gct cca ggg gtc tac cag tgg cac atc agc aaa        144
Pro Leu Ala Leu Ile Ala Pro Gly Val Tyr Gln Trp His Ile Ser Lys
             35                  40                  45 aca cag ggt cac ttt gga gct ttc ctg ctc cgg atg aac cag ctc ttt        192
Thr Gln Gly His Phe Gly Ala Phe Leu Leu Arg Met Asn Gln Leu Phe
 50                  55                  60 gcg ccg tca gat att gtc ttg aca ggg gac gag agt gtc agg gga atc        240
Ala Pro Ser Asp Ile Val Leu Thr Gly Asp Glu Ser Val Arg Gly Ile
 65                  70                  75                  80 gtc aag gtc tac aaa gga cgg aac ctg aag gag gcc ggt gag cca ggc        288
Val Lys Val Tyr Lys Gly Arg Asn Leu Lys Glu Ala Gly Glu Pro Gly
                 85                  90                  95 agc ggt cag gga gag gac att ctt ctg gat atg ccc gag agg atg gtt        336
Ser Gly Gln Gly Glu Asp Ile Leu Leu Asp Met Pro Glu Arg Met Val
            100                 105                 110 ttc att gcg aac cac cag atc tac tct gac tgg atg tac ctc tgg tgc        384
Phe Ile Ala Asn His Gln Ile Tyr Ser Asp Trp Met Tyr Leu Trp Cys
        115                 120                 125 ttc tcc tat ttt gca gag agg cac agg gca ctg aag att att ctt cgg        432
Phe Ser Tyr Phe Ala Glu Arg His Arg Ala Leu Lys Ile Ile Leu Arg
130                 135                 140 ggc gac ctg acc tgg atc cct gtc ttt ggc tgg ggt atg cgg ttc ttt        480
Gly Asp Leu Thr Trp Ile Pro Val Phe Gly Trp Gly Met Arg Phe Phe
145                 150                 155                 160 gac ttt atc ttt ttg aaa cgt aat gac tgg gca cac gat cgc cgt gcc        528
Asp Phe Ile Phe Leu Lys Arg Asn Asp Trp Ala His Asp Arg Arg Ala
                165                 170                 175 att gag gaa aac ttg gga cgt gtc aag gaa aag gat ccc ctc tgg ctc        576
Ile Glu Glu Asn Leu Gly Arg Val Lys Glu Lys Asp Pro Leu Trp Leu
            180                 185                 190 gtg gtc ttc ccc gag gga aca gtc gtc tcc aag gaa acg cgt ctc cga        624
Val Val Phe Pro Glu Gly Thr Val Val Ser Lys Glu Thr Arg Leu Arg
        195                 200                 205 tcc gtt gcc ttt tca aag aag gct agt ctg tcg gat cac cgc cat gtg        672
Ser Val Ala Phe Ser Lys Lys Ala Ser Leu Ser Asp His Arg His Val
210                 215                 220 ctg ctt cca agg acc agc ggt ctg ttt gtg tgc atc aac aag ttg cgt        720
Leu Leu Pro Arg Thr Ser Gly Leu Phe Val Cys Ile Asn Lys Leu Arg
225                 230                 235                 240 gga tct gtc gac tac ttg tac gat gca acc gtt ggc tac tcg aat gtc        768
Gly Ser Val Asp Tyr Leu Tyr Asp Ala Thr Val Gly Tyr Ser Asn Val
                245                 250                 255 gag tat ggc gag att ccg cag gag ctt tac ccg tta cca gga ctg tat        816
Glu Tyr Gly Glu Ile Pro Gln Glu Leu Tyr Pro Leu Pro Gly Leu Tyr
            260                 265                 270 atc aac aaa gca cag ccc aag gag atc aac atg cac ctg cgt cga ttt        864
Ile Asn Lys Ala Gln Pro Lys Glu Ile Asn Met His Leu Arg Arg Phe
        275                 280                 285 gcg atc aag gat atc ccc acg tca gaa ccc gaa ttt gtg gaa tgg gtc        912
Ala Ile Lys Asp Ile Pro Thr Ser Glu Pro Glu Phe Val Glu Trp Val
290                 295                 300 cga gct cgg tgg gtg gag aag gat gag ttg atg gaa gag ttt tat acc        960
Arg Ala Arg Trp Val Glu Lys Asp Glu Leu Met Glu Glu Phe Tyr Thr
305                 310                 315                 320 aag ggc cga ttt cca tca caa ctg acg gcc gcc gac att ggt gag aag        1008
Lys Gly Arg Phe Pro Ser Gln Leu Thr Ala Ala Asp Ile Gly Glu Lys
                325                 330                 335
```

```
gag gtc aag acg gca gga ggt cca acg gag gga cag agt gtc agg atc      1056
Glu Val Lys Thr Ala Gly Gly Pro Thr Glu Gly Gln Ser Val Arg Ile
        340                 345                 350 ccg ctc aag gcg cga ggc atg atg gac tac ctc atg ccc tcg gtc atg      1104
Pro Leu Lys Ala Arg Gly Met Met Asp Tyr Leu Met Pro Ser Val Met
355                 360                 365 aat ctg atc gcc ctt cct gtg ctg gcg ttt gcg atg aga tat gca gtg      1152
Asn Leu Ile Ala Leu Pro Val Leu Ala Phe Ala Met Arg Tyr Ala Val
    370                 375                 380 cag caa gca tcg ggc tga                                              1170
Gln Gln Ala Ser Gly
385

<210> SEQ ID NO 19
<211> LENGTH: 389
<212> TYPE: PRT
<213> ORGANISM: Mortierella alpina

<400> SEQUENCE: 19

Met Asn Pro Ile Tyr Lys Gly Leu Arg Ala Ile Val Trp Ala Phe Tyr
1               5                   10                  15

Phe Asn Leu Gly Ala Ser Leu Ile Ser Ile Thr Gln Val Leu Ser Leu
            20                  25                  30

Pro Leu Ala Leu Ile Ala Pro Gly Val Tyr Gln Trp His Ile Ser Lys
        35                  40                  45

Thr Gln Gly His Phe Gly Ala Phe Leu Leu Arg Met Asn Gln Leu Phe
    50                  55                  60

Ala Pro Ser Asp Ile Val Leu Thr Gly Asp Glu Ser Val Arg Gly Ile
65                  70                  75                  80

Val Lys Val Tyr Lys Gly Arg Asn Leu Lys Glu Ala Gly Glu Pro Gly
                85                  90                  95

Ser Gly Gln Gly Glu Asp Ile Leu Leu Asp Met Pro Glu Arg Met Val
            100                 105                 110

Phe Ile Ala Asn His Gln Ile Tyr Ser Asp Trp Met Tyr Leu Trp Cys
        115                 120                 125

Phe Ser Tyr Phe Ala Glu Arg His Arg Ala Leu Lys Ile Ile Leu Arg
    130                 135                 140

Gly Asp Leu Thr Trp Ile Pro Val Phe Gly Trp Gly Met Arg Phe Phe
145                 150                 155                 160

Asp Phe Ile Phe Leu Lys Arg Asn Asp Trp Ala His Asp Arg Arg Ala
                165                 170                 175

Ile Glu Glu Asn Leu Gly Arg Val Lys Glu Asp Pro Leu Trp Leu
            180                 185                 190

Val Val Phe Pro Glu Gly Thr Val Val Ser Lys Glu Thr Arg Leu Arg
        195                 200                 205

Ser Val Ala Phe Ser Lys Lys Ala Ser Leu Ser Asp His Arg His Val
    210                 215                 220

Leu Leu Pro Arg Thr Ser Gly Leu Phe Val Cys Ile Asn Lys Leu Arg
225                 230                 235                 240

Gly Ser Val Asp Tyr Leu Tyr Asp Ala Thr Val Gly Tyr Ser Asn Val
                245                 250                 255

Glu Tyr Gly Glu Ile Pro Gln Glu Leu Tyr Pro Leu Pro Gly Leu Tyr
            260                 265                 270

Ile Asn Lys Ala Gln Pro Lys Glu Ile Asn Met His Leu Arg Arg Phe
        275                 280                 285

Ala Ile Lys Asp Ile Pro Thr Ser Glu Pro Glu Phe Val Glu Trp Val
```

```
                290                 295                 300
Arg Ala Arg Trp Val Glu Lys Asp Glu Leu Met Glu Glu Phe Tyr Thr
305                 310                 315                 320

Lys Gly Arg Phe Pro Ser Gln Leu Thr Ala Ala Asp Ile Gly Glu Lys
                325                 330                 335

Glu Val Lys Thr Ala Gly Gly Pro Thr Glu Gly Gln Ser Val Arg Ile
            340                 345                 350

Pro Leu Lys Ala Arg Gly Met Met Asp Tyr Leu Met Pro Ser Val Met
        355                 360                 365

Asn Leu Ile Ala Leu Pro Val Leu Ala Phe Ala Met Arg Tyr Ala Val
    370                 375                 380

Gln Gln Ala Ser Gly
385

<210> SEQ ID NO 20
<211> LENGTH: 687
<212> TYPE: DNA
<213> ORGANISM: Shewanella hanedai
<220> FEATURE:
<221> NAME/KEY: CDS
<222> LOCATION: (1)..(684)
<223> OTHER INFORMATION: LPAAT

<400> SEQUENCE: 20 atg tta ctg cta gca ttt gtt ttt ggt ggt ctt gtt tgt tta tta aga    48
Met Leu Leu Leu Ala Phe Val Phe Gly Gly Leu Val Cys Leu Leu Arg
1               5                   10                  15 ccg aga cat cgt gac aat gta cac atg ttc gct aaa att ttc tcc tat    96
Pro Arg His Arg Asp Asn Val His Met Phe Ala Lys Ile Phe Ser Tyr
                20                  25                  30 gct gcg cca gta tta ggt atc aag gtc ata gta cgt aaa cct agc gta   144
Ala Ala Pro Val Leu Gly Ile Lys Val Ile Val Arg Lys Pro Ser Val
            35                  40                  45 gcg acg act gag cct tgt gtc ttt ttg gca aat cat cag aat aat ttc   192
Ala Thr Thr Glu Pro Cys Val Phe Leu Ala Asn His Gln Asn Asn Phe
        50                  55                  60 gat atg ttt acc cat act gcg gca gta ccg aaa ggg acg gtc agt ctt   240
Asp Met Phe Thr His Thr Ala Ala Val Pro Lys Gly Thr Val Ser Leu
65                  70                  75                  80 gga aag aag agt tta gct tgg gtg cct ttt ttt ggt cag att tac tgg   288
Gly Lys Lys Ser Leu Ala Trp Val Pro Phe Phe Gly Gln Ile Tyr Trp
                85                  90                  95 ttg tcc ggt aat att cta att gac aga aaa aac cgc aat aga gcg ttt   336
Leu Ser Gly Asn Ile Leu Ile Asp Arg Lys Asn Arg Asn Arg Ala Phe
                100                 105                 110 gaa acc atg gcg caa acc gcc aaa aag att aaa gat aag tgc tta tct   384
Glu Thr Met Ala Gln Thr Ala Lys Lys Ile Lys Asp Lys Cys Leu Ser
            115                 120                 125 atc tgg ata ttt ccg gaa ggt acg cgc tct cgt ggc aag ggc tta ttg   432
Ile Trp Ile Phe Pro Glu Gly Thr Arg Ser Arg Gly Lys Gly Leu Leu
        130                 135                 140 cct ttt aaa tct ggt gca ttt cat act gca ata gat gcg gga gtg gct   480
Pro Phe Lys Ser Gly Ala Phe His Thr Ala Ile Asp Ala Gly Val Ala
145                 150                 155                 160 atg gta cct gtg ttg gca tca aat caa agc cat ata aaa ctt aat cgt   528
Met Val Pro Val Leu Ala Ser Asn Gln Ser His Ile Lys Leu Asn Arg
                165                 170                 175 tgg aat aat ggt gtg gtt att atc gag atg atg gat cca atc gaa act   576
Trp Asn Asn Gly Val Val Ile Ile Glu Met Met Asp Pro Ile Glu Thr
                180                 185                 190
```

```
aaa ggt ttg gct aag tct cag gta aag gag ttg tct aaa cgt atc cac    624
Lys Gly Leu Ala Lys Ser Gln Val Lys Glu Leu Ser Lys Arg Ile His
        195                 200                 205 gct atg atg tcg aat cgt tta act cag ttg gat caa gaa gct tca gcc    672
Ala Met Met Ser Asn Arg Leu Thr Gln Leu Asp Gln Glu Ala Ser Ala
    210                 215                 220 tta atg gca aag taa                                                687
Leu Met Ala Lys
225

<210> SEQ ID NO 21
<211> LENGTH: 228
<212> TYPE: PRT
<213> ORGANISM: Shewanella hanedai

<400> SEQUENCE: 21

Met Leu Leu Leu Ala Phe Val Phe Gly Gly Leu Val Cys Leu Leu Arg
1               5                   10                  15

Pro Arg His Arg Asp Asn Val His Met Phe Ala Lys Ile Phe Ser Tyr
            20                  25                  30

Ala Ala Pro Val Leu Gly Ile Lys Val Ile Val Arg Lys Pro Ser Val
        35                  40                  45

Ala Thr Thr Glu Pro Cys Val Phe Leu Ala Asn His Gln Asn Asn Phe
    50                  55                  60

Asp Met Phe Thr His Thr Ala Ala Val Pro Lys Gly Thr Val Ser Leu
65                  70                  75                  80

Gly Lys Lys Ser Leu Ala Trp Val Pro Phe Gly Gln Ile Tyr Trp
                85                  90                  95

Leu Ser Gly Asn Ile Leu Ile Asp Arg Lys Asn Arg Asn Arg Ala Phe
            100                 105                 110

Glu Thr Met Ala Gln Thr Ala Lys Lys Ile Lys Asp Lys Cys Leu Ser
        115                 120                 125

Ile Trp Ile Phe Pro Glu Gly Thr Arg Ser Arg Gly Lys Gly Leu Leu
    130                 135                 140

Pro Phe Lys Ser Gly Ala Phe His Thr Ala Ile Asp Ala Gly Val Ala
145                 150                 155                 160

Met Val Pro Val Leu Ala Ser Asn Gln Ser His Ile Lys Leu Asn Arg
                165                 170                 175

Trp Asn Asn Gly Val Val Ile Ile Glu Met Met Asp Pro Ile Glu Thr
            180                 185                 190

Lys Gly Leu Ala Lys Ser Gln Val Lys Glu Leu Ser Lys Arg Ile His
        195                 200                 205

Ala Met Met Ser Asn Arg Leu Thr Gln Leu Asp Gln Glu Ala Ser Ala
    210                 215                 220

Leu Met Ala Lys
225

<210> SEQ ID NO 22
<211> LENGTH: 1352
<212> TYPE: DNA
<213> ORGANISM: Physcomitrella patens
<220> FEATURE:
<221> NAME/KEY: CDS
<222> LOCATION: (39)..(1340)
<223> OTHER INFORMATION: GPAT

<400> SEQUENCE: 22
ggccgcaagg taaccgcctt ctgccgcaag ccttgact atg ccg tcg ctg ttt cgg    56
```

```
                        Met Pro Ser Leu Phe Arg
                         1               5 gcg aaa cgc aat ggc aga agg acg ccg ggg aat gcc gtg acc aat ttc    104
Ala Lys Arg Asn Gly Arg Arg Thr Pro Gly Asn Ala Val Thr Asn Phe
         10              15              20 ggg aaa tct gaa ttc cat cgt gaa att agt ggg agt acg cgg gcg acc    152
Gly Lys Ser Glu Phe His Arg Glu Ile Ser Gly Ser Thr Arg Ala Thr
             25              30              35 acg cag gtg gct gaa gcc acc aca gct ggt ctt agg gag acc att gag    200
Thr Gln Val Ala Glu Ala Thr Thr Ala Gly Leu Arg Glu Thr Ile Glu
 40              45              50 gac cgc gct att atc gac ggt cat tct cac agt ttt gaa gga att caa    248
Asp Arg Ala Ile Ile Asp Gly His Ser His Ser Phe Glu Gly Ile Gln
 55              60              65              70 tcg gaa gaa gag ttg atg cag gta att gaa aag gag gtg gaa tcc ggt    296
Ser Glu Glu Glu Leu Met Gln Val Ile Glu Lys Glu Val Glu Ser Gly
             75              80              85 cgg ctg ccg aag cgt gct ggc gcg gga atg gta gag ttg tat cgc aat    344
Arg Leu Pro Lys Arg Ala Gly Ala Gly Met Val Glu Leu Tyr Arg Asn
             90              95             100 tat cga gat gct gta gtg agc agt ggc gta gaa aat gcg atg gat att    392
Tyr Arg Asp Ala Val Val Ser Ser Gly Val Glu Asn Ala Met Asp Ile
             105             110             115 gtt gtg aaa gtc atg tca act gtg ttg gac cgg att ctt ctg cag ttc    440
Val Val Lys Val Met Ser Thr Val Leu Asp Arg Ile Leu Leu Gln Phe
 120             125             130 gag gag cca ttc aca ttt gga tcg cac cac aag aga atg gtg gag ccg    488
Glu Glu Pro Phe Thr Phe Gly Ser His His Lys Arg Met Val Glu Pro
135             140             145             150 tat gat tac tac aca ttt ggt cag aac tat gtg cgt cct ctc cta gat    536
Tyr Asp Tyr Tyr Thr Phe Gly Gln Asn Tyr Val Arg Pro Leu Leu Asp
             155             160             165 ttc agg aac tct tac ctt ggg aac tta aag atc ttt gac cag ata gag    584
Phe Arg Asn Ser Tyr Leu Gly Asn Leu Lys Ile Phe Asp Gln Ile Glu
             170             175             180 aag aac ctg aaa gag ggg cac aac gtc att ttt cta tcc aat cac cag    632
Lys Asn Leu Lys Glu Gly His Asn Val Ile Phe Leu Ser Asn His Gln
             185             190             195 act gag gca gat cct gct gtt atg gcg ctg ttg ctt gag cac tct cac    680
Thr Glu Ala Asp Pro Ala Val Met Ala Leu Leu Leu Glu His Ser His
 200             205             210 ccc tat ttg gca gag aac ttg acc tat gtg gct gga gac agg gtt gtg    728
Pro Tyr Leu Ala Glu Asn Leu Thr Tyr Val Ala Gly Asp Arg Val Val
215             220             225             230 ctg gat cca ttc tgc aaa cct ttt agt atg ggc agg aat ctc ttg tgc    776
Leu Asp Pro Phe Cys Lys Pro Phe Ser Met Gly Arg Asn Leu Leu Cys
             235             240             245 gtg tat tca aaa aag cac att cac gat gta ccg gac ctt gct gaa atg    824
Val Tyr Ser Lys Lys His Ile His Asp Val Pro Asp Leu Ala Glu Met
             250             255             260 aaa atc aaa gct aat gcg aag act ttg aga cag atg acg atc ctg ctg    872
Lys Ile Lys Ala Asn Ala Lys Thr Leu Arg Gln Met Thr Ile Leu Leu
             265             270             275 agg cag gga ggt caa tta tta tgg gta gca ccc agt ggt gga cgc gat    920
Arg Gln Gly Gly Gln Leu Leu Trp Val Ala Pro Ser Gly Gly Arg Asp
             280             285             290 cgc cct gat cct gag acc aac gaa tgg gtt cct gca cat ttt gac tcg    968
Arg Pro Asp Pro Glu Thr Asn Glu Trp Val Pro Ala His Phe Asp Ser
295             300             305             310
```

```
tct gct gtg gag aat atg aag cga cta tct gac att gtc cga gta cct    1016
Ser Ala Val Glu Asn Met Lys Arg Leu Ser Asp Ile Val Arg Val Pro
            315                 320                 325 gct cat tta cat gcc cta tca tta cta tgt ttt gag att atg cca cct    1064
Ala His Leu His Ala Leu Ser Leu Leu Cys Phe Glu Ile Met Pro Pro
            330                 335                 340 cct gtc cag gta caa aag gag cta gga gag cga aga gca gta gga ttt    1112
Pro Val Gln Val Gln Lys Glu Leu Gly Glu Arg Arg Ala Val Gly Phe
            345                 350                 355 agc gga gtt ggt cta gcc gtt tcc gag caa cta gat tat gat tcc att    1160
Ser Gly Val Gly Leu Ala Val Ser Glu Gln Leu Asp Tyr Asp Ser Ile
            360                 365                 370 gcg aag tta gtc gac gat tcc aaa aat gcg aag gat gcc ttt tcg gat    1208
Ala Lys Leu Val Asp Asp Ser Lys Asn Ala Lys Asp Ala Phe Ser Asp
375                 380                 385                 390 gcg gca tgg agc gaa gtc aat gat atg tat aac gtg tta aaa gaa gca    1256
Ala Ala Trp Ser Glu Val Asn Asp Met Tyr Asn Val Leu Lys Glu Ala
                395                 400                 405 att tat ggt gac caa ggt tgt gct gtt agc aca gat tcc ttg aga ctg    1304
Ile Tyr Gly Asp Gln Gly Cys Ala Val Ser Thr Asp Ser Leu Arg Leu
            410                 415                 420 gaa cag ccc tgg ttt gat gga agc agg cga act gat tgaaaatagg gc     1352
Glu Gln Pro Trp Phe Asp Gly Ser Arg Arg Thr Asp
            425                 430
```

<210> SEQ ID NO 23
<211> LENGTH: 434
<212> TYPE: PRT
<213> ORGANISM: Physcomitrella patens

<400> SEQUENCE: 23

```
Met Pro Ser Leu Phe Arg Ala Lys Arg Asn Gly Arg Thr Pro Gly
1               5                   10                  15

Asn Ala Val Thr Asn Phe Gly Lys Ser Glu Phe His Arg Glu Ile Ser
                20                  25                  30

Gly Ser Thr Arg Ala Thr Thr Gln Val Ala Glu Ala Thr Thr Ala Gly
            35                  40                  45

Leu Arg Glu Thr Ile Glu Asp Arg Ala Ile Ile Asp Gly His Ser His
        50                  55                  60

Ser Phe Glu Gly Ile Gln Ser Glu Glu Glu Leu Met Gln Val Ile Glu
65                  70                  75                  80

Lys Glu Val Glu Ser Gly Arg Leu Pro Lys Arg Ala Gly Ala Gly Met
                85                  90                  95

Val Glu Leu Tyr Arg Asn Tyr Arg Asp Ala Val Val Ser Ser Gly Val
            100                 105                 110

Glu Asn Ala Met Asp Ile Val Val Lys Val Met Ser Thr Val Leu Asp
        115                 120                 125

Arg Ile Leu Leu Gln Phe Glu Glu Pro Phe Thr Phe Gly Ser His His
    130                 135                 140

Lys Arg Met Val Glu Pro Tyr Asp Tyr Tyr Thr Phe Gly Gln Asn Tyr
145                 150                 155                 160

Val Arg Pro Leu Leu Asp Phe Arg Asn Ser Tyr Leu Gly Asn Leu Lys
                165                 170                 175

Ile Phe Asp Gln Ile Glu Lys Asn Leu Lys Glu Gly His Asn Val Ile
            180                 185                 190

Phe Leu Ser Asn His Gln Thr Glu Ala Asp Pro Ala Val Met Ala Leu
        195                 200                 205
```

```
Leu Leu Glu His Ser His Pro Tyr Leu Ala Glu Asn Leu Thr Tyr Val
    210             215                 220

Ala Gly Asp Arg Val Val Leu Asp Pro Phe Cys Lys Pro Phe Ser Met
225             230                 235                 240

Gly Arg Asn Leu Leu Cys Val Tyr Ser Lys Lys His Ile His Asp Val
                245                 250                 255

Pro Asp Leu Ala Glu Met Lys Ile Lys Ala Asn Ala Lys Thr Leu Arg
            260                 265                 270

Gln Met Thr Ile Leu Leu Arg Gln Gly Gly Gln Leu Leu Trp Val Ala
        275                 280                 285

Pro Ser Gly Gly Arg Asp Arg Pro Asp Pro Glu Thr Asn Glu Trp Val
    290                 295                 300

Pro Ala His Phe Asp Ser Ser Ala Val Glu Asn Met Lys Arg Leu Ser
305             310                 315                 320

Asp Ile Val Arg Val Pro Ala His Leu His Ala Leu Ser Leu Leu Cys
                325                 330                 335

Phe Glu Ile Met Pro Pro Val Gln Val Gln Lys Glu Leu Gly Glu
            340                 345                 350

Arg Arg Ala Val Gly Phe Ser Gly Val Gly Leu Ala Val Ser Glu Gln
        355                 360                 365

Leu Asp Tyr Asp Ser Ile Ala Lys Leu Val Asp Ser Lys Asn Ala
    370                 375                 380

Lys Asp Ala Phe Ser Asp Ala Ala Trp Ser Glu Val Asn Asp Met Tyr
385             390                 395                 400

Asn Val Leu Lys Glu Ala Ile Tyr Gly Asp Gln Gly Cys Ala Val Ser
                405                 410                 415

Thr Asp Ser Leu Arg Leu Glu Gln Pro Trp Phe Asp Gly Ser Arg Arg
            420                 425                 430

Thr Asp
```

<210> SEQ ID NO 24
<211> LENGTH: 444
<212> TYPE: DNA
<213> ORGANISM: Physcomitrella patens
<220> FEATURE:
<221> NAME/KEY: CDS
<222> LOCATION: (1)..(444)
<223> OTHER INFORMATION: GPAT/LPAAT

<400> SEQUENCE: 24

```
atg atc cgg att ttc aga ggg caa cca tct gtg gtt cat gtg cac gtg    48
Met Ile Arg Ile Phe Arg Gly Gln Pro Ser Val Val His Val His Val
1               5                   10                  15 agg cgg gtc cct atg tct gat ctg cct gag gga gcc aac gcg att tct    96
Arg Arg Val Pro Met Ser Asp Leu Pro Glu Gly Ala Asn Ala Ile Ser
            20                  25                  30 aaa tgg tgt cac gat gcc ttt cac atc aag gac gat cgg ctg gag cag   144
Lys Trp Cys His Asp Ala Phe His Ile Lys Asp Asp Arg Leu Glu Gln
        35                  40                  45 cac gaa aaa gag aat acg ttt ggg gag gac ttg tat att cct att gaa   192
His Glu Lys Glu Asn Thr Phe Gly Glu Asp Leu Tyr Ile Pro Ile Glu
    50                  55                  60 cgg cca ctt aaa cct ctt att att gtg atc tcc tgg gcc atc act ttg   240
Arg Pro Leu Lys Pro Leu Ile Ile Val Ile Ser Trp Ala Ile Thr Leu
65                  70                  75                  80 ctg gct gca gca tgg tgg ttt cta aga cga gtt tta tcc act tgg aaa   288
Leu Ala Ala Ala Trp Trp Phe Leu Arg Arg Val Leu Ser Thr Trp Lys
                85                  90                  95
```

```
gga atc gcc tgg gtg gca gga gta ctc gtg gtc gtc atg ctg tgt gtc      336
Gly Ile Ala Trp Val Ala Gly Val Leu Val Val Val Met Leu Cys Val
            100                 105                 110 cag att tta gtg atg tcg tca caa tcg gaa aga agt tca gat cct gca      384
Gln Ile Leu Val Met Ser Ser Gln Ser Glu Arg Ser Ser Asp Pro Ala
        115                 120                 125 gct aag aag gcc aat caa aaa cag gcg gct tct gtt gct cac ctc ggc      432
Ala Lys Lys Ala Asn Gln Lys Gln Ala Ala Ser Val Ala His Leu Gly
    130                 135                 140 aaa acg gac tga                                                      444
Lys Thr Asp
145

<210> SEQ ID NO 25
<211> LENGTH: 147
<212> TYPE: PRT
<213> ORGANISM: Physcomitrella patens

<400> SEQUENCE: 25

Met Ile Arg Ile Phe Arg Gly Gln Pro Ser Val Val His Val His Val
1               5                   10                  15

Arg Arg Val Pro Met Ser Asp Leu Pro Glu Gly Ala Asn Ala Ile Ser
            20                  25                  30

Lys Trp Cys His Asp Ala Phe His Ile Lys Asp Asp Arg Leu Glu Gln
        35                  40                  45

His Glu Lys Glu Asn Thr Phe Gly Glu Asp Leu Tyr Ile Pro Ile Glu
    50                  55                  60

Arg Pro Leu Lys Pro Leu Ile Ile Val Ile Ser Trp Ala Ile Thr Leu
65                  70                  75                  80

Leu Ala Ala Ala Trp Trp Phe Leu Arg Arg Val Leu Ser Thr Trp Lys
                85                  90                  95

Gly Ile Ala Trp Val Ala Gly Val Leu Val Val Val Met Leu Cys Val
            100                 105                 110

Gln Ile Leu Val Met Ser Ser Gln Ser Glu Arg Ser Ser Asp Pro Ala
        115                 120                 125

Ala Lys Lys Ala Asn Gln Lys Gln Ala Ala Ser Val Ala His Leu Gly
    130                 135                 140

Lys Thr Asp
145

<210> SEQ ID NO 26
<211> LENGTH: 1710
<212> TYPE: DNA
<213> ORGANISM: Physcomitrella patens
<220> FEATURE:
<221> NAME/KEY: CDS
<222> LOCATION: (246)..(1394)
<223> OTHER INFORMATION: GPAT/LPAAT

<400> SEQUENCE: 26
gaattcgccc tttctctttt tcgtgctgct ccagccgata ttcatgacct gcccgggcag     60
gtcacattgc gtgttggcca tgtcctggtt gcagctctcg tgaccctcac gctcgcgagc    120
ggcaccgctc gtcttctgcc tcttgcttgc tcttgcttgc tttctgagga acagccccag    180
ctccggcacc agcataaggt cgtgtaggga gagagagaga gggggagaga agtaagcttg    240 gagtc atg gag ggc ggg ggc tcc ata atc gct ctt cct ctg ggg ctt atg    290
      Met Glu Gly Gly Gly Ser Ile Ile Ala Leu Pro Leu Gly Leu Met
      1               5                   10                  15
```

```
ttc ctc ttc tcc ggg ttc ttt atc aat atc ctg cag ctg ctg tcg gtg         338
Phe Leu Phe Ser Gly Phe Phe Ile Asn Ile Leu Gln Leu Leu Ser Val
                20                  25                  30 tta ttc att ttg ccg ttt tcg agg agg gcg tac cga gta gta aat atg         386
Leu Phe Ile Leu Pro Phe Ser Arg Arg Ala Tyr Arg Val Val Asn Met
        35                  40                  45 att atg atg gag gtg ctg tgg tcg gag ctt ata tgg ctg ctg gat tgg         434
Ile Met Met Glu Val Leu Trp Ser Glu Leu Ile Trp Leu Leu Asp Trp
    50                  55                  60 tgg gcg aat gtg aag gtg aag gtt tac acg cca aag gag tcg tgg gag         482
Trp Ala Asn Val Lys Val Lys Val Tyr Thr Pro Lys Glu Ser Trp Glu
65                  70                  75 cac tta gga aag gag cac gca tta ctc att tgt aat cac cgc agt gac         530
His Leu Gly Lys Glu His Ala Leu Leu Ile Cys Asn His Arg Ser Asp
80                  85                  90                  95 ata gat tgg ctc gta gga tgg att att gcc cag aga ttg ggt tgt cta         578
Ile Asp Trp Leu Val Gly Trp Ile Ile Ala Gln Arg Leu Gly Cys Leu
                100                 105                 110 ggt ggg act cga gct gtt atg aag aag tcc acc aaa ttt ctt ccg gtc         626
Gly Gly Thr Arg Ala Val Met Lys Lys Ser Thr Lys Phe Leu Pro Val
        115                 120                 125 att ggc tgg tct atg tgg ttt tca gag tat gtg ttt tta tca aga gat         674
Ile Gly Trp Ser Met Trp Phe Ser Glu Tyr Val Phe Leu Ser Arg Asp
    130                 135                 140 tgg gcc aaa gat gag aag gtc ttg aag aat ggt tat tca agt ctt aag         722
Trp Ala Lys Asp Glu Lys Val Leu Lys Asn Gly Tyr Ser Ser Leu Lys
145                 150                 155 ggc ttc ccc agg acc ttg tgg gtg gct ctt ttt gtg gaa ggc act cga         770
Gly Phe Pro Arg Thr Leu Trp Val Ala Leu Phe Val Glu Gly Thr Arg
160                 165                 170                 175 ttt acg aag gcc aaa ctt gag gct gcc caa aaa ttt gca gcg gat aca         818
Phe Thr Lys Ala Lys Leu Glu Ala Ala Gln Lys Phe Ala Ala Asp Thr
                180                 185                 190 ggg cta cgt gtt cca agg cat gtg ctt gtt cct cgc aca aaa ggg ttc         866
Gly Leu Arg Val Pro Arg His Val Leu Val Pro Arg Thr Lys Gly Phe
        195                 200                 205 gtt tcg gct gtg gag aac ttg cgt gaa ttt gtt ccg gta gtt tat gac         914
Val Ser Ala Val Glu Asn Leu Arg Glu Phe Val Pro Val Val Tyr Asp
    210                 215                 220 atg acc gtt gct ata tct aaa gag ctg ccc aat cct aca atg atc cgg         962
Met Thr Val Ala Ile Ser Lys Glu Leu Pro Asn Pro Thr Met Ile Arg
225                 230                 235 att ttc aga ggg caa cca tct gtg gtt cat gtg cac gtg aga cgg gtc        1010
Ile Phe Arg Gly Gln Pro Ser Val Val His Val His Val Arg Arg Val
240                 245                 250                 255 cct atg tct gat ctg cct gag gga gcc aac gcg att tct aaa tgg tgt        1058
Pro Met Ser Asp Leu Pro Glu Gly Ala Asn Ala Ile Ser Lys Trp Cys
                260                 265                 270 cac gat gcc ttt cac atc aag gac gat cgg ctg gag cag cac gaa aaa        1106
His Asp Ala Phe His Ile Lys Asp Asp Arg Leu Glu Gln His Glu Lys
        275                 280                 285 gag aat acg ttt ggg gag gac ttg tat att cct att gaa cgg cca ctt        1154
Glu Asn Thr Phe Gly Glu Asp Leu Tyr Ile Pro Ile Glu Arg Pro Leu
    290                 295                 300 aaa cct ctt att att gtg atc tcc tgg gcc atc act ttg ctg gct gca        1202
Lys Pro Leu Ile Ile Val Ile Ser Trp Ala Ile Thr Leu Leu Ala Ala
305                 310                 315 gca tgg tgg ttt cta aga cga gtt tta tcc act tgg aaa gga atc gcc        1250
Ala Trp Trp Phe Leu Arg Arg Val Leu Ser Thr Trp Lys Gly Ile Ala
320                 325                 330                 335
```

```
tgg gtg gca gga gta ctc gtg gtc gtc atg ctg tgt gtc cag att tta     1298
Trp Val Ala Gly Val Leu Val Val Val Met Leu Cys Val Gln Ile Leu
            340                 345                 350 gtg atg tcg tca caa tcg gaa aga agt tca gat cct gca gct aag aag     1346
Val Met Ser Ser Gln Ser Glu Arg Ser Ser Asp Pro Ala Ala Lys Lys
        355                 360                 365 gcc aat caa aaa cag gcg gct tct gtt gct cac ctc ggc aaa acg gac     1394
Ala Asn Gln Lys Gln Ala Ala Ser Val Ala His Leu Gly Lys Thr Asp
370                 375                 380 tgagaacttt tgctttaacg caatccaaga cttaggcgtg ctagtctcag ttacaattag    1454
cattcaggca ctccagatgt gtcaagaaat tttagttact ctagccaaga attgtttgac    1514
accttgtagt ccacctaatt tccttgaacg attaagagca gcggccatta gatgattcga    1574 tttggttct tgatagtatc tggtaccttc ttcttcaagc attgtgtatt ccgcttcagc     1634
cattcctttt tttaagatgt attgcttctc gttcgagggt aggtcatttc tgatctaatt    1694
ttgaaagcac taattc                                                   1710

<210> SEQ ID NO 27
<211> LENGTH: 383
<212> TYPE: PRT
<213> ORGANISM: Physcomitrella patens

<400> SEQUENCE: 27

Met Glu Gly Gly Gly Ser Ile Ile Ala Leu Pro Leu Gly Leu Met Phe
1               5                   10                  15

Leu Phe Ser Gly Phe Phe Ile Asn Ile Leu Gln Leu Leu Ser Val Leu
            20                  25                  30

Phe Ile Leu Pro Phe Ser Arg Arg Ala Tyr Arg Val Val Asn Met Ile
        35                  40                  45

Met Met Glu Val Leu Trp Ser Glu Leu Ile Trp Leu Leu Asp Trp Trp
    50                  55                  60

Ala Asn Val Lys Val Lys Val Tyr Thr Pro Lys Glu Ser Trp Glu His
65                  70                  75                  80

Leu Gly Lys Glu His Ala Leu Leu Ile Cys Asn His Arg Ser Asp Ile
                85                  90                  95

Asp Trp Leu Val Gly Trp Ile Ile Ala Gln Arg Leu Gly Cys Leu Gly
            100                 105                 110

Gly Thr Arg Ala Val Met Lys Lys Ser Thr Lys Phe Leu Pro Val Ile
        115                 120                 125

Gly Trp Ser Met Trp Phe Ser Glu Tyr Val Phe Leu Ser Arg Asp Trp
    130                 135                 140

Ala Lys Asp Glu Lys Val Leu Lys Asn Gly Tyr Ser Ser Leu Lys Gly
145                 150                 155                 160

Phe Pro Arg Thr Leu Trp Val Ala Leu Phe Val Glu Gly Thr Arg Phe
                165                 170                 175

Thr Lys Ala Lys Leu Glu Ala Ala Gln Lys Phe Ala Ala Asp Thr Gly
            180                 185                 190

Leu Arg Val Pro Arg His Val Leu Val Pro Arg Thr Lys Gly Phe Val
        195                 200                 205

Ser Ala Val Glu Asn Leu Arg Glu Phe Val Pro Val Val Tyr Asp Met
    210                 215                 220

Thr Val Ala Ile Ser Lys Glu Leu Pro Asn Pro Thr Met Ile Arg Ile
225                 230                 235                 240

Phe Arg Gly Gln Pro Ser Val Val His Val His Val Arg Arg Val Pro
```

```
                   245                 250                 255
Met Ser Asp Leu Pro Glu Gly Ala Asn Ala Ile Ser Lys Trp Cys His
            260                 265                 270

Asp Ala Phe His Ile Lys Asp Asp Arg Leu Glu Gln His Glu Lys Glu
            275                 280                 285

Asn Thr Phe Gly Glu Asp Leu Tyr Ile Pro Ile Glu Arg Pro Leu Lys
            290                 295                 300

Pro Leu Ile Ile Val Ile Ser Trp Ala Ile Thr Leu Leu Ala Ala Ala
305                 310                 315                 320

Trp Trp Phe Leu Arg Arg Val Leu Ser Thr Trp Lys Gly Ile Ala Trp
                325                 330                 335

Val Ala Gly Val Leu Val Val Met Leu Cys Val Gln Ile Leu Val
            340                 345                 350

Met Ser Ser Gln Ser Glu Arg Ser Ser Asp Pro Ala Ala Lys Lys Ala
            355                 360                 365

Asn Gln Lys Gln Ala Ala Ser Val Ala His Leu Gly Lys Thr Asp
        370                 375                 380

<210> SEQ ID NO 28
<211> LENGTH: 628
<212> TYPE: DNA
<213> ORGANISM: Cryptocodinium cohnii
<220> FEATURE:
<221> NAME/KEY: CDS
<222> LOCATION: (3)..(578)
<223> OTHER INFORMATION: DAGAT

<400> SEQUENCE: 28 tt gat gat tgg atc gcc gcg ttg gcg act gct tgt gca agc acg gat       47
   Asp Asp Trp Ile Ala Ala Leu Ala Thr Ala Cys Ala Ser Thr Asp
   1               5                  10                  15 ggg gtt acg gac gtc gac agc ctg aag ccc tca gca agt gca gtt ccc      95
Gly Val Thr Asp Val Asp Ser Leu Lys Pro Ser Ala Ser Ala Val Pro
                20                  25                  30 cat gga ccc ccc aag gcg aag gtc agt gag cta tcg gcc ctg cgc aag    143
His Gly Pro Pro Lys Ala Lys Val Ser Glu Leu Ser Ala Leu Arg Lys
            35                  40                  45 gtg cac aat cga aac cgg acc agc gtt ttg acc aac gag gac gga ggc    191
Val His Asn Arg Asn Arg Thr Ser Val Leu Thr Asn Glu Asp Gly Gly
        50                  55                  60 att cct gag tgc aac gtt gtg ggg atc gtg aac ctc tgt gtt act gtg    239
Ile Pro Glu Cys Asn Val Val Gly Ile Val Asn Leu Cys Val Thr Val
65                  70                  75 atg gtc ttg atc cac ctg cgc ctc att tat gag agc atc cgg aag cac    287
Met Val Leu Ile His Leu Arg Leu Ile Tyr Glu Ser Ile Arg Lys His
80                  85                  90                  95 ggt gtt ttg ttg gac acc ttc cgg gtg gcg gcc cac acc gca ctc aag    335
Gly Val Leu Leu Asp Thr Phe Arg Val Ala Ala His Thr Ala Leu Lys
                100                 105                 110 cca ggt aac ttc cag tgt acg ctt tgt ttc ttc gct ttg ccg gtc ctg    383
Pro Gly Asn Phe Gln Cys Thr Leu Cys Phe Phe Ala Leu Pro Val Leu
            115                 120                 125 gcc atc ttg gcg acc ttc att gag gtc ttg gcg agc aag gga cag ttg    431
Ala Ile Leu Ala Thr Phe Ile Glu Val Leu Ala Ser Lys Gly Gln Leu
        130                 135                 140 ggg atc tcg ctt cgc gag cac cct gca tgc cgg gct ttg tac aat ctg    479
Gly Ile Ser Leu Arg Glu His Pro Ala Cys Arg Ala Leu Tyr Asn Leu
145                 150                 155 cct tac cat ccc tgt cct ggt cat cca cca ctt tca ggc aac tcc tct    527
```

```
Pro Tyr His Pro Cys Pro Gly His Pro Pro Leu Ser Gly Asn Ser Ser
160                 165                 170                 175 cgt ggg agc ctc gtt gct gat tgc tgc gac cac tct ctt ctt gaa agt      575
Arg Gly Ser Leu Val Ala Asp Cys Cys Asp His Ser Leu Leu Glu Ser
                180                 185                 190 tgg tgagcttcgc ccacgtgaat tggctctcgg cgacagtgga aggcgatgga           628
Trp
```

<210> SEQ ID NO 29
<211> LENGTH: 192
<212> TYPE: PRT
<213> ORGANISM: Cryptocodinium cohnii

<400> SEQUENCE: 29

```
Asp Asp Trp Ile Ala Ala Leu Ala Thr Ala Cys Ala Ser Thr Asp Gly
1               5                   10                  15

Val Thr Asp Val Asp Ser Leu Lys Pro Ser Ala Ser Ala Val Pro His
                20                  25                  30

Gly Pro Pro Lys Ala Lys Val Ser Glu Leu Ser Ala Leu Arg Lys Val
            35                  40                  45

His Asn Arg Asn Arg Thr Ser Val Leu Thr Asn Glu Asp Gly Gly Ile
        50                  55                  60

Pro Glu Cys Asn Val Val Gly Ile Val Asn Leu Cys Val Thr Val Met
65                  70                  75                  80

Val Leu Ile His Leu Arg Leu Ile Tyr Glu Ser Ile Arg Lys His Gly
                85                  90                  95

Val Leu Leu Asp Thr Phe Arg Val Ala Ala His Thr Ala Leu Lys Pro
            100                 105                 110

Gly Asn Phe Gln Cys Thr Leu Cys Phe Phe Ala Leu Pro Val Leu Ala
        115                 120                 125

Ile Leu Ala Thr Phe Ile Glu Val Leu Ala Ser Lys Gly Gln Leu Gly
    130                 135                 140

Ile Ser Leu Arg Glu His Pro Ala Cys Arg Ala Leu Tyr Asn Leu Pro
145                 150                 155                 160

Tyr His Pro Cys Pro Gly His Pro Pro Leu Ser Gly Asn Ser Ser Arg
                165                 170                 175

Gly Ser Leu Val Ala Asp Cys Cys Asp His Ser Leu Leu Glu Ser Trp
            180                 185                 190
```

<210> SEQ ID NO 30
<211> LENGTH: 1272
<212> TYPE: DNA
<213> ORGANISM: Cryptocodinium cohnii
<220> FEATURE:
<221> NAME/KEY: CDS
<222> LOCATION: (164)..(1120)
<223> OTHER INFORMATION: DAGAT

<400> SEQUENCE: 30

```
ggacactgac atggactgaa ggagtagaaa gccgtagcca ttttggctca agctccagtg    60
aacagtcgcg ccctgactgc agaggggtgc ggcacaaacc ctcagataca cacacatccc   120
gtgagtttat agattcttgt ctcgcgctct tcttgtgcaa gcg atg gct gga aag    175
                                                Met Ala Gly Lys
                                                1 tgg atg ctg ctc agt ggt ggt gca gca gct gca gcg ttg gcg ctt ctg    223
Trp Met Leu Leu Ser Gly Gly Ala Ala Ala Ala Ala Leu Ala Leu Leu
5                   10                  15                  20 gag ggc acc cag ctt cga gcg tcg aca tcg gca cgc gcc cgg ata ttg    271
```

```
Glu Gly Thr Gln Leu Arg Ala Ser Thr Ser Ala Arg Ala Arg Ile Leu
             25                  30                  35 ctg gtt tcg ttg gca gca tat ctc cca acg tac ctc gat gga agc gag      319
Leu Val Ser Leu Ala Ala Tyr Leu Pro Thr Tyr Leu Asp Gly Ser Glu
         40                  45                  50 tac cgg gct gcc cct cga cga agc gag cga gcc tca cgg gtc ctg cgg      367
Tyr Arg Ala Ala Pro Arg Arg Ser Glu Arg Ala Ser Arg Val Leu Arg
             55                  60                  65 cag ttg tac aaa gtc atg gta aat tgg ttc ttc aca atc aaa cgg cca      415
Gln Leu Tyr Lys Val Met Val Asn Trp Phe Phe Thr Ile Lys Arg Pro
     70                  75                  80 gta atc gag gct tcc gaa gag ctg aca gct tgt gac cag tgc atc ttg      463
Val Ile Glu Ala Ser Glu Glu Leu Thr Ala Cys Asp Gln Cys Ile Leu
 85                  90                  95                 100 gcg gtc cat ccc cat gga gta cct tct ctc gac cat ttg ctg acg gtc      511
Ala Val His Pro His Gly Val Pro Ser Leu Asp His Leu Leu Thr Val
                105                 110                 115 atc gcc tat gat cct gac ttg gaa cgg gtg ttg ccc cag ttg cgg aga      559
Ile Ala Tyr Asp Pro Asp Leu Glu Arg Val Leu Pro Gln Leu Arg Arg
            120                 125                 130 agt gcc ttg agt gca ggt gtc ctg ttc aag att ccc att ctg cgc gag      607
Ser Ala Leu Ser Ala Gly Val Leu Phe Lys Ile Pro Ile Leu Arg Glu
        135                 140                 145 gtc ctt ctg tgg act ggc tgt gtc gac gct ggc ggg aag acc gtg gac      655
Val Leu Leu Trp Thr Gly Cys Val Asp Ala Gly Gly Lys Thr Val Asp
    150                 155                 160 tct tgc ttg aag gct ggt ctc agc ctt tct gtt gtg ccc ggc ggc gaa      703
Ser Cys Leu Lys Ala Gly Leu Ser Leu Ser Val Val Pro Gly Gly Glu
165                 170                 175                 180 cgc gag caa ctt ctc gca cag cga ggg aac aag gaa atc ctc gtg ctg      751
Arg Glu Gln Leu Leu Ala Gln Arg Gly Asn Lys Glu Ile Leu Val Leu
                185                 190                 195 aaa cac agg aag ggc ttt gtc aag tac gcc ttg agg cat ggc att ccg      799
Lys His Arg Lys Gly Phe Val Lys Tyr Ala Leu Arg His Gly Ile Pro
            200                 205                 210 ttg gta cct gtg tat tgc ttc ggc gag aac caa ctt ttt tgg cag tcc      847
Leu Val Pro Val Tyr Cys Phe Gly Glu Asn Gln Leu Phe Trp Gln Ser
        215                 220                 225 tcc ttc ctc ttc aag gtt cgc agt tgg ctg cgg cgc act ctg gga gtg      895
Ser Phe Leu Phe Lys Val Arg Ser Trp Leu Arg Arg Thr Leu Gly Val
    230                 235                 240 gcg ctc gtg ttg ccc tac gga ggc tgc tgc aat ctg cct ggt gtg ccc      943
Ala Leu Val Leu Pro Tyr Gly Gly Cys Cys Asn Leu Pro Gly Val Pro
245                 250                 255                 260 ttc tcg gag ccg gtg cag ctc gtc gtc gga gct ccc ttg aag ctt ccg      991
Phe Ser Glu Pro Val Gln Leu Val Val Gly Ala Pro Leu Lys Leu Pro
                265                 270                 275 aag atc gaa gag ccg agc gga gtg gaa ata gcc aag tgg cac gct cgg     1039
Lys Ile Glu Glu Pro Ser Gly Val Glu Ile Ala Lys Trp His Ala Arg
            280                 285                 290 tac atg gag tgt ttg gaa gcc ttg ttc aag cgg cac cga gtt gaa gct     1087
Tyr Met Glu Cys Leu Glu Ala Leu Phe Lys Arg His Arg Val Glu Ala
        295                 300                 305 gga tat cct gaa ttg gaa ctc gag ttc atc tga aggtttcaag tttacatgtg   1140
Gly Tyr Pro Glu Leu Glu Leu Glu Phe Ile
    310                 315 tctcacagtc ctccgctctg agccccactc attgtagtta ctcttctatg tgtgcaacgt   1200
cgaccacagg agttaccgtc aaagacggtt gctccttgct gcttcgagag aaaaaaaaaa   1260
```
aaaaaaaaaa aa                                                          1272

<210> SEQ ID NO 31
<211> LENGTH: 318
<212> TYPE: PRT
<213> ORGANISM: Cryptocodinium cohnii

<400> SEQUENCE: 31

Met Ala Gly Lys Trp Met Leu Leu Ser Gly Ala Ala Ala Ala
1               5                   10                  15

Leu Ala Leu Leu Glu Gly Thr Gln Leu Arg Ala Ser Thr Ser Ala Arg
            20                  25                  30

Ala Arg Ile Leu Leu Val Ser Leu Ala Ala Tyr Leu Pro Thr Tyr Leu
        35                  40                  45

Asp Gly Ser Glu Tyr Arg Ala Ala Pro Arg Arg Ser Glu Arg Ala Ser
    50                  55                  60

Arg Val Leu Arg Gln Leu Tyr Lys Val Met Val Asn Trp Phe Phe Thr
65                  70                  75                  80

Ile Lys Arg Pro Val Ile Glu Ala Ser Glu Glu Leu Thr Ala Cys Asp
                85                  90                  95

Gln Cys Ile Leu Ala Val His Pro His Gly Val Pro Ser Leu Asp His
            100                 105                 110

Leu Leu Thr Val Ile Ala Tyr Asp Pro Asp Leu Glu Arg Val Leu Pro
        115                 120                 125

Gln Leu Arg Arg Ser Ala Leu Ser Ala Gly Val Leu Phe Lys Ile Pro
    130                 135                 140

Ile Leu Arg Glu Val Leu Leu Trp Thr Gly Cys Val Asp Ala Gly Gly
145                 150                 155                 160

Lys Thr Val Asp Ser Cys Leu Lys Ala Gly Leu Ser Leu Ser Val Val
                165                 170                 175

Pro Gly Gly Glu Arg Glu Gln Leu Leu Ala Gln Arg Gly Asn Lys Glu
            180                 185                 190

Ile Leu Val Leu Lys His Arg Lys Gly Phe Val Lys Tyr Ala Leu Arg
        195                 200                 205

His Gly Ile Pro Leu Val Pro Val Tyr Cys Phe Gly Glu Asn Gln Leu
    210                 215                 220

Phe Trp Gln Ser Ser Phe Leu Phe Lys Val Arg Ser Trp Leu Arg Arg
225                 230                 235                 240

Thr Leu Gly Val Ala Leu Val Leu Pro Tyr Gly Gly Cys Cys Asn Leu
                245                 250                 255

Pro Gly Val Pro Phe Ser Glu Pro Val Gln Leu Val Val Gly Ala Pro
            260                 265                 270

Leu Lys Leu Pro Lys Ile Glu Glu Pro Ser Gly Val Glu Ile Ala Lys
        275                 280                 285

Trp His Ala Arg Tyr Met Glu Cys Leu Glu Ala Leu Phe Lys Arg His
    290                 295                 300

Arg Val Glu Ala Gly Tyr Pro Glu Leu Glu Leu Glu Phe Ile
305                 310                 315

<210> SEQ ID NO 32
<211> LENGTH: 448
<212> TYPE: DNA
<213> ORGANISM: Cryptocodinium cohnii
<220> FEATURE:
<221> NAME/KEY: CDS
<222> LOCATION: (1)..(426)
<223> OTHER INFORMATION: DAGAT

<400> SEQUENCE: 32

```
atc aag atg gtg ccg ttt ttg aag aac gtg ctg ggg ctc ttt ggg ctg     48
Ile Lys Met Val Pro Phe Leu Lys Asn Val Leu Gly Leu Phe Gly Leu
1               5                   10                  15 atc gac gcg agc aag cag gtg ttg gtc aag cga ttg aag cgc cca ggt     96
Ile Asp Ala Ser Lys Gln Val Leu Val Lys Arg Leu Lys Arg Pro Gly
            20                  25                  30 ggt tcc ctg gtg att tac atc gga ggg atg gtg gag ctc ttc atg tcc    144
Gly Ser Leu Val Ile Tyr Ile Gly Gly Met Val Glu Leu Phe Met Ser
        35                  40                  45 agc ccc aag cag gaa gtc gtc ttc ttg aag aag agg aag ggt ttt atc    192
Ser Pro Lys Gln Glu Val Val Phe Leu Lys Lys Arg Lys Gly Phe Ile
50                  55                  60 cga ctc gct ctg agc aca ggt gcc gat gtc gtg ccg atc tac ttg ttc    240
Arg Leu Ala Leu Ser Thr Gly Ala Asp Val Val Pro Ile Tyr Leu Phe
65                  70                  75                  80 ggc aac acc acc gtg ctc tca gtg ctg acc gct ggc cct ctg gcc tct    288
Gly Asn Thr Thr Val Leu Ser Val Leu Thr Ala Gly Pro Leu Ala Ser
                85                  90                  95 ctg agc cgt gcc gcc ggg gtg tca gtg acc att ttt tgg gga cgc ttc    336
Leu Ser Arg Ala Ala Gly Val Ser Val Thr Ile Phe Trp Gly Arg Phe
            100                 105                 110 ggc ttg ccg atg ccc tac ccc gtc aag ctc acc tat gcc cgt ggc cgt    384
Gly Leu Pro Met Pro Tyr Pro Val Lys Leu Thr Tyr Ala Arg Gly Arg
        115                 120                 125 ccc atc ggt ctc cct cat atc gaa atc cta cag atg aga cat            426
Pro Ile Gly Leu Pro His Ile Glu Ile Leu Gln Met Arg His
    130                 135                 140 tgaccgttgg catgacgtgt ac                                           448
```

<210> SEQ ID NO 33
<211> LENGTH: 142
<212> TYPE: PRT
<213> ORGANISM: Cryptocodinium cohnii

<400> SEQUENCE: 33

```
Ile Lys Met Val Pro Phe Leu Lys Asn Val Leu Gly Leu Phe Gly Leu
1               5                   10                  15

Ile Asp Ala Ser Lys Gln Val Leu Val Lys Arg Leu Lys Arg Pro Gly
            20                  25                  30

Gly Ser Leu Val Ile Tyr Ile Gly Gly Met Val Glu Leu Phe Met Ser
        35                  40                  45

Ser Pro Lys Gln Glu Val Val Phe Leu Lys Lys Arg Lys Gly Phe Ile
50                  55                  60

Arg Leu Ala Leu Ser Thr Gly Ala Asp Val Val Pro Ile Tyr Leu Phe
65                  70                  75                  80

Gly Asn Thr Thr Val Leu Ser Val Leu Thr Ala Gly Pro Leu Ala Ser
                85                  90                  95

Leu Ser Arg Ala Ala Gly Val Ser Val Thr Ile Phe Trp Gly Arg Phe
            100                 105                 110

Gly Leu Pro Met Pro Tyr Pro Val Lys Leu Thr Tyr Ala Arg Gly Arg
        115                 120                 125

Pro Ile Gly Leu Pro His Ile Glu Ile Leu Gln Met Arg His
    130                 135                 140
```

<210> SEQ ID NO 34
<211> LENGTH: 1757

-continued

```
<212> TYPE: DNA
<213> ORGANISM: Physcomitrella patens
<220> FEATURE:
<221> NAME/KEY: CDS
<222> LOCATION: (76)..(1578)
<223> OTHER INFORMATION: LCAT

<400> SEQUENCE: 34
ggcgcgccag aggacgagac aaggggact tgtgagaatc ttcgagcttc aacctgtcaa      60
gcttcggtct ccacc atg tgt tca att tct tgt gga tcc act ccg cag caa    111
                 Met Cys Ser Ile Ser Cys Gly Ser Thr Pro Gln Gln
                 1               5                   10 ctc tgt cat tac agg aag agc ggg gag ctg att aca aga aag agt cgc    159
Leu Cys His Tyr Arg Lys Ser Gly Glu Leu Ile Thr Arg Lys Ser Arg
        15                  20                  25 gca gct att cgg tgg tgg agg tat ggc caa caa tgc aag gtg ctg ttg    207
Ala Ala Ile Arg Trp Trp Arg Tyr Gly Gln Gln Cys Lys Val Leu Leu
    30                  35                  40 ccg ttg gat ttg att cga tca tcg tct caa ttc ttc atc gta gtt ctc    255
Pro Leu Asp Leu Ile Arg Ser Ser Ser Gln Phe Phe Ile Val Val Leu
45                  50                  55                  60 act ctg acg ctc ttc ctg ttc acc acg tgt gga gct gtg cat act gcg    303
Thr Leu Thr Leu Phe Leu Phe Thr Thr Cys Gly Ala Val His Thr Ala
                65                  70                  75 gca caa gac aga tca ttc gca aca ttg agc caa aga tca aga gcg tct    351
Ala Gln Asp Arg Ser Phe Ala Thr Leu Ser Gln Arg Ser Arg Ala Ser
            80                  85                  90 ctc ttc agt gtg gga cgg gca caa gca agg aac aaa cac cat ttg gcg    399
Leu Phe Ser Val Gly Arg Ala Gln Ala Arg Asn Lys His His Leu Ala
        95                  100                 105 ccg gtg gtc ata gtt cca ggc acc ggc ggg aat caa cta gag gcc agg    447
Pro Val Val Ile Val Pro Gly Thr Gly Gly Asn Gln Leu Glu Ala Arg
    110                 115                 120 ttg aca gct gat tac gag gct aac aag cca tgg tgc tac agc ttc aga    495
Leu Thr Ala Asp Tyr Glu Ala Asn Lys Pro Trp Cys Tyr Ser Phe Arg
125                 130                 135                 140 aaa gat tac ttc agg ttg tgg ctg gat gtg aaa aca ctg ttt cca cct    543
Lys Asp Tyr Phe Arg Leu Trp Leu Asp Val Lys Thr Leu Phe Pro Pro
                145                 150                 155 ttc acg acg tgt ttc gcc gac cgc ctg agc ttg gac tac aac ccg cag    591
Phe Thr Thr Cys Phe Ala Asp Arg Leu Ser Leu Asp Tyr Asn Pro Gln
            160                 165                 170 tcc gat gcc tat agc aac atc aag ggc gtg aag acg cgg gta ccg ttt    639
Ser Asp Ala Tyr Ser Asn Ile Lys Gly Val Lys Thr Arg Val Pro Phe
        175                 180                 185 ttt ggt act acc gaa gga atg gag tac ctg gat ccc tca ctc aaa ttc    687
Phe Gly Thr Thr Glu Gly Met Glu Tyr Leu Asp Pro Ser Leu Lys Phe
    190                 195                 200 ttg aca ggc tac atg ata cac ttg gtg aac gca tta aaa gct cat ggt    735
Leu Thr Gly Tyr Met Ile His Leu Val Asn Ala Leu Lys Ala His Gly
205                 210                 215                 220 tac gag aac gga aag tca tta tac gga gct cca tac gac ttt cgg ttc    783
Tyr Glu Asn Gly Lys Ser Leu Tyr Gly Ala Pro Tyr Asp Phe Arg Phe
                225                 230                 235 gca ccg ggg cca cat gca tcc aac gta gct cta gag tac ctg aaa gac    831
Ala Pro Gly Pro His Ala Ser Asn Val Ala Leu Glu Tyr Leu Lys Asp
            240                 245                 250 ctg aaa gat ctc ata gaa acc gcg tac tca gta aat gcc aac gag ccg    879
Leu Lys Asp Leu Ile Glu Thr Ala Tyr Ser Val Asn Ala Asn Glu Pro
        255                 260                 265
```

```
gtg gtc atc ctc gct cac agc atg ggc ggg ttg tgg act ctc ttc ttc      927
Val Val Ile Leu Ala His Ser Met Gly Gly Leu Trp Thr Leu Phe Phe
    270             275                 280 ctg aac cag caa tcc atg gag tgg agg aac aaa tac gtt tcc cgc ttt      975
Leu Asn Gln Gln Ser Met Glu Trp Arg Asn Lys Tyr Val Ser Arg Phe
285                 290                 295                 300 gtg tct gta gct acc ccg tgg gga ggg gcg gtc gaa cag atg atg acc     1023
Val Ser Val Ala Thr Pro Trp Gly Gly Ala Val Glu Gln Met Met Thr
                305                 310                 315 ttc gca tcc ggc aat ccg gag gga gtt ccc ttt gtg aac tcc ctg gtc     1071
Phe Ala Ser Gly Asn Pro Glu Gly Val Pro Phe Val Asn Ser Leu Val
                320                 325                 330 gtg cgc gaa gag cag cgg cgc tca gag tct aac ttg tgg ctg ctg cca     1119
Val Arg Glu Glu Gln Arg Arg Ser Glu Ser Asn Leu Trp Leu Leu Pro
    335                 340                 345 gtg cgg cgc tgc ttc aga gac cga cca ttg gta att acc tcg tcg cgc     1167
Val Arg Arg Cys Phe Arg Asp Arg Pro Leu Val Ile Thr Ser Ser Arg
    350                 355                 360 aac tac aca gct ggg gac atg gaa cag ttt ctg tgc gac atc ggt ttc     1215
Asn Tyr Thr Ala Gly Asp Met Glu Gln Phe Leu Cys Asp Ile Gly Phe
365                 370                 375                 380 cct gaa ggg gtc gcg cca tac aaa tcc cgg ata ccg cac cta acg gac     1263
Pro Glu Gly Val Ala Pro Tyr Lys Ser Arg Ile Pro His Leu Thr Asp
                385                 390                 395 att cta caa cct cct caa gtc ccc gtc acc cta att cac ggc tat ggc     1311
Ile Leu Gln Pro Pro Gln Val Pro Val Thr Leu Ile His Gly Tyr Gly
                400                 405                 410 gtg ccg acg gcg gag aca cta agc tac gag aag aag gga ttc gac aac     1359
Val Pro Thr Ala Glu Thr Leu Ser Tyr Glu Lys Lys Gly Phe Asp Asn
    415                 420                 425 cat ccc gaa atc aca gaa ggt gat ggc gac ggg acg gtg aat gtg tgc     1407
His Pro Glu Ile Thr Glu Gly Asp Gly Asp Gly Thr Val Asn Val Cys
    430                 435                 440 agc ttg acc gcg gtg gtt gag gaa tgg gag cga gtc gca ggt cag gag     1455
Ser Leu Thr Ala Val Val Glu Glu Trp Glu Arg Val Ala Gly Gln Glu
445                 450                 455                 460 ttg gaa atg att gcg ctg cat ggc aaa caa cat atg caa atc ttg cac     1503
Leu Glu Met Ile Ala Leu His Gly Lys Gln His Met Gln Ile Leu His
                465                 470                 475 gac gac cat tct gtg caa gtg atc gtg gac gcc att ctc aat gtt acc     1551
Asp Asp His Ser Val Gln Val Ile Val Asp Ala Ile Leu Asn Val Thr
                480                 485                 490 cca cag gaa cag ctt atg ttc cac taa gccctaatcg taaccctaaa            1598
Pro Gln Glu Gln Leu Met Phe His
                495                 500 cctagctcca atcctcacag gatcaggcca cattctcctt gaaaaacagc ataaggtcga   1658
ttctccgcag cctctcttcc attccacctc ccccttgta tctctctcca ttcaattgta    1718
caattgtttt tttattcaaa aaaaaaaaaa aaaaaaaa                           1757

<210> SEQ ID NO 35
<211> LENGTH: 500
<212> TYPE: PRT
<213> ORGANISM: Physcomitrella patens

<400> SEQUENCE: 35

Met Cys Ser Ile Ser Cys Gly Ser Thr Pro Gln Gln Leu Cys His Tyr
1               5                   10                  15

Arg Lys Ser Gly Glu Leu Ile Thr Arg Lys Ser Arg Ala Ala Ile Arg
            20                  25                  30
```

```
Trp Trp Arg Tyr Gly Gln Gln Cys Lys Val Leu Leu Pro Leu Asp Leu
         35                  40                  45

Ile Arg Ser Ser Gln Phe Phe Ile Val Leu Thr Leu Thr Leu
 50                  55                  60

Phe Leu Phe Thr Thr Cys Gly Ala Val His Thr Ala Ala Gln Asp Arg
 65              70                  75                  80

Ser Phe Ala Thr Leu Ser Gln Arg Ser Arg Ala Ser Leu Phe Ser Val
                 85                  90                  95

Gly Arg Ala Gln Ala Arg Asn Lys His His Leu Ala Pro Val Val Ile
             100                 105                 110

Val Pro Gly Thr Gly Gly Asn Gln Leu Glu Ala Arg Leu Thr Ala Asp
             115                 120                 125

Tyr Glu Ala Asn Lys Pro Trp Cys Tyr Ser Phe Arg Lys Asp Tyr Phe
         130                 135                 140

Arg Leu Trp Leu Asp Val Lys Thr Leu Phe Pro Pro Phe Thr Thr Cys
145                 150                 155                 160

Phe Ala Asp Arg Leu Ser Leu Asp Tyr Asn Pro Gln Ser Asp Ala Tyr
                 165                 170                 175

Ser Asn Ile Lys Gly Val Lys Thr Arg Val Pro Phe Phe Gly Thr Thr
             180                 185                 190

Glu Gly Met Glu Tyr Leu Asp Pro Ser Leu Lys Phe Leu Thr Gly Tyr
         195                 200                 205

Met Ile His Leu Val Asn Ala Leu Lys Ala His Gly Tyr Glu Asn Gly
     210                 215                 220

Lys Ser Leu Tyr Gly Ala Pro Tyr Asp Phe Arg Phe Ala Pro Gly Pro
225                 230                 235                 240

His Ala Ser Asn Val Ala Leu Glu Tyr Leu Lys Asp Leu Lys Asp Leu
                 245                 250                 255

Ile Glu Thr Ala Tyr Ser Val Asn Ala Asn Glu Pro Val Val Ile Leu
             260                 265                 270

Ala His Ser Met Gly Gly Leu Trp Thr Leu Phe Phe Leu Asn Gln Gln
         275                 280                 285

Ser Met Glu Trp Arg Asn Lys Tyr Val Ser Arg Phe Val Ser Val Ala
     290                 295                 300

Thr Pro Trp Gly Gly Ala Val Glu Gln Met Met Thr Phe Ala Ser Gly
305                 310                 315                 320

Asn Pro Glu Gly Val Pro Phe Val Asn Ser Leu Val Val Arg Glu Glu
                 325                 330                 335

Gln Arg Arg Ser Glu Ser Asn Leu Trp Leu Leu Pro Val Arg Arg Cys
             340                 345                 350

Phe Arg Asp Arg Pro Leu Val Ile Thr Ser Ser Arg Asn Tyr Thr Ala
         355                 360                 365

Gly Asp Met Glu Gln Phe Leu Cys Asp Ile Gly Phe Pro Glu Gly Val
     370                 375                 380

Ala Pro Tyr Lys Ser Arg Ile Pro His Leu Thr Asp Ile Leu Gln Pro
385                 390                 395                 400

Pro Gln Val Pro Val Thr Leu Ile His Gly Tyr Gly Val Pro Thr Ala
                 405                 410                 415

Glu Thr Leu Ser Tyr Glu Lys Lys Gly Phe Asp Asn His Pro Glu Ile
             420                 425                 430

Thr Glu Gly Asp Gly Asp Gly Thr Val Asn Val Cys Ser Leu Thr Ala
         435                 440                 445
```

```
Val Val Glu Glu Trp Glu Arg Val Ala Gly Gln Glu Leu Glu Met Ile
    450                 455                 460

Ala Leu His Gly Lys Gln His Met Gln Ile Leu His Asp Asp His Ser
465                 470                 475                 480

Val Gln Val Ile Val Asp Ala Ile Leu Asn Val Thr Pro Gln Glu Gln
                485                 490                 495

Leu Met Phe His
            500

<210> SEQ ID NO 36
<211> LENGTH: 1893
<212> TYPE: DNA
<213> ORGANISM: Fusarium graminaeum
<220> FEATURE:
<221> NAME/KEY: CDS
<222> LOCATION: (1)..(1893)
<223> OTHER INFORMATION: LCAT

<400> SEQUENCE: 36 atg gga aag tcc act tta cga cgc cgg aat ggc caa gat gcg aca aat       48
Met Gly Lys Ser Thr Leu Arg Arg Arg Asn Gly Gln Asp Ala Thr Asn
1               5                   10                  15 aac gat agc gcc gac gct gac gac act ccg aga gaa gaa agc cca acg       96
Asn Asp Ser Ala Asp Ala Asp Asp Thr Pro Arg Glu Glu Ser Pro Thr
            20                  25                  30 gct gag ccg acc aca cac gtt cga gtt gtt caa cac gcc gtg ccc aga      144
Ala Glu Pro Thr Thr His Val Arg Val Val Gln His Ala Val Pro Arg
        35                  40                  45 acc cga aaa cgc cgc aac acc ttc gtc ttc ttc ctt ggt agt ttg ttt      192
Thr Arg Lys Arg Arg Asn Thr Phe Val Phe Phe Leu Gly Ser Leu Phe
    50                  55                  60 gga att ata gcc gcc gga ttt ttc gct tcc agc aat gat ctt att gac      240
Gly Ile Ile Ala Ala Gly Phe Phe Ala Ser Ser Asn Asp Leu Ile Asp
65                  70                  75                  80 ctc ccc gag ttt acc gac ttg tcg atg gat aac ttg atg gat gtt ctg      288
Leu Pro Glu Phe Thr Asp Leu Ser Met Asp Asn Leu Met Asp Val Leu
                85                  90                  95 cct gcc ggc ttg ata aag gac atg cgc gac ctt gtt cag ggc gag cgg      336
Pro Ala Gly Leu Ile Lys Asp Met Arg Asp Leu Val Gln Gly Glu Arg
            100                 105                 110 gac att gcc gaa tcg tac gag cca ttc tct gtt ggc gaa aag gct cga      384
Asp Ile Ala Glu Ser Tyr Glu Pro Phe Ser Val Gly Glu Lys Ala Arg
        115                 120                 125 tcc gag ggt cta gga gtt cac cat cct atg atc atg ata cct ggt gtt      432
Ser Glu Gly Leu Gly Val His His Pro Met Ile Met Ile Pro Gly Val
    130                 135                 140 atc tca act gga ctc gaa tcg tgg ggt acg gct aat atc tcg aaa ccc      480
Ile Ser Thr Gly Leu Glu Ser Trp Gly Thr Ala Asn Ile Ser Lys Pro
145                 150                 155                 160 tac ttt aga aaa cga ctt tgg ggt agt tgg aca atg atg aga gct ctg      528
Tyr Phe Arg Lys Arg Leu Trp Gly Ser Trp Thr Met Met Arg Ala Leu
                165                 170                 175 gtt atg gac aag gag gtt tgg aag aag cac gtc atg ctc gac aag agg      576
Val Met Asp Lys Glu Val Trp Lys Lys His Val Met Leu Asp Lys Arg
            180                 185                 190 acg ggc ctt gac ccg cct gac gta aag ttg agg gct gcc caa ggg ttc      624
Thr Gly Leu Asp Pro Pro Asp Val Lys Leu Arg Ala Ala Gln Gly Phe
        195                 200                 205 gat gcg acc gat ttc ttc atc acg gga tat tgg atc tgg agc aaa atc      672
Asp Ala Thr Asp Phe Phe Ile Thr Gly Tyr Trp Ile Trp Ser Lys Ile
    210                 215                 220
```

```
ttt gag aat ctc gca tcc atc ggc tac gac cca acg aac tcg ttc acg      720
Phe Glu Asn Leu Ala Ser Ile Gly Tyr Asp Pro Thr Asn Ser Phe Thr
225                 230                 235                 240 gct gct tac gat tgg cgc ttg tcg tat ccc aac ctt gag gta cgg gac      768
Ala Ala Tyr Asp Trp Arg Leu Ser Tyr Pro Asn Leu Glu Val Arg Asp
                245                 250                 255 cgc tac ttc act cgg cta aag tcg cat atc gaa atc gcg gtg gcc act      816
Arg Tyr Phe Thr Arg Leu Lys Ser His Ile Glu Ile Ala Val Ala Thr
            260                 265                 270 gag gac aaa aaa gtc gtc ctc gca tca cac agt atg ggg agc caa gtc      864
Glu Asp Lys Lys Val Val Leu Ala Ser His Ser Met Gly Ser Gln Val
        275                 280                 285 ctt tac tat ttt ctc cac tgg gtg cag tca gaa aga ggc gga cgc ggt      912
Leu Tyr Tyr Phe Leu His Trp Val Gln Ser Glu Arg Gly Gly Arg Gly
    290                 295                 300 ggg ccg gat tgg gtt gag cgt cac att gac gcc tgg atc aac atc agc      960
Gly Pro Asp Trp Val Glu Arg His Ile Asp Ala Trp Ile Asn Ile Ser
305                 310                 315                 320 gga tgc atg ctt gga gca gtc aag gat ttg acc gct gtg ctc tcc ggc     1008
Gly Cys Met Leu Gly Ala Val Lys Asp Leu Thr Ala Val Leu Ser Gly
                325                 330                 335 gag atg cgc gac aca gct caa ctg aac ccg ttc gct att tac ggc ctg     1056
Glu Met Arg Asp Thr Ala Gln Leu Asn Pro Phe Ala Ile Tyr Gly Leu
            340                 345                 350 gaa aag ttc ttg agt aaa gag gag aga gcc gag atc ttt cgc ggc atg     1104
Glu Lys Phe Leu Ser Lys Glu Glu Arg Ala Glu Ile Phe Arg Gly Met
        355                 360                 365 ccc ggg ata tcc tcc atg ttg ccc atc ggc ggc aac tct gta tgg ggt     1152
Pro Gly Ile Ser Ser Met Leu Pro Ile Gly Gly Asn Ser Val Trp Gly
    370                 375                 380 aac ttg acc tgg gct cca gac gac ttg cca ggc cag aac cgt tca tat     1200
Asn Leu Thr Trp Ala Pro Asp Asp Leu Pro Gly Gln Asn Arg Ser Tyr
385                 390                 395                 400 gga tct ctc ttg aac ttt agg gtc ggt tcg aac tgg aca act cct gat     1248
Gly Ser Leu Leu Asn Phe Arg Val Gly Ser Asn Trp Thr Thr Pro Asp
                405                 410                 415 cgt aac ttt acc gtc gag gaa ggt gtg tcc tat ttg ctt aac aca acg     1296
Arg Asn Phe Thr Val Glu Glu Gly Val Ser Tyr Leu Leu Asn Thr Thr
            420                 425                 430 gag gac tgg tat caa gac cag atc aag ggc agt tat tct cgg ggc att     1344
Glu Asp Trp Tyr Gln Asp Gln Ile Lys Gly Ser Tyr Ser Arg Gly Ile
        435                 440                 445 gct cat tcc ata gat gag gtc gaa gcc aat gag aat gac ccc aag aag     1392
Ala His Ser Ile Asp Glu Val Glu Ala Asn Glu Asn Asp Pro Lys Lys
    450                 455                 460 tgg atc aat cct ctc gag acg cga ttg cca ctt gct cct agc ctc aag     1440
Trp Ile Asn Pro Leu Glu Thr Arg Leu Pro Leu Ala Pro Ser Leu Lys
465                 470                 475                 480 atc tac tgc ttt tat ggt gtt gga aaa ccg acc gag cga ggg tac ttc     1488
Ile Tyr Cys Phe Tyr Gly Val Gly Lys Pro Thr Glu Arg Gly Tyr Phe
                485                 490                 495 tat aag cca ccg gat cag cca tca ttg acc aac ctc aac atc aca ata     1536
Tyr Lys Pro Pro Asp Gln Pro Ser Leu Thr Asn Leu Asn Ile Thr Ile
            500                 505                 510 gat acg ggc tat acc gaa gga gac gtg gat cat ggc gtt gtc atg ggc     1584
Asp Thr Gly Tyr Thr Glu Gly Asp Val Asp His Gly Val Val Met Gly
        515                 520                 525 gag gga gat ggt acc gtg aac ctc ctc agt aca ggc tac atg tgt aat     1632
Glu Gly Asp Gly Thr Val Asn Leu Leu Ser Thr Gly Tyr Met Cys Asn
```

```
                530                 535                 540
cat ggc tgg aat atg aaa cgc tac aac cca gca ggc gtc aag gtt aca    1680
His Gly Trp Asn Met Lys Arg Tyr Asn Pro Ala Gly Val Lys Val Thr
545                 550                 555                 560 gtt gtc gag atg cct cac gag ccg gac cgc ttc aat cct cga gga ggg    1728
Val Val Glu Met Pro His Glu Pro Asp Arg Phe Asn Pro Arg Gly Gly
                565                 570                 575 cct cgc acg gcc gac cac gtt gac atc ttg ggg cga tac aac ctg aac    1776
Pro Arg Thr Ala Asp His Val Asp Ile Leu Gly Arg Tyr Asn Leu Asn
            580                 585                 590 gag ttg ctg tta cga gta gcg agc ggc aaa ggt gac acg att acg aac    1824
Glu Leu Leu Leu Arg Val Ala Ser Gly Lys Gly Asp Thr Ile Thr Asn
        595                 600                 605 tat gtt gtg agc aac atc aaa gaa tat gca tcc agg gtt aag att tac    1872
Tyr Val Val Ser Asn Ile Lys Glu Tyr Ala Ser Arg Val Lys Ile Tyr
    610                 615                 620 gat gat gag gag act tca tag                                        1893
Asp Asp Glu Glu Thr Ser
625                 630

<210> SEQ ID NO 37
<211> LENGTH: 630
<212> TYPE: PRT
<213> ORGANISM: Fusarium graminaeum

<400> SEQUENCE: 37

Met Gly Lys Ser Thr Leu Arg Arg Arg Asn Gly Gln Asp Ala Thr Asn
1               5                   10                  15

Asn Asp Ser Ala Asp Ala Asp Asp Thr Pro Arg Glu Glu Ser Pro Thr
            20                  25                  30

Ala Glu Pro Thr Thr His Val Arg Val Gln His Ala Val Pro Arg
        35                  40                  45

Thr Arg Lys Arg Arg Asn Thr Phe Val Phe Leu Gly Ser Leu Phe
    50                  55                  60

Gly Ile Ile Ala Ala Gly Phe Phe Ala Ser Ser Asn Asp Leu Ile Asp
65                  70                  75                  80

Leu Pro Glu Phe Thr Asp Leu Ser Met Asp Asn Leu Met Asp Val Leu
                85                  90                  95

Pro Ala Gly Leu Ile Lys Asp Met Arg Asp Leu Val Gln Gly Glu Arg
            100                 105                 110

Asp Ile Ala Glu Ser Tyr Glu Pro Phe Ser Val Gly Glu Lys Ala Arg
        115                 120                 125

Ser Glu Gly Leu Gly Val His His Pro Met Ile Met Ile Pro Gly Val
    130                 135                 140

Ile Ser Thr Gly Leu Glu Ser Trp Gly Thr Ala Asn Ile Ser Lys Pro
145                 150                 155                 160

Tyr Phe Arg Lys Arg Leu Trp Gly Ser Trp Thr Met Met Arg Ala Leu
                165                 170                 175

Val Met Asp Lys Glu Val Trp Lys Lys His Val Met Leu Asp Lys Arg
            180                 185                 190

Thr Gly Leu Asp Pro Pro Asp Val Lys Leu Arg Ala Ala Gln Gly Phe
        195                 200                 205

Asp Ala Thr Asp Phe Phe Ile Thr Gly Tyr Trp Ile Trp Ser Lys Ile
    210                 215                 220

Phe Glu Asn Leu Ala Ser Ile Gly Tyr Asp Pro Thr Asn Ser Phe Thr
225                 230                 235                 240
```

```
Ala Ala Tyr Asp Trp Arg Leu Ser Tyr Pro Asn Leu Glu Val Arg Asp
                245                 250                 255

Arg Tyr Phe Thr Arg Leu Lys Ser His Ile Glu Ile Ala Val Ala Thr
            260                 265                 270

Glu Asp Lys Lys Val Val Leu Ala Ser His Ser Met Gly Ser Gln Val
        275                 280                 285

Leu Tyr Tyr Phe Leu His Trp Val Gln Ser Glu Arg Gly Gly Arg Gly
    290                 295                 300

Gly Pro Asp Trp Val Glu Arg His Ile Asp Ala Trp Ile Asn Ile Ser
305                 310                 315                 320

Gly Cys Met Leu Gly Ala Val Lys Asp Leu Thr Ala Val Leu Ser Gly
                325                 330                 335

Glu Met Arg Asp Thr Ala Gln Leu Asn Pro Phe Ala Ile Tyr Gly Leu
            340                 345                 350

Glu Lys Phe Leu Ser Lys Glu Glu Arg Ala Glu Ile Phe Arg Gly Met
        355                 360                 365

Pro Gly Ile Ser Ser Met Leu Pro Ile Gly Gly Asn Ser Val Trp Gly
    370                 375                 380

Asn Leu Thr Trp Ala Pro Asp Asp Leu Pro Gly Gln Asn Arg Ser Tyr
385                 390                 395                 400

Gly Ser Leu Leu Asn Phe Arg Val Gly Ser Asn Trp Thr Thr Pro Asp
                405                 410                 415

Arg Asn Phe Thr Val Glu Glu Gly Val Ser Tyr Leu Leu Asn Thr Thr
            420                 425                 430

Glu Asp Trp Tyr Gln Asp Gln Ile Lys Gly Ser Tyr Ser Arg Gly Ile
        435                 440                 445

Ala His Ser Ile Asp Glu Val Glu Ala Asn Glu Asn Asp Pro Lys Lys
    450                 455                 460

Trp Ile Asn Pro Leu Glu Thr Arg Leu Pro Leu Ala Pro Ser Leu Lys
465                 470                 475                 480

Ile Tyr Cys Phe Tyr Gly Val Gly Lys Pro Thr Glu Arg Gly Tyr Phe
                485                 490                 495

Tyr Lys Pro Pro Asp Gln Pro Ser Leu Thr Asn Leu Asn Ile Thr Ile
            500                 505                 510

Asp Thr Gly Tyr Thr Glu Gly Asp Val Asp His Gly Val Val Met Gly
        515                 520                 525

Glu Gly Asp Gly Thr Val Asn Leu Leu Ser Thr Gly Tyr Met Cys Asn
    530                 535                 540

His Gly Trp Asn Met Lys Arg Tyr Asn Pro Ala Gly Val Lys Val Thr
545                 550                 555                 560

Val Val Glu Met Pro His Glu Pro Asp Arg Phe Asn Pro Arg Gly Gly
                565                 570                 575

Pro Arg Thr Ala Asp His Val Asp Ile Leu Gly Arg Tyr Asn Leu Asn
            580                 585                 590

Glu Leu Leu Leu Arg Val Ala Ser Gly Lys Gly Asp Thr Ile Thr Asn
        595                 600                 605

Tyr Val Val Ser Asn Ile Lys Glu Tyr Ala Ser Arg Val Lys Ile Tyr
    610                 615                 620

Asp Asp Glu Glu Thr Ser
625                 630

<210> SEQ ID NO 38
<211> LENGTH: 849
<212> TYPE: DNA
```

```
<213> ORGANISM: Caenorhabditis elegans
<220> FEATURE:
<221> NAME/KEY: CDS
<222> LOCATION: (1)..(849)
<223> OTHER INFORMATION: Acyl-CoA:lysophospholipid acyltransferase

<400> SEQUENCE: 38
```

| | | | | | | | | | | | | | | | | |
|---|---|---|---|---|---|---|---|---|---|---|---|---|---|---|---|---|
| atg | gag | aac | ttc | tgg | tcg | atc | gtc | gtg | ttt | ttt | cta | ctc | tca | att | ctc | 48 |
| Met | Glu | Asn | Phe | Trp | Ser | Ile | Val | Val | Phe | Phe | Leu | Leu | Ser | Ile | Leu | |
| 1 | | | | 5 | | | | | 10 | | | | | 15 | | |

```
ttc att tta tat aac ata tcg aca gta tgc cac tac tat atg cgg att        96
Phe Ile Leu Tyr Asn Ile Ser Thr Val Cys His Tyr Tyr Met Arg Ile
             20                  25                  30 tcg ttt tat tac ttc aca att tta ttg cat gga atg gaa gtt tgt gtt       144
Ser Phe Tyr Tyr Phe Thr Ile Leu Leu His Gly Met Glu Val Cys Val
         35                  40                  45 aca atg atc cct tct tgg cta aat ggg aag ggt gct gat tac gtg ttt       192
Thr Met Ile Pro Ser Trp Leu Asn Gly Lys Gly Ala Asp Tyr Val Phe
     50                  55                  60 cac tcg ttt ttc tat tgg tgt aaa tgg act ggt gtt cat aca aca gtc       240
His Ser Phe Phe Tyr Trp Cys Lys Trp Thr Gly Val His Thr Thr Val
 65                  70                  75                  80 tat gga tat gaa aaa aca caa gtt gaa ggt ccg gct gta gtt att tgt       288
Tyr Gly Tyr Glu Lys Thr Gln Val Glu Gly Pro Ala Val Val Ile Cys
                 85                  90                  95 aat cat cag agt tct ctc gac att cta tcg atg gca tca atc tgg ccg       336
Asn His Gln Ser Ser Leu Asp Ile Leu Ser Met Ala Ser Ile Trp Pro
             100                 105                 110 aag aat tgt gtt gta atg atg aaa cga att ctt gcc tat gtt cca ttc       384
Lys Asn Cys Val Val Met Met Lys Arg Ile Leu Ala Tyr Val Pro Phe
         115                 120                 125 ttc aat ctc gga gcc tac ttt tcc aac aca atc ttc atc gat cga tat       432
Phe Asn Leu Gly Ala Tyr Phe Ser Asn Thr Ile Phe Ile Asp Arg Tyr
     130                 135                 140 aac cgt gaa cgt gcg atg gct tca gtt gat tat tgt gca tct gaa atg       480
Asn Arg Glu Arg Ala Met Ala Ser Val Asp Tyr Cys Ala Ser Glu Met
 145                 150                 155                 160 aag aac aga aat ctt aaa ctt tgg gta ttt ccg gaa gga aca aga aat       528
Lys Asn Arg Asn Leu Lys Leu Trp Val Phe Pro Glu Gly Thr Arg Asn
                 165                 170                 175 cgt gaa gga ggg ttc att cca ttc aag aaa gga gca ttc aat att gca       576
Arg Glu Gly Gly Phe Ile Pro Phe Lys Lys Gly Ala Phe Asn Ile Ala
             180                 185                 190 gtt cgt gcg cag att ccc att att cca gtt gta ttc tca gac tat cgg       624
Val Arg Ala Gln Ile Pro Ile Ile Pro Val Val Phe Ser Asp Tyr Arg
         195                 200                 205 gat ttc tac tca aag cca ggc cga tat ttc aag aat gat gga gaa gtt       672
Asp Phe Tyr Ser Lys Pro Gly Arg Tyr Phe Lys Asn Asp Gly Glu Val
     210                 215                 220 gtt att cga gtt ctg gat gcg att cca aca aaa ggg ctc act ctt gat       720
Val Ile Arg Val Leu Asp Ala Ile Pro Thr Lys Gly Leu Thr Leu Asp
 225                 230                 235                 240 gac gtc agc gag ttg tct gat atg tgt cgg gac gtt atg ttg gca gcc       768
Asp Val Ser Glu Leu Ser Asp Met Cys Arg Asp Val Met Leu Ala Ala
                 245                 250                 255 tat aag gaa gtt act cta gaa gct cag caa cga aat gcg aca cgg cgt       816
Tyr Lys Glu Val Thr Leu Glu Ala Gln Gln Arg Asn Ala Thr Arg Arg
             260                 265                 270 gga gaa aca aaa gac ggg aag aaa tct gag taa                           849
Gly Glu Thr Lys Asp Gly Lys Lys Ser Glu
         275                 280
```

<210> SEQ ID NO 39
<211> LENGTH: 282
<212> TYPE: PRT
<213> ORGANISM: Caenorhabditis elegans

<400> SEQUENCE: 39

Met Glu Asn Phe Trp Ser Ile Val Val Phe Phe Leu Leu Ser Ile Leu
1               5                   10                  15

Phe Ile Leu Tyr Asn Ile Ser Thr Val Cys His Tyr Tyr Met Arg Ile
            20                  25                  30

Ser Phe Tyr Tyr Phe Thr Ile Leu Leu His Gly Met Glu Val Cys Val
        35                  40                  45

Thr Met Ile Pro Ser Trp Leu Asn Gly Lys Gly Ala Asp Tyr Val Phe
    50                  55                  60

His Ser Phe Phe Tyr Trp Cys Lys Trp Thr Gly Val His Thr Thr Val
65                  70                  75                  80

Tyr Gly Tyr Glu Lys Thr Gln Val Glu Gly Pro Ala Val Val Ile Cys
                85                  90                  95

Asn His Gln Ser Ser Leu Asp Ile Leu Ser Met Ala Ser Ile Trp Pro
            100                 105                 110

Lys Asn Cys Val Val Met Met Lys Arg Ile Leu Ala Tyr Val Pro Phe
        115                 120                 125

Phe Asn Leu Gly Ala Tyr Phe Ser Asn Thr Ile Phe Ile Asp Arg Tyr
    130                 135                 140

Asn Arg Glu Arg Ala Met Ala Ser Val Asp Tyr Cys Ala Ser Glu Met
145                 150                 155                 160

Lys Asn Arg Asn Leu Lys Leu Trp Val Phe Pro Glu Gly Thr Arg Asn
                165                 170                 175

Arg Glu Gly Gly Phe Ile Pro Phe Lys Lys Gly Ala Phe Asn Ile Ala
            180                 185                 190

Val Arg Ala Gln Ile Pro Ile Ile Pro Val Val Phe Ser Asp Tyr Arg
        195                 200                 205

Asp Phe Tyr Ser Lys Pro Gly Arg Tyr Phe Lys Asn Asp Gly Glu Val
    210                 215                 220

Val Ile Arg Val Leu Asp Ala Ile Pro Thr Lys Gly Leu Thr Leu Asp
225                 230                 235                 240

Asp Val Ser Glu Leu Ser Asp Met Cys Arg Asp Val Met Leu Ala Ala
                245                 250                 255

Tyr Lys Glu Val Thr Leu Glu Ala Gln Gln Arg Asn Ala Thr Arg Arg
            260                 265                 270

Gly Glu Thr Lys Asp Gly Lys Lys Ser Glu
        275                 280

<210> SEQ ID NO 40
<211> LENGTH: 849
<212> TYPE: DNA
<213> ORGANISM: Caenorhabditis elegans
<220> FEATURE:
<221> NAME/KEY: CDS
<222> LOCATION: (1)..(849)
<223> OTHER INFORMATION: Acyl-CoA:lysophospholipid acyltransferase

<400> SEQUENCE: 40 atg gag aac ttc tgg tcg atc gtc gtg ttt ttt cta ctc tca att ctc         48
Met Glu Asn Phe Trp Ser Ile Val Val Phe Phe Leu Leu Ser Ile Leu
1               5                   10                  15

| | | |
|---|---|---|
| ttc att tta tat aac ata tcg aca gta tgc cac tac tat atg cgg att<br>Phe Ile Leu Tyr Asn Ile Ser Thr Val Cys His Tyr Tyr Met Arg Ile<br>20 25 30 | | 96 |
| tcg ttt tat tac ttc aca att tta ttg cat gga atg gaa gtt tgt gtt<br>Ser Phe Tyr Tyr Phe Thr Ile Leu Leu His Gly Met Glu Val Cys Val<br>35 40 45 | | 144 |
| aca atg atc cct tct tgg cta aat ggg aag ggt gct gat tac gtg ttt<br>Thr Met Ile Pro Ser Trp Leu Asn Gly Lys Gly Ala Asp Tyr Val Phe<br>50 55 60 | | 192 |
| cac tcg ttt ttc tat tgg tgt aaa tgg act ggt gtt cat aca aca gtc<br>His Ser Phe Phe Tyr Trp Cys Lys Trp Thr Gly Val His Thr Thr Val<br>65 70 75 80 | | 240 |
| tat gga tat gaa aaa aca caa gtt gaa ggt ccg gct gta gtt att tgt<br>Tyr Gly Tyr Glu Lys Thr Gln Val Glu Gly Pro Ala Val Val Ile Cys<br>85 90 95 | | 288 |
| aat cat cag agt tct ctc gac att cta tcg atg gca tca atc tgg ccg<br>Asn His Gln Ser Ser Leu Asp Ile Leu Ser Met Ala Ser Ile Trp Pro<br>100 105 110 | | 336 |
| aag aat tgt gtt gta atg atg aaa cga att ctt gcc tat gtt cca ttc<br>Lys Asn Cys Val Val Met Met Lys Arg Ile Leu Ala Tyr Val Pro Phe<br>115 120 125 | | 384 |
| ttc aat ctc gga gcc tac ttt tcc aac aca atc ttc atc gat cga tat<br>Phe Asn Leu Gly Ala Tyr Phe Ser Asn Thr Ile Phe Ile Asp Arg Tyr<br>130 135 140 | | 432 |
| aac cgt gaa cgt gcg atg gct tca gtt gat tat tgt gca tct gaa atg<br>Asn Arg Glu Arg Ala Met Ala Ser Val Asp Tyr Cys Ala Ser Glu Met<br>145 150 155 160 | | 480 |
| aag aac aga aat ctt aaa ctt tgg gta tct ccg gaa gga aca aga aat<br>Lys Asn Arg Asn Leu Lys Leu Trp Val Ser Pro Glu Gly Thr Arg Asn<br>165 170 175 | | 528 |
| cgt gaa gga ggg ttc att cca ttc aag aaa gga gca ttc aat att gca<br>Arg Glu Gly Gly Phe Ile Pro Phe Lys Lys Gly Ala Phe Asn Ile Ala<br>180 185 190 | | 576 |
| gtt cgt gcg cag att ccc att att cca gtt gta ttc tca gac tat cgg<br>Val Arg Ala Gln Ile Pro Ile Ile Pro Val Val Phe Ser Asp Tyr Arg<br>195 200 205 | | 624 |
| gat ttc tac tca aag cca ggc cga tat ttc aag aat gat gga gaa gtt<br>Asp Phe Tyr Ser Lys Pro Gly Arg Tyr Phe Lys Asn Asp Gly Glu Val<br>210 215 220 | | 672 |
| gtt att cga gtt ctg gat gcg att cca aca aaa ggg ctc act ctt gat<br>Val Ile Arg Val Leu Asp Ala Ile Pro Thr Lys Gly Leu Thr Leu Asp<br>225 230 235 240 | | 720 |
| gac gtc agc gag ttg tct gat atg tgt cgg gac gtt atg ttg gca gcc<br>Asp Val Ser Glu Leu Ser Asp Met Cys Arg Asp Val Met Leu Ala Ala<br>245 250 255 | | 768 |
| tat aag gaa gtt act cta gaa gct cag caa cga aat gcg aca cgg cgt<br>Tyr Lys Glu Val Thr Leu Glu Ala Gln Gln Arg Asn Ala Thr Arg Arg<br>260 265 270 | | 816 |
| gga gaa aca aaa gac ggg aag aaa tct gag taa<br>Gly Glu Thr Lys Asp Gly Lys Lys Ser Glu<br>275 280 | | 849 |

<210> SEQ ID NO 41
<211> LENGTH: 282
<212> TYPE: PRT
<213> ORGANISM: Caenorhabditis elegans

<400> SEQUENCE: 41

Met Glu Asn Phe Trp Ser Ile Val Val Phe Phe Leu Leu Ser Ile Leu
1               5                   10                  15

```
Phe Ile Leu Tyr Asn Ile Ser Thr Val Cys His Tyr Met Arg Ile
         20                  25                  30

Ser Phe Tyr Tyr Phe Thr Ile Leu His Gly Met Glu Val Cys Val
         35                  40                  45

Thr Met Ile Pro Ser Trp Leu Asn Gly Lys Gly Ala Asp Tyr Val Phe
 50                  55                  60

His Ser Phe Phe Tyr Trp Cys Lys Trp Thr Gly Val His Thr Val
 65                  70                  75                  80

Tyr Gly Tyr Glu Lys Thr Gln Val Glu Gly Pro Ala Val Ile Cys
                 85                  90                  95

Asn His Gln Ser Ser Leu Asp Ile Leu Ser Met Ala Ser Ile Trp Pro
                100                 105                 110

Lys Asn Cys Val Val Met Met Lys Arg Ile Leu Ala Tyr Val Pro Phe
                115                 120                 125

Phe Asn Leu Gly Ala Tyr Phe Ser Asn Thr Ile Phe Ile Asp Arg Tyr
130                 135                 140

Asn Arg Glu Arg Ala Met Ala Ser Val Asp Tyr Cys Ala Ser Glu Met
145                 150                 155                 160

Lys Asn Arg Asn Leu Lys Leu Trp Val Ser Pro Glu Gly Thr Arg Asn
                165                 170                 175

Arg Glu Gly Gly Phe Ile Pro Phe Lys Lys Gly Ala Phe Asn Ile Ala
                180                 185                 190

Val Arg Ala Gln Ile Pro Ile Pro Val Val Phe Ser Asp Tyr Arg
                195                 200                 205

Asp Phe Tyr Ser Lys Pro Gly Arg Tyr Phe Lys Asn Asp Gly Glu Val
                210                 215                 220

Val Ile Arg Val Leu Asp Ala Ile Pro Thr Lys Gly Leu Thr Leu Asp
225                 230                 235                 240

Asp Val Ser Glu Leu Ser Asp Met Cys Arg Asp Val Met Leu Ala Ala
                245                 250                 255

Tyr Lys Glu Val Thr Leu Glu Ala Gln Gln Arg Asn Ala Thr Arg Arg
                260                 265                 270

Gly Glu Thr Lys Asp Gly Lys Lys Ser Glu
                275                 280
```

<210> SEQ ID NO 42
<211> LENGTH: 849
<212> TYPE: DNA
<213> ORGANISM: Caenorhabditis elegans
<220> FEATURE:
<221> NAME/KEY: CDS
<222> LOCATION: (1)..(849)
<223> OTHER INFORMATION: Acyl-CoA:lysophospholipid acyltransferase

<400> SEQUENCE: 42

```
atg gag aac ttc tgg tcg atc gtc gtg ttt ttt cta ctc tca att ctc        48
Met Glu Asn Phe Trp Ser Ile Val Val Phe Phe Leu Leu Ser Ile Leu
 1               5                  10                  15 ttc att tta tat aac ata tcg aca gta tgc cac tac tat gtg cgg att       96
Phe Ile Leu Tyr Asn Ile Ser Thr Val Cys His Tyr Tyr Val Arg Ile
                20                  25                  30 tcg ttt tat tac ttc aca att tta ttg cat gga atg gaa gtt tgt gtt      144
Ser Phe Tyr Tyr Phe Thr Ile Leu Leu His Gly Met Glu Val Cys Val
            35                  40                  45 aca atg atc cct tct tgg cta aat ggg aag ggt gct gat tac gtg ttt      192
Thr Met Ile Pro Ser Trp Leu Asn Gly Lys Gly Ala Asp Tyr Val Phe
 50                  55                  60
```

```
cac tcg ttt ttc tat tgg tgt aaa tgg act ggt gtt cat aca aca gtc    240
His Ser Phe Phe Tyr Trp Cys Lys Trp Thr Gly Val His Thr Thr Val
 65                  70                  75                  80 tat gga tat gaa aaa aca caa gtt gaa ggt ccg gct gta gtt att tgt    288
Tyr Gly Tyr Glu Lys Thr Gln Val Glu Gly Pro Ala Val Val Ile Cys
                 85                  90                  95 aat cat cag agt tct ctc gac att cta tcg atg gca tca atc tgg ccg    336
Asn His Gln Ser Ser Leu Asp Ile Leu Ser Met Ala Ser Ile Trp Pro
            100                 105                 110 aag aat tgt gtt gta atg atg aaa cga att ctt gcc tat gtt cca ttc    384
Lys Asn Cys Val Val Met Met Lys Arg Ile Leu Ala Tyr Val Pro Phe
        115                 120                 125 ttc aat ctc gga gcc tac ttt tcc aac aca atc ttc atc gat cga tat    432
Phe Asn Leu Gly Ala Tyr Phe Ser Asn Thr Ile Phe Ile Asp Arg Tyr
    130                 135                 140 aac cgt gaa cgt gcg atg gct tca gtt gat tat tgt gca tct gaa atg    480
Asn Arg Glu Arg Ala Met Ala Ser Val Asp Tyr Cys Ala Ser Glu Met
145                 150                 155                 160 aag aac aga aat ctt aaa ctt tgg gta ttt ccg gaa gga aca aga aat    528
Lys Asn Arg Asn Leu Lys Leu Trp Val Phe Pro Glu Gly Thr Arg Asn
                165                 170                 175 cgt gaa gga ggg ttc att cca ttc aag aaa gga gca ttc aat att gca    576
Arg Glu Gly Gly Phe Ile Pro Phe Lys Lys Gly Ala Phe Asn Ile Ala
            180                 185                 190 gtt cgt gcg cag att ccc att att cca gtt gta ttc tca gac tat cgg    624
Val Arg Ala Gln Ile Pro Ile Ile Pro Val Val Phe Ser Asp Tyr Arg
        195                 200                 205 gat ttc tac tca aag cca ggc cga tat ttc aag aat gat gga gaa gtt    672
Asp Phe Tyr Ser Lys Pro Gly Arg Tyr Phe Lys Asn Asp Gly Glu Val
    210                 215                 220 gtt att cga gtt ctg gat gcg att cca aca aaa ggg ctc act ctt gat    720
Val Ile Arg Val Leu Asp Ala Ile Pro Thr Lys Gly Leu Thr Leu Asp
225                 230                 235                 240 gac gtc agc gag ttg tct gat atg tgt cgg gac gtt atg ttg gca gcc    768
Asp Val Ser Glu Leu Ser Asp Met Cys Arg Asp Val Met Leu Ala Ala
                245                 250                 255 tat aag gaa gtt act cta gaa gct cag caa cga aat gcg aca cgg cgt    816
Tyr Lys Glu Val Thr Leu Glu Ala Gln Gln Arg Asn Ala Thr Arg Arg
            260                 265                 270 gga gaa aca aaa gac ggg aag aaa tct gag taa                        849
Gly Glu Thr Lys Asp Gly Lys Lys Ser Glu
        275                 280

<210> SEQ ID NO 43
<211> LENGTH: 282
<212> TYPE: PRT
<213> ORGANISM: Caenorhabditis elegans

<400> SEQUENCE: 43

Met Glu Asn Phe Trp Ser Ile Val Val Phe Phe Leu Leu Ser Ile Leu
1               5                   10                  15

Phe Ile Leu Tyr Asn Ile Ser Thr Val Cys His Tyr Tyr Val Arg Ile
            20                  25                  30

Ser Phe Tyr Tyr Phe Thr Ile Leu Leu His Gly Met Glu Val Cys Val
        35                  40                  45

Thr Met Ile Pro Ser Trp Leu Asn Gly Lys Gly Ala Asp Tyr Val Phe
    50                  55                  60

His Ser Phe Phe Tyr Trp Cys Lys Trp Thr Gly Val His Thr Thr Val
65                  70                  75                  80
```

-continued

```
Tyr Gly Tyr Glu Lys Thr Gln Val Glu Gly Pro Ala Val Val Ile Cys
                 85                  90                  95

Asn His Gln Ser Ser Leu Asp Ile Leu Ser Met Ala Ser Ile Trp Pro
            100                 105                 110

Lys Asn Cys Val Val Met Met Lys Arg Ile Leu Ala Tyr Val Pro Phe
        115                 120                 125

Phe Asn Leu Gly Ala Tyr Phe Ser Asn Thr Ile Phe Ile Asp Arg Tyr
    130                 135                 140

Asn Arg Glu Arg Ala Met Ala Ser Val Asp Tyr Cys Ala Ser Glu Met
145                 150                 155                 160

Lys Asn Arg Asn Leu Lys Leu Trp Val Phe Pro Glu Gly Thr Arg Asn
                165                 170                 175

Arg Glu Gly Gly Phe Ile Pro Phe Lys Lys Gly Ala Phe Asn Ile Ala
            180                 185                 190

Val Arg Ala Gln Ile Pro Ile Ile Pro Val Val Phe Ser Asp Tyr Arg
        195                 200                 205

Asp Phe Tyr Ser Lys Pro Gly Arg Tyr Phe Lys Asn Asp Gly Glu Val
    210                 215                 220

Val Ile Arg Val Leu Asp Ala Ile Pro Thr Lys Gly Leu Thr Leu Asp
225                 230                 235                 240

Asp Val Ser Glu Leu Ser Asp Met Cys Arg Asp Val Met Leu Ala Ala
                245                 250                 255

Tyr Lys Glu Val Thr Leu Glu Ala Gln Gln Arg Asn Ala Thr Arg Arg
            260                 265                 270

Gly Glu Thr Lys Asp Gly Lys Lys Ser Glu
        275                 280
```

```
<210> SEQ ID NO 44
<211> LENGTH: 849
<212> TYPE: DNA
<213> ORGANISM: Caenorhabditis elegans
<220> FEATURE:
<221> NAME/KEY: CDS
<222> LOCATION: (1)..(849)
<223> OTHER INFORMATION: Acyl-CoA:lysophospholipid acyltransferase

<400> SEQUENCE: 44
```

```
atg gag aac ttc tgg tcg atc gtc gtg ttt ttt cta ctc tca att ctc     48
Met Glu Asn Phe Trp Ser Ile Val Val Phe Phe Leu Leu Ser Ile Leu
1               5                   10                  15 ttc att tta tat aac ata tcg aca gta tgc cac tac tat atg cgg att    96
Phe Ile Leu Tyr Asn Ile Ser Thr Val Cys His Tyr Tyr Met Arg Ile
            20                  25                  30 tcg ttt tat tac ttc aca att tta ttg cat gga atg gaa gtt tgt gtt   144
Ser Phe Tyr Tyr Phe Thr Ile Leu Leu His Gly Met Glu Val Cys Val
        35                  40                  45 aca atg atc cct tct tgg cta aat ggg aag ggt gct gat tac gtg ttt   192
Thr Met Ile Pro Ser Trp Leu Asn Gly Lys Gly Ala Asp Tyr Val Phe
    50                  55                  60 cac tcg ttt ttc tat tgg tgt aaa tgg act ggt gtt cat aca aca gtc   240
His Ser Phe Phe Tyr Trp Cys Lys Trp Thr Gly Val His Thr Thr Val
65                  70                  75                  80 tat gga tat gaa aaa aca caa gtt gaa ggt ccg gcc gta gtt att tgt   288
Tyr Gly Tyr Glu Lys Thr Gln Val Glu Gly Pro Ala Val Val Ile Cys
                85                  90                  95 aat cat cag ggt tct ctc gac att cta tcg atg gca tca atc tgg ccg   336
Asn His Gln Gly Ser Leu Asp Ile Leu Ser Met Ala Ser Ile Trp Pro
            100                 105                 110
```

```
aag aat tgt gtt gta atg atg aaa cga att ctt gcc tat gtt cca ttc      384
Lys Asn Cys Val Val Met Met Lys Arg Ile Leu Ala Tyr Val Pro Phe
            115                 120                 125 ttc aat ctc gga gcc tac ttt tcc aac aca atc ttc atc gat cga tat      432
Phe Asn Leu Gly Ala Tyr Phe Ser Asn Thr Ile Phe Ile Asp Arg Tyr
    130                 135                 140 aac cgt gaa cgt gcg atg gct tca gtt gat tat tgt gca tct gaa atg      480
Asn Arg Glu Arg Ala Met Ala Ser Val Asp Tyr Cys Ala Ser Glu Met
145                 150                 155                 160 aag aac aga aat ctt aaa ctt tgg gta ttt ccg gaa gga aca aga aat      528
Lys Asn Arg Asn Leu Lys Leu Trp Val Phe Pro Glu Gly Thr Arg Asn
                165                 170                 175 cgt gaa gga ggg ttc att cca ttc aag aaa gga gca ttc aat att gca      576
Arg Glu Gly Gly Phe Ile Pro Phe Lys Lys Gly Ala Phe Asn Ile Ala
            180                 185                 190 gtt cgt gcg cag att ccc att att cca gtt gta ttc tca gac tat cgg      624
Val Arg Ala Gln Ile Pro Ile Ile Pro Val Val Phe Ser Asp Tyr Arg
        195                 200                 205 gat ttc tac tca aag cca ggc cga tat ttc aag aat gat gga gaa gtt      672
Asp Phe Tyr Ser Lys Pro Gly Arg Tyr Phe Lys Asn Asp Gly Glu Val
210                 215                 220 gtt att cga gtt ctg gat gcg att cca aca aaa ggg ctc act ctt gat      720
Val Ile Arg Val Leu Asp Ala Ile Pro Thr Lys Gly Leu Thr Leu Asp
225                 230                 235                 240 gac gtc agc gag ttg tct gat atg tgt cgg gac gtt atg ttg gca gcc      768
Asp Val Ser Glu Leu Ser Asp Met Cys Arg Asp Val Met Leu Ala Ala
                245                 250                 255 tat aag gaa gtt act cta gaa gct cag caa cga aat gcg aca cgg cgt      816
Tyr Lys Glu Val Thr Leu Glu Ala Gln Gln Arg Asn Ala Thr Arg Arg
            260                 265                 270 gga gaa aca aaa gac ggg aag aaa tct gag taa                          849
Gly Glu Thr Lys Asp Gly Lys Lys Ser Glu
        275                 280

<210> SEQ ID NO 45
<211> LENGTH: 282
<212> TYPE: PRT
<213> ORGANISM: Caenorhabditis elegans

<400> SEQUENCE: 45

Met Glu Asn Phe Trp Ser Ile Val Val Phe Leu Leu Ser Ile Leu
1               5                   10                  15

Phe Ile Leu Tyr Asn Ile Ser Thr Val Cys His Tyr Tyr Met Arg Ile
            20                  25                  30

Ser Phe Tyr Tyr Phe Thr Ile Leu Leu His Gly Met Glu Val Cys Val
        35                  40                  45

Thr Met Ile Pro Ser Trp Leu Asn Gly Lys Gly Ala Asp Tyr Val Phe
    50                  55                  60

His Ser Phe Phe Tyr Trp Cys Lys Trp Thr Gly Val His Thr Thr Val
65                  70                  75                  80

Tyr Gly Tyr Glu Lys Thr Gln Val Glu Gly Pro Ala Val Val Ile Cys
                85                  90                  95

Asn His Gln Gly Ser Leu Asp Ile Leu Ser Met Ala Ser Ile Trp Pro
            100                 105                 110

Lys Asn Cys Val Val Met Met Lys Arg Ile Leu Ala Tyr Val Pro Phe
        115                 120                 125

Phe Asn Leu Gly Ala Tyr Phe Ser Asn Thr Ile Phe Ile Asp Arg Tyr
    130                 135                 140
```

```
Asn Arg Glu Arg Ala Met Ala Ser Val Asp Tyr Cys Ala Ser Glu Met
145                 150                 155                 160

Lys Asn Arg Asn Leu Lys Leu Trp Val Phe Pro Glu Gly Thr Arg Asn
            165                 170                 175

Arg Glu Gly Gly Phe Ile Pro Phe Lys Lys Gly Ala Phe Asn Ile Ala
        180                 185                 190

Val Arg Ala Gln Ile Pro Ile Ile Pro Val Val Phe Ser Asp Tyr Arg
    195                 200                 205

Asp Phe Tyr Ser Lys Pro Gly Arg Tyr Phe Lys Asn Asp Gly Glu Val
    210                 215                 220

Val Ile Arg Val Leu Asp Ala Ile Pro Thr Lys Gly Leu Thr Leu Asp
225                 230                 235                 240

Asp Val Ser Glu Leu Ser Asp Met Cys Arg Asp Val Met Leu Ala Ala
                245                 250                 255

Tyr Lys Glu Val Thr Leu Glu Ala Gln Gln Arg Asn Ala Thr Arg Arg
            260                 265                 270

Gly Glu Thr Lys Asp Gly Lys Lys Ser Glu
            275                 280

<210> SEQ ID NO 46
<211> LENGTH: 1578
<212> TYPE: DNA
<213> ORGANISM: Physcomitrella patens
<220> FEATURE:
<221> NAME/KEY: CDS
<222> LOCATION: (1)..(1578)
<223> OTHER INFORMATION: Delta-6-desaturase

<400> SEQUENCE: 46 atg gta ttc gcg ggc ggt gga ctt cag cag ggc tct ctc gaa gaa aac      48
Met Val Phe Ala Gly Gly Gly Leu Gln Gln Gly Ser Leu Glu Glu Asn
1               5                   10                  15 atc gac gtc gag cac att gcc agt atg tct ctc ttc agc gac ttc ttc      96
Ile Asp Val Glu His Ile Ala Ser Met Ser Leu Phe Ser Asp Phe Phe
                20                  25                  30 agt tat gtg tct tca act gtt ggt tcg tgg agc gta cac agt ata caa     144
Ser Tyr Val Ser Ser Thr Val Gly Ser Trp Ser Val His Ser Ile Gln
            35                  40                  45 cct ttg aag cgc ctg acg agt aag aag cgt gtt tcg gaa agc gct gcc     192
Pro Leu Lys Arg Leu Thr Ser Lys Lys Arg Val Ser Glu Ser Ala Ala
        50                  55                  60 gtg caa tgt ata tca gct gaa gtt cag aga aat tcg agt acc cag gga     240
Val Gln Cys Ile Ser Ala Glu Val Gln Arg Asn Ser Ser Thr Gln Gly
65                  70                  75                  80 act gcg gag gca ctc gca gaa tca gtc gtg aag ccc acg aga cga agg     288
Thr Ala Glu Ala Leu Ala Glu Ser Val Val Lys Pro Thr Arg Arg Arg
                85                  90                  95 tca tct cag tgg aag aag tcg aca cac ccc cta tca gaa gta gca gta     336
Ser Ser Gln Trp Lys Lys Ser Thr His Pro Leu Ser Glu Val Ala Val
            100                 105                 110 cac aac aag cca agc gat tgc tgg att gtt gta aaa aac aag gtg tat     384
His Asn Lys Pro Ser Asp Cys Trp Ile Val Val Lys Asn Lys Val Tyr
        115                 120                 125 gat gtt tcc aat ttt gcg gac gag cat ccc gga gga tca gtt att agt     432
Asp Val Ser Asn Phe Ala Asp Glu His Pro Gly Gly Ser Val Ile Ser
130                 135                 140 act tat ttt gga cga gac ggc aca gat gtt ttc tct agt ttt cat gca     480
Thr Tyr Phe Gly Arg Asp Gly Thr Asp Val Phe Ser Ser Phe His Ala
145                 150                 155                 160
```

```
gct tct aca tgg aaa att ctt caa gac ttt tac att ggt gac gtg gag      528
Ala Ser Thr Trp Lys Ile Leu Gln Asp Phe Tyr Ile Gly Asp Val Glu
            165                 170                 175 agg gtg gag ccg act cca gag ctg ctg aaa gat ttc gaa atg aga          576
Arg Val Glu Pro Thr Pro Glu Leu Leu Lys Asp Phe Arg Glu Met Arg
                180                 185                 190 gct ctt ttc ctg agg gag caa ctt ttc aaa agt tcg aaa ttg tac tat      624
Ala Leu Phe Leu Arg Glu Gln Leu Phe Lys Ser Ser Lys Leu Tyr Tyr
            195                 200                 205 gtt atg aag ctg ctc acg aat gtt gct att ttt gct gcg agc att gca      672
Val Met Lys Leu Leu Thr Asn Val Ala Ile Phe Ala Ala Ser Ile Ala
        210                 215                 220 ata ata tgt tgg agc aag act att tca gcg gtt ttg gct tca gct tgt      720
Ile Ile Cys Trp Ser Lys Thr Ile Ser Ala Val Leu Ala Ser Ala Cys
225                 230                 235                 240 atg atg gct ctg tgt ttc caa cag tgc gga tgg cta tcc cat gat ttt      768
Met Met Ala Leu Cys Phe Gln Gln Cys Gly Trp Leu Ser His Asp Phe
                245                 250                 255 ctc cac aat cag gtg ttt gag aca cgc tgg ctt aat gaa gtt gtc ggg      816
Leu His Asn Gln Val Phe Glu Thr Arg Trp Leu Asn Glu Val Val Gly
            260                 265                 270 tat gtg atc ggc aac gcc gtt ctg ggg ttt agt aca ggg tgg tgg aag      864
Tyr Val Ile Gly Asn Ala Val Leu Gly Phe Ser Thr Gly Trp Trp Lys
        275                 280                 285 gag aag cat aac ctt cat cat gct gct cca aat gaa tgc gat cag act      912
Glu Lys His Asn Leu His His Ala Ala Pro Asn Glu Cys Asp Gln Thr
                290                 295                 300 tac caa cca att gat gaa gat att gat act ctc ccc ctc att gcc tgg      960
Tyr Gln Pro Ile Asp Glu Asp Ile Asp Thr Leu Pro Leu Ile Ala Trp
305                 310                 315                 320 agc aag gac ata ctg gcc aca gtt gag aat aag aca ttc ttg cga atc     1008
Ser Lys Asp Ile Leu Ala Thr Val Glu Asn Lys Thr Phe Leu Arg Ile
                325                 330                 335 ctc caa tac cag cat ctg ttc ttc atg ggt ctg tta ttt ttc gcc cgt     1056
Leu Gln Tyr Gln His Leu Phe Phe Met Gly Leu Leu Phe Phe Ala Arg
            340                 345                 350 ggt agt tgg ctc ttt tgg agc tgg aga tat acc tct aca gca gtg ctc     1104
Gly Ser Trp Leu Phe Trp Ser Trp Arg Tyr Thr Ser Thr Ala Val Leu
        355                 360                 365 tca cct gtc gac agg ttg ttg gag aag gga act gtt ctg ttt cac tac     1152
Ser Pro Val Asp Arg Leu Leu Glu Lys Gly Thr Val Leu Phe His Tyr
    370                 375                 380 ttt tgg ttc gtc ggg aca gcg tgc tat ctt ctc cct ggt tgg aag cca     1200
Phe Trp Phe Val Gly Thr Ala Cys Tyr Leu Leu Pro Gly Trp Lys Pro
385                 390                 395                 400 tta gta tgg atg gcg gtg act gag ctc atg tcc ggc atg ctg ctg ggc     1248
Leu Val Trp Met Ala Val Thr Glu Leu Met Ser Gly Met Leu Leu Gly
                405                 410                 415 ttt gta ttt gta ctt agc cac aat ggg atg gag gtt tat aat tcg tct     1296
Phe Val Phe Val Leu Ser His Asn Gly Met Glu Val Tyr Asn Ser Ser
            420                 425                 430 aaa gaa ttc gtg agt gca cag atc gta tcc aca cgg gat atc aaa gga     1344
Lys Glu Phe Val Ser Ala Gln Ile Val Ser Thr Arg Asp Ile Lys Gly
        435                 440                 445 aac ata ttc aac gac tgg ttc act ggt ggc ctt aac agg caa ata gag     1392
Asn Ile Phe Asn Asp Trp Phe Thr Gly Gly Leu Asn Arg Gln Ile Glu
    450                 455                 460 cat cat ctt ttc cca aca atg ccc agg cat aat tta aac aaa ata gca     1440
His His Leu Phe Pro Thr Met Pro Arg His Asn Leu Asn Lys Ile Ala
465                 470                 475                 480
```

```
cct aga gtg gag gtg ttc tgt aag aaa cac ggt ctg gtg tac gaa gac    1488
Pro Arg Val Glu Val Phe Cys Lys Lys His Gly Leu Val Tyr Glu Asp
            485                 490                 495 gta tct att gct acc ggc act tgc aag gtt ttg aaa gca ttg aag gaa    1536
Val Ser Ile Ala Thr Gly Thr Cys Lys Val Leu Lys Ala Leu Lys Glu
        500                 505                 510 gtc gcg gag gct gcg gca gag cag cat gct acc acc agt taa            1578
Val Ala Glu Ala Ala Ala Glu Gln His Ala Thr Thr Ser
            515                 520                 525

<210> SEQ ID NO 47
<211> LENGTH: 525
<212> TYPE: PRT
<213> ORGANISM: Physcomitrella patens

<400> SEQUENCE: 47

Met Val Phe Ala Gly Gly Leu Gln Gln Gly Ser Leu Glu Glu Asn
1               5                   10                  15

Ile Asp Val Glu His Ile Ala Ser Met Ser Leu Phe Ser Asp Phe Phe
            20                  25                  30

Ser Tyr Val Ser Ser Thr Val Gly Ser Trp Ser Val His Ser Ile Gln
        35                  40                  45

Pro Leu Lys Arg Leu Thr Ser Lys Lys Arg Val Ser Glu Ser Ala Ala
    50                  55                  60

Val Gln Cys Ile Ser Ala Glu Val Gln Arg Asn Ser Ser Thr Gln Gly
65                  70                  75                  80

Thr Ala Glu Ala Leu Ala Glu Ser Val Val Lys Pro Thr Arg Arg Arg
                85                  90                  95

Ser Ser Gln Trp Lys Lys Ser Thr His Pro Leu Ser Glu Val Ala Val
            100                 105                 110

His Asn Lys Pro Ser Asp Cys Trp Ile Val Val Lys Asn Lys Val Tyr
        115                 120                 125

Asp Val Ser Asn Phe Ala Asp Glu His Pro Gly Gly Ser Val Ile Ser
    130                 135                 140

Thr Tyr Phe Gly Arg Asp Gly Thr Asp Val Phe Ser Ser Phe His Ala
145                 150                 155                 160

Ala Ser Thr Trp Lys Ile Leu Gln Asp Phe Tyr Ile Gly Asp Val Glu
                165                 170                 175

Arg Val Glu Pro Thr Pro Glu Leu Leu Lys Asp Phe Arg Glu Met Arg
            180                 185                 190

Ala Leu Phe Leu Arg Glu Gln Leu Phe Lys Ser Ser Lys Leu Tyr Tyr
        195                 200                 205

Val Met Lys Leu Leu Thr Asn Val Ala Ile Phe Ala Ala Ser Ile Ala
    210                 215                 220

Ile Ile Cys Trp Ser Lys Thr Ile Ser Ala Val Leu Ala Ser Ala Cys
225                 230                 235                 240

Met Met Ala Leu Cys Phe Gln Gln Cys Gly Trp Leu Ser His Asp Phe
                245                 250                 255

Leu His Asn Gln Val Phe Glu Thr Arg Trp Leu Asn Glu Val Val Gly
            260                 265                 270

Tyr Val Ile Gly Asn Ala Val Leu Gly Phe Ser Thr Gly Trp Trp Lys
        275                 280                 285

Glu Lys His Asn Leu His His Ala Ala Pro Asn Glu Cys Asp Gln Thr
    290                 295                 300

Tyr Gln Pro Ile Asp Glu Asp Ile Asp Thr Leu Pro Leu Ile Ala Trp
```

```
                    305                 310                 315                 320
Ser Lys Asp Ile Leu Ala Thr Val Glu Asn Lys Thr Phe Leu Arg Ile
                325                 330                 335

Leu Gln Tyr Gln His Leu Phe Phe Met Gly Leu Leu Phe Phe Ala Arg
            340                 345                 350

Gly Ser Trp Leu Phe Trp Ser Trp Arg Tyr Thr Ser Thr Ala Val Leu
        355                 360                 365

Ser Pro Val Asp Arg Leu Leu Glu Lys Gly Thr Val Leu Phe His Tyr
    370                 375                 380

Phe Trp Phe Val Gly Thr Ala Cys Tyr Leu Leu Pro Gly Trp Lys Pro
385                 390                 395                 400

Leu Val Trp Met Ala Val Thr Glu Leu Met Ser Gly Met Leu Leu Gly
                405                 410                 415

Phe Val Phe Val Leu Ser His Asn Gly Met Glu Val Tyr Asn Ser Ser
            420                 425                 430

Lys Glu Phe Val Ser Ala Gln Ile Val Ser Thr Arg Asp Ile Lys Gly
        435                 440                 445

Asn Ile Phe Asn Asp Trp Phe Thr Gly Gly Leu Asn Arg Gln Ile Glu
    450                 455                 460

His His Leu Phe Pro Thr Met Pro Arg His Asn Leu Asn Lys Ile Ala
465                 470                 475                 480

Pro Arg Val Glu Val Phe Cys Lys Lys His Gly Leu Val Tyr Glu Asp
                485                 490                 495

Val Ser Ile Ala Thr Gly Thr Cys Lys Val Leu Lys Ala Leu Lys Glu
            500                 505                 510

Val Ala Glu Ala Ala Glu Gln His Ala Thr Thr Ser
        515                 520                 525

<210> SEQ ID NO 48
<211> LENGTH: 1192
<212> TYPE: DNA
<213> ORGANISM: Physcomitrella patens
<220> FEATURE:
<221> NAME/KEY: CDS
<222> LOCATION: (58)..(930)
<223> OTHER INFORMATION: Delta-6-elongase

<400> SEQUENCE: 48
ctgcttcgtc tcatcttggg ggtgtgattc gggagtgggt tgagttggtg gagcgca          57 atg gag gtc gtg gag aga ttc tac ggt gag ttg gat ggg aag gtc tcg        105
Met Glu Val Val Glu Arg Phe Tyr Gly Glu Leu Asp Gly Lys Val Ser
 1               5                  10                  15 cag ggc gtg aat gca ttg ctg ggt agt ttt ggg gtg gag ttg acg gat        153
Gln Gly Val Asn Ala Leu Leu Gly Ser Phe Gly Val Glu Leu Thr Asp
             20                  25                  30 acg ccc act acc aaa ggc ttg ccc ctc gtt gac agt ccc aca ccc atc        201
Thr Pro Thr Thr Lys Gly Leu Pro Leu Val Asp Ser Pro Thr Pro Ile
         35                  40                  45 gtc ctc ggt gtt tct gta tac ttg act att gtc att gga ggg ctt ttg        249
Val Leu Gly Val Ser Val Tyr Leu Thr Ile Val Ile Gly Gly Leu Leu
     50                  55                  60 tgg ata aag gcc agg gat ctg aaa ccg cgc gcc tcg gag cca ttt ttg        297
Trp Ile Lys Ala Arg Asp Leu Lys Pro Arg Ala Ser Glu Pro Phe Leu
 65                  70                  75                  80 ctc caa gct ttg gtg ctt gtg cac aac ctg ttc tgt ttt gcg ctc agt        345
Leu Gln Ala Leu Val Leu Val His Asn Leu Phe Cys Phe Ala Leu Ser
                 85                  90                  95
```

```
ctg tat atg tgc gtg ggc atc gct tat cag gct att acc tgg cgg tac      393
Leu Tyr Met Cys Val Gly Ile Ala Tyr Gln Ala Ile Thr Trp Arg Tyr
            100                 105                 110 tct ctc tgg ggc aat gca tac aat cct aaa cat aaa gag atg gcg att      441
Ser Leu Trp Gly Asn Ala Tyr Asn Pro Lys His Lys Glu Met Ala Ile
        115                 120                 125 ctg gta tac ttg ttc tac atg tct aag tac gtg gaa ttc atg gat acc      489
Leu Val Tyr Leu Phe Tyr Met Ser Lys Tyr Val Glu Phe Met Asp Thr
    130                 135                 140 gtt atc atg ata ctg aag cgc agc acc agg caa ata agc ttc ctc cac      537
Val Ile Met Ile Leu Lys Arg Ser Thr Arg Gln Ile Ser Phe Leu His
145                 150                 155                 160 gtt tat cat cat tct tca att tcc ctc att tgg tgg gct att gct cat      585
Val Tyr His His Ser Ser Ile Ser Leu Ile Trp Trp Ala Ile Ala His
                165                 170                 175 cac gct cct ggc ggt gaa gca tat tgg tct gcg gct ctg aac tca gga      633
His Ala Pro Gly Gly Glu Ala Tyr Trp Ser Ala Ala Leu Asn Ser Gly
            180                 185                 190 gtg cat gtt ctc atg tat gcg tat tac ttc ttg gct gcc tgc ctt cga      681
Val His Val Leu Met Tyr Ala Tyr Tyr Phe Leu Ala Ala Cys Leu Arg
        195                 200                 205 agt agc cca aag tta aaa aat aag tac ctt ttt tgg ggc agg tac ttg      729
Ser Ser Pro Lys Leu Lys Asn Lys Tyr Leu Phe Trp Gly Arg Tyr Leu
    210                 215                 220 aca caa ttc caa atg ttc cag ttt atg ctg aac tta gtg cag gct tac      777
Thr Gln Phe Gln Met Phe Gln Phe Met Leu Asn Leu Val Gln Ala Tyr
225                 230                 235                 240 tac gac atg aaa acg aat gcg cca tat cca caa tgg ctg atc aag att      825
Tyr Asp Met Lys Thr Asn Ala Pro Tyr Pro Gln Trp Leu Ile Lys Ile
                245                 250                 255 ttg ttc tac tac atg atc tcg ttg ctg ttt ctt ttc ggc aat ttt tac      873
Leu Phe Tyr Tyr Met Ile Ser Leu Leu Phe Leu Phe Gly Asn Phe Tyr
            260                 265                 270 gta caa aaa tac atc aaa ccc tct gac gga aag caa aag gga gct aaa      921
Val Gln Lys Tyr Ile Lys Pro Ser Asp Gly Lys Gln Lys Gly Ala Lys
        275                 280                 285 act gag tga gctgtatcaa gccatagaaa ctctattatg ttagaacctg              970
Thr Glu
    290 aagttggtgc tttcttatct ccacttatct tttaagcagc atcagttttg aaatgatgtg   1030 tgggcgtggt ctgcaagtag tcatcaatat aatcggcctg agcacttcag atggattgtt   1090 agaacatgag taaaagcggt tattacggtg tttattttgt accaaatcac cgcacgggtg   1150 aattgaaata tttcagattt gatcaatttc atctgaaaaa aa                      1192

<210> SEQ ID NO 49
<211> LENGTH: 290
<212> TYPE: PRT
<213> ORGANISM: Physcomitrella patens

<400> SEQUENCE: 49

Met Glu Val Val Glu Arg Phe Tyr Gly Glu Leu Asp Gly Lys Val Ser
1               5                   10                  15

Gln Gly Val Asn Ala Leu Leu Gly Ser Phe Gly Val Glu Leu Thr Asp
            20                  25                  30

Thr Pro Thr Thr Lys Gly Leu Pro Leu Val Asp Ser Pro Thr Pro Ile
        35                  40                  45

Val Leu Gly Val Ser Val Tyr Leu Thr Ile Val Ile Gly Gly Leu Leu
    50                  55                  60
```

```
Trp Ile Lys Ala Arg Asp Leu Lys Pro Arg Ala Ser Glu Pro Phe Leu
 65                  70                  75                  80

Leu Gln Ala Leu Val Leu Val His Asn Leu Phe Cys Phe Ala Leu Ser
             85                  90                  95

Leu Tyr Met Cys Val Gly Ile Ala Tyr Gln Ala Ile Thr Trp Arg Tyr
            100                 105                 110

Ser Leu Trp Gly Asn Ala Tyr Asn Pro Lys His Lys Glu Met Ala Ile
        115                 120                 125

Leu Val Tyr Leu Phe Tyr Met Ser Lys Tyr Val Glu Phe Met Asp Thr
    130                 135                 140

Val Ile Met Ile Leu Lys Arg Ser Thr Arg Gln Ile Ser Phe Leu His
145                 150                 155                 160

Val Tyr His His Ser Ile Ser Leu Ile Trp Trp Ala Ile Ala His
                165                 170                 175

His Ala Pro Gly Gly Glu Ala Tyr Trp Ser Ala Ala Leu Asn Ser Gly
            180                 185                 190

Val His Val Leu Met Tyr Ala Tyr Tyr Phe Leu Ala Ala Cys Leu Arg
    195                 200                 205

Ser Ser Pro Lys Leu Lys Asn Lys Tyr Leu Phe Trp Gly Arg Tyr Leu
    210                 215                 220

Thr Gln Phe Gln Met Phe Gln Phe Met Leu Asn Leu Val Gln Ala Tyr
225                 230                 235                 240

Tyr Asp Met Lys Thr Asn Ala Pro Tyr Pro Gln Trp Leu Ile Lys Ile
                245                 250                 255

Leu Phe Tyr Tyr Met Ile Ser Leu Leu Phe Leu Phe Gly Asn Phe Tyr
            260                 265                 270

Val Gln Lys Tyr Ile Lys Pro Ser Asp Gly Lys Gln Lys Gly Ala Lys
        275                 280                 285

Thr Glu
    290

<210> SEQ ID NO 50
<211> LENGTH: 1410
<212> TYPE: DNA
<213> ORGANISM: Phaeodactylum tricornutum
<220> FEATURE:
<221> NAME/KEY: CDS
<222> LOCATION: (1)..(1410)
<223> OTHER INFORMATION: Delta-5-desaturase

<400> SEQUENCE: 50 atg gct ccg gat gcg gat aag ctt cga caa cgc cag acg act gcg gta      48
Met Ala Pro Asp Ala Asp Lys Leu Arg Gln Arg Gln Thr Thr Ala Val
 1               5                  10                  15 gcg aag cac aat gct gct acc ata tcg acg cag gaa cgc ctt tgc agt      96
Ala Lys His Asn Ala Ala Thr Ile Ser Thr Gln Glu Arg Leu Cys Ser
             20                  25                  30 ctg tct tcg ctc aaa ggc gaa gaa gtc tgc atc gac gga atc atc tat     144
Leu Ser Ser Leu Lys Gly Glu Glu Val Cys Ile Asp Gly Ile Ile Tyr
         35                  40                  45 gac ctc caa tca ttc gat cat ccc ggg ggt gaa acg atc aaa atg ttt     192
Asp Leu Gln Ser Phe Asp His Pro Gly Gly Glu Thr Ile Lys Met Phe
     50                  55                  60 ggt ggc aac gat gtc act gta cag tac aag atg att cac ccg tac cat     240
Gly Gly Asn Asp Val Thr Val Gln Tyr Lys Met Ile His Pro Tyr His
 65                  70                  75                  80 acc gag aag cat ttg gaa aag atg aag cgt gtc ggc aag gtg acg gat     288
```

```
Thr Glu Lys His Leu Glu Lys Met Lys Arg Val Gly Lys Val Thr Asp
             85                  90                  95 ttc gtc tgc gag tac aag ttc gat acc gaa ttt gaa cgc gaa atc aaa        336
Phe Val Cys Glu Tyr Lys Phe Asp Thr Glu Phe Glu Arg Glu Ile Lys
            100                 105                 110 cga gaa gtc ttc aag att gtg cga cga ggc aag gat ttc ggt act ttg        384
Arg Glu Val Phe Lys Ile Val Arg Arg Gly Lys Asp Phe Gly Thr Leu
            115                 120                 125 gga tgg ttc ttc cgt gcg ttt tgc tac att gcc att ttc ttc tac ctg        432
Gly Trp Phe Phe Arg Ala Phe Cys Tyr Ile Ala Ile Phe Phe Tyr Leu
    130                 135                 140 cag tac cat tgg gtc acc acg gga acc tct tgg ctg ctg gcc gtg gcc        480
Gln Tyr His Trp Val Thr Thr Gly Thr Ser Trp Leu Leu Ala Val Ala
145                 150                 155                 160 tac gga atc tcc caa gcg atg att ggc atg aat gtc cag cac gat gcc        528
Tyr Gly Ile Ser Gln Ala Met Ile Gly Met Asn Val Gln His Asp Ala
                165                 170                 175 aac cac ggg gcc acc tcc aag cgt ccc tgg gtc aac gac atg cta ggc        576
Asn His Gly Ala Thr Ser Lys Arg Pro Trp Val Asn Asp Met Leu Gly
            180                 185                 190 ctc ggt gcg gat ttt att ggt ggt tcc aag tgg ctc tgg cag gaa caa        624
Leu Gly Ala Asp Phe Ile Gly Gly Ser Lys Trp Leu Trp Gln Glu Gln
        195                 200                 205 cac tgg acc cac cac gct tac acc aat cac gcc gag atg gat ccc gat        672
His Trp Thr His His Ala Tyr Thr Asn His Ala Glu Met Asp Pro Asp
    210                 215                 220 agc ttt ggt gcc gaa cca atg ctc cta ttc aac gac tat ccc ttg gat        720
Ser Phe Gly Ala Glu Pro Met Leu Leu Phe Asn Asp Tyr Pro Leu Asp
225                 230                 235                 240 cat ccc gct cgt acc tgg cta cat cgc ttt caa gca ttc ttt tac atg        768
His Pro Ala Arg Thr Trp Leu His Arg Phe Gln Ala Phe Phe Tyr Met
                245                 250                 255 ccc gtc ttg gct gga tac tgg ttg tcc gct gtc ttc aat cca caa att        816
Pro Val Leu Ala Gly Tyr Trp Leu Ser Ala Val Phe Asn Pro Gln Ile
            260                 265                 270 ctt gac ctc cag caa cgc ggc gca ctt tcc gtc ggt atc cgt ctc gac        864
Leu Asp Leu Gln Gln Arg Gly Ala Leu Ser Val Gly Ile Arg Leu Asp
        275                 280                 285 aac gct ttc att cac tcg cga cgc aag tat gcg gtt ttc tgg cgg gct        912
Asn Ala Phe Ile His Ser Arg Arg Lys Tyr Ala Val Phe Trp Arg Ala
    290                 295                 300 gtg tac att gcg gtg aac gtg att gct ccg ttt tac aca aac tcc ggc        960
Val Tyr Ile Ala Val Asn Val Ile Ala Pro Phe Tyr Thr Asn Ser Gly
305                 310                 315                 320 ctc gaa tgg tcc tgg cgt gtc ttt gga aac atc atg ctc atg ggt gtg       1008
Leu Glu Trp Ser Trp Arg Val Phe Gly Asn Ile Met Leu Met Gly Val
                325                 330                 335 gcg gaa tcg ctc gcg ctg gcg gtc ctg ttt tcg ttg tcg cac aat ttc       1056
Ala Glu Ser Leu Ala Leu Ala Val Leu Phe Ser Leu Ser His Asn Phe
            340                 345                 350 gaa tcc gcg gat cgc gat ccg acc gcc cca ctg aaa aag acg gga gaa       1104
Glu Ser Ala Asp Arg Asp Pro Thr Ala Pro Leu Lys Lys Thr Gly Glu
        355                 360                 365 cca gtc gac tgg ttc aag aca cag gtc gaa act tcc tgc act tac ggt       1152
Pro Val Asp Trp Phe Lys Thr Gln Val Glu Thr Ser Cys Thr Tyr Gly
    370                 375                 380 gga ttc ctt tcc ggt tgc ttc acg gga ggt ctc aac ttt cag gtt gaa       1200
Gly Phe Leu Ser Gly Cys Phe Thr Gly Gly Leu Asn Phe Gln Val Glu
385                 390                 395                 400
```

-continued

```
cac cac ttg ttc cca cgc atg agc agc gct tgg tat ccc tac att gcc    1248
His His Leu Phe Pro Arg Met Ser Ser Ala Trp Tyr Pro Tyr Ile Ala
            405                 410                 415 ccc aag gtc cgc gaa att tgc gcc aaa cac ggc gtc cac tac gcc tac    1296
Pro Lys Val Arg Glu Ile Cys Ala Lys His Gly Val His Tyr Ala Tyr
        420                 425                 430 tac ccg tgg atc cac caa aac ttt ctc tcc acc gtc cgc tac atg cac    1344
Tyr Pro Trp Ile His Gln Asn Phe Leu Ser Thr Val Arg Tyr Met His
    435                 440                 445 gcg gcc ggg acc ggt gcc aac tgg cgc cag atg gcc aga gaa aat ccc    1392
Ala Ala Gly Thr Gly Ala Asn Trp Arg Gln Met Ala Arg Glu Asn Pro
450                 455                 460 ttg acc gga cgg gcg taa                                            1410
Leu Thr Gly Arg Ala
465
```

<210> SEQ ID NO 51
<211> LENGTH: 469
<212> TYPE: PRT
<213> ORGANISM: Phaeodactylum tricornutum

<400> SEQUENCE: 51

```
Met Ala Pro Asp Ala Asp Lys Leu Arg Gln Arg Gln Thr Thr Ala Val
1               5                   10                  15

Ala Lys His Asn Ala Ala Thr Ile Ser Thr Gln Glu Arg Leu Cys Ser
            20                  25                  30

Leu Ser Ser Leu Lys Gly Glu Glu Val Cys Ile Asp Gly Ile Ile Tyr
        35                  40                  45

Asp Leu Gln Ser Phe Asp His Pro Gly Gly Glu Thr Ile Lys Met Phe
    50                  55                  60

Gly Gly Asn Asp Val Thr Val Gln Tyr Lys Met Ile His Pro Tyr His
65                  70                  75                  80

Thr Glu Lys His Leu Glu Lys Met Lys Arg Val Gly Lys Val Thr Asp
                85                  90                  95

Phe Val Cys Glu Tyr Lys Phe Asp Thr Glu Phe Glu Arg Glu Ile Lys
            100                 105                 110

Arg Glu Val Phe Lys Ile Val Arg Arg Gly Lys Asp Phe Gly Thr Leu
        115                 120                 125

Gly Trp Phe Phe Arg Ala Phe Cys Tyr Ile Ala Ile Phe Phe Tyr Leu
    130                 135                 140

Gln Tyr His Trp Val Thr Thr Gly Thr Ser Trp Leu Leu Ala Val Ala
145                 150                 155                 160

Tyr Gly Ile Ser Gln Ala Met Ile Gly Met Asn Val Gln His Asp Ala
                165                 170                 175

Asn His Gly Ala Thr Ser Lys Arg Pro Trp Val Asn Asp Met Leu Gly
            180                 185                 190

Leu Gly Ala Asp Phe Ile Gly Gly Ser Lys Trp Leu Trp Gln Glu Gln
        195                 200                 205

His Trp Thr His His Ala Tyr Thr Asn His Ala Glu Met Asp Pro Asp
    210                 215                 220

Ser Phe Gly Ala Glu Pro Met Leu Leu Phe Asn Asp Tyr Pro Leu Asp
225                 230                 235                 240

His Pro Ala Arg Thr Trp Leu His Arg Phe Gln Ala Phe Phe Tyr Met
                245                 250                 255

Pro Val Leu Ala Gly Tyr Trp Leu Ser Ala Val Phe Asn Pro Gln Ile
            260                 265                 270
```

-continued

```
Leu Asp Leu Gln Gln Arg Gly Ala Leu Ser Val Gly Ile Arg Leu Asp
        275                 280                 285

Asn Ala Phe Ile His Ser Arg Arg Lys Tyr Ala Val Phe Trp Arg Ala
        290                 295                 300

Val Tyr Ile Ala Val Asn Val Ile Ala Pro Phe Tyr Thr Asn Ser Gly
305                 310                 315                 320

Leu Glu Trp Ser Trp Arg Val Phe Gly Asn Ile Met Leu Met Gly Val
                325                 330                 335

Ala Glu Ser Leu Ala Leu Ala Val Leu Phe Ser Leu Ser His Asn Phe
            340                 345                 350

Glu Ser Ala Asp Arg Asp Pro Thr Ala Pro Leu Lys Lys Thr Gly Glu
        355                 360                 365

Pro Val Asp Trp Phe Lys Thr Gln Val Glu Thr Ser Cys Thr Tyr Gly
    370                 375                 380

Gly Phe Leu Ser Gly Cys Phe Thr Gly Gly Leu Asn Phe Gln Val Glu
385                 390                 395                 400

His His Leu Phe Pro Arg Met Ser Ser Ala Trp Tyr Pro Tyr Ile Ala
                405                 410                 415

Pro Lys Val Arg Glu Ile Cys Ala Lys His Gly Val His Tyr Ala Tyr
            420                 425                 430

Tyr Pro Trp Ile His Gln Asn Phe Leu Ser Thr Val Arg Tyr Met His
        435                 440                 445

Ala Ala Gly Thr Gly Ala Asn Trp Arg Gln Met Ala Arg Glu Asn Pro
    450                 455                 460

Leu Thr Gly Arg Ala
465

<210> SEQ ID NO 52
<211> LENGTH: 3598
<212> TYPE: DNA
<213> ORGANISM: artificial sequence
<220> FEATURE:
<221> NAME/KEY: misc_feature
<223> OTHER INFORMATION: Sequence of a plant promoter-terminator
      expression cassette in pUC19

<400> SEQUENCE: 52
tcgcgcgttt cggtgatgac ggtgaaaacc tctgacacat gcagctcccg gagacggtca      60
cagcttgtct gtaagcggat gccgggagca gacaagcccg tcagggcgcg tcagcgggtg     120
ttggcgggtg tcggggctgg cttaactatg cggcatcaga gcagattgta ctgagagtgc     180
accatatgcg gtgtgaaata ccgcacagat gcgtaaggag aaaataccgc atcaggcgcc     240
attcgccatt caggctgcgc aactgttggg aagggcgatc ggtgcgggcc tcttcgctat     300
tacgccagct ggcgaaaggg ggatgtgctg caaggcgatt aagttgggta acgccagggt     360
tttcccagtc acgacgttgt aaaacgacgg ccagtgaatt cggcgcgccg agctcctcga     420
gcaaatttac acattgccac taaacgtcta aaccctttgta atttgttttt gttttactat     480
gtgtgttatg tatttgattt gcgataaatt tttatatttg gtactaaatt tataacacct     540
tttatgctaa cgtttgccaa cacttagcaa tttgcaagtt gattaattga ttctaaatta     600
tttttgtctt ctaaatacat atactaatca actggaaatg taaatatttg ctaatatttc     660
tactatagga gaattaaagt gagtgaatat ggtaccacaa ggtttggaga tttaattgtt     720
gcaatgctgc atggatggca tatacaccaa acattcaata attcttgagg ataataatgg     780
taccacacaa gatttgaggt gcatgaacgt cacgtggaca aaaggtttag taattttca      840
```

```
agacaacaat gttaccacac acaagttttg aggtgcatgc atggatgccc tgtggaaagt      900
ttaaaaatat tttggaaatg atttgcatgg aagccatgtg taaaaccatg acatccactt      960
ggaggatgca ataatgaaga aaactacaaa tttacatgca actagttatg catgtagtct     1020
atataatgag gattttgcaa tactttcatt catacacact cactaagttt tacacgatta     1080
taatttcttc atagccagcc caccgcggtg ggcggccgcc tgcagtctag aaggcctcct     1140
gctttaatga gatatgcgag acgcctatga tcgcatgata tttgctttca attctgttgt     1200
gcacgttgta aaaacctga gcatgtgtag ctcagatcct taccgccggt ttcggttcat     1260
tctaatgaat atatcacccg ttactatcgt atttttatga ataatattct ccgttcaatt     1320
tactgattgt ccgtcgacga attcgagctc ggcgcgccaa gcttggcgta atcatggtca     1380
tagctgtttc ctgtgtgaaa ttgttatccg ctcacaattc cacacaacat acgagccgga     1440
agcataaagt gtaaagcctg gggtgcctaa tgagtgagct aactcacatt aattgcgttg     1500
cgctcactgc ccgctttcca gtcgggaaac ctgtcgtgcc agctgcatta atgaatcggc     1560
caacgcgcgg ggagaggcgg tttgcgtatt gggcgctctt ccgcttcctc gctcactgac     1620
tcgctgcgct cggtcgttcg gctgcggcga gcggtatcag ctcactcaaa ggcggtaata     1680
cggttatcca cagaatcagg ggataacgca ggaaagaaca tgtgagcaaa aggccagcaa     1740
aaggccagga accgtaaaaa ggccgcgttg ctggcgtttt tccataggct ccgcccccct     1800
gacgagcatc acaaaaatcg acgctcaagt cagaggtggc gaaacccgac aggactataa     1860
agataccagg cgtttccccc tggaagctcc ctcgtgcgct ctcctgttcc gaccctgccg     1920
cttaccggat acctgtccgc ctttctccct tcgggaagcg tggcgctttc tcatagctca     1980
cgctgtaggt atctcagttc ggtgtaggtc gttcgctcca agctgggctg tgtgcacgaa     2040
ccccccgttc agcccgaccg ctgcgcctta tccggtaact atcgtcttga gtccaacccg     2100
gtaagacacg acttatcgcc actggcagca gccactggta acaggattag cagagcgagg     2160
tatgtaggcg gtgctacaga gttcttgaag tggtggccta actacggcta cactagaagg     2220
acagtatttg gtatctgcgc tctgctgaag ccagttacct tcggaaaaag agttggtagc     2280
tcttgatccg gcaaacaaac caccgctggt agcggtggtt tttttgtttg caagcagcag     2340
attacgcgca gaaaaaaagg atctcaagaa gatcctttga tcttttctac ggggtctgac     2400
gctcagtgga acgaaaactc acgttaaggg attttggtca tgagattatc aaaaaggatc     2460
ttcacctaga tccttttaaa ttaaaaatga agttttaaat caatctaaag tatatatgag     2520
taaacttggt ctgacagtta ccaatgctta atcagtgagg cacctatctc agcgatctgt     2580
ctatttcgtt catccatagt tgcctgactc cccgtcgtgt agataactac gatacgggag     2640
ggcttaccat ctggccccag tgctgcaatg ataccgcgag acccacgctc accggctcca     2700
gatttatcag caataaacca gccagccgga agggccgagc gcagaagtgg tcctgcaact     2760
ttatccgcct ccatccagtc tattaattgt tgccgggaag ctagagtaag tagttcgcca     2820
gttaatagtt tgcgcaacgt tgttgccatt gctacaggca tcgtggtgtc acgctcgtcg     2880
tttggtatgg cttcattcag ctccggttcc caacgatcaa ggcgagttac atgatccccc     2940
atgttgtgca aaaaagcggt tagctccttc ggtcctccga tcgttgtcag aagtaagttg     3000
gccgcagtgt tatcactcat ggttatggca gcactgcata attctcttac tgtcatgcca     3060
tccgtaagat gcttttctgt gactggtgag tactcaacca agtcattctg agaatagtgt     3120
atgcggcgac cgagttgctc ttgcccggcg tcaatacggg ataataccgc gccacatagc     3180
agaactttaa aagtgctcat cattggaaaa cgttcttcgg ggcgaaaact ctcaaggatc     3240
```

| | |
|---|---|
| ttaccgctgt tgagatccag ttcgatgtaa cccactcgtg cacccaactg atcttcagca | 3300 |
| tcttttactt tcaccagcgt ttctgggtga gcaaaaacag gaaggcaaaa tgccgcaaaa | 3360 |
| aagggaataa gggcgacacg gaaatgttga atactcatac tcttcctttt tcaatattat | 3420 |
| tgaagcattt atcagggtta ttgtctcatg agcggataca tatttgaatg tatttagaaa | 3480 |
| aataaacaaa taggggttcc gcgcacattt ccccgaaaag tgccacctga cgtctaagaa | 3540 |
| accattatta tcatgacatt aacctataaa aataggcgta tcacgaggcc ctttcgtc | 3598 |

<210> SEQ ID NO 53
<211> LENGTH: 3590
<212> TYPE: DNA
<213> ORGANISM: artificial sequence
<220> FEATURE:
<221> NAME/KEY: misc_feature
<223> OTHER INFORMATION: Sequence of a plant promoter-terminator
    expression cassette in pUC19

<400> SEQUENCE: 53

| | |
|---|---|
| tcgcgcgttt cggtgatgac ggtgaaaacc tctgacacat gcagctcccg gagacggtca | 60 |
| cagcttgtct gtaagcggat gccgggagca gacaagcccg tcagggcgcg tcagcgggtg | 120 |
| ttggcgggtg tcggggctgg cttaactatg cggcatcaga gcagattgta ctgagagtgc | 180 |
| accatatgcg gtgtgaaata ccgcacagat gcgtaaggag aaaataccgc atcaggcgcc | 240 |
| attcgccatt caggctgcgc aactgttggg aagggcgatc ggtgcgggcc tcttcgctat | 300 |
| tacgccagct ggcgaaaggg ggatgtgctg caaggcgatt aagttgggta acgccagggt | 360 |
| tttcccagtc acgacgttgt aaaacgacgg ccagtgaatt cggcgcgccg agctcctcga | 420 |
| gcaaatttac acattgccac taaacgtcta aacccttgta atttgttttt gttttactat | 480 |
| gtgtgttatg tatttgattt gcgataaatt tttatatttg gtactaaatt tataacacct | 540 |
| tttatgctaa cgtttgccaa cacttagcaa tttgcaagtt gattaattga ttctaaatta | 600 |
| tttttgtctt ctaaatacat atactaatca actggaaatg taaatatttg ctaatatttc | 660 |
| tactatagga gaattaaagt gagtgaatat ggtaccacaa ggtttggaga tttaattgtt | 720 |
| gcaatgctgc atggatggca tatacaccaa acattcaata attcttgagg ataataatgg | 780 |
| taccacacaa gatttgaggt gcatgaacgt cacgtggaca aaaggtttag taattttttca | 840 |
| agacaacaat gttaccacac acaagttttg aggtgcatgc atggatgccc tgtggaaagt | 900 |
| ttaaaaatat tttggaaatg atttgcatgg aagccatgtg taaaaccatg acatccactt | 960 |
| ggaggatgca ataatgaaga aaactacaaa tttacatgca actagttatg catgtagtct | 1020 |
| atataatgag gattttgcaa tactttcatt catacacact cactaagttt tacacgatta | 1080 |
| taatttcttc atagccagcg gatccgatat cgggcccgct agcgttaacc ctgctttaat | 1140 |
| gagatatgcg agacgcctat gatcgcatga tatttgcttt caattctgtt gtgcacgttg | 1200 |
| taaaaaaacct gagcatgtgt agctcagatc cttaccgccg gtttcggttc attcaatga | 1260 |
| atatatcacc cgttactatc gtattttat gaataatatt ctccgttcaa tttactgatt | 1320 |
| gtccgtcgac gaattcgagc tcggcgcgcc aagcttggcg taatcatggt catagctgtt | 1380 |
| tcctgtgtga aattgttatc cgctcacaat tccacacaac atacgagccg gaagcataaa | 1440 |
| gtgtaaagcc tggggtgcct aatgagtgag ctaactcaca ttaattgcgt tgcgctcact | 1500 |
| gcccgctttc cagtcgggaa acctgtcgtg ccagctgcat taatgaatcg gccaacgcgc | 1560 |
| ggggagaggc ggtttgcgta ttgggcgctc ttccgcttcc tcgctcactg actcgctgcg | 1620 |

```
ctcggtcgtt cggctgcggc gagcggtatc agctcactca aaggcggtaa tacggttatc    1680
cacagaatca ggggataacg caggaaagaa catgtgagca aaaggccagc aaaaggccag    1740
gaaccgtaaa aaggccgcgt tgctggcgtt tttccatagg ctccgccccc ctgacgagca    1800
tcacaaaaat cgacgctcaa gtcagaggtg gcgaaacccg acaggactat aaagatacca    1860
ggcgtttccc cctggaagct ccctcgtgcg ctctcctgtt ccgaccctgc cgcttaccgg    1920
atacctgtcc gcctttctcc cttcgggaag cgtggcgctt tctcatagct cacgctgtag    1980
gtatctcagt tcggtgtagg tcgttcgctc caagctgggc tgtgtgcacg aaccccccgt    2040
tcagcccgac cgctgcgcct tatccggtaa ctatcgtctt gagtccaacc cggtaagaca    2100
cgacttatcg ccactggcag cagccactgg taacaggatt agcagagcga ggtatgtagg    2160
cggtgctaca gagttcttga agtggtggcc taactacggc tacactagaa ggacagtatt    2220
tggtatctgc gctctgctga agccagttac cttcggaaaa agagttggta gctcttgatc    2280
cggcaaacaa accaccgctg gtagcggtgg tttttttgtt tgcaagcagc agattacgcg    2340
cagaaaaaaa ggatctcaag aagatccttt gatcttttct acggggtctg acgctcagtg    2400
gaacgaaaac tcacgttaag ggattttggt catgagatta tcaaaaagga tcttcaccta    2460 gatccttta aattaaaaat gaagttttaa atcaatctaa agtatatatg agtaaacttg    2520
gtctgacagt taccaatgct taatcagtga ggcacctatc tcagcgatct gtctatttcg    2580
ttcatccata gttgcctgac tccccgtcgt gtagataact acgatacggg agggcttacc    2640
atctggcccc agtgctgcaa tgataccgcg agacccacgc tcaccggctc cagatttatc    2700
agcaataaac cagccagccg gaagggccga gcgcagaagt ggtcctgcaa ctttatccgc    2760
ctccatccag tctattaatt gttgccggga agctagagta agtagttcgc cagttaatag    2820
tttgcgcaac gttgttgcca ttgctacagg catcgtggtg tcacgctcgt cgtttggtat    2880
ggcttcattc agctccggtt cccaacgatc aaggcgagtt acatgatccc ccatgttgtg    2940
caaaaaagcg gttagctcct tcggtcctcc gatcgttgtc agaagtaagt tggccgcagt    3000
gttatcactc atggttatgg cagcactgca taattctctt actgtcatgc catccgtaag    3060
atgcttttct gtgactggtg agtactcaac caagtcattc tgagaatagt gtatgcggcg    3120
accgagttgc tcttgcccgg cgtcaatacg ggataatacc gcgccacata gcagaacttt    3180
aaaagtgctc atcattggaa aacgttcttc ggggcgaaaa ctctcaagga tcttaccgct    3240
gttgagatcc agttcgatgt aacccactcg tgcacccaac tgatcttcag catcttttac    3300
tttcaccagc gtttctgggt gagcaaaaac aggaaggcaa aatgccgcaa aaaagggaat    3360
aagggcgaca cggaaatgtt gaatactcat actcttcctt tttcaatatt attgaagcat    3420
ttatcagggt tattgtctca tgagcggata catatttgaa tgtatttaga aaataaaca    3480 aataggggtt ccgcgcacat ttccccgaaa agtgccacct gacgtctaag aaaccattat    3540
tatcatgaca ttaacctata aaaataggcg tatcacgagg ccctttcgtc              3590
```

<210> SEQ ID NO 54
<211> LENGTH: 3584
<212> TYPE: DNA
<213> ORGANISM: artificial sequence
<220> FEATURE:
<221> NAME/KEY: misc_feature
<223> OTHER INFORMATION: Sequence of a plant promoter-terminator
    expression cassette in pUC19

<400> SEQUENCE: 54

```
tcgcgcgttt cggtgatgac ggtgaaaacc tctgacacat gcagctcccg gagacggtca    60
```

```
cagcttgtct gtaagcggat gccgggagca gacaagcccg tcagggcgcg tcagcgggtg      120
ttggcgggtg tcgggctgg cttaactatg cggcatcaga gcagattgta ctgagagtgc       180
accatatgcg gtgtgaaata ccgcacagat gcgtaaggag aaaataccgc atcaggcgcc      240
attcgccatt caggctgcgc aactgttggg aagggcgatc ggtgcgggcc tcttcgctat      300
tacgccagct ggcgaaaggg ggatgtgctg caaggcgatt aagttgggta acgccagggt      360
tttcccagtc acgacgttgt aaaacgacgg ccagtgaatt cggcgcgccg agctcctcga      420
gcaaatttac acattgccac taaacgtcta aacccttgta atttgttttt gttttactat      480
gtgtgttatg tatttgattt gcgataaatt tttatatttg gtactaaatt tataacacct      540
tttatgctaa cgtttgccaa cacttagcaa tttgcaagtt gattaattga ttctaaatta      600
tttttgtctt ctaaatacat atactaatca actggaaatg taaatatttg ctaatatttc      660
tactatagga gaattaaagt gagtgaatat ggtaccacaa ggtttggaga tttaattgtt      720
gcaatgctgc atggatggca tataccacaa acattcaata attcttgagg ataataatgg      780
taccacacaa gatttgaggt gcatgaacgt cacgtggaca aaaggtttag taattttttca     840 agacaacaat gttaccacac acaagttttg aggtgcatgc atggatgccc tgtggaaagt      900
ttaaaaatat tttggaaatg atttgcatgg aagccatgtg taaaaccatg acatccactt      960
ggaggatgca ataatgaaga aaactacaaa tttacatgca actagttatg catgtagtct     1020
atataatgag gattttgcaa tactttcatt catacacact cactaagttt tacacgatta     1080
taatttcttc atagccagca gatctgccgg catcgatccc gggccatggc ctgctttaat     1140
gagatatgcg agacgcctat gatcgcatga tatttgcttt caattctgtt gtgcacgttg     1200
taaaaaacct gagcatgtgt agctcagatc cttaccgccg gtttcggttc attctaatga     1260
atatatcacc cgttactatc gtattttttat gaataatatt ctccgttcaa tttactgatt     1320
gtccgtcgac gagctcggcg cgccaagctt ggcgtaatca tggtcatagc tgtttcctgt     1380
gtgaaattgt tatccgctca caattccaca acaatacga gccggaagca taaagtgtaa      1440
agcctggggt gcctaatgag tgagctaact cacattaatt gcgttgcgct cactgcccgc     1500
tttccagtcg ggaaacctgt cgtgccagct gcattaatga atcggccaac gcgcggggag     1560
aggcggtttg cgtattgggc gctcttccgc ttcctcgctc actgactcgc tgcgctcggt     1620
cgttcggctg cggcgagcgg tatcagctca ctcaaaggcg gtaatacggt tatccacaga     1680
atcaggggat aacgcaggaa agaacatgtg agcaaaaggc cagcaaaagg ccaggaaccg     1740
taaaaaggcc gcgttgctgg cgttttttcca taggctccgc cccctgacg agcatcacaa     1800 aaatcgacgc tcaagtcaga ggtggcgaaa cccgacagga ctataaagat accaggcgtt     1860
tccccctgga agctccctcg tgcgctctcc tgttccgacc ctgccgctta ccggatacct     1920
gtccgccttt ctcccttcgg gaagcgtggc gctttctcat agctcacgct gtaggtatct     1980
cagttcggtg taggtcgttc gctccaagct gggctgtgtg cacgaaccc ccgttcagcc      2040 cgaccgctgc gccttatccg gtaactatcg tcttgagtcc aacccggtaa gacacgactt     2100
atcgccactg gcagcagcca ctggtaacag gattagcaga gcgaggtatg taggcggtgc     2160
tacagagttc ttgaagtggt ggcctaacta cggctacact agaaggacag tatttggtat     2220
ctgcgctctg ctgaagccag ttaccttcgg aaaaagagtt ggtagctctt gatccggcaa     2280
acaaaccacc gctggtagcg gtggtttttt tgtttgcaag cagcagatta cgcgcagaaa     2340
aaaaggatct caagaagatc ctttgatctt ttctacgggg tctgacgctc agtggaacga     2400
```

```
aaactcacgt taagggattt tggtcatgag attatcaaaa aggatcttca cctagatcct    2460
tttaaattaa aaatgaagtt ttaaatcaat ctaaagtata tatgagtaaa cttggtctga    2520
cagttaccaa tgcttaatca gtgaggcacc tatctcagcg atctgtctat ttcgttcatc    2580
catagttgcc tgactccccg tcgtgtagat aactacgata cgggagggct taccatctgg    2640
ccccagtgct gcaatgatac cgcgagaccc acgctcaccg gctccagatt tatcagcaat    2700
aaaccagcca gccggaaggg ccgagcgcag aagtggtcct gcaactttat ccgcctccat    2760
ccagtctatt aattgttgcc gggaagctag agtaagtagt tcgccagtta atagtttgcg    2820
caacgttgtt gccattgcta caggcatcgt ggtgtcacgc tcgtcgtttg gtatggcttc    2880
attcagctcc ggttcccaac gatcaaggcg agttacatga tcccccatgt tgtgcaaaaa    2940
agcggttagc tccttcggtc ctccgatcgt tgtcagaagt aagttggccg cagtgttatc    3000
actcatggtt atggcagcac tgcataattc tcttactgtc atgccatccg taagatgctt    3060
ttctgtgact ggtgagtact caaccaagtc attctgagaa tagtgtatgc ggcgaccgag    3120
ttgctcttgc ccggcgtcaa tacgggataa taccgcgcca catagcagaa ctttaaaagt    3180
gctcatcatt ggaaaacgtt cttcggggcg aaaactctca aggatcttac cgctgttgag    3240
atccagttcg atgtaaccca ctcgtgcacc caactgatct tcagcatctt ttactttcac    3300
cagcgtttct gggtgagcaa aaacaggaag gcaaaatgcc gcaaaaaagg gaataagggc    3360
gacacggaaa tgttgaatac tcatactctt ccttttcaa tattattgaa gcatttatca    3420
gggttattgt ctcatgagcg gatacatatt tgaatgtatt tagaaaaata aacaaatagg    3480
ggttccgcgc acatttcccc gaaaagtgcc acctgacgtc taagaaacca ttattatcat    3540
gacattaacc tataaaaata ggcgtatcac gaggcccttt cgtc                    3584

<210> SEQ ID NO 55
<211> LENGTH: 4507
<212> TYPE: DNA
<213> ORGANISM: artificial sequence
<220> FEATURE:
<221> NAME/KEY: misc_feature
<223> OTHER INFORMATION: Sequence of a plant promoter-terminator
      expression cassette in pUC19

<400> SEQUENCE: 55
tcgcgcgttt cggtgatgac ggtgaaaacc tctgacacat gcagctcccg gagacggtca      60
cagcttgtct gtaagcggat gccgggagca gacaagcccg tcagggcgcg tcagcgggtg     120
ttggcgggtg tcggggctgg cttaactatg cggcatcaga gcagattgta ctgagagtgc     180
accatatgcg gtgtgaaata ccgcacagat gcgtaaggag aaaataccgc atcaggcgcc     240
attcgccatt caggctgcgc aactgttggg aagggcgatc ggtgcgggcc tcttcgctat     300
tacgccagct ggcgaaaggg ggatgtgctg caaggcgatt aagttgggta acgccagggt     360
tttcccagtc acgacgttgt aaaacgacgg ccagtgaatt cggcgcgccg agctcctcga     420
gcaaatttac acattgccac taaacgtcta aacccttgta atttgttttt gttttactat     480
gtgtgttatg tatttgattt gcgataaatt tttatatttg gtactaaatt tataacacct     540
tttatgctaa cgtttgccaa cacttagcaa tttgcaagtt gattaattga ttctaaatta     600
tttttgtctt ctaaatacat atactaatca actggaaatg taaatatttg ctaatatttc     660
tactatagga gaattaaagt gagtgaatat ggtaccacaa ggtttggaga tttaattgtt     720
gcaatgctgc atggatggca tatacaccaa acattcaata attcttgagg ataataatgg     780
taccacacaa gatttgaggt gcatgaacgt cacgtggaca aaaggtttag taattttca      840
```

```
agacaacaat gttaccacac acaagttttg aggtgcatgc atggatgccc tgtggaaagt    900
ttaaaaatat tttggaaatg atttgcatgg aagccatgtg taaaaccatg acatccactt    960
ggaggatgca ataatgaaga aaactacaaa tttacatgca actagttatg catgtagtct   1020
atataatgag gattttgcaa tactttcatt catacacact cactaagttt tacacgatta   1080
taatttcttc atagccagcc caccgcgtg gcggccgcc tgcagtctag aaggcctcct     1140
gctttaatga gatatgcgag acgcctatga tcgcatgata tttgctttca attctgttgt   1200
gcacgttgta aaaacctga gcatgtgtag ctcagatcct taccgccggt ttcggttcat    1260
tctaatgaat atatcacccg ttactatcgt attttatga ataatattct ccgttcaatt    1320
tactgattgt ccgtcgagca aatttacaca ttgccactaa acgtctaaac ccttgtaatt   1380
tgtttttgtt ttactatgtg tgttatgtat ttgatttgcg ataaattttt atatttggta   1440
ctaaatttat aacaccttt atgctaacgt ttgccaacac ttagcaattt gcaagttgat    1500
taattgattc taaattattt ttgtcttcta aatacatata ctaatcaact ggaaatgtaa   1560
atatttgcta atatttctac tataggagaa ttaaagtgag tgaatatggt accacaaggt   1620
ttggagattt aattgttgca atgctgcatg gatggcatat acaccaaaca ttcaataatt   1680
cttgaggata ataatggtac cacacaagat ttgaggtgca tgaacgtcac gtggacaaaa   1740
ggtttagtaa tttttcaaga caacaatgtt accacacaca agttttgagg tgcatgcatg   1800
gatgccctgt ggaaagttta aaaatatttt ggaaatgatt tgcatggaag ccatgtgtaa   1860
aaccatgaca tccacttgga ggatgcaata atgaagaaaa ctacaaattt acatgcaact   1920
agttatgcat gtagtctata taatgaggat tttgcaatac tttcattcat acacactcac   1980
taagttttac acgattataa tttcttcata gccagcggat ccgatatcgg gcccgctagc   2040
gttaaccctg ctttaatgag atatgcgaga cgcctatgat cgcatgatat ttgctttcaa   2100
ttctgttgtg cacgttgtaa aaacctgagc atgtgtagc tcagatcctt accgccggtt   2160
tcggttcatt ctaatgaata tatcacccgt tactatcgta ttttatgaa taatattctc    2220
cgttcaattt actgattgtc cgtcgacgaa ttcgagctcg cgcgccaag cttggcgtaa    2280
tcatggtcat agctgtttcc tgtgtgaaat tgttatccgc tcacaattcc acacaacata   2340
cgagccggaa gcataaagtg taaagcctgg ggtgcctaat gagtgagcta actcacatta   2400
attgcgttgc gctcactgcc cgctttccag tcgggaaacc tgtcgtgcca gctgcattaa   2460
tgaatcggcc aacgcgcggg gagaggcggt ttgcgtattg ggcgctcttc cgcttcctcg   2520
ctcactgact cgctgcgctc ggtcgttcgg ctgcggcgag cggtatcagc tcactcaaag   2580
gcggtaatac ggttatccac agaatcaggg gataacgcag gaaagaacat gtgagcaaaa   2640
ggccagcaaa aggccaggaa ccgtaaaaag gccgcgttgc tggcgttttt ccataggctc   2700
cgcccccctg acgagcatca aaaaatcga cgctcaagtc agaggtggcg aaacccgaca    2760
ggactataaa gataccaggc gtttccccct ggaagctccc tcgtgcgctc tcctgttccg   2820
accctgccgc ttaccggata cctgtccgcc tttctccctt cgggaagcgt ggcgctttct   2880
catagctcac gctgtaggta tctcagttcg gtgtaggtcg ttcgctccaa gctgggctgt   2940
gtgcacgaac cccccgttca gcccgaccgc tgcgccttat ccggtaacta tcgtcttgag   3000
tccaacccgg taagacacga cttatcgcca ctggcagcag ccactggtaa caggattagc   3060
agagcgaggt atgtaggcgg tgctacagag ttcttgaagt ggtggcctaa ctacggctac   3120
actagaagga cagtatttgg tatctgcgct ctgctgaagc cagttacctt cggaaaaaga   3180
```

```
gttggtagct cttgatccgg caaacaaacc accgctggta gcggtggttt ttttgtttgc    3240
aagcagcaga ttacgcgcag aaaaaaagga tctcaagaag atcctttgat cttttctacg    3300
gggtctgacg ctcagtggaa cgaaaactca cgttaaggga ttttggtcat gagattatca    3360
aaaaggatct tcacctagat ccttttaaat taaaaatgaa gttttaaatc aatctaaagt    3420
atatatgagt aaacttggtc tgacagttac caatgcttaa tcagtgaggc acctatctca    3480
gcgatctgtc tatttcgttc atccatagtt gcctgactcc ccgtcgtgta gataactacg    3540
atacgggagg gcttaccatc tggccccagt gctgcaatga taccgcgaga cccacgctca    3600
ccggctccag atttatcagc aataaaccag ccagccggaa gggccgagcg cagaagtggt    3660
cctgcaactt tatccgcctc catccagtct attaattgtt gccgggaagc tagagtaagt    3720
agttcgccag ttaatagttt gcgcaacgtt gttgccattg ctacaggcat cgtggtgtca    3780
cgctcgtcgt ttggtatggc ttcattcagc tccggttccc aacgatcaag gcgagttaca    3840
tgatccccca tgttgtgcaa aaaagcggtt agctccttcg gtcctccgat cgttgtcaga    3900
agtaagttgg ccgcagtgtt atcactcatg gttatggcag cactgcataa ttctcttact    3960
gtcatgccat ccgtaagatg cttttctgtg actggtgagt actcaaccaa gtcattctga    4020
gaatagtgta tgcggcgacc gagttgctct tgcccggcgt caatacggga taataccgcg    4080
ccacatagca gaactttaaa agtgctcatc attggaaaac gttcttcggg gcgaaaactc    4140
tcaaggatct taccgctgtt gagatccagt tcgatgtaac ccactcgtgc acccaactga    4200
tcttcagcat cttttacttt caccagcgtt tctgggtgag caaaaacagg aaggcaaaat    4260
gccgcaaaaa agggaataag ggcgacacgg aaatgttgaa tactcatact cttcctttt     4320 caatattatt gaagcattta tcagggttat tgtctcatga gcggatacat atttgaatgt    4380
atttagaaaa ataaacaaat aggggttccg cgcacatttc cccgaaaagt gccacctgac    4440
gtctaagaaa ccattattat catgacatta acctataaaa ataggcgtat cacgaggccc    4500
tttcgtc                                                              4507

<210> SEQ ID NO 56
<211> LENGTH: 17752
<212> TYPE: DNA
<213> ORGANISM: Artificial sequence
<220> FEATURE:
<223> OTHER INFORMATION: Vector comprising Physcomitrella patens
      Delta-6-elongase gene
<220> FEATURE:
<223> OTHER INFORMATION: Vector comprising Physcomitrella patens
      Delta-6-desaturase gene
<220> FEATURE:
<223> OTHER INFORMATION: Vector comprising Phaeodactylum tricornutum
      Delta-5-desaturase gene
<220> FEATURE:
<221> NAME/KEY: CDS
<222> LOCATION: (11543)..(12415)
<223> OTHER INFORMATION: Delta-6-elongase
<220> FEATURE:
<221> NAME/KEY: CDS
<222> LOCATION: (13313)..(14890)
<223> OTHER INFORMATION: Delta-6-desaturase
<220> FEATURE:
<221> NAME/KEY: CDS
<222> LOCATION: (15791)..(17200)
<223> OTHER INFORMATION: Delta-5-desaturase

<400> SEQUENCE: 56
gatctggcgc cggccagcga gacgagcaag attggccgcc gcccgaaacg atccgacagc      60
gcgcccagca caggtgcgca ggcaaattgc accaacgcat acagcgccag cagaatgcca     120
```

```
tagtgggcgg tgacgtcgtt cgagtgaacc agatcgcgca ggaggcccgg cagcaccggc    180
ataatcaggc cgatgccgac agcgtcgagc gcgacagtgc tcagaattac gatcaggggt    240
atgttgggtt tcacgtctgg cctccggacc agcctccgct ggtccgattg aacgcgcgga    300
ttctttatca ctgataagtt ggtggacata ttatgtttat cagtgataaa gtgtcaagca    360
tgacaaagtt gcagccgaat acagtgatcc gtgccgccct ggacctgttg aacgaggtcg    420
gcgtagacgg tctgacgaca cgcaaactgg cggaacggtt gggggttcag cagccggcgc    480
tttactggca cttcaggaac aagcgggcgc tgctcgacgc actggccgaa gccatgctgg    540
cggagaatca tacgcattcg gtgccgagag ccgacgacga ctggcgctca tttctgatcg    600
ggaatgcccg cagcttcagg caggcgctgc tcgcctaccg cgatggcgcg cgcatccatg    660
ccggcacgcg accgggcgca ccgcagatgg aaacggccga cgcgcagctt cgcttcctct    720
gcgaggcggg ttttcggcc ggggacgccg tcaatgcgct gatgacaatc agctacttca    780
ctgttggggc cgtgcttgag gagcaggccg gcgacagcga tgccggcgag cgcggcggca    840
ccgttgaaca ggctccgctc tcgccgctgt tgcgggccgc gatagacgcc ttcgacgaag    900
ccggtccgga cgcagcgttc gagcaggac tcgcggtgat tgtcgatgga ttggcgaaaa    960
ggaggctcgt tgtcaggaac gttgaaggac cgagaaaggg tgacgattga tcaggaccgc    1020
tgccggagcg caacccactc actacagcag agccatgtag acaacatccc ctcccccttt    1080
ccaccgcgtc agacgcccgt agcagcccgc tacgggcttt tcatgccct gccctagcgt     1140 ccaagcctca cggccgcgct cggcctctct ggcggccttc tggcgctctt ccgcttcctc    1200
gctcactgac tcgctgcgct cggtcgttcg gctgcggcga cggtatcag ctcactcaaa    1260 ggcggtaata cggttatcca cagaatcagg ggataacgca ggaaagaaca tgtgagcaaa    1320
aggccagcaa aaggccagga accgtaaaaa ggccgcgttg ctggcgtttt tccataggct    1380
ccgcccccct gacgagcatc acaaaaatcg acgctcaagt cagaggtggc gaaacccgac    1440
aggactataa agataccagg cgtttccccc tggaagctcc ctcgtgcgct ctcctgttcc    1500
gaccctgccg cttaccggat acctgtccgc ctttctccct cgggaagcg tggcgctttt    1560 ccgctgcata cccctgcttc ggggtcatta tagcgatttt tcggtatat ccatccttt     1620 tcgcacgata tacaggattt tgccaaaggg ttcgtgtaga ctttccttgg tgtatccaac    1680
ggcgtcagcc gggcaggata ggtgaagtag gcccacccgc gagcgggtgt tccttcttca    1740
ctgtccctta ttcgcacctg gcggtgctca acgggaatcc tgctctgcga ggctggccgg    1800
ctaccgccgg cgtaacagat gagggcaagc ggatggctga tgaaaccaag ccaaccagga    1860
agggcagccc acctatcaag gtgtactgcc ttccagacga acgaagagcg attgaggaaa    1920
aggcggcggc ggccggcatg agcctgtcgg cctacctgct ggccgtcggc cagggctaca    1980
aaatcacggg cgtcgtggac tatgagcacg tccgcgagct ggcccgcatc aatggcgacc    2040
tgggccgcct gggcggcctg ctgaaactct ggctcaccga cgaccgcgc acggcgcggt    2100 tcggtgatgc cacgatcctc gccctgctgg cgaagatcga agagaagcag gacgagcttg    2160
gcaaggtcat gatgggcgtg gtccgcccga ggcagagcc atgactttt tagccgctaa     2220 aacggccggg gggtgcgcgt gattgccaag cacgtcccca tgcgctccat caagaagagc    2280
gacttcgcgc agctggtgaa gtacatcacc gacgagcaag gcaagaccga cgccttttgc    2340
gacgctcacc gggctggttg ccctcgccgc tgggctggcg ccgtctatg gccctgcaaa    2400 cgcgccagaa acgccgtcga agccgtgtgc gagacaccgc ggccgccggc gttgtggata    2460
cctcgcggaa aacttggccc tcactgacag atgaggggcg gacgttgaca cttgagggc    2520
```

```
cgactcaccc ggcgcggcgt tgacagatga ggggcaggct cgatttcggc cggcgacgtg    2580
gagctggcca gcctcgcaaa tcggcgaaaa cgcctgattt tacgcgagtt tcccacagat    2640
gatgtggaca agcctgggga taagtgccct gcggtattga cacttgaggg gcgcgactac    2700
tgacagatga ggggcgcgat ccttgacact tgaggggcag agtgctgaca gatgaggggc    2760
gcacctattg acatttgagg ggctgtccac aggcagaaaa tccagcattt gcaagggttt    2820
ccgcccgttt ttcggccacc gctaacctgt cttttaacct gcttttaaac caatatttat    2880
aaaccttgtt tttaaccagg gctgcgccct gtgcgcgtga ccgcgcacgc gaaggggggg    2940 tgcccccccct tctcgaaccc tcccggcccg ctaacgcggg cctcccatcc ccccaggggc    3000
tgcgcccctc ggccgcgaac ggcctcaccc caaaaatggc agcgctggca gtccttgcca    3060
ttgccgggat cggggcagta acgggatggg cgatcagccc gagcgcgacg cccggaagca    3120
ttgacgtgcc gcaggtgctg gcatcgacat tcagcgacca ggtgccgggc agtgagggcg    3180
gcggcctggg tggcggcctg cccttcactt cggccgtcgg ggcattcacg gacttcatgg    3240
cggggccggc aatttttacc ttgggcattc ttggcatagt ggtcgcgggt gccgtgctcg    3300
tgttcggggg tgcgataaac ccagcgaacc atttgaggtg ataggtaaga ttataccgag    3360
gtatgaaaac gagaattgga cctttacaga attactctat gaagcgccat atttaaaaag    3420
ctaccaagac gaagaggatg aagaggatga ggaggcagat tgccttgaat atattgacaa    3480
tactgataag ataatatatc ttttatatag aagatatcgc cgtatgtaag gatttcaggg    3540
ggcaaggcat aggcagcgcg cttatcaata tatctataga atgggcaaag cataaaaact    3600
tgcatggact aatgcttgaa acccaggaca ataaccttat agcttgtaaa ttctatcata    3660
attgggtaat gactccaact tattgatagt gttttatgtt cagataatgc ccgatgactt    3720
tgtcatgcag ctccaccgat tttgagaacg acagcgactt ccgtcccagc cgtgccaggt    3780
gctgcctcag attcaggtta tgccgctcaa ttcgctgcgt atatcgcttg ctgattacgt    3840
gcagctttcc cttcaggcgg gattcataca gcggccagcc atccgtcatc catatcacca    3900
cgtcaaaggg tgacagcagg ctcataagac gccccagcgt cgccatagtg cgttcaccga    3960
atacgtgcgc aacaaccgtc ttccggagac tgtcatacgc gtaaaacagc cagcgctggc    4020
gcgatttagc cccgacatag ccccactgtt cgtccatttc cgcgcagacg atgacgtcac    4080
tgcccggctg tatgcgcgag gttaccgact gcggcctgag ttttttaagt gacgtaaaat    4140
cgtgttgagg ccaacgccca taatgcgggc tgttgcccgg catccaacgc cattcatggc    4200
catatcaatg attttctggt gcgtaccggg ttgagaagcg gtgtaagtga actgcagttg    4260
ccatgtttta cggcagtgag agcagagata gcgctgatgt ccggcggtgc ttttgccgtt    4320
acgcaccacc ccgtcagtag ctgaacagga gggacagctg atagacacag aagccactgg    4380
agcacctcaa aaaccatcc atacactaaa tcagtaagtt ggcagcatca cccataattg    4440
tggtttcaaa atcggctccg tcgatactat gttatacgcc aactttgaaa acaactttga    4500
aaaagctgtt ttctggtatt taaggtttta gaatgcaagg aacagtgaat tggagttcgt    4560
cttgttataa ttagcttctt ggggtatctt taaatactgt agaaagagg  aaggaaataa    4620 taaatggcta aaatgagaat atcaccggaa ttgaaaaaac tgatcgaaaa ataccgctgc    4680
gtaaaagata cggaaggaat gtctcctgct aaggtatata agctggtggg agaaaatgaa    4740
aacctatatt taaaaatgac ggacagccgg tataaaggga ccacctatga tgtggaacgg    4800
gaaaaggaca tgatgctatg gctggaagga aagctgcctg ttccaaaggt cctgcacttt    4860
```

```
gaacggcatg atggctggag caatctgctc atgagtgagg ccgatggcgt cctttgctcg    4920
gaagagtatg aagatgaaca aagccctgaa agattatcg agctgtatgc ggagtgcatc     4980
aggctctttc actccatcga catatcggat tgtccctata cgaatagctt agacagccgc    5040
ttagccgaat tggattactt actgaataac gatctggccg atgtggattg cgaaaactgg    5100
gaagaagaca ctccatttaa agatccgcgc gagctgtatg attttttaaa gacggaaaag    5160
cccgaagagg aacttgtctt ttcccacggc gacctggag acagcaacat ctttgtgaaa     5220
gatggcaaag taagtggctt tattgatctt gggagaagcg gcagggcgga caagtggtat    5280
gacattgcct tctgcgtccg gtcgatcagg gaggatatcg gggaagaaca gtatgtcgag    5340
ctattttttg acttactggg gatcaagcct gattgggaga aaataaaata ttatatttta    5400
ctggatgaat tgttttagta cctagatgtg gcgcaacgat gccggcgaca agcaggagcg    5460
caccgacttc ttccgcatca agtgttttgg ctctcaggcc gaggcccacg gcaagtattt    5520
gggcaagggg tcgctggtat tcgtgcaggg caagattcgg aataccaagt acgagaagga    5580
cggccagacg gtctacggga ccgacttcat tgccgataag gtggattatc tggacaccaa    5640
ggcaccaggc gggtcaaatc aggaataagg gcacattgcc ccggcgtgag tcggggcaat    5700
cccgcaagga gggtgaatga atcggacgtt tgaccggaag gcatacaggc aagaactgat    5760
cgacgcgggg ttttccgccg aggatgccga aaccatcgca agccgcaccg tcatgcgtgc    5820
gccccgcgaa accttccagt ccgtcggctc gatggtccag caagctacgg ccaagatcga    5880
gcgcgacagc gtgcaactgg ctcccccctgc cctgcccgcg ccatcggccg ccgtgggagcg   5940
ttcgcgtcgt ctcgaacagg aggcggcagg tttggcgaag tcgatgacca tcgacacgcg    6000
aggaactatg acgaccaaga agcgaaaaac cgccggcgag gacctggcaa acaggtcag     6060
cgaggccaag caggccgcgt tgctgaaaca cacgaagcag cagatcaagg aaatgcagct    6120
ttccttgttc gatattgcgc cgtggccgga cacgatgcga gcgatgccaa acgacacggc    6180
ccgctctgcc ctgttcacca cgcgcaacaa gaaaatcccg cgcgaggcgc tgcaaaacaa    6240
ggtcattttc cacgtcaaca aggacgtgaa gatcacctac accggcgtcg agctgcgggc    6300
cgacgatgac gaactggtgt ggcagcaggt gttggagtac gcgaagcgca ccctatcgg     6360
cgagccgatc accttcacgt tctacgagct ttgccaggac ctgggctggt cgatcaatgg    6420
ccggtattac acgaaggccg aggaatgcct gtcgcgccta caggcgacgg cgatgggctt    6480
cacgtccgac cgcgttgggc acctggaatc ggtgtcgctg ctgcaccgct tccgcgtcct    6540
ggaccgtggc aagaaaacgt cccgttgcca ggtcctgatc gacgaggaaa tcgtcgtgct    6600
gtttgctggc gaccactaca cgaaattcat atgggagaag taccgcaagc tgtcgccgac    6660
ggcccgacgg atgttcgact atttcagctc gcaccgggag ccgtacccgc tcaagctgga    6720
aaccttccgc ctcatgtgcg gatcggattc caccccgcgtg aagaagtggc gcgagcaggt    6780
cggcgaagcc tgcgaagagt tgcgaggcag cggcctggtg aacacgcct gggtcaatga     6840
tgacctggtg cattgcaaac gctagggcct tgtggggtca gttccggctg ggggttcagc    6900
agccagcgct ttactggcat ttcaggaaca agcgggcact gctcgacgca cttgcttcgc    6960
tcagtatcgc tcgggacgca cggcgcgctc tacgaactgc cgataaacag aggattaaaa    7020
ttgacaattg tgattaaggc tcagattcga cggcttggag cggccgacgt gcaggatttc    7080
cgcgagatcc gattgtcggc cctgaagaaa gctccagaga tgttcgggtc cgtttacgag    7140
cacgaggaga aaaagcccat ggaggcgttc gctgaacggt tgcgagatgc cgtggcattc    7200
ggcgcctaca tcgacggcga gatcattggg ctgtcggtct tcaaacagga ggacggcccc    7260
```

```
aaggacgctc acaaggcgca tctgtccggc gttttcgtgg agcccgaaca gcgaggccga    7320
ggggtcgccg gtatgctgct gcgggcgttg ccggcgggtt tattgctcgt gatgatcgtc    7380
cgacagattc aacgggaat ctggtggatg cgcatcttca tcctcggcgc acttaatatt     7440
tcgctattct ggagcttgtt gtttatttcg gtctaccgcc tgccgggcgg ggtcgcggcg    7500
acggtaggcg ctgtgcagcc gctgatggtc gtgttcatct ctgccgctct gctaggtagc    7560
ccgatacgat tgatggcggt cctgggggct atttgcggaa ctgcgggcgt ggcgctgttg    7620
gtgttgacac caaacgcagc gctagatcct gtcggcgtcg cagcgggcct ggcggggcg     7680 gtttccatgg cgttcggaac cgtgctgacc cgcaagtggc aacctcccgt gcctctgctc    7740
acctttaccg cctggcaact ggcggccgga ggacttctgc tcgttccagt agctttagtg    7800
tttgatccgc caatcccgat gcctacagga accaatgttc tcggcctggc gtggctcggc    7860
ctgatcggag cgggtttaac ctacttcctt tggttccggg ggatctcgcg actcgaacct    7920
acagttgttt ccttactggg ctttctcagc cccagatctg gggtcgatca gccggggatg    7980
catcaggccg acagtcggaa cttcgggtcc ccgacctgta ccattcggtg agcaatggat    8040
aggggagttg atatcgtcaa cgttcacttc taaagaaata gcgccactca gcttcctcag    8100
cggctttatc cagcgatttc ctattatgtc ggcatagttc tcaagatcga cagcctgtca    8160
cggttaagcg agaaatgaat aagaaggctg ataattcgga tctctgcgag ggagatgata    8220
tttgatcaca ggcagcaacg ctctgtcatc gttacaatca acatgctacc ctccgcgaga    8280
tcatccgtgt ttcaaacccg gcagcttagt tgccgttctt ccgaatagca tcggtaacat    8340
gagcaaagtc tgccgcctta caacggctct cccgctgacg ccgtcccgga ctgatgggct    8400
gcctgtatcg agtggtgatt tgtgccgag ctgccggtcg gggagctgtt ggctggctgg     8460
tggcaggata tattgtggtg taaacaaatt gacgcttaga caacttaata acacattgcg    8520
gacgttttta atgtactggg gtggttttc ttttcaccag tgagacgggc aacagctgat     8580
tgcccttcac cgcctggccc tgagagagtt gcagcaagcg gtccacgctg gtttgcccca    8640
gcaggcgaaa atcctgtttg atggtggttc cgaaatcggc aaaatccctt ataaatcaaa    8700
agaatagccc gagatagggt tgagtgttgt tccagtttgg aacaagagtc cactattaaa    8760
gaacgtggac tccaacgtca aagggcgaaa aacgtctat caggggcgatg gcccactacg     8820 tgaaccatca cccaaatcaa gttttttggg gtcgaggtgc cgtaaagcac taaatcggaa    8880
ccctaaaggg agcccccgat ttagagcttg acggggaaag ccggcgaacg tggcgagaaa    8940
ggaagggaag aaagcgaaag gagcgggcgc cattcaggct gcgcaactgt gggaagggc     9000 gatcggtgcg ggcctcttcg ctattacgcc agctggcgaa aggggatgt gctgcaaggc     9060 gattaagttg ggtaacgcca gggttttccc agtcacgacg ttgtaaaacg acggccagtg    9120
aattaattcc catcttgaaa gaaatatagt ttaaatattt attgataaaa taacaagtca    9180
ggtattatag tccaagcaaa aacataaatt tattgatgca agtttaaatt cagaaatatt    9240
tcaataactg attatatcag ctggtacatt gccgtagatg aaagactgag tgcgatatta    9300
tgtgtaatac ataaattgat gatatagcta gcttagctca tcggggatc cgtcgaagct    9360 agcttgggtc ccgctcagaa gaactcgtca agaaggcgat agaaggcgat gcgctgcgaa    9420
tcgggagcgg cgataccgta agcacgagg aagcggtcag cccattcgcc gccaagctct     9480
tcagcaatat cacgggtagc caacgctatg tcctgatagc ggtccgccac acccagccgg    9540
ccacagtcga tgaatccaga aaagcggcca ttttccacca tgatattcgg caagcaggca    9600
```

```
tcgccatggg tcacgacgag atcctcgccg tcgggcatgc gcgccttgag cctggcgaac    9660
agttcggctg gcgcgagccc ctgatgctct tcgtccagat catcctgatc gacaagaccg    9720
gcttccatcc gagtacgtgc tcgctcgatg cgatgtttcg cttggtggtc gaatgggcag    9780
gtagccggat caagcgtatg cagccgccgc attgcatcag ccatgatgga tactttctcg    9840
gcaggagcaa ggtgagatga caggagatcc tgccccggca cttcgcccaa tagcagccag    9900
tcccttcccg cttcagtgac aacgtcgagc acagctgcgc aaggaacgcc cgtcgtggcc    9960
agccacgata gccgcgctgc ctcgtcctgc agttcattca gggcaccgga caggtcggtc   10020
ttgacaaaaa gaaccgggcg cccctgcgct gacagccgga acacggcggc atcagagcag   10080
ccgattgtct gttgtgccca gtcatagccg aatagcctct ccacccaagc ggccggagaa   10140
cctgcgtgca atccatcttg ttcaatccaa gctcccatgg gccctcgact agagtcgaga   10200
tctggattga gagtgaatat gagactctaa ttggataccg aggggaattt atggaacgtc   10260
agtggagcat ttttgacaag aaatatttgc tagctgatag tgaccttagg cgacttttga   10320
acgcgcaata atggtttctg acgtatgtgc ttagctcatt aaactccaga aacccgcggc   10380
tgagtggctc cttcaacgtt gcggttctgt cagttccaaa cgtaaaacgg cttgtcccgc   10440
gtcatcggcg ggggtcataa cgtgactccc ttaattctcc gctcatgatc ttgatcccct   10500
gcgccatcag atccttggcg gcaagaaagc catccagttt actttgcagg gcttcccaac   10560
cttaccagag ggcgccccag ctggcaattc cggttcgctt gctgtccata aaaccgccca   10620
gtctagctat cgccatgtaa gcccactgca agctacctgc tttctctttg cgcttgcgtt   10680
ttcccttgtc cagatagccc agtagctgac attcatccgg ggtcagcacc gtttctgcgg   10740
actggctttc tacgtgttcc gcttccttta gcagcccttg cgccctgagt gcttgcggca   10800
gcgtgaagct tgcatgcctg caggtcgacg gcgcgccgag ctcctcgagc aaatttacac   10860
attgccacta aacgtctaaa cccttgtaat ttgttttttgt tttactatgt gtgttatgta   10920
tttgatttgc gataaatttt tatatttggt actaaattta taacacccttt tatgctaacg   10980 tttgccaaca cttagcaatt tgcaagttga ttaattgatt ctaaattatt tttgtcttct   11040
aaatacatat actaatcaac tggaaatgta aatatttgct aatatttcta ctataggaga   11100
attaaagtga gtgaatatgg taccacaagg tttggagatt taattgttgc aatgctgcat   11160
ggatggcata tacaccaaac attcaataat tcttgaggat aataatggta ccacacaaga   11220
tttgaggtgc atgaacgtca cgtggacaaa aggtttagta attttttcaag acaacaatgt   11280 taccacacac aagttttgag gtgcatgcat ggatgccctg tggaaagttt aaaaatattt   11340
tggaaatgat ttgcatggaa gccatgtgta aaaccatgac atccacttgg aggatgcaat   11400
aatgaagaaa actacaaatt tacatgcaac tagttatgca tgtagtctat ataatgagga   11460
ttttgcaata ctttcattca tacacactca ctaagtttta cacgattata atttcttcat   11520
agccagccca ccgcggtgga aa atg gag gtc gtg gag aga ttc tac ggt gag   11572
                           Met Glu Val Val Glu Arg Phe Tyr Gly Glu
                             1               5                  10 ttg gat ggg aag gtc tcg cag ggc gtg aat gca ttg ctg ggt agt ttt   11620
Leu Asp Gly Lys Val Ser Gln Gly Val Asn Ala Leu Leu Gly Ser Phe
             15                  20                  25 ggg gtg gag ttg acg gat acg ccc act acc aaa ggc ttg ccc ctc gtt   11668
Gly Val Glu Leu Thr Asp Thr Pro Thr Thr Lys Gly Leu Pro Leu Val
         30                  35                  40 gac agt ccc aca ccc atc gtc ctc ggt gtt tct gta tac ttg act att   11716
Asp Ser Pro Thr Pro Ile Val Leu Gly Val Ser Val Tyr Leu Thr Ile
     45                  50                  55
```

```
gtc att gga ggg ctt ttg tgg ata aag gcc agg gat ctg aaa ccg cgc     11764
Val Ile Gly Gly Leu Leu Trp Ile Lys Ala Arg Asp Leu Lys Pro Arg
60                  65                  70 gcc tcg gag cca ttt ttg ctc caa gct ttg gtg ctt gtg cac aac ctg     11812
Ala Ser Glu Pro Phe Leu Leu Gln Ala Leu Val Leu Val His Asn Leu
75                  80                  85                  90 ttc tgt ttt gcg ctc agt ctg tat atg tgc gtg ggc atc gct tat cag     11860
Phe Cys Phe Ala Leu Ser Leu Tyr Met Cys Val Gly Ile Ala Tyr Gln
                95                  100                 105 gct att acc tgg cgg tac tct ctc tgg ggc aat gca tac aat cct aaa     11908
Ala Ile Thr Trp Arg Tyr Ser Leu Trp Gly Asn Ala Tyr Asn Pro Lys
            110                 115                 120 cat aaa gag atg gcg att ctg gta tac ttg ttc tac atg tct aag tac     11956
His Lys Glu Met Ala Ile Leu Val Tyr Leu Phe Tyr Met Ser Lys Tyr
        125                 130                 135 gtg gaa ttc atg gat acc gtt atc atg ata ctg aag cgc agc acc agg     12004
Val Glu Phe Met Asp Thr Val Ile Met Ile Leu Lys Arg Ser Thr Arg
    140                 145                 150 caa ata agc ttc ctc cac gtt tat cat cat tct tca att tcc ctc att     12052
Gln Ile Ser Phe Leu His Val Tyr His His Ser Ser Ile Ser Leu Ile
155                 160                 165                 170 tgg tgg gct att gct cat cac gct cct ggc ggt gaa gca tat tgg tct     12100
Trp Trp Ala Ile Ala His His Ala Pro Gly Gly Glu Ala Tyr Trp Ser
                175                 180                 185 gcg gct ctg aac tca gga gtg cat gtt ctc atg tat gcg tat tac ttc     12148
Ala Ala Leu Asn Ser Gly Val His Val Leu Met Tyr Ala Tyr Tyr Phe
            190                 195                 200 ttg gct gcc tgc ctt cga agt agc cca aag tta aaa aat aag tac ctt     12196
Leu Ala Ala Cys Leu Arg Ser Ser Pro Lys Leu Lys Asn Lys Tyr Leu
        205                 210                 215 ttt tgg ggc agg tac ttg aca caa ttc caa atg ttc cag ttt atg ctg     12244
Phe Trp Gly Arg Tyr Leu Thr Gln Phe Gln Met Phe Gln Phe Met Leu
    220                 225                 230 aac tta gtg cag gct tac tac gac atg aaa acg aat gcg cca tat cca     12292
Asn Leu Val Gln Ala Tyr Tyr Asp Met Lys Thr Asn Ala Pro Tyr Pro
235                 240                 245                 250 caa tgg ctg atc aag att ttg ttc tac tac atg atc tcg ttg ctg ttt     12340
Gln Trp Leu Ile Lys Ile Leu Phe Tyr Tyr Met Ile Ser Leu Leu Phe
                255                 260                 265 ctt ttc ggc aat ttt tac gta caa aaa tac atc aaa ccc tct gac gga     12388
Leu Phe Gly Asn Phe Tyr Val Gln Lys Tyr Ile Lys Pro Ser Asp Gly
            270                 275                 280 aag caa aag gga gct aaa act gag tga tctagaaggc ctcctgcttt          12435
Lys Gln Lys Gly Ala Lys Thr Glu
        285                 290 aatgagatat gcgagacgcc tatgatcgca tgatatttgc tttcaattct gttgtgcacg   12495
ttgtaaaaaa cctgagcatg tgtagctcag atccttaccg ccggtttcgg ttcattctaa   12555
tgaatatatc acccgttact atcgtatttt tatgaataat attctccgtt caatttactg   12615
attgtccgtc gagcaaattt acacattgcc actaaacgtc taaacccttg taatttgttt   12675
ttgttttact atgtgtgtta tgtatttgat ttgcgataaa ttttttatatt tggtactaaa  12735 tttataacac cttttatgct aacgtttgcc aacacttagc aatttgcaag ttgattaatt   12795
gattctaaat tattttttgtc ttctaaatac atatactaat caactggaaa tgtaaatatt  12855
tgctaatatt tctactatag gagaattaaa gtgagtgaat atggtaccac aaggtttgga   12915
gatttaattg ttgcaatgct gcatggatgg catatacacc aaacattcaa taattcttga   12975
```

-continued

```
ggataataat ggtaccacac aagatttgag gtgcatgaac gtcacgtgga caaaaggttt       13035
agtaattttt caagacaaca atgttaccac acacaagttt tgaggtgcat gcatggatgc       13095
cctgtggaaa gtttaaaaat attttggaaa tgatttgcat ggaagccatg tgtaaaacca       13155
tgacatccac ttggaggatg caataatgaa gaaaactaca aatttacatg caactagtta       13215
tgcatgtagt ctatataatg aggattttgc aatactttca ttcatacaca ctcactaagt       13275
tttacacgat tataatttct tcatagccag cggatcc atg gta ttc gcg ggc ggt       13330
                                         Met Val Phe Ala Gly Gly
                                                             295
```

```
gga ctt cag cag ggc tct ctc gaa gaa aac atc gac gtc gag cac att        13378
Gly Leu Gln Gln Gly Ser Leu Glu Glu Asn Ile Asp Val Glu His Ile
    300                 305                 310 gcc agt atg tct ctc ttc agc gac ttc ttc agt tat gtg tct tca act        13426
Ala Ser Met Ser Leu Phe Ser Asp Phe Phe Ser Tyr Val Ser Ser Thr
            315                 320                 325 gtt ggt tcg tgg agc gta cac agt ata caa cct ttg aag cgc ctg acg        13474
Val Gly Ser Trp Ser Val His Ser Ile Gln Pro Leu Lys Arg Leu Thr
330                 335                 340 agt aag aag cgt gtt tcg gaa agc gct gcc gtg caa tgt ata tca gct        13522
Ser Lys Lys Arg Val Ser Glu Ser Ala Ala Val Gln Cys Ile Ser Ala
345                 350                 355                 360 gaa gtt cag aga aat tcg agt acc cag gga act gcg gag gca ctc gca        13570
Glu Val Gln Arg Asn Ser Ser Thr Gln Gly Thr Ala Glu Ala Leu Ala
                365                 370                 375 gaa tca gtc gtg aag ccc acg aga cga agg tca tct cag tgg aag aag        13618
Glu Ser Val Val Lys Pro Thr Arg Arg Arg Ser Ser Gln Trp Lys Lys
            380                 385                 390 tcg aca cac ccc cta tca gaa gta gca gta cac aac aag cca agc gat        13666
Ser Thr His Pro Leu Ser Glu Val Ala Val His Asn Lys Pro Ser Asp
        395                 400                 405 tgc tgg att gtt gta aaa aac aag gtg tat gat gtt tcc aat ttt gcg        13714
Cys Trp Ile Val Val Lys Asn Lys Val Tyr Asp Val Ser Asn Phe Ala
    410                 415                 420 gac gag cat ccc gga gga tca gtt att agt act tat ttt gga cga gac        13762
Asp Glu His Pro Gly Gly Ser Val Ile Ser Thr Tyr Phe Gly Arg Asp
425                 430                 435                 440 ggc aca gat gtt ttc tct agt ttt cat gca gct tct aca tgg aaa att        13810
Gly Thr Asp Val Phe Ser Ser Phe His Ala Ala Ser Thr Trp Lys Ile
                445                 450                 455 ctt caa gac ttt tac att ggt gac gtg gag agg gtg gag ccg act cca        13858
Leu Gln Asp Phe Tyr Ile Gly Asp Val Glu Arg Val Glu Pro Thr Pro
            460                 465                 470 gag ctg ctg aaa gat ttc cga gaa atg aga gct ctt ttc ctg agg gag        13906
Glu Leu Leu Lys Asp Phe Arg Glu Met Arg Ala Leu Phe Leu Arg Glu
        475                 480                 485 caa ctt ttc aaa agt tcg aaa ttg tac tat gtt atg aag ctc ctc acg        13954
Gln Leu Phe Lys Ser Ser Lys Leu Tyr Tyr Val Met Lys Leu Leu Thr
    490                 495                 500 aat gtt gct att ttt gct gcg agc att gca ata ata tgt tgg agc aag        14002
Asn Val Ala Ile Phe Ala Ala Ser Ile Ala Ile Ile Cys Trp Ser Lys
505                 510                 515                 520 act att tca gcg gtt ttg gct tca gct tgt atg atg gct ctg tgt ttc        14050
Thr Ile Ser Ala Val Leu Ala Ser Ala Cys Met Met Ala Leu Cys Phe
                525                 530                 535 caa cag tgc gga tgg cta tcc cat gat ttt ctc cac aat cag gtg ttt        14098
Gln Gln Cys Gly Trp Leu Ser His Asp Phe Leu His Asn Gln Val Phe
            540                 545                 550 gag aca cgc tgg ctt aat gaa gtt gtc ggg tat gtg atc ggc aac gcc        14146
Glu Thr Arg Trp Leu Asn Glu Val Val Gly Tyr Val Ile Gly Asn Ala
```

-continued

```
                Glu Thr Arg Trp Leu Asn Glu Val Val Gly Tyr Val Ile Gly Asn Ala
                                555                 560                 565 gtt ctg ggg ttt agt aca ggg tgg tgg aag gag aag cat aac ctt cat                 14194
Val Leu Gly Phe Ser Thr Gly Trp Trp Lys Glu Lys His Asn Leu His
        570                 575                 580 cat gct gct cca aat gaa tgc gat cag act tac caa cca att gat gaa                 14242
His Ala Ala Pro Asn Glu Cys Asp Gln Thr Tyr Gln Pro Ile Asp Glu
585                 590                 595                 600 gat att gat act ctc ccc ctc att gcc tgg agc aag gac ata ctg gcc                 14290
Asp Ile Asp Thr Leu Pro Leu Ile Ala Trp Ser Lys Asp Ile Leu Ala
                605                 610                 615 aca gtt gag aat aag aca ttc ttg cga atc ctc caa tac cag cat ctg                 14338
Thr Val Glu Asn Lys Thr Phe Leu Arg Ile Leu Gln Tyr Gln His Leu
                620                 625                 630 ttc ttc atg ggt ctg tta ttt ttc gcc cgt ggt agt tgg ctc ttt tgg                 14386
Phe Phe Met Gly Leu Leu Phe Phe Ala Arg Gly Ser Trp Leu Phe Trp
                635                 640                 645 agc tgg aga tat acc tct aca gca gtg ctc tca cct gtc gac agg ttg                 14434
Ser Trp Arg Tyr Thr Ser Thr Ala Val Leu Ser Pro Val Asp Arg Leu
        650                 655                 660 ttg gag aag gga act gtt ctg ttt cac tac ttt tgg ttc gtc ggg aca                 14482
Leu Glu Lys Gly Thr Val Leu Phe His Tyr Phe Trp Phe Val Gly Thr
665                 670                 675                 680 gcg tgc tat ctt ctc cct ggt tgg aag cca tta gta tgg atg gcg gtg                 14530
Ala Cys Tyr Leu Leu Pro Gly Trp Lys Pro Leu Val Trp Met Ala Val
                685                 690                 695 act gag ctc atg tcc ggc atg ctg ctg ggc ttt gta ttt gta ctt agc                 14578
Thr Glu Leu Met Ser Gly Met Leu Leu Gly Phe Val Phe Val Leu Ser
                700                 705                 710 cac aat ggg atg gag gtt tat aat tcg tct aaa gaa ttc gtg agt gca                 14626
His Asn Gly Met Glu Val Tyr Asn Ser Ser Lys Glu Phe Val Ser Ala
        715                 720                 725 cag atc gta tcc aca cgg gat atc aaa gga aac ata ttc aac gac tgg                 14674
Gln Ile Val Ser Thr Arg Asp Ile Lys Gly Asn Ile Phe Asn Asp Trp
730                 735                 740 ttc act ggt ggc ctt aac agg caa ata gag cat cat ctt ttc cca aca                 14722
Phe Thr Gly Gly Leu Asn Arg Gln Ile Glu His His Leu Phe Pro Thr
745                 750                 755                 760 atg ccc agg cat aat tta aac aaa ata gca cct aga gtg gag gtg ttc                 14770
Met Pro Arg His Asn Leu Asn Lys Ile Ala Pro Arg Val Glu Val Phe
                765                 770                 775 tgt aag aaa cac ggt ctg gtg tac gaa gac gta tct att gct acc ggc                 14818
Cys Lys Lys His Gly Leu Val Tyr Glu Asp Val Ser Ile Ala Thr Gly
                780                 785                 790 act tgc aag gtt ttg aaa gca ttg aag gaa gtc gcg gag gct gcg gca                 14866
Thr Cys Lys Val Leu Lys Ala Leu Lys Glu Val Ala Glu Ala Ala Ala
        795                 800                 805 gag cag cat gct acc acc agt taa gctagcgtta accctgcttt aatgagatat               14920
Glu Gln His Ala Thr Thr Ser
        810                 815 gcgagacgcc tatgatcgca tgatatttgc tttcaattct gttgtgcacg ttgtaaaaaa               14980
cctgagcatg tgtagctcag atccttaccg ccggtttcgg ttcattctaa tgaatatatc               15040
acccgttact atcgtatttt tatgaataat attctccgtt caatttactg attgtccgtc               15100
gagcaaattt acacattgcc actaaacgtc taaacccttg taatttgttt ttgttttact               15160
atgtgtgtta tgtatttgat ttgcgataaa ttttttatatt tggtactaaa tttataacac              15220
cttttatgct aacgtttgcc aacacttagc aatttgcaag ttgattaatt gattctaaat               15280
```

```
tattttttgtc ttctaaatac atatactaat caactggaaa tgtaaatatt tgctaatatt   15340
tctactatag gagaattaaa gtgagtgaat atggtaccac aaggtttgga gatttaattg   15400
ttgcaatgct gcatggatgg catatacacc aaacattcaa taattcttga ggataataat   15460
ggtaccacac aagatttgag gtgcatgaac gtcacgtgga caaaaggttt agtaattttt   15520
caagacaaca atgttaccac acacaagttt tgaggtgcat gcatggatgc cctgtggaaa   15580
gtttaaaaat attttggaaa tgatttgcat ggaagccatg tgtaaaacca tgacatccac   15640
ttggaggatg caataatgaa gaaaactaca aatttacatg caactagtta tgcatgtagt   15700
ctatataatg aggattttgc aatactttca ttcatacaca ctcactaagt tttacacgat   15760
tataatttct tcatagccag cagatctaaa atg gct ccg gat gcg gat aag ctt   15814
                                 Met Ala Pro Asp Ala Asp Lys Leu
                                                  820 cga caa cgc cag acg act gcg gta gcg aag cac aat gct gct acc ata   15862
Arg Gln Arg Gln Thr Thr Ala Val Ala Lys His Asn Ala Ala Thr Ile
    825                 830                 835 tcg acg cag gaa cgc ctt tgc agt ctg tct tcg ctc aaa ggc gaa gaa   15910
Ser Thr Gln Glu Arg Leu Cys Ser Leu Ser Ser Leu Lys Gly Glu Glu
840                 845                 850                 855 gtc tgc atc gac gga atc atc tat gac ctc caa tca ttc gat cat ccc   15958
Val Cys Ile Asp Gly Ile Ile Tyr Asp Leu Gln Ser Phe Asp His Pro
                860                 865                 870 ggg ggt gaa acg atc aaa atg ttt ggt ggc aac gat gtc act gta cag   16006
Gly Gly Glu Thr Ile Lys Met Phe Gly Gly Asn Asp Val Thr Val Gln
            875                 880                 885 tac aag atg att cac ccg tac cat acc gag aag cat ttg gaa aag atg   16054
Tyr Lys Met Ile His Pro Tyr His Thr Glu Lys His Leu Glu Lys Met
        890                 895                 900 aag cgt gtc ggc aag gtg acg gat ttc gtc tgc gag tac aag ttc gat   16102
Lys Arg Val Gly Lys Val Thr Asp Phe Val Cys Glu Tyr Lys Phe Asp
    905                 910                 915 acc gaa ttt gaa cgc gaa atc aaa cga gaa gtc ttc aag att gtg cga   16150
Thr Glu Phe Glu Arg Glu Ile Lys Arg Glu Val Phe Lys Ile Val Arg
920                 925                 930                 935 cga ggc aag gat ttc ggt act ttg gga tgg ttc ttc cgt gcg ttt tgc   16198
Arg Gly Lys Asp Phe Gly Thr Leu Gly Trp Phe Phe Arg Ala Phe Cys
                940                 945                 950 tac att gcc att ttc ttc tac ctg cag tac cat tgg gtc acc acg gga   16246
Tyr Ile Ala Ile Phe Phe Tyr Leu Gln Tyr His Trp Val Thr Thr Gly
            955                 960                 965 acc tct tgg ctg ctg gcc gtg gcc tac gga atc tcc caa gcg atg att   16294
Thr Ser Trp Leu Leu Ala Val Ala Tyr Gly Ile Ser Gln Ala Met Ile
        970                 975                 980 ggc atg aat gtc cag cac gat gcc aac cac ggg gcc acc tcc aag cgt   16342
Gly Met Asn Val Gln His Asp Ala Asn His Gly Ala Thr Ser Lys Arg
    985                 990                 995 ccc tgg gtc aac gac atg cta ggc ctc ggt gcg gat ttt att ggt       16387
Pro Trp Val Asn Asp Met Leu Gly Leu Gly Ala Asp Phe Ile Gly
1000                1005                1010 ggt tcc aag tgg ctc tgg cag gaa caa cac tgg acc cac cac gct       16432
Gly Ser Lys Trp Leu Trp Gln Glu Gln His Trp Thr His His Ala
1015                1020                1025 tac acc aat cac gcc gag atg gat ccc gat agc ttt ggt gcc gaa       16477
Tyr Thr Asn His Ala Glu Met Asp Pro Asp Ser Phe Gly Ala Glu
1030                1035                1040 cca atg ctc cta ttc aac gac tat ccc ttg gat cat ccc gct cgt       16522
Pro Met Leu Leu Phe Asn Asp Tyr Pro Leu Asp His Pro Ala Arg
1045                1050                1055
```

```
acc tgg cta cat cgc ttt caa gca ttc ttt tac atg ccc gtc ttg    16567
Thr Trp Leu His Arg Phe Gln Ala Phe Phe Tyr Met Pro Val Leu
1060            1065                1070 gct gga tac tgg ttg tcc gct gtc ttc aat cca caa att ctt gac    16612
Ala Gly Tyr Trp Leu Ser Ala Val Phe Asn Pro Gln Ile Leu Asp
1075            1080                1085 ctc cag caa cgc ggc gca ctt tcc gtc ggt atc cgt ctc gac aac    16657
Leu Gln Gln Arg Gly Ala Leu Ser Val Gly Ile Arg Leu Asp Asn
1090            1095                1100 gct ttc att cac tcg cga cgc aag tat gcg gtt ttc tgg cgg gct    16702
Ala Phe Ile His Ser Arg Arg Lys Tyr Ala Val Phe Trp Arg Ala
1105            1110                1115 gtg tac att gcg gtg aac gtg att gct ccg ttt tac aca aac tcc    16747
Val Tyr Ile Ala Val Asn Val Ile Ala Pro Phe Tyr Thr Asn Ser
1120            1125                1130 ggc ctc gaa tgg tcc tgg cgt gtc ttt gga aac atc atg ctc atg    16792
Gly Leu Glu Trp Ser Trp Arg Val Phe Gly Asn Ile Met Leu Met
1135            1140                1145 ggt gtg gcg gaa tcg ctc gcg ctg gcg gtc ctg ttt tcg ttg tcg    16837
Gly Val Ala Glu Ser Leu Ala Leu Ala Val Leu Phe Ser Leu Ser
1150            1155                1160 cac aat ttc gaa tcc gcg gat cgc gat ccg acc gcc cca ctg aaa    16882
His Asn Phe Glu Ser Ala Asp Arg Asp Pro Thr Ala Pro Leu Lys
1165            1170                1175 aag acg gga gaa cca gtc gac tgg ttc aag aca cag gtc gaa act    16927
Lys Thr Gly Glu Pro Val Asp Trp Phe Lys Thr Gln Val Glu Thr
1180            1185                1190 tcc tgc act tac ggt gga ttc ctt tcc ggt tgc ttc acg gga ggt    16972
Ser Cys Thr Tyr Gly Gly Phe Leu Ser Gly Cys Phe Thr Gly Gly
1195            1200                1205 ctc aac ttt cag gtt gaa cac cac ttg ttc cca cgc atg agc agc    17017
Leu Asn Phe Gln Val Glu His His Leu Phe Pro Arg Met Ser Ser
1210            1215                1220 gct tgg tat ccc tac att gcc ccc aag gtc cgc gaa att tgc gcc    17062
Ala Trp Tyr Pro Tyr Ile Ala Pro Lys Val Arg Glu Ile Cys Ala
1225            1230                1235 aaa cac ggc gtc cac tac gcc tac tac ccg tgg atc cac caa aac    17107
Lys His Gly Val His Tyr Ala Tyr Tyr Pro Trp Ile His Gln Asn
1240            1245                1250 ttt ctc tcc acc gtc cgc tac atg cac gcg gcc ggg acc ggt gcc    17152
Phe Leu Ser Thr Val Arg Tyr Met His Ala Ala Gly Thr Gly Ala
1255            1260                1265 aac tgg cgc cag atg gcc aga gaa aat ccc ttg acc gga cgg gcg    17197
Asn Trp Arg Gln Met Ala Arg Glu Asn Pro Leu Thr Gly Arg Ala
1270            1275                1280 taa agatctgccg gcatcgatcc cgggccatgg cctgctttaa tgagatatgc    17250
gagacgccta tgatcgcatg atatttgctt tcaattctgt tgtgcacgtt gtaaaaacc    17310 tgagcatgtg tagctcagat ccttaccgcc ggtttcggtt cattctaatg aatatatcac    17370
ccgttactat cgtattttta tgaataatat tctccgttca atttactgat tgtccgtcga    17430
cgagctcggc gcgcctctag aggatcgatg aattcagatc ggctgagtgg ctccttcaac    17490
gttgcggttc tgtcagttcc aaacgtaaaa cggcttgtcc cgcgtcatcg gcggggtca    17550 taacgtgact cccttaattc tccgctcatg atcagattgt cgtttcccgc cttcagttta    17610
aactatcagt gtttgacagg atatattggc gggtaaacct aagagaaaag agcgtttatt    17670
agaataatcg gatatttaaa agggcgtgaa aaggtttatc cttcgtccat ttgtatgtgc    17730
```
atgccaacca cagggttccc ca                                            17752

<210> SEQ ID NO 57
<211> LENGTH: 290
<212> TYPE: PRT
<213> ORGANISM: Physcomitrella patens

<400> SEQUENCE: 57

Met Glu Val Val Glu Arg Phe Tyr Gly Glu Leu Asp Gly Lys Val Ser
1               5                   10                  15

Gln Gly Val Asn Ala Leu Leu Gly Ser Phe Gly Val Glu Leu Thr Asp
            20                  25                  30

Thr Pro Thr Thr Lys Gly Leu Pro Leu Val Asp Ser Pro Thr Pro Ile
        35                  40                  45

Val Leu Gly Val Ser Val Tyr Leu Thr Ile Val Ile Gly Gly Leu Leu
    50                  55                  60

Trp Ile Lys Ala Arg Asp Leu Lys Pro Arg Ala Ser Glu Pro Phe Leu
65                  70                  75                  80

Leu Gln Ala Leu Val Leu Val His Asn Leu Phe Cys Phe Ala Leu Ser
                85                  90                  95

Leu Tyr Met Cys Val Gly Ile Ala Tyr Gln Ala Ile Thr Trp Arg Tyr
            100                 105                 110

Ser Leu Trp Gly Asn Ala Tyr Asn Pro Lys His Lys Glu Met Ala Ile
        115                 120                 125

Leu Val Tyr Leu Phe Tyr Met Ser Lys Tyr Val Glu Phe Met Asp Thr
    130                 135                 140

Val Ile Met Ile Leu Lys Arg Ser Thr Arg Gln Ile Ser Phe Leu His
145                 150                 155                 160

Val Tyr His His Ser Ser Ile Ser Leu Ile Trp Trp Ala Ile Ala His
                165                 170                 175

His Ala Pro Gly Gly Glu Ala Tyr Trp Ser Ala Ala Leu Asn Ser Gly
            180                 185                 190

Val His Val Leu Met Tyr Ala Tyr Tyr Phe Leu Ala Ala Cys Leu Arg
        195                 200                 205

Ser Ser Pro Lys Leu Lys Asn Lys Tyr Leu Phe Trp Gly Arg Tyr Leu
    210                 215                 220

Thr Gln Phe Gln Met Phe Gln Phe Met Leu Asn Leu Val Gln Ala Tyr
225                 230                 235                 240

Tyr Asp Met Lys Thr Asn Ala Pro Tyr Pro Gln Trp Leu Ile Lys Ile
                245                 250                 255

Leu Phe Tyr Tyr Met Ile Ser Leu Leu Phe Leu Phe Gly Asn Phe Tyr
            260                 265                 270

Val Gln Lys Tyr Ile Lys Pro Ser Asp Gly Lys Gln Lys Gly Ala Lys
        275                 280                 285

Thr Glu
    290

<210> SEQ ID NO 58
<211> LENGTH: 525
<212> TYPE: PRT
<213> ORGANISM: Physcomitrella patens

<400> SEQUENCE: 58

Met Val Phe Ala Gly Gly Gly Leu Gln Gln Gly Ser Leu Glu Glu Asn
1               5                   10                  15

Ile Asp Val Glu His Ile Ala Ser Met Ser Leu Phe Ser Asp Phe Phe

-continued

```
                20                  25                  30
Ser Tyr Val Ser Ser Thr Val Gly Ser Trp Ser Val His Ser Ile Gln
         35                  40                  45

Pro Leu Lys Arg Leu Thr Ser Lys Lys Arg Val Ser Glu Ser Ala Ala
 50                  55                  60

Val Gln Cys Ile Ser Ala Glu Val Gln Arg Asn Ser Ser Thr Gln Gly
 65                  70                  75                  80

Thr Ala Glu Ala Leu Ala Glu Ser Val Val Lys Pro Thr Arg Arg Arg
                 85                  90                  95

Ser Ser Gln Trp Lys Lys Ser Thr His Pro Leu Ser Val Ala Val
                100                 105                 110

His Asn Lys Pro Ser Asp Cys Trp Ile Val Val Lys Asn Lys Val Tyr
            115                 120                 125

Asp Val Ser Asn Phe Ala Asp Glu His Pro Gly Gly Ser Val Ile Ser
        130                 135                 140

Thr Tyr Phe Gly Arg Asp Gly Thr Asp Val Phe Ser Ser Phe His Ala
145                 150                 155                 160

Ala Ser Thr Trp Lys Ile Leu Gln Asp Phe Tyr Ile Gly Asp Val Glu
                165                 170                 175

Arg Val Glu Pro Thr Pro Glu Leu Leu Lys Asp Phe Arg Glu Met Arg
            180                 185                 190

Ala Leu Phe Leu Arg Glu Gln Leu Phe Lys Ser Ser Lys Leu Tyr Tyr
        195                 200                 205

Val Met Lys Leu Leu Thr Asn Val Ala Ile Phe Ala Ala Ser Ile Ala
210                 215                 220

Ile Ile Cys Trp Ser Lys Thr Ile Ser Ala Val Leu Ala Ser Ala Cys
225                 230                 235                 240

Met Met Ala Leu Cys Phe Gln Gln Cys Gly Trp Leu Ser His Asp Phe
                245                 250                 255

Leu His Asn Gln Val Phe Glu Thr Arg Trp Leu Asn Glu Val Val Gly
            260                 265                 270

Tyr Val Ile Gly Asn Ala Val Leu Gly Phe Ser Thr Gly Trp Trp Lys
        275                 280                 285

Glu Lys His Asn Leu His His Ala Ala Pro Asn Glu Cys Asp Gln Thr
    290                 295                 300

Tyr Gln Pro Ile Asp Glu Asp Ile Asp Thr Leu Pro Leu Ile Ala Trp
305                 310                 315                 320

Ser Lys Asp Ile Leu Ala Thr Val Glu Asn Lys Thr Phe Leu Arg Ile
                325                 330                 335

Leu Gln Tyr Gln His Leu Phe Phe Met Gly Leu Leu Phe Phe Ala Arg
            340                 345                 350

Gly Ser Trp Leu Phe Trp Ser Trp Arg Tyr Thr Ser Thr Ala Val Leu
        355                 360                 365

Ser Pro Val Asp Arg Leu Leu Glu Lys Gly Thr Val Leu Phe His Tyr
    370                 375                 380

Phe Trp Phe Val Gly Thr Ala Cys Tyr Leu Leu Pro Gly Trp Lys Pro
385                 390                 395                 400

Leu Val Trp Met Ala Val Thr Glu Leu Met Ser Gly Met Leu Leu Gly
                405                 410                 415

Phe Val Phe Val Leu Ser His Asn Gly Met Glu Val Tyr Asn Ser Ser
            420                 425                 430

Lys Glu Phe Val Ser Ala Gln Ile Val Ser Thr Arg Asp Ile Lys Gly
        435                 440                 445
```

```
Asn Ile Phe Asn Asp Trp Phe Thr Gly Gly Leu Asn Arg Gln Ile Glu
        450                 455                 460

His His Leu Phe Pro Thr Met Pro Arg His Asn Leu Asn Lys Ile Ala
465                 470                 475                 480

Pro Arg Val Glu Val Phe Cys Lys Lys His Gly Leu Val Tyr Glu Asp
                485                 490                 495

Val Ser Ile Ala Thr Gly Thr Cys Lys Val Leu Lys Ala Leu Lys Glu
            500                 505                 510

Val Ala Glu Ala Ala Glu Gln His Ala Thr Thr Ser
        515                 520                 525

<210> SEQ ID NO 59
<211> LENGTH: 469
<212> TYPE: PRT
<213> ORGANISM: Phaeodactylum tricornutum

<400> SEQUENCE: 59

Met Ala Pro Asp Ala Asp Lys Leu Arg Gln Arg Gln Thr Thr Ala Val
1               5                   10                  15

Ala Lys His Asn Ala Ala Thr Ile Ser Thr Gln Glu Arg Leu Cys Ser
            20                  25                  30

Leu Ser Ser Leu Lys Gly Glu Glu Val Cys Ile Asp Gly Ile Ile Tyr
        35                  40                  45

Asp Leu Gln Ser Phe Asp His Pro Gly Gly Glu Thr Ile Lys Met Phe
    50                  55                  60

Gly Gly Asn Asp Val Thr Val Gln Tyr Lys Met Ile His Pro Tyr His
65                  70                  75                  80

Thr Glu Lys His Leu Glu Lys Met Lys Arg Val Gly Lys Val Thr Asp
                85                  90                  95

Phe Val Cys Glu Tyr Lys Phe Asp Thr Glu Phe Glu Arg Glu Ile Lys
            100                 105                 110

Arg Glu Val Phe Lys Ile Val Arg Arg Gly Lys Asp Phe Gly Thr Leu
        115                 120                 125

Gly Trp Phe Phe Arg Ala Phe Cys Tyr Ile Ala Ile Phe Phe Tyr Leu
    130                 135                 140

Gln Tyr His Trp Val Thr Thr Gly Thr Ser Trp Leu Leu Ala Val Ala
145                 150                 155                 160

Tyr Gly Ile Ser Gln Ala Met Ile Gly Met Asn Val Gln His Asp Ala
                165                 170                 175

Asn His Gly Ala Thr Ser Lys Arg Pro Trp Val Asn Asp Met Leu Gly
            180                 185                 190

Leu Gly Ala Asp Phe Ile Gly Gly Ser Lys Trp Leu Trp Gln Glu Gln
        195                 200                 205

His Trp Thr His His Ala Tyr Thr Asn His Ala Glu Met Asp Pro Asp
    210                 215                 220

Ser Phe Gly Ala Glu Pro Met Leu Leu Phe Asn Asp Tyr Pro Leu Asp
225                 230                 235                 240

His Pro Ala Arg Thr Trp Leu His Arg Phe Gln Ala Phe Phe Tyr Met
                245                 250                 255

Pro Val Leu Ala Gly Tyr Trp Leu Ser Ala Val Phe Asn Pro Gln Ile
            260                 265                 270

Leu Asp Leu Gln Gln Arg Gly Ala Leu Ser Val Gly Ile Arg Leu Asp
        275                 280                 285

Asn Ala Phe Ile His Ser Arg Arg Lys Tyr Ala Val Phe Trp Arg Ala
```

```
                290             295             300
Val Tyr Ile Ala Val Asn Val Ile Ala Pro Phe Tyr Thr Asn Ser Gly
305                 310                 315                 320

Leu Glu Trp Ser Trp Arg Val Phe Gly Asn Ile Met Leu Met Gly Val
                325                 330                 335

Ala Glu Ser Leu Ala Leu Ala Val Leu Phe Ser Leu Ser His Asn Phe
            340                 345                 350

Glu Ser Ala Asp Arg Asp Pro Thr Ala Pro Leu Lys Lys Thr Gly Glu
        355                 360                 365

Pro Val Asp Trp Phe Lys Thr Gln Val Glu Thr Ser Cys Thr Tyr Gly
370                 375                 380

Gly Phe Leu Ser Gly Cys Phe Thr Gly Gly Leu Asn Phe Gln Val Glu
385                 390                 395                 400

His His Leu Phe Pro Arg Met Ser Ser Ala Trp Tyr Pro Tyr Ile Ala
                405                 410                 415

Pro Lys Val Arg Glu Ile Cys Ala Lys His Gly Val His Tyr Ala Tyr
                420                 425                 430

Tyr Pro Trp Ile His Gln Asn Phe Leu Ser Thr Val Arg Tyr Met His
                435                 440                 445

Ala Ala Gly Thr Gly Ala Asn Trp Arg Gln Met Ala Arg Glu Asn Pro
    450                 455                 460

Leu Thr Gly Arg Ala
465

<210> SEQ ID NO 60
<211> LENGTH: 26
<212> TYPE: DNA
<213> ORGANISM: Artificial sequence
<220> FEATURE:
<223> OTHER INFORMATION: Polylinker

<400> SEQUENCE: 60
gaattcggcg cgccgagctc ctcgag                                          26

<210> SEQ ID NO 61
<211> LENGTH: 265
<212> TYPE: DNA
<213> ORGANISM: Artificial sequence
<220> FEATURE:
<223> OTHER INFORMATION: Polylinker

<400> SEQUENCE: 61
ccaccgcggt gggcggccgc ctgcagtcta gaaggcctcc tgctttaatg agatatgcga     60
gacgcctatg atcgcatgat atttgctttc aattctgttg tgcacgttgt aaaaaacctg   120
agcatgtgta gctcagatcc ttaccgccgg tttcggttca ttctaatgaa tatatcaccc   180
gttactatcg tattttatg aataatattc tccgttcaat ttactgattg tccgtcgacg   240
aattcgagct cggcgcgcca agctt                                         265

<210> SEQ ID NO 62
<211> LENGTH: 257
<212> TYPE: DNA
<213> ORGANISM: artificial sequence
<220> FEATURE:
<223> OTHER INFORMATION: Polylinker

<400> SEQUENCE: 62
ggatccgata tcgggcccgc tagcgttaac cctgctttaa tgagatatgc gagacgccta     60
```

```
tgatcgcatg atatttgctt tcaattctgt tgtgcacgtt gtaaaaaacc tgagcatgtg    120
tagctcagat ccttaccgcc ggtttcggtt cattctaatg aatatatcac ccgttactat    180
cgtattttta tgaataatat tctccgttca atttactgat tgtccgtcga cgaattcgag    240
ctcggcgcgc caagctt                                                   257

<210> SEQ ID NO 63
<211> LENGTH: 5410
<212> TYPE: DNA
<213> ORGANISM: artificial sequence
<220> FEATURE:
<223> OTHER INFORMATION: vector

<400> SEQUENCE: 63
ttttggaaat gatttgcatg gaagccatgt gtaaaaccat gacatccact tggaggatgc     60
aataatgaag aaaactacaa atttacatgc aactagttat gcatgtagtc tatataatga    120
ggattttgca atactttcat tcatacacac tcactaagtt ttacacgatt ataatttctt    180
catagccagc ggatccgata tcgggcccgc tagcgttaac cctgctttaa tgagatatgc    240
gagacgccta tgatcgcatg atatttgctt tcaattctgt tgtgcacgtt gtaaaaaacc    300
tgagcatgtg tagctcagat ccttaccgcc ggtttcggtt cattctaatg aatatatcac    360
ccgttactat cgtattttta tgaataatat tctccgttca atttactgat tgtccgtcga    420
gcaaatttac acattgccac taaacgtcta aacccttgta atttgttttt gttttactat    480
gtgtgttatg tatttgattt gcgataaatt tttatatttg gtactaaatt tataacacct    540
tttatgctaa cgtttgccaa cacttagcaa tttgcaagtt gattaattga ttctaaatta    600
tttttgtctt ctaaatacat atactaatca actggaaatg taaatatttg ctaatatttc    660
tactatagga gaattaaagt gagtgaatat ggtaccacaa ggtttggaga tttaattgtt    720
gcaatgctgc atggatggca tatacaccaa acattcaata attcttgagg ataataatgg    780
taccacacaa gatttgaggt gcatgaacgt cacgtggaca aaaggtttag taattttca     840 agacaacaat gttaccacac acaagttttg aggtgcatgc atggatgccc tgtggaaagt    900
ttaaaaatat tttggaaatg atttgcatgg aagccatgtg taaaaccatg acatccactt    960
ggaggatgca ataatgaaga aaactacaaa tttacatgca actagttatg catgtagtct   1020
atataatgag gattttgcaa tactttcatt catacacact cactaagttt tacacgatta   1080
taatttcttc atagccagca gatctgccgg catcgatccc gggccatggc ctgctttaat   1140
gagatatgcg agacgcctat gatcgcatga tatttgcttt caattctgtt gtgcacgttg   1200
taaaaaacct gagcatgtgt agctcagatc cttaccgccg gtttcggttc attctaatga   1260
atatatcacc cgttactatc gtatttttat gaataatatt ctccgttcaa tttactgatt   1320
gtccgtcgac gagctcggcg cgccaagctt ggcgtaatca tggtcatagc tgtttcctgt   1380
gtgaaattgt tatccgctca caattccaca acatacga gccggaagca taaagtgtaa   1440
agcctggggt gcctaatgag tgagctaact cacattaatt gcgttgcgct cactgcccgc   1500
tttccagtcg ggaaacctgt cgtgccagct gcattaatga atcggccaac gcgcggggag   1560
aggcggtttg cgtattgggc gctcttccgc ttcctcgctc actgactcgc tgcgctcggt   1620
cgttcggctg cggcgagcgg tatcagctca ctcaaaggcg gtaatacggt tatccacaga   1680
atcaggggat aacgcaggaa agaacatgtg agcaaaaggc cagcaaaagg ccaggaaccg   1740
taaaaaggcc gcgttgctgg cgtttttcca taggctccgc ccccctgacg agcatcacaa   1800
aaatcgacgc tcaagtcaga ggtggcgaaa cccgacagga ctataaagat accaggcgtt   1860
```

```
tcccccctgga agctccctcg tgcgctctcc tgttccgacc ctgccgctta ccggataccT    1920
gtccgccttt ctcccttcgg gaagcgtggc gctttctcat agctcacgct gtaggtatct    1980
cagttcggtg taggtcgttc gctccaagct gggctgtgtg cacgaacccc ccgttcagcc    2040
cgaccgctgc gccttatccg gtaactatcg tcttgagtcc aacccggtaa gacacgactt    2100
atcgccactg gcagcagcca ctggtaacag gattagcaga gcgaggtatg taggcggtgc    2160
tacagagttc ttgaagtggt ggcctaacta cggctacact agaaggacag tatttggtat    2220
ctgcgctctg ctgaagccag ttaccttcgg aaaagagtt ggtagctctt gatccggcaa    2280
acaaaccacc gctggtagcg gtggttttttt tgtttgcaag cagcagatta cgcgcagaaa    2340
aaaaggatct caagaagatc ctttgatctt ttctacgggg tctgacgctc agtggaacga    2400
aaactcacgt taagggattt tggtcatgag attatcaaaa aggatcttca cctagatcct    2460
tttaaattaa aaatgaagtt ttaaatcaat ctaaagtata tatgagtaaa cttggtctga    2520
cagttaccaa tgcttaatca gtgaggcacc tatctcagcg atctgtctat ttcgttcatc    2580
catagttgcc tgactccccg tcgtgtagat aactacgata cgggagggct taccatctgg    2640
ccccagtgct gcaatgatac cgcgagaccc acgctcaccg gctccagatt tatcagcaat    2700
aaaccagcca gccggaaggg ccgagcgcag aagtggtcct gcaactttat ccgcctccat    2760
ccagtctatt aattgttgcc gggaagctag agtaagtagt tcgccagtta atagtttgcg    2820
caacgttgtt gccattgcta caggcatcgt ggtgtcacgc tcgtcgtttg gtatggcttc    2880
attcagctcc ggttcccaac gatcaaggcg agttacatga tcccccatgt tgtgcaaaaa    2940
agcggttagc tccttcggtc ctccgatcgt tgtcagaagt aagttggccg cagtgttatc    3000
actcatggtt atggcagcac tgcataattc tcttactgtc atgccatccg taagatgctt    3060
ttctgtgact ggtgagtact caaccaagtc attctgagaa tagtgtatgc ggcgaccgag    3120
ttgctcttgc ccggcgtcaa tacgggataa taccgcgcca catagcagaa ctttaaaagt    3180
gctcatcatt ggaaaacgtt cttcggggcg aaaactctca aggatcttac cgctgttgag    3240
atccagttcg atgtaaccca ctcgtgcacc caactgatct tcagcatctt ttactttcac    3300
cagcgtttct gggtgagcaa aaacaggaag gcaaaatgcc gcaaaaaagg gaataagggc    3360
gacacggaaa tgttgaatac tcatactctt ccttttcaa tattattgaa gcatttatca    3420
gggttattgt ctcatgagcg gatacatatt tgaatgtatt tagaaaaata aacaaatagg    3480
ggttccgcgc acatttcccc gaaaagtgcc acctgacgtc taagaaacca ttattatcat    3540
gacattaacc tataaaaata ggcgtatcac gaggcccttt cgtctcgcgc gtttcggtga    3600
tgacggtgaa aacctctgac acatgcagct cccggagacg gtcacagctt gtctgtaagc    3660
ggatgccggg agcagacaag cccgtcaggg cgcgtcagcg ggtgttggcg ggtgtcgggg    3720
ctggcttaac tatgcggcat cagagcagat tgtactgaga gtgcaccata tgcggtgtga    3780
aataccgcac agatgcgtaa ggagaaaata ccgcatcagg cgccattcgc cattcaggct    3840
gcgcaactgt tgggaagggc gatcggtgcg ggcctcttcg ctattacgcc agctggcgaa    3900
agggggatgt gctgcaaggc gattaagttg ggtaacgcca gggttttccc agtcacgacg    3960
ttgtaaaacg acggccagtg aattcggcgc gccgagctcc tcgagcaaat ttacacattg    4020
ccactaaacg tctaaaccct tgtaatttgt ttttgtttta ctatgtgtgt tatgtatttg    4080
atttgcgata aatttttata tttggtacta aatttataac acctttatg ctaacgtttg    4140
ccaacactta gcaatttgca agttgattaa ttgattctaa attattttg tcttctaaat    4200
```

```
acatatacta atcaactgga aatgtaaata tttgctaata tttctactat aggagaatta      4260
aagtgagtga atatggtacc acaaggtttg gagatttaat tgttgcaatg ctgcatggat      4320
ggcatataca ccaaacattc aataattctt gaggataata atggtaccac acaagatttg      4380
aggtgcatga acgtcacgtg gacaaaaggt ttagtaattt ttcaagacaa caatgttacc      4440
acacacaagt tttgaggtgc atgcatggat gccctgtgga agtttaaaa atattttgga       4500 aatgatttgc atggaagcca tgtgtaaaac catgacatcc acttggagga tgcaataatg      4560
aagaaaacta caaatttaca tgcaactagt tatgcatgta gtctatataa tgaggatttt      4620
gcaatacttt cattcataca cactcactaa gttttacacg attataattt cttcatagcc      4680
agcccaccgc ggtgggcggc cgcctgcagt ctagaaggcc tcctgcttta atgagatatg      4740
cgagacgcct atgatcgcat gatatttgct ttcaattctg ttgtgcacgt tgtaaaaaac      4800
ctgagcatgt gtagctcaga tccttaccgc cggtttcggt tcattctaat gaatatatca      4860
cccgttacta tcgtatttt atgaataata ttctccgttc aatttactga ttgtccgtcg       4920
agcaaattta cacattgcca ctaaacgtct aaacccttgt aatttgtttt tgttttacta      4980
tgtgtgttat gtatttgatt tgcgataaat ttttatattt ggtactaaat ttataacacc      5040
ttttatgcta acgtttgcca acacttagca atttgcaagt tgattaattg attctaaatt      5100 attttgtct tctaaataca tatactaatc aactggaaat gtaaatattt gctaatattt       5160
ctactatagg agaattaaag tgagtgaata tggtaccaca aggtttggag atttaattgt      5220
tgcaatgctg catggatggc atatacacca aacattcaat aattcttgag gataataatg      5280
gtaccacaca agatttgagg tgcatgaacg tcacgtggac aaaaggttta gtaattttc       5340 aagacaacaa tgttaccaca cacaagtttt gaggtgcatg catggatgcc ctgtggaaag      5400
tttaaaaata                                                             5410
```

<210> SEQ ID NO 64
<211> LENGTH: 12093
<212> TYPE: DNA
<213> ORGANISM: artificial sequence
<220> FEATURE:
<223> OTHER INFORMATION: vector

<400> SEQUENCE: 64

```
gatctggcgc cggccagcga gacgagcaag attggccgcc gcccgaaacg atccgacagc        60
gcgcccagca caggtgcgca ggcaaattgc accaacgcat acagcgccag cagaatgcca       120
tagtgggcgg tgacgtcgtt cgagtgaacc agatcgcgca ggaggcccgg cagcaccggc       180
ataatcaggc cgatgccgac agcgtcgagc gcgacagtgc tcagaattac gatcaggggt       240
atgttgggtt tcacgtctgg cctccggacc agcctccgct ggtccgattg aacgcgcgga      300
ttctttatca ctgataagtt ggtggacata ttatgtttat cagtgataaa gtgtcaagca      360
tgacaaagtt gcagccgaat acagtgatcc gtgccgccct ggacctgttg aacgaggtcg      420
gcgtagacgg tctgacgaca cgcaaactgg cggaacggtt gggggttcag cagccggcgc      480
tttactggca cttcaggaac aagcgggcgc tgctcgacgc actggccgaa gccatgctgg      540
cggagaatca tacgcattcg gtgccgagag ccgacgacga ctggcgctca tttctgatcg      600
ggaatgcccg cagcttcagg caggcgctgc tcgcctaccg cgatgcgcgc gcatccatg       660 ccggcacgcg accgggcgca ccgcagatgg aaacggccga cgcgcagctt cgcttcctct      720
gcgaggcggg ttttcggcc ggggacgccg tcaatgcgct gatgacaatc agctacttca       780
ctgttggggc cgtgcttgag gagcaggccg gcgacagcga tgccggcgag cgcggcggca      840
```

-continued

```
ccgttgaaca ggctccgctc tcgccgctgt tgcgggccgc gatagacgcc ttcgacgaag      900
ccggtccgga cgcagcgttc gagcagggac tcgcggtgat tgtcgatgga ttggcgaaaa      960
ggaggctcgt tgtcaggaac gttgaaggac cgagaaaggg tgacgattga tcaggaccgc     1020
tgccggagcg caacccactc actacagcag agccatgtag acaacatccc ctcccccttt     1080
ccaccgcgtc agacgcccgt agcagcccgc tacgggcttt ttcatgccct gccctagcgt     1140
ccaagcctca cggccgcgct cggcctctct ggcggccttc tggcgctctt ccgcttcctc     1200
gctcactgac tcgctgcgct cggtcgttcg gctgcggcga gcggtatcag ctcactcaaa     1260
ggcggtaata cggttatcca cagaatcagg ggataacgca ggaaagaaca tgtgagcaaa     1320
aggccagcaa aaggccagga accgtaaaaa ggccgcgttg ctggcgtttt tccataggct     1380
ccgcccccct gacgagcatc acaaaaatcg acgctcaagt cagaggtggc gaaacccgac     1440
aggactataa agataccagg cgtttccccc tggaagctcc ctcgtgcgct ctcctgttcc     1500
gaccctgccg cttaccggat acctgtccgc ctttctccct tcgggaagcg tggcgctttt     1560
ccgctgcata cccctgcttc ggggtcatta tagcgatttt ttcggtatat ccatcctttt     1620
tcgcacgata tacaggattt tgccaagggg ttcgtgtaga cttccttggt gtatccaac      1680
ggcgtcagcc gggcaggata ggtgaagtag gcccacccgc gagcgggtgt tccttcttca     1740
ctgtccctta ttcgcacctg gcggtgctca acgggaatcc tgctctgcga ggctggccgg     1800
ctaccgccgg cgtaacagat gagggcaagc ggatggctga tgaaaccaag ccaaccagga     1860
agggcagccc acctatcaag gtgtactgcc ttccagacga acgaagagcg attgaggaaa     1920
aggcggcggc ggccggcatg agcctgtcgg cctacctgct ggcgtcggc cagggctaca      1980
aaatcacggg cgtcgtggac tatgagcacg tccgcgagct ggcccgcatc aatggcgacc     2040
tgggccgcct gggcggcctg ctgaaactct ggctcaccga cgacccgcgc acggcgcggt     2100
tcggtgatgc cacgatcctc gccctgctgg cgaagatcga agagaagcag gacgagcttg     2160
gcaaggtcat gatgggcgtg gtccgcccga gggcagagcc atgactttt tagccgctaa      2220
aacgccgggg ggtgcgcgt gattgccaag cacgtcccca tgcgctccat caagaagagc      2280
gacttcgcgg agctggtgaa gtacatcacc gacgagcaag gcaagaccga gcgcctttgc     2340
gacgctcacc gggctggttg ccctcgccgc tgggctggcg gccgtctatg gccctgcaaa     2400
cgcgccagaa acgccgtcga agccgtgtgc gagacaccgc ggccgccggc gttgtggata     2460
cctcgcggaa aacttggccc tcactgacag atgaggggcg gacgttgaca cttgaggggc     2520
cgactcaccc ggcgcggcgt tgacagatga ggggcaggct cgatttcggc cggcgacgtg     2580
gagctggcca gcctcgcaaa tcggcgaaaa cgcctgattt tacgcgagtt tcccacagat     2640
gatgtggaca agcctgggga taagtgccct gcggtattga cacttgaggg gcgcgactac     2700
tgacagatga ggggcgcgat ccttgacact tgaggggcag agtgctgaca gatgaggggc     2760
gcacctattg acatttgagg ggctgtccac aggcagaaaa tccagcattt gcaagggttt     2820
ccgcccgttt ttcggccacc gctaacctgt cttttaacct gctttttaaac caatatttat     2880
aaaccttgtt tttaaccagg gctgcgccct gtgcgcgtga ccgcgcacgc cgaaggggg      2940
tgcccccct tctcgaaccc tcccggcccg ctaacgcggg cctcccatcc ccccagggc       3000
tgcgcccctc ggccgcgaac ggcctcaccc caaaaatggc agcgctggca gtccttgcca     3060
ttgccgggat cggggcagta acggatgggc gatcagccc gagcgcgacg cccggaagca      3120
ttgacgtgcc gcaggtgctg gcatcgacat tcagcgacca ggtgccgggc agtgagggcg     3180
```

```
gcggcctggg tggcggcctg cccttcactt cggccgtcgg ggcattcacg gacttcatgg    3240
cggggccggc aattttttacc ttgggcattc ttggcatagt ggtcgcgggt gccgtgctcg    3300
tgttcggggg tgcgataaac ccagcgaacc atttgaggtg ataggtaaga ttataccgag    3360
gtatgaaaac gagaattgga cctttacaga attactctat gaagcgccat atttaaaaag    3420
ctaccaagac gaagaggatg aagaggatga ggaggcagat tgccttgaat atattgacaa    3480
tactgataag ataatatatc ttttatatag aagatatcgc cgtatgtaag gatttcaggg    3540
ggcaaggcat aggcagcgcg cttatcaata tatctataga atgggcaaag cataaaaact    3600
tgcatggact aatgcttgaa acccaggaca ataaccttat agcttgtaaa ttctatcata    3660
attgggtaat gactccaact tattgatagt gttttatgtt cagataatgc ccgatgactt    3720
tgtcatgcag ctccaccgat tttgagaacg acagcgactt ccgtcccagc cgtgccaggt    3780
gctgcctcag attcaggtta tgccgctcaa ttcgctgcgt atatcgcttg ctgattacgt    3840
gcagctttcc cttcaggcgg gattcataca gcggccagcc atccgtcatc catatccacca   3900 cgtcaaaggg tgacagcagg ctcataagac gccccagcgt cgccatagtg cgttcaccga    3960
atacgtgcgc aacaaccgtc ttccggagac tgtcatacgc gtaaaacagc cagcgctggc    4020
gcgatttagc cccgacatag ccccactgtt cgtccatttc cgcgcagacg atgacgtcac    4080
tgcccggctg tatgcgcgag gttaccgact gcggcctgag ttttttaagt gacgtaaaat    4140
cgtgttgagg ccaacgccca taatgcgggc tgttgcccgg catccaacgc cattcatggc    4200
catatcaatg attttctggt gcgtaccggg ttgagaagcg gtgtaagtga actgcagttg    4260
ccatgtttta cggcagtgag agcagagata gcgctgatgt ccggcggtgc ttttgccgtt    4320
acgcaccacc ccgtcagtag ctgaacagga gggacagctg atagacacag aagccactgg    4380
agcacctcaa aaacaccatc atacactaaa tcagtaagtt ggcagcatca cccataattg    4440
tggtttcaaa atcggctccg tcgatactat gttatacgcc aactttgaaa caactttga    4500 aaaagctgtt ttctggtatt taaggttttta gaatgcaagg aacagtgaat tggagttcgt    4560
cttgttataa ttagcttctt ggggtatctt taaatactgt agaaaagagg aaggaaataa    4620
taaatggcta aaatgagaat atcaccggaa ttgaaaaaac tgatcgaaaa ataccgctgc    4680
gtaaaagata cggaaggaat gtctcctgct aaggtatata agctggtggg agaaaatgaa    4740
aacctatatt taaaaatgac ggacagccgg tataagggga ccacctatga tgtggaacgg    4800
gaaaaggaca tgatgctatg gctggaagga agctgcctg ttccaaaggt cctgcacttt    4860
gaacggcatg atggctggag caatctgctc atgagtgagg ccgatggcgt cctttgctcg    4920
gaagagtatg aagatgaaca aagccctgaa aagattatcg agctgtatgc ggagtgcatc    4980
aggctctttc actccatcga catatcggat tgtccctata cgaatagctt agacagccgc    5040
ttagccgaat tggattactt actgaataac gatctggccg atgtggattg cgaaaactgg    5100
gaagaagaca ctccatttaa agatccgcgc gagctgtatg atttttttaaa gacggaaaag    5160 cccgaagagg aacttgtctt ttcccacggc gacctgggag acagcaacat ctttgtgaaa    5220
gatggcaaag taagtggctt tattgatctt gggagaagcg gcagggcgga caagtggtat    5280
gacattgcct tctgcgtccg gtcgatcagg gaggatatcg ggaagaaca gtatgtcgag    5340 ctatttttttg acttactggg gatcaagcct gattgggaga aaataaaata ttatatttta    5400
ctggatgaat tgtttttagta cctagatgtg gcgcaacgat gccggcgaca agcaggagcg    5460
caccgacttc ttccgcatca agtgttttgg ctctcaggcc gaggcccacg gcaagtattt    5520
gggcaagggg tcgctggtat tcgtgcaggg caagattcgg aataccaagt acgagaagga    5580
```

```
cggccagacg gtctacggga ccgacttcat tgccgataag gtggattatc tggacaccaa    5640
ggcaccaggc gggtcaaatc aggaataagg gcacattgcc ccggcgtgag tcgggcaat     5700 cccgcaagga gggtgaatga atcggacgtt tgaccgaaag gcatacaggc aagaactgat    5760
cgacgcgggg ttttccgccg aggatgccga aaccatcgca agccgcaccg tcatgcgtgc    5820
gccccgcgaa accttccagt ccgtcggctc gatggtccag caagctacgg ccaagatcga    5880
gcgcgacagc gtgcaactgg ctcccctgc cctgcccgcg ccatcggccg ccgtggagcg     5940
ttcgcgtcgt ctcgaacagg aggcggcagg tttggcgaag tcgatgacca tcgacacgcg    6000
aggaactatg acgaccaaga agcgaaaaac cgccggcgag gacctggcaa aacaggtcag    6060
cgaggccaag caggccgcgt tgctgaaaca cacgaagcag cagatcaagg aaatgcagct    6120
ttccttgttc gatattgcgc cgtggccgga cacgatgcga gcgatgccaa acgacacggc    6180
ccgctctgcc ctgttcacca cgcgcaacaa gaaaatcccg cgcgaggcgc tgcaaaacaa    6240
ggtcattttc cacgtcaaca aggacgtgaa gatcacctac accggcgtcg agctgcgggc    6300
cgacgatgac gaactggtgt ggcagcaggt gttggagtac gcgaagcgca cccctatcgg    6360
cgagccgatc accttcacgt tctacgagct ttgccaggac ctgggctggt cgatcaatgg    6420
ccggtattac acgaaggccg aggaatgcct gtcgcgccta caggcgacgg cgatgggctt    6480
cacgtccgac cgcgttgggc acctggaatc ggtgtcgctg ctgcaccgct tccgcgtcct    6540
ggaccgtggc aagaaaaacgt cccgttgcca ggtcctgatc gacgaggaaa tcgtcgtgct    6600
gtttgctggc gaccactaca cgaaattcat atgggagaag taccgcaagc tgtcgccgac    6660
ggcccgacgg atgttcgact atttcagctc gcaccggag ccgtacccgc tcaagctgga     6720
aaccttccgc ctcatgtgcg gatcggattc cacccgcgtg aagaagtggc gcgagcaggt    6780
cggcgaagcc tgcgaagagt tgcgaggcag cggcctggtg aacacgcct gggtcaatga     6840 tgacctggtg cattgcaaac gctagggcct tgtgggtca gttccggctg ggggttcagc     6900
agccagcgct ttactggcat ttcaggaaca agcgggcact gctcgacgca cttgcttcgc    6960
tcagtatcgc tcgggacgca cggcgcgctc tacgaactgc cgataaacag aggattaaaa    7020
ttgacaattg tgattaaggc tcagattcga cggcttggag cggccgacgt gcaggatttc    7080
cgcgagatcc gattgtcggc cctgaagaaa gctccagaga tgttcgggtc cgtttacgag    7140
cacgaggaga aaaagcccat ggaggcgttc gctgaacggt tgcgagatgc cgtggcattc    7200
ggcgcctaca tcgacggcga gatcattggg ctgtcggtct tcaaacagga ggacggcccc    7260
aaggacgctc acaaggcgca tctgtccggc gttttcgtgg agcccgaaca gcgaggccga    7320
ggggtcgccg gtatgctgct gcgggcgttg ccggcgggtt tattgctcgt gatgatcgtc    7380
cgacagattc caacgggaat ctggtggatg cgcatcttca tcctcggcgc acttaatatt    7440
tcgctattct ggagcttgtt gtttatttcg gtctaccgcc tgccgggcgg ggtcgcggcg    7500
acggtaggcg ctgtgcagcc gctgatggtc gtgttcatct ctgccgctct gctaggtagc    7560
ccgatacgat tgatggcggt cctgggggct atttgcggaa ctgcgggcgt ggcgctgttg    7620
gtgttgacac caaacgcagc gctagatcct gtcggcgtcg cagcggggcct ggcggggggcg   7680 gtttccatgg cgttcggaac cgtgctgacc cgcaagtggc aacctcccgt gcctctgctc    7740 accttaccg cctggcaact ggcggccgga ggacttctgc tcgttccagt agctttagtg      7800
tttgatccgc caatcccgat gcctacagga accaatgttc tcggcctggc gtggctcggc    7860
ctgatcggag cgggtttaac ctacttcctt tggttccggg ggatctcgcg actcgaacct    7920
```

```
acagttgttt ccttactggg ctttctcagc cccagatctg gggtcgatca gccggggatg    7980
catcaggccg acagtcggaa cttcgggtcc ccgacctgta ccattcggtg agcaatggat    8040
aggggagttg atatcgtcaa cgttcacttc taaagaaata gcgccactca gcttcctcag    8100
cggctttatc cagcgatttc ctattatgtc ggcatagttc tcaagatcga cagcctgtca    8160
cggttaagcg agaaatgaat aagaaggctg ataattcgga tctctgcgag ggagatgata    8220
tttgatcaca ggcagcaacg ctctgtcatc gttacaatca acatgctacc ctccgcgaga    8280
tcatccgtgt ttcaaacccg gcagcttagt tgccgttctt ccgaatagca tcggtaacat    8340
gagcaaagtc tgccgcctta caacggctct cccgctgacg ccgtcccgga ctgatgggct    8400
gcctgtatcg agtggtgatt ttgtgccgag ctgccggtcg gggagctgtt ggctggctgg    8460
tggcaggata tattgtggtg taaacaaatt gacgcttaga caacttaata acacattgcg    8520
gacgtttta atgtactggg gtggtttttc ttttcaccag tgagacgggc aacagctgat    8580
tgcccttcac cgcctggccc tgagagagtt gcagcaagcg gtccacgctg gtttgcccca    8640
gcaggcgaaa atcctgtttg atggtggttc cgaaatcggc aaaatccctt ataaatcaaa    8700
agaatagccc gagatagggt tgagtgttgt tccagttggg aacaagagtc cactattaaa    8760
gaacgtggac tccaacgtca aagggcgaaa accgtctat cagggcgatg cccactacg    8820
tgaaccatca cccaaatcaa gttttttggg gtcgaggtgc cgtaaagcac taaatcggaa    8880
ccctaaaggg agccccgat ttagagcttg acggggaaag ccggcgaacg tggcgagaaa    8940
ggaagggaag aaagcgaaag gagcgggcgc cattcaggct gcgcaactgt tgggaagggc    9000
gatcggtgcg ggcctcttcg ctattacgcc agctggcgaa aggggatgt gctgcaaggc    9060
gattaagttg ggtaacgcca gggttttccc agtcacgacg ttgtaaaacg acggccagtg    9120
aattaattcc catcttgaaa gaaatatagt ttaaatattt attgataaaa taacaagtca    9180
ggtattatag tccaagcaaa aacataaatt tattgatgca agtttaaatt cagaaatatt    9240
tcaataactg attatatcag ctggtacatt gccgtagatg aaagactgag tgcgatatta    9300
tgtgtaatac ataaattgat gatatagcta gcttagctca tcgggggatc cgtcgaagct    9360
agcttgggtc ccgctcagaa gaactcgtca agaaggcgat agaaggcgat gcgctgcgaa    9420
tcgggagcgg cgataccgta aagcacgagg aagcggtcag cccattcgcc gccaagctct    9480
tcagcaatat cacgggtagc caacgctatg tcctgatagc ggtccgccac acccagccgg    9540
ccacagtcga tgaatccaga aaagcggcca ttttccacca tgatattcgg caagcaggca    9600
tcgccatggg tcacgacgag atcctcgccg tcggcatgc gcgccttgag cctggcgaac    9660
agttcggctg cgcgagccc ctgatgctct tcgtccagat catcctgatc gacaagaccg    9720
gcttccatcc gagtacgtgc tcgctcgatg cgatgtttcg cttggtggtc gaatgggcag    9780
gtagccggat caagcgtatg cagccgccgc attgcatcag ccatgatgga ctttctcg    9840
gcaggagcaa ggtgagatga caggagatcc tgccccggca cttcgcccaa tagcagccag    9900
tcccttcccg cttcagtgac aacgtcgagc acagctgcgc aaggaacgcc cgtcgtggcc    9960
agccacgata gccgcgctgc ctcgtcctgc agttcattca gggcaccgga caggtcggtc   10020
ttgacaaaaa gaaccgggcg cccctgcgct gacagccgga acacggcggc atcagagcag   10080
ccgattgtct gttgtgccca gtcatagccg aatagcctct ccacccaagc ggccggagaa   10140
cctgcgtgca atccatcttg ttcaatccaa gctcccatgg gccctcgact agagtcgaga   10200
tctggattga gagtgaatat gagactctaa ttggataccg aggggaattt atggaacgtc   10260
agtggagcat ttttgacaag aaatatttgc tagctgatag tgaccttagg cgactttga   10320
```

```
acgcgcaata atggtttctg acgtatgtgc ttagctcatt aaactccaga aacccgcggc    10380
tgagtggctc cttcaacgtt gcggttctgt cagttccaaa cgtaaaacgg cttgtcccgc    10440
gtcatcggcg ggggtcataa cgtgactccc ttaattctcc gctcatgatc ttgatcccct    10500
gcgccatcag atccttggcg gcaagaaagc catccagttt actttgcagg gcttcccaac    10560
cttaccagag ggcgcccag ctggcaattc cggttcgctt gctgtccata aaaccgccca    10620
gtctagctat cgccatgtaa gcccactgca agctacctgc tttctctttg cgcttgcgtt    10680
ttcccttgtc cagatagccc agtagctgac attcatccgg ggtcagcacc gtttctgcgg    10740
actggctttc tacgtgttcc gcttccttta gcagcccttg cgcctgagt gcttgcggca    10800 gcgtgaagct tgcatgcctg caggtcgacg gcgcgccgag ctcctcgagc aaatttacac    10860
attgccacta aacgtctaaa cccttgtaat ttgttttgt tttactatgt gtgttatgta    10920
tttgatttgc gataaatttt tatatttggt actaaattta taacaccttt tatgctaacg    10980
tttgccaaca cttagcaatt tgcaagttga ttaattgatt ctaaattatt tttgtcttct    11040
aaatacatat actaatcaac tggaaatgta aatatttgct aatatttcta ctataggaga    11100
attaaagtga gtgaatatgg taccacaagg tttggagatt taattgttgc aatgctgcat    11160
ggatggcata tacaccaaac attcaataat tcttgaggat aataatggta ccacacaaga    11220
tttgaggtgc atgaacgtca cgtggacaaa aggtttagta attttttcaag acaacaatgt    11280 taccacacac aagttttgag gtgcatgcat ggatgccctg tggaaagttt aaaaatattt    11340
tggaaatgat ttgcatggaa gccatgtgta aaaccatgac atccacttgg aggatgcaat    11400
aatgaagaaa actacaaatt tacatgcaac tagttatgca tgtagtctat ataatgagga    11460
ttttgcaata ctttcattca tacacactca ctaagtttta cacgattata atttcttcat    11520
agccagccca ccgcggtggg cggccgcctg cagtctagaa ggcctcctgc tttaatgaga    11580
tatgcgagac gcctatgatc gcatgatatt tgctttcaat tctgttgtgc acgttgtaaa    11640
aaacctgagc atgtgtagct cagatcctta ccgccggttt cggttcattc taatgaatat    11700
atcacccgtt actatcgtat ttttatgaat aatattctcc gttcaattta ctgattgtcc    11760
gtcgacgaat tcgagctcgg cgcgcctcta gaggatcgat gaattcagat cggctgagtg    11820
gctccttcaa cgttgcggtt ctgtcagttc caaacgtaaa acggcttgtc ccgcgtcatc    11880
ggcgggggtc ataacgtgac tcccttaatt ctccgctcat gatcagattg tcgtttcccg    11940
ccttcagttt aaactatcag tgtttgacag gatatattgg cgggtaaacc taagagaaaa    12000
gagcgtttat tagaataatc ggatatttaa aagggcgtga aaaggtttat ccttcgtcca    12060
tttgtatgtg catgccaacc acagggttcc cca                                 12093
```

<210> SEQ ID NO 65
<211> LENGTH: 12085
<212> TYPE: DNA
<213> ORGANISM: artificial sequence
<220> FEATURE:
<221> NAME/KEY: misc_feature
<223> OTHER INFORMATION: Plant expression vector with a
      promoter-terminator expression cassette

<400> SEQUENCE: 65

```
gatctggcgc cggccagcga gacgagcaag attggccgcc gcccgaaacg atccgacagc    60
gcgcccagca caggtgcgca ggcaaattgc accaacgcat acagcgccag cagaatgcca   120
tagtgggcgg tgacgtcgtt cgagtgaacc agatcgcgca ggaggcccgg cagcaccggc   180
```

```
ataatcaggc cgatgccgac agcgtcgagc gcgacagtgc tcagaattac gatcaggggt      240
atgttgggtt tcacgtctgg cctccggacc agcctccgct ggtccgattg aacgcgcgga      300
ttctttatca ctgataagtt ggtggacata ttatgtttat cagtgataaa gtgtcaagca      360
tgacaaagtt gcagccgaat acagtgatcc gtgccgccct ggacctgttg aacgaggtcg      420
gcgtagacgg tctgacgaca cgcaaactgg cggaacggtt gggggttcag cagccggcgc      480
tttactggca cttcaggaac aagcgggcgc tgctcgacgc actggccgaa gccatgctgg      540
cggagaatca tacgcattcg gtgccgagag ccgacgacga ctggcgctca tttctgatcg      600
ggaatgcccg cagcttcagg caggcgctgc tcgcctaccg cgatggcgcg cgcatccatg      660
ccggcacgcg accgggcgca ccgcagatgg aaacggccga cgcgcagctt cgcttcctct      720
gcgaggcggg ttttcggcc ggggacgccg tcaatgcgct gatgacaatc agctacttca      780
ctgttggggc cgtgcttgag gagcaggccg gcgacagcga tgccggcgag cgcggcggca      840
ccgttgaaca ggctccgctc tcgccgctgt tgcgggccgc gatagacgcc ttcgacgaag      900
ccggtccgga cgcagcgttc gagcagggac tcgcggtgat tgtcgatgga ttggcgaaaa      960
ggaggctcgt tgtcaggaac gttgaaggac cgagaaaggg tgacgattga tcaggaccgc     1020
tgccggagcg caacccactc actacagcag agccatgtag acaacatccc ctccccttt      1080 ccaccgcgtc agacgcccgt agcagcccgc tacgggcttt ttcatgccct gcctagcgt      1140 ccaagcctca cggccgcgct cggcctctct ggcggccttc tggcgctctt ccgcttcctc     1200
gctcactgac tcgctgcgct cggtcgttcg gctgcggcga gcggtatcag ctcactcaaa     1260
ggcggtaata cggttatcca cagaatcagg ggataacgca ggaaagaaca tgtgagcaaa     1320
aggccagcaa aaggccagga accgtaaaaa ggccgcgttg ctggcgtttt tccataggct     1380
ccgcccccct gacgagcatc acaaaaatcg acgctcaagt cagaggtggc gaaacccgac     1440
aggactataa agataccagg cgtttccccc tggaagctcc ctcgtgcgct ctcctgttcc     1500
gaccctgccg cttaccggat acctgtccgc ctttctccct tcgggaagcg tggcgctttt     1560
ccgctgcata accctgcttc ggggtcatta gcgattttt tcggtatat ccatccttt       1620 tcgcacgata tacaggattt tgccaaaggg ttcgtgtaga cttttcttgg tgtatccaac     1680
ggcgtcagcc gggcaggata ggtgaagtag gcccacccgc gagcgggtgt tccttcttca     1740
ctgtccctta ttcgcacctg gcggtgctca acgggaatcc tgctctgcga ggctggccgg     1800
ctaccgccgg cgtaacagat gagggcaagc ggatggctga tgaaaccaag ccaaccagga     1860
agggcagccc acctatcaag gtgtactgcc ttccagacga acgaagagcg attgaggaaa     1920
aggcggcggc ggccgcatg agcctgtcgg cctacctgct ggcgtcggc cagggctaca      1980 aaatcacggg cgtcgtggac tatgagcacg tccgcgagct ggcccgcatc aatggcgacc     2040
tgggccgcct gggcggcctg ctgaaactct ggctcaccga cgacccgcgc acggcgcggt     2100
tcggtgatgc cacgatcctc gccctgctgg cgaagatcga agagaagcag gacgagcttg     2160
gcaaggtcat gatgggcgtg gtccgcccga gggcagagcc atgacttttt tagccgctaa     2220
aacggccggg gggtgcgcgt gattgccaag cacgtcccca tgcgctccat caagaagagc     2280
gacttcgcgg agctggtgaa gtacatcacc gacgagcaag gcaagaccga gcgcctttgc     2340
gacgctcacc gggctggttg ccctcgccgc tgggctggcg gccgtctatg gcctgcaaa      2400 cgcgccagaa acgccgtcga agccgtgtgc gagacaccgc ggccgccggc gttgtggata     2460
cctcgcggaa aacttggccc tcactgacag atgaggggcg gacgttgaca cttgagggcg     2520
cgactcaccc ggcgcggcgt tgacagatga ggggcaggct cgatttcggc cggcgacgtg     2580
```

```
gagctggcca gcctcgcaaa tcggcgaaaa cgcctgattt tacgcgagtt tcccacagat    2640
gatgtggaca agcctgggga taagtgccct gcggtattga cacttgaggg gcgcgactac    2700
tgacagatga ggggcgcgat ccttgacact tgaggggcag agtgctgaca gatgaggggc    2760
gcacctattg acatttgagg ggctgtccac aggcagaaaa tccagcattt gcaagggttt    2820
ccgcccgttt ttcggccacc gctaacctgt cttttaacct gcttttaaac caatatttat    2880
aaaccttgtt tttaaccagg gctgcgccct gtgcgcgtga ccgcgcacgc cgaaggggg    2940 tgccccccct tctcgaaccc tcccggcccg ctaacgcggg cctcccatcc ccccagggc    3000 tgcgcccctc ggccgcgaac ggcctcaccc caaaaatggc agcgctggca gtccttgcca    3060
ttgccgggat cggggcagta acgggatggg cgatcagccc gagcgcgacg cccggaagca    3120
ttgacgtgcc gcaggtgctg gcatcgacat tcagcgacca ggtgccgggc agtgagggcg    3180
gcggcctggg tggcggcctg cccttcactt cggccgtcgg ggcattcacg gacttcatgg    3240
cggggccggc aattttacc ttgggcattc ttggcatagt ggtcgcgggt gccgtgctcg    3300
tgttcggggg tgcgataaac ccagcgaacc atttgaggtg ataggtaaga ttataccgag    3360
gtatgaaaac gagaattgga cctttacaga attactctat gaagcgccat atttaaaaag    3420
ctaccaagac gaagaggatg aagaggatga ggaggcagat tgccttgaat atattgacaa    3480
tactgataag ataatatatc ttttatatag aagatatcgc cgtatgtaag gatttcaggg    3540
ggcaaggcat aggcagcgcg cttatcaata tatctataga atgggcaaag cataaaaact    3600
tgcatggact aatgcttgaa acccaggaca ataaccttat agcttgtaaa ttctatcata    3660
attgggtaat gactccaact tattgatagt gttttatgtt cagataatgc ccgatgactt    3720
tgtcatgcag ctccaccgat tttgagaacg acagcgactt ccgtcccagc cgtgccaggt    3780
gctgcctcag attcaggtta tgccgctcaa ttcgctgcgt atatcgcttg ctgattacgt    3840 gcagcttttcc cttcaggcgg gattcataca gcggccagcc atccgtcatc catatccacca    3900 cgtcaaaggg tgacagcagg ctcataagac gccccagcgt cgccatagtg cgttcaccga    3960
atacgtgcgc aacaaccgtc ttccggagac tgtcatacgc gtaaaacagc cagcgctggc    4020
gcgatttagc cccgacatag ccccactgtt cgtccatttc cgcgcagacg atgacgtcac    4080
tgcccggctg tatgcgcgag gttaccgact gcggcctgag ttttttaagt gacgtaaaat    4140
cgtgttgagg ccaacgccca taatgcgggc tgttgcccgg catccaacgc cattcatggc    4200
catatcaatg atttttctggt gcgtaccggg ttgagaagcg gtgtaagtga actgcagttg    4260
ccatgtttta cggcagtgag agcagagata gcgctgatgt ccggcggtgc ttttgccgtt    4320
acgcaccacc ccgtcagtag ctgaacagga gggacagctg atagacacag aagccactgg    4380
agcacctcaa aaacaccatc atacactaaa tcagtaagtt ggcagcatca cccataattg    4440
tggtttcaaa atcggctccg tcgatactat gttatacgcc aactttgaaa caactttga    4500 aaaagctgtt ttctggtatt taaggttta gaatgcaagg aacagtgaat ggagttcgt    4560 cttgttataa ttagcttctt ggggtatctt taaatactgt agaaaagagg aaggaaataa    4620
taaatggcta aaatgagaat atcaccggaa ttgaaaaaac tgatcgaaaa ataccgctgc    4680
gtaaaagata cggaaggaat gtctcctgct aaggtatata agctggtggg agaaaatgaa    4740
aacctatatt taaaaatgac ggacagccgg tataaaggga ccacctatga tgtggaacgg    4800
gaaaaggaca tgatgctatg gctggaagga agctgcctg ttccaaaggt cctgcacttt    4860
gaacggcatg atggctggag caatctgctc atgagtgagg ccgatggcgt cctttgctcg    4920
```

```
gaagagtatg aagatgaaca aagccctgaa aagattatcg agctgtatgc ggagtgcatc    4980
aggctctttc actccatcga catatcggat tgtccctata cgaatagctt agacagccgc    5040
ttagccgaat tggattactt actgaataac gatctggccg atgtggattg cgaaaactgg    5100
gaagaagaca ctccatttaa agatccgcgc gagctgtatg attttttaaa gacggaaaag    5160
cccgaagagg aacttgtctt ttcccacggc gacctgggag acagcaacat ctttgtgaaa    5220
gatggcaaag taagtggctt tattgatctt gggagaagcg gcagggcgga caagtggtat    5280
gacattgcct tctgcgtccg gtcgatcagg gaggatatcg gggaagaaca gtatgtcgag    5340
ctattttttg acttactggg gatcaagcct gattgggaga aaataaaata ttatatttta    5400
ctggatgaat tgttttagta cctagatgtg gcgcaacgat gccggcgaca agcaggagcg    5460
caccgacttc ttccgcatca agtgttttgg ctctcaggcc gaggcccacg gcaagtattt    5520
gggcaagggg tcgctggtat tcgtgcaggg caagattcgg aataccaagt acgagaagga    5580
cggccagacg gtctacggga ccgacttcat tgccgataag gtggattatc tggacaccaa    5640
ggcaccaggc gggtcaaatc aggaataagg gcacattgcc ccggcgtgag tcgggcaat     5700 cccgcaagga gggtgaatga atcggacgtt tgaccgaaag gcatacaggc aagaactgat    5760
cgacgcgggg ttttccgccg aggatgccga aaccatcgca agccgcaccg tcatgcgtgc    5820
gccccgcgaa accttccagt ccgtcggctc gatggtccag caagctacgg ccaagatcga    5880
gcgcgacagc gtgcaactgg ctcccccctgc cctgcccgcg ccatcggccg ccgtggagcg    5940
ttcgcgtcgt ctcgaacagg aggcggcagg tttggcgaag tcgatgacca tcgacacgcg    6000
aggaactatg acgaccaaga agcgaaaaac cgccggcgag gacctggcaa aacaggtcag    6060
cgaggccaag caggccgcgt tgctgaaaca cacgaagcag cagatcaagg aaatgcagct    6120
ttccttgttc gatattgcgc cgtggccgga cacgatgcga gcgatgccaa acgacacggc    6180
ccgctctgcc ctgttcacca cgcgcaacaa gaaaatcccg cgcgaggcgc tgcaaaacaa    6240
ggtcattttc cacgtcaaca aggacgtgaa gatcacctac accggcgtcg agctgcgggc    6300
cgacgatgac gaactggtgt ggcagcaggt gttggagtac gcgaagcgca ccctatcgg    6360 cgagccgatc accttcacgt tctacgagct ttgccaggac ctgggctggt cgatcaatgg    6420
ccggtattac acgaaggccg aggaatgcct gtcgcgccta caggcgacgg cgatgggctt    6480
cacgtccgac cgcgttgggc acctggaatc ggtgtcgctg ctgcaccgct tccgcgtcct    6540
ggaccgtggc aagaaaacgt cccgttgcca ggtcctgatc gacgaggaaa tcgtcgtgct    6600
gtttgctggc gaccactaca cgaaattcat atgggagaag taccgcaagc tgtcgccgac    6660
ggcccgacgg atgttcgact atttcagctc gcaccgggag ccgtacccgc tcaagctgga    6720
aaccttccgc ctcatgtgcg gatcggattc caccgcgtg aagaagtggc gcgagcaggt    6780
cggcgaagcc tgcgaagagt tgcgaggcag cggcctggtg aacacgcct gggtcaatga    6840 tgacctggtg cattgcaaac gctagggcct tgtgggtca gttccggctg ggggttcagc    6900
agccagcgct ttactggcat ttcaggaaca agcgggcact gctcgacgca cttgcttcgc    6960
tcagtatcgc tcgggacgca cggcgcgctc tacgaactgc cgataaacag aggattaaaa    7020
ttgacaattg tgattaaggc tcagattcga cggcttggag cggccgacgt gcaggatttc    7080
cgcgagatcc gattgtcggc cctgaagaaa gctccagaga tgttcgggtc cgtttacgag    7140
cacgaggaga aaaagcccat ggaggcgttc gctgaacggt tgcgagatgc cgtggcattc    7200
ggcgcctaca tcgacggcga gatcattggg ctgtcggtct tcaaacagga ggacggcccc    7260
aaggacgctc acaaggcgca tctgtccggc gttttcgtgg agcccgaaca gcgaggccga    7320
```

-continued

```
ggggtcgccg gtatgctgct gcgggcgttg ccggcgggtt tattgctcgt gatgatcgtc    7380
cgacagattc caacgggaat ctggtggatg cgcatcttca tcctcggcgc acttaatatt    7440
tcgctattct ggagcttgtt gtttatttcg gtctaccgcc tgccgggcgg ggtcgcggcg    7500
acggtaggcg ctgtgcagcc gctgatggtc gtgttcatct ctgccgctct gctaggtagc    7560
ccgatacgat tgatggcggt cctggggggct atttgcggaa ctgcgggcgt ggcgctgttg    7620
gtgttgacac caaacgcagc gctagatcct gtcggcgtcg cagcgggcct ggcggggggcg    7680 gtttccatgg cgttcggaac cgtgctgacc cgcaagtggc aacctcccgt gcctctgctc    7740
acctttaccg cctggcaact ggcggccgga ggacttctgc tcgttccagt agctttagtg    7800
tttgatccgc caatcccgat gcctacagga accaatgttc tcggcctggc gtggctcggc    7860
ctgatcggag cgggtttaac ctacttcctt tggttccggg ggatctcgcg actcgaacct    7920
acagttgttt ccttactggg ctttctcagc cccagatctg gggtcgatca gccggggatg    7980
catcaggccg acagtcggaa cttcgggtcc ccgacctgta ccattcggtg agcaatggat    8040
aggggagttg atatcgtcaa cgttcacttc taaagaaata cgccactca gcttcctcag     8100 cggctttatc cagcgatttc ctattatgtc ggcatagttc tcaagatcga cagcctgtca    8160
cggttaagcg agaaatgaat aagaaggctg ataattcgga tctctgcgag ggagatgata    8220
tttgatcaca ggcagcaacg ctctgtcatc gttacaatca acatgctacc ctccgcgaga    8280
tcatccgtgt ttcaaacccg gcagcttagt tgccgttctt ccgaatagca tcggtaacat    8340
gagcaaagtc tgccgcctta caacggctct cccgctgacg ccgtcccgga ctgatgggct    8400
gcctgtatcg agtggtgatt ttgtgccgag ctgccggtcg gggagctgtt ggctggctgg    8460
tggcaggata tattgtggtg taaacaaatt gacgcttaga caacttaata acacattgcg    8520 gacgtttta atgtactggg gtggttttc ttttcaccag tgagacgggc aacagctgat      8580
tgcccttcac cgcctggccc tgagagagtt gcagcaagcg gtccacgctg gtttgcccca    8640
gcaggcgaaa atcctgtttg atggtggttc cgaaatcggc aaaatcccct ataaatcaaa    8700
agaatagccc gagatagggt tgagtgttgt tccagtttgg aacaagagtc cactattaaa    8760
gaacgtggac tccaacgtca aagggcgaaa aaccgtctat cagggcgatg cccactacg     8820 tgaaccatca cccaaatcaa gttttttggg gtcgaggtgc cgtaaagcac taatcggaa     8880 ccctaaaggg agccccccgat ttagagcttg acggggaaag ccggcgaacg tggcgagaaa   8940
ggaagggaag aaagcgaaag gagcgggcgc cattcaggct gcgcaactgt tgggaagggc    9000
gatcggtgcg ggcctcttcg ctattacgcc agctggcgaa aggggggatgt gctgcaaggc   9060 gattaagttg ggtaacgcca gggttttccc agtcacgacg ttgtaaaacg acggccagtg    9120
aattaattcc catcttgaaa gaaatatagt ttaaatattt attgataaaa taacaagtca    9180
ggtattatag tccaagcaaa aacataaatt tattgatgca agtttaaatt cagaaatatt    9240
tcaataactg attatatcag ctggtacatt gccgtagatg aaagactgag tgcgatatta    9300
tgtgtaatac ataaattgat gatatagcta gcttagctca tcgggggatc cgtcgaagct    9360
agcttgggtc ccgctcagaa gaactcgtca agaaggcgat agaaggcgat gcgctgcgaa    9420
tcgggagcgg cgataccgta aagcacgagg aagcggtcag cccattcgcc gccaagctct    9480
tcagcaatat cacgggtagc caacgctatg tcctgatagc ggtccgccac acccagccgg    9540
ccacagtcga tgaatccaga aaagcggcca ttttccacca tgatattcgg caagcaggca    9600
tcgccatggg tcacgacgag atcctcgccg tcgggcatgc gcgccttgag cctggcgaac    9660
```

```
agttcggctg gcgcgagccc ctgatgctct tcgtccagat catcctgatc gacaagaccg    9720
gcttccatcc gagtacgtgc tcgctcgatg cgatgtttcg cttggtggtc gaatgggcag    9780
gtagccggat caagcgtatg cagccgccgc attgcatcag ccatgatgga tactttctcg    9840
gcaggagcaa ggtgagatga caggagatcc tgccccggca cttcgcccaa tagcagccag    9900
tcccttcccg cttcagtgac aacgtcgagc acagctgcgc aaggaacgcc cgtcgtggcc    9960
agccacgata gccgcgctgc ctcgtcctgc agttcattca gggcaccgga caggtcggtc   10020
ttgacaaaaa gaaccgggcg cccctgcgct gacagccgga acacggcggc atcagagcag   10080
ccgattgtct gttgtgccca gtcatagccg aatagcctct ccacccaagc ggccggagaa   10140
cctgcgtgca atccatcttg ttcaatccaa gctcccatgg gccctcgact agagtcgaga   10200
tctggattga gagtgaatat gagactctaa ttggataccg aggggaattt atggaacgtc   10260
agtggagcat ttttgacaag aaatatttgc tagctgatag tgaccttagg cgacttttga   10320
acgcgcaata atggtttctg acgtatgtgc ttagctcatt aaactccaga aacccgcggc   10380
tgagtggctc cttcaacgtt gcggttctgt cagttccaaa cgtaaaacgg cttgtcccgc   10440
gtcatcggcg ggggtcataa cgtgactccc ttaattctcc gctcatgatc ttgatcccct   10500
gcgccatcag atccttggcg gcaagaaagc catccagttt actttgcagg gcttcccaac   10560
cttaccagag ggcgcccag ctggcaattc cggttcgctt gctgtccata aaaccgccca   10620
gtctagctat cgccatgtaa gcccactgca agctacctgc tttctctttg cgcttgcgtt   10680
ttcccttgtc cagatagccc agtagctgac attcatccgg ggtcagcacc gtttctgcgg   10740
actggctttc tacgtgttcc gcttcctta gcagcccttg cgccctgagt gcttgcggca   10800
gcgtgaagct tgcatgcctg caggtcgacg gcgcgccgag ctcctcgagc aaatttacac   10860
attgccacta acgtctaaa cccttgtaat ttgttttgt tttactatgt gtgttatgta   10920
tttgatttgc gataaatttt tatatttggt actaaattta taacacctttt tatgctaacg   10980
tttgccaaca cttagcaatt tgcaagttga ttaattgatt ctaaattatt tttgtcttct   11040
aaatacatat actaatcaac tggaaatgta aatatttgct aatatttcta ctataggaga   11100
attaaagtga gtgaatatgg taccacaagg tttggagatt taattgttgc aatgctgcat   11160
ggatggcata tacaccaaac attcaataat tcttgaggat aataatggta ccacacaaga   11220
tttgaggtgc atgaacgtca cgtggacaaa aggtttagta attttttcaag acaacaatgt   11280
taccacacac aagttttgag gtgcatgcat ggatgccctg tggaaagttt aaaaatattt   11340
tggaaatgat ttgcatggaa gccatgtgta aaaccatgac atccacttgg aggatgcaat   11400
aatgaagaaa actacaaatt tacatgcaac tagttatgca tgtagtctat ataatgagga   11460
ttttgcaata ctttcattca tacacactca ctaagtttta cacgattata atttcttcat   11520
agccagcgga tccgatatcg ggcccgctag cgttaaccct gctttaatga gatatgcgag   11580
acgcctatga tcgcatgata tttgctttca attctgttgt gcacgttgta aaaacctga   11640
gcatgtgtag ctcagatcct taccgccggt ttcggttcat tctaatgaat atatcacccg   11700
ttactatcgt atttttatga ataatattct ccgttcaatt tactgattgt ccgtcgacga   11760
attcgagctc ggcgcgcctc tagaggatcg atgaattcag atcggctgag tggctccttc   11820
aacgttgcgg ttctgtcagt tccaaacgta aacggcttg tcccgcgtca tcggcggggg   11880
tcataacgtg actcccttaa ttctccgctc atgatcagat tgtcgtttcc cgccttcagt   11940
ttaaactatc agtgtttgac aggatatatt ggcgggtaaa cctaagagaa aagagcgttt   12000
attagaataa tcggatattt aaaagggcgt gaaaaggttt atccttcgtc catttgtatg   12060
```

<210> SEQ ID NO 66
<211> LENGTH: 12079
<212> TYPE: DNA
<213> ORGANISM: artificial sequence
<220> FEATURE:
<223> OTHER INFORMATION: vector

<400> SEQUENCE: 66

```
gatctggcgc cggccagcga gacgagcaag attggccgcc gcccgaaacg atccgacagc      60
gcgcccagca caggtgcgca ggcaaattgc accaacgcat acagcgccag cagaatgcca     120
tagtgggcgg tgacgtcgtt cgagtgaacc agatcgcgca ggaggcccgg cagcaccggc     180
ataatcaggc cgatgccgac agcgtcgagc gcgacagtgc tcagaattac gatcaggggt     240
atgttgggtt tcacgtctgg cctccggacc agcctccgct ggtccgattg aacgcgcgga     300
ttctttatca ctgataagtt ggtggacata ttatgtttat cagtgataaa gtgtcaagca     360
tgacaaagtt gcagccgaat acagtgatcc gtgccgccct ggacctgttg aacgaggtcg     420
gcgtagacgg tctgacgaca cgcaaactgg cggaacggtt gggggttcag cagccggcgc     480
tttactggca cttcaggaac aagcgggcgc tgctcgacgc actggccgaa gccatgctgg     540
cggagaatca tacgcattcg gtgccgagag ccgacgacga ctggcgctca tttctgatcg     600
ggaatgcccg cagcttcagg caggcgctgc tcgcctaccg cgatggcgcg cgcatccatg     660
ccggcacgcg accgggcgca ccgcagatgg aaacggccga cgcgcagctt cgcttcctct     720
gcgaggcggg ttttcggcc ggggacgccg tcaatgcgct gatgacaatc agctacttca     780
ctgttggggc cgtgcttgag gagcaggccg gcgacagcga tgccggcgag gcggcggca     840
ccgttgaaca ggctccgctc tcgccgctgt tgcgggccgc gatagacgcc ttcgacgaag     900
ccggtccgga cgcagcgttc gagcaggac tcgcggtgat tgtcgatgga ttggcgaaaa     960
ggaggctcgt tgtcaggaac gttgaaggac cgagaaaggg tgacgattga tcaggaccgc    1020
tgccggagcg caacccactc actacagcag agccatgtag acaacatccc ctccccttt    1080
ccaccgcgtc agacgcccgt agcagcccgc tacgggcttt ttcatgccct gccctagcgt    1140
ccaagcctca cggccgcgct cggcctctct ggcggccttc tggcgctctt ccgcttcctc    1200
gctcactgac tcgctgcgct cggtcgttcg gctgcggcga gcggtatcag ctcactcaaa    1260
ggcggtaata cggttatcca cagaatcagg ggataacgca ggaaagaaca tgtgagcaaa    1320
aggccagcaa aaggccagga accgtaaaaa ggccgcgttg ctggcgtttt tccataggct    1380
ccgccccct gacgagcatc acaaaaatcg acgctcaagt cagaggtggc gaaacccgac    1440
aggactataa agataccagg cgtttccccc tggaagctcc ctcgtgcgct ctcctgttcc    1500
gaccctgccg cttaccggat acctgtccgc ctttctccct tcgggaagcg tggcgctttt    1560
ccgctgcata accctgcttc ggggtcatta tagcgatttt ttcggtatat ccatcctttt    1620
tcgcacgata tacaggattt tgccaaaggg ttcgtgtaga cttttccttgg tgtatccaac    1680
ggcgtcagcc gggcaggata ggtgaagtag gcccaccccgc gagcgggtgt tccttcttca    1740
ctgtcccttta ttcgcacctg gcggtgctca acgggaatcc tgctctgcga ggctggccgg    1800
ctaccgccgg cgtaacagat gagggcaagc ggatggctga tgaaaccaag ccaaccagga    1860
agggcagccc acctatcaag gtgtactgcc ttccagacga acgaagagcg attgaggaaa    1920
aggcggcggc ggccggcatg agcctgtcgg cctacctgct ggccgtcggc cagggctaca    1980
```

-continued

```
aaatcacggg cgtcgtggac tatgagcacg tccgcgagct ggcccgcatc aatggcgacc    2040
tgggccgcct gggcggcctg ctgaaactct ggctcaccga cgaccgcgc acggcgcggt     2100 tcggtgatgc cacgatcctc gccctgctgg cgaagatcga agagaagcag gacgagcttg    2160
gcaaggtcat gatgggcgtg gtccgcccga gggcagagcc atgacttttt tagccgctaa   2220
aacggccggg gggtgcgcgt gattgccaag cacgtcccca tgcgctccat caagaagagc    2280
gacttcgcgg agctggtgaa gtacatcacc gacgagcaag gcaagaccga gcgcctttgc    2340
gacgctcacc gggctggttg ccctcgccgc tgggctggcg gccgtctatg gccctgcaaa    2400
cgcgccagaa acgccgtcga agccgtgtgc gagacaccgc ggccgccggc gttgtggata    2460
cctcgcggaa aacttggccc tcactgacag atgaggggcg gacgttgaca cttgaggggc    2520
cgactcaccc ggcgcggcgt tgacagatga ggggcaggct cgatttcggc cggcgacgtg    2580
gagctggcca gcctcgcaaa tcggcgaaaa cgcctgattt tacgcgagtt tcccacagat    2640 gatgtgaca agcctgggga taagtgccct gcggtattga cacttgaggg gcgcgactac    2700
tgacagatga ggggcgcgat ccttgacact tgaggggcag agtgctgaca gatgaggggc    2760
gcacctattg acatttgagg ggctgtccac aggcagaaaa tccagcattt gcaagggttt    2820
ccgcccgttt ttcggccacc gctaacctgt cttttaacct gcttttaaac caatatttat    2880
aaaccttgtt tttaaccagg gctgcgccct gtgcgcgtga ccgcgcacgc cgaaggggg     2940 tgccccccct tctcgaaccc tcccggcccg ctaacgcggg cctcccatcc ccccagggc    3000 tgcgcccctc ggccgcgaac ggcctcaccc caaaaatggc agcgctggca gtccttgcca    3060
ttgccgggat cggggcagta acgggatggg cgatcagccc gagcgcgacg cccggaagca    3120
ttgacgtgcc gcaggtgctg gcatcgacat tcagcgacca ggtgccgggc agtgagggcg    3180
gcggcctggg tggcggcctg cccttcactt cggccgtcgg ggcattcacg gacttcatgg    3240
cggggccggc aattttacc ttgggcattc ttggcatagt ggtcgcgggt gccgtgctcg     3300
tgttcggggg tgcgataaac ccagcgaacc atttgaggtg ataggtaaga ttataccgag    3360
gtatgaaaac gagaattgga cctttacaga attactctat gaagcgccat atttaaaaag    3420
ctaccaagac gaagaggatg aagaggatga ggaggcagat tgccttgaat atattgacaa    3480
tactgataag ataatatatc ttttatatag aagatatcgc cgtatgtaag gatttcaggg    3540
ggcaaggcat aggcagcgcg cttatcaata tatctataga atgggcaaag cataaaaact    3600
tgcatggact aatgcttgaa acccaggaca ataaccttat agcttgtaaa ttctatcata    3660
attgggtaat gactccaact tattgatagt gttttatgtt cagataatgc ccgatgactt    3720
tgtcatgcag ctccaccgat tttgagaacg acagcgactt ccgtcccagc cgtgccaggt    3780
gctgcctcag attcaggtta tgccgctcaa ttcgctgcgt atatcgcttg ctgattacgt    3840 gcagcttttcc cttcaggcgg gattcataca gcggccagcc atccgtcatc catatccacca   3900 cgtcaaaggg tgacagcagg ctcataagac gccccagcgt cgcccatagt cgttcaccga    3960
atacgtgcgc aacaaccgtc ttccggagac tgtcatacgc gtaaaacagc cagcgctggc    4020
gcgatttagc cccgacatag ccccactgtt cgtccatttc cgcgcagacg atgacgtcac    4080
tgcccggctg tatgcgcgag gttaccgact gcggcctgag ttttttaagt gacgtaaaat    4140
cgtgttgagg ccaacgccca taatgcgggc tgttgcccgg catccaacgc cattcatggc    4200
catatcaatg attttctggt gcgtaccggg ttgagaagcg gtgtaagtga actgcagttg    4260
ccatgtttta cggcagtgag agcagagata gcgctgatgt ccggcggtgc ttttgccgtt    4320
acgcaccacc ccgtcagtag ctgaacagga gggacagctg atagacacag aagccactgg    4380
```

```
agcacctcaa aaacaccatc atacactaaa tcagtaagtt ggcagcatca cccataattg    4440
tggtttcaaa atcggctccg tcgatactat gttatacgcc aactttgaaa acaactttga    4500
aaaagctgtt ttctggtatt taaggtttta gaatgcaagg aacagtgaat tggagttcgt    4560
cttgttataa ttagcttctt ggggtatctt taaatactgt agaaagagg aaggaaataa     4620 taaatggcta aaatgagaat atcaccggaa ttgaaaaaac tgatcgaaaa ataccgctgc    4680
gtaaaagata cggaaggaat gtctcctgct aaggtatata agctggtggg agaaaatgaa    4740
aacctatatt taaaaatgac ggacagccgg tataaaggga ccacctatga tgtggaacgg    4800
gaaaaggaca tgatgctatg gctggaagga aagctgcctg ttccaaaggt cctgcacttt    4860
gaacggcatg atggctggag caatctgctc atgagtgagg ccgatggcgt cctttgctcg    4920
gaagagtatg aagatgaaca aagccctgaa aagattatcg agctgtatgc ggagtgcatc    4980
aggctctttc actccatcga catatcggat tgtccctata cgaatagctt agacagccgc    5040
ttagccgaat tggattactt actgaataac gatctggccg atgtggattg cgaaaactgg    5100
gaagaagaca ctccatttaa agatccgcgc gagctgtatg atttttttaaa gacgggaaaag   5160 cccgaagagg aacttgtctt ttcccacggc gacctgggag acagcaacat ctttgtgaaa    5220
gatggcaaag taagtggctt tattgatctt gggagaagcg gcagggcgga caagtggtat    5280
gacattgcct tctgcgtccg gtcgatcagg gaggatatcg gggaagaaca gtatgtcgag    5340 ctatttttg acttactggg gatcaagcct gattgggaga aaataaaata ttatattta     5400 ctggatgaat tgttttagta cctagatgtg gcgcaacgat gccggcgaca agcaggagcg    5460
caccgacttc ttccgcatca agtgttttgg ctctcaggcc gaggcccacg gcaagtattt    5520
gggcaagggg tcgctggtat tcgtgcaggg caagattcgg aataccaagt acgagaagga    5580
cggccagacg gtctacggga ccgacttcat tgccgataag gtggattatc tggacaccaa    5640
ggcaccaggc gggtcaaatc aggaataagg gcacattgcc ccggcgtgag tcggggcaat    5700
cccgcaagga gggtgaatga atcggacgtt tgaccggaag gcatacaggc aagaactgat    5760
cgacgcgggg ttttccgccg aggatgccga aaccatcgca agccgcaccg tcatgcgtgc    5820
gccccgcgaa accttccagt ccgtcggctc gatggtccag caagctacgg ccaagatcga    5880
gcgcgacagc gtgcaactgg ctcccccctgc cctgcccgcg ccatcggccg ccgtggagcg    5940
ttcgcgtcgt ctcgaacagg aggcggcagg tttggcgaag tcgatgacca tcgacacgcg    6000
aggaactatg acgaccaaga agcgaaaaac cgccggcgag gacctggcaa acaggtcag    6060 cgaggccaag caggccgcgt tgctgaaaca cacgaagcag cagatcaagg aaatgcagct    6120
ttccttgttc gatattgcgc cgtggccgga cacgatgcga gcgatgccaa acgacacggc    6180
ccgctctgcc ctgttcacca cgcgcaacaa gaaaatcccg cgcgaggcgc tgcaaaacaa    6240
ggtcattttc cacgtcaaca aggacgtgaa gatcacctac accggcgtcg agctgcgggc    6300
cgacgatgac gaactggtgt ggcagcaggt gttggagtac gcgaagcgca ccctatcgg    6360 cgagccgatc accttcacgt tctacgagct ttgccaggac ctgggctggt cgatcaatgg    6420
ccggtattac acgaaggccg aggaatgcct gtcgcgccta caggcgacgg cgatgggctt    6480
cacgtccgac cgcgttgggc acctggaatc ggtgtcgctg ctgcaccgct tccgcgtcct    6540
ggaccgtggc aagaaaacgt cccgttgcca ggtcctgatc gacgaggaaa tcgtcgtgct    6600
gtttgctggc gaccactaca cgaaattcat atgggagaag taccgcaagc tgtcgccgac    6660
ggcccgacgg atgttcgact atttcagctc gcaccgggag ccgtacccgc tcaagctgga    6720
```

```
aaccttccgc ctcatgtgcg gatcggattc cacccgcgtg aagaagtggc gcgagcaggt    6780
cggcgaagcc tgcgaagagt tgcgaggcag cggcctggtg gaacacgcct gggtcaatga    6840
tgacctggtg cattgcaaac gctagggcct tgtggggtca gttccggctg ggggttcagc    6900
agccagcgct ttactggcat ttcaggaaca agcgggcact gctcgacgca cttgcttcgc    6960
tcagtatcgc tcgggacgca cggcgcgctc tacgaactgc cgataaacag aggattaaaa    7020
ttgacaattg tgattaaggc tcagattcga cggcttggag cggccgacgt gcaggatttc    7080
cgcgagatcc gattgtcggc cctgaagaaa gctccagaga tgttcgggtc cgtttacgag    7140
cacgaggaga aaaagcccat ggaggcgttc gctgaacggt tgcgagatgc cgtggcattc    7200
ggcgcctaca tcgacggcga gatcattggg ctgtcggtct tcaaacagga ggacggcccc    7260
aaggacgctc acaaggcgca tctgtccggc gttttcgtgg agcccgaaca gcgaggccga    7320
ggggtcgccg gtatgctgct gcgggcgttg ccggcgggtt tattgctcgt gatgatcgtc    7380
cgacagattc caacgggaat ctggtggatg cgcatcttca tcctcggcgc acttaatatt    7440
tcgctattct ggagcttgtt gtttatttcg gtctaccgcc tgccgggcgg ggtcgcggcg    7500
acggtaggcg ctgtgcagcc gctgatggtc gtgttcatct ctgccgctct gctaggtagc    7560
ccgatacgat tgatggcggt cctggggggct atttgcggaa ctgcgggcgt ggcgctgttg    7620
gtgttgacac caaacgcagc gctagatcct gtcggcgtcg cagcgggcct ggcggggggcg    7680 gtttccatgg cgttcggaac cgtgctgacc cgcaagtggc aacctcccgt gcctctgctc    7740
acctttaccg cctggcaact ggcggccgga ggacttctgc tcgttccagt agctttagtg    7800
tttgatccgc caatcccgat gcctacagga accaatgttc tcggcctggc gtggctcggc    7860
ctgatcggag cgggtttaac ctacttcctt tggttccggg ggatctcgcg actcgaacct    7920
acagttgttt ccttactggg cttttctcagc cccagatctg gggtcgatca gccggggatg    7980
catcaggccg acagtcggaa cttcgggtcc ccgacctgta ccattcggtg agcaatggat    8040
aggggagttg atatcgtcaa cgttcacttc taaagaaata gcgccactca gcttcctcag    8100
cggctttatc cagcgatttc ctattatgtc ggcatagttc tcaagatcga cagcctgtca    8160
cggttaagcg agaaatgaat aagaaggctg ataattcgga tctctgcgag ggagatgata    8220
tttgatcaca gcagcaacg ctctgtcatc gttacaatca acatgctacc ctccgcgaga    8280
tcatccgtgt ttcaaacccg gcagcttagt tgccgttctt ccgaatagca tcggtaacat    8340
gagcaaagtc tgccgcctta caacggctct cccgctgacg ccgtcccgga ctgatgggct    8400
gcctgtatcg agtggtgatt tgtgccgag ctgccggtcg gggagctgtt ggctggctgg    8460
tggcaggata tattgtggtg taaacaaatt gacgcttaga caacttaata acacattgcg    8520
gacgttttta atgtactggg gtggttttc ttttcaccag tgagacgggc aacagctgat    8580
tgcccttcac cgcctggccc tgagagagtt gcagcaagcg gtccacgctg gtttgcccca    8640
gcaggcgaaa atcctgtttg atggtggttc cgaaatcggc aaaatccctt ataaatcaaa    8700
agaatagccc gagatagggt tgagtgttgt tccagtttgg aacaagagtc cactattaaa    8760
gaacgtggac tccaacgtca aagggcgaaa aaccgtctat cagggcgatg cccactacg    8820 tgaaccatca cccaaatcaa gttttttggg gtcgaggtgc cgtaaagcac taaatcggaa    8880
ccctaaaggg agccccgat ttagagcttg acggggaaag ccggcgaacg tggcgagaaa    8940
ggaagggaag aaagcgaaag gagcgggcgc cattcaggct gcgcaactgt tgggaagggc    9000
gatcggtgcg ggcctcttcg ctattacgcc agctggcgaa aggggggatgt gctgcaaggc    9060 gattaagttg ggtaacgcca gggttttccc agtcacgacg ttgtaaaacg acggccagtg    9120
```

```
aattaattcc catcttgaaa gaaatatagt ttaaatattt attgataaaa taacaagtca   9180
ggtattatag tccaagcaaa aacataaatt tattgatgca agtttaaatt cagaaatatt   9240
tcaataactg attatatcag ctggtacatt gccgtagatg aaagactgag tgcgatatta   9300
tgtgtaatac ataaattgat gatatagcta gcttagctca tcgggggatc cgtcgaagct   9360
agcttgggtc ccgctcagaa gaactcgtca agaaggcgat agaaggcgat gcgctgcgaa   9420
tcgggagcgg cgataccgta aagcacgagg aagcggtcag cccattcgcc gccaagctct   9480
tcagcaatat cacgggtagc caacgctatg tcctgatagc ggtccgccac acccagccgg   9540
ccacagtcga tgaatccaga aaagcggcca ttttccacca tgatattcgg caagcaggca   9600
tcgccatggg tcacgacgag atcctcgccg tcgggcatgc gcgccttgag cctggcgaac   9660
agttcggctg gcgcgagccc ctgatgctct tcgtccagat catcctgatc gacaagaccg   9720
gcttccatcc gagtacgtgc tcgctcgatg cgatgtttcg cttggtggtc gaatgggcag   9780
gtagccggat caagcgtatg cagccgccgc attgcatcag ccatgatgga tactttctcg   9840
gcaggagcaa ggtgagatga caggagatcc tgccccggca cttcgcccaa tagcagccag   9900
tcccttcccg cttcagtgac aacgtcgagc acagctgcgc aaggaacgcc cgtcgtggcc   9960
agccacgata gccgcgctgc ctcgtcctgc agttcattca gggcaccgga caggtcggtc  10020
ttgacaaaaa gaaccgggcg cccctgcgct gacagccgga cacggcggc atcagagcag  10080
ccgattgtct gttgtgccca gtcatagccg aatagcctct ccacccaagc ggccggagaa  10140
cctgcgtgca atccatcttg ttcaatccaa gctcccatgg gccctcgact agagtcgaga  10200
tctggattga gagtgaatat gagactctaa ttggataccg aggggaattt atggaacgtc  10260
agtggagcat ttttgacaag aaatatttgc tagctgatag tgaccttagg cgacttttga  10320
acgcgcaata atggtttctg acgtatgtgc ttagctcatt aaactccaga acccgcggc  10380
tgagtggctc cttcaacgtt gcggttctgt cagttccaaa cgtaaaacgg cttgtcccgc  10440
gtcatcggcg ggggtcataa cgtgactccc ttaattctcc gctcatgatc ttgatcccct  10500
gcgccatcag atccttggcg gcaagaaagc catccagttt actttgcagg gcttcccaac  10560
cttaccagag ggcgccccag ctggcaattc cggttcgctt gctgtccata aaaccgccca  10620
gtctagctat cgccatgtaa gcccactgca agctacctgc tttctctttg cgcttgcgtt  10680
ttcccttgtc cagatagccc agtagctgac attcatccgg ggtcagcacc gtttctgcgg  10740
actggctttc tacgtgttcc gcttccttta gcagcccttg cgccctgagt gcttgcggca  10800
gcgtgaagct tgcatgcctg caggtcgacg gcgcgccgag ctcctcgagc aaatttacac  10860
attgccacta aacgtctaaa cccttgtaat ttgttttttgt tttactatgt gtgttatgta  10920
tttgatttgc gataaatttt tatatttggt actaaattta taacaccttt tatgctaacg  10980
tttgccaaca cttagcaatt tgcaagttga ttaattgatt ctaaattatt tttgtcttct  11040
aaatacatat actaatcaac tggaaatgta aatatttgct aatatttcta ctataggaga  11100
attaaagtga gtgaatatgg taccacaagg tttggagatt taattgttgc aatgctgcat  11160
ggatggcata taccaaaac attcaataat tcttgaggat aataatggta ccacacaaga  11220
tttgaggtgc atgaacgtca cgtggacaaa aggtttagta atttttcaag acaacaatgt  11280
taccacacac aagttttgag gtgcatgcat ggatgccctg tggaaagttt aaaaatattt  11340
tggaaatgat ttgcatggaa gccatgtgta aaaccatgac atcccacttgg aggatgcaat  11400
aatgaagaaa actacaaatt tacatgcaac tagttatgca tgtagtctat ataatgagga  11460
```

```
ttttgcaata ctttcattca tacacactca ctaagtttta cacgattata atttcttcat   11520
agccagcaga tctgccggca tcgatcccgg gccatggcct gctttaatga gatatgcgag   11580
acgcctatga tcgcatgata tttgctttca attctgttgt gcacgttgta aaaaacctga   11640
gcatgtgtag ctcagatcct taccgccggt ttcggttcat tctaatgaat atatcacccg   11700
ttactatcgt atttttatga ataatattct ccgttcaatt tactgattgt ccgtcgacga   11760
gctcggcgcg cctctagagg atcgatgaat tcagatcggc tgagtggctc cttcaacgtt   11820
gcggttctgt cagttccaaa cgtaaaacgg cttgtcccgc gtcatcggcg ggggtcataa   11880
cgtgactccc ttaattctcc gctcatgatc agattgtcgt ttcccgcctt cagttttaaac  11940 tatcagtgtt tgacaggata tattggcggg taaacctaag agaaagagc gtttattaga    12000 ataatcggat atttaaaagg gcgtgaaaag gtttatcctt cgtccatttg tatgtgcatg   12060
ccaaccacag ggttcccca                                                12079
```

<210> SEQ ID NO 67
<211> LENGTH: 13002
<212> TYPE: DNA
<213> ORGANISM: artificial sequence
<220> FEATURE:
<223> OTHER INFORMATION: Plant expression vector with 2
      promoter-terminator expression cassettes

<400> SEQUENCE: 67

```
gatctggcgc cggccagcga gacgagcaag attggccgcc gcccgaaacg atccgacagc     60
gcgcccagca caggtgcgca ggcaaattgc accaacgcat acagcgccag cagaatgcca    120
tagtgggcgg tgacgtcgtt cgagtgaacc agatcgcgca ggaggcccgg cagcaccggc    180
ataatcaggc cgatgccgac agcgtcgagc gcgacagtgc tcagaattac gatcaggggt    240
atgttgggtt tcacgtctgg cctccggacc agcctccgct ggtccgattg aacgcgcgga    300
ttctttatca ctgataagtt ggtggacata ttatgtttat cagtgataaa gtgtcaagca    360
tgacaaagtt gcagccgaat acagtgatcc gtgccgccct ggacctgttg aacgaggtcg    420
gcgtagacgt tctgacgaca cgcaaactgg cggaacggtt gggggttcag cagccggcgc    480
tttactggca cttcaggaac aagcgggcgc tgctcgacgc actggccgaa gccatgctgg    540
cggagaatca tacgcattcg gtgccgagag ccgacgacga ctggcgctca tttctgatcg    600
ggaatgcccg cagcttcagg caggcgctgc tcgcctaccg cgatggcgcg cgcatccatg    660
ccggcacgcg accgggcgca ccgcagatgg aaacggccga cgcgcagctt cgcttcctct    720
gcgaggcggg ttttcggcc ggggacgccg tcaatgcgct gatgacaatc agctacttca    780
ctgttggggc cgtgcttgag gagcaggccg cgacagcga tgccggcgag gcggcggca    840 ccgttgaaca ggctccgctc tcgccgctgt tgcgggccgc gatagacgcc ttcgacgaag    900
ccggtccgga cgcagcgttc gagcaggac tcgcggtgat tgtcgatgga ttggcgaaa    960 ggaggctcgt tgtcaggaac gttgaaggac cgagaaggg tgacgattga tcaggaccgc   1020
tgccggagcg caacccactc actacagcag agccatgtag acaacatccc ctccccttt   1080 ccaccgcgtc agacgcccgt agcagcccgc tacgggcttt ttcatgccct gccctagcgt   1140
ccaagcctca cggccgcgct cggcctctct ggcggccttc tggcgctctt ccgcttcctc   1200
gctcactgac tcgctgcgct cggtcgttcg gctgcggcga gcggtatcag ctcactcaaa   1260
ggcggtaata cggttatcca cagaatcagg ggataacgca ggaaagaaca tgtgagcaaa   1320
aggccagcaa aaggccagga accgtaaaaa ggccgcgttg ctggcgtttt tccataggct   1380
```

-continued

```
ccgccccct  gacgagcatc  acaaaaatcg  acgctcaagt  cagaggtggc  gaaacccgac   1440
aggactataa  agataccagg  cgtttccccc  tggaagctcc  ctcgtgcgct  ctcctgttcc   1500
gaccctgccg  cttaccggat  acctgtccgc  ctttctccct  tcgggaagcg  tggcgctttt   1560
ccgctgcata  accctgcttc  ggggtcatta  tagcgatttt  ttcggtatat  ccatccttt    1620 tcgcacgata  tacaggattt  tgccaaaggg  ttcgtgtaga  ctttccttgg  tgtatccaac   1680
ggcgtcagcc  gggcaggata  ggtgaagtag  gcccacccgc  gagcggtgt   tccttcttca   1740 ctgtcccta   ttcgcacctg  gcggtgctca  acgggaatcc  tgctctgcga  ggctggccgg   1800
ctaccgccgg  cgtaacagat  gagggcaagc  ggatggctga  tgaaaccaag  ccaaccagga   1860
agggcagccc  acctatcaag  gtgtactgcc  ttccagacga  acgaagagcg  attgaggaaa   1920 aggcggcgg   ggccggcatg  agcctgtcgg  cctacctgct  ggccgtcggc  cagggctaca   1980
aaatcacggg  cgtcgtggac  tatgagcacg  tccgcgagct  ggcccgcatc  aatggcgacc   2040
tgggccgcct  gggcggcctg  ctgaaactct  ggctcaccga  cgacccgcgc  acggcgcggt   2100
tcggtgatgc  cacgatcctc  gccctgctgg  cgaagatcga  agagaagcag  gacgagcttg   2160
gcaaggtcat  gatgggcgtg  gtccgcccga  gggcagagcc  atgacttttt  tagccgctaa   2220
aacggccggg  gggtgcgcgt  gattgccaag  cacgtcccca  tgcgctccat  caagaagagc   2280
gacttcgcgg  agctggtgaa  gtacatcacc  gacgagcaag  gcaagaccga  gcgccttgc    2340 gacgctcacc  gggctggttg  ccctcgccgc  tgggctggcg  gccgtctatg  gccctgcaaa   2400
cgcgccagaa  acgccgtcga  agccgtgtgc  gagacaccgc  ggccgccggc  gttgtggata   2460
cctcgcggaa  aacttggccc  tcactgacag  atgaggggcg  gacgttgaca  cttgagggc    2520 cgactcaccc  ggcgcggcgt  tgacagatga  ggggcaggct  cgatttcggc  cggcgacgtg   2580
gagctggcca  gcctcgcaaa  tcggcgaaaa  cgcctgattt  tacgcgagtt  tcccacagat   2640
gatgtggaca  agcctgggga  taagtgccct  gcggtattga  cacttgaggg  gcgcgactac   2700
tgacagatga  ggggcgcgat  ccttgacact  tgaggggcag  agtgctgaca  gatgaggggc   2760
gcacctattg  acatttgagg  ggctgtccac  aggcagaaaa  tccagcattt  gcaagggttt   2820
ccgcccgttt  ttcggccacc  gctaacctgt  cttttaacct  gcttttaaac  caatatttat   2880
aaaccttgtt  tttaaccagg  gctgcgccct  gtgcgcgtga  ccgcgcacgc  cgaagggggg   2940 tgcccccct   tctcgaaccc  tcccggcccg  ctaacgcggg  cctcccatcc  ccccaggggc   3000
tgcgcccctc  ggccgcgaac  ggcctcaccc  caaaaatggc  agcgctggca  gtccttgcca   3060
ttgccgggat  cggggcagta  acgggatggg  cgatcagccc  gagcgcgacg  cccggaagca   3120
ttgacgtgcc  gcaggtgctg  gcatcgacat  tcagcgacca  ggtgccgggc  agtgagggcg   3180
gcggcctggg  tggcggcctg  cccttcactt  cggccgtcgg  ggcattcacg  gacttcatgg   3240
cggggccggc  aattttttacc  ttgggcattc  ttggcatagt  ggtcgcgggt  gccgtgctcg   3300
tgttcggggg  tgcgataaac  ccagcgaacc  atttgaggtg  ataggtaaga  ttataccgag   3360
gtatgaaaac  gagaattgga  cctttacaga  attactctat  gaagcgccat  atttaaaaag   3420
ctaccaagac  gaagaggatg  aagaggatga  ggaggcagat  tgccttgaat  atattgacaa   3480
tactgataag  ataatatatc  ttttatatag  aagatatcgc  cgtatgtaag  gatttcaggg   3540
ggcaaggcat  aggcagcgcg  cttatcaata  tatctataga  atgggcaaag  cataaaaact   3600
tgcatggact  aatgcttgaa  acccaggaca  ataaccttat  agcttgtaaa  ttctatcata   3660
attgggtaat  gactccaact  tattgatagt  gttttatgtt  cagataatgc  ccgatgactt   3720
tgtcatgcag  ctccaccgat  tttgagaacg  acagcgactt  ccgtcccagc  cgtgccaggt   3780
```

```
gctgcctcag attcaggtta tgccgctcaa ttcgctgcgt atatcgcttg ctgattacgt    3840
gcagctttcc cttcaggcgg gattcataca gcggccagcc atccgtcatc catatcacca    3900
cgtcaaaggg tgacagcagg ctcataagac gccccagcgt cgccatagtg cgttcaccga    3960
atacgtgcgc aacaaccgtc ttccggagac tgtcatacgc gtaaaacagc cagcgctggc    4020
gcgatttagc cccgacatag ccccactgtt cgtccatttc cgcgcagacg atgacgtcac    4080
tgcccggctg tatgcgcgag gttaccgact gcggcctgag ttttttaagt gacgtaaaat    4140
cgtgttgagg ccaacgccca taatgcgggc tgttgcccgg catccaacgc cattcatggc    4200
catatcaatg attttctggt gcgtaccggg ttgagaagcg gtgtaagtga actgcagttg    4260
ccatgtttta cggcagtgag agcagagata gcgctgatgt ccggcggtgc ttttgccgtt    4320
acgcaccacc ccgtcagtag ctgaacagga gggacagctg atagacacag aagccactgg    4380
agcacctcaa aaacaccatc atacactaaa tcagtaagtt ggcagcatca cccataattg    4440
tggtttcaaa atcggctccg tcgatactat gttatacgcc aactttgaaa caactttga    4500
aaaagctgtt ttctggtatt taaggtttta gaatgcaagg aacagtgaat tggagttcgt    4560
cttgttataa ttagcttctt ggggtatctt taaatactgt agaaagagg aaggaaataa    4620
taaatggcta aaatgagaat atcaccggaa ttgaaaaaac tgatcgaaaa ataccgctgc    4680
gtaaaagata cggaaggaat gtctcctgct aaggtatata agctggtggg agaaaatgaa    4740
aacctatatt taaaaatgac ggacagccgg tataaaggga ccacctatga tgtggaacgg    4800
gaaaaggaca tgatgctatg gctggaagga aagctgcctg ttccaaaggt cctgcacttt    4860
gaacggcatg atggctggag caatctgctc atgagtgagg ccgatggcgt cctttgctcg    4920
gaagagtatg aagatgaaca aagccctgaa aagattatcg agctgtatgc ggagtgcatc    4980
aggctctttc actccatcga catatcggat tgtccctata cgaatagctt agacagccgc    5040
ttagccgaat tggattactt actgaataac gatctggccg atgtggattg cgaaaactgg    5100
gaagaagaca ctccatttaa agatccgcgc gagctgtatg atttttaaa gacggaaaag    5160
cccgaagagg aacttgtctt ttcccacggc gacctgggag acagcaacat ctttgtgaaa    5220
gatggcaaag taagtggctt tattgatctt gggagaagcg gcagggcgga caagtggtat    5280
gacattgcct tctgcgtccg gtcgatcagg gaggatatcg gggaagaaca gtatgtcgag    5340
ctattttttg acttactggg gatcaagcct gattgggaga aaataaaata ttatatttta    5400
ctggatgaat tgttttagta cctagatgtg gcgcaacgat gccggcgaca agcaggagcg    5460
caccgacttc ttccgcatca agtgttttgg ctctcaggcc gaggcccacg gcaagtattt    5520
gggcaagggt tcgctggtat tcgtgcaggg caagattcgg aataccaagt acgaaagga    5580
cggccagacg gtctacggga ccgacttcat tgccgataag gtggattatc tggacaccaa    5640
ggcaccaggc gggtcaaatc aggaataagg gcacattgcc ccggcgtgag tcggggcaat    5700
cccgcaagga gggtgaatga atcggacgtt tgaccggaag gcatacaggc aagaactgat    5760
cgacgcgggg ttttccgccg aggatgccga aaccatcgca agccgcaccg tcatgcgtgc    5820
gccccgcgaa accttccagt ccgtcggctc gatggtccag caagctacgg ccaagatcga    5880
gcgcgacagc gtgcaactgg ctcccctgc cctgccgcg ccatcggccg ccgtggagcg    5940
ttcgcgtcgt ctcgaacagg aggcggcagg tttggcgaag tcgatgacca tcgacacgcg    6000
aggaactatg acgaccaaga agcgaaaaac cgcggcgag gacctggcaa acaggtcag    6060
cgaggccaag caggccgcgt tgctgaaaca cacgaagcag cagatcaagg aaatgcagct    6120
```

```
ttccttgttc gatattgcgc cgtggccgga cacgatgcga gcgatgccaa acgacacggc    6180
ccgctctgcc ctgttcacca cgcgcaacaa gaaaatcccg cgcgaggcgc tgcaaaacaa    6240
ggtcattttc cacgtcaaca aggacgtgaa gatcacctac accggcgtcg agctgcgggc    6300
cgacgatgac gaactggtgt ggcagcaggt gttggagtac gcgaagcgca cccctatcgg    6360
cgagccgatc accttcacgt tctacgagct tgccaggac ctgggctggt cgatcaatgg     6420
ccggtattac acgaaggccg aggaatgcct gtcgcgccta caggcgacgg cgatgggctt    6480
cacgtccgac cgcgttgggc acctggaatc ggtgtcgctg ctgcaccgct tccgcgtcct    6540
ggaccgtggc aagaaaacgt cccgttgcca ggtcctgatc gacgaggaaa tcgtcgtgct    6600
gtttgctggc gaccactaca cgaaattcat atgggagaag taccgcaagc tgtcgccgac    6660
ggcccgacgg atgttcgact atttcagctc gcaccgggag ccgtacccgc tcaagctgga    6720
aaccttccgc ctcatgtgcg gatcggattc cacccgcgtg aagaagtggc gcgagcaggt    6780
cggcgaagcc tgcgaagagt tgcgaggcag cggcctggtg gaacacgcct gggtcaatga    6840
tgacctggtg cattgcaaac gctagggcct tgtggggtca gttccggctg ggggttcagc    6900
agccagcgct ttactggcat ttcaggaaca agcgggcact gctcgacgca cttgcttcgc    6960
tcagtatcgc tcgggacgca cggcgcgctc tacgaactgc cgataaacag aggattaaaa    7020
ttgacaattg tgattaaggc tcagattcga cggcttggag cggccgacgt gcaggatttc    7080
cgcgagatcc gattgtcggc cctgaagaaa gctccagaga tgttcgggtc cgtttacgag    7140
cacgaggaga aaaagcccat ggaggcgttc gctgaacggt tgcgagatgc cgtggcattc    7200
ggcgcctaca tcgacggcga gatcattggg ctgtcggtct tcaaacagga ggacggcccc    7260
aaggacgctc acaaggcgca tctgtccggc gttttcgtgg agcccgaaca gcgaggccga    7320
ggggtcgccg gtatgctgct gcgggcgttg ccggcgggtt tattgctcgt gatgatcgtc    7380
cgacagattc caacgggaat ctggtggatg cgcatcttca tcctcggcgc acttaatatt    7440
tcgctattct ggagcttgtt gtttatttcg gtctaccgcc tgccgggcgg ggtcgcggcg    7500
acggtaggcg ctgtgcagcc gctgatggtc gtgttcatct ctgccgctct gctaggtagc    7560
ccgatacgat tgatggcggt cctggggggct atttgcggaa ctgcgggcgt ggcgctgttg    7620
gtgttgacac caaacgcagc gctagatcct gtcggcgtcg cagcgggcct ggcggggggcg    7680 gtttccatgg cgttcggaac cgtgctgacc cgcaagtggc aacctcccgt gcctctgctc    7740
acctttaccg cctggcaact ggcggccgga ggacttctgc tcgttccagt agctttagtg    7800
tttgatccgc caatcccgat gcctacagga accaatgttc tcggcctggc gtggctcggc    7860
ctgatcggag cgggtttaac ctacttcctt tggttccggg ggatctcgcg actcgaacct    7920
acagttgttt ccttactggg ctttctcagc cccagatctg gggtcgatca gccggggatg    7980
catcaggccg acagtcggaa cttcgggtcc ccgacctgta ccattcggtg agcaatggat    8040
aggggagttg atatcgtcaa cgttcacttc taaagaaata gcgccactca gcttcctcag    8100
cggctttatc cagcgatttc ctattatgtc ggcatagttc tcaagatcga cagcctgtca    8160
cggttaagcg agaaatgaat aagaaggctg ataattcgga tctctgcgag ggagatgata    8220
tttgatcaca ggcagcaacg ctctgtcatc gttacaatca acatgctacc ctccgcgaga    8280
tcatccgtgt ttcaaacccg gcagcttagt tgccgttctt ccgaatagca tcggtaacat    8340
gagcaaagtc tgccgcctta caacggctct cccgctgacg ccgtcccgga ctgatgggct    8400
gcctgtatcg agtggtgatt ttgtgccgag ctgccggtcg gggagctgtt ggctggctgg    8460
tggcaggata tattgtggtg taaacaaatt gacgcttaga caacttaata acacattgcg    8520
```

```
gacgttttta atgtactggg gtggttttt ctttcaccag tgagacgggc aacagctgat    8580
tgcccttcac cgcctggccc tgagagagtt gcagcaagcg gtccacgctg gtttgccca    8640
gcaggcgaaa atcctgtttg atggtggttc cgaaatcggc aaaatccctt ataaatcaaa    8700
agaatagccc gagatagggt tgagtgttgt tccagtttgg aacaagagtc cactattaaa    8760
gaacgtggac tccaacgtca aagggcgaaa aaccgtctat cagggcgatg gcccactacg    8820
tgaaccatca cccaaatcaa gttttttggg gtcgaggtgc cgtaaagcac taaatcggaa    8880
ccctaaaggg agcccccgat ttagagcttg acggggaaag ccggcgaacg tggcgagaaa    8940
ggaagggaag aaagcgaaag gagcgggcgc cattcaggct gcgcaactgt tgggaagggc    9000
gatcggtgcg ggcctcttcg ctattacgcc agctggcgaa aggggggatgt gctgcaaggc    9060
gattaagttg ggtaacgcca gggttttccc agtcacgacg ttgtaaaacg acggccagtg    9120
aattaattcc catcttgaaa gaaatatagt ttaaatattt attgataaaa taacaagtca    9180
ggtattatag tccaagcaaa acataaaatt tattgatgca agtttaaatt cagaaatatt    9240
tcaataactg attatatcag ctggtacatt gccgtagatg aaagactgag tgcgatatta    9300
tgtgtaatac ataaattgat gatatagcta gcttagctca tcgggggatc cgtcgaagct    9360
agcttgggtc ccgctcagaa gaactcgtca agaaggcgat agaaggcgat gcgctgcgaa    9420
tcgggagcgg cgataccgta aagcacgagg aagcggtcag cccattcgcc gccaagctct    9480
tcagcaatat cacgggtagc caacgctatg tcctgatagc ggtccgccac acccagccgg    9540
ccacagtcga tgaatccaga aaagcggcca ttttccacca tgatattcgg caagcaggca    9600
tcgccatggg tcacgacgag atcctcgccg tcgggcatgc gcgccttgag cctggcgaac    9660
agttcggctg cgcgagcccc tgatgctct tcgtccagat catcctgatc gacaagaccg    9720
gcttccatcc gagtacgtgc tcgctcgatg cgatgtttcg cttggtggtc gaatgggcag    9780
gtagccggat caagcgtatg cagccgccgc attgcatcag ccatgatgga tactttctcg    9840
gcaggagcaa ggtgagatga caggagatcc tgccccggca cttcgcccaa tagcagccag    9900
tcccttcccg cttcagtgac aacgtcgagc acagctgcgc aaggaacgcc cgtcgtggcc    9960
agccacgata ccgcgctgc ctcgtcctgc agttcattca gggcaccgga caggtcggtc   10020
ttgacaaaaa gaaccgggcg cccctgcgct gacagccgga acacggcggc atcagagcag   10080
ccgattgtct gttgtgccca gtcatagccg aatagcctct ccacccaagc ggccggagaa   10140
cctgcgtgca atccatcttg ttcaatccaa gctcccatgg gccctcgact agagtcgaga   10200
tctggattga gagtgaatat gagactctaa ttggataccg aggggaattt atggaacgtc   10260
agtggagcat ttttgacaag aaatatttgc tagctgatag tgaccttagg cgactttga    10320
acgcgcaata atggtttctg acgtatgtgc ttagctcatt aaactccaga aacccgcggc   10380
tgagtggctc cttcaacgtt gcggttctgt cagttccaaa cgtaaaacgg cttgtcccgc   10440
gtcatcggcg ggggtcataa cgtgactccc ttaattctcc gctcatgatc ttgatcccct   10500
gcgccatcag atccttggcg gcaagaaagc catccagttt actttgcagg gcttcccaac   10560
cttaccagag ggcgccccag ctggcaattc cggttcgctt gctgtccata aaaccgccca   10620
gtctagctat cgccatgtaa gcccactgca agctacctgc tttctctttg cgcttgcgtt   10680
ttcccttgtc cagatagccc agtagctgac attcatccgg ggtcagcacc gtttctgcgg   10740
actggctttc tacgtgttcc gcttccttta gcagccctg cgccctgagt gcttgcggca   10800
gcgtgaagct tgcatgcctg caggtcgacg gcgcgccgag ctcctcgagc aaatttacac   10860
```

```
attgccacta aacgtctaaa cccttgtaat ttgttttgt tttactatgt gtgttatgta    10920
tttgatttgc gataaatttt tatatttggt actaaattta taacacctt tatgctaacg    10980 tttgccaaca cttagcaatt tgcaagttga ttaattgatt ctaaattatt tttgtcttct    11040
aaatacatat actaatcaac tggaaatgta aatatttgct aatatttcta ctataggaga    11100
attaaagtga gtgaatatgg taccacaagg tttggagatt taattgttgc aatgctgcat    11160
ggatggcata tacaccaaac attcaataat tcttgaggat aataatggta ccacacaaga    11220
tttgaggtgc atgaacgtca cgtggacaaa aggtttagta atttttcaag caacaatgt    11280 taccacacac aagttttgag gtgcatgcat ggatgccctg tggaaagttt aaaaatattt    11340
tggaaatgat ttgcatggaa gccatgtgta aaaccatgac atccacttgg aggatgcaat    11400
aatgaagaaa actacaaatt tacatgcaac tagttatgca tgtagtctat ataatgagga    11460
ttttgcaata ctttcattca tacacactca ctaagttta cacgattata atttcttcat    11520
agccagccca ccgcggtggg cggccgcctg cagtctagaa ggcctcctgc tttaatgaga    11580
tatgcgagac gcctatgatc gcatgatatt tgctttcaat tctgttgtgc acgttgtaaa    11640
aaacctgagc atgtgtagct cagatcctta ccgccggttt cggttcattc taatgaatat    11700
atcacccgtt actatcgtat ttttatgaat aatattctcc gttcaattta ctgattgtcc    11760
gtcgagcaaa tttacacatt gccactaaac gtctaaaccc ttgtaatttg tttttgtttt    11820
actatgtgtg ttatgtattt gatttgcgat aaattttat atttggtact aaatttataa    11880
caccttttat gctaacgttt gccaacactt agcaatttgc aagttgatta attgattcta    11940 aattatttt gtcttctaaa tacatatact aatcaactgg aaatgtaaat atttgctaat    12000
atttctacta taggagaatt aaagtgagtg aatatggtac cacaaggttt ggagatttaa    12060
ttgttgcaat gctgcatgga tggcatatac accaaacatt caataattct tgaggataat    12120
aatggtacca cacaagattt gaggtgcatg aacgtcacgt ggacaaaagg tttagtaatt    12180
tttcaagaca acaatgttac cacacacaag ttttgaggtg catgcatgga tgccctgtgg    12240
aaagtttaaa aatattttgg aaatgatttg catggaagcc atgtgtaaaa ccatgacatc    12300
cacttggagg atgcaataat gaagaaaact acaaatttac atgcaactag ttatgcatgt    12360
agtctatata tgaggatttt gcaatactt tcattcatac acactcacta agttttacac    12420
gattataatt tcttcatagc cagcggatcc gatatcgggc ccgctagcgt taaccctgct    12480
ttaatgagat atgcgagacg cctatgatcg catgatattt gctttcaatt ctgttgtgca    12540
cgttgtaaaa aacctgagca tgtgtagctc agatccttac cgccggtttc ggttcattct    12600
aatgaatata tcacccgtta ctatcgtatt tttatgaata atattctccg ttcaatttac    12660
tgattgtccg tcgacgaatt cgagctcggc gcgcctctag aggatcgatg aattcagatc    12720
ggctgagtgg ctccttcaac gttgcggttc tgtcagttcc aaacgtaaaa cggcttgtcc    12780
cgcgtcatcg gcggggtca taacgtgact cccttaattc tccgctcatg atcagattgt    12840
cgtttcccgc cttcagttta aactatcagt gtttgacagg atatattggc gggtaaacct    12900
aagagaaaag agcgttttat tagaataatcg gatatttaaa agggcgtgaa aaggtttatc    12960
cttcgtccat ttgtatgtgc atgccaacca cagggttccc ca                      13002
```

<210> SEQ ID NO 68
<211> LENGTH: 13905
<212> TYPE: DNA
<213> ORGANISM: artificial sequence
<220> FEATURE:
<223> OTHER INFORMATION: Plant expression vector with 3 promoter-terminator expression cassettes

<400> SEQUENCE: 68

```
gatctggcgc cggccagcga gacgagcaag attggccgcc gcccgaaacg atccgacagc      60
gcgcccagca caggtgcgca ggcaaattgc accaacgcat acagcgccag cagaatgcca     120
tagtgggcgg tgacgtcgtt cgagtgaacc agatcgcgca ggaggccgg cagcaccggc     180
ataatcaggc cgatgccgac agcgtcgagc gcgacagtgc tcagaattac gatcaggggt     240
atgttgggtt tcacgtctgg cctccggacc agcctccgct ggtccgattg aacgcgcgga     300
ttctttatca ctgataagtt ggtggacata ttatgtttat cagtgataaa gtgtcaagca     360
tgacaaagtt gcagccgaat acagtgatcc gtgccgccct ggacctgttg aacgaggtcg     420
gcgtagacgg tctgacgaca cgcaaactgg cggaacggtt gggggttcag cagccggcgc     480
tttactggca cttcaggaac aagcgggcgc tgctcgacgc actggccgaa gccatgctgg     540
cggagaatca tacgcattcg gtgccgagag ccgacgacga ctggcgctca tttctgatcg     600
ggaatgcccg cagcttcagg caggcgctgc tcgcctaccg cgatggcgcg cgcatccatg     660
ccggcacgcg accgggcgca ccgcagatgg aaacggccga cgcgcagctt cgcttcctct     720
gcgaggcggg ttttccggcc ggggacgccg tcaatgcgct gatgacaatc agctacttca     780
ctgttggggc cgtgcttgag gagcaggccg gcgacagcga tgccggcgag cgcggcggca     840
ccgttgaaca ggctccgctc tcgccgctgt tgcgggccgc gatagacgcc ttcgacgaag     900
ccggtccgga cgcagcgttc gagcaggac tcgcggtgat tgtcgatgga ttggcgaaaa     960
ggaggctcgt tgtcaggaac gttgaaggac cgagaaaggg tgacgattga tcaggaccgc    1020
tgccggagcg caacccactc actacagcag agccatgtag acaacatccc ctcccccttt    1080
ccaccgcgtc agacgcccgt agcagcccgc tacgggcttt ttcatgccct gccctagcgt    1140
ccaagcctca cggccgcgct cggcctctct ggcggccttc tggcgctctt ccgcttcctc    1200
gctcactgac tcgctgcgct cggtcgttcg gctgcggcga cggtatcag ctcactcaaa    1260
ggcggtaata cggttatcca cagaatcagg ggataacgca ggaaagaaca tgtgagcaaa    1320
aggccagcaa aaggccagga accgtaaaaa ggccgcgttg ctggcgtttt tccataggct    1380
ccgcccccct gacgagcatc acaaaaatcg acgctcaagt cagaggtggc gaaacccgac    1440
aggactataa agataccagg cgtttccccc tggaagctcc ctcgtgcgct ctcctgttcc    1500
gaccctgccg cttaccggat acctgtccgc ctttctccct tcgggaagcg tggcgctttt    1560
ccgctgcata accctgcttc ggggtcatta tagcgatttt tcggtatat ccatcctttt    1620
tcgcacgata tacaggattt tgccaaaggg ttcgtgtaga cttccttgg tgtatccaac    1680
ggcgtcagcc gggcaggata ggtgaagtag gcccacccgc gagcgggtgt tccttcttca    1740
ctgtccctta ttcgcacctg gcggtgctca acgggaatcc tgctctgcga ggctggccgg    1800
ctaccgccgg cgtaacagat gagggcaagc ggatggctga tgaaaccaag ccaaccagga    1860
agggcagccc acctatcaag gtgtactgcc ttccagacga acgaagagcg attgaggaaa    1920
aggcggcggc ggccggcatg agcctgtcgg cctacctgct ggccgtcggc cagggctaca    1980
aaatcacggg cgtcgtggac tatgagcacg tccgcgagct ggcccgcatc aatggcgacc    2040
tgggcgcct gggcggcctg ctgaaactct ggctcaccga cgaccgcgc acggcgcggt    2100
tcggtgatgc cacgatcctc gccctgctgg cgaagatcga agagaagcag gacgagcttg    2160
gcaaggtcat gatgggcgtg gtccgcccga gggcagagcc atgactttt tagccgctaa    2220
aacggccggg gggtgcgcgt gattgccaag cacgtcccca tgcgctccat caagaagagc    2280
```

```
gacttcgcgg agctggtgaa gtacatcacc gacgagcaag gcaagaccga gcgcctttgc   2340
gacgctcacc gggctggttg ccctcgccgc tgggctggcg gccgtctatg gccctgcaaa   2400
cgcgccagaa acgccgtcga agccgtgtgc gagacaccgc ggccgccggc gttgtggata   2460
cctcgcggaa aacttggccc tcactgacag atgaggggcg gacgttgaca cttgaggggc   2520
cgactcaccc ggcgcggcgt tgacagatga ggggcaggct cgatttcggc cggcgacgtg   2580
gagctggcca gcctcgcaaa tcggcgaaaa cgcctgattt tacgcgagtt tcccacagat   2640
gatgtggaca gcctgggga taagtgccct gcggtattga cacttgaggg gcgcgactac   2700
tgacagatga ggggcgcgat ccttgacact tgaggggcag agtgctgaca gatgaggggc   2760
gcacctattg acatttgagg ggctgtccac aggcagaaaa tccagcattt gcaagggttt   2820
ccgcccgttt ttcggccacc gctaacctgt cttttaacct gcttttaaac caatatttat   2880
aaaccttgtt tttaaccagg gctgcgccct gtgcgcgtga ccgcgcacgc cgaaggggg   2940 tgccccccct tctcgaaccc tcccggcccg ctaacgcggg cctccatcc ccccagggc   3000 tgcgcccctc ggccgcgaac ggcctcaccc caaaaatggc agcgctggca gtccttgcca   3060
ttgccgggat cggggcagta acgggatggg cgatcagccc gagcgcgacg cccggaagca   3120
ttgacgtgcc gcaggtgctg gcatcgacat tcagcgacca ggtgccgggc agtgaggggcg   3180 gcggcctggg tggcggcctg cccttcactt cggccgtcgg ggcattcacg gacttcatgg   3240
cggggccggc aatttttacc ttgggcattc ttggcatagt ggtcgcgggt gccgtgctcg   3300
tgttcggggg tgcgataaac ccagcgaacc atttgaggtg ataggtaaga ttataccgag   3360
gtatgaaaac gagaattgga cctttacaga attactctat gaagcgccat atttaaaaag   3420
ctaccaagac gaagaggatg aagaggatga ggaggcagat tgccttgaat atattgacaa   3480
tactgataag ataatatatc ttttatatag aagatatcgc cgtatgtaag gatttcaggg   3540
ggcaaggcat aggcagcgcg cttatcaata tatctataga atgggcaaag cataaaaact   3600
tgcatggact aatgcttgaa acccaggaca ataaccttat agcttgtaaa ttctatcata   3660
attgggtaat gactccaact tattgatagt gttttatgtt cagataatgc ccgatgactt   3720
tgtcatgcag ctccaccgat tttgagaacg acagcgactt ccgtcccagc cgtgccaggt   3780
gctgcctcag attcaggtta tgccgctcaa ttcgctgcgt atatcgcttg ctgattacgt   3840
gcagctttcc cttcaggcgg gattcataca gcggccagcc atccgtcatc catatcacca   3900
cgtcaaaggt gacacgcagg ctcataagac gccccagcgt cgccatagtg cgttcaccga   3960
atacgtgcgc aacaaccgtc ttccggagac tgtcatacgc gtaaaacagc cagcgctggc   4020
gcgatttagc cccgacatag ccccactgtt cgtccatttc cgcgcagacg atgacgtcac   4080
tgcccggctg tatgcgcgag gttaccgact gcggcctgag ttttttaagt gacgtaaaat   4140
cgtgttgagg ccaacgccca taatgcgggc tgttgcccgg catccaacgc cattcatggc   4200
catatcaatg attttctggt gcgtaccggg ttgagaagcg gtgtaagtga actgcagttg   4260
ccatgtttta cggcagtgag agcagagata cgctgatgt ccggcggtgc ttttgccgtt   4320
acgcaccacc ccgtcagtag ctgaacagga gggacagctg atagacacag aagccactgg   4380
agcacctcaa aaacaccatc atacactaaa tcagtaagtt ggcagcatca cccataattg   4440
tggtttcaaa atcggctccg tcgatactat gttatacgcc aactttgaaa caactttga   4500 aaaagctgtt ttctggtatt taaggtttta gaatgcaagg aacagtgaat tggagttcgt   4560
cttgttataa ttagcttctt ggggtatctt taaatactgt agaaaagagg aaggaaataa   4620
```

```
taaatggcta aaatgagaat atcaccggaa ttgaaaaaac tgatcgaaaa ataccgctgc    4680
gtaaaagata cggaaggaat gtctcctgct aaggtatata agctggtggg agaaaatgaa    4740
aacctatatt taaaaatgac ggacagccgg tataaaggga ccacctatga tgtggaacgg    4800
gaaaaggaca tgatgctatg gctggaagga aagctgcctg ttccaaaggt cctgcacttt    4860
gaacggcatg atggctggag caatctgctc atgagtgagg ccgatggcgt cctttgctcg    4920
gaagagtatg aagatgaaca aagccctgaa agattatcg agctgtatgc ggagtgcatc     4980
aggctctttc actccatcga catatcggat tgtccctata cgaatagctt agacagccgc    5040
ttagccgaat tggattactt actgaataac gatctggccg atgtggattg cgaaaactgg    5100
gaagaagaca ctccatttaa agatccgcgc gagctgtatg atttttaaa gacggaaaag     5160
cccgaagagg aacttgtctt tcccacggc gacctgggag acagcaacat ctttgtgaaa     5220
gatggcaaag taagtggctt tattgatctt gggagaagcg gcagggcgga caagtggtat    5280
gacattgcct tctgcgtccg gtcgatcagg gaggatatcg gggaagaaca gtatgtcgag    5340
ctatttttg acttactggg gatcaagcct gattgggaga aaataaaata ttatattta      5400
ctggatgaat tgttttagta cctagatgtg gcgcaacgat gccggcgaca agcaggagcg    5460
caccgacttc ttccgcatca agtgttttgg ctctcaggcc gaggcccacg gcaagtattt    5520
gggcaagggg tcgctggtat tcgtgcaggg caagattcgg aataccaagt acgagaagga    5580
cggccagacg gtctacggga ccgacttcat tgccgataag gtggattatc tggacaccaa    5640
ggcaccaggc gggtcaaatc aggaataagg gcacattgcc ccggcgtgag tcggggcaat    5700
cccgcaagga gggtgaatga atcggacgtt tgaccggaag gcatacaggc aagaactgat    5760
cgacgcgggg ttttccgccg aggatgccga aaccatcgca agccgcaccg tcatgcgtgc    5820
gccccgcgaa accttccagt ccgtcggctc gatggtccag caagctacgg ccaagatcga    5880
gcgcgacagc gtgcaactgg ctcccccctgc cctgcccgcg ccatcggccg ccgtggagcg    5940
ttcgcgtcgt ctcgaacagg aggcggcagg tttggcgaag tcgatgacca tcgacacgcg    6000
aggaactatg acgaccaaga agcgaaaaac cgccggcgag gacctggcaa acaggtcag     6060
cgaggccaag caggccgcgt tgctgaaaca cacgaagcag cagatcaagg aaatgcagct    6120
ttccttgttc gatattgcgc cgtggccgga cacgatgcga gcgatgccaa acgacacggc    6180
ccgctctgcc ctgttcacca cgcgcaacaa gaaaatcccg cgcgaggcgc tgcaaaacaa    6240
ggtcattttc cacgtcaaca aggacgtgaa gatcacctac accggcgtcg agctgcgggc    6300
cgacgatgac gaactggtgt ggcagcaggt gttggagtac gcgaagcgca ccctatcgg    6360
cgagccgatc accttcacgt tctacgagct ttgccaggac ctgggctggt cgatcaatgg    6420
ccggtattac acgaaggccg aggaatgcct gtcgcgccta caggcgacgg cgatgggctt    6480
cacgtccgac cgcgttgggc acctggaatc ggtgtcgctg ctgcaccgct tccgcgtcct    6540
ggaccgtggc aagaaaacgt cccgttgcca ggtcctgatc gacgaggaaa tcgtcgtgct    6600
gtttgctggc gaccactaca cgaaattcat atgggagaag taccgcaagc tgtcgccgac    6660
ggcccgacgg atgttcgact atttcagctc gcaccgggag ccgtacccgc tcaagctgga    6720
aaccttccgc ctcatgtgcg gatcggattc caccgcgtg aagaagtggc gcgagcaggt     6780
cggcgaagcc tgcgaagagt tgcgaggcag cggcctggtg aacacgcct gggtcaatga     6840
tgacctggtg cattgcaaac gctagggcct tgtggggtca gttccggctg ggggttcagc    6900
agccagcgct ttactggcat ttcaggaaca agcgggcact gctcgacgca cttgcttcgc    6960
tcagtatcgc tcgggacgca cggcgcgctc tacgaactgc cgataaacag aggattaaaa    7020
```

```
ttgacaattg tgattaaggc tcagattcga cggcttggag cggccgacgt gcaggatttc    7080
cgcgagatcc gattgtcggc cctgaagaaa gctccagaga tgttcgggtc cgtttacgag    7140
cacgaggaga aaaagcccat ggaggcgttc gctgaacggt tgcgagatgc cgtggcattc    7200
ggcgcctaca tcgacggcga gatcattggg ctgtcggtct tcaaacagga ggacggcccc    7260
aaggacgctc acaaggcgca tctgtccggc gttttcgtgg agcccgaaca gcgaggccga    7320
ggggtcgccg gtatgctgct gcgggcgttg ccggcgggtt tattgctcgt gatgatcgtc    7380
cgacagattc caacgggaat ctggtggatg cgcatcttca tcctcggcgc acttaatatt    7440
tcgctattct ggagcttgtt gtttatttcg gtctaccgcc tgccgggcgg ggtcgcggcg    7500
acggtaggcg ctgtgcagcc gctgatggtc gtgttcatct ctgccgctct gctaggtagc    7560
ccgatacgat tgatggcggt cctggggggct atttgcggaa ctgcgggcgt ggcgctgttg    7620
gtgttgacac caaacgcagc gctagatcct gtcggcgtcg cagcgggcct ggcggggggcg    7680 gtttccatgg cgttcggaac cgtgctgacc cgcaagtggc aacctcccgt gcctctgctc    7740
acctttaccg cctggcaact ggcggccgga ggacttctgc tcgttccagt agctttagtg    7800
tttgatccgc caatcccgat gcctacagga accaatgttc tcggcctggc gtggctcggc    7860
ctgatcggag cgggtttaac ctacttcctt tggttccggg ggatctcgcg actcgaacct    7920
acagttgttt ccttactggg ctttctcagc cccagatctg gggtcgatca gccggggatg    7980
catcaggccg acagtcggaa cttcgggtcc ccgacctgta ccattcggtg agcaatggat    8040
aggggagttg atatcgtcaa cgttcacttc taaagaaata gcgccactca gcttcctcag    8100
cggctttatc cagcgatttc ctattatgtc ggcatagttc tcaagatcga cagcctgtca    8160
cggttaagcg agaaatgaat aagaaggctg ataattcgga tctctgcgag ggagatgata    8220
tttgatcaca ggcagcaacg ctctgtcatc gttacaatca acatgctacc ctccgcgaga    8280
tcatccgtgt ttcaaacccg gcagcttagt tgccgttctt ccgaatagca tcggtaacat    8340
gagcaaagtc tgccgcctta caacggctct cccgctgacg ccgtcccgga ctgatgggct    8400
gcctgtatcg agtggtgatt tgtgccgagc tgccggtcg gggagctgtt ggctggctgg     8460
tggcaggata tattgtggtg taaacaaatt gacgcttaga caacttaata acacattgcg    8520
gacgttttta atgtactggg gtggtttttc ttttcaccag tgagacgggc aacagctgat    8580
tgcccttcac cgcctggccc tgagagagtt gcagcaagcg gtccacgctg gtttgcccca    8640
gcaggcgaaa atcctgtttg atggtggttc cgaaatcggc aaaatccctt ataaatcaaa    8700
agaatagccc gagatagggt tgagtgttgt tccagtttgg aacaagagtc cactattaaa    8760
gaacgtggac tccaacgtca aagggcgaaa aaccgtctat cagggcgatg cccactacg     8820 tgaaccatca cccaaatcaa gttttttggg gtcgaggtgc cgtaaagcac taaatcggaa    8880
ccctaaaggg agccccgat ttagagcttg acggggaaag ccggcgaacg tggcgagaaa     8940
ggaagggaag aaagcgaaag gagcgggcgc cattcaggct gcgcaactgt tgggaagggc    9000
gatcggtgcg ggcctcttcg ctattacgcc agctggcgaa aggggatgt gctgcaaggc     9060 gattaagttg ggtaacgcca gggttttccc agtcacgacg ttgtaaaacg acggccagtg    9120
aattaattcc catcttgaaa gaaatatagt ttaaatattt attgataaaa taacaagtca    9180
ggtattatag tccaagcaaa aacataaatt tattgatgca agtttaaatt cagaaatatt    9240
tcaataactg attatatcag ctggtacatt gccgtagatg aaagactgag tgcgatatta    9300
tgtgtaatac ataaattgat gatatagcta gcttagctca tcgggggatc cgtcgaagct    9360
```

```
agcttgggtc cgctcagaa gaactcgtca agaaggcgat agaaggcgat gcgctgcgaa    9420
tcgggagcgg cgataccgta agcacgagg aagcggtcag cccattcgcc gccaagctct    9480
tcagcaatat cacgggtagc caacgctatg tcctgatagc ggtccgccac acccagccgg   9540
ccacagtcga tgaatccaga aaagcggcca ttttccacca tgatattcgg caagcaggca   9600
tcgccatggg tcacgacgag atcctcgccg tcgggcatgc gcgccttgag cctggcgaac   9660
agttcggctg gcgcgagccc ctgatgctct tcgtccagat catcctgatc gacaagaccg   9720
gcttccatcc gagtacgtgc tcgctcgatg cgatgtttcg cttggtggtc gaatgggcag   9780
gtagccggat caagcgtatg cagccgccgc attgcatcag ccatgatgga tactttctcg   9840
gcaggagcaa ggtgagatga caggagatcc tgccccggca cttcgcccaa tagcagccag   9900
tcccttcccg cttcagtgac aacgtcgagc acagctgcgc aaggaacgcc cgtcgtggcc   9960
agccacgata gccgcgctgc ctcgtcctgc agttcattca gggcaccgga caggtcggtc  10020
ttgacaaaaa gaaccgggcg cccctgcgct gacagccgga acacggcggc atcagagcag  10080
ccgattgtct gttgtgccca gtcatagccg aatagcctct ccacccaagc ggccggagaa  10140
cctgcgtgca atccatcttg ttcaatccaa gctcccatgg gccctcgact agagtcgaga  10200
tctggattga gagtgaatat gagactctaa ttggataccg aggggaattt atggaacgtc  10260
agtggagcat ttttgacaag aaatatttgc tagctgatag tgaccttagg cgacttttga  10320
acgcgcaata atggtttctg acgtatgtgc ttagctcatt aaactccaga aacccgcggc  10380
tgagtggctc cttcaacgtt gcggttctgt cagttccaaa cgtaaaacgg cttgtcccgc  10440
gtcatcggcg ggggtcataa cgtgactccc ttaattctcc gctcatgatc ttgatcccct  10500
gcgccatcag atccttggcg gcaagaaagc catccagttt actttgcagg gcttcccaac  10560
cttaccagag ggcgcccag ctggcaattc cggttcgctt gctgtccata aaaccgccca   10620
gtctagctat cgccatgtaa gcccactgca agctacctgc tttctctttg cgcttgcgtt  10680
ttcccttgtc cagatagccc agtagctgac attcatccgg ggtcagcacc gtttctgcgg  10740
actggctttc tacgtgttcc gcttccttta gcagcccttg cgccctgagt gcttgcggca  10800
gcgtgaagct tgcatgcctg caggtcgacg gcgcgccgag ctcctcgagc aaatttacac  10860
attgccacta aacgtctaaa cccttgtaat ttgttttttgt tttactatgt gtgttatgta  10920
tttgatttgc gataaatttt tatatttggt actaaattta taacacccttt tatgctaacg  10980
tttgccaaca cttagcaatt tgcaagttga ttaattgatt ctaaattatt tttgtcttct  11040
aaatacatat actaatcaac tggaaatgta aatatttgct aatatttcta ctataggaga  11100
attaaagtga gtgaatatgg taccacaagg tttggagatt taattgttgc aatgctgcat  11160
ggatggcata tacaccaaac attcaataat tcttgaggat aataatggta ccacacaaga  11220
tttgaggtgc atgaacgtca cgtggacaaa aggtttagta attttttcaag acaacaatgt  11280
taccacacac aagttttgag gtgcatgcat ggatgccctg tggaaagttt aaaaatattt  11340
tggaaatgat ttgcatggaa gccatgtgta aaaccatgac atccacttgg aggatgcaat  11400
aatgaagaaa actacaaatt tacatgcaac tagttatgca tgtagtctat ataatgagga  11460
ttttgcaata ctttcattca tacacactca ctaagtttta cacgattata atttcttcat  11520
agccagccca ccgcggtggg cggccgcctg cagtctagaa ggcctcctgc tttaatgaga  11580
tatgcgagac gcctatgatc gcatgatatt tgctttcaat tctgttgtgc acgttgtaaa  11640
aaacctgagc atgtgtagct cagatcctta ccgccggttt cggttcattc taatgaatat  11700
atcacccgtt actatcgtat ttttatgaat aatattctcc gttcaattta ctgattgtcc  11760
```

```
gtcgagcaaa tttacacatt gccactaaac gtctaaaccc ttgtaatttg tttttgtttt   11820
actatgtgtg ttatgtattt gatttgcgat aaattttat atttggtact aaatttataa    11880 cacctttat gctaacgttt gccaacactt agcaatttgc aagttgatta attgattcta    11940 aattatttt gtcttctaaa tacatatact aatcaactgg aaatgtaaat atttgctaat    12000
atttctacta taggagaatt aaagtgagtg aatatggtac cacaaggttt ggagatttaa   12060
ttgttgcaat gctgcatgga tggcatatac accaaacatt caataattct tgaggataat   12120
aatggtacca cacaagattt gaggtgcatg aacgtcacgt ggacaaaagg tttagtaatt   12180
tttcaagaca acaatgttac cacacacaag ttttgaggtg catgcatgga tgccctgtgg   12240
aaagtttaaa aatattttgg aaatgatttg catggaagcc atgtgtaaaa ccatgacatc   12300
cacttggagg atgcaataat gaagaaaact acaaatttac atgcaactag ttatgcatgt   12360
agtctatata tgaggatttt gcaatacttt cattcatac acactcacta agttttacac      12420
gattataatt tcttcatagc cagcggatcc gatatcgggc ccgctagcgt taaccctgct   12480
ttaatgagat atgcgagacg cctatgatcg catgatattt gctttcaatt ctgttgtgca   12540
cgttgtaaaa aacctgagca tgtgtagctc agatccttac cgccggtttc ggttcattct   12600
aatgaatata tcacccgtta ctatcgtatt tttatgaata atattctccg ttcaatttac   12660
tgattgtccg tcgagcaaat ttacacattg ccactaaacg tctaaaccct tgtaatttgt   12720
ttttgtttta ctatgtgtgt tatgtatttg atttgcgata aattttata tttggtacta   12780 aatttataac acctttatg ctaacgtttg ccaacactta gcaatttgca agttgattaa     12840
ttgattctaa attatttttg tcttctaaat acatatacta atcaactgga aatgtaaata   12900
tttgctaata tttctactat aggagaatta aagtgagtga atatggtacc acaaggtttg   12960
gagatttaat tgttgcaatg ctgcatggat ggcatataca ccaaacattc aataattctt   13020
gaggataata atggtaccac acaagatttg aggtgcatga acgtcacgtg acaaaaggt    13080 ttagtaattt ttcaagacaa caatgttacc acacacaagt tttgaggtgc atgcatggat   13140
gccctgtgga aagtttaaaa atattttgga aatgatttgc atggaagcca tgtgtaaaac   13200
catgacatcc acttggagga tgcaataatg aagaaaacta caaatttaca tgcaactagt   13260
tatgcatgta gtctatataa tgaggatttt gcaatacttt cattcataca cactcactaa   13320
gttttacacg attataattt cttcatagcc agcagatctg ccggcatcga tcccgggcca   13380
tggcctgctt taatgagata tgcgagacgc ctatgatcgc atgatatttg ctttcaattc   13440
tgttgtgcac gttgtaaaaa acctgagcat gtgtagctca gatccttacc gccggtttcg   13500
gttcattcta atgaatatat cacccgttac tatcgtattt ttatgaataa tattctccgt   13560
tcaatttact gattgtccgt cgacgagctc ggcgcgcctc tagaggatcg atgaattcag   13620
atcggctgag tggctccttc aacgttgcgg ttctgtcagt tccaaacgta aacggcttg    13680 tcccgcgtca tcggcggggg tcataacgtg actcccttaa ttctccgctc atgatcagat   13740
tgtcgtttcc cgccttcagt ttaaactatc agtgtttgac aggatatatt ggcgggtaaa   13800
cctaagagaa aagagcgttt attagaataa tcggatattt aaaagggcgt gaaaaggttt   13860
atccttcgtc catttgtatg tgcatgccaa ccacagggt ccccca                   13905
```

<210> SEQ ID NO 69
<211> LENGTH: 1443
<212> TYPE: DNA
<213> ORGANISM: Phaeodactylum tricornutum
<220> FEATURE:

<221> NAME/KEY: CDS
<222> LOCATION: (9)..(1442)
<223> OTHER INFORMATION: Delta-6-desaturase

<400> SEQUENCE: 69

```
gatctaaa atg ggc aaa gga ggg gac gct cgg gcc tcg aag ggc tca acg        50
         Met Gly Lys Gly Gly Asp Ala Arg Ala Ser Lys Gly Ser Thr
         1               5                   10 gcg gct cgc aag atc agt tgg cag gaa gtc aag acc cac gcg tct ccg        98
Ala Ala Arg Lys Ile Ser Trp Gln Glu Val Lys Thr His Ala Ser Pro
15                  20                  25                  30 gag gac gcc tgg atc att cac tcc aat aag gtc tac gac gtg tcc aac       146
Glu Asp Ala Trp Ile Ile His Ser Asn Lys Val Tyr Asp Val Ser Asn
                35                  40                  45 tgg cac gaa cat ccc gga ggc gcc gtc att ttc acg cac gcc ggt gac       194
Trp His Glu His Pro Gly Gly Ala Val Ile Phe Thr His Ala Gly Asp
            50                  55                  60 gac atg acg gac att ttc gct gcc ttt cac gca ccc gga tcg cag tcg       242
Asp Met Thr Asp Ile Phe Ala Ala Phe His Ala Pro Gly Ser Gln Ser
        65                  70                  75 ctc atg aag aag ttc tac att ggc gaa ttg ctc ccg gaa acc acc ggc       290
Leu Met Lys Lys Phe Tyr Ile Gly Glu Leu Leu Pro Glu Thr Thr Gly
    80                  85                  90 aag gag ccg cag caa atc gcc ttt gaa aag ggc tac cgc gat ctg cgc       338
Lys Glu Pro Gln Gln Ile Ala Phe Glu Lys Gly Tyr Arg Asp Leu Arg
95                  100                 105                 110 tcc aaa ctc atc atg atg ggc atg ttc aag tcc aac aag tgg ttc tac       386
Ser Lys Leu Ile Met Met Gly Met Phe Lys Ser Asn Lys Trp Phe Tyr
                115                 120                 125 gtc tac aag tgc ctc agc aac atg gcc att tgg gcc gcc gcc tgt gct       434
Val Tyr Lys Cys Leu Ser Asn Met Ala Ile Trp Ala Ala Ala Cys Ala
            130                 135                 140 ctc gtc ttt tac tcg gac cgc ttc tgg gta cac ctg gcc agc gcc gtc       482
Leu Val Phe Tyr Ser Asp Arg Phe Trp Val His Leu Ala Ser Ala Val
        145                 150                 155 atg ctg gga aca ttc ttt cag cag tcg gga tgg ttg gca cac gac ttt       530
Met Leu Gly Thr Phe Phe Gln Gln Ser Gly Trp Leu Ala His Asp Phe
    160                 165                 170 ctg cac cac cag gtc ttc acc aag cgc aag cac ggg gat ctc gga gga       578
Leu His His Gln Val Phe Thr Lys Arg Lys His Gly Asp Leu Gly Gly
175                 180                 185                 190 ctc ttt tgg ggg aac ctc atg cag ggt tac tcc gta cag tgg tgg aaa       626
Leu Phe Trp Gly Asn Leu Met Gln Gly Tyr Ser Val Gln Trp Trp Lys
                195                 200                 205 aac aag cac aac gga cac cac gcc gtc ccc aac ctc cac tgc tcc tcc       674
Asn Lys His Asn Gly His His Ala Val Pro Asn Leu His Cys Ser Ser
            210                 215                 220 gca gtc gcg caa gat ggg gac ccg gac atc gat acc atg ccc ctt ctc       722
Ala Val Ala Gln Asp Gly Asp Pro Asp Ile Asp Thr Met Pro Leu Leu
        225                 230                 235 gcc tgg tcc gtc cag caa gcc cag tct tac cgg gaa ctc caa gcc gac       770
Ala Trp Ser Val Gln Gln Ala Gln Ser Tyr Arg Glu Leu Gln Ala Asp
    240                 245                 250 gga aag gat tcg ggt ttg gtc aag ttc atg atc cgt aac caa tcc tac       818
Gly Lys Asp Ser Gly Leu Val Lys Phe Met Ile Arg Asn Gln Ser Tyr
255                 260                 265                 270 ttt tac ttt ccc atc ttg ttg ctc gcc cgc ctg tcg tgg ttg aac gag       866
Phe Tyr Phe Pro Ile Leu Leu Leu Ala Arg Leu Ser Trp Leu Asn Glu
                275                 280                 285 tcc ttc aag tgc gcc ttt ggg ctt gga gct gcg tcg gag aac gct gct       914
```

```
Ser Phe Lys Cys Ala Phe Gly Leu Gly Ala Ala Ser Glu Asn Ala Ala
            290                 295                 300 ctc gaa ctc aag gcc aag ggt ctt cag tac ccc ctt ttg gaa aag gct    962
Leu Glu Leu Lys Ala Lys Gly Leu Gln Tyr Pro Leu Leu Glu Lys Ala
        305                 310                 315 ggc atc ctg ctg cac tac gct tgg atg ctt aca gtt tcg tcc ggc ttt    1010
Gly Ile Leu Leu His Tyr Ala Trp Met Leu Thr Val Ser Ser Gly Phe
    320                 325                 330 gga cgc ttc tcg ttc gcg tac acc gca ttt tac ttt cta acc gcg acc    1058
Gly Arg Phe Ser Phe Ala Tyr Thr Ala Phe Tyr Phe Leu Thr Ala Thr
335                 340                 345                 350 gcg tcc tgt gga ttc ttg ctc gcc att gtc ttt ggc ctc ggc cac aac    1106
Ala Ser Cys Gly Phe Leu Leu Ala Ile Val Phe Gly Leu Gly His Asn
                355                 360                 365 ggc atg gcc acc tac aat gcc gac gcc cgt ccg gac ttc tgg aag ctc    1154
Gly Met Ala Thr Tyr Asn Ala Asp Ala Arg Pro Asp Phe Trp Lys Leu
            370                 375                 380 caa gtc acc acg act cgc aac gtc acg ggc gga cac ggt ttc ccc caa    1202
Gln Val Thr Thr Thr Arg Asn Val Thr Gly Gly His Gly Phe Pro Gln
        385                 390                 395 gcc ttt gtc gac tgg ttc tgt ggt ggc ctc cag tac caa gtc gac cac    1250
Ala Phe Val Asp Trp Phe Cys Gly Gly Leu Gln Tyr Gln Val Asp His
    400                 405                 410 cac tta ttc ccc agc ctg ccc cga cac aat ctg gcc aag aca cac gca    1298
His Leu Phe Pro Ser Leu Pro Arg His Asn Leu Ala Lys Thr His Ala
415                 420                 425                 430 ctg gtc gaa tcg ttc tgc aag gag tgg ggt gtc cag tac cac gaa gcc    1346
Leu Val Glu Ser Phe Cys Lys Glu Trp Gly Val Gln Tyr His Glu Ala
                435                 440                 445 gac ctt gtg gac ggg acc atg gaa gtc ttg cac cat ttg ggc agc gtg    1394
Asp Leu Val Asp Gly Thr Met Glu Val Leu His His Leu Gly Ser Val
            450                 455                 460 gcc ggc gaa ttc gtc gtg gat ttt gta cgc gat gga ccc gcc atg taa a  1443
Ala Gly Glu Phe Val Val Asp Phe Val Arg Asp Gly Pro Ala Met
        465                 470                 475

<210> SEQ ID NO 70
<211> LENGTH: 477
<212> TYPE: PRT
<213> ORGANISM: Phaeodactylum tricornutum

<400> SEQUENCE: 70

Met Gly Lys Gly Gly Asp Ala Arg Ala Ser Lys Gly Ser Thr Ala Ala
1               5                   10                  15

Arg Lys Ile Ser Trp Gln Glu Val Lys Thr His Ala Ser Pro Glu Asp
            20                  25                  30

Ala Trp Ile Ile His Ser Asn Lys Val Tyr Asp Val Ser Asn Trp His
        35                  40                  45

Glu His Pro Gly Gly Ala Val Ile Phe Thr His Ala Gly Asp Asp Met
    50                  55                  60

Thr Asp Ile Phe Ala Ala Phe His Ala Pro Gly Ser Gln Ser Leu Met
65                  70                  75                  80

Lys Lys Phe Tyr Ile Gly Glu Leu Leu Pro Glu Thr Thr Gly Lys Glu
                85                  90                  95

Pro Gln Gln Ile Ala Phe Glu Lys Gly Tyr Arg Asp Leu Arg Ser Lys
            100                 105                 110

Leu Ile Met Met Gly Met Phe Lys Ser Asn Lys Trp Phe Tyr Val Tyr
        115                 120                 125
```

```
Lys Cys Leu Ser Asn Met Ala Ile Trp Ala Ala Ala Cys Ala Leu Val
            130                 135                 140

Phe Tyr Ser Asp Arg Phe Trp Val His Leu Ala Ser Ala Val Met Leu
145                 150                 155                 160

Gly Thr Phe Phe Gln Gln Ser Gly Trp Leu Ala His Asp Phe Leu His
                165                 170                 175

His Gln Val Phe Thr Lys Arg Lys His Gly Asp Leu Gly Gly Leu Phe
            180                 185                 190

Trp Gly Asn Leu Met Gln Gly Tyr Ser Val Gln Trp Lys Asn Lys
            195                 200                 205

His Asn Gly His His Ala Val Pro Asn Leu His Cys Ser Ser Ala Val
    210                 215                 220

Ala Gln Asp Gly Asp Pro Asp Ile Asp Thr Met Pro Leu Leu Ala Trp
225                 230                 235                 240

Ser Val Gln Gln Ala Gln Ser Tyr Arg Glu Leu Gln Ala Asp Gly Lys
                245                 250                 255

Asp Ser Gly Leu Val Lys Phe Met Ile Arg Asn Gln Ser Tyr Phe Tyr
            260                 265                 270

Phe Pro Ile Leu Leu Leu Ala Arg Leu Ser Trp Leu Asn Glu Ser Phe
        275                 280                 285

Lys Cys Ala Phe Gly Leu Gly Ala Ala Ser Glu Asn Ala Ala Leu Glu
    290                 295                 300

Leu Lys Ala Lys Gly Leu Gln Tyr Pro Leu Leu Glu Lys Ala Gly Ile
305                 310                 315                 320

Leu Leu His Tyr Ala Trp Met Leu Thr Val Ser Ser Gly Phe Gly Arg
                325                 330                 335

Phe Ser Phe Ala Tyr Thr Ala Phe Tyr Phe Leu Thr Ala Thr Ala Ser
            340                 345                 350

Cys Gly Phe Leu Leu Ala Ile Val Phe Gly Leu Gly His Asn Gly Met
        355                 360                 365

Ala Thr Tyr Asn Ala Asp Ala Arg Pro Asp Phe Trp Lys Leu Gln Val
    370                 375                 380

Thr Thr Thr Arg Asn Val Thr Gly Gly His Gly Phe Pro Gln Ala Phe
385                 390                 395                 400

Val Asp Trp Phe Cys Gly Gly Leu Gln Tyr Gln Val Asp His His Leu
                405                 410                 415

Phe Pro Ser Leu Pro Arg His Asn Leu Ala Lys Thr His Ala Leu Val
            420                 425                 430

Glu Ser Phe Cys Lys Glu Trp Gly Val Gln Tyr His Glu Ala Asp Leu
        435                 440                 445

Val Asp Gly Thr Met Glu Val Leu His His Leu Gly Ser Val Ala Gly
    450                 455                 460

Glu Phe Val Val Asp Phe Val Arg Asp Gly Pro Ala Met
465                 470                 475

<210> SEQ ID NO 71
<211> LENGTH: 17061
<212> TYPE: DNA
<213> ORGANISM: Artificial sequence
<220> FEATURE:
<223> OTHER INFORMATION: Vector comprising Phaeodactylum tricornutum
      delta-6-desaturase gene
<220> FEATURE:
<223> OTHER INFORMATION: Vector comprising Physcomitrella patens
      delta-6-elongase gene
<220> FEATURE:
<223> OTHER INFORMATION: Vector comprising Caenorhabditis elegans LPLAT
```

```
            gene
<220> FEATURE:
<221> NAME/KEY: CDS
<222> LOCATION: (4554)..(5987)
<223> OTHER INFORMATION: Phaeodactylum tricornutum delta-6-desaturase
<220> FEATURE:
<221> NAME/KEY: CDS
<222> LOCATION: (2805)..(3653)
<223> OTHER INFORMATION: Caenorhabditis elegans LPLAT
<220> FEATURE:
<221> NAME/KEY: CDS
<222> LOCATION: (1026)..(1898)
<223> OTHER INFORMATION: Physcomitrella patens delta-6-elongase

<400> SEQUENCE: 71
tggggaaccc tgtggttggc atgcacatac aaatggacga aggataaacc ttttcacgcc      60
cttttaaata tccgattatt ctaataaacg ctctttttctc ttaggtttac ccgccaatat    120
atcctgtcaa acactgatag tttaaactga aggcgggaaa cgacaatctg atcatgagcg    180
gagaattaag ggagtcacgt tatgaccccc gccgatgacg cggacaagc cgttttacgt     240 ttggaactga cagaaccgca acgttgaagg agccactcag ccgatctgaa ttcatcgatc    300
ctctagaggc gcgccgagct cctcgagcaa atttacacat tgccactaaa cgtctaaacc    360
cttgtaattt gttttgttt tactatgtgt gttatgtatt tgatttgcga taaatttta     420 tatttggtac taaatttata acaccttta tgctaacgtt tgccaacact tagcaattg     480 caagttgatt aattgattct aaattattt tgtcttctaa atacatatac taatcaactg    540
gaaatgtaaa tatttgctaa tatttctact ataggagaat taaagtgagt gaatatggta    600
ccacaaggtt tggagattta attgttgcaa tgctgcatgg atggcatata caccaaacat    660
tcaataattc ttgaggataa taatggtacc acacaagatt tgaggtgcat gaacgtcacg    720
tggacaaaag gtttagtaat ttttcaagac aacaatgtta ccacacacaa gttttgaggt    780
gcatgcatgg atgccctgtg gaaagtttaa aaatattttg gaaatgattt gcatggaagc    840
catgtgtaaa accatgacat ccacttggag gatgcaataa tgaagaaaac tacaaattta    900
catgcaacta gttatgcatg tagtctctat aatgaggatt ttgcaatact ttcattcata    960
cacactcact aagttttaca cgattataat ttcttcatag ccagcccacc gcggtgggcg   1020 gccgc atg gag gtc gtg gag aga ttc tac ggt gag ttg gat ggg aag gtc   1070
      Met Glu Val Val Glu Arg Phe Tyr Gly Glu Leu Asp Gly Lys Val
        1               5                  10                  15 tcg cag ggc gtg aat gca ttg ctg ggt agt ttt ggg gtg gag ttg acg      1118
Ser Gln Gly Val Asn Ala Leu Leu Gly Ser Phe Gly Val Glu Leu Thr
                 20                  25                  30 gat acg ccc act acc aaa ggc ttg ccc ctc gtt gac agt ccc aca ccc      1166
Asp Thr Pro Thr Thr Lys Gly Leu Pro Leu Val Asp Ser Pro Thr Pro
             35                  40                  45 atc gtc ctc ggt gtt tct gta tac ttg act att gtc att gga ggg ctt      1214
Ile Val Leu Gly Val Ser Val Tyr Leu Thr Ile Val Ile Gly Gly Leu
         50                  55                  60 ttg tgg ata aag gcc agg gat ctg aaa ccg cgc gcc tcg gag cca ttt      1262
Leu Trp Ile Lys Ala Arg Asp Leu Lys Pro Arg Ala Ser Glu Pro Phe
 65                  70                  75 ttg ctc caa gct ttg gtg ctt gtg cac aac ctg ttc tgt ttt gcg ctc      1310
Leu Leu Gln Ala Leu Val Leu Val His Asn Leu Phe Cys Phe Ala Leu
 80                  85                  90                  95 agt ctg tat atg tgc gtg ggc atc gct tat cag gct att acc tgg cgg      1358
Ser Leu Tyr Met Cys Val Gly Ile Ala Tyr Gln Ala Ile Thr Trp Arg
                100                 105                 110 tac tct ctc tgg ggc aat gca tac aat cct aaa cat aaa gag atg gcg      1406
```

```
                Tyr Ser Leu Trp Gly Asn Ala Tyr Asn Pro Lys His Lys Glu Met Ala
                            115                 120                 125 att ctg gta tac ttg ttc tac atg tct aag tac gtg gaa ttc atg gat        1454
Ile Leu Val Tyr Leu Phe Tyr Met Ser Lys Tyr Val Glu Phe Met Asp
            130                 135                 140 acc gtt atc atg ata ctg aag cgc agc acc agg caa ata agc ttc ctc        1502
Thr Val Ile Met Ile Leu Lys Arg Ser Thr Arg Gln Ile Ser Phe Leu
        145                 150                 155 cac gtt tat cat cat tct tca att tcc ctc att tgg tgg gct att gct        1550
His Val Tyr His His Ser Ser Ile Ser Leu Ile Trp Trp Ala Ile Ala
160                 165                 170                 175 cat cac gct cct ggc ggt gaa gca tat tgg tct gcg gct ctg aac tca        1598
His His Ala Pro Gly Gly Glu Ala Tyr Trp Ser Ala Ala Leu Asn Ser
                180                 185                 190 gga gtg cat gtt ctc atg tat gcg tat tac ttc ttg gct gcc tgc ctt        1646
Gly Val His Val Leu Met Tyr Ala Tyr Tyr Phe Leu Ala Ala Cys Leu
            195                 200                 205 cga agt agc cca aag tta aaa aat aag tac ctt ttt tgg ggc agg tac        1694
Arg Ser Ser Pro Lys Leu Lys Asn Lys Tyr Leu Phe Trp Gly Arg Tyr
        210                 215                 220 ttg aca caa ttc caa atg ttc cag ttt atg ctg aac tta gtg cag gct        1742
Leu Thr Gln Phe Gln Met Phe Gln Phe Met Leu Asn Leu Val Gln Ala
    225                 230                 235 tac tac gac atg aaa acg aat gcg cca tat cca caa tgg ctg atc aag        1790
Tyr Tyr Asp Met Lys Thr Asn Ala Pro Tyr Pro Gln Trp Leu Ile Lys
240                 245                 250                 255 att ttg ttc tac tac atg atc tcg ttg ctg ttt ctt ttc ggc aat ttt        1838
Ile Leu Phe Tyr Tyr Met Ile Ser Leu Leu Phe Leu Phe Gly Asn Phe
                260                 265                 270 tac gta caa aaa tac atc aaa ccc tct gac gga aag caa aag gga gct        1886
Tyr Val Gln Lys Tyr Ile Lys Pro Ser Asp Gly Lys Gln Lys Gly Ala
            275                 280                 285 aaa act gag tga tctagaaggc ctcctgcttt aatgagatat gcgagacgcc           1938
Lys Thr Glu
        290 tatgatcgca tgatatttgc tttcaattct gttgtgcacg ttgtaaaaaa cctgagcatg     1998 tgtagctcag atccttaccg ccggtttcgg ttcattctaa tgaatatatc acccgttact     2058 atcgtatttt tatgaataat attctccgtt caatttactg attgtccgtc gagcaaattt     2118 acacattgcc actaaacgtc taaacccttg taatttgttt ttgttttact atgtgtgtta     2178 tgtatttgat ttgcgataaa tttttatatt tggtactaaa tttataacac cttttatgct     2238 aacgtttgcc aacacttagc aatttgcaag ttgattaatt gattctaaat tatttttgtc     2298 ttctaaatac atatactaat caactggaaa tgtaaatatt tgctaatatt tctactatag     2358 gagaattaaa gtgagtgaat atggtaccac aaggtttgga gatttaattg ttgcaatgct     2418 gcatggatgg catatacacc aaacattcaa taattcttga ggataataat ggtaccacac     2478 aagatttgag gtgcatgaac gtcacgtgga caaaaggttt agtaattttt caagacaaca     2538 atgttaccac acacaagttt tgaggtgcat gcatggatgc cctgtggaaa gtttaaaaat     2598 attttggaaa tgatttgcat ggaagccatg tgtaaaacca tgacatccac ttggaggatg     2658 caataatgaa gaaaactaca aatttacatg caactagtta tgcatgtagt ctatataatg     2718 aggattttgc aatactttca ttcatacaca ctcactaagt tttacacgat tataatttct     2778 tcatagccag cggatccgcc cacata atg gag aac ttc tgg tct att gtt gtg      2831
                               Met Glu Asn Phe Trp Ser Ile Val Val
                               295
```

```
ttt ttt cta ctc tca att ctc ttc att tta tat aac ata tcg aca gta    2879
Phe Phe Leu Leu Ser Ile Leu Phe Ile Leu Tyr Asn Ile Ser Thr Val
300             305                 310                 315 tgc cac tac tat atg cgg att tcg ttt tat tac ttc aca att tta ttg    2927
Cys His Tyr Tyr Met Arg Ile Ser Phe Tyr Tyr Phe Thr Ile Leu Leu
                320                 325                 330 cat gga atg gaa gtt tgt gtt aca atg atc cct tct tgg cta aat ggg    2975
His Gly Met Glu Val Cys Val Thr Met Ile Pro Ser Trp Leu Asn Gly
            335                 340                 345 aag ggt gct gat tac gtg ttt cac tcg ttt ttc tat tgg tgt aaa tgg    3023
Lys Gly Ala Asp Tyr Val Phe His Ser Phe Phe Tyr Trp Cys Lys Trp
        350                 355                 360 act ggt gtt cat aca aca gtc tat gga tat gaa aaa aca caa gtt gaa    3071
Thr Gly Val His Thr Thr Val Tyr Gly Tyr Glu Lys Thr Gln Val Glu
    365                 370                 375 ggt ccg gct gta gtt att tgt aat cat cag agt tct ctc gac att cta    3119
Gly Pro Ala Val Val Ile Cys Asn His Gln Ser Ser Leu Asp Ile Leu
380             385                 390                 395 tcg atg gca tca atc tgg ccg aag aat tgt gtt gta atg atg aaa cga    3167
Ser Met Ala Ser Ile Trp Pro Lys Asn Cys Val Val Met Met Lys Arg
                400                 405                 410 att ctt gcc tat gtt cca ttc ttc aat ctc gga gcc tac ttt tcc aac    3215
Ile Leu Ala Tyr Val Pro Phe Phe Asn Leu Gly Ala Tyr Phe Ser Asn
            415                 420                 425 aca atc ttc atc gat cga tat aac cgt gaa cgt gcg atg gct tca gtt    3263
Thr Ile Phe Ile Asp Arg Tyr Asn Arg Glu Arg Ala Met Ala Ser Val
        430                 435                 440 gat tat tgt gca tct gaa atg aag aac aga aat ctt aaa ctt tgg gta    3311
Asp Tyr Cys Ala Ser Glu Met Lys Asn Arg Asn Leu Lys Leu Trp Val
    445                 450                 455 ttt ccg gaa gga aca aga aat cgt gaa gga ggg ttc att cca ttc aag    3359
Phe Pro Glu Gly Thr Arg Asn Arg Glu Gly Gly Phe Ile Pro Phe Lys
460             465                 470                 475 aaa gga gca ttc aat att gca gtt cgt gcg cag att ccc att att cca    3407
Lys Gly Ala Phe Asn Ile Ala Val Arg Ala Gln Ile Pro Ile Ile Pro
                480                 485                 490 gtt gta ttc tca gac tat cgg gat ttc tac tca aag cca ggc cga tat    3455
Val Val Phe Ser Asp Tyr Arg Asp Phe Tyr Ser Lys Pro Gly Arg Tyr
            495                 500                 505 ttc aag aat gat gga gaa gtt gtt att cga gtt ctg gat gcg att cca    3503
Phe Lys Asn Asp Gly Glu Val Val Ile Arg Val Leu Asp Ala Ile Pro
        510                 515                 520 aca aaa ggg ctc act ctt gat gac gtc agc gag ttg tct gat atg tgt    3551
Thr Lys Gly Leu Thr Leu Asp Asp Val Ser Glu Leu Ser Asp Met Cys
    525                 530                 535 cgg gac gtt atg ttg gca gcc tat aag gaa gtt act cta gaa gct cag    3599
Arg Asp Val Met Leu Ala Ala Tyr Lys Glu Val Thr Leu Glu Ala Gln
540             545                 550                 555 caa cga aat gcg aca cgg cgt gga gaa aca aaa gac ggg aag aaa tct    3647
Gln Arg Asn Ala Thr Arg Arg Gly Glu Thr Lys Asp Gly Lys Lys Ser
                560                 565                 570 gag taa gctagcgtta accctgcttt aatgagatat gcgagacgcc tatgatcgca     3703
Glu tgatatttgc tttcaattct gttgtgcacg ttgtaaaaaa cctgagcatg tgtagctcag   3763
atccttaccg ccggtttcgg ttcattctaa tgaatatatc acccgttact atcgtatttt   3823
tatgaataat attctccgtt caatttactg attgtccgtc gagcaaattt acacattgcc   3883
actaaacgtc taaccctttg taatttgttt ttgttttact atgtgtgtta tgtatttgat   3943
```

-continued

```
ttgcgataaa ttttatatt tggtactaaa tttataacac cttttatgct aacgtttgcc   4003
aacacttagc aatttgcaag ttgattaatt gattctaaat tattttgtc ttctaaatac    4063 atatactaat caactggaaa tgtaaatatt tgctaatatt tctactatag gagaattaaa   4123
gtgagtgaat atggtaccac aaggtttgga gatttaattg ttgcaatgct gcatggatgg   4183
catatacacc aaacattcaa taattcttga ggataataat ggtaccacac aagatttgag   4243
gtgcatgaac gtcacgtgga caaaaggttt agtaatttt caagacaaca atgttaccac    4303
acacaagttt tgaggtgcat gcatggatgc cctgtggaaa gtttaaaaat attttggaaa   4363
tgatttgcat ggaagccatg tgtaaaacca tgacatccac ttggaggatg caataatgaa   4423
gaaaactaca aatttacatg caactagtta tgcatgtagt ctatataatg aggattttgc   4483
aatactttca ttcatacaca ctcactaagt tttacacgat tataatttct tcatagccag   4543
cagatctaaa atg ggc aaa gga ggg gac gct cgg gcc tcg aag ggc tca     4592
          Met Gly Lys Gly Gly Asp Ala Arg Ala Ser Lys Gly Ser
              575                 580                 585 acg gcg gct cgc aag atc agt tgg cag gaa gtc aag acc cac gcg tct    4640
Thr Ala Ala Arg Lys Ile Ser Trp Gln Glu Val Lys Thr His Ala Ser
            590                 595                 600 ccg gag gac gcc tgg atc att cac tcc aat aag gtc tac gac gtg tcc    4688
Pro Glu Asp Ala Trp Ile Ile His Ser Asn Lys Val Tyr Asp Val Ser
        605                 610                 615 aac tgg cac gaa cat ccc gga ggc gcc gtc att ttc acg cac gcc ggt    4736
Asn Trp His Glu His Pro Gly Gly Ala Val Ile Phe Thr His Ala Gly
        620                 625                 630 gac gac atg acg gac att ttc gct gcc ttt cac gca ccc gga tcg cag    4784
Asp Asp Met Thr Asp Ile Phe Ala Ala Phe His Ala Pro Gly Ser Gln
        635                 640                 645 tcg ctc atg aag aag ttc tac att ggc gaa ttg ctc ccg gaa acc acc    4832
Ser Leu Met Lys Lys Phe Tyr Ile Gly Glu Leu Leu Pro Glu Thr Thr
650                 655                 660                 665 ggc aag gag ccg cag caa atc gcc ttt gaa aag ggc tac cgc gat ctg    4880
Gly Lys Glu Pro Gln Gln Ile Ala Phe Glu Lys Gly Tyr Arg Asp Leu
            670                 675                 680 cgc tcc aaa ctc atc atg atg ggc atg ttc aag tcc aac aag tgg ttc    4928
Arg Ser Lys Leu Ile Met Met Gly Met Phe Lys Ser Asn Lys Trp Phe
        685                 690                 695 tac gtc tac aag tgc ctc agc aac atg gcc att tgg gcc gcc gcc tgt    4976
Tyr Val Tyr Lys Cys Leu Ser Asn Met Ala Ile Trp Ala Ala Ala Cys
        700                 705                 710 gct ctc gtc ttt tac tcg gac cgc ttc tgg gta cac ctg gcc agc gcc    5024
Ala Leu Val Phe Tyr Ser Asp Arg Phe Trp Val His Leu Ala Ser Ala
        715                 720                 725 gtc atg ctg gga aca ttc ttt cag cag tcg gga tgg ttg gca cac gac    5072
Val Met Leu Gly Thr Phe Phe Gln Gln Ser Gly Trp Leu Ala His Asp
730                 735                 740                 745 ttt ctg cac cac cag gtc ttc acc aag cgc aag cac ggg gat ctc gga    5120
Phe Leu His His Gln Val Phe Thr Lys Arg Lys His Gly Asp Leu Gly
            750                 755                 760 gga ctc ttt tgg ggg aac ctc atg cag ggt tac tcc gta cag tgg tgg    5168
Gly Leu Phe Trp Gly Asn Leu Met Gln Gly Tyr Ser Val Gln Trp Trp
        765                 770                 775 aaa aac aag cac aac gga cac cac gcc gtc ccc aac ctc cac tgc tcc    5216
Lys Asn Lys His Asn Gly His His Ala Val Pro Asn Leu His Cys Ser
        780                 785                 790 tcc gca gtc gcg caa gat ggg gac ccg gac atc gat acc atg ccc ctt    5264
Ser Ala Val Ala Gln Asp Gly Asp Pro Asp Ile Asp Thr Met Pro Leu
        795                 800                 805
```

| | | |
|---|---|---|
| ctc gcc tgg tcc gtc cag caa gcc cag tct tac cgg gaa ctc caa gcc<br>Leu Ala Trp Ser Val Gln Gln Ala Gln Ser Tyr Arg Glu Leu Gln Ala<br>810                        815                         820                        825 | | 5312 |
| gac gga aag gat tcg ggt ttg gtc aag ttc atg atc cgt aac caa tcc<br>Asp Gly Lys Asp Ser Gly Leu Val Lys Phe Met Ile Arg Asn Gln Ser<br>                       830                         835                        840 | | 5360 |
| tac ttt tac ttt ccc atc ttg ttg ctc gcc cgc ctg tcg tgg ttg aac<br>Tyr Phe Tyr Phe Pro Ile Leu Leu Leu Ala Arg Leu Ser Trp Leu Asn<br>                       845                         850                       855 | | 5408 |
| gag tcc ttc aag tgc gcc ttt ggg ctt gga gct gcg tcg gag aac gct<br>Glu Ser Phe Lys Cys Ala Phe Gly Leu Gly Ala Ala Ser Glu Asn Ala<br>         860                        865                         870 | | 5456 |
| gct ctc gaa ctc aag gcc aag ggt ctt cag tac ccc ctt ttg gaa aag<br>Ala Leu Glu Leu Lys Ala Lys Gly Leu Gln Tyr Pro Leu Leu Glu Lys<br>875                        880                         885 | | 5504 |
| gct ggc atc ctg ctg cac tac gct tgg atg ctt aca gtt tcg tcc ggc<br>Ala Gly Ile Leu Leu His Tyr Ala Trp Met Leu Thr Val Ser Ser Gly<br>890                        895                         900                       905 | | 5552 |
| ttt gga cgc ttc tcg ttc gcg tac acc gca ttt tac ttt cta acc gcg<br>Phe Gly Arg Phe Ser Phe Ala Tyr Thr Ala Phe Tyr Phe Leu Thr Ala<br>                       910                         915                       920 | | 5600 |
| acc gcg tcc tgt gga ttc ttg ctc gcc att gtc ttt ggc ctc ggc cac<br>Thr Ala Ser Cys Gly Phe Leu Leu Ala Ile Val Phe Gly Leu Gly His<br>                       925                         930                       935 | | 5648 |
| aac ggc atg gcc acc tac aat gcc gac gcc cgt ccg gac ttc tgg aag<br>Asn Gly Met Ala Thr Tyr Asn Ala Asp Ala Arg Pro Asp Phe Trp Lys<br>         940                        945                         950 | | 5696 |
| ctc caa gtc acc acg act cgc aac gtc acg ggc gga cac ggt ttc ccc<br>Leu Gln Val Thr Thr Thr Arg Asn Val Thr Gly Gly His Gly Phe Pro<br>955                        960                         965 | | 5744 |
| caa gcc ttt gtc gac tgg ttc tgt ggt ggc ctc cag tac caa gtc gac<br>Gln Ala Phe Val Asp Trp Phe Cys Gly Gly Leu Gln Tyr Gln Val Asp<br>970                        975                         980                       985 | | 5792 |
| cac cac tta ttc ccc agc ctg ccc cga cac aat ctg gcc aag aca cac<br>His His Leu Phe Pro Ser Leu Pro Arg His Asn Leu Ala Lys Thr His<br>                       990                         995                     1000 | | 5840 |
| gca ctg gtc gaa tcg ttc tgc aag gag tgg ggt gtc cag tac cac<br>Ala Leu Val Glu Ser Phe Cys Lys Glu Trp Gly Val Gln Tyr His<br>                       1005                   1010                 1015 | | 5885 |
| gaa gcc gac ctt gtg gac ggg acc atg gaa gtc ttg cac cat ttg<br>Glu Ala Asp Leu Val Asp Gly Thr Met Glu Val Leu His His Leu<br>                    1020                  1025                 1030 | | 5930 |
| ggc agc gtg gcc ggc gaa ttc gtc gtg gat ttt gta cgc gat gga<br>Gly Ser Val Ala Gly Glu Phe Val Val Asp Phe Val Arg Asp Gly<br>                 1035                   1040                 1045 | | 5975 |
| ccc gcc atg taa agatctgccg gcatcgatcc cgggccatgg cctgctttaa<br>Pro Ala Met | | 6027 |
| tgagatatgc gagacgccta tgatcgcatg atatttgctt tcaattctgt tgtgcacgtt | | 6087 |
| gtaaaaaacc tgagcatgtg tagctcagat ccttaccgcc ggtttcggtt cattctaatg | | 6147 |
| aatatatcac ccgttactat cgtattttta tgaataat tctccgttca atttactgat | | 6207 |
| tgtccgtcga cgagctcggc gcgccgtcga cctgcaggca tgcaagcttc acgctgccgc | | 6267 |
| aagcactcag ggcgcaaggg ctgctaaagg aagcggaaca cgtagaaagc cagtccgcag | | 6327 |
| aaacggtgct gaccccggat gaatgtcagc tactgggcta tctggacaag gaaaacgca | | 6387 |
| agcgcaaaga gaaagcaggt agcttgcagt gggcttacat ggcgatagct agactgggcg | | 6447 |
| gttttatgga cagcaagcga accggaattg ccagctgggg cgccctctgg taaggttggg | | 6507 |

```
aagccctgca aagtaaactg gatggctttc ttgccgccaa ggatctgatg gcgcagggga    6567
tcaagatcat gagcggagaa ttaagggagt cacgttatga cccccgccga tgacgcggga    6627
caagccgttt tacgtttgga actgacagaa ccgcaacgtt gaaggagcca ctcagccgcg    6687
ggtttctgga gtttaatgag ctaagcacat acgtcagaaa ccattattgc gcgttcaaaa    6747
gtcgcctaag gtcactatca gctagcaaat atttcttgtc aaaaatgctc cactgacgtt    6807
ccataaattc ccctcggtat ccaattagag tctcatattc actctcaatc cagatctcga    6867
ctctagtcga gggcccatgg gagcttggat tgaacaagat ggattgcacg caggttctcc    6927
ggccgcttgg gtggagaggc tattcggcta tgactgggca caacagacaa tcggctgctc    6987
tgatgccgcc gtgttccggc tgtcagcgca ggggcgcccg gttcttttg tcaagaccga     7047 cctgtccggt gccctgaatg aactgcagga cgaggcagcg cggctatcgt ggctggccac    7107
gacgggcgtt ccttgcgcag ctgtgctcga cgttgtcact gaagcgggaa gggactggct    7167
gctattgggc gaagtgccgg ggcaggatct cctgtcatct caccttgctc ctgccgagaa    7227
agtatccatc atggctgatg caatgcgcg gctgcatacg cttgatccgg ctacctgccc     7287
attcgaccac caagcgaaac atcgcatcga gcgagcacgt actcggatgg aagccggtct    7347
tgtcgatcag gatgatctgg acgaagagca tcaggggctc gcgccagccg aactgttcgc    7407
caggctcaag gcgcgcatgc ccgacggcga ggatctcgtc gtgacccatg gcgatgcctg    7467
cttgccgaat atcatggtgg aaaatggccg cttttctgga ttcatcgact gtggccggct    7527
gggtgtggcg gaccgctatc aggacatagc gttggctacc cgtgatattg ctgaagagct    7587
tggcggcgaa tgggctgacc gcttcctcgt gctttacggt atcgccgctc ccgattcgca    7647
gcgcatcgcc ttctatcgcc ttcttgacga gttcttctga gcgggaccca agctagcttc    7707
gacggatccc ccgatgagct aagctagcta tatcatcaat ttatgtatta cacataatat    7767
cgcactcagt ctttcatcta cggcaatgta ccagctgata taatcagtta ttgaaatatt    7827
tctgaattta aacttgcatc aataaattta tgttttgct tggactataa acctgactt      7887 gttattttat caataaatat ttaaactata tttctttcaa gatgggaatt aattcactgg    7947
ccgtcgtttt acaacgtcgt gactgggaaa accctggcgt tacccaactt aatcgccttg    8007
cagcacatcc ccctttcgcc agctggcgta atagcgaaga ggcccgcacc gatcgccctt    8067
cccaacagtt gcgcagcctg aatggcgccc gctcctttcg ctttcttccc ttcctttctc    8127
gccacgttcg ccggctttcc ccgtcaagct ctaaatcggg ggctcccttt agggttccga    8187
tttagtgctt tacggcacct cgaccccaaa aaacttgatt tgggtgatgg ttcacgtagt    8247
gggccatcgc cctgatagac ggtttttcgc cctttgacgt tggagtccac gttctttaat    8307
agtggactct tgttccaaac tggaacaaca ctcaaccta tctcgggcta ttcttttgat     8367
ttataaggga ttttgccgat ttcggaacca ccatcaaaca ggattttcgc ctgctggggc    8427
aaaccagcgt ggaccgcttg ctgcaactct ctcagggcca ggcggtgaag gcaatcagc     8487 tgttgcccgt ctcactggtg aaaagaaaaa ccacccagt acattaaaaa cgtccgcaat     8547
gtgttattaa gttgtctaag cgtcaatttg tttacaccac aatatatcct gccaccagcc    8607
agccaacagc tccccgaccg gcagctcggc acaaaatcac cactcgatac aggcagccca    8667
tcagtccggg acggcgtcag cgggagagcc gttgtaaggc ggcagacttt gctcatgtta    8727
ccgatgctat tcggaagaac ggcaactaag ctgccgggtt tgaaacacgg atgatctcgc    8787
ggagggtagc atgttgattg taacgatgac agagcgttgc tgcctgtgat caaatatcat    8847
```

```
ctccctcgca gagatccgaa ttatcagcct tcttattcat ttctcgctta accgtgacag    8907
gctgtcgatc ttgagaacta tgccgacata ataggaaatc gctggataaa gccgctgagg    8967
aagctgagtg gcgctatttc tttagaagtg aacgttgacg atatcaactc ccctatccat    9027
tgctcaccga atggtacagg tcggggaccc gaagttccga ctgtcggcct gatgcatccc    9087
cggctgatcg accccagatc tggggctgag aaagcccagt aaggaaacaa ctgtaggttc    9147
gagtcgcgag atccccggga accaaaggaa gtaggttaaa cccgctccga tcaggccgag    9207
ccacgccagg ccgagaacat tggttcctgt aggcatcggg attggcggat caaacactaa    9267
agctactgga acgagcagaa gtcctccggc cgccagttgc caggcggtaa aggtgagcag    9327
aggcacggga ggttgccact tgcgggtcag cacggttccg aacgccatgg aaaccgcccc    9387
cgccaggccc gctgcgacgc cgacaggatc tagcgctgcg tttggtgtca acaccaacag    9447
cgccacgccc gcagttccgc aaatagcccc caggaccgcc atcaatcgta tcgggctacc    9507
tagcagagcg gcagagatga acacgaccat cagcggctgc acagcgccta ccgtcgccgc    9567
gaccccgccc ggcaggcggt agaccgaaat aaacaacaag ctccagaata gcgaaatatt    9627
aagtgcgccg aggatgaaga tgcgcatcca ccagattccc gttggaatct gtcggacgat    9687
catcacgagc aataaacccg ccggcaacgc ccgcagcagc ataccggcga cccctcggcc    9747
tcgctgttcg ggctccacga aaacgccgga cagatgcgcc ttgtgagcgt ccttggggcc    9807
gtcctcctgt ttgaagaccg acagcccaat gatctcgccg tcgatgtagg cgccgaatgc    9867
cacggcatct cgcaaccgtt cagcgaacgc ctccatgggc ttttttctcct cgtgctcgta    9927
aacggacccg aacatctctg gagctttctt cagggccgac aatcggatct cgcggaaatc    9987
ctgcacgtcg gccgctccaa gccgtcgaat ctgagcctta atcacaattg tcaattttaa   10047
tcctctgttt atcggcagtt cgtagagcgc gccgtgcgtc ccgagcgata ctgagcgaag   10107
caagtgcgtc gagcagtgcc cgcttgttcc tgaaatgcca gtaaagcgct ggctgctgaa   10167
cccccagccg gaactgaccc cacaaggccc tagcgtttgc aatgcaccag gtcatcattg   10227
acccaggcgt gttccaccag gccgctgcct cgcaactctt cgcaggcttc gccgacctgc   10287
tcgcgccact tcttcacgcg ggtggaatcc gatccgcaca tgaggcggaa ggtttccagc   10347
ttgagcgggt acggctcccg gtgcgagctg aaatagtcga acatccgtcg ggccgtcggc   10407
gacagcttgc ggtacttctc ccatatgaat ttcgtgtagt ggtcgccagc aaacagcacg   10467
acgatttcct cgtcgatcag gacctggcaa cgggacgttt tcttgccacg gtccaggacg   10527
cggaagcggt gcagcagcga caccgattcc aggtgcccaa cgcggtcgga cgtgaagccc   10587
atcgccgtcg cctgtaggcg cgacaggcat tcctcggcct tcgtgtaata ccggccattg   10647
atcgaccagc ccaggtcctg gcaaagctcg tagaacgtga aggtgatcgg ctcgccgata   10707
ggggtgcgct tcgcgtactc caacacctgc tgccacacca gttcgtcatc gtcggcccgc   10767
agctcgacgc cggtgtaggt gatcttcacg tccttgttga cgtggaaaat gaccttgttt   10827
tgcagcgcct cgcgcgggat tttcttgttg cgcgtggtga acagggcaga gcgggccgtg   10887
tcgtttggca tcgctcgcat cgtgtccggc cacggcgcaa tatcgaacaa ggaaagctgc   10947
atttccttga tctgctgctt cgtgtgtttc agcaacgcgg cctgcttggc ctcgctgacc   11007
tgttttgcca ggtcctcgcc ggcggttttt cgcttcttgg tcgtcatagt tcctcgcgtg   11067
tcgatggtca tcgacttcgc caaacctgcc gcctcctgtt cgagacgacg cgaacgctcc   11127
acggcggcca atggcgcggg cagggcaggg ggagccagtt gcacgctgtc gcgctcgatc   11187
ttggccgtag cttgctggac catcgagccg acggactgga aggtttcgcg gggcgcacgc   11247
```

```
atgacggtgc ggcttgcgat ggtttcggca tcctcggcgg aaaacccgc gtcgatcagt    11307 tcttgcctgt atgccttccg gtcaaacgtc cgattcattc accctccttg cgggattgcc    11367
ccgactcacg ccggggcaat gtgcccttat tcctgatttg acccgcctgg tgccttggtg    11427
tccagataat ccaccttatc ggcaatgaag tcggtcccgt agaccgtctg gccgtccttc    11487
tcgtacttgg tattccgaat cttgccctgc acgaatacca gcgacccctt gcccaaatac    11547
ttgccgtggg cctcggcctg agagccaaaa cacttgatgc ggaagaagtc ggtgcgctcc    11607
tgcttgtcgc cggcatcgtt gcgccacatc taggtactaa acaattcat ccagtaaaat    11667 ataatatttt attttctccc aatcaggctt gatccccagt aagtcaaaaa atagctcgac    11727
atactgttct tccccgatat cctccctgat cgaccggacg cagaaggcaa tgtcatacca    11787
cttgtccgcc ctgccgcttc tcccaagatc aataaagcca cttactttgc catctttcac    11847
aaagatgttg ctgtctccca ggtcgccgtg ggaaaagaca agttcctctt cgggcttttc    11907 cgtcttaaa aaatcataca gctcgcgcgg atctttaaat ggagtgtctt cttcccagtt    11967
ttcgcaatcc acatcggcca gatcgttatt cagtaagtaa tccaattcgg ctaagcggct    12027
gtctaagcta ttcgtatagg gacaatccga tatgtcgatg gagtgaaaga gcctgatgca    12087
ctccgcatac agctcgataa tcttttcagg gctttgttca tcttcatact cttccgagca    12147
aaggacgcca tcggcctcac tcatgagcag attgctccag ccatcatgcc gttcaaagtg    12207
caggaccttt ggaacaggca gctttccttc cagccatagc atcatgtcct tttcccgttc    12267
cacatcatag gtggtccctt tataccggct gtccgtcatt tttaaatata ggttttcatt    12327
ttctcccacc agcttatata ccttagcagg agacattcct tccgtatctt ttacgcagcg    12387 gtattttcg atcagttttt tcaattccgg tgatattctc attttagcca tttattattt    12447
ccttcctctt ttctacagta tttaaagata ccccaagaag ctaattataa caagacgaac    12507
tccaattcac tgttccttgc attctaaaac cttaaatacc agaaaacagc tttttcaaag    12567
ttgttttcaa agttggcgta taacatagta tcgacggagc cgattttgaa accacaatta    12627
tgggtgatgc tgccaactta ctgatttagt gtatgatggt gttttgagg tgctccagtg    12687 gcttctgtgt ctatcagctg tccctcctgt tcagctactg acggggtggt gcgtaacggc    12747
aaaagcaccg ccggacatca gcgctatctc tgctctcact gccgtaaaac atggcaactg    12807
cagttcactt acaccgcttc tcaacccggt acgcaccaga aaatcattga tatggccatg    12867
aatggcgttg gatgccgggc aacagcccgc attatgggcg ttggcctcaa cacgatttta    12927
cgtcacttaa aaaactcagg ccgcagtcgg taacctcgcg catacagccg ggcagtgacg    12987
tcatcgtctg cgcggaaatg gacgaacagt ggggctatgt cggggctaaa tcgcgccagc    13047
gctggctgtt ttacgcgtat gacagtctcc ggaagacggt tgttgcgcac gtattcggtg    13107
aacgcactat ggcgacgctg gggcgtctta tgagcctgct gtcaccctt gacgtggtga    13167 tatggatgac ggatggctgg ccgctgtatg aatcccgcct gaagggaaag ctgcacgtaa    13227
tcagcaagcg atatacgcag cgaattgagc ggcataacct gaatctgagg cagcacctgg    13287
cacggctggg acggaagtcg ctgtcgttct caaaatcggt ggagctgcat gacaaagtca    13347
tcgggcatta tctgaacata aaacactatc aataagttgg agtcattacc caattatgat    13407
agaatttaca agctataagg ttattgtcct gggtttcaag cattagtcca tgcaagtttt    13467
tatgctttgc ccattctata gatatattga taagcgcgct gcctatgcct tgccccctga    13527
aatccttaca tacggcgata tcttctatat aaaagatata ttatcttatc agtattgtca    13587
```

-continued

```
atatattcaa ggcaatctgc ctcctcatcc tcttcatcct cttcgtcttg gtagcttttt    13647
aaatatggcg cttcatagag taattctgta aaggtccaat tctcgttttc atacctcggt    13707
ataatcttac ctatcacctc aaatggttcg ctgggtttat cgcaccccg  aacacgagca    13767 cggcacccgc gaccactatg ccaagaatgc ccaaggtaaa aattgccggc cccgccatga    13827
agtccgtgaa tgccccgacg gccgaagtga agggcaggcc gccacccagg ccgccgccct    13887
cactgcccgg cacctggtcg ctgaatgtcg atgccagcac ctgcggcacg tcaatgcttc    13947
cgggcgtcgc gctcgggctg atcgcccatc ccgttactgc cccgatcccg gcaatggcaa    14007
ggactgccag cgctgccatt tttggggtga ggccgttcgc ggccgagggg cgcagccct    14067 gggggatgg  gaggcccgcg ttagcgggcc gggagggttc gagaagggg  ggcaccccc     14127 ttcggcgtgc gcggtcacgc gcacagggcg cagccctggt taaaaacaag gtttataaat    14187
attggtttaa aagcaggtta aaagacaggt tagcggtggc cgaaaacgg  gcggaaaccc    14247 ttgcaaatgc tggattttct gcctgtggac agcccctcaa atgtcaatag gtgcgcccct    14307
catctgtcag cactctgccc ctcaagtgtc aaggatcgcg cccctcatct gtcagtagtc    14367
gcgcccctca agtgtcaata ccgcagggca cttatcccca ggcttgtcca catcatctgt    14427
gggaaactcg cgtaaaatca ggcgttttcg ccgatttgcg aggctggcca gctccacgtc    14487 gccgccgaa  atcgagcctg cccctcatct gtcaacgccg cgccgggtga gtcggcccct    14547
caagtgtcaa cgtccgcccc tcatctgtca gtgagggcca agttttccgc gaggtatcca    14607
caacgccggc ggccgcggtg tctcgcacac ggcttcgacg gcgtttctgg cgcgtttgca    14667
gggccataga cggccgccag cccagcggcg agggcaacca gcccggtgag cgtcgcaaag    14727
gcgctcggtc ttgccttgct cgtcggtgat gtacttcacc agctccgcga agtcgctctt    14787
cttgatggag cgcatgggga cgtgcttggc aatcacgcgc accccccggc cgttttagcg    14847
gctaaaaaag tcatggctct gccctcgggc ggaccacgcc catcatgacc ttgccaagct    14907
cgtcctgctt ctcttcgatc ttcgccagca gggcgaggat cgtggcatca ccgaaccgcg    14967
ccgtgcgcgg gtcgtcggtg agccagagtt tcagcaggcc gcccaggcgg cccaggtcgc    15027
cattgatgcg ggccagctcg cggacgtgct catagtccac gacgcccgtg attttgtagc    15087
cctggccgac ggccagcagg taggccgaca ggctcatgcc ggccgccgcc gccttttcct    15147
caatcgctct tcgttcgtct ggaaggcagt acaccttgat aggtgggctg cccttcctgg    15207
ttggcttggt ttcatcagcc atccgcttgc cctcatctgt tacgccggcg gtagccggcc    15267
agcctcgcag agcaggattc ccgttgagca ccgccaggtg cgaataaggg acagtgaaga    15327
aggaacaccc gctcgcgggt gggcctactt cacctatcct gcccggctga cgccgttgga    15387
tacaccaagg aaagtctaca cgaacccttt ggcaaaatcc tgtatatcgt gcgaaaaagg    15447
atggatatac cgaaaaaatc gctataatga ccccgaagca gggttatgca gcggaaaagc    15507
gccacgcttc ccgaagggag aaaggcggac aggtatccgg taagcggcag ggtcggaaca    15567
ggagagcgca cgagggagct tccagggga  aacgcctggt atctttatag tcctgtcggg    15627
tttcgccacc tctgacttga gcgtcgattt ttgtgatgct cgtcaggggg gcggagccta    15687
tggaaaaacg ccagcaacgc ggccttttta cggttcctgg ccttttgctg gccttttgct    15747
cacatgttct ttcctgcgtt atcccctgat tctgtggata accgtattac cgcctttgag    15807
tgagctgata ccgctcgccg cagccgaacg accgagcgca gcgagtcagt gagcgaggaa    15867
gcggaagagc gccagaaggc cgccagagag gccgagcgcg gccgtgaggc ttggacgcta    15927
gggcagggca tgaaaaagcc cgtagcgggc tgctacgggc gtctgacgcg gtggaagggg    15987
```

```
ggaggggatg ttgtctacat ggctctgctg tagtgagtgg gttgcgctcc ggcagcggtc   16047
ctgatcaatc gtcacccttt ctcggtcctt caacgttcct gacaacgagc ctccttttcg   16107
ccaatccatc gacaatcacc gcgagtccct gctcgaacgc tgcgtccgga ccggcttcgt   16167
cgaaggcgtc tatcgcggcc cgcaacagcg gcgagagcgg agcctgttca acggtgccgc   16227
cgcgctcgcc ggcatcgctg tcgccggcct gctcctcaag cacggcccca acagtgaagt   16287
agctgattgt catcagcgca ttgacggcgt ccccggccga aaaacccgcc tcgcagagga   16347
agcgaagctg cgcgtcggcc gtttccatct gcggtgcgcc cggtcgcgtg ccggcatgga   16407
tgcgcgcgcc atcgcggtag gcgagcagcg cctgcctgaa gctgcgggca ttcccgatca   16467
gaaatgagcg ccagtcgtcg tcggctctcg gcaccgaatg cgtatgattc tccgccagca   16527
tggcttcggc cagtgcgtcg agcagcgccc gcttgttcct gaagtgccag taaagcgccg   16587
gctgctgaac ccccaaccgt tccgccagtt tgcgtgtcgt cagaccgtct acgccgacct   16647
cgttcaacag gtccagggcg gcacggatca ctgtattcgg ctgcaacttt gtcatgcttg   16707
acactttatc actgataaac ataatatgtc caccaactta tcagtgataa gaatccgcg   16767
cgttcaatcg gaccagcgga ggctggtccg gaggccagac gtgaaaccca acatacccct   16827
gatcgtaatt ctgagcactg tcgcgctcga cgctgtcggc atcggcctga ttatgccggt   16887
gctgccgggc ctcctgcgcg atctggttca ctcgaacgac gtcaccgccc actatggcat   16947
tctgctggcg ctgtatgcgt tggtgcaatt tgcctgcgca cctgtgctgg gcgcgctgtc   17007
ggatcgtttc gggcggcggc caatcttgct cgtctcgctg ccggcgcca gatc          17061
```

<210> SEQ ID NO 72
<211> LENGTH: 290
<212> TYPE: PRT
<213> ORGANISM: Physcomitrella patens

<400> SEQUENCE: 72

```
Met Glu Val Val Glu Arg Phe Tyr Gly Glu Leu Asp Gly Lys Val Ser
1               5                   10                  15

Gln Gly Val Asn Ala Leu Leu Gly Ser Phe Gly Val Glu Leu Thr Asp
            20                  25                  30

Thr Pro Thr Thr Lys Gly Leu Pro Leu Val Asp Ser Pro Thr Pro Ile
        35                  40                  45

Val Leu Gly Val Ser Val Tyr Leu Thr Ile Val Ile Gly Gly Leu Leu
    50                  55                  60

Trp Ile Lys Ala Arg Asp Leu Lys Pro Arg Ala Ser Glu Pro Phe Leu
65                  70                  75                  80

Leu Gln Ala Leu Val Leu Val His Asn Leu Phe Cys Phe Ala Leu Ser
                85                  90                  95

Leu Tyr Met Cys Val Gly Ile Ala Tyr Gln Ala Ile Thr Trp Arg Tyr
            100                 105                 110

Ser Leu Trp Gly Asn Ala Tyr Asn Pro Lys His Lys Glu Met Ala Ile
        115                 120                 125

Leu Val Tyr Leu Phe Tyr Met Ser Lys Tyr Val Glu Phe Met Asp Thr
    130                 135                 140

Val Ile Met Ile Leu Lys Arg Ser Thr Arg Gln Ile Ser Phe Leu His
145                 150                 155                 160

Val Tyr His His Ser Ser Ile Ser Leu Ile Trp Trp Ala Ile Ala His
                165                 170                 175

His Ala Pro Gly Gly Glu Ala Tyr Trp Ser Ala Ala Leu Asn Ser Gly
```

```
              180                 185                 190
Val His Val Leu Met Tyr Ala Tyr Tyr Phe Leu Ala Ala Cys Leu Arg
        195                 200                 205

Ser Ser Pro Lys Leu Lys Asn Lys Tyr Leu Phe Trp Gly Arg Tyr Leu
    210                 215                 220

Thr Gln Phe Gln Met Phe Gln Phe Met Leu Asn Leu Val Gln Ala Tyr
225                 230                 235                 240

Tyr Asp Met Lys Thr Asn Ala Pro Tyr Pro Gln Trp Leu Ile Lys Ile
                245                 250                 255

Leu Phe Tyr Tyr Met Ile Ser Leu Leu Phe Leu Phe Gly Asn Phe Tyr
            260                 265                 270

Val Gln Lys Tyr Ile Lys Pro Ser Asp Gly Lys Gln Lys Gly Ala Lys
        275                 280                 285

Thr Glu
    290

<210> SEQ ID NO 73
<211> LENGTH: 282
<212> TYPE: PRT
<213> ORGANISM: Caenorhabditis elegans

<400> SEQUENCE: 73

Met Glu Asn Phe Trp Ser Ile Val Val Phe Phe Leu Leu Ser Ile Leu
1               5                   10                  15

Phe Ile Leu Tyr Asn Ile Ser Thr Val Cys His Tyr Tyr Met Arg Ile
            20                  25                  30

Ser Phe Tyr Tyr Phe Thr Ile Leu Leu His Gly Met Glu Val Cys Val
        35                  40                  45

Thr Met Ile Pro Ser Trp Leu Asn Gly Lys Gly Ala Asp Tyr Val Phe
    50                  55                  60

His Ser Phe Phe Tyr Trp Cys Lys Trp Thr Gly Val His Thr Thr Val
65                  70                  75                  80

Tyr Gly Tyr Glu Lys Thr Gln Val Glu Gly Pro Ala Val Val Ile Cys
                85                  90                  95

Asn His Gln Ser Ser Leu Asp Ile Leu Ser Met Ala Ser Ile Trp Pro
            100                 105                 110

Lys Asn Cys Val Val Met Met Lys Arg Ile Leu Ala Tyr Val Pro Phe
        115                 120                 125

Phe Asn Leu Gly Ala Tyr Phe Ser Asn Thr Ile Phe Ile Asp Arg Tyr
130                 135                 140

Asn Arg Glu Arg Ala Met Ala Ser Val Asp Tyr Cys Ala Ser Glu Met
145                 150                 155                 160

Lys Asn Arg Asn Leu Lys Leu Trp Val Phe Pro Glu Gly Thr Arg Asn
                165                 170                 175

Arg Glu Gly Gly Phe Ile Pro Phe Lys Lys Gly Ala Phe Asn Ile Ala
            180                 185                 190

Val Arg Ala Gln Ile Pro Ile Ile Pro Val Val Phe Ser Asp Tyr Arg
        195                 200                 205

Asp Phe Tyr Ser Lys Pro Gly Arg Tyr Phe Lys Asn Asp Gly Glu Val
    210                 215                 220

Val Ile Arg Val Leu Asp Ala Ile Pro Thr Lys Gly Leu Thr Leu Asp
225                 230                 235                 240

Asp Val Ser Glu Leu Ser Asp Met Cys Arg Asp Val Met Leu Ala Ala
                245                 250                 255
```

Tyr Lys Glu Val Thr Leu Glu Ala Gln Gln Arg Asn Ala Thr Arg Arg
            260                 265                 270

Gly Glu Thr Lys Asp Gly Lys Lys Ser Glu
            275                 280

<210> SEQ ID NO 74
<211> LENGTH: 477
<212> TYPE: PRT
<213> ORGANISM: Phaeodactylum tricornutum

<400> SEQUENCE: 74

Met Gly Lys Gly Gly Asp Ala Arg Ala Ser Lys Gly Ser Thr Ala Ala
1               5                   10                  15

Arg Lys Ile Ser Trp Gln Glu Val Lys Thr His Ala Ser Pro Glu Asp
            20                  25                  30

Ala Trp Ile Ile His Ser Asn Lys Val Tyr Asp Val Ser Asn Trp His
            35                  40                  45

Glu His Pro Gly Gly Ala Val Ile Phe Thr His Ala Gly Asp Asp Met
        50                  55                  60

Thr Asp Ile Phe Ala Ala Phe His Ala Pro Gly Ser Gln Ser Leu Met
65                  70                  75                  80

Lys Lys Phe Tyr Ile Gly Glu Leu Leu Pro Glu Thr Thr Gly Lys Glu
                85                  90                  95

Pro Gln Gln Ile Ala Phe Glu Lys Gly Tyr Arg Asp Leu Arg Ser Lys
            100                 105                 110

Leu Ile Met Met Gly Met Phe Lys Ser Asn Lys Trp Phe Tyr Val Tyr
        115                 120                 125

Lys Cys Leu Ser Asn Met Ala Ile Trp Ala Ala Cys Ala Leu Val
130                 135                 140

Phe Tyr Ser Asp Arg Phe Trp Val His Leu Ala Ser Ala Val Met Leu
145                 150                 155                 160

Gly Thr Phe Phe Gln Gln Ser Gly Trp Leu Ala His Asp Phe Leu His
                165                 170                 175

His Gln Val Phe Thr Lys Arg Lys His Gly Asp Leu Gly Gly Leu Phe
            180                 185                 190

Trp Gly Asn Leu Met Gln Gly Tyr Ser Val Gln Trp Trp Lys Asn Lys
        195                 200                 205

His Asn Gly His His Ala Val Pro Asn Leu His Cys Ser Ser Ala Val
210                 215                 220

Ala Gln Asp Gly Asp Pro Asp Ile Asp Thr Met Pro Leu Leu Ala Trp
225                 230                 235                 240

Ser Val Gln Gln Ala Gln Ser Tyr Arg Glu Leu Gln Ala Asp Gly Lys
                245                 250                 255

Asp Ser Gly Leu Val Lys Phe Met Ile Arg Asn Gln Ser Tyr Phe Tyr
            260                 265                 270

Phe Pro Ile Leu Leu Leu Ala Arg Leu Ser Trp Leu Asn Glu Ser Phe
        275                 280                 285

Lys Cys Ala Phe Gly Leu Gly Ala Ala Ser Glu Asn Ala Ala Leu Glu
290                 295                 300

Leu Lys Ala Lys Gly Leu Gln Tyr Pro Leu Leu Glu Lys Ala Gly Ile
305                 310                 315                 320

Leu Leu His Tyr Ala Trp Met Leu Thr Val Ser Ser Gly Phe Gly Arg
                325                 330                 335

Phe Ser Phe Ala Tyr Thr Ala Phe Tyr Leu Thr Ala Thr Ala Ser
            340                 345                 350

```
Cys Gly Phe Leu Leu Ala Ile Val Phe Gly Leu Gly His Asn Gly Met
        355                 360                 365

Ala Thr Tyr Asn Ala Asp Ala Arg Pro Asp Phe Trp Lys Leu Gln Val
    370                 375                 380

Thr Thr Thr Arg Asn Val Thr Gly Gly His Gly Phe Pro Gln Ala Phe
385                 390                 395                 400

Val Asp Trp Phe Cys Gly Gly Leu Gln Tyr Gln Val Asp His His Leu
                405                 410                 415

Phe Pro Ser Leu Pro Arg His Asn Leu Ala Lys Thr His Ala Leu Val
            420                 425                 430

Glu Ser Phe Cys Lys Glu Trp Gly Val Gln Tyr His Glu Ala Asp Leu
        435                 440                 445

Val Asp Gly Thr Met Glu Val Leu His His Leu Gly Ser Val Ala Gly
    450                 455                 460

Glu Phe Val Val Asp Phe Val Arg Asp Gly Pro Ala Met
465                 470                 475

<210> SEQ ID NO 75
<211> LENGTH: 47
<212> TYPE: DNA
<213> ORGANISM: unknown
<220> FEATURE:
<221> NAME/KEY: misc_feature
<222> LOCATION: (1)..(47)
<223> OTHER INFORMATION: Oligonucleotide "USP1 upstream"

<400> SEQUENCE: 75
ccggaattcg gcgcgccgag ctcctcgagc aaatttacac attgcca                47

<210> SEQ ID NO 76
<211> LENGTH: 47
<212> TYPE: DNA
<213> ORGANISM: unknown
<220> FEATURE:
<221> NAME/KEY: misc_feature
<222> LOCATION: (1)..(47)
<223> OTHER INFORMATION: Oligonucleotide "USP2 upstream"

<400> SEQUENCE: 76
ccggaattcg gcgcgccgag ctcctcgagc aaatttacac attgcca                47

<210> SEQ ID NO 77
<211> LENGTH: 47
<212> TYPE: DNA
<213> ORGANISM: unknown
<220> FEATURE:
<221> NAME/KEY: misc_feature
<222> LOCATION: (1)..(47)
<223> OTHER INFORMATION: Oligonucleotide "USP3 upstream"

<400> SEQUENCE: 77
ccggaattcg gcgcgccgag ctcctcgagc aaatttacac attgcca                47

<210> SEQ ID NO 78
<211> LENGTH: 48
<212> TYPE: DNA
<213> ORGANISM: unknown
<220> FEATURE:
<221> NAME/KEY: misc_feature
<222> LOCATION: (1)..(48)
<223> OTHER INFORMATION: Oligonucleotide "USP1 downstream"

<400> SEQUENCE: 78
```
aaaactgcag gcggccgccc accgcggtgg gctggctatg aagaaatt        48

<210> SEQ ID NO 79
<211> LENGTH: 27
<212> TYPE: DNA
<213> ORGANISM: unknown
<220> FEATURE:
<221> NAME/KEY: misc_feature
<222> LOCATION: (1)..(27)
<223> OTHER INFORMATION: Oligonucleotide "USP2 downstream"

<400> SEQUENCE: 79
cgcggatccg ctggctatga agaaatt        27

<210> SEQ ID NO 80
<211> LENGTH: 45
<212> TYPE: DNA
<213> ORGANISM: unknown
<220> FEATURE:
<221> NAME/KEY: misc_feature
<222> LOCATION: (1)..(45)
<223> OTHER INFORMATION: Oligonucleotide "USP3 downstream"

<400> SEQUENCE: 80
tcccccggga tcgatgccgg cagatctgct ggctatgaag aaatt        45

<210> SEQ ID NO 81
<211> LENGTH: 40
<212> TYPE: DNA
<213> ORGANISM: unknown
<220> FEATURE:
<221> NAME/KEY: misc_feature
<222> LOCATION: (1)..(40)
<223> OTHER INFORMATION: Oligonucleotide "OCS1 upstream"

<400> SEQUENCE: 81
aaaactgcag tctagaaggc ctcctgcttt aatgagatat        40

<210> SEQ ID NO 82
<211> LENGTH: 51
<212> TYPE: DNA
<213> ORGANISM: unknown
<220> FEATURE:
<221> NAME/KEY: misc_feature
<222> LOCATION: (1)..(51)
<223> OTHER INFORMATION: Oligonucleotide "OCS2 upstream"

<400> SEQUENCE: 82
cgcggatccg atatcgggcc cgctagcgtt aaccctgctt taatgagata t        51

<210> SEQ ID NO 83
<211> LENGTH: 33
<212> TYPE: DNA
<213> ORGANISM: unknown
<220> FEATURE:
<221> NAME/KEY: misc_feature
<222> LOCATION: (1)..(33)
<223> OTHER INFORMATION: Oligonucleotide "OCS3 upstream"

<400> SEQUENCE: 83
tcccccgggc catggcctgc tttaatgaga tat        33

<210> SEQ ID NO 84
<211> LENGTH: 53
<212> TYPE: DNA
<213> ORGANISM: unknown
<220> FEATURE:
<221> NAME/KEY: misc_feature
<222> LOCATION: (1)..(53)
<223> OTHER INFORMATION: Oligonucleotide "OCS1 downstream"

<400> SEQUENCE: 84
cccaagcttg gcgcgccgag ctcgaattcg tcgacggaca atcagtaaat tga    53

<210> SEQ ID NO 85
<211> LENGTH: 53
<212> TYPE: DNA
<213> ORGANISM: unknown
<220> FEATURE:
<221> NAME/KEY: misc_feature
<222> LOCATION: (1)..(53)
<223> OTHER INFORMATION: Oligonucleotide "OCS2 downstream"

<400> SEQUENCE: 85
cccaagcttg gcgcgccgag ctcgaattcg tcgacggaca atcagtaaat tga    53

<210> SEQ ID NO 86
<211> LENGTH: 47
<212> TYPE: DNA
<213> ORGANISM: unknown
<220> FEATURE:
<221> NAME/KEY: misc_feature
<222> LOCATION: (1)..(47)
<223> OTHER INFORMATION: Oligonucleotide "OCS3 downstream"

<400> SEQUENCE: 86
cccaagcttg gcgcgccgag ctcgtcgacg gacaatcagt aaattga    47

<210> SEQ ID NO 87
<211> LENGTH: 29
<212> TYPE: DNA
<213> ORGANISM: unknown
<220> FEATURE:
<221> NAME/KEY: misc_feature
<222> LOCATION: (1)..(29)
<223> OTHER INFORMATION: Primer "5' T06E8.1f"

<400> SEQUENCE: 87
acataatgga gaacttctgg tcgatcgtc    29

<210> SEQ ID NO 88
<211> LENGTH: 24
<212> TYPE: DNA
<213> ORGANISM: unknown
<220> FEATURE:
<221> NAME/KEY: misc_feature
<222> LOCATION: (1)..(24)
<223> OTHER INFORMATION: Primer "3' T06E8.1r"

<400> SEQUENCE: 88
ttactcagat ttcttcccgt cttt    24

<210> SEQ ID NO 89
<211> LENGTH: 26
<212> TYPE: DNA
<213> ORGANISM: unknown
<220> FEATURE:
<221> NAME/KEY: misc_feature
<222> LOCATION: (1)..(26)
<223> OTHER INFORMATION: Primer "5' F59F4.4f"

<400> SEQUENCE: 89
acataatgac cttcctagcc atatta    26

<210> SEQ ID NO 90

```
<211> LENGTH: 24
<212> TYPE: DNA
<213> ORGANISM: unknown
<220> FEATURE:
<221> NAME/KEY: misc_feature
<222> LOCATION: (1)..(24)
<223> OTHER INFORMATION: Primer "3' F59F4.4r"

<400> SEQUENCE: 90
tcagatattc aaattggcgg cttc                                              24

<210> SEQ ID NO 91
<211> LENGTH: 32
<212> TYPE: DNA
<213> ORGANISM: unknown
<220> FEATURE:
<221> NAME/KEY: misc_feature
<222> LOCATION: (1)..(32)
<223> OTHER INFORMATION: Primer "ARe503f"

<400> SEQUENCE: 91
ttaagcgcgg ccgcatggag aacttctggt cg                                     32

<210> SEQ ID NO 92
<211> LENGTH: 31
<212> TYPE: DNA
<213> ORGANISM: unknown
<220> FEATURE:
<221> NAME/KEY: misc_feature
<222> LOCATION: (1)..(31)
<223> OTHER INFORMATION: Primer "ARe504r"

<400> SEQUENCE: 92
acctcggcgg ccgcccttttt actcagattt c                                     31

<210> SEQ ID NO 93
<211> LENGTH: 41
<212> TYPE: DNA
<213> ORGANISM: unknown
<220> FEATURE:
<221> NAME/KEY: misc_feature
<222> LOCATION: (1)..(41)
<223> OTHER INFORMATION: Forward primer

<400> SEQUENCE: 93
acataatgga gaacttctgg tctattgttg tgttttttct a                           41

<210> SEQ ID NO 94
<211> LENGTH: 41
<212> TYPE: DNA
<213> ORGANISM: unknown
<220> FEATURE:
<221> NAME/KEY: misc_feature
<222> LOCATION: (1)..(41)
<223> OTHER INFORMATION: Reverse primer

<400> SEQUENCE: 94
ctagctagct tactcagatt tcttcccgtc ttttgtttct c                           41

<210> SEQ ID NO 95
<211> LENGTH: 18
<212> TYPE: DNA
<213> ORGANISM: unknown
<220> FEATURE:
<221> NAME/KEY: misc_feature
<222> LOCATION: (1)..(18)
<223> OTHER INFORMATION: primer

<400> SEQUENCE: 95
```
caggaaacag ctatgacc                         18

<210> SEQ ID NO 96
<211> LENGTH: 19
<212> TYPE: DNA
<213> ORGANISM: unknown
<220> FEATURE:
<221> NAME/KEY: misc_feature
<222> LOCATION: (1)..(19)
<223> OTHER INFORMATION: primer

<400> SEQUENCE: 96
ctaaagggaa caaaagctg                        19

<210> SEQ ID NO 97
<211> LENGTH: 18
<212> TYPE: DNA
<213> ORGANISM: unknown
<220> FEATURE:
<221> NAME/KEY: misc_feature
<222> LOCATION: (1)..(18)
<223> OTHER INFORMATION: primer

<400> SEQUENCE: 97
tgtaaaacga cggccagt                         18

<210> SEQ ID NO 98
<211> LENGTH: 18
<212> TYPE: DNA
<213> ORGANISM: unknown
<220> FEATURE:
<221> NAME/KEY: misc_feature
<222> LOCATION: (1)..(18)
<223> OTHER INFORMATION: Primer "LPAAT069-5'"

<400> SEQUENCE: 98
gctacattgc catggagc                         18

<210> SEQ ID NO 99
<211> LENGTH: 19
<212> TYPE: DNA
<213> ORGANISM: unknown
<220> FEATURE:
<221> NAME/KEY: misc_feature
<222> LOCATION: (1)..(19)
<223> OTHER INFORMATION: Primer "LPAAT069-3'"

<400> SEQUENCE: 99
gctacaagag gtcaggtcg                        19

<210> SEQ ID NO 100
<211> LENGTH: 25
<212> TYPE: DNA
<213> ORGANISM: unknown
<220> FEATURE:
<221> NAME/KEY: misc_feature
<222> LOCATION: (1)..(25)
<223> OTHER INFORMATION: Primer "ACtrau-5'"

<400> SEQUENCE: 100
ctggatccat gagcgcgtgg acgag                 25

<210> SEQ ID NO 101
<211> LENGTH: 25
<212> TYPE: DNA
<213> ORGANISM: unknown
<220> FEATURE:

```
<221> NAME/KEY: misc_feature
<222> LOCATION: (1)..(25)
<223> OTHER INFORMATION: Primer "ACtrau-3'"

<400> SEQUENCE: 101
ttggatccca agaggtcagg tcgga                                              25

<210> SEQ ID NO 102
<211> LENGTH: 26
<212> TYPE: DNA
<213> ORGANISM: unknown
<220> FEATURE:
<221> NAME/KEY: misc_feature
<222> LOCATION: (1)..(26)
<223> OTHER INFORMATION: Primer "ACtrau-3'stop"

<400> SEQUENCE: 102
ttggatccct acaagaggtc aggtcg                                             26

<210> SEQ ID NO 103
<211> LENGTH: 22
<212> TYPE: DNA
<213> ORGANISM: unknown
<220> FEATURE:
<221> NAME/KEY: misc_feature
<222> LOCATION: (1)..(22)
<223> OTHER INFORMATION: Primer "YES-HIS-5'"

<400> SEQUENCE: 103
ctgagctcat gagcgcgtgg ag                                                 22

<210> SEQ ID NO 104
<211> LENGTH: 35
<212> TYPE: DNA
<213> ORGANISM: unknown
<220> FEATURE:
<221> NAME/KEY: misc_feature
<222> LOCATION: (1)..(35)
<223> OTHER INFORMATION: Primer "YES-HIS-3'"

<400> SEQUENCE: 104
atggatccgt gatggtgatg gtgatgcaag aggtc                                   35

<210> SEQ ID NO 105
<211> LENGTH: 18
<212> TYPE: DNA
<213> ORGANISM: unknown
<220> FEATURE:
<221> NAME/KEY: misc_feature
<222> LOCATION: (1)..(18)
<223> OTHER INFORMATION: Primer "LPAAT069-5'"

<400> SEQUENCE: 105
gctacattgc catggagc                                                      18

<210> SEQ ID NO 106
<211> LENGTH: 19
<212> TYPE: DNA
<213> ORGANISM: unknown
<220> FEATURE:
<221> NAME/KEY: misc_feature
<222> LOCATION: (1)..(19)
<223> OTHER INFORMATION: Primer "LPAAT069-3'"

<400> SEQUENCE: 106
gctacaagag gtcaggtcg                                                     19
```

```
<210> SEQ ID NO 107
<211> LENGTH: 41
<212> TYPE: DNA
<213> ORGANISM: unknown
<220> FEATURE:
<223> OTHER INFORMATION: primer
<220> FEATURE:
<221> NAME/KEY: misc_feature
<222> LOCATION: (1)..(41)
<223> OTHER INFORMATION: Primer

<400> SEQUENCE: 107
atggatgaat ccaccacgac catcagcccg atgcttgctg c                    41

<210> SEQ ID NO 108
<211> LENGTH: 40
<212> TYPE: DNA
<213> ORGANISM: unknown
<220> FEATURE:
<221> NAME/KEY: misc_feature
<222> LOCATION: (1)..(40)
<223> OTHER INFORMATION: Primer

<400> SEQUENCE: 108
atgaacccta tctacaaggg ttcagcccga tgcttgctgc                      40

<210> SEQ ID NO 109
<211> LENGTH: 37
<212> TYPE: DNA
<213> ORGANISM: unknown
<220> FEATURE:
<221> NAME/KEY: misc_feature
<222> LOCATION: (1)..(37)
<223> OTHER INFORMATION: Primer

<400> SEQUENCE: 109
atgttactgc tagcatttgt ttactttgcc attaagg                         37

<210> SEQ ID NO 110
<211> LENGTH: 46
<212> TYPE: DNA
<213> ORGANISM: unknown
<220> FEATURE:
<221> NAME/KEY: misc_feature
<222> LOCATION: (1)..(46)
<223> OTHER INFORMATION: Primer

<400> SEQUENCE: 110
atgagcgcgt ggacgagggc ctacaagagg tcaggtcgga cgtaca               46

<210> SEQ ID NO 111
<211> LENGTH: 40
<212> TYPE: DNA
<213> ORGANISM: unknown
<220> FEATURE:
<221> NAME/KEY: misc_feature
<222> LOCATION: (1)..(40)
<223> OTHER INFORMATION: Primer

<400> SEQUENCE: 111
atggctttga tgtatatctg ttacacgatt tttcttttag                      40

<210> SEQ ID NO 112
<211> LENGTH: 41
<212> TYPE: DNA
<213> ORGANISM: unknown
<220> FEATURE:
<221> NAME/KEY: misc_feature
<222> LOCATION: (1)..(41)
```

<223> OTHER INFORMATION: Primer

<400> SEQUENCE: 112
atgctgatat tacagcccctt cctaatgaac aggaagaccg t                41

<210> SEQ ID NO 113
<211> LENGTH: 39
<212> TYPE: DNA
<213> ORGANISM: unknown
<220> FEATURE:
<221> NAME/KEY: misc_feature
<222> LOCATION: (1)..(39)
<223> OTHER INFORMATION: Primer

<400> SEQUENCE: 113
atgatccgga ttttcagagt cagtccgttt tgccgaggt                39

<210> SEQ ID NO 114
<211> LENGTH: 39
<212> TYPE: DNA
<213> ORGANISM: unknown
<220> FEATURE:
<221> NAME/KEY: misc_feature
<222> LOCATION: (1)..(39)
<223> OTHER INFORMATION: Primer

<400> SEQUENCE: 114
atgccgtcgc tgtttcgggt caatcagttc gcctgcttc                39

<210> SEQ ID NO 115
<211> LENGTH: 41
<212> TYPE: DNA
<213> ORGANISM: unknown
<220> FEATURE:
<221> NAME/KEY: misc_feature
<222> LOCATION: (1)..(41)
<223> OTHER INFORMATION: Primer

<400> SEQUENCE: 115
atgctgatat tacagcccctt cctaatgaac aggaagaccg t                41

<210> SEQ ID NO 116
<211> LENGTH: 39
<212> TYPE: DNA
<213> ORGANISM: unknown
<220> FEATURE:
<221> NAME/KEY: misc_feature
<222> LOCATION: (1)..(39)
<223> OTHER INFORMATION: Primer

<400> SEQUENCE: 116
atgaccagca cggaaaatac ctagatgtta gtttcactc                39

<210> SEQ ID NO 117
<211> LENGTH: 40
<212> TYPE: DNA
<213> ORGANISM: unknown
<220> FEATURE:
<221> NAME/KEY: misc_feature
<222> LOCATION: (1)..(40)
<223> OTHER INFORMATION: Primer

<400> SEQUENCE: 117
atgattatga tggaggtgct gtcagtccgt tttgccgagg                40

<210> SEQ ID NO 118
<211> LENGTH: 40

```
<212> TYPE: DNA
<213> ORGANISM: unknown
<220> FEATURE:
<221> NAME/KEY: misc_feature
<222> LOCATION: (1)..(40)
<223> OTHER INFORMATION: Primer

<400> SEQUENCE: 118
atgtgttcaa tttcttgtgg ttagtggaac ataagctgtt                                40

<210> SEQ ID NO 119
<211> LENGTH: 41
<212> TYPE: DNA
<213> ORGANISM: unknown
<220> FEATURE:
<221> NAME/KEY: misc_feature
<222> LOCATION: (1)..(41)
<223> OTHER INFORMATION: Primer

<400> SEQUENCE: 119
atgggaaagt ccactttacc tatgaagtct cctcatcatc g                              41

<210> SEQ ID NO 120
<211> LENGTH: 27
<212> TYPE: DNA
<213> ORGANISM: unknown
<220> FEATURE:
<221> NAME/KEY: misc_feature
<222> LOCATION: (1)..(27)
<223> OTHER INFORMATION: Primer GSP

<400> SEQUENCE: 120 tctcttttc gtgctgctcc agccgat                                               27

<210> SEQ ID NO 121
<211> LENGTH: 52
<212> TYPE: DNA
<213> ORGANISM: unknown
<220> FEATURE:
<223> OTHER INFORMATION: primer
<220> FEATURE:
<221> NAME/KEY: misc_feature
<222> LOCATION: (1)..(52)
<223> OTHER INFORMATION: 5' primer att1ThLPAAT

<400> SEQUENCE: 121
ggggacaagt ttgtacaaaa aagcaggctc catgagcgcg tggacgaggg cc                  52

<210> SEQ ID NO 122
<211> LENGTH: 72
<212> TYPE: DNA
<213> ORGANISM: unknown
<220> FEATURE:
<221> NAME/KEY: misc_feature
<222> LOCATION: (1)..(72)
<223> OTHER INFORMATION: 3' primer att2ThLPAAT

<400> SEQUENCE: 122
ggggaccact ttgtacaaga aagctgggtc tagtggtggt ggtggtggtg caagaggtca          60
ggtcggacgt ac                                                              72

<210> SEQ ID NO 123
<211> LENGTH: 22
<212> TYPE: DNA
<213> ORGANISM: Artificial sequence
<220> FEATURE:
<223> OTHER INFORMATION: primer
```

```
<400> SEQUENCE: 123
atggatgaat ccaccacgac ca                                              22

<210> SEQ ID NO 124
<211> LENGTH: 19
<212> TYPE: DNA
<213> ORGANISM: Artificial sequence
<220> FEATURE:
<223> OTHER INFORMATION: primer

<400> SEQUENCE: 124
tcagcccgat gcttgctgc                                                  19

<210> SEQ ID NO 125
<211> LENGTH: 21
<212> TYPE: DNA
<213> ORGANISM: Artificial sequence
<220> FEATURE:
<223> OTHER INFORMATION: primer

<400> SEQUENCE: 125 atgaaccta tctacaaggg t                                                21

<210> SEQ ID NO 126
<211> LENGTH: 19
<212> TYPE: DNA
<213> ORGANISM: Artificial sequence
<220> FEATURE:
<223> OTHER INFORMATION: primer

<400> SEQUENCE: 126
tcagcccgat gcttgctgc                                                  19

<210> SEQ ID NO 127
<211> LENGTH: 20
<212> TYPE: DNA
<213> ORGANISM: Artificial sequence
<220> FEATURE:
<223> OTHER INFORMATION: primer

<400> SEQUENCE: 127
atgttactgc tagcatttgt                                                 20

<210> SEQ ID NO 128
<211> LENGTH: 17
<212> TYPE: DNA
<213> ORGANISM: Artificial sequence
<220> FEATURE:
<223> OTHER INFORMATION: primer

<400> SEQUENCE: 128
ttactttgcc attaagg                                                    17

<210> SEQ ID NO 129
<211> LENGTH: 20
<212> TYPE: DNA
<213> ORGANISM: Artificial sequence
<220> FEATURE:
<223> OTHER INFORMATION: primer

<400> SEQUENCE: 129
atgagcgcgt ggacgagggc                                                 20

<210> SEQ ID NO 130
<211> LENGTH: 26
```

```
<212> TYPE: DNA
<213> ORGANISM: Artificial sequence
<220> FEATURE:
<223> OTHER INFORMATION: primer

<400> SEQUENCE: 130
ctacaagagg tcaggtcgga cgtaca                                      26

<210> SEQ ID NO 131
<211> LENGTH: 20
<212> TYPE: DNA
<213> ORGANISM: Artificial sequence
<220> FEATURE:
<223> OTHER INFORMATION: primer

<400> SEQUENCE: 131
atggctttga tgtatatctg                                             20

<210> SEQ ID NO 132
<211> LENGTH: 20
<212> TYPE: DNA
<213> ORGANISM: Artificial sequence
<220> FEATURE:
<223> OTHER INFORMATION: primer

<400> SEQUENCE: 132
ttacacgatt tttcttttag                                             20

<210> SEQ ID NO 133
<211> LENGTH: 21
<212> TYPE: DNA
<213> ORGANISM: Artificial sequence
<220> FEATURE:
<223> OTHER INFORMATION: primer

<400> SEQUENCE: 133
atgctgatat tacagcccctt c                                          21

<210> SEQ ID NO 134
<211> LENGTH: 20
<212> TYPE: DNA
<213> ORGANISM: Artificial sequence
<220> FEATURE:
<223> OTHER INFORMATION: primer

<400> SEQUENCE: 134
ctaatgaaca ggaagaccgt                                             20

<210> SEQ ID NO 135
<211> LENGTH: 19
<212> TYPE: DNA
<213> ORGANISM: Artificial sequence
<220> FEATURE:
<223> OTHER INFORMATION: primer

<400> SEQUENCE: 135
atgatccgga ttttcagag                                              19

<210> SEQ ID NO 136
<211> LENGTH: 20
<212> TYPE: DNA
<213> ORGANISM: Artificial sequence
<220> FEATURE:
<223> OTHER INFORMATION: primer

<400> SEQUENCE: 136
```

```
tcagtccgtt ttgccgaggt                                              20

<210> SEQ ID NO 137
<211> LENGTH: 19
<212> TYPE: DNA
<213> ORGANISM: Artificial sequence
<220> FEATURE:
<223> OTHER INFORMATION: primer

<400> SEQUENCE: 137
atgccgtcgc tgtttcggg                                               19

<210> SEQ ID NO 138
<211> LENGTH: 20
<212> TYPE: DNA
<213> ORGANISM: Artificial sequence
<220> FEATURE:
<223> OTHER INFORMATION: primer

<400> SEQUENCE: 138
tcaatcagtt cgcctgcttc                                              20

<210> SEQ ID NO 139
<211> LENGTH: 21
<212> TYPE: DNA
<213> ORGANISM: Artificial sequence
<220> FEATURE:
<223> OTHER INFORMATION: primer

<400> SEQUENCE: 139
atgctgatat tacagcccttt c                                           21

<210> SEQ ID NO 140
<211> LENGTH: 20
<212> TYPE: DNA
<213> ORGANISM: Artificial sequence
<220> FEATURE:
<223> OTHER INFORMATION: primer

<400> SEQUENCE: 140
ctaatgaaca ggaagaccgt                                              20

<210> SEQ ID NO 141
<211> LENGTH: 20
<212> TYPE: DNA
<213> ORGANISM: Artificial sequence
<220> FEATURE:
<223> OTHER INFORMATION: primer

<400> SEQUENCE: 141
atgaccagca cggaaaatac                                              20

<210> SEQ ID NO 142
<211> LENGTH: 19
<212> TYPE: DNA
<213> ORGANISM: Artificial sequence
<220> FEATURE:
<223> OTHER INFORMATION: primer

<400> SEQUENCE: 142
ctagatgtta gtttcactc                                               19

<210> SEQ ID NO 143
<211> LENGTH: 21
<212> TYPE: DNA
<213> ORGANISM: Artificial sequence
```

```
<220> FEATURE:
<223> OTHER INFORMATION: primer

<400> SEQUENCE: 143
atgattatga tggaggtgct g                                              21

<210> SEQ ID NO 144
<211> LENGTH: 19
<212> TYPE: DNA
<213> ORGANISM: Artificial sequence
<220> FEATURE:
<223> OTHER INFORMATION: primer

<400> SEQUENCE: 144
tcagtccgtt ttgccgagg                                                 19

<210> SEQ ID NO 145
<211> LENGTH: 20
<212> TYPE: DNA
<213> ORGANISM: Artificial sequence
<220> FEATURE:
<223> OTHER INFORMATION: primer

<400> SEQUENCE: 145
atgtgttcaa tttcttgtgg                                                20

<210> SEQ ID NO 146
<211> LENGTH: 20
<212> TYPE: DNA
<213> ORGANISM: Artificial sequence
<220> FEATURE:
<223> OTHER INFORMATION: primer

<400> SEQUENCE: 146
ttagtggaac ataagctgtt                                                20

<210> SEQ ID NO 147
<211> LENGTH: 19
<212> TYPE: DNA
<213> ORGANISM: Artificial sequence
<220> FEATURE:
<223> OTHER INFORMATION: primer

<400> SEQUENCE: 147
atgggaaagt ccactttac                                                 19

<210> SEQ ID NO 148
<211> LENGTH: 22
<212> TYPE: DNA
<213> ORGANISM: Artificial sequence
<220> FEATURE:
<223> OTHER INFORMATION: primer

<400> SEQUENCE: 148
ctatgaagtc tcctcatcat cg                                             22
```